(12) United States Patent
Lippincott et al.

(10) Patent No.: US 11,873,339 B2
(45) Date of Patent: *Jan. 16, 2024

(54) ANTI-C10ORF54 ANTIBODIES AND USES THEREOF

(71) Applicant: PIERRE FABRE MEDICAMENT, Boulogne-Billancourt (FR)

(72) Inventors: John Lippincott, Burlingame, CA (US); Edward Thein Htun Van Der Horst, Burlingame, CA (US); Sung Young Kim, Burlingame, CA (US); Leonard G Presta, Burlingame, CA (US); Jan-Willem Theunissen, Burlingame, CA (US)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 513 days.

This patent is subject to a terminal disclaimer.

(21) Appl. No.: 16/908,347

(22) Filed: Jun. 22, 2020

(65) Prior Publication Data

US 2020/0385473 A1 Dec. 10, 2020

Related U.S. Application Data

(63) Continuation of application No. 15/534,982, filed as application No. PCT/US2015/065331 on Dec. 11, 2015, now Pat. No. 10,766,959.

(60) Provisional application No. 62/090,880, filed on Dec. 11, 2014.

(51) Int. Cl.
| | |
|---|---|
| *C07K 16/28* | (2006.01) |
| *A61K 39/395* | (2006.01) |
| *A61K 47/68* | (2017.01) |
| *A61P 35/00* | (2006.01) |
| *A61K 31/4025* | (2006.01) |
| *A61K 31/404* | (2006.01) |
| *A61K 31/5517* | (2006.01) |
| *A61K 39/00* | (2006.01) |

(52) U.S. Cl.
CPC ........ *C07K 16/2827* (2013.01); *A61K 31/404* (2013.01); *A61K 31/4025* (2013.01); *A61K 31/5517* (2013.01); *A61K 39/39558* (2013.01); *A61K 47/6803* (2017.08); *A61K 47/6851* (2017.08); *A61K 47/6873* (2017.08); *A61P 35/00* (2018.01); *A61K 2039/505* (2013.01); *C07K 2317/24* (2013.01); *C07K 2317/565* (2013.01); *C07K 2317/567* (2013.01); *C07K 2317/73* (2013.01); *C07K 2317/74* (2013.01); *C07K 2317/92* (2013.01)

(58) Field of Classification Search
CPC ................ C07K 2317/565; C07K 2317/24
USPC .................................................. 424/133.1
See application file for complete search history.

(56) References Cited

U.S. PATENT DOCUMENTS

| | | |
|---|---|---|
| 3,710,795 A | 1/1973 | Higuchi et al. |
| 3,773,919 A | 11/1973 | Boswell et al. |
| RE28,819 E | 5/1976 | Thompson |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Cook et al. |
| 4,414,209 A | 11/1983 | Cook et al. |
| 4,444,887 A | 4/1984 | Hoffmann |
| 4,485,045 A | 11/1984 | Regen |
| 4,522,811 A | 6/1985 | Eppstein et al. |
| 4,526,938 A | 7/1985 | Churchill et al. |
| 4,544,545 A | 10/1985 | Ryan et al. |
| 4,676,980 A | 6/1987 | Segal et al. |
| 4,716,111 A | 12/1987 | Osband et al. |
| 4,816,397 A | 3/1989 | Boss et al. |
| 4,816,567 A | 3/1989 | Cabilly et al. |
| 4,880,078 A | 11/1989 | Inoue et al. |
| 4,980,286 A | 12/1990 | Morgan et al. |
| 5,013,556 A | 5/1991 | Woodle et al. |
| 5,112,946 A | 5/1992 | Maione |
| 5,122,464 A | 6/1992 | Wilson et al. |
| 5,128,326 A | 7/1992 | Balazs et al. |
| 5,223,409 A | 6/1993 | Ladner et al. |
| 5,225,539 A | 7/1993 | Winter |
| 5,290,540 A | 3/1994 | Prince et al. |
| 5,314,995 A | 5/1994 | Fell, Jr. et al. |
| 5,336,603 A | 8/1994 | Capon et al. |
| 5,349,053 A | 9/1994 | Landolfi |
| 5,359,046 A | 10/1994 | Capon et al. |

(Continued)

FOREIGN PATENT DOCUMENTS

| | | |
|---|---|---|
| EP | 0 239 400 B1 | 9/1987 |
| EP | 037 166 A1 | 10/1988 |

(Continued)

OTHER PUBLICATIONS

Ames, R. et al. "Conversion of murine Fabs isolated from a combinatorial phage display library to full length immunoglobulins," *Journal of Immunological Methods.*, 184:177-186 (1995).
Al-Lazikani, B. et al. "Standard Conformations for the Canonical Structures of Immunoglobulins," *J. Mol. Biol.* 273: 927-948 (1997).
Ashkenazi, A. et al. "Protection Against Endotoxic Shock by a Tumor Necrosis Factor Receptor Immunoadhesin," *Proc. Natl. Acad. Sci.*, 88:10535-10539 (1991).

(Continued)

*Primary Examiner* — Lynn A Bristol
(74) *Attorney, Agent, or Firm* — Finnegan, Henderson, Farabow, Garrett & Dunner, L.L.P.

(57) ABSTRACT

The present disclosure relates generally to anti-C10orf54 antibodies, including antibody-drug conjugates comprising the antibodies, and methods of their use.

24 Claims, 51 Drawing Sheets

Specification includes a Sequence Listing.

(56) References Cited

U.S. PATENT DOCUMENTS

| | | |
|---|---|---|
| 5,403,484 A | 4/1995 | Ladner et al. |
| 5,413,923 A | 5/1995 | Kucherlapati et al. |
| 5,427,908 A | 6/1995 | Dower et al. |
| 5,441,050 A | 8/1995 | Thurston et al. |
| 5,447,851 A | 9/1995 | Beutler et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,605,793 A | 2/1997 | Stemmer |
| 5,618,709 A | 4/1997 | Gewirtz et al. |
| 5,622,929 A | 4/1997 | Willner et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,679,377 A | 10/1997 | Bernstein et al. |
| 5,698,426 A | 12/1997 | Huse |
| 5,709,874 A | 1/1998 | Hanson et al. |
| 5,723,125 A | 3/1998 | Chang et al. |
| 5,733,743 A | 3/1998 | Johnson et al. |
| 5,734,033 A | 3/1998 | Reed |
| 5,750,753 A | 5/1998 | Kimae et al. |
| 5,759,542 A | 6/1998 | Gurewich |
| 5,766,886 A | 6/1998 | Studnicka et al. |
| 5,780,225 A | 7/1998 | Wigler et al. |
| 5,783,181 A | 7/1998 | Browne et al. |
| 5,807,715 A | 9/1998 | Morrison et al. |
| 5,811,238 A | 9/1998 | Stemmer et al. |
| 5,814,318 A | 9/1998 | Lonberg et al. |
| 5,821,047 A | 10/1998 | Garrard et al. |
| 5,824,307 A | 10/1998 | Johnson |
| 5,830,721 A | 11/1998 | Stemmer et al. |
| 5,834,252 A | 11/1998 | Stemmer et al. |
| 5,837,458 A | 11/1998 | Minshull et al. |
| 5,840,674 A | 11/1998 | Yatvin et al. |
| 5,844,095 A | 12/1998 | Linsley et al. |
| 5,855,913 A | 1/1999 | Hanes et al. |
| 5,860,957 A | 1/1999 | Jacobsen et al. |
| 5,874,064 A | 2/1999 | Edwards et al. |
| 5,885,834 A | 3/1999 | Epstein |
| 5,900,252 A | 5/1999 | Calanchi et al. |
| 5,908,626 A | 6/1999 | Chang et al. |
| 5,916,597 A | 6/1999 | Lee et al. |
| 5,934,272 A | 8/1999 | Lloyd et al. |
| 5,939,598 A | 8/1999 | Kucherlapati et al. |
| 5,948,433 A | 9/1999 | Burton et al. |
| 5,969,108 A | 10/1999 | McCafferty et al. |
| 5,972,366 A | 10/1999 | Haynes et al. |
| 5,983,134 A | 11/1999 | Ostrow |
| 5,985,307 A | 11/1999 | Hanson et al. |
| 5,985,309 A | 11/1999 | Edwards et al. |
| 5,985,317 A | 11/1999 | Venkateshwaran et al. |
| 5,985,320 A | 11/1999 | Edwards et al. |
| 5,989,463 A | 11/1999 | Tracy et al. |
| 5,998,596 A | 12/1999 | Bergan et al. |
| 6,004,534 A | 12/1999 | Langer et al. |
| 6,005,079 A | 12/1999 | Casterman et al. |
| 6,010,715 A | 1/2000 | Wick et al. |
| 6,019,968 A | 2/2000 | Platz et al. |
| 6,024,975 A | 2/2000 | D'Angelo et al. |
| 6,039,975 A | 3/2000 | Shah et al. |
| 6,048,736 A | 4/2000 | Kosak |
| 6,054,297 A | 4/2000 | Carter et al. |
| 6,060,082 A | 5/2000 | Chen et al. |
| 6,071,495 A | 6/2000 | Unger et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,256,533 B1 | 7/2001 | Yuzhakov et al. |
| 6,261,595 B1 | 7/2001 | Stanley et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,277,832 B1 | 8/2001 | Sugiyama et al. |
| 6,316,652 B1 | 11/2001 | Steliou |
| 6,331,415 B1 | 12/2001 | Cabilly et al. |
| 6,407,213 B1 | 6/2002 | Carter et al. |
| 6,639,055 B1 | 10/2003 | Carter et al. |
| 6,719,971 B1 | 4/2004 | Carter et al. |
| 6,800,738 B1 | 10/2004 | Carter et al. |
| 10,766,959 B2 * | 9/2020 | Lippincott ......... A61K 47/6873 |
| 2005/0042664 A1 | 2/2005 | Wu et al. |
| 2011/0021568 A1 | 1/2011 | Ellman et al. |
| 2013/0177557 A1 | 7/2013 | Noelle et al. |
| 2014/0341920 A1 | 11/2014 | Noelle |

FOREIGN PATENT DOCUMENTS

| | | |
|---|---|---|
| EP | 0 307 434 B1 | 3/1989 |
| EP | 0 394 827 A1 | 10/1990 |
| EP | 0 396 387 B1 | 11/1990 |
| EP | 0 519 596 B1 | 12/1992 |
| EP | 0 592 106 B1 | 4/1994 |
| KR | 10-2013-0010906 | 1/2013 |
| WO | WO 86/05807 | 10/1986 |
| WO | WO 89/01036 | 2/1989 |
| WO | WO 89/12624 | 12/1989 |
| WO | WO 90/02809 | 3/1990 |
| WO | WO 91/05548 | 5/1991 |
| WO | WO 91/06570 | 5/1991 |
| WO | WO 91/09967 | 7/1991 |
| WO | WO 91/10737 | 7/1991 |
| WO | WO 91/10741 | 7/1991 |
| WO | WO 91/14438 | 10/1991 |
| WO | WO 92/01047 | 1/1992 |
| WO | WO 92/08495 | 5/1992 |
| WO | WO 92/18619 | 10/1992 |
| WO | WO 91/19244 | 11/1992 |
| WO | WO 92/22324 | 12/1992 |
| WO | WO 93/11236 | 6/1993 |
| WO | WO 93/17105 | 9/1993 |
| WO | WO 94/04678 | 3/1994 |
| WO | WO 94/25591 | 11/1994 |
| WO | WO 95/15982 | 6/1995 |
| WO | WO 95/20401 | 8/1995 |
| WO | WO 96/04388 | 2/1996 |
| WO | WO 96/20698 | 7/1996 |
| WO | WO 96/22024 | 7/1996 |
| WO | WO 96/33735 | 10/1996 |
| WO | WO 96/34096 | 10/1996 |
| WO | WO 97/13844 | 4/1997 |
| WO | WO 97/32572 | 9/1997 |
| WO | WO 97/33899 | 9/1997 |
| WO | WO 97/34631 | 9/1997 |
| WO | WO 97/34911 | 9/1997 |
| WO | WO 97/44013 | 9/1997 |
| WO | WO 98/16654 | 4/1998 |
| WO | WO 98/24893 | 6/1998 |
| WO | WO 98/31346 | 7/1998 |
| WO | WO 98/45479 | 10/1998 |
| WO | WO 98/46645 | 10/1998 |
| WO | WO 98/50433 | 11/1998 |
| WO | WO 99/04813 | 2/1999 |
| WO | WO 99/15154 | 4/1999 |
| WO | WO 99/20253 | 4/1999 |
| WO | WO 99/23105 | 5/1999 |
| WO | WO 99/66903 | 12/1999 |
| WO | WO 2007/044515 A1 | 4/2007 |
| WO | WO 2014/039983 A1 | 3/2014 |

OTHER PUBLICATIONS

Baca, M. et al. "Antibody Humanization Using Monovalent Phage Display," *J. Bio. Chem.*, 272:10678-10684 (1997).

Berman, H. et al. "The Protein Data Bank," *Nucl. Acids. Res.*, 28:235-242 (2000).

(56) References Cited

OTHER PUBLICATIONS

Better, M. et al. "*Escherichia coli* Secretion of an Active Chimeric Antibody Fragment," International Genetic Engineering, Inc. 1041 (1988).

Bitter, G. et al. "Vectors for Expression of Cloned Genes," 153: 516-544 (1987).

Brickmann, U. et al. "Phage display of disulfide-stabilized Fv fragments," *Journal of Immunological Methods*., 182: 41-50 (1995).

Buchwald, H. et al. "Long-term, continuous intravenous heparin administration by an implantable infusion pump in ambulatory patients with recurrent venous thrombosis," Surgery., 507.

Burton, D. et al. "Human Antibodies From Combinatorial Libraries," Adv. Immunol., 57:191-280 (1994).

Caldas, C. et al. "Design and synthesis of germline-based hemi-humanized single-chain Fv against the CD18 surface antigen," *Protein Engineering*., 13:353-360 (2000).

Carter, P. et al. "Humanization of an anti-p185$^{HER2}$ antibody for human cancer therapy," *Proc. Natl. Acad. Sci.*, 89:4285-4289 (1992).

Chothia, C. et al. "Canonical Structures for the Hypervariable Regions of Immunoglobulins," *J. Mol. Biol.* 196:901-917 (1987).

Chothia, C. et al. "Structural Determinants in the Sequences of Immunoglobulin Variable Domain," *J. Mol. Biol.* 278: 457-479 (1998).

Cleek, R. et al. "Biodegradable Polymeric Carriers for a bFGF Antibody for Cardiovascular Application," Institute of Biosciences and Bioengineering., 853 (1997).

Colbere-Garapin, F. et al. "A New Dominant Hybrid Selective Marker for Higher Eukaryotic Cells," *J. Mol. Biol.* 150:1-14 (1981).

Couto, J. et al. "Designing Human Consensus Antibodies with Minimal Positional Templates," *American Association for Cancer Research*., 55:5973-5977 (1995).

Crouse, G. et al. "Expression and Amplification of Engineered Mouse Dihydrofolate Reductase Minigenes," *American Society for Microbiology*., 3:257-266 (1983).

DeNardo, G. et al. "Comparison of 1,4,7,10-Tetraazacyclododecane-N,N',N'',N'''-tetraacetic acid (DOTA)-Peptide-ChL6, a Novel Immunoconjugate with Catabolizable Linker, to 2-Iminothiolane-2-[p-(Bromoacetamido)benzyle]-DOTA-ChL6 in Breast Cancer Xenografts[1] ," *American Association for Cancer Research*., 4:2483-2490 (1998).

During, M. et al. "Controlled release of dopamine from a polymeric brain implant: in vivo characterization," *Annals of Neurology*., 25:351-356(1989).

Edelman, G. et al. "The covalent structure of an entire-yG immunoglobulin molecule*," *Biochem*., 63:78-81, (1969).

Ellman, G. et al. "A New and Rapid Colorimetric Determination of Cetylcholinesterase Activity," *Biochemical Pharmacology*., 7:88-95 (1960).

Eppstein, D. et al. "Biological activity of liposome-encapsulated murine interferon y is mediated by a cell membrane receptor," *Proc. Natl. Acad. Sci.*, 82:3688-3692 (1985).

Flajnik, M. et al. "Evolution of the 87 family: Co-evolution of 87H6 and NKp30, identification of a new 87 family member, 87H7, and of 87's historical relationship with the MHC," *NIH Public Access*., 64(8):571-590 (2012).

Flies, D. et al. "Cutting Edge: a Monoclonal Antibody Specific for the Programmed Death-1 Homolog Prevents Graft-versus-Host Disease in Mouse Models," *The Journal of Immunology*., 187:1537-1541 (2017).

Foecking, M. et al. "Powerful and versatile enhancer-promoter unit for mammalian expression vectors." *Elsevier Science Publishers*., 45:101-105 (1986).

Gabizon, A. et al. "Pharmacokinetics and Tissue Distribution of Doxorubicin Encapsulated in Stable Liposomes With Long Circulation Times," *J Natl Cancer Inst*. 81:1484-1488 (1989).

Gentz, R. et al. "Bioassay for trans-activation using purified human immunodeficiency virus tat-encoded protein:Trans-activation requires mRNA synthesis," *Proc. Natl. Acad. Sci. USA*., 86:821-824 (1989).

Gillies, S. et al. "High-level expression of chimeric antibodies using adapted cDNA variable region cassettes," Journal of Immunological Methods., 125:191-202 (1989).

Greenspan, N. et al. "I diotypes: structure and immunogenicity[1] ," *The FASEB Journal*., 7:437-444 (2017).

Guex, N. et al. "Swiss-Model and the Swiss-PdbViewer: an environment for comparative protein modeling," Electrophoresis., 18:2714-2723 (1997).

Hansson, L. et al. "Evolution of Differential Substrate Specificities in Mu Class Glutathione Transferases Probed by DNA Shuffling," *J. Mol. Biol.* 287:265-276 (1999).

Harayama, S. "Artificial evolution by DNA shuffling," *Tibtech*., 16:76-82 (1998).

Hellstrom, K. et al. "Antibodies for Drug Delivery," *Tumor Institute*., 623-653 (1987).

Howard, M. et al. "Intracerebral drug delivery in rats with lesion-induced memory deficits," *J. Neurosurg.* 71:105-112 (1989).

Hwang, K. et al. "Hepatic uptake and degradation of unilamellar sphingomyelin/ cholesterol liposomes: A kinetic study," *Proc. Natl. Acad. Set USA*., 77:4030-4034 (1980).

International Search Report for PCT/US2015/065331 dated Jun. 13, 2014.

Inouye, S. et al. "Up-promoter mutations in the Ipp gene or *Escherichia coli,"* Nucleic Acids Res., 13: 3101-3110 (1985).

Jalkanen, M. et al. "Cell Surface Proteoglycan of Mouse Mammary Epithelial Cells Is Shed by Cleavage of Its Matrix-binding Ectodomain from Its Membrane-associated Domain," *The Journal of Cell Biology*., 105:3087-3096 (1987).

Jalkanen, M. et al. "Heparan Sulfate Proteoglycans from Mouse Mammary Epithelial Cells: Localization on the Cell Surface with a Monoclonal Antibody," *The Journal of Cell Biology*., 101: 976-984 (1985).

Johnson, S. et al. "Development of a Humanized Monoclonal Antibody (MEDI-493) with Potent in Vitro and in Vivo Activity against Respiratory Syncytial Virus," *The Journal of Infectious Diseases* 176:1215-24. (1997).

Joliot, A. et al. "Antennapedia homeobox peptide regulates neural morphogenesis," *Proc. Natl. Acad. Sci USA*., 88:1864-1868 (1991).

Jones, P. et al. "Replacing the complementarity determining regions in a human antibody with those from a mouse," *Nature* 321:1-4 (1986).

Kabat, E. et al. "Unusual Distributions of Amino Acids in Complementarity determining (Hypervariable) Segments of Heavy and Light Chains of Immunoglobulins and Their Possible Roles in Specificity of Antibody-combining Sites," *The Journal of Biological Chemistry*., 252:6609-6616 (1977).

Goelz, S. et al. "Inhibition of Calcification of Bioprosthetic Heart Valves by Local Controlled-Release Diphosphonate," Science., 228:190.

Kantarjian, H. et al. "Treatment of Philadelphia Chromosome-positive, Accelerated-phase Chronic Myelogenous Leukemia with Imatinib Mesylate[1] ," *American Association for Cancer Research*., 8:2167-2176 (2002).

Keller, A. et al. "Empirical Statistical Model to Estimate the Accuracy of Peptide Identifications Made by MSAVIS and Database Search," *Institute for Systems Biology*., 74:5383-5392 (2002).

Kettleboroug, C. et al. "Isolation of tumor cell-specific single-chain Fv from immunized mice using phage-antibody libraries and the re-construction of whole antibodies from these antibody fragments," *Eur. J. Immunol*., 24:952-958 (1994).

Kilpatrick, K. et al. "Rapid Development of Affinity Matured Monoclonal Antibodies Using RIMMS," *Hybridoma*., 16:381— (1997).

Kohler, G. et al. "Immunoglobulin chain loss in hybridoma lines," *Proc. Natl. Acad. Sci. USA*., 77:2197-2199 (1980).

Kohler, G. et al. "Pillars Article: Continuous cultures of fused cells secreting antibody of predefined Specificity," *The Journal of Immunology*., 174:495-497 (2017).

Lam, X. et al. "Microencapsulation of Recombinant Humanized Monoclonal Antibody for Local Delivery." *Proceed Int'l. Symp Contorl Rel. Bioact Matter*, 24:759-760 (1997).

(56) References Cited

OTHER PUBLICATIONS

Langer, R. et al. "Chemical and Physical Structure of Polymers as Carriers for Controlled Release of Bioactive Agents: A Review," *Journal of Macromolecular Science, Part C.*, 23:1 61-126 (1983).
Langer, R. et al. "New Methods of Drug Delivery," *Science*, 1527-1533 (1990).
Lefranc, M. et al. "IMGT unique numbering for immunoglobulin and T cell receptor variable domains and Ig superfamily V-like domains," *Developmental and Comparative Immunology.*, 27:55-77 (2002).
Liu, H. et al. "A Model for Random Sampling and Estimation of Relative Protein Abundance in Shotgun Proteomics," *Analytical Chemistry* 76:4193-4201 (2004).
Logan, J. et al. "Adenovirus tripartite leader sequence enhances translation of mRNAs late after infection," *Proc. Natl. Acad. Sci. USA* 81:3655-3659 (1984).
Lonberg, N. et al. "Human Antibodies from Transgenic Mice," *International Review of Immunology.*, 13:65-93(1995).
Lorennzo, M. et al. "PCR-Based Method for the Introduction of Mutations in Genes Cloned and Expressed in Vaccinia Virus," *Bio Techniques.*, 24:308-313 (1998).
Lowry, I. et al. "Isolation of Transforming DNA: Cloning the Hamster aprt Gene," *College of Physicians and Surgeons, Columbia University.*, 22:817-823 (1980).
Lowry, O. et al. "Protein Measurement With the Folin Phenol Reagent," *J. Biol. Chem.*, 193:265-275. (1951).
Lundgren, D. et al. "Protein Identification Using Sorcerer 2 and Sequest," *Current Protocols in Bioinformatics.*, 13.3. 1-13.3.21 (2009).
Martin, F. et al. "Irreversible Coupling of Immunoglobulin Fragments to Preformed Vesicles," *Cancer Research Institute.*, 257:286-288 (1982).
Mohammad, R. et al. "A new tubulin polymerization inhibitor, auristatin PE, induces tumor regression in a human Waldenstrom's macroglobulinemia xenograft model," *International Journal of Oncology.*, 15:367-372 (1999).
Mohammad, R. et al. "Bryostatin 1 induces differentiation and potentiates the antitumor effect of Auristatin PE in a human pancreatic tumor (PANC-1) xenograft model," *Anti-Cancer Drugs.*, 12:735-740 (2001).
Moore, A. et al. "Apoptosis in CHO cell batch cultures: examination by flow cytometry," *Cytotechnology.*, 17:1-11 (1995).
Morgan, R. et al. "Human Gene Therapy," *Annu. Rev. Biochem.*, 62:191-217 (1993).
Morrison, S. et al. "Chimeric human antibody molecules: Mouse antigen-binding domains with human constant region domains," *Proc. Natl. Acad. Sci. USA.*, 81: 6851-6855 (1984).
Morrison, S. et al. "Transfectomas Provide Novel Chimeric Antibodies," *Science.*, 229:1202-1207 (1985).
Mulligan, R et al. "The Basic Science of Gene Therapy," *Science.*, 260:926 (1993).
Mulligan, R et al. "Selection for animal cells that express the *Escherichia coli* gene coding for xanthine-guanine phosphoribosyltransferase," *Proc. Natl. Acad. Sci.* USA 78:2072-2076 (1981).
Mullinax, R. et al. "Expression of a Heterodimeric Fab Antibody Protein in One Cloning Step," Research Report, 1-5.
Muyldermans, S. "Single domain camel antibodies: current status," 74:277-302 (2001).
Neilson, K. et al. "Less label, more free: Approaches in label-free quantitative mass spectrometry," *Proteomics.*, 11:535-553 (2011).
Nesvizhskii, A. et al. "A Statistical Model for Identifying Proteins by Tandem Mass Spectrometry," *Anal. Chem.*, 75:4646-4658 (2003).
Nicolaou, K. et al. "Calicheamicin $\theta^1{}_1$: A Rationally Designed Molecule with Extremely Potent and Selective DNA Cleaving Properties and Apoptosis Inducing Activity," *Angew. Chem. Int. Ed. Engl.*, 33:183-186 (1994).
Ning, S. et al. "Intratumoral radioimmunotherapy of a human colon cancer xenograft using a sustained-release gel," *Radiotherapy & Oncology.*, 39:179-189 (1996).

Nisonoff, A. "Idiotypes: concepts and applications.," *The Journal of Immunology.*, 147:2429-2438 (2017).
Nuttall, S. et al. "Immunoglobulin $V_H$ Domains and Beyond: Design and Selection of Single-Domain Binding and Targeting Reagents," *Current pharmaceutical Biotechnology.*, 253-263 (2000).
O'Hare, K. et al. "Transformation of mouse fibroblasts to methotrexate resistance by a recombinant plasmid expressing a prokaryotic dihydrofolate reductase," *Proc. Natl. Acad. Sci. USA.*, 78: 1527-1531 (1981).
Oi, V. et al. "Chimeric Antibodies," *BioTechniques*, 4:214 (1986).
Olsen, J. et al. "A Dual Pressure Linear Ion Trap Orbitrap Instrument with Very High Sequencing Speed," *The American Society for Biochemistry and Molecular Biology, Inc.*, 8:2759-2769 (2009).
Oppermann, H. et al. "Antigen recognition and targeted delivery by the single-chain Fv," *ResearchGate.*, (1993).
Padlan, E. "A Possible Procedure for Reducing the Immunogenicity of Antibody Variable Domains While Preserving Their Ligand-Binding Properties," *Molecular Immunology.*, 28:489-498 (1991).
Patten, P. et al. "Applications of DNA shuffling to pharmaceuticals and vaccines," *Current Opinion in Biotechnology.*, 8:724-733 (1997).
Pedersen, J. et al. "Comparison of Surface Accessible Residues in Human and Murine Immunoglobulin Fv Domains," *J. Mol. Biol.* 235:959-973 (1994).
Persic, L. et al. "An integrated vector system for the eukaryotic expression of antibodies or their fragments after selection from phage display libraries," *Gene.*, 187:9-18 (1997).
Peterson, J. et al. "Enzymatic Cleavage of Peptide-Linked Radiolabels from Immunoconjugates," *The American Chemical Society.*, 10:553-557 (1999).
Presta, L. "Antibody engineering," *Current Opinion in Structural Biology.*, 2:593-596 (1992).
Proudfoot, N. "Transcriptional interference and termination between duplicated α-globin gene constructs suggests a novel mechanism for gene regulation," Nature., 322:562-565 (1986).
Riechmann, L. et al. "Reshaping human antibodies for therapy," *Nature.*, 332:1-5 (1988).
Rogushka, M. et al. "A comparison of two murine monoclonal antibodies humanized by CDR-grafting and variable domain resurfacing," *Protein Engineering.*, 9:895-904 (1996).
Rüther, U. et al. "Easy identification of cDNA clones," *The EMBO Journal.*, 2:1791-1794 (1983).
Sandhu, J. "A rapid procedure for the humanization of monoclonal antibodies," *Gene.*, 150:409-410 (1994).
Santerre, R. et al. "Expression of prokaryotic genes for hygromycin B and G418 resistance as dominant-selection markers in mouse L cells," Lilly Research Laboratories., 147-146 (1984).
Sauder, C. et al. "A Preliminary Trial of the Programmable Implantable Medication System for Insulin Delivery," *The New England Journal of Medicine.*, 574 (1989).
Sawai, H. et al. "Direct Production of the Fab Fragment Derived From the Sperm Immobilizing Antibody Using Polymerase Chain Reaction and cDNA Expression Vectors," *American Journal of Reproductive Immunology.*, 34:26-34 (1995).
Song, Y. et al. "Antibody Mediated Lung Targeting of Long-Circulating Emulsions," *PDS Journal Pharmaceutical Science and Techology.*, 50:372-377 (1996).
Studinicka, G. et al. "Human-engineered monoclonal antibodies retain full specific binding activity by preserving non-CDR complementaritymodulating residues," *Protein Engineering.*, 7:805-814 (1994).
Szybalska, E. et al. "Genetics of Human Cell Lines, Iv. Dna-Mediated Heritable Transformation of a Biochemical Trait," *Proc. N. A. S.*, 2026 (1962).
Tan, P. et al. ""Superhumanized" Antibodies: Reduction of Immunogenic Potential by Complementarity-Determining Region Grafting with Human Germline Sequences: Application to an Anti-CD28," *J Immunol* 169:1119-1125 (2017).
Thorpe, P. et al. "The Preparation and Cytotoxic Properties of Antibody-Toxin Conjugates," *Immunological Rev.*, 62 (1982).
Tolstoshev, P. "Gene Therapy, Concepts, Current Trials and Future Directions," *Annu. Rev. Pharmacol. Toxicol.*, 32:573-96 (1993).
Traunecker, A. et al. "Soluble CD4 molecules neutralize human immunodeficiency virus type 1," *Nature.*, 331: 84-86 (1988).

(56) References Cited

OTHER PUBLICATIONS

Van Heeke, G. et al. "Expression of Human Asparagine Synthetase in *Escherichia coli*," *The Journal of Biological Chemistry.*, 264:5503-5509 (1989).
Vie, H. et al. "Human fusion proteins between interleukin 2 and IgM heavy chain are cytotoxic for cells expressing the interleukin 2 receptor," *Proc. Natl. Acad. Sci. USA.*, 89:11337-11341 (1992).
Wall, N. et al. "Modulation of cIAP-1 by Novel Antitubulin Agents When Combined with Bryostatin 1 Results in Increased Apoptosis in the Human Early Pre-B Acute Lymphoblastic Leukemia Cell Line Reh," *Biochemical and Biophysical Research Communications.*, 266:76-80 (1999).
Wang, L. et al. "VISTA, a novel mouse Ig superfamily ligand that negatively regulates T cell responses," *The Journal of Experimental Medicine.*, 208:577-592 (2011).
Wigler, M. et al. "Transformation of mammalian cells with an amplifiable dominant-acting gene," *Proc. Natl. Acad. Sci. USA.*, 77:3567-3570 (1980).
Wigler, M. et al. "Transfer of Purified Herpes Virus Thymidine Kinase Gene to Cultured Mouse Cells," *Cell.*, 11:223-232 (1977).
Wilson, I. et al. "The Structure of an Antigenic Determinant in a Protein," *Cell.*, 37:767-778 (1984).
Woyke, T. et al. "In Vitro Activities and Postantifungal Effects of the Potent Dolastatin 10 Derivative Auristatin PHE." *Antimicrobial Agents and Chemotherapy.*, 45:3580-3584 (2001).
Woyke, T. et al. "Effect of Auristatin PHE on Microtubule Integrity and Nuclear Localization in Cryptococcus neoformans," *Antimicrobial Agents and Chemotherapy.*, 46:3802-3808 (2002).
Wu, G. et al. "Receptor-mediated in Vitro Gene Transformation by a Soluble DNA Carrier System," *The Journal of Biological Chemistry.*, 262:4429-4432 (1987).
Wu, G. et al. "Delivery systems for gene therapy," *Biotherapy.*, 3:87-95 (1991).
Yates, J. et al. "Proteomics by Mass Spectrometry: Approaches, Advances, and Applications," *Annu. Rev. Biomed. Eng.*, 11:49-79 (2009).
Zhang, Z. et al. "Signal peptide prediction based on analysis of experimentally verified cleavage sites," *Protein Science.*, 13:2819-2824 (2004).
Zheng, X. et al. "Administration of noncytolytic Il-10/Fc in murine models of lipopolysaccharide-induced septic shock and allogeneic islet transplantation," *The Journal of Immunology.*, 154:5590-5600 (1995).
Zimmermann, K. et al. "A Triglycine Linker Improves Tumor Uptake and Biodistributions of 67-Cu-Labeled Anti-Neuroblastoma MAb chCE7 F(ab')$_2$ Fragments," *Nuclear Medicine & Biology.*, 26:943-950 (2000).
Zybailov, B. et al. "Statistical Analysis of Membrane Proteome Expression Changes in *Saccharomyces cerevisiae*," *Journal of Proteome Research.*, 5:2339-2347 (2006).
J. L. Lines, et al., "VISTA is an immune checkpoint molecule for human T cells," Cancer Res., 74(7): 1924-1932 (2014).

\* cited by examiner

| C10ORF54 | CD13+/CD33+ | | CD34+/CD33+ | | | CD34+/CD33− | | |
|---|---|---|---|---|---|---|---|---|
| | Incidence* | Pos, [%] | Fold MFI | Incidence* | Pos, [%] | Fold MFI | Incidence* | Pos, [%] | Fold MFI |
| AML | 18/23 (3 relapses) | 31 | 48.6 | 10/21 (3 relapses) | 41 | 50.9 | 9/21 (3 relapses) | 25 | 8.5 |
| BMNC | 3/3 | 75 | 28.1 | 1/3 | 31 | 0.9 | 0/3 | 1.5 | 0.5 |

FIG. 2 huVH1
Potential humanized sequence based on IMGT IGHV1-18 acceptor framework (method 1)
QVQLVQSGAEVKKPGASVKVSCKAS GYTFTSYGIS WVRQAPGQGLEWMG WISAYNGNTNYAQKLQG RVTMTDTSISTAYMELRSLRSDDTAVYYCAR Joining region
IMGT J00256|IGHJ4*01|YFDYWGQTLVTVSS

```
                 10         20         30         40         50         60         70         80         90
                  b b b       b b b   b b   b  b i i   i b b      b b b        b b b      b b b b    b b i b
seq
76E1     EVQLLQSGPELEKPGASVKISCKAS GYSFTGYNMN WVKQSNGKSLEWIG NIDPYYDYTSYNLKFKD KATLTVDKSSSTAYMQLKSLTSEDSAVYYCAT
          * ***                   *    *  *   * *  **    *                 **    *****     *   **  * *
huVH1a   QVQLVQSGAEVKRPGASVKVSCKAS GYSFTGYNMN WVRQAPGQGLEWMG NIDPYYDYTSYNLKFKD RVTMTDTSTAYMELRSLRSDDTAVYYCAR
                             I          S     Q       E        Q                    A L V K                   T
AbM                                     S     S       S        S                                              
huVH1b   QVQLVQSGAEVKKPGASVKVSCKAS GYSFTGYNMN WVRQAPGQGLEWMG NIDPYYDYTSYAQKLQG RVTMTDTSISTAYMELRSLRSDDTAVYYCAR
                             I                                                       A L V K                  T
                                                                                   F
```

```
           100      110
            i b   b b b
seq                                
76E1    STMITPFDY WGQGTTLVTVSS
                **
huVH1a  STMITPFDY WGQGTLVTVSS
           L         L
AbM       100a      110
huVH1b  STMITPFDY WGQGTLVTVSS
           L
```

(1) CDR sequences noted in bold.
(2) Human germline and joining sequences from IMGT® the international ImMunoGeneTics information system® www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted below sequence in red; underlined residues are positions to alter first.
(7) Potential changes in CDR sequence noted below each CDR sequence. These may prevent asparagines (N) deamidation (N), methionine (M) oxidation, Asp-Gly (DG) isoaspartate formation or Asp-Pro (DP) bond cleavage.

FIG. 3A huVH3
Potential humanized sequence based on IMGT IGHV3-48 acceptor framework (method 2)
EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR Joining region
IMGT J00256|IGHJ4*01|YFDYWGQTLVTVSS

```
                                  b b b                      b b b       b b i i       i b b  b b               i b b                 b b b            b b b b      b bib
seq          10          20          30          40          50          60          70          80          90
76E1    EVQLLQSGPELEKPGASVKISCKAS GFTFSSYSMN WVKQSNGKSLEWIG NIDPYYDYTSYNLKFKD KATLTVDKSSSTAYMQLKSLTSEDSAVYYCAT
         ** ** *** * *** ***          *               **  **                 ** *** ******* * ** *** ******        *
             Q         V I                              Q  S   IG      E    Q                 A L V K   S A M L                T
                                                        S  S           S
                                                        D  A           D
                                                        A                                                                       A AbM           10         ib    b b b  20       30         40   50   a     60              70  abc    80           90
huVH3b  EVQLVESGGGLVQPGGSLRLSCAAS GYSFTGYNMN WVRQAPGKGLEWVS NIDPYYDYTSYADSVKG RFTISRDNAKNSLYLQMNSLRAEDTAVYYCAR
             Q           V I                            Q  S   IG      E    Q                 A L V K   S A M L                T
                                                        S  S           S     F
                                                        D  A           D
                                                        A seq          100      ib    i     b b b  110
76E1    STWITPFDY WGQGTLVTVSS
                 **
             AbM  100a         110
huVH3a  STWITPFDY WGQGTLVTVSS
             L                     L
huVH3b  STWITPFDY WGQGTLVTVSS
             L                     L
```

(1) CDR sequences noted in bold.
(2) Human germline and joining sequences from IMGT® the international ImMunoGeneTics information system® www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterisk (*).
(6) Potential humanized framework mutations from human sequence to parental mouse sequence are noted below sequence in red; underlined residues are positions to alter first.
(7) Potential changes in CDR sequence noted below each CDR sequence. These may prevent asparagines (N) deamidation (N), methionine (M) oxidation, Asp-Gly (DG) isoaspartate formation or Asp-Pro (DP) bond cleavage.

FIG. 3B huVH1
Potential humanized sequence based on IMGT IGHV1-18 acceptor framework (method 1)
QVQLVQSGAEVKKPGASVKVSCKAS GYTFTSYGIS WVRQAPGQGLEWMG WISAYNGNTNYAQKLQG RVTMTDTSTSTAYMELRSLRSDDTAVYYCAR Joining region
IMGT 00256|IGHJ4*01|YFDYWGQGTLVTVSS

```
seq         10          20           30            40            50           60            70           80          90
        b   bbb      bbbb         bb  b bii       iibb bb       b       i    bbb          b  bbb       bbb    b bib
141A    QVQLQQSGAELMKPGASVKISCKAT GYTFSRYWIE WVKQRPGHGLEWIG EILPGSGSTNYNEKFKG KATFTADTSSNTAYMQLSSLTSEDSAVYYCAG
          *    **                **         **  * ***  *             *    **          **  ***   * *  ****    *
huVH1a  QVQLVQSGAEVKKPGASVKVSCKAS GYTFSRYWIE WVRQAPGQGLEWMG EILPGSGSTNYNEKFKG RVTMTDTSTSTAYMELRSLRSDDTAVYYCAR
                    M    I                                           I         QQ        AF A   N
                                                                     SS        DD
                                                                     A AbM                                                                  50 a         60            70 abc         80          90
huVH1b  QVQLVQSGAEVKKPGASVKVSCKAS GYTFSRYWIE WVRQAPGQGLEWMG EILPGSGSTNYAQKLQG RVTMTDTSTSTAYMELRSLRSDDTAVYYCAR
                                                                       L          Q  F   AF A   N            G
                                                                                  S
                                                                                  D
                                                                                  A seq     100         110         120
         ib    i     b  b   b
141A    EEVYDGYPMFGY WCQGTLVTVSA
           *
huVH1a  EEVYDGYPMFGY WCQGTLVTVSS
         E
         S
         A AbM     100abcd       110
huVH1b  EEVYDGYPMFGY WCQGTLVTVSS
         E
         S
         A
```

(1) CDR sequences noted in bold.
(2) Human germline and joining sequences from IMGT® the international ImMunoGeneTics information system®
    www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted
    below sequence in red; underlined residues are positions to alter first.
(7) Potential changes in CDR sequence noted below each CDR sequence. These may prevent asparagines
    (N) deamidation, methionine (M) oxidation, Asp-Gly (DG) isoaspartate formation or Asp-Pro (DP) bond cleavage.

FIG. 4A

FIG. 4B huVH3
Potential humanized sequence based on IMGT IGHV3-48 acceptor framework (method 2)
EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR Joining region
IMGT J00256|IGHJ4*01|YFDYWGQTLVTVSS

```
seq           10         20         30         40         50         60         70         80         90
         b b b      b b b b    b b   b b i i   i i b b  b b      i      b b b    b b b b    b b b     b b i b
141A QVQLQQSGAELMKPGASVKISCKAT GYTFSRYWIE WVKQRPGHGLEWIG EILPGSGSTNYNEKFKG KATFTADTSSNTAYMQLSSLTSEDSAVYYCAG
       * **  **** ****  **** *           **  *           **                *** **   *** ***  **   *
huVH3a EVQLVESGGGLVQPGGSLRLSCAAS GYTFSRYWIE WVRQAPGKGLEWVS EILPGSGSTNYNEKFKG RFTISRDNAKNSLYLQMNSLRAEDTAVYYCAR
                    Q    M   V I                          IG     Q Q                AFAI  A M L                G
                                                                 S S                                  
                                                                 D D                                  
                                                                 A A                                  
AbM                                                              60                       70 abc    80         90
huVH3b EVQLVESGGGLVQPGGSLRLSCAAS GYTFSRYWIE WVRQAPGKGLEWVS EILPGSGSTNYADSVKG RFTISRDNAKNSLYLQMNSLRAEDTAVYYCAR
                    Q    M   V I                          IG     Q                  F   AFAI  A M L            G
                                                                 S                                    
                                                                 D                                    
                                                                 A seq   100        110        120
     ib i  b b b
141A EEVYDGYPMFGY WCQGTLVTVSA
            *
huVH3a EEVYDGYPMFGY WCQGTLVTVSS
         E
         S
         A
AbM   100abcd        110
huVH3b EEVYDGYPMFGY WCQGTLVTVSS
         E
         S
         A
```

(1) CDR sequences noted in bold.
(2) Human germline and joining sequences from IMGT® the international ImMunoGeneTics information system®
    www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted
    below sequence in red; underlined residues are positions to alter first.
(7) Potential changes in CDR sequence noted below each CDR sequence. These may prevent asparagines
    (N) deamidation (N), methionine (M) oxidation, Asp-Gly (DG) isoaspartate formation or Asp-Pro (DP) bond cleavage.

huVH1
Potential humanized sequence based on IMGT IGHV1-18 acceptor framework (method 1)
QVQLVQSGAEVKKPGASVKVSCKAS GYTFTSYGIS WVRQAPGQGLEWMG WISAYNGNTNYAQKLQG RVTMTTDTSTSTAYMELRSLRSDDTAVYYCAR Joining region
IMGT J00256|IGHJ4*01|YFDYWGQTLVTVSS

```
               b b b             b b b            b b  b bii  i ibb b b       i b        b b b              b b  b bib
seq                10               20               30               40               50               60               70               80               90
175A   QVQLQQSGAELMKPGASVKISCKAT GYTFSTHWIE WVKQRPGHGLEWIG EILPGSGSTSYNEKFKG KATFTADTSSNTAYMQLSSLTSEDSAVYYCAR
        *     **        *   *              * *  *           *                      *      ** ** *  * ** *
AbM                                                                           I                     Q                                      A F A
huVH1a QVQLVQSGAEVKPGASVKVSCKAS GYTFSTHWIE WVRQAPGQGLEWMG EILPGSGSTSYNEKFKG RVTMTTDTSTSTAYMELRSLRSDDTAVYYCAR
                                                                              I                     S
                                                                                                    D
                                                                                                    A ib    b b b                     i                                                    i
AbM                10               20               30               40               50   a       60              70  abc         80               90
huVH1b QVQLVQSGAEVKPGASVKVSCKAS GYTFSTHWIE WVRQAPGQGLEWMG EILPGSGSTSYAQKLQG RVTMTTDTSTSTAYMELRSLRSDDTAVYYCAR
                                   I                                          I      F               A F A ib i  b b b
seq   100             110
175A  MLLYYYAMDY WGQGTSVTVSS
                  *
huVH1a MLLYYYAMDY WGQGTLVTVSS AbM   100ab         110
huVH1b MLLYYYAMDY WGQGTLVTVSS
```

(1) CDR sequences noted in bold.
(2) Human germline and joining sequences from IMGT® the international ImMunoGeneTics information system®
    www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted
    below sequence in red; underlined residues are positions to alter first.
(7) Potential changes in CDR sequence noted below each CDR sequence. These may prevent asparagines
    (N) deamidation (N), methionine (M) oxidation, Asp-Gly (DG) isoaspartate formation or Asp-Pro (DP) bond cleavage.

FIG. 5A huVH3
Potential humanized sequence based on IMGT IGHV3-48 acceptor framework (method 2)
EVQLVESGGGLVQPGGSLRLSCAAS GFTFSSYSMN WVRQAPGKGLEWVS YISSSSSTIYYADSVKG RFTISRDNAKNSLYLQMNSLRAEDTAVYYCAR Joining region
IMGT J00256|IGHJ4*01|YFDYWGQGTLVTVSS

```
seq              10          20          30          40          50          60          70          80          90
            b b b      b b b b      b b  b bi i  i bb b b       i b                             b b b   b b b b  b bib
175A    QVQLQQSGAELMKPGASVKISCKAT GYTFSSHWIE WVKQRPGHGLEWIG EILPGSGSTSYNEKFKG KATFTADTSSNTAYMQLSSLTSEDSAVYYCAR
         *  ** **  **   ***            * * *         * *         **            ** *** *** ** ** ** **  ** *
                        Q                  VI                    IG                            Q    A F A I  A M L
                                                                                                 S
                                                                                                 D
                                                                                                 A
AbM                                                                                          70 abc         80        90
huVH3a  EVQLVESGGGLVQPGGSLRLSCAAS GYTFSSHWIE WVRQAPGKGLEWVS EILPGSGSTSYNEKFKG RFTISRDNAKNSLYLQMNSLRAEDTAVYYCAR
                        Q                  VI                    IG                           F    A F A I  A M L
```

```
seq     100         110
         ib  i   b b b
175A    MLLYYYAMDY WGQGTSVTVSS
                 *
huVH3a  MLLYYYAMDY WGQGTLVTVSS
AbM     100ab         110
huVH3b  MLLYYYAMDY WGQGTLVTVSS
```

(1) CDR sequences noted in bold.
(2) Human germline and joining sequences from IMGT® the international ImMunoGeneTics information system® www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted below sequence in red; underlined residues are positions to alter first.
(7) Potential changes in CDR sequence noted below each CDR sequence. These may prevent asparagines (N) deamidation (N), methionine (M) oxidation, Asp-Gly (DG) isoaspartate formation or Asp-Pro (DP) bond cleavage.

FIG. 5B huVK2
Potential humanized sequence based on IMGT IGKV2-28 acceptor framework (method 1)
DIVMTQSPLSLPVTPGEPASISC RSSQSLLHSNGYNYLD WYLQKPGQSPQLLIY LGSNRAS GVPDRFSGSGSGTDFTLKISRVEAEDVGVYYC MQALQTP

Joining region
IMGT J00242|IGKJ2*01|YTFGQGTKLEIK

```
seq        10         20         30         40         50         60         70         80         90
AbM        10         20         30abcde    40         50         60         70         80         90
           b b b  b b  bbb  b     bi bi i   ii ibbi   i     b b    bbb  b    bb bib
76E1  DVLMTQTPLSLPVSLGDQASISC RSSQSIVHSNGNTYLE WYLQKPGQSPKLLIY KVSNRFS GVPDRFSGSGSGTDFTLKINRVEAEDLGVYYC
      **    *       *** ***                                                            *
huVK2 DIVMTQSPLSLPVTPGEPASISC RSSQSIVHSNGNTYLE WYLQKPGQSPQLLIY KVSNRFS GVPDRFSGSGSGTDFTLKISRVEAEDVGVYYC
      V                            Q                Q                                                   L
                                   S                S
                                   A                A
                                   D                D
```

```
seq        90        100        110
AbM        90        100        110
       ibi  iib i    b b b
76E1   FQGSNVPWT FGGGTKLEIK
              *
huVK2  FQGSNVPWT FGQGTKLEIK
```

FIG. 6A (1) CDR sequences noted in bold.
(2) Human germline and joining sequences from IMGT® the international ImMunoGeneTics information system®
    www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterisk (*).
(6) Potential humanized framework mutations from human sequence to parental mouse sequence are noted
    below sequence in red; underlined residues are positions to alter first.
(7) Potential changes in CDR sequence noted below each CDR sequence. These may prevent asparagines
    (N) deamidation (N), methionine (M) oxidation, Asp-Gly (DG) isoaspartate formation or Asp-Pro (DP) bond cleavage.

huVK1
Potential humanized sequence based on IMGT IGKV1-39 acceptor framework (method 2)
DIQMTQSPSSLSASVGDRVTITC RASQSISSYLN WYQQKPGKAPKLLIY AASSLQS GVPSRFSGSGSGTDFTLTISSLQPEDFATYYC QQSYSTP Joining region
IMGT J00242|IGKJ2*01|YTFGQGTKLEIK

```
seq              10         20         30  30abcde  40         50         60         70         80         90
AbM              10         20         30           40         50         60         70         80         90
                 b b b  b b  b b b   b  b      bi bi i  ii ibbi      i     b  b       b b b b      b b  bib
76E1  DVLMTQTPLSLPVSLGDQASISC RSSQSIVHSNGNTYLE WYLQKPGQSPKLLIY KVSNRFS GVPDRFSGSGSGTDFTLKINRVEAEDLGVYYC
      **   * *** ***  ****   *     *   **        **    *          *        *  ****  * *****   ***
huVK1 DIQMTQSPSSLSASVGDRVTITC RSSQSIVHSNGNTYLE WYQQKPGKAPKLLIY KVSNRFS GVPSRFSGSGSGTDFTLTISSLQPEDFATYYC
         V       V     A                      QQ              Q                                V    LG
                                               SS              S
                                               A A              D
                                                 D               A seq   90         100        110
AbM   90         100
      ibi  iib i  b b b
76E1  FQQSNWPWT FGGGTKLEIK
         *
huVK1 FQQSNWPWT FGGGTKLEIK
```

(1) CDR sequences noted in bold.
(2) Human germline and joining sequences from IMGT® the international ImMunoGeneTics information system®
    www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted
    below sequence in red; underlined residues are positions to alter first.
(7) Potential changes in CDR sequence noted below each CDR sequence. These may prevent asparagines
    (N) deamidation (N), methionine (M) oxidation, Asp-Gly (DG) isoaspartate formation or Asp-Pro (DP) bond cleavage.

FIG. 6B huVK3
Potential humanized sequence based on IMGT IGKV3-20 acceptor framework (method 1)
EIVLTQSPGTLSLSPGERATLSC RASQSVSSSYLA WYQQKPGQAPRLLIY GASSRAT GIPDRFSGSGSGTDFTLTISRLEPEDFAVYYC QQYGSSP Joining region
IMGT J00242|IGKJ2*01|YTFGQGTKLEIK

```
                       10            20           30         40          50         60          70         80
seq                    10            20           30         40          50         60          70         80
AbM         b b b    bb       bbb  b  b  b  bi bi i    ii ibbi     i    b  b        b b b b     b bib
141A        QIVLSQSPAILSASPGEKVTMTC RASSSLSYMH WYQQKPGSSPKPWIY ATSNLAS GVPARFSGSGSGTSYSLTISRVEAEDAATYYC
             *  ***   *  *  * ***                   ** ***       ** ***                *  ***         *   *   ***
huVK3       EIVLTQSPGTLSLSPGERATLSC RASSSLSYMH WYQQKPGQAPRLLIY ATSNLAS GIPDRFSGSGSGTDFTLTISRLEPEDFAVYYC
                      A    V M                              S  PW                                  Y      V
                                                             Q                                     V
                                                             S
                                                             D
                                                             A 90          100
seq             90          100
AbM       ibi  iib i   b b b
141A      QQWSSNPYT FGGGTKLEIK
               *
huVK3     QQWSSNPYT FGGGTKLEIK
          Q
          S
          A
```

FIG. 7A (1) CDR sequences noted in bold.
(2) Human germline and joining sequences from IMGT® the international ImMunoGeneTics information system® www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted below sequence in red; underlined residues are positions to alter first.
(7) Potential changes in CDR sequence noted below each CDR sequence. These may prevent asparagines (N) deamidation (N), methionine (M) oxidation, Asp-Gly (DG) isoaspartate formation or Asp-Pro (DP) bond cleavage.

huVK1
Potential humanized sequence based on IMGT IGKV1-39 acceptor framework (method 2)
DIQMTQSPSSLSASVGDRVTITC RASQSISSYLN WYQQKPGKAPKLLIY AASSLQS GVPSRFSGSGSGTDFTLTISSLQPEDFATYYC QQSYSTP

Joining region
IMGT J00242|IGKJ2*01|YTFGQGTKLEIK

```
                   10           20           30          40           50           60           70         80
seq                10           20        30    34       40           50           60           70         80
AbM            b b b    b b    b b b     b  b bi bi i    ii ibbi   i  b  b        b b b     b b b     b bib
141A      QIVLSQSPAILSASPGEKVTMTC RASSSLSYMH WYQQKPGSSPKPWIY ATSNLAS GVPARFSGSGSGTSYSLTISRVEAEDAATYYC
          * ****   ** * **** *           **  **           ** *             *     ***            **** *
                                          L                    S  PW                         Y       V
huVK1     DIQMTQSPSSLSASVGDRVTITC RASSSLSYMH WYQQKPGKAPKLLIY ATSNLAS GVPSRFSGSGSGTDFTLTISSLQPEDFATYYC
                                          M                    Q                                    Y   V
                                                               S
                                                               D
                                                               A
```

```
                 90         100
seq              90         100
AbM        ibi    iib  i    b b b
141A       QQWSSNPYT FGGGTKLEIK
               *
huVK1      QQWSSNPYT FGQGTKLEIK
           Q
           S
           A
```

FIG. 7B

(1) CDR sequences noted in bold.
(2) Human germline and joining sequences from IMGT® the international ImMunoGeneTics information system® www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted below sequence in red; underlined residues are positions to alter first.
(7) Potential changes in CDR sequence noted below each CDR sequence. These may prevent asparagines (N) deamidation (N), methionine (M) oxidation, Asp-Gly (DG) isoaspartate formation or Asp-Pro (DP) bond cleavage.

huVK2
Potential humanized sequence based on IMGT IGKV2-28 acceptor framework (method 1)
DIVMTQSPLSLPVTPGEPASISC RSSQSLLHSNGYNYLD WYLQKPGQSPQLLIY LGSNRAS GVPDRFSGSGSGTDFTLKISRVEAEDVGVYYC MQALQTP

Joining region
IMGT J00242|IGKJ2*01|YTFGQGTKLEIK

```
seq        10          20          30  30abcde    40          50          60          70          80          90
AbM        10          20                         40          50          60          70          80
           b b b  b b   b b b b        b  b i b i   i i b b i    i    b  b           b b       b b b  b  bb bib
175A       DVLMTQTPLSLPVSLGDQASISC RSSQSIVHSNGNTYLE WYLQKPGQSPKLLIY KLSNRFS GVPDRFSGSGSGTDFTLKISRVEAEDLGVYYC
           **  *          ** **             Q Q                       Q                                    *
                                             S S                       S                                    L
                                            A A                       D
                                             D                        A
huVK2      DIVMTQSPLSLPVTPGEPASISC RSSQSIVHSNGNTYLE WYLQKPGQSPQLLIY KLSNRFS GVPDRFSGSGSGTDFTLKISRVEAEDVGVYYC
              V
```

```
seq        90         100        110
AbM        90         100
           i b i   i i b  i   b b b b
175A       FQGSHFPYT FGGGTKLEIK
                *
huVK2      FQGSHFPYT FGGGTKLEIK
```

(1) CDR sequences noted in bold.
(2) Human germline and joining sequences from IMGT® the international ImMunoGeneTics information system®
    www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain; "i" notes sidechain at interface between VH and VL domains.
(5) Sequence differences between each humanized sequence and murine sequence noted by asterick (*).
(6) Potential humanized framework mutations from human sequence to parental mouse sequence are noted
    below sequence in red; underlined residues are positions to alter first.
(7) Potential changes in CDR sequence noted below each CDR sequence. These may prevent asparagines
    (N) deamidation (N), methionine (M) oxidation, Asp-Gly (DG) isoaspartate formation or Asp-Pro (DP) bond cleavage.

FIG. 8A huVK1
Potential humanized sequence based on IMGT IGKV1-39 acceptor framework (method 2)
DIQMTQSPSSLSASVGDRVTITC RASQSISSYLN WYQQKPGKAPKLLIY AASSLQS GVPSRFSGSGSGTDFTLTISSLQPEDFATYYC QQSYSTP

Joining region
IMGT J00242|IGKJ2*01|YTFGQGTKLEIK

```
        10          20          30   30abcde    40         50           60          70          80         90
seq                                                                                                                
AbM     10          20                           40         50           60          70          80
        b b b   bb bbb b   b b    bi bi i    ii ibbi      i  b   b     b b bbb b     bb bib 175A    DVLMTQTPLSLPVSLGDQASISC  RSSQSIVHSNGNTYLE  WYLQKPGQSPKLLIY  KLSNRFS  GVPDRFSGSGSGTDFTLKISRVEAEDLGVYYC
         **  * *  * *        ****      *                  **                   *     **    * ***
                                                 Q   Q                             Q
                                                 S   S                             S
                                                 A   A                             D
                                                     D                             A huVK1   DIQMTQSPSSLSASVGDRVTITC  RSSQSIVHSNGNTYLE  WYQQKPGKAPKLLIY  KLSNRFS  GVPSRFSGSGSGTDFTLTISSLQPEDFATYYC
             V    V                                                                            V     LG
             A 90         100         110
seq                100
AbM     90                                      
         ibi   iib i   b b b 175A    FQGSHFPYT  FGGGTKLEIK
            *
huVK1   FQGSHFPYT  FGGGTKLEIK
```

(1) CDR sequences noted in bold.
(2) Human germline and joining sequences from IMGT® the international ImMunoGeneTics information system®
    www.imgt.org (founder and director: Marie-Paule Lefranc, Montpellier, France).
(3) Residue numbering shown as sequential (seq) or according to website www.bioinf.org.uk/abs/ (AbM).
(4) "b" notes buried sidechain, "i" notes sidechain at interface between VH and VL domains.
(5) Sequence differences between each humanized sequence and murine sequence noted by asterick (*).
(6) Potential humanized framework mutations from human sequence to parental mouse sequence are noted
    below sequence in red; underlined residues are positions to alter first.
(7) Potential changes in CDR sequence noted below each CDR sequence. These may prevent asparagines
    (N) deamidation (N), methionine (M) oxidation, Asp-Gly (DG) isoaspartate formation or Asp-Pro (DP) bond cleavage.

FIG. 8B

76E1 VH
EVQLQSGPELEKPGASVKISCKASGYSFAAAAAAAAAAAAAAAAAAAWKQSNGKSLEWIGAIAAAAAAAAAAAAAAAAAAAAAAAAAAAAAAKATLTVDKSSSTAYMQLKSLTSEDSAVYYC
ATAAAAAAFDYWGQGTLTVSS (SEQ ID NO: 1143)
human subgroup I 141A VH
QVQLQQSGAELMKPGASVKISCKATGYTFAAAAAAAAAAAAAAAAAAAWKQRPGHGLEWIGAIAAAAAAAAAAAAAAAAAAAAAAAAAAAAAAKATFTADTSSNTAYMQLSSLTSEDSAVYYC
AGAAAAAAAAAAAAAAAWGQGTLVTVSA (SEQ ID NO: 1144)
human subgroup I 175A VH
QVQLQQSGAELMKPGASVKISCKATGYTFAAAAAAAAAAAAAAAAAAAWKQRPGHGLEWIGAIAAAAAAAAAAAAAAAAAAAAAAAAAAAAAAKATFTADTSSNTAYMQLSSLTSEDSAVYYC
ARAAAAAYAMDYWGQGTSVTVSS (SEQ ID NO: 1145)
human subgroup I 76E1 VL
DVLMTQTPLSLPVSLGDQASISCRSSQSAAAAAAAAAAAAAAAAAAAWYLQKPGQSPKLLIYAAAAAAAAAAAAGVPDRFSGSGSGTDFTLKINRVEAEDLGVYYCAQA
AAAPATFGGGTKLEIK (SEQ ID NO: 1146)
human kappa II 141A VL
QIVLSQSPAILSASPGEKVTMTCRASAAAAAAAAAAAAAWYQQKPGSSPKPWIYAAANLASGVPARFSGSGSGTSYSLTISRVEAEDAATYYCQQAAAAAPAT
FGGGTKLEIK (SEQ ID NO: 1147)
human kappa III 175A VL
DVLMTQTPLSLPVSLGDQASISCRSSQSAAAAAAAAAAAAAAAAAAAWYLQKPGQSPKLLIYAAAAAAAAAAAAGVPDRFSGSGSGTDFTLKISRVEAEDLGVYYCAQA
AAAPATFGGGTKLEIK (SEQ ID NO: 1148)
human kappa II

FIG. 9

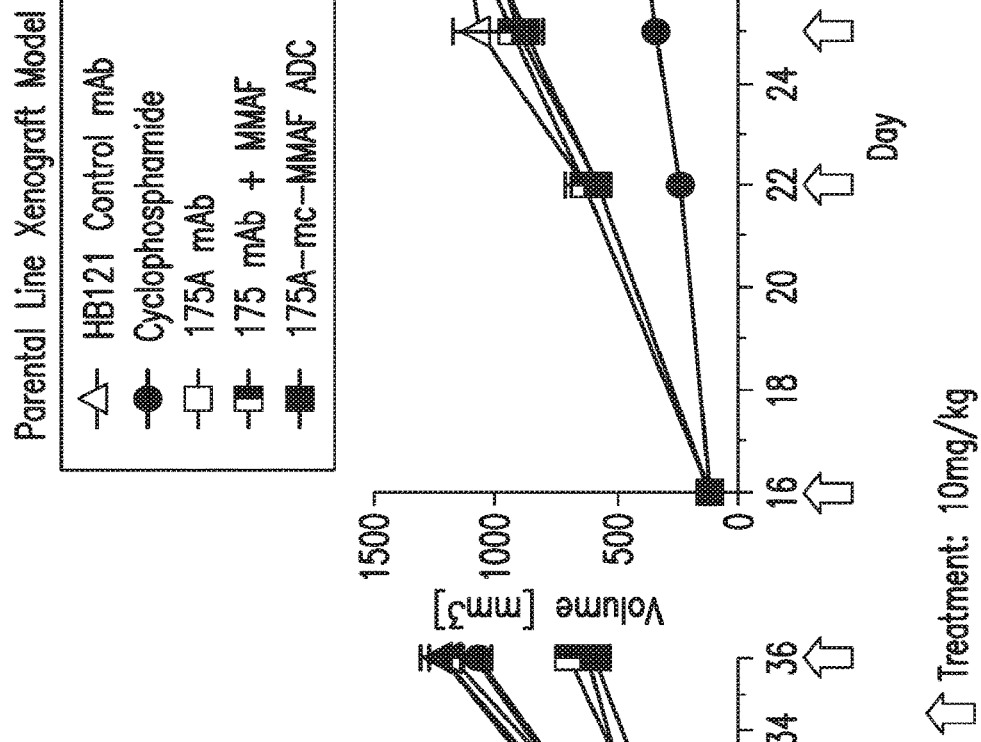
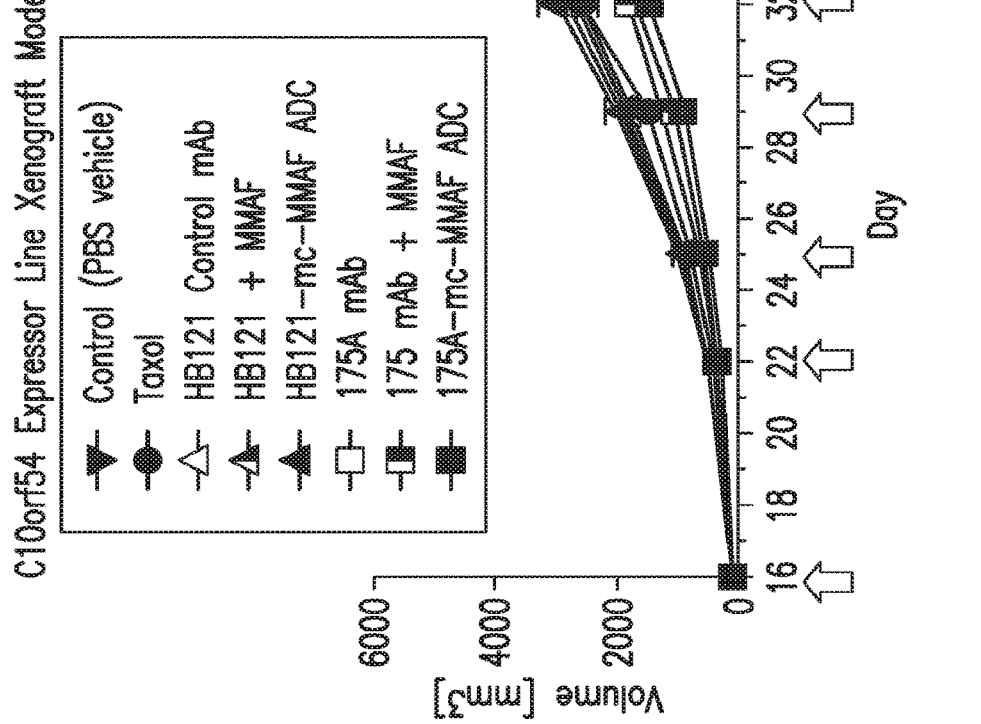
FIG. 15

R13 VH

R13-3610-76E1   MGWTWIFILILSVTTGVHS
R13-3610-141A   MEWTWVFLFLLSVTAGVHS
R13-3610-175A   MEWTWVFLFLLSVTAGVHS

```
Kabat     1    10    22       31—35    40    50—a—60—65
AbM       1    10    22  26—35         40    50—a—58—65
Chothia   1    10    22  26—32         40       a—55—65
Contact   1    10    22       30—35    40    50—a—58—65
IMGT      1          23  27—38  41                56—65   74
76E1   EVQLLQSGPELEKPGASVKISCKAS GYSFTGYNMN WVKQSNGKSLEWIG NIDPYYDYTSYNLKFKD
141A   QVQLQQSGAELMKPGASVKISCKAT GYTFSRYWIE WVKQRPGHGLEWIG EILPGSGSTNYNEKFKG
175A   QVQLQQSGAELMKPGASVKISCKAT GYTFSTHWIE WVKQRPGHGLEWIG EILPGSGSTSYNEKFKG Kabat     70    80   abc   90   95—100—102   110
AbM       70    80   abc   90   95—100—102   110
Chothia   70    80   abc   90   96—100—101   110
Contact   70    80   abc   90   93—100—101   110
IMGT      75         89         105—117
76E1   KATLTVDKSSSTAYMQLKSLTSEDSAVYYCAT STMITP——FDY  WGQGTTLTVSS
141A   KATFTADTSSNTAYMQLSSLTSEDSAVYYCAG EEVDGYPWFGY  WGQGTLVTVSA
175A   KATFTADTSSNTAYMQLSSLTSEDSAVYYCAR WLYYYA——MDY  WGQGTSVTVSS
```

R13-3610-76E1    MKLPVRLLVLMFWIPASSS
R13-3610-141A    MDFQVQIFSFLLISASVIMSRG
R13-3610-175A    MKLPVRLLVLMFWIPASSS

```
             1          10         20          24-27abcd—34     40        50—56
Kabat        1          10         20          24—30abcd—34     40        50—56
AbM          1          10         20          26—30abcd-32     40        50—
Chothia      1          10         20              30abcd—36    40        46—55
Contact      1                         23   27—         —38   41           56-65 69
IMGT         1                                                              ├──┤

76E1    DVLMTQTPLSLPVSLGDQASISC  RSSQSIVHSNGNTYLE  WYLQKPGQSPKLLIY  KVSNRFS
141A    QIVLSQSPAILSASPGEKVTMTC  RASSSL——SYMH       WYQQKPGSSPKPWIY  ATSNLAS
175A    DVLMTQTPLSLPVSLGDQASISC  RSSQSIVHSNGNTYLE  WYLQKPGQSPKLLIY  KLSNRFS 60         70         80         89——97
Kabat        60         70         80         89——97
AbM          60         70         80         91——96
Chothia      60         70         80         89——96
Contact      60         70         80         105———117
IMGT         70             89
76E1    GVPDRFSGSGSGTDFTLKINRVEAEDLGVYYC  FQGSHVPWT   FGGGTKLEIK
141A    GVPARFSGSGSGTSYSLTISRVEAEDAATYYC  QQWSSNPYT   FGGGTKLEIK
175A    GVPDRFSGSGSGTDFTLKISRVEAEDLGVYYC  FQGSHFPYT   FGGGTKLEIK
```

| | 1 | 10 | 22 | 26————35 | 40 | 50—a—58 | 65 |
|---|---|---|---|---|---|---|---|
| AbM | | | | | | | |
| hu76E1 | QVQLVQSGAEVKKPGASVKVSCKAS | GYSFTGYNMN | WVRQAPGQGLEWIG | NIDPYDYTSYNLKFKD | hu141A    QVQLVQSGAEVKKPGASVKVSCKAS GYTFSRYWIE WVRQAPGQGLEWIG EILPGSGSTNYNEKFKG
hu175A    QVQLVQSGAEVKKPGASVKVSCKAS GYTFSTHWIE WVRQAPGQGLEWIG EILPGSGSTSYNEKFKG
consen    QVQLVQSGAEVKKPGASVKVSCKAS GYTFSXXWIE WVRQAPGQGLEWIG EILPGSGSTXYNEKFKG
                                     RY                              N
                                     TH                              S

| | 70 | 80 abc | 90 | 95—100—102 | 110 | |
|---|---|---|---|---|---|---|
| AbM | | | | | | |
| hu76E1 | RVTMTVDKSTSTAYMELRSLRSDDTAVYYCAT | STMITP--FDY | WGQGTLVTVSS | (SEQ ID NO: 1135) | hu141A    RVTMTADTSTSTAYMELRSLRSDDTAVYYCAG EEVYDGYPWFGY WGQGTLVTVSS (SEQ ID NO: 1136)
hu175A    RVTMTADTSTSTAYMELRSLRSDDTAVYYCAR WLYYYA--MDY WGQGTLVTVSS (SEQ ID NO: 1137)
consen    RVTMTADTSTSTAYMELRSLRSDDTAVYYCAR xxxxxxxxxXXY WGQGTLVTVSS (SEQ ID NO: 1138)
                                              WG
                                              FD

FIG. 17A

```
R13 VL 1         10        20    24————30abcd————34        40             50————56
AbM        EIVLTQSPGTLSLSPGERATLSC RASSSL————SYMH WYQQKPGQAPRPWIY ATSNLAS hu141A     DIVMTQSPLSLPVTGEPASISC  RSSQSIVHSNGNTYLE WYLQKPGQSPQLLIY KVSNRFS
hu76E1     DIVMTQSPLSLPVTGEPASISC  RSSQSIVHSNGNTYLE WYLQKPGQSPQLLIY KLSNRFS
hu175A     DIVMTQSPLSLPVTGEPASISC  RSSQSIVHSNGNTYLE WYLQKPGQSPQLLIY KXSNRFS
consen                                                                 V
                                                                       L 60        70        80   89————97
AbM        GIPDRFSGSGSGTDYTLTISRLEPEDFAVYYC QQWSSNPYT  FGQGTKLEIK
hu141A     GVPDRFSGSGSGTDFTLKISRVEAEDVGVYYC FQGSHVPWT  FGQGTKLEIK (SEQ ID NO: 1139)
hu76E1     GVPDRFSGSGSGTDFTLKISRVEAEDVGVYYC FQGSHFPYT  FGQGTKLEIK (SEQ ID NO: 1140)
hu175A     GVPDRFSGSGSGTDFTLKISRVEAEDVGVYYC FQGSHXPYT  FGQGTKLEIK (SEQ ID NO: 1141)
consen     GVPDRFSGSGSGTDFTLKISRVEAEDVGVYYC FQGSHXPXT  FGQGTKLEIK (SEQ ID NO: 1142)
                                                 V W
                                                 F Y
```

FIG. 17B

| VH Domains | | | | | | | |
|---|---|---|---|---|---|---|---|
| AbM# | | 10 | 20 | 26 30 | 35 | 40 | 50 a | 65 |
| 5B | QVQLQQSGAELVRPGVSVKISCKGS | GYTFTD-YGMH | WVKQSHAKSLEWIG | IDTYYGDATYNQKFKG |
| 46A | QVQLQQSGAGGELVRPGVSVKISCKGS | GYTFTD-YGMH | WVKQSHAKSLEWIG | IINTYYGDATYNQKFKG |
| 97A | QVQLQQSGAELVRPGVSVKISCKGS | GYTFTD-YGMH | WVKQSHAKSLEWIG | VIDTYYGDASNNQKFKG |
| 128A | QVQLQQSGAELVRPGVSVKISCKGS | GYTFTD-YGMH | WVKQSHAKSLEWIG | LIDTYYGDATYNHKFKG |
| 146C | QVQLQQSGAELVRPGVSVKISCKGS | GYTFTD-YGMH | WVKQSHAKSLEWIG | LIDTYYGDATYNHKFKG |
| 208A | QVQLQQSGAELVRPGVSVKISCKGS | GYTFTD-YGMH | WVKQSHAKSLEWIG | VIDTYYGDAGYNQKFKG |
| consensus | | GYTFTD-YGMH | | *I*TYYGDA**N*KFKG |
| 215A | EVQLQQSGPELVKPGASMKISCKAS | GFSFTG-YTMN | WVKQSHGKNLEWIG | LISPYNGGTSYNQKFKG |
| 26A | EVQLQQSGPELVKPGASMKISCKAS | GFSFTG-YTMN | WVKQSHVKNLEWIG | LISPYNGGTSYNQKFKG |
| 164A | EVQLQQSGPELEKPGASVKISCKAS | GYSFTG-YNMN | WVKQSNGKSLEWIG | NIDPYYGSASYNQKFKG |
| 230A | EVQLQQSGPELEKPGASVKISCKAS | GYSFTG-SNMN | WVKQNNGKSLEWIG | NIDPYYGTTYNQKFKG |
| 76E1 | EVQLLQSGPELEKPGASVKISCKAS | GYSFTG-YNMN | WVKQSNGKSLEWIG | NIDPYYDYTSYNLKFKD |
| 53A | EVQLQQSGPELVKPGASVKMSCKAS | GYTFTS-YFMH | WVKQKPGQGLEWIG | YIYPYNDGTKYNEKFKG |
| 259A | EVQLQQSGPELVKPGASVKMSCKAS | GYTFTS-YFMH | WVKQKPGQGLEWIG | YIYPYNDGTKYNEKFKG |
| consensus | | GYTFTS-YFMH | | YIYPYNDGTKYNEKFKG |
| 33A | QVQLQQSGAELMKPGASVKISCKAT | GYTFTS-YWIE | WVKQRPGHGLEWIG | EILPGSGSTSYNEKFKG |
| 39A | QVQLQQSGAELMKPGASVKISCKAT | GYTFSS-NWIE | WVKQRPGHGLEWIG | EILPGSGSTSYNEKFKG |
| 124A | QVQLQQSGAELMKPGASVKISCKAT | GYTFSS-NWIE | WVKQRPGHGLEWMG | EILPGSGSTSYNEKFKG |
| 175A | QVQLQQSGAELMKPGASVKISCKAT | GYTFST-HWIE | WVKQRPGHGLEWIG | EILPGSGSTSYNEKFKG |
| 321D | QVQLQQSGAELMKPGAAVKISCKAT | GYTFSS-HWIE | WVKQRPGHGLEWIG | EILPGSGSTDYNEKFKG |
| consensus | | GYTFS*-*WIE | | EILPGSGST*YNEKFKG |
| 141A | QVQLQQSGAELMKPGASVKISCKAT | GYTFSR-YWIE | WVKQRPGHGLEWIG | EILPGSGSTNYNEKFKG |
| 51A | QVQLQQSGAELMKPGASVKISCKAT | GYTFSR-YWIE | WVKQRPGHGLEWIG | EILPGSGSTNYNEKFKG |
| consensus | | GYTFSR-YWIE | | EILPGSGSTNYNEKFKG |
| 353A | EVKLLESGGGLVQPGGSLKLSCAAS | GFDFSR-YWMN | WVRQAPGKGLEWIG | EINPDSSTINYTPSLKD |
| 305A | DVQLQESGPGLVKPSQSLSLTCSVT | GYSITSGYYWN | WIRQFPGNKLEWMG | YIS-YDGSNNYNPSLKN |

FIG. 18A

| AbM# | 70 | 80 abc | 90 | 95 100 | 102 | 110 |
|---|---|---|---|---|---|---|
| 5B | KATMTVDKSSSSTAYMELARLTSEDSAIYYCAR | RAGNAM | ---DY | WGQGTSVTVSS |
| 46A | KATMTVDKSSSSTAYMELARLTSEDSAIYYCAR | RAGTAM | ---DY | WGQGTSVTVSS |
| 97A | KATMTVDKSSSRTAYMELARLTSEDSAIYYCAR | RAGNAM | ---DY | WGQGTSVTVSS |
| 128A | KATMTVDKSSSSTAYMELARLTSEDSAIYYCAR | RAGNAM | ---DY | WGQGTSVTASS |
| 146C | KATMTVDKSSSRTAYMELARLTSEDSAIYYCAR | RAGNAM | ---DY | WGQGTSVTASS |
| 208A | KATMTVDKSSSSTAYMELARLTSEDSAIYYCAR | RAGNAM | ---DY | WGQGTSVTVSS |
| consensus | | | RAGNAM | ---DY | |
| 215A | KATLTVDKSSSSTAYMELLSLTSEDSAVYYCAR | RAYGYAM | ---DY | WGQGTSVTVSS |
| 26A | KATLTVDKSSSSTAYMELLSLTSEDSAVYYCAR | RAYGYAM | ---DY | WGQGTSVTVSS |
| 164A | KATLTVDKSSSTAYMQLKSLTSEDSAVYYCTR | SNYGYGYF | ---DV | WGAGTTVTVSS |
| 230A | KATLTVDKSSSSTAYMQLKSLTSEDSAVYYCAR | DYDYALGYF | ---DV | WGAGTTVTVSS |
| 76E1 | KATLTVDKSSSSTAYMQLKSLTSEDSAVYYCAT | STMITPF | ---DY | WGQGTLTLVSS |
| 53A | KATLTSDKSSSSTAYMELSSLTSEDSAVYYCAR | FDYDTL | ---RY | WGQGTLTLVSS |
| 259A | KATLTSDKSSSTAYMDLSSLTSEDSAVYYCAR | FDYDTL | ---RY | WGQGTLTLVSS |
| consensus | | | FDYDTL | ---RY | |
| 33A | KATFTADTSSNTAYMQLSGLTSEDSAVYYCAR | WLLYYYAM | ---VY | WGQGTSVTVSS |
| 39A | KATFTADTSSNTAYMQLSSLTSEDSAVYYCAR | WLLYYYAM | ---DY | WGQGTSVTVSS |
| 124A | KATFTADTSSNTAYMQLSSLTSEDSAVYYCAR | WLLYYYAM | ---DF | WGQGTSVTVSS |
| 175A | KATFTADTSSNTAYMQLSSLTSEDSAVYYCAR | WLLYYYAM | ---DY | WGQGTSVTVSS |
| 321D | KATFTADTSSNTAYMQLSSLTSEDSAVYYCAR | WLLYYYAM | ---DY | WGQGTSVTVSS |
| consensus | | | WLLYYYAM | ---DY | |
| 141A | KATFTADTSSNTAYMQLSSLTSEDSAVYYCAG | EEVYDGYPWF | ---GY | WGQGTLVTVSA |
| 51A | KATFTADTSSNTAYMQLSSLTSEDSAVYYCAS | EEVYDGYPWF | ---GY | WGQGTLVTVSA |
| consensus | | | EEVYDGYPWF | ---GY | |
| 353A | KFIISRDNAKNTLYLQMSKVRVEDTALYYCAR | PCEIYYGSYWFAY | | WGQGTLVTVSA |
| 305A | RISITRDTSKNQFLKLNSVTTEDTATYYCAR | RHDYLSF | ---AY | WGQGTLVIVSA |

FIG. 18B

| VL Domains | | | | | | |
|---|---|---|---|---|---|---|
| AbM# | | 10 | 20 24 | 30 | 34 | 40 | 50 56 |

```
VL Domains
AbM#              10        20 24     30        34        40        50 56
5B       NIWMTQTPKFLLVSAGDRVTITC KASQSVS------NDVA WYQQKPGSPKLLIY YASNRYT
46A      SIWMTQTPKFLLVSAGDRVTITC KASQSVS------NDVA WYQQKPGSPKLLIY YASNRYT
97A      SIWMTQTPKFLLVSAGDRVAITC KASQSVS------NDVA WYQQKPGSPKLLIY YASNRYT
128A     NIAMTQTPKFLLVSAGDRVTITC KASQSVS------NDIA WYQQKPGSPKLLIY YASNRYT
146C     NIAMTQTPKFLLVSAGDRVTITC KASQSVS------NDIA WYQQKPGSPRLLIY YASNRYT
208A     SIWMTQTPKFLLVSAGDRVTITC KASQSVS------NDVA WYQQKPGSPKLLIY YASNRYT
consensus                        KASQSVS------ND*A                 YASNRYT

215A     QIVLTQSPAIMSASPGEKVTMTC SASSSVS------YMF WYQQKPGSSPRLLIY DTSNLAS

26A      QIVLTQSPAIMSASPGEKVTMTC SASSSVS------YMY WYQQKPGSSPRLLIY DTSNLAS 164A-1   NIMMTQSPSSLAVSAGEKVTMSC KSSQSVLYSSNQKNYLA WYQQKPGQSPKLLIY WASTRES
164A-2   ENVLTQSPAIMAASPGEKVTMTC SASSSVSS-----SNLH WYQQKSGTSTKFWIY RTSNLAS

230A     DVVMTQTPLSLPVSLGDQASISC RSSQSLVHSNGN-TYLH WYLQKPGQSPKLLIY KVSNRFS

76E1     DVLMTQTPLSLPVSLGDQASISC RSSQSIVHSNGN-TYLE WYLQKPGQSPKLLIY KVSNRFS

53A      DVLTQTPLSLPVNIGDQASISC KSTKSLLNSDGF-TYLD WYLQKPGQSPQLLIY LYSNRFS
259A     DVLTQTPLSLPVNIGDQASISC KSTKSLLNSDGF-TYLD WYLQKPGQSPQLLIY LISNRFS
consensus                     KSTKSLLNSDGF-TYLD                 L*SNRFS 33A      DVLMTQTPLSLPVSLGDQASISC RSSQSIVHSNGN-TYLE WYLQKPGQSPKLLIY KVSNRFS
39A      DVLMTQTPLSLPVSLGDPASISC RSSQSIVHNNGN-TYLE WYLQKPGQSPKLLIY KVSNRFS
124A     DVLMTQTPLSLPVSLGDQASISC RSSQSIVHNNGN-TYLE WYLQKPGQSPKLLIY KVSNRFS
175A     DVLMTQTPLSLPVSLGDQASISC RSSQSIVHSNGN-TYLE WYLQKPGQSPKLLIY KLSNRFS
321D     DVLMTQTPLSLPVSLGDQASISC RSSQSIVH*NGN-TYLE WYLQKPGQSPKLLIY KVSNRFS
                                RSSQSIVH*NGN-TYLE                 K*SNRFS 141A     QIVLSQSPAILSASPGEKVTMTC RASSSL--------SYMH WYQQKPGSSPKPWIY ATSNLAS
51A      QIVLSQSPAILSASPGEKVTMTC RASSSL--------SYMH WYQQRPGSSPKPWIY ATSNLAS
consensus                     RASSSL--------SYMH                 ATSNLAS

353A     DIVLTQSPASLAVSLGQRATISC RASESVEYYGT--SLMQ WFQQKPGQPPKLLIY AASNVES

305A     DIVLTQSPASLAVSLGQRATISC KASQSVDYDGD--SYMN WYQQKPGQPPKLLIY AASNLES
```

FIG. 18C

```
AbM#       60         70         80         89-------97
5B         GVPDRFTGSGYGTDFTFTISTVQAEDLAVYFC QQDYSSPRT FGGGTKLEIK
46A        GVPDRFTGSGYGTDFTFTISTVQAEDLAVYFC QQDYGSPRT FGGGTKLEIK
97A        GVPDRFTGSGYGTDFTFTISTVQAEDLAVYFC QQDYGSPRT FGGGTKLEIK
128A       GVPDRFTGSGYGTDFTFTISTVQAEDLAVYFC QQDYSSPRT FGGGTKLEIK
146C       GVPDRFTGSGYGTDFTFTISTVQAEDLAVYFC QQDYSSPRT FGGGTKLEIK
208A       GVPDRFTGSGYGTDFTFTISTVQAEDLAVYFC QQDYSSPRT FGGGTKLEIK
consensus                                   QQDY*SPRT

215A       GVPLRFSGSGSGTSYSLTISRMEAEDAATYYC QQWSSYPFT FGSGTKLEIK

26A        GVPLRFSGSGSGTSYSLTISRMEAEDAATYYC QQWSSYPFT FGSGTKLEIK 164A-1     GVPDRFTGSGSGTDFTLTISSVQAEDLAVYYC HQFLSS-YT FGGGTKLEMK
164A-2     EVPAPFSGSGSGTSYSLTISSVEAEDAATYYC QQWSGYPRT FGGGTKLEIK

230A       GVPDRFSGSGSGTDFTLKISRVEAEDLGVYFC SQSTHVPYT FGGGTKLEIK

76E1       GVPDRFSGSGSGTDFTLKINRVEAEDLGVYYC FQGSHVPWT FGGGTKLEIK

53A        GVPDRFSGSGSGTDFTLKISRVEAEDLGVYYC FQSNYFPWT FGGGTKLEIK
259A       GVPDRFSGSGSGTDFTLKISRVEAEDLGVYYC FQSNYFPWT FGGGTKLEIK
consensus                                   FQSNYFPWT 33A        GVPDRFSGSGSGTDFTLKISRVEAEDLGVYYC FQGSHVPYT FGGGTKLEIK
39A        GVPDRFSGSGSGTDFTLKISRVEAEDLGVYYC FQGSHVPYT FGGGTKLEIK
124A       GVPDRFSGSGSGTDFTLKISRVEAEDLGVYYC FQGSHVPYT FGGGTKLEIK
175A       GVPDRFSGSGSGTDFTLKISRVEAEDLGVYYC FQGSHFPYT FGGGTKLEIK
321D       GVPDRFSGSGSGTDFTLKITRVEAEDLGVYYC FQGSHVPFT FGGGTKLEIK
consensus                                   FQGSH*PFT 141A       GVPARFSGSGSGTSYSLTISRVEAEDAATYYC QQWSSNPYT FGGGTKLEIK
51A        GVPARFSGSGSGTSYSLTISRVEAEDAATYYC QQWSSNPYT FGGGTKLEIK
consensus                                   QQWSSNPYT

353A       RVPARFSGSGSGTDFSLNIHPVEEDIAMYFC  QQSRKDPWT FGGGTKLEIK

305A       GIPARFSGSGSGTDFTLNIHPVEEEDAATYYC QQSDEDPYT FGGGTKLEIK
```

FIG. 18D

| mAb | Human VH Germline | Human VL Germline | Paratope Bin |
|---|---|---|---|
| 5B | IGHV1-46 | IGKV1-39 | 1 |
| 46A | IGHV1-46 | IGKV1-39 | 1 |
| 97A | IGHV1-46 | IGKV1-39 | 1 |
| 128A | IGHV1-46 | IGKV1-39 | 1 |
| 146C | IGHV1-46 | IGKV1-39 | 1 |
| 208A | IGHV1-46 | IGKV1-39 | 1 |
| 215A | IGHV1-46 | IGKV1-39 | 2 |
| 26A | IGHV1-46 | IGKV3-11 | 3 |
| 164A | IGHV1-46 | IGKV3-11 | 4 |
| | | IGKV4-1 | 4 |
| 230A | IGHV1-46 | IGKV3D-20 | 5 |
| 76E1 | IGHV1-46 | IGKV2-30 | 6 |
| 53A | IGHV1-18 | IGKV2-28 | 7 |
| 259A | IGHV1-46 | IGKV2-29 | 7 |
| 33A | IGHV1-46 | IGKV2-29 | 8 |
| 39A | IGHV1-46 | IGKV2-30 | 8 |
| 124A | IGHV1-46 | IGKV2-30 | 8 |
| 175A | IGHV1-46 | IGKV2-30 | 8 |
| 321D | IGHV1-18 | IGKV2-28 | 8 |
| 141A | IGHV1-46 | IGKV2-30 | 9 |
| 51A | IGHV1-18 | IGKV3-20 | 9 |
| 353A | IGHV3-74 | IGKV1-39 | 10 |
| 305A | IGHV4-61 | IGKV1-39 | 11 |

FIG. 19

Human VH germline sequences

IGHV1-18*01
QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAR

IGHV1-46*01
QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR

IGHV3-74*01
EVQLVESGGGLVQPGGSLRLSCAASGFTFSSYWMHWVRQAPGKGLVWVSRINSDGSSTSYADSVKGRFTISRDNAKNTLYLQMNSLRAEDTAVYYCAR

IGHV4-61*01
QVQLQESGPGLVKPSETLSLTCTVSGGSVSSGSYYWSWIRQPPGKGLEWIGYIYYSGSTNYNPSLKSRVTISVDTSKNQFSLKLSSVTAADTAVYYCAR

FIG. 20A

Human VL kappa germline sequences

IGKV1-39*01
DIQMTQSPSSLSASVGDRVTITCRASQSISSYLNWYQQKPGKAPKLLIYAASSLQSGVPSRFSGSGSGTDFTLTISSLQPEDFATYYCQQSYSTPP

IGKV2-28*01
DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPP

IGKV2-29*02
DIVMTQTPLSLSVTPGQPASISCKSSQSLLHSDGKTYLYWYLQKPGQSPQLLIYEVSSRFSGVPDRFSGSGSGTDFTLKISRVEAEDVGVYYCMQGIHLPP

IGKV2-30*02
DVVMTQSPLSLPVTLGQPASISCRSSQSLVHSDGNTYLNWFQQRPGQSPRRLIYKVSNRDSGVPDRFSGSGSGTDFTLKISRVEAEDVGVYYCMQGTHWPP

IGKV3-11*01
EIVLTQSPATLSLSPGERATLSCRASQSVSSYLAWYQQKPGQAPRLLIYDASNRATGIPARFSGSGSGTDFTLTISSLEPEDFAVYYCQQRSNWPP

IGKV3-20*01
EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPP

IGKV3D-20*01
EIVLTQSPATLSLSPGERATLSCGASQSVSSSYLAWYQQKPGLAPRLLIYDASSRATGIPDRFSGSGSGTDFTLTISRLEPEDFAVYYCQQYGSSPP

IGKV4-1*01
DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPP

FIG. 20B

```
                    1         10                20                30                40                50                60
human   MGVPTALEAGSWRWGSLLFALFLAASLGPVAAFKVATPYSLYVCPEGQNVTLTCRLLGPV
mouse   MGVPAVPEASSPRWGTLLLAIFLAASRGLVAAFKVTTPYSLYVCPEGQNATLTCRILGPV 70                80                90               100               110               120               130
        DKGHDVTFYKTWYRSSSRGEVQTCSERRPIRNLTFQDLHLHHGGHQAANTSHDLAQRHGLESASDHHGNFS
        SKGHDVTIYKTWYLSSRGEVQMCKEHRPIRNFTLQHLQ-HHGSHLKANASHDQPQKHGLELASDHHGNFS 140               150               160               170               180               190
        ITMRNLTLLDSGLYCCLVVEIRHHHSEHRVHGAMELQVQGKKDAPSNCVVYPSSSQDSENITA
        ITLRNVTPRDSGLYCCLVIELKNHHPEQRFYGSMELQVQAGKGSGSTCMA--SNEQDSDSITA
```

FIG. 21A CONTINUED

```
Potential humanized sequence based on IMGT IGHV1-46*01 acceptor framework (AbM CDR definition)
IGHV1-46*01 QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR
Joining region    IMGT J00256|IGHJ4*01|YFDYWGQGTLVTVSS seq                       10         20         30         40         50         60         70         80         90
AbM                       10         20         30         40         50         60         70         80   abc    90
26A              b b b           b b b       b     b    b i i   i bb b  b     a  b b                b b b x           b b b     b bibibb
        EVQLQQSGPELVKPGASMKISCKAS GYTFTSYYMH WVKQSHVKNLEWIG LISPYNGGTS YNQKFKGKATLVDKSSSTAYMELLSLTSEDSAVYYCAR
         *    *          *        *  *  *    *  *    * *  *****     *           *   * * **  * *     *

1-46*01 QVQLVQSGAEVKKPGASVKVSCKAS GYTFTSYYMH WVRQAPGQGLEWMG IINPSGGSTS YAQKFQGRVTMTRDTSTSTVYMELSSLRSEDTAVYYCAR
h26AH1  QVQLVQSGAEVKKPGASVKISCKAS GFSFTGYTMN WVRQAPGQGLEWMG LISPYNGGTS YAQKFQGRVTMTRDTSTSTVYMELSSLRSEDTAVYYCAR
h26AH2  QVQLVQSGAEVKKPGASVKISCKAS GFSFTGYTMN WVRQAPGQGLEWIG LISPYNGGTS YAQKFQGRATLTVDTSTSTAYMELSSLRSEDTAVYYCAR
h26AH3  QVQLVQSGAEVKKPGASVKISCKAS GFSFTGYTMN WVRQAPGQGLEWIG LISPYNGGTS YAQKFQGRATLTVDKSTSTAYMELSSLRSEDTAVYYCAR
                    V                   M                               N
                                                              # seq     100        110
AbM     100        110
                b   i  b b b
26A     RAYGYAMDY WGQGTSVTVSS
                    *
h26AH1  RAYGYAMDY WGQGTLVTVSS
h26AH2  RAYGYAMDY WGQGTLVTVSS
h26AH3  RAYGYAMDY WGQGTLVTVSS (1) CDR sequences noted in bold. CDR definitions are AbM definition from website www.bioinf.org.uk/abs/.

(2) Human germline and joining sequences from IMGT® the international ImMunoGeneTics® information system
    www.imgt.org (founder and director: Marie-Paule Lefranc, Montpellier, France).

(3) Residue numbering shown as sequential (seq) or according to Chothia from website
    www.bioinf.org.uk/abs/ (AbM).

(4) "b" notes buried sidechain; "p" notes partially buried; "i" notes sidechain at interface between
    VH and VL domains.

(5) Sequence differences between human and murine germlines noted by asterisk (*).

(6) Potential changes in CDR sequences noted below each CDR sequence. These may prevent asparagine
    (N) deamidation.
```

FIG. 22A

```
Potential humanized sequence based on IMGT IGKV3-11*01 acceptor framework (AbM CDR definition)
IGHV3-11*01 EIVLTQSPATLSLSPGERATLSCRASQSVSSYLAWYQQKPGQAPRLLIYDASNRATGIPARFSGSGSGTDFTLTISSLEPEDFAVYYCQQRSNWPP
Joining region IMGT J00242|IGKJ2*01|YTFGQGTKLEIK seq              10         20         30         40         50         60         70         80
AbM              10         20         30         40         50         60         70         80
                 b b b      b    b b b b    b    b i    b i      i i ibbi              b                          bb bib
26A    QIVLTQSPAIMSASPGEKVTMTC SASSSVS--YMY WYQQKPGSSPRLLIY DTSNLAS GVPLRFSGSGSGTSYSLTISRMEAEDAATYYC
        *           *      **                    *            #                *   *  ** *  *   *   A IGKV3-11  EIVLTQSPATLSLSPGERATLSC RASQSVSSYLA  WYQQKPGQAPRLLIY DASNRAT GIPARFSGSGSGTDFTLTISSLEPEDFAVYYC
h26AL1    EIVLTQSPATLSLSPGERATLSC SASSSVS--YMY WYQQKPGQAPRLLIY DTSNLAS GIPARFSGSGSGTDFTLTISSLEPEDFAVYYC
h26AL2    EIVLTQSPATLSLSPGERVTMSC SASSSVS--YMY WYQQKPGQAPRLLIY DTSNLAS GVPARFSGSGSGTDYTLTISSMEPEDFAVYYC
h26AL3    EIVLTQSPATMSASPGERVTMSC SASSSVS--YMY WYQQKPGQAPRLLIY DTSNLAS GVPARFSGSGSGTDYTLTISSMEPEDFAVYYC seq       90         100
AbM       90         100
          ibi  iib  i    b  b b
26A       QQRSNWPP
IGKV3-11  QQWSSYPFT  FGQGTKLEIK
h26AL1    QQWSSYPFT  FGQGTKLEIK
h26AL2    QQWSSYPFT  FGQGTKLEIK
h26AL3    QQWSSYPFT  FGQGTKLEIK
                *
```

(1) CDR sequences noted in bold. CDR definitions are AbM definition from website www.bioinf.org.uk/abs/.

(2) Human germline and joining sequences from IMGT® the international ImMunoGeneTics® information system www.imgt.org (founder and director: Marie-Paule Lefranc, Montpellier, France).

(3) Residue numbering shown as sequential (seq) or according to Chothia from website www.bioinf.org.uk/abs/ (AbM).

(4) "b" notes buried sidechain; "i" notes sidechain at interface between VH and VL domains.

(5) Sequence differences between human and murine germlines noted by asterisk (*).

(6) Potential additional mutations in frameworks are noted below sequence.

(7) Potential changes in CDR sequences noted below each CDR sequence.

FIG. 22B

Potential humanized sequence based on IMGT IGHV1-46*01 acceptor framework (AbM CDR definition)
IGHV1-46*01 QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR
Joining region  IMGT J00256|IGHJ4*01|YFDYWGQGTLVTVSS

```
seq              10         20         30         40         50         60         70         80         90
AbM    b b b      b b b b    b b b      b i i b b  i b b      b     b b b    b b b      b  b b        b i b i b b
1-46*01 QVQLQQSGAELVRPGSVKISCKGS GYTFTDYGMH WVKQSHAKSLEWIG LIDTYYGDAT YNHKFKGKATMTVDKSSRTAYMELARLTSEDSAIYYCAR
128A    * ***      * ***       ******      ******   *****     *       *  ** *** *** *  **  * * **** * *
h128AH1 QVQLVQSGAEVKKPGASVKVSCKAS GYTFTSYYMH WVRQAPGQGLEWMG IINPSGGSTS YAQKFQGRVTMTRDTSTSTVYMELSSLRSEDTAVYYCAR
h128AH2 QVQLVQSGAEVKKPGASVKVSCKAS GYTFTDYGMH WVRQAPGQGLEWMG LIDTYYGDAT YAQKFQGRCTMTRDTSTSTVYMELSSLRSEDTAVYYCAR
h128AH3 QVQLVQSGAEVKKPGASVKISCKGS GYTFTDYGMH WVRQAPGQGLEWIG LIDTYYGDAT YAQKFQGRATMTVDKSTSTVYMELSSLRSEDTAVYYCAR
                V                                                  N                                         i seq    100        110
AbM     b         b b
128A   RAGNAMDY  WGQGTSVTASS
h128AH1 RAGNAMDY  WGQGTSVTASS
h128AH2 RAGNAMDY  WGQGTLVTVSS
h128AH3 RAGNAMDY  WGQGTLVTVSS
                 A
```

(1) CDR sequences noted in bold. CDR definitions are AbM definition from website www.bioinf.org.uk/abs/.

(2) Human germline and joining sequences from IMGT® the international ImMunoGeneTics® information system www.imgt.org (founder and director: Marie-Paule Lefranc, Montpellier, France).

(3) Residue numbering shown as sequential (seq) or according to Chothia from website www.bioinf.org.uk/abs/ (AbM).

(4) "b" notes buried sidechain; "p" notes partially buried; "i" notes sidechain at interface between VH and VL domains.

(5) Sequence differences between human and murine germlines noted by asterisk (*).

(6) Potential additional mutations in frameworks are noted below sequence.

FIG. 23A

```
Potential humanized sequence based on IMGT IGKV1-39*01 acceptor framework (AbM CDR definition)
IGKV1-39*01 DIQMTQSPSSLSASVGDRVTITCRASQSISSYLNWYQQKPGKAPKLLIYAASSLQSGVPSRFSGSGSGTDFTLTISSLQPEDFATYYCQQSYSTPP
Joining region IMGT J00242|IGKJ2*01|YTFGQGTKLEIK 10         20         30         40         50         60         70         80
seq           10         20         30         40         50         60         70         80
AbM         b  b  b  b  b     b  bi bi   b   bi bi    ii ibbi        b                b b    bb bib
128A        NIAMTQTPKFLLVSAGDRVTITC KASQSVSNDIA WYQQKPGQSPRLLIY YASNRYT GVPDRFTGSGYGTDFTFTISTVQAEDLAVYFC
              *        ***       *         *   *           ***  #       *  *    *   * **  *   *   * *
IGKV1-39    DIQMTQSPSSLSASVGDRVTITC RASQSISSYLN WYQQKPGKAPKLLIY AASSLQS GVPSRFSGSGSGTDFTLTISSLQPEDFATYYC
h128AL1     DIQMTQSPSSLSASVGDRVTITC KASQSVSNDIA WYQQKPGKAPKLLIY YASNRYT GVPSRFSGSGSGTDFTLTISSLQPEDFATYYC
h128AL2     DIQMTQSPSSLSVSVGDRVTITC KASQSVSNDIA WYQQKPGKAPKLLIY YASNRYT GVPSRFSGSGSGTDFTFTISSVQPEDFATYYC
h128AL3     DIQMTQSPSSLSVSVGDRVTITC KASQSVSNDIA WYQQKPGKAPKLLIY YASNRYT GVPSRFSGSGSGTDFTFTISSVQPEDFATYYC
                                           #                   #                                   L  F 90        100
seq           90        100
AbM         ibi   iib    b b b
128A        QQDYSSPRT FGQGTKLEIK
               *
IGKV1-39    QQSYSTPP
h128AL1     QQDYSSPRT FGQGTKLEIK
h128AL2     QQDYSSPRT FGQGTKLEIK
h128AL3     QQDYSSPRT FGQGTKLEIK
```

(1) CDR sequences noted in bold. CDR definitions are AbM definition from website www.bioinf.org.uk/abs/.

(2) Human germline and joining sequences from IMGT® the international ImMunoGeneTics® information system www.imgt.org (founder and director: Marie-Paule Lefranc, Montpellier, France).

(3) Residue numbering shown as sequential (seq) or according to Chothia from website www.bioinf.org.uk/abs/ (AbM).

(4) "b" notes buried sidechain; "i" notes sidechain at interface between VH and VL domains.

(5) Sequence differences between human and murine germlines noted by asterisk (*).

(6) Potential additional mutations in frameworks are noted below sequence.

(7) Potential changes in CDR sequences noted below each CDR sequence. These may prevent asparagine (N) deamidation.

FIG. 23B

```
Potential humanized sequence based on IMGT IGHV1-46*01 acceptor framework (AbM CDR definition)
IGHV1-46*01_QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR
Joining region IMGT J00256|IGHJ4*01|YFDYWGQGTLVTVSS bibibb
seq              b b b    p        b b b                b b b  b i i   i bb b                b b b b  x   b b b b  b
AbM                10       20        30         40        50          60         70       80   abc    90
                 *  *     *  *      *      *    *    *    *           *  *     *  *       *  *  *    *     *
124A             QVQLVQSGAELMKPGASVKISCKAT GYTFSSNWIE     WVKQRPGHGLEWMG EILPGSGSTS YNEKFKGKATFTADTSSNTAYMQLSSLTSEDSAVYYCAR
                                M                                                     N                x
1-46*01          QVQLVQSGAEVKKPGASVKVSCKAS GYTFTSYYMH     WVRQAPGQGLEWMG IINPSGGSTS YAQKFQGRVTMTRDTSTSTVYMELSSLRSEDTAVYYCAR
h124AH1          QVQLVQSGAEVKKPGASVKVSCKAS GYTFSSNWIE     WVRQAPGQGLEWMG EILPGSGSTS YAQKFQGRVTMTRDTSTSTVYMELSSLRSEDTAVYYCAR
h124AH2          QVQLVQSGAEVKKPGASVKISCKAS GYTFSSNWIE     WVRQAPGQGLEWMG EILPGSGSTS YAQKFQGRATFTADTSTSTAYMELSSLRSEDTAVYYCAR
                                                  # seq                      b    b b b
AbM                100     110
                  *   *      *
124A             WLLYYYAMDF WGQGTSVTVSS
                                   *
h124AH1          WLLYYYAMDF WGQGTLVTVSS
h124AH2          WLLYYYAMDF WGQGTLVTVSS
```

(1) CDR sequences noted in bold. CDR definitions are AbM definition from website www.bioinf.org.uk/abs/.

(2) Human germline and joining sequences from IMGT® the international ImMunoGeneTics® information system www.imgt.org (founder and director: Marie-Paule Lefranc, Montpellier, France).

(3) Residue numbering shown as sequential (seq) or according to Chothia from website www.bioinf.org.uk/abs/ (AbM).

(4) "b" notes buried sidechain; "p" notes partially buried; "i" notes sidechain at interface between VH and VL domains.

(5) Sequence differences between human and murine germlines noted by asterisk (*).

(6) Potential changes in CDR sequences noted below each CDR sequence. These may prevent asparagine (N) deamidation.

FIG. 24A

```
Potential humanized sequence based on IMGT IGKV2-30*01 acceptor framework (AbM CDR definition)
IGKV2-30*01 DVVMTQSPLSLPVTLGQPASISCRSSQSLVYSDGNTYLNWFQQRPGQSPRRLIYKVSNRDSGVPDRFSGSGSGTDFTLKISRVEAEDVGVYYCMQGTHWPP
Joining region IMGT J00242|IGKJ2*01|YTFGQGTKLEIK seq                  10         20         30         40         50         60         70         80         90
AbM                  10         20         30abcde    40         50         60         70         80         90
         b b b      b   b b   b b         b           bi bi      ibbi         i          b        b b b       bb bib
124A  DVLMTQTPLSLPVSLGDQASISC RSSQSIVHNNGNTYLE WYLQKPGQSPKLLIY KVSNRFS GVPDRFSGSGSTDFTLKISRVEAEDLGVYYC
         *                 * *    *                  *  *               *                                  *
IGKV2-30  DVVMTQSPLSLPVTLGQPASISC RSSQSLVYSDGNTYLN WFQQRPGQSPRRLIY KVSNRDS GVPDRFSGSGSGTDFTLKISRVEAEDVGVYYC
h124AL1   DVVMTQSPLSLPVTLGQPASISC RSSQSIVHNNGNTYLE WFQQRPGQSPRRLIY KVSNRFS GVPDRFSGSGSGTDFTLKISRVEAEDVGVYYC
h124AL2   DVVMTQSPLSLPVTLGQPASISC RSSQSIVHNNGNTYLE WYQQRPGQSPRLLIY KVSNRFS GVPDRFSGSGSGTDFTLKISRVEAEDVGVYYC
                                      #@ #                # seq       90        100       110
AbM       90        100
          ibi  iib  i  b b b
124A    FQGSHVPYT FGGGTKLEIK
          *
IGKV2-30   MQGTHWPP
h124AL1    FQGSHVPYT FGQGTKLEIK
h124AL2    FQGSHVPYT FGQGTKLEIK
```

(1) CDR sequences noted in bold. CDR definitions are AbM definition from website www.bioinf.org.uk/abs/.

(2) Human germline and joining sequences from IMGT® the international ImMunoGeneTics® information system www.imgt.org (founder and director: Marie-Paule Lefranc, Montpellier, France).

(3) Residue numbering shown as sequential (seq) or according to Chothia from website www.bioinf.org.uk/abs/ (AbM).

(4) "b" notes buried sidechain; "i" notes sidechain at interface between VH and VL domains.

(5) Sequence differences between human and murine germlines noted by asterisk (*).

(6) Potential additional mutations in frameworks are noted below sequence.

(7) Potential changes in CDR sequences noted below each CDR sequence. These may prevent asparagine (N) deamidation or isoaspartate formation (DG).

FIG. 24B

```
Potential humanized sequence based on IMGT IGHV1-46*01 acceptor framework (AbM CDR definition)
IGHV1-46*01 QVQLVQSGAEVKKPGASVKVSCKASGYTFTSYYMHWVRQAPGQGLEWMGIINPSGGSTSYAQKFQGRVTMTRDTSTSTVYMELSSLRSEDTAVYYCAR
Joining region  IMGT J00256|IGHJ4*01|YFDYWGQGTLVTVSS seq             10         20         30         40         50    a      60         70  b   b  b  80  abc  90
AbM            b b b     p b  b   b     b    b i    i  i bb  b          b         b b x           b   b      bibibb
259A    EVQLQQSGPELVKPGASVKMSCKASGYTFTSYFMHWVKQKPGQGLEWIGYIYPYNDGTKYNEKFKGKATLTSDKSSTAYMDLSSLTSEDSAVYYCAR
        *       **                *    ***                *       *           *    *      *     * *

1-46*01 QVQLVQSGAEVKKPGASVKVSCKAS GYTFTSYYMH WVRQAPGQGLEWMG IINPSGGSTS YAQKFQGRVTMTRDTSTSTVYMELSSLRSEDTAVYYCAR
h259AH1 QVQLVQSGAEVKKPGASVKVSCKAS GYTFTSYFMH WVRQAPGQGLEWMG YIYPYNDGTK YAQKFQGRVTMTRDTSTSTAYMELSSLRSEDTAVYYCAR
h259AH2 QVQLVQSGAEVKKPGASVKMSCKAS GYTFTSYFMH WVRQAPGQGLEWIG YIYPYNDGTK YAQKFQGRATLTSDTSTSTAYMELSSLRSEDTAVYYCAR
h259AH3 QVQLVQSGAEVKKPGASVKMSCKAS GYTFTSYFMH WVRQAPGQGLEWIG YIYPYNDGTK YAQKFQGRATLTSDKSTSTAYMELSSLRSEDTAVYYCAR
                    v                                          #@      N seq    100       110
AbM   b          b b b
      b    i
259A  FDYDTLRY WGQGTTLTVSS h259AH1 FDYDTLRY WGQGTLLTVSS
h259AH2 FDYDTLRY WGQGTLLTVSS
h259AH3 FDYDTLRY WGQGTLLTVSS
                   *  *
```

(1) CDR sequences noted in bold. CDR definitions are AbM definition from website www.bioinf.org.uk/abs/.

(2) Human germline and joining sequences from IMGT® the international ImMunoGeneTics® information system www.imgt.org (founder and director: Marie-Paule Lefranc, Montpellier, France).

(3) Residue numbering shown as sequential (seq) or according to Chothia from website www.bioinf.org.uk/abs/(AbM).

(4) "b" notes buried sidechain; "p" notes partially buried; "i" notes sidechain at interface between VH and VL domains.

(5) Sequence differences between human and murine germlines noted by asterisk (*).

(6) Potential additional mutations in frameworks are noted below sequence.

(7) Potential changes in CDR sequences noted below each CDR sequence. These may prevent asparagine (N) deamidation or isoaspartate formation (DG).

FIG. 25A

```
Potential humanized sequence based on IMGT IGKV2-28*01 acceptor framework (AbM CDR definition)
IGKV2-28*01 DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPP
Joining region IMGT J00242|IGKJ2*01|YTFGQGTKLEIK 10         20         30         40         50         60         70         80         90
seq               b b  b      b b b    b       b   bi bi  i  ii ibbi      i          b b    b  b   b      bb bib
AbM               b    ibi   iib  b     b    30abcde         ii ibbi    SNRFS        b                    bb bib
259A         DVLTQTPLSLPVNIGDQASISC    KSTKSLLNSDGFTYLD WYLQKPGQSPQLLIY LISNRFS GVPDRFSGSGSGTDFTLKISRVEAEDLGVYYC
                 * *              * **  ****      *                #                                      *
IGKV2-28     DIVMTQSPLSLPVTPGEPASISC    RSSQSLLHSNGYNYLD WYLQKPGQSPQLLIY LGSNRAS GVPDRFSGSGSGTDFTLKISRVEAEDVGVYYC
h259AL1      DIVMTQSPLSLPVTPGEPASISC    KSTKSLLNSDGFTYLD WYLQKPGQSPQLLIY LISNRFS GVPDRFSGSGSGTDFTLKISRVEAEDVGVYYC
h259AL1      DIVLTQSPLSLPVTPGEPASISC    KSTKSLLNSDGFTYLD WYLQKPGQSPQLLIY LISNRFS GVPDRFSGSGSGTDFTLKISRVEAEDVGVYYC
                V                                                          #

90        100        110
seq                    i            b b  b
AbM               ibi  iib          b b  b
259A         FQSNYFPWT FGGGTKLEIK
                                   *
IGKV2-28     MQALQTPP
h259AH2      FQSNYFPWT FGQGTKLEIK
h259AL1      FQSNYFPWT FGQGTKLEIK
```

(1) CDR sequences noted in bold. CDR definitions are AbM definition from website www.bioinf.org.uk/abs/.

(2) Human germline and joining sequences from IMGT® the international ImMunoGeneTics® information system www.imgt.org (founder and director: Marie-Paule Lefranc, Montpellier, France).

(3) Residue numbering shown as sequential (seq) or according to Chothia from website www.bioinf.org.uk/abs/ (AbM).

(4) "b" notes buried sidechain; "i" notes sidechain at interface between VH and VL domains.

(5) Sequence differences between human and murine germlines noted by asterisk (*).

(6) Potential additional mutations in frameworks are noted below sequence.

(7) Potential changes in CDR sequences noted below each CDR sequence. These may prevent asparagine (N) deamidation or isoaspartate formation (DG).

FIG. 25B

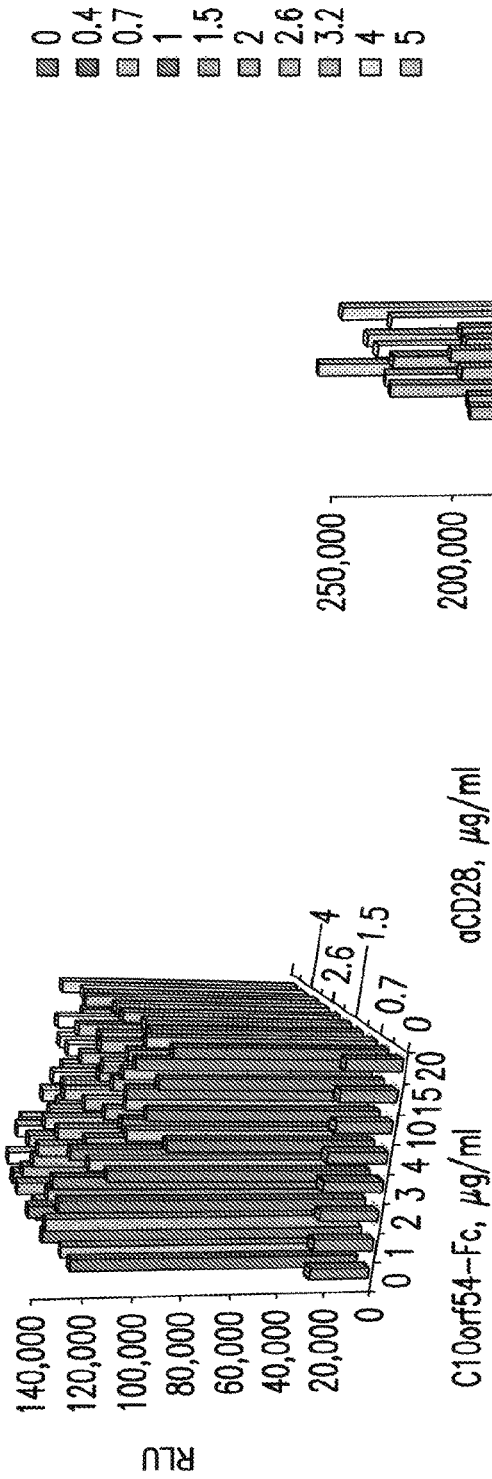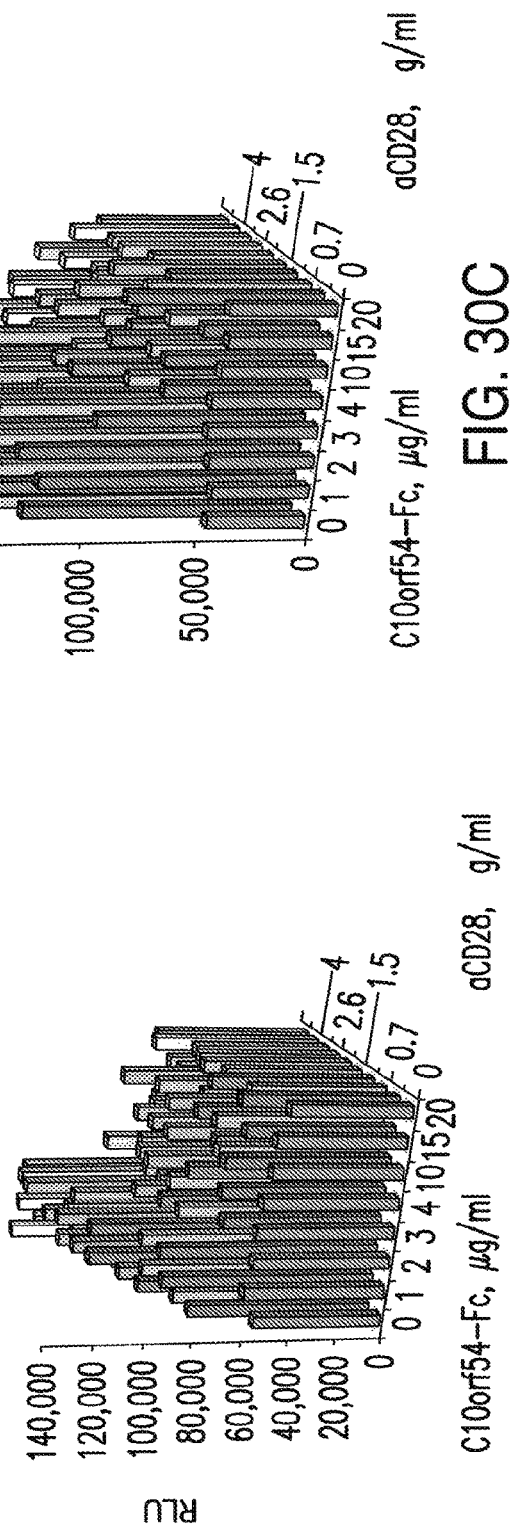
FIG. 30A
FIG. 30B
FIG. 30C

ANTI-C10ORF54 ANTIBODIES AND USES THEREOF

CROSS REFERENCE TO RELATED APPLICATIONS

This application is a continuation of U.S. patent application Ser. No. 15/534,982, filed Jun. 9, 2017, which is a National Stage Entry of International Application No. PCT/US2015/065331, filed Dec. 11, 2015, which claims the benefit of priority of U.S. Provisional Application No. 62/090,880, filed Dec. 11, 2014. The entire contents of each of these applications is incorporated herein by reference.

FIELD

The present disclosure relates generally to anti-C10orf54 antibodies, including antibody-drug conjugates comprising the antibodies, and methods of their use.

BACKGROUND

C10orf54 is a single-pass type I transmembrane protein that is 311 amino acids in length and includes a signal sequence and one IgV-like domain in its intracellular region. It is potentially a member of the B7 family of proteins and it has approximately 24% sequence identity to B7-H1/PD-L1 (Flajnik et al., *Immunogenetic* 64:571-590 (2012)). The mouse ortholog to C10orf54 is known as V-region Immunoglobulin-containing Suppressor of T Cell Activation (VISTA; also known as PD-L3). VISTA was cloned from a library of CD4 positive regulatory T cells ($T_{reg}$) (Wang et al., *JEM* 208(3):577-592 (2011)). VISTA is primarily expressed on hematopoietic cells, and VISTA expression is highly regulated on myeloid antigen-presenting cells (APCs) and T cells (Wang et al., supra).

VISTA appears to have functional activities that are nonredundant with other Ig superfamily members and may play a role in the development of autoimmunity and immune surveillance in cancer. For example, expression of a VISTA-Ig fusion protein has been shown to inhibit T cell proliferation and cytokine production in vitro and overexpression of VISTA on MCA105 tumor cells interferes with a host's protective antitumor immunity (Wang et al., supra). Moreover, administration of a VISTA-specific monoclonal antibody enhanced CD4 positive T cell response in vivo and the development of autoimmunity (Wang et al., supra). Monoclonal antibodies against C10orf54 have also been shown to prevent acute graft-versus-host disease in mice (Flies et al., *J. Immunology* 187(4):1537-1541 (2011)).

Citation or discussion of a reference herein shall not be construed as an admission that such is prior art to the present disclosure.

SUMMARY

The present disclosure provides antibodies that bind C10orf54, including humanized antibodies and antibody-drug conjugates comprising the humanized antibodies, and methods of use of the antibodies and the antibody-drug conjugates, including for the diagnosis and treatment of cancers. The present disclosure further provides proteins that bind to C10orf54, including binding proteins, such as antibodies, that bind to one or more C10orf54 proteins or chimeric proteins. Such binding proteins, including antibodies, may be antagonists (e.g., inhibit one or more of the biological activities of C10orf54).

In a first aspect, provided herein are antibodies that bind to C10orf54, including a C10orf54 polypeptide, a C10orf54 polypeptide fragment or a C10orf54 epitope, collectively referred to herein as anti-C10orf54 antibodies. Also provided herein are anti-C10orf54 antibodies that are conjugated to drugs as antibody-drug conjugates (ADCs), including ADCs of the formula A-L-CTX, wherein A is an antibody, L is a linker, and CTX is cytotoxin. In some embodiments the anti-C10orf54 antibodies are humanized antibodies that bind to a C10orf54 polypeptide, a C10orf54 polypeptide fragment or a C10orf54 epitope. In certain embodiments, the anti-C10orf54 antibody comprises a VH domain, VL domain, VH CDR1, VH CDR2, VH CDR3, VL CDR1, VL CDR2, and/or VL CDR3 of monoclonal antibody 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33), or a humanized variant thereof. In certain embodiments, the anti-C10orf54 antibody can further comprise a VH FR1, VH FR2, VH FR3, VH FR4, VL FR1, VL FR2, VL FR3, and/or VL FR4 of a human germline immunoglobulin amino acid sequence or a variant thereof.

In certain embodiments, the antibody comprises less than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3. In specific embodiments, the antibody comprises or consists of one, two, three, four, or five CDRs selected from the group consisting of VH CDR1, VH CDR2, VH CDR3, VL CDR1, VL CDR2, and/or VL CDR3 of the monoclonal antibody 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33), or a humanized variant thereof. In specific embodiments, the antibody further comprises a VH FR1, VH FR2, VH FR3, VH FR4, VL FR1, VL FR2, VL FR3, and/or VL FR4 of a human germline immunoglobulin amino acid sequence or a variant thereof.

In specific embodiments, the antibody is a humanized antibody, a monoclonal antibody, a recombinant antibody, an antigen binding fragment or any combination thereof. In particular embodiments, the antibody is a humanized monoclonal antibody as described herein (e.g., 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3), or antigen binding fragment thereof, that binds to a C10orf54 polypeptide (e.g., a cell surface-expressed or soluble C10orf54), a C10orf54 fragment, or a C10orf54 epitope.

In a second aspect, provided herein are antibodies, including humanized antibodies, (i) that competitively block (e.g., in a dose-dependent manner) an anti-C10orf54 antibody provided herein from binding to a C10orf54 polypeptide (e.g., a cell surface-expressed or soluble C10orf54), a C10orf54 fragment, or a C10orf54 epitope and/or (ii) that bind to a C10orf54 epitope that is bound by an anti-C10orf54 antibody (e.g., humanized anti-C10orf54 antibodies) provided herein. In other embodiments, the antibody competitively blocks (e.g., in a dose-dependent manner) monoclonal antibody 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) or a humanized variant thereof from binding to a C10orf54 polypeptide (e.g., a cell surface-expressed or soluble C10orf54), a C10orf54 fragment, or a C10orf54 epitope. In other embodiments, the antibody binds to a C10orf54 epitope that is bound (e.g., recognized) by monoclonal antibody 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) or a humanized variant thereof (e.g. humanized anti-C10orf54 antibodies).

In certain embodiments, the anti-C10orf54 antibodies (e.g., humanized anti-C10orf54 antibodies) provided herein (e.g., 5B, 46A, 97A, 128A, 146C, 208A, 215A, 26A, 164A, 230A, 76E1, 53A, 259A, 33A, 39A, 124A, 175A, 321 D, 141 A, 51 A, 353A, or 305A described herein (e.g., Tables 12-33) with a VH domain, VL domain, VH CDR1, VH CDR2, VH CDR3, VL CDR1, VL CDR2, and/or VL CDR3) are conjugated or recombinantly fused to a diagnostic agent, detectable agent or therapeutic agent. In some aspects, the therapeutic agent is a chemotherapeutic agent (e.g., a cystotoxic agent such as cytotoxin). In some aspects, the detectable agent is a radioisotope, an enzyme, a fluorescent compound, a bioluminescent compound or a chemiluminescent compound. In certain embodiments, the anti-C10orf54 antibodies provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) are conjugated to drugs as antibody-drug conjugates (ADCs). In some aspects, the antibody-drug conjugate (ADC) is of the formula A-L-CTX, wherein A is an antibody, L is a linker, and CTX is a cytotoxin.

In certain embodiments, provided are compositions comprising an anti-C10orf54 antibody (e.g., humanized anti-C10orf54 antibodies) described herein. In some embodiments, the compositions comprise an antibody-drug conjugate wherein the antibody is an anti-C10orf54 antibody provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3). Also provided herein are pharmaceutical compositions comprising an anti-C10orf54 antibody, including a humanized anti-C10orf54 antibody, provided herein (e.g., 5B, 46A, 97A, 128A, 146C, 208A, 215A, 26A, 164A, 230A, 76E1, 53A, 259A, 33A, 39A, 124A, 175A, 321D, 141 A, 51 A, 353A, or 305A described herein (e.g., Tables 12-33) with a VH domain, VL domain, VH CDR1, VH CDR2, VH CDR3, VL CDR1, VL CDR2, and/or VL CDR3).

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC10 (SEQ ID NO: 1251), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), and CC9 (SEQ ID NO: 1250).

In certain embodiments, the antibody provided herein binds a first group of C10orf54 proteins or chimeric proteins designated CC1 (SEQ ID NO: 1079), CC4 (SEQ ID NO: 1245), CC5 (SEQ ID NO: 1246), and CC8 (SEQ ID NO: 1249), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251). In some aspected, such an antibody does not comprise one or more CDR sequences selected from the group consisting of 30, 1099, 1104, 1105, 1110, 31, 1100, 1106, 1111, 1116, 32, 1101, 1107, 1112, 45, 1102, 1108, 1113, 40, 1103, 1114, 41, 1109, and 1115.

In certain embodiments, the antibody provided herein binds to a first group of C10orf54 proteins or chimeric proteins designated CC1 (SEQ ID NO: 1079), CC4 (SEQ ID NO: 1245), and CC5 (SEQ ID NO: 1246), and does not bind to a second group of C10orf54 proteins or chimeric proteins designated (SEQ ID NO: 1243), CC3 (SEQ ID NO: 1244), CC6 (SEQ ID NO: 1247), CC7 (SEQ ID NO: 1248), CC8 (SEQ ID NO: 1249), CC9 (SEQ ID NO: 1250), and CC10 (SEQ ID NO: 1251). In some aspects, such an antibody does not comprise one or more CDR sequences selected from the group consisting of 36, 1081, 1086, 1087, 1092, 37, 1082, 1088, 1093, 1098, 38, 1083, 1089, 1094, 45, 1084, 1090, 1095, 46, 1085, 1096, 47, 1091, and 1097.

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC9 (SEQ ID NO: 1250), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251). In some aspects, such an antibody does not comprise one or more CDR sequences selected from the group consisting of 33, 1117, 1122, 1123, 1128, 34, 1118, 1124, 1129, 1134, 35, 1119, 1125, 1130, 42, 1120, 1126, 1131, 43, 1121, 1132, 44, 1127, and 1133.

In certain embodiments, the antibody provided herein binds to a first group of C10orf54 proteins or chimeric proteins designated CC1 (SEQ ID NO: 1079), CC3 (SEQ ID NO: 1244), CC4 (SEQ ID NO: 1245), CC5 (SEQ ID NO: 1246), CC8 (SEQ ID NO: 1249), and CC9 (SEQ ID NO: 1250), and does not bind to a second group of C10orf54 proteins or chimeric proteins designated CC2 (SEQ ID NO: 1243), CC6 (SEQ ID NO: 1247), CC7 (SEQ ID NO: 1248), and CC10 (SEQ ID NO: 1251).

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC10 (SEQ ID NO: 1251), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251).

In a third aspect, provided are isolated nucleic acid molecules encoding a VH chain, VL chain, VH domain, VL domain, VH CDR1, VH CDR2, VH CDR3, VL CDR1, VL CDR2, and/or VL CDR3 of anti-C10orf54 antibodies as described herein (e.g., 5B, 46A, 97A, 128A, 146C, 208A, 215A, 26A, 164A, 230A, 76E1, 53A, 259A, 33A, 39A, 124A, 175A, 321D, 141 A, 51 A, 353A, or 305A described herein (e.g., Tables 12-33) with a VH domain, VL domain, VH CDR1, VH CDR2, VH CDR3, VL CDR1, VL CDR2, and/or VL CDR3), including humanized anti-C10orf54 antibodies, that bind to a C10orf54 polypeptide, a C10orf54 polypeptide fragment, or a C10orf54 epitope. In certain embodiments, the nucleic acid molecule encodes a VH domain, VL domain, VH CDR1, VH CDR2, VH CDR3, VL CDR1, VL CDR2, and/or VL CDR3 of monoclonal antibody 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33), or a humanized variant thereof. In certain embodiments, the nucleic acid molecule further encodes a VH FR1, VH FR2, VH FR3, VH FR4, VL FR1, VL FR2, VL FR3, and/or VL FR4 of a human germline immunoglobulin amino acid sequence or a variant thereof. Also provided herein are vectors and host cells comprising the nucleic acid molecules encoding an anti-C10orf54 antibody (e.g., humanized anti-C10orf54 antibodies), as well as methods of producing an anti-C10orf54 antibody by culturing the host cells provided herein under conditions that promote the production of the anti-C10orf54 antibody.

In a fourth aspect, provided herein are methods of treating, preventing or alleviating a disease, disorder or condition, including one or more symptoms of a disease, disorder or condition, comprising administering a therapeutically effective amount of an anti-C10orf54 antibody as described herein (e.g., 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3), including an antibody-drug conjugate (ADC) comprising an anti-C10orf54 antibody, provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) to a subject, thereby treating, preventing or alleviating the disease, disorder or condition, including one or more symptoms of the disease, disorder or condition. In some embodiments the anti-C10orf54 antibodies are humanized antibodies that bind to a C10orf54 polypeptide, a C10orf54 polypeptide fragment or a C10orf54 epitope. In one embodiment, the disease, disorder or condition is caused by or otherwise associated with C10orf54, including by or associated with C10orf54-expressing cells (e.g., tumor cells, myeloid-derived suppressor cells (MDSC), suppressive dendritic cells (suppressive DC), and/or regulatory T cells (T regs)). In certain embodiments, the disease is a cancer, such as a leukemia, a bladder cancer, a skin cancer, a colon cancer, a breast cancer, a liver cancer, a kidney cancer, a lung cancer, a stomach cancer, a pancreas cancer, an esophagus cancer or a fibrosarcoma. In one embodiment, the leukemia is an acute myeloid leukemia (AML). In other embodiments, the disease is graft-versus-host disease (GVHD). Additional methods provided include using an anti-C10orf54 antibody with C10orf54 binding activity for C10orf54-expressing cells, provided herein (e.g., 5B, 46A, 97A, 128A, 146C, 208A, 215A, 26A, 164A, 230A, 76E1, 53A, 259A, 33A, 39A, 124A, 175A, 321 D, 141 A, 51 A, 353A, or 305A described herein (e.g., Tables 12-33) with a VH domain, VL domain, VH CDR1, VH CDR2, VH CDR3, VL CDR1, VL CDR2, and/or VL CDR3), for example, as an unconjugated antibody or conjugated antibody (ADC), including to inhibit and/or kill the C10orf54-expressing cells (e.g., with anti-tumor activity to mediate an anti-tumor effect). In certain embodiments, the anti-C10orf54 antibodies, including ADCs comprising the anti-C10orf54 antibodies, provided herein (e.g., 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) inhibit C10orf54-mediated suppressor activity on T cells (e.g., to allow an effective anti-tumor immune response). In certain embodiments, the anti-C10orf54 antibodies provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) directly kill C10orf54-expressing cells (e.g., C10orf54-bearing tumor cells, myeloid-derived suppressor cells (MDSC), suppressive dendritic cells (suppressive DC), and/or regulatory T cells (T regs)), for example, via antibody-dependent cellular cytotoxicity (ADCC) and/or complement-dependent cytotoxicity (CDC) In certain embodiments, antibody drug conjugates (ADCs) comprising anti-C10orf54 antibodies provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) directly kill C10orf54-expressing cells including by binding to cells expressing C10orf54 (e.g., tumor cells, myeloid-derived suppressor cells (MDSC), suppressive dendritic cells (suppressive DC), and/or regulatory T cells (T regs)), for example, by allowing internalization of the cytotoxic drug. In certain embodiments, the anti-C10orf54 antibodies provided herein or antibody drug conjugates (ADCs) comprising anti-C10orf54 antibodies provided herein are used in methods for treating cancers (e.g., bladder, breast, colon, connective tissue, rectal, gastric, esophageal, lung, laryx, kidney, oral, ovarian, or prostate cancer, or a sarcoma, melanoma, glioma, lymphoma or leukemia) or tumors associated with myeloid-derived suppressor cells (MDSC) (e.g., colon carcinoma, mammary carcinoma, fibrosarcoma, thymoma, lung carcinoma, renal cell carcinoma, mesothelioma, glioma, lymphoma, sarcoma, prostate carcinoma, sarcoma, or head and neck carcinoma). In any of the above embodiments, the anti-C10orf54 antibody can be a humanized anti-C10orf54 antibody provided herein (e.g., 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) that binds to a C10orf54 polypeptide, a C10orf54 polypeptide fragment or a C10orf54 epitope.

In a fifth aspect, provided herein are methods of inhibiting the growth of cells and/or killing cells having cell surface expression of C10orf54 comprising contacting the cells with an effective amount of an anti-C10orf54 antibody or antibody-drug conjugates comprising the anti-C10orf54 antibody provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3). In one embodiment, the cell is a regulatory T cell (e.g., a CD4$^+$ Foxp3$^+$ regulatory T cell). In certain embodiments, provided herein is a method of inhibiting the growth of a tumor with inflammation in a subject comprising administering an effective amount of the anti-C10orf54 antibodies, including ADCs comprising the anti-C10orf54 antibodies, provided herein (e.g., 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3). In other embodiments, the cell is a myeloid-derived suppressor cell (e.g., a CD11 b$^+$ or CD11 b$^{high}$ myeloid-derived suppressor cell) or a suppressive dendritic cell (e.g., a CD11 b+ or CD11b$^{high}$ dendritic cell). In other embodiments, the cell is a cancerous or pre-cancerous cell. Additional methods provided include using an anti-C10orf54 antibody with C10orf54 binding activity for C10orf54-expressing cells provided herein (e.g., 5B, 46A, 97A, 128A, 146C, 208A, 215A, 26A, 164A, 230A, 76E1, 53A, 259A, 33A, 39A, 124A, 175A, 321D, 141 A, 51 A, 353A, or 305A described herein (e.g., Tables 12-33) with a VH domain, VL domain, VH CDR1, VH CDR2, VH CDR3, VL CDR1, VL CDR2, and/or VL CDR3), for example, as an unconjugated antibody or conjugated antibody (ADC) including to inhibit and/or kill C10orf54-expressing cells (e.g., with anti-tumor activity to mediate an anti-tumor effect). In certain embodiments, the anti-C10orf54 antibodies, including ADCs comprising the anti-C10orf54 antibodies, provided herein (e.g., 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) inhibit C10orf54-mediated suppressor activity on T cells (e.g., to allow an effective anti-tumor immune response). In certain embodiments, the anti-C10orf54 antibodies provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) directly kill C10orf54-expressing cells (e.g., C10orf54-bearing tumor cells, myeloid-derived suppressor cells (MDSC), suppressive dendritic cells (suppressive DC), and/or regulatory T cells (T regs)), for example, via antibody-dependent cellular cytotoxicity (ADCC) and/or complement-dependent cytotoxicity (CDC) In certain embodiments, antibody drug conjugates (ADCs) comprising anti-C10orf54 antibodies provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) directly kill C10orf54-expressing cells including by binding to cells expressing C10orf54 (e.g., tumor cells, myeloid-derived suppressor cells (MDSC), suppressive dendritic cells (suppressive DC), and/or regulatory T cells (T regs)), for example, by allowing internalization of the cytotoxic drug. In any of the above embodiments, the anti-C10orf54 antibody can be a humanized anti-C10orf54 antibody provided herein (e.g., 5B, 46A, 97A, 128A, 146C, 208A, 215A, 26A, 164A, 230A, 76E1, 53A, 259A, 33A, 39A, 124A, 175A, 321 D, 141 A, 51 A, 353A, or 305A described herein (e.g., Tables 12-33) with a VH domain, VL domain, VH CDR1, VH CDR2, VH CDR3, VL CDR1, VL CDR2, and/or VL CDR3) that binds to a C10orf54 polypeptide, a C10orf54 polypeptide fragment or a C10orf54 epitope.

In a sixth aspect, provided herein are methods of modulating an immune response in a subject comprising administering an effective amount of an anti-C10orf54 antibody (e.g., a humanized anti-C10orf54 antibody) provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) to a subject. In one embodiment, the modulating comprises increasing T cell activation. In other embodiment, the modulating comprises increasing T cell proliferation. In another embodiment, the modulating comprises increasing cytokine production.

In a seventh aspect, provided herein are methods for detecting C10orf54 in a sample comprising contacting the sample with an anti-C10orf54 antibody (e.g., a humanized anti-C10orf54 antibody) provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3), such as an antibody that comprises a detectible agent. In certain embodiments, the sample comprises a cell expressing C10orf54 on its surface.

In an eighth aspect, provided herein are methods of treating cancers comprising administering to a subject an anti-C10orf54 antibody (e.g., a humanized anti-C10orf54 antibody) or an antibody-drug conjugate (ADC) comprising the anti-C10orf54 antibody (e.g., an ADC of the formula A-L-CTX, wherein A is the antibody, L is a linker, and CTX is a cytotoxic agent) provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) in a therapeutically effective amount, including in an amount effective to kill a C10orf54-expressing cell (e.g., tumor cell, myeloid-derived suppressor cell (MDSC), suppressive dendritic cell (suppressive DC), and/or regulatory T cell (T reg)). In some embodiments the cancer is acute myeloid leukemia (AML). In any of the above embodiments, the anti-C10orf54 antibody can be a humanized anti-C10orf54 antibody provided herein (e.g., 5B, 46A, 97A, 128A, 146C, 208A, 215A, 26A, 164A, 230A, 76E1, 53A, 259A, 33A, 39A, 124A, 175A, 321 D, 141 A, 51 A, 353A, or 305A described herein (e.g., Tables 12-33) with a VH domain, VL domain, VH CDR1, VH CDR2, VH CDR3, VL CDR1, VL CDR2, and/or VL CDR3) that binds to a C10orf54 polypeptide, a C10orf54 polypeptide fragment or a C10orf54 epitope.

In a ninth aspect, provided herein are methods of killing C10orf54-expressing cells (e.g., tumor cells, myeloid-derived suppressor cells (MDSC), suppressive dendritic cells (suppressive DC), and/or regulatory T cells (T reg)) comprising contacting a C10orf54-expressing cell (e.g., tumor cell, myeloid-derived suppressor cell (MDSC), suppressive dendritic cell (suppressive DC), and/or regulatory T cell (T regs)) with an amount of an anti-C10orf54 antibody or an antibody-drug conjugate (ADC) comprising an anti-C10orf54 antibody (e.g., an ADC of the formula A-L-CTX, wherein A is the antibody, L is a linker, and CTX is a cytotoxic agent) provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3) effective to kill the cell (e.g., tumor cell, myeloid-derived suppressor cell (MDSC), suppressive dendritic cell (suppressive DC), and/or regulatory T cell (T reg)). In some embodiments, the tumor cell is an AML cell. In any of the above embodiments, the anti-C10orf54 antibody can be a humanized anti-C10orf54 antibody provided herein (e.g., 5B, 46A, 97A, 128A, 146C, 208A, 215A, 26A, 164A, 230A, 76E1, 53A, 259A, 33A, 39A, 124A, 175A, 321 D, 141 A, 51 A, 353A, or 305A described herein (e.g., Tables 12-33) with a VH domain, VL domain, VH CDR1, VH CDR2, VH CDR3, VL CDR1, VL CDR2, and/or VL CDR3) that binds to a C10orf54 polypeptide, a C10orf54 polypeptide fragment or a C10orf54 epitope.

In a tenth aspect, provided herein is a kit comprising an anti-C10orf54 antibody (e.g., a humanized anti-C10orf54 antibody) that binds to a C10orf54 polypeptide, a C10orf54 polypeptide fragment, or a C10orf54 epitope provided herein (e.g., 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3). In some embodiments, the kits comprise an antibody-drug conjugate (ADC) wherein the antibody is an anti-C10orf54 antibody (e.g., a humanized anti-C10orf54 antibody) provided herein (e.g., 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A described herein (e.g., Tables 12-33) with a VH domain, VL domain, VH CDR1, VH CDR2, VH CDR3, VL CDR1, VL CDR2, and/or VL CDR3).

TERMINOLOGY

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

The term "about" or "approximately" means within 20%, such as within 10%, or within 5% (or 1% or less) of a given value or range.

As used herein, "administer" or "administration" refers to the act of injecting or otherwise physically delivering a substance as it exists outside the body (e.g., an anti-C10orf54 antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

As used herein, an "agonist" of C10orf54 refers to a molecule that is capable of activating or otherwise increasing one or more of the biological activities of C10orf54, such as in a cell expressing C10orf54 or in a cell expressing a C10orf54 ligand, such as a C10orf54 receptor. In some embodiments, an agonist of C10orf54 (e.g., an agonistic antibody provided herein) may, for example, act by activating or otherwise increasing the activation and/or cell signaling pathways of the cell expressing a C10orf54 or a C10orf54 receptor, thereby increasing a C10orf54-mediated biological activity of the cell the relative to the C10orf54-mediated biological activity in the absence of agonist. In certain embodiments the antibodies provided herein are agonistic anti-C10orf54 antibodies.

The term "alkyl," as used herein, means a straight, branched chain, or cyclic (in this case, it would also be known as "cycloalkyl") hydrocarbon containing from 1-10 carbon atoms. Examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl. In certain embodiments, alkyl groups are optionally substituted.

The term "$C_{1-6}$alkyl," as used herein, means a straight, branched chain, or cyclic (in this case, it would also be known as "cycloalkyl") hydrocarbon containing from 1-6 carbon atoms.

The term "$C_{1-3}$ alkyl," as used herein, means a straight or branched chain hydrocarbon containing from 1-3 carbon atoms.

The term "alkenyl," as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (e.g., an alkenylene group). In some embodiments, alkenyl groups are optionally substituted. Examples of alkenyl include, but are not limited to, ethenyl, 2-propenyl, 2-methyl-2-propenyl, 3-butenyl, 4-pentenyl, 5-hexenyl, 2-heptenyl, and 2-methyl-1-heptenyl. In certain embodiments, alkenyl groups are optionally substituted.

The term "$C_{2-6}$ alkenyl," as used herein, means a straight, branched chain, or cyclic (in this case, it would also be known as "cycloalkyl") hydrocarbon containing from 2-6 carbon atoms and at least one carbon-carbon double bond formed by the removal of two hydrogens.

The term "alkoxy," as used herein, means an alkyl group, as defined herein, appended to the parent molecular moiety through an oxygen atom. Examples of alkoxy include, but are not limited to, methoxy, ethoxy, propoxy, 2-propoxy, butoxy, tert-butoxy, pentyloxy, and hexyloxy.

An "amino acid" (or AA) or amino acid residue include but are not limited to the 20 naturally occurring amino acids acids commonly designated by three letter symbols and also includes 4-hydroxyproline, hydroxyysine, demosine, isodemosine, 3-methylhistidine, norvalin, beta-alanine, gamma-aminobutyric acid, homocysteine, homoserine, ornithine and methionine sulfone. The amino acid residue of the present application also include the corresponding N-methyl amino acids, such as —N(CH$_3$)CH$_2$C(O)O—, —NHC(O)CH$_2$CH$_2$CH(NHCH$_3$)C(O)O—, etc. The amino acids, dipeptides, tripeptides, oligomers and polypeptides designated as -(AA)$_r$- of the present application may include the corresponding non-N-alkylated amino acids and peptides (such as non-N-methylated amino acids in the peptides), as well as a mixture of the non-N-alkylated amino acids and the N-alkylated amino acids of the peptides.

An "antibody-drug conjugate" or "ADC" is an antibody that is conjugated to one or more cytotoxins, through one or more linkers. An antibody-drug conjugate (ADC) may be of the formula A-L-CTX, wherein A is an antibody, L is a linker, and CTX is a cytotoxin.

In the context of a polypeptide, the term "analog" as used herein refers to a polypeptide that possesses a similar or identical function as a C10orf54 polypeptide, a fragment of a C10orf54 polypeptide, or an anti-C10orf54 antibody but does not necessarily comprise a similar or identical amino acid sequence of a C10orf54 polypeptide, a fragment of a C10orf54 polypeptide, or an anti-C10orf54 antibody, or possess a similar or identical structure of a C10orf54 polypeptide, a fragment of a C10orf54 polypeptide, or an anti-C10orf54 antibody. A polypeptide that has a similar amino acid sequence refers to a polypeptide that satisfies at least one of the following: (a) a polypeptide having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of a C10orf54 polypeptide (e.g., SEQ ID NO:1079), a fragment of a C10orf54 polypeptide, or an anti-C10orf54 antibody described herein; (b) a polypeptide encoded by a nucleotide sequence that hybridizes under stringent conditions to a nucleotide sequence encoding a C10orf54 polypeptide, a fragment of a C10orf54 polypeptide, or an anti-C10orf54 antibody (or VH or VL region thereof) described herein of at least 5 amino acid residues, at least 10 amino acid residues, at least 15 amino acid residues, at least 20 amino acid residues, at least 25 amino acid residues, at least 40 amino acid residues, at least 50 amino acid residues, at least 60 amino residues, at least 70 amino acid residues, at least 80 amino acid residues, at least 90 amino acid residues, at least 100 amino acid residues, at least 125 amino acid residues, or at least 150 amino acid residues (see, e.g., Sambrook et al. (2001) *Molecular Cloning: A Laboratory Manual*, Cold Spring Harbor Laboratory Press, Cold Spring Harbor, NY; Maniatis et al. (1982) *Molecular Cloning: A Laboratory Manual*, Cold Spring Harbor Press, Cold Spring Harbor, NY); and (c) a polypeptide encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical to the nucleotide sequence encoding a C10orf54 polypeptide, a fragment of a C10orf54 polypeptide, or an anti-C10orf54 antibody (or VH or VL region thereof) described herein. A polypeptide with similar structure to a C10orf54 polypeptide, a fragment of a C10orf54 polypeptide, or an anti-C10orf54 antibody described herein refers to a polypeptide that has a similar secondary, tertiary or quaternary structure of a C10orf54 polypeptide, a fragment of a C10orf54, or a C10orf54 antibody described herein. The structure of a polypeptide can determined by methods known to those skilled in the art, including but not limited to, X-ray crystallography, nuclear magnetic resonance, and crystallographic electron microscopy.

As used herein, an "antagonist" or "inhibitor" of C10orf54 refers to a molecule that is capable of inhibiting or otherwise decreasing one or more of the biological activities of C10orf54, such as in a cell expressing C10orf54 or in a cell expressing a C10orf54 ligand, such as a C10orf54 receptor. In some embodiments, an antagonist of C10orf54 (e.g., an antagonistic antibody provided herein) may, for example, act by inhibiting or otherwise decreasing the activation and/or cell signaling pathways of the cell expressing a C10orf54 or a C10orf54 receptor, thereby inhibiting a C10orf54-mediated biological activity of the cell the relative to the C10orf54-mediated biological activity in the absence of antagonist. In certain embodiments the antibodies provided herein are antagonistic anti-C10orf54 antibodies.

The terms "antibody" and "immunoglobulin" or "Ig" are used interchangeably herein, and are intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See, Borrebaeck (ed.) (1995) *Antibody Engineering*, Second Ed., Oxford University Press; Kuby (1997) *Immunology*, Third Ed., W.H. Freeman and Company, New York). In specific embodiments, the specific molecular antigen can be bound by an antibody provided herein includes the target C10orf54 polypeptide, fragment or epitope.

Antibodies also include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments of any of the above, which refers a portion of an antibody heavy or light chain polypeptide that retains some or all of the binding activity of the antibody from which the fragment was derived. Non-limiting examples of functional fragments include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (sdFv), Fd fragments, Fv fragments, diabody, triabody, tetrabody and minibody. In particular, antibodies provided herein include immunoglobulin molecules and immunologically active portions of immunoglobulin molecules, e.g., antigen binding domains or molecules that contain an antigen-binding site that binds to a C10orf54 antigen (e.g., one or more complementarity determining regions (CDRs) of an anti-C10orf54 antibody). Such antibody fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics*, 22:189-224 (1993); Plückthun and Skerra, *Meth. Enzymol.*, 178:497-515 (1989) and in Day, E. D., *Advanced Immunochemistry*, Second Ed., Wiley-Liss, Inc., New York, NY (1990). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. An anti-C10orf54 antibodies provided herein can be agonistic antibodies or antagonistic antibodies.

The terms "antibodies that specifically bind to C10orf54," "antibodies that specifically bind to a C10orf54 epitope," "anti-C10orf54 antibodies" and analogous terms are also used interchangeably herein and refer to antibodies that specifically bind to a C10orf54 polypeptide, such as a C10orf54 antigen or epitope. Such antibodies include humanized antibodies. An antibody that specifically binds to a C10orf54 antigen may be cross-reactive with related antigens. In certain embodiments, an antibody that specifically binds to a C10orf54 antigen does not cross-react with other antigens. An antibody that specifically binds to a C10orf54 antigen can be identified, for example, by immunoassays, BIAcore, or other techniques known to those of skill in the art. An antibody binds specifically to a C10orf54 antigen when it binds to a C10orf54 antigen with higher affinity than to any cross-reactive antigen as determined using experimental techniques, such as radioimmunoassays (RIA) and enzyme-linked immunosorbent assays (ELISAs). Typically a specific or selective reaction will be at least twice background signal or noise and more typically more than 10 times background. See, e.g., Paul, ed., 1989, *Fundamental Immunology Second Edition*, Raven Press, New York at pages 332-336 for a discussion regarding antibody specificity. In certain embodiments, an antibody "which binds" an antigen of interest is one that binds the antigen with sufficient affinity such that the antibody is useful as a diagnostic and/or therapeutic agent in targeting a cell or tissue expressing the antigen, and does not significantly cross-react with other proteins. In such embodiments, the extent of binding of the antibody to a "non-target" protein will be less than about 10% of the binding of the antibody to its particular target protein as determined by fluorescence activated cell sorting (FACS) analysis or radioimmunoprecipitation (RIA). With regard to the binding of an antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope. In certain embodiments, an antibody that binds to C10orf54 has a dissociation constant (Kd) of ≤1 µM, ≤100 nM, ≤10 nM, ≤1 nM, or ≤0.1 nM. In certain embodiments, anti-C10orf54 antibody binds to an epitope of C10orf54 that is conserved among C10orf54 from different species.

An "anti-c10orf54 antibody" or "an antibody that binds to C10orf54" refers to an antibody that is capable of binding C10orf54, including, for example, an antibody, with sufficient affinity such that the antibody is useful as a diagnostic and/or therapeutic agent in targeting C10orf54. Such antibodies include humanized antibodies. Preferably, the extent of binding of an anti-C10orf54 antibody to an unrelated, non-C10orf54 protein is less than about 10% of the binding of the antibody to C10orf54 as measured, e.g., by fluorescence activated cell sorting (FACS) analysis or a radioimmunoassay (RIA). An antibody that "specifically binds to" or is "specific for" C10orf54 is defined as above. In certain embodiments, an antibody that binds to C10orf54 has a dissociation constant (Kd) of <1 µM, <100 nM, <10 nM, <1 nM, or <0.1 nM. In certain embodiments, anti-C10orf54 antibody binds to an epitope of C10orf54 that is conserved among C10orf54 from different species.

An "antigen" is a predetermined antigen to which an antibody can selectively bind. The target antigen may be a polypeptide, carbohydrate, nucleic acid, lipid, hapten or other naturally occurring or synthetic compound. In specific embodiments, the target antigen is a polypeptide.

The term "antigen binding fragment," "antigen binding domain," "antigen binding region," and similar terms refer to that portion of an antibody which comprises the amino acid residues that interact with an antigen and confer on the binding agent its specificity and affinity for the antigen (e.g., the complementarity determining regions (CDRs)).

The terms "binds" or "binding" as used herein refer to an interaction between molecules to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces.

The strength of the total non-covalent interactions between a single antigen-binding site on an antibody and a single epitope of a target molecule, such as C10orf54, is the affinity of the antibody or functional fragment for that epitope. The ratio of association ($k_1$) to dissociation ($k_{-1}$) of an antibody to a monovalent antigen ($k_1/k_{-1}$) is the association constant K, which is a measure of affinity. The value of K varies for different complexes of antibody and antigen and depends on both $k_1$ and $k_{-1}$. The association constant K for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent C10orf54, come in contact with antibodies containing multiple binding sites, the interaction of antibody with antigen at one site will increase the probability of a reaction at a second site. The strength of such multiple interactions between a multivalent antibody and antigen is called the avidity. The avidity of an antibody can be a better measure of its binding capacity than is the affinity of its individual binding sites. For example, high avidity can compensate for low affinity as is sometimes found for pentameric IgM antibodies, which can have a lower affinity than IgG, but the high avidity of IgM, resulting from its multivalence, enables it to bind antigen effectively.

The term "C10orf54" or "C10orf54 polypeptide" and similar terms refers to the polypeptide ("polypeptide," "peptide" and "protein" are used interchangeably herein) encoded by the human Chromosome 10 Open Reading Frame 54 (C10orf54) gene, which is also known in the art as B7-H5, platelet receptor Gi24, Gl24, Stress Induced Secreted Protein1, SISP1, and PP2135, comprising the amino acid sequence of:

(SEQ ID NO: 1079)

```
  1 mgvptaleag swrwgsllfa lflaaslgpv aafkvatpys lyvcpegqnv tltcrllgpv 61 dkghdvtfyk twyrssrgev qtcserrpir nitfqdlhlh hgghqaants hdlaqrhgle 121 sasdhhgnfs itmrnltlld sglycclvve irhhhsehrv hgamelqvqt gkdapsncvv 181 ypsssqdsen itaaalatga civgilclpl illlvykqrq aasnrraqel vrmdsniqgi 241 enpgfeaspp aqgipeakvr hplsyvaqrq psesgrhlls epstplsppg pgdvffpsld 301 pvpdspnfev i
``` and related polypeptides, including SNP variants thereof. The C10orf54 polypeptide has been shown to or is predicted to comprise several distinct regions within the amino acid sequence including: a signal sequence (residues 1-32; see Zhang et al., *Protein Sci.* 13:2819-2824 (2004)); an immunoglobulin domain—IgV-like (residues 33-162); and a transmembrane region (residues 195-215). The mature C10orf54 protein includes amino acid residues 33-311 of SEQ ID NO: 1079. The extracellular domain of the C10orf54 protein includes amino acid residues 33-194 of SEQ ID NO: 1079. Related polypeptides include allelic variants (e.g., SNP variants); splice variants; fragments; derivatives; substitution, deletion, and insertion variants; fusion polypeptides (e.g., chimeric proteins); and interspecies homologs, preferably, which retain C10orf54 activity and/or are sufficient to generate an anti-C10orf54 immune response. As those skilled in the art will appreciate, an anti-C10orf54 antibody provided herein can bind to a C10orf54 polypeptide, polypeptide fragment, antigen, and/or epitope, as an epitope is part of the larger antigen, which is part of the larger polypeptide fragment, which, in turn, is part of the larger polypeptide. C10orf54 can exist in a native or denatured form. The C10orf54 polypeptides described herein may be isolated from a variety of sources, such as from human tissue types or from another source, or prepared by recombinant or synthetic methods. A "native sequence C10orf54 polypeptide" comprises a polypeptide having the same amino acid sequence as the corresponding C10orf54 polypeptide derived from nature. Such native sequence C10orf54 polypeptides can be isolated from nature or can be produced by recombinant or synthetic means. The term "native sequence C10orf54 polypeptide" specifically encompasses naturally-occurring truncated or secreted forms of the specific C10orf54 polypeptide (e.g., an extracellular domain sequence), naturally-occurring variant forms (e.g., alternatively spliced forms) and naturally-occurring allelic variants of the polypeptide.

A cDNA nucleic acid sequence encoding the C10orf54 polypeptide comprises:

(SEQ ID NO: 1080)

```
  1 atgggcgtcc ccacggccct ggaggccggc agctggcgct ggggatccct gctcttcgct 61 ctcttcctgg ctgcgtccct aggtccggtg gcagccttca aggtcgccac gccgtattcc 121 ctgtatgtct gtcccgaggg gcagaacgtc accctcacct gcaggctctt gggccctgtg 181 gacaaagggc acgatgtgac cttctacaag acgtggtacc gcagctcgag gggcgaggtg 241 cagacctgct cagagcgccg gcccatccgc aacctcacgt tccaggacct tcacctgcac 301 catggaggcc accaggctgc caacaccagc cacgacctgg ctcagcgcca cgggctggag 361 tcggcctccg accaccatgg caacttctcc atcaccatgc gcaacctgac cctgctggat 421 agcggcctct actgctgcct ggtggtggag atcaggcacc accactcgga gcacagggtc 481 catggtgcca tggagctgca ggtgcagaca ggcaaagatg caccatccaa ctgtgtggtg 541 tacccatcct cctcccagga tagtgaaaac atcacggctg cagccctggc tacgggtgcc 601 tgcatcgtag gaatcctctg cctccccctc atcctgctcc tggtctacaa gcaaaggcag 661 gcagcctcca accgccgtgc ccaggagctg gtgcggatgg acagcaacat tcaagggatt 721 gaaaacccgg gctttgaagc ctcaccacct gcccagggga tacccgaggc caaagtcagg 781 cacccctgt cctatgtggc ccagcggcag ccttctgagt ctgggcggca tctgctttcg 841 gagcccagca ccccctgtc tcctccaggc cccggagacg tcttcttccc atccctggac 901 cctgtccctg actctccaaa ctttgaggtc atctag
```

Orthologs to the C10orf54 polypeptide are also well known in the art. For example, the mouse ortholog to the C10orf54 polypeptide is V-region Immunoglobulin-containing Suppressor of T cell Activation (VISTA) (also known as PD-L3, PD-1H, PD-XL, Pro1412 and UNQ730), which shares approximately 70% sequence identity to the human polypeptide. Orthologs of C10orf54 can also be found in additional organisms including chimpanzee, cow, rat and zebrafish.

A "C10orf54-expressing cell," "a cell having expression of C10orf54" or a grammatical equivalent thereof refers to a cell that expresses endogenous or transfected C10orf54 on the cell surface. C10orf54 expressing cells include a C10orf54-berring tumor cells, regulatory tumor cells (e.g., $CD4^+$ $Foxp3^+$ regulatory T cells), myeloid-derived suppressor cells (e.g., CD11 $b^+$ or CD11 $b^{high}$ myeloid-derived suppressor cells) and/or suppressive dendritic cells (e.g., CD11 $b^+$ or CD11 $b^{high}$ dendritic cells). A cell expressing C10orf54 produces sufficient levels of C10orf54 on its surface, such that an anti-C10orf54 antibody can bind thereto. In some aspect, such binding may have a therapeutic effect with respect to the cancer. A cell that "overexpresses" C10orf54 is one that has significantly higher levels of C10orf54 at the cell surface thereof, compared to a cell of the same tissue type that is known to express C10orf54. Such overexpression may be caused by gene amplification or by increased transcription or translation. C10orf54 overexpression may be determined in a diagnostic or prognostic assay by evaluating increased levels of the C10orf54 protein present on the surface of a cell (e.g. via an immunohistochemistry assay; FACS analysis). Alternatively, or additionally, one may measure levels of C10orf54-encoding nucleic acid or mRNA in the cell, e.g. via fluorescent in situ hybridization; (FISH; see WO98/45479 published October, 1998), Southern blotting, Northern blotting, or polymerase chain reaction (PCR) techniques, such as real time quantitative PCR (RT-PCR). Aside from the above assays, various in vivo assays are available to the skilled practitioner. For example, one may expose cells within the body of the patient to an antibody which is optionally labeled with a detectable agent, and binding of the antibody to cells in the patient can be evaluated, e.g. by external scanning for radioactivity or by analyzing a biopsy taken from a patient previously exposed to the antibody. A C10orf54-expressing tumor cell includes, but is not limited to, acute myeloid leukemia (AML) tumor cells.

A "C10orf54-mediated disease," "C10orf54-mediated disorder" and "C10orf54-mediated condition" are used interchangeably and refer to any disease, disorder or condition that is completely or partially caused by or is the result of C10orf54. Such diseases, disorders or conditions include those caused by or otherwise associated with C10orf54, including by or associated with C10orf54-expressing cells (e.g., tumor cells, myeloid-derived suppressor cells (MDSC), suppressive dendritic cells (suppressive DC), and/or regulatory T cells (T regs)). In certain embodiments, C10orf54 is aberrantly (e.g., highly) expressed on the surface of a cell. In some embodiments, C10orf54 may be aberrantly upregulated on a particular cell type. In other embodiments, normal, aberrant or excessive cell signaling is caused by binding of C10orf54 to a C10orf54 ligand, which can bind or otherwise interact with C10orf54.

The terms "cell proliferative disorder" and "proliferative disorder" refer to disorders that are associated with some degree of abnormal cell proliferation. In one embodiment, the cell proliferative disorder is a tumor or cancer. "Tumor," as used herein, refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein. The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, oral cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain cancer, skin cancer, esophagus cancer as well as head and neck cancer, and associated metastases.

The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a exemplary carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in *Remington's Pharmaceutical Sciences* (1990) Mack Publishing Co., Easton, PA. Such compositions will contain a prophylactically or therapeutically effective amount of the antibody, e.g., in isolated or purified form, together with a suitable amount of carrier so as to provide the form for proper administration to the patient. The formulation should suit the mode of administration.

The term "chemical group," as used herein, refers to two or more atoms bound together as a single unit and forming part of a molecule.

A "chemotherapeutic agent" is a chemical agent (e.g., compound or drug) useful in the treatment of cancer, regardless of mechanism of action. Chemotherapeutic agents include compounds used in targeted therapy and conventional chemotherapy. Examples of chemotherapeutic agents include, but are not limited to, alkylating agents such as thiotepa and CYTOXAN® cyclophosphamide; alkyl sulfonates such as busulfan, improsulfan and piposulfan;

aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, AR1 NOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammal I and calicheamicin omega II (see, e.g., Agnew, *Chem Intl. Ed. Engl.* 33:183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN®, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, IL.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin. Additional chemotherapeutic agents include cytotoxic agents useful as antibody drug conjugates, such as maytansinoids (DM1 and DM4, for example) and auristatins (MMAE and MMAF, for example).

Also included in the definition of chemotherapeutic agent are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY 117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RI VISor® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as ME inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAX1 D®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above The antibodies provided herein can include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)).

As used herein, the term "composition" is intended to encompass a product containing the specified ingredients (e.g., an antibody provided herein) in, optionally, the specified amounts, as well as any product which results, directly or indirectly, from combination of the specified ingredients in, optionally, the specified amounts.

A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. CDR region sequences have also been defined by AbM, Contact and IMGT. CDR region sequences are illustrated in FIGS. 16A and 16B. The positions of CDRs within a canonical antibody variable domain have been determined by comparison of numerous structures (Al-Lazikani et al., *J. Mol. Biol.* 273: 927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

The term "hypervariable region", "HVR", or "HV", when used herein refers to the regions of an antibody variable domain that are hypervariable in sequence and/or form structurally defined loops. Generally, antibodies comprise six hypervariable regions; three in the VH (H 1, H2, H3), and three in the VL (LI, L2, L3). A number of hypervariable region delineations are in use and are encompassed herein. The Kabat CDRs are based on sequence variability and are the most commonly used (Kabat et al., *Sequences of Proteins of Immunological Interest,* 5th Ed. Public Health Service, National Institutes of Health, Bethesda, MD. (1991)). Chothia refers instead to the location of the structural loops (Chothia and Lesk *J Mol. Biol.* 196:901-917 (1987)). The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

Recently, a universal numbering system has been developed and widely adopted, ImMunoGeneTics (IMGT) Information System© (Lafranc et al., *Dev. Comp. Immunol.* 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. Correspondence between the Kabat numbering and the IMGT unique numbering system is also well known to one skilled in the art (e.g. Lefranc et al., supra) and is also illustrated in FIGS. 16A and 16B. An Exemplary system, shown herein, combines Kabat and Chothia.

TABLE 1

CDR Definitions

| | Exemplary (Kabat + Chothia) | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

Hypervariable regions may comprise "extended hypervariable regions" as follows: 24-36 or 24-34 (LI), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. The variable domain residues are numbered according to Kabat et al., supra, for each of these definitions. As used herein, the terms "HVR" and "CDR" are used interchangeably.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CL domain of the light chain.

The term "cycloalkyl," as used herein, means a monocyclic or polycyclic radical that contains only carbon and hydrogen, and includes those that are saturated, partially unsaturated, or fully unsaturated. Cycloalkyl groups include groups having from 3 to 10 ring atoms.

In the context of a polypeptide, the term "derivative" as used herein refers to a polypeptide that comprises an amino acid sequence of a C10orf54 polypeptide, a fragment of a C10orf54 polypeptide, or an antibody that binds to a C10orf54 polypeptide which has been altered by the introduction of amino acid residue substitutions, deletions or additions. The term "derivative" as used herein also refers to a C10orf54 polypeptide, a fragment of a C10orf54 polypeptide, or an antibody that binds to a C10orf54 polypeptide which has been chemically modified, e.g., by the covalent attachment of any type of molecule to the polypeptide. For example, but not by way of limitation, a C10orf54 polypeptide, a fragment of a C10orf54 polypeptide, or a C10orf54 antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a C10orf54 polypeptide, a fragment of a C10orf54 polypeptide, or a C10orf54 antibody may be chemically modified by chemical modifications using techniques known to those of skill in the art, including, but not limited to specific chemical cleavage, acetylation, formulation, metabolic synthesis of tunicamycin, etc. Further, a derivative of a C10orf54 polypeptide, a fragment of a C10orf54 polypeptide, or a C10orf54 antibody may contain one or more non-classical amino acids. A polypeptide derivative possesses a similar or identical function as a C10orf54 polypeptide, a fragment of a C10orf54 polypeptide, or a C10orf54 antibody described herein.

The term "cytotoxic agent" or "cytotoxin" or "CTX" as used herein refers to a substance that inhibits or prevents the function of cells and/or has a cytotoxic effect on cells (e.g., causes destruction of cells). The term is intended to include alkylating agents, an anthracyclines, a cytoskeletal disruptors (taxanes), an epothilones, an histone deacetylase Inhibitor (HDAC), an inhibitor of Topoisomerase I, an Inhibitor of Topoisomerase II, a kinase inhibitor, a monoclonal antibodies, a nucleotide analog, a peptide antibiotic, a platinum-based agent, a retinoids, a Vinca alkaloid or a derivative thereof, and radioisotope. The term is also intended to include Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine. The term is also intended to include a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite. The term is also intended to include Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. Preferred cytotoxins include an auristatin, a calicheamicin, a maytansinoid, and a tubulysin. Other preferred cytotoxins include monomethylauristatin E (MMAE), monomethylauristatin F (MMAF), calicheamicin γ, mertansine, tubulysin T3, and tubulysin T4. Still other preferred cytotoxins include calicheamicin, doxorubicin, camptothecin, duocarmycin, DM1, DM4, a maytansinoid, and a tubulysin. Still other preferred cytotoxins include MMAE, MMAF, and a pyrrolobenzodiazepine (PBD).

The term "MMAF" generally refers to monomethylauristatin F, for which a chemical name is (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid. A person of ordinary skill in the art will understand that MMAF is also described in the art as MeVal-Val-Dil-Dap-Phe, where "Dil" is dolaisoleuine, and "Dap" is dolaproine.

The term "MMAE" generally refers to refers to monomethylauristatin E, for which a chemical name is (S)—N-((3R,4S,5S)-1-((S)-2-((1R,2R)-3-(((1 S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide.

The term "pyrrolobenzodiazepine" or "pyrrolobenzodiazepines" generally refers to a family of pyrrolo[2,1-c][1,4] benzodiazepine (PBD) dimers which are synthetic sequence-selective interstrand DNA minor-groove cross-linking agents developed from anthramycins. Examples of pyrrolobenzodiazepines include, but are not limited to, abbeymycin, chicamycin, DC-81, mazethramycin, neothramycins A and B, porothramycin, prothracarcin, sibanomicin (DC-102), sibiromycin and tomamycin.

Exemplary pyrrolobenzodiazepines include those disclosed in U.S. Pat. Nos. 7,049,311, 7,741,319, 8,697,688 (see, e.g., (26) in Example 5), and 8,765,740; International Publication Nos. WO 2011/130598 A1, WO 2012/112708 A1, WO 2013/055987 A1, WO 2013/165940 A1; and Jeffrey et al., *Bioconjugate Chem.* 2013, 24, 1256-1263, and Sutherland et al., *Blood* 2013, 122(8), 1455-1463; the content of each of which is incorporated by reference in its entirety.

The structures for T3 and T4 are provided below:

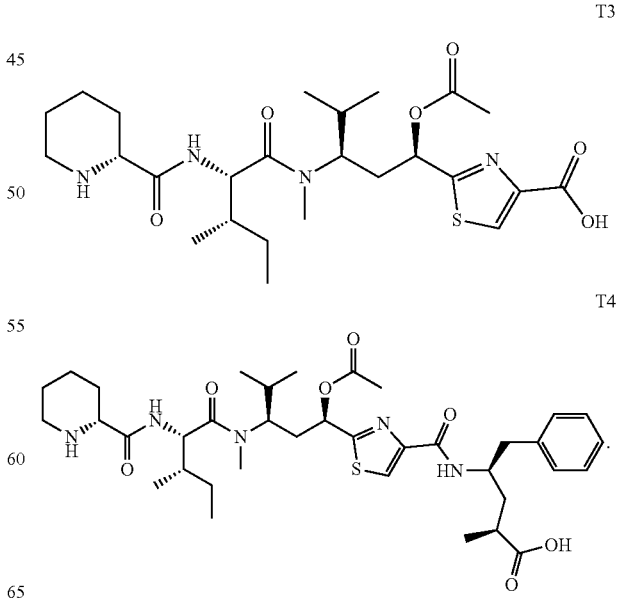

25

The structure for MMAF is provided below:

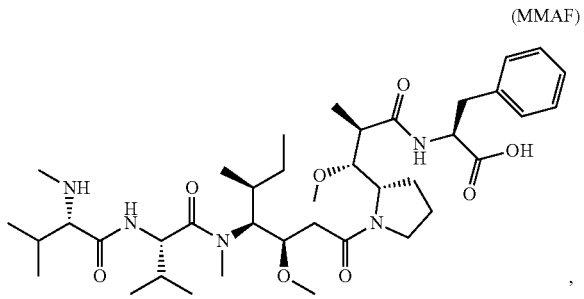 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

(MMAF)

, which the chemical name is "(S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid." A person of ordinary skill in the art will understand that MMAF is also described in the art as MeVal-Val-Dil-Dap-Phe, where "Dil" is dolaisoleuine, and "Dap" is dolaproine

26

The structure for MMAE is provided below:

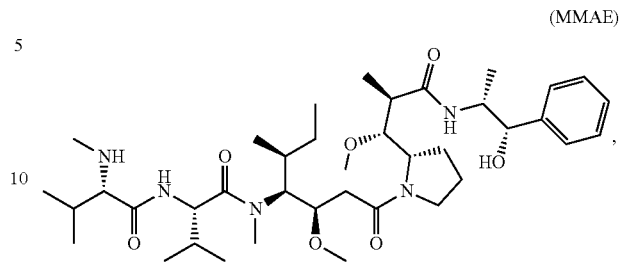

(MMAE)

, for which the chemical name is "(S)—N-((3R,4S,5S)-1-((S)-2-((1R,2R)-3-(((1 S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide." A person of ordinary skill in the art will understand that MMAE is also described in the art as MeVal-Val-Dil-Dap-Norephedrine, where "Dil" is dolaisoleuine, and "Dap" is dolaproine.

The structures for three PBDs is provided below:

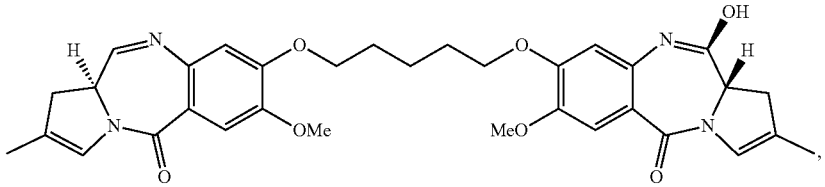

for which the chemical name is "(S)-11-hydroxy-7-methoxy-8-((5-(((S)-7-methoxy-2-methyl-5-oxo-5,11a-dihydro-1H-benzo[e]pyrrolo[1,2-a][1,4]diazepin-8-yl)oxy)pentyl)oxy)-2-methyl-1H-benzo[e]pyrrolo[1,2-a][1,4]diazepin-5(11 aH-one"; and

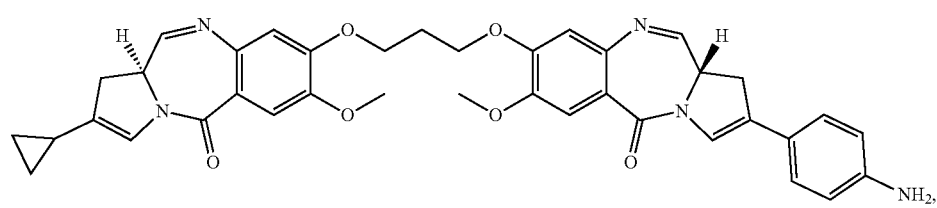 [SMILES: COc1cc2c(cc1OCCCOc1cc3c(cc1OC)C(=O)N1C=C(C4CC4)C[C@H]1C=N3)N=C[C@@H]1CC(c3ccc(N)cc3)=CN1C2=O]

, for which the chemical name is "(S)-2-(4-aminophenyl)-8-(3-(((S)-2-cyclopropyl-7-methoxy-5-oxo-5,11a-dihydro-1H-benzo[e]pyrrolo[1,2-a][1,4]diazepin-8-yl)oxy)propoxy)-7-methoxy-1H-benzo[e]pyrrolo[1,2-a][1,4]diazepin-5(11 aH-one" (see, e.g., compound (26) in Example 5 of U.S. Pat. No. 8,697,688); and

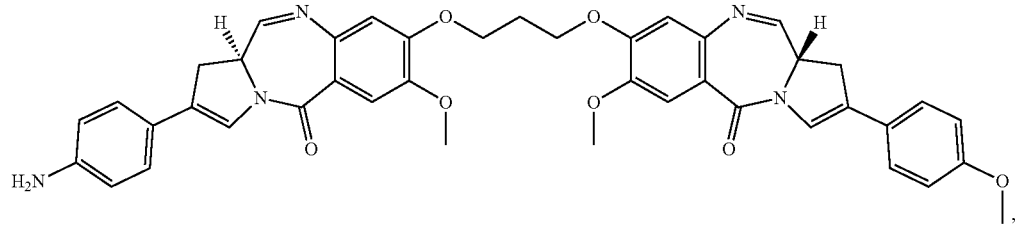 [SMILES: COc1ccc(C2=CN3C(=O)c4cc(OC)c(OCCCOc5cc6c(cc5OC)C(=O)N5C=C(c7ccc(N)cc7)C[C@H]5C=N6)cc4N=C[C@@H]3C2)cc1]

for which the chemical name is (S)-2-(4-aminophenyl)-7-methoxy-8-(3-(((S)-7-methoxy-2-(4-methoxyphenyl)-5-oxo-5,11a-dihydro-1H-benzo[e]pyrrolo[1,2-a][1,4]diazepin-8-yl)oxy)propoxy)-1H-benzo[e]pyrrolo[1,2-a][1,4]diazepin-5(11 aH)-one.

Other cytotoxic agents including various antitumor or anticancer agents are known in the art.

The term "detectable probe," as used herein, refers to a composition that provides a detectable signal. The term includes, without limitation, any fluorophore, chromophore, radiolabel, enzyme, antibody or antibody fragment, and the like, that provide a detectable signal via its activity.

The term "diagnostic agent" refers to a substance administered to a subject that aids in the diagnosis of a disease. Such substances can be used to reveal, pinpoint, and/or define the localization of a disease causing process. In certain embodiments, a diagnostic agent includes a substance that is conjugated to an antibody provided herein, that when administered to a subject or contacted to a sample from a subject aids in the diagnosis of cancer, tumor formation, or any other C10orf54-mediated disease.

The term "detectable agent" refers to a substance that can be used to ascertain the existence or presence of a desired molecule, such as an antibody provided herein, in a sample or subject. A detectable agent can be a substance that is capable of being visualized or a substance that is otherwise able to be determined and/or measured (e.g., by quantitation).

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the agent, the route of administration, etc. In some embodiments, effective amount also refers to the amount of an antibody provided herein to achieve a specified result (e.g., inhibition of a C10orf54 biological activity of a cell, such as modulating T cell activation and/or proliferation). In some embodiments, this term refers to the amount of a therapy (e.g., an antibody or pharmaceutical composition provided herein) which is sufficient to reduce and/or ameliorate the severity and/or duration of a given disease and/or a symptom related thereto. This term also encompasses an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than anti-C10orf54 antibody provided herein). In some embodiments, the effective amount of an antibody is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein).

The term "electrophilic leaving group," as used herein, refers to a leaving group that accepts an electron pair to make a covalent bond. In general, electrophiles are susceptible to attack by complementary nucleophiles, including the reduced thiols from the disulfide bond of an antibody.

The term "electrophilic leaving group that reacts selectively with thiols," as used herein, refers to electrophilic leaving group that reacts selectively with thiols, over other nucleophiles. In certain embodiments, an electrophilic leaving group that reacts selectively with thiols reacts selectively with the reduced thiols from the disulfide bond of an antibody.

The term "encode" or grammatical equivalents thereof as it is used in reference to nucleic acid molecule refers to a nucleic acid molecule in its native state or when manipulated by methods well known to those skilled in the art that can be transcribed to produce mRNA, which is then translated into a polypeptide and/or a fragment thereof. The antisense strand is the complement of such a nucleic acid molecule, and the encoding sequence can be deduced therefrom.

The term "epitope" as used herein refers to a localized region on the surface of an antigen, such as C10orf54 polypeptide or C10orf54 polypeptide fragment, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits an antibody response in an animal. An epitope having antigenic activity is a portion of a polypeptide to which an antibody binds as determined by any method well known in the art, for example, by an immunoassay. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a C10orf54 epitope is a three-dimensional surface feature of a C10orf54 polypeptide. In other embodiments, a C10orf54 epitope is linear feature of a C10orf54 polypeptide. Generally an antigen has several or many different epitopes and reacts with many different antibodies.

The term "excipient" as used herein refers to an inert substance which is commonly used as a diluent, vehicle, preservative, binder, or stabilizing agent, and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, *Remington's Pharmaceutical Sciences* (1990) Mack Publishing Co., Easton, PA, which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, C10orf54 fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a C10orf54 polypeptide or an antibody that binds to a C10orf54 polypeptide. In a specific embodiment, a fragment of a C10orf54 polypeptide or an antibody that binds to a C10orf54 antigen retains at least 1, at least 2, or at least 3 functions of the polypeptide or antibody.

The term "framework" or "FR" residues are those variable domain residues flanking the CDRs. FR residues are present, e.g., in chimeric, humanized, human, domain antibodies, diabodies, linear antibodies, and bispecific antibodies. FR residues are those variable domain residues other than the hypervariable region residues herein defined.

A "functional fragment" of an antibody will exhibit at least one if not some or all of the biological functions attributed to the intact antibody, the function comprising at least specific binding to the target antigen.

The term "fusion protein" as used herein refers to a polypeptide that comprises an amino acid sequence of an antibody and an amino acid sequence of a heterologous polypeptide or protein (e.g., a polypeptide or protein not normally a part of the antibody (e.g., a non-anti-C10orf54 antigen antibody)). The term "fusion" when used in relation to C10orf54 or to an anti-C10orf54 antibody refers to the joining of a peptide or polypeptide, or fragment, variant and/or derivative thereof, with a heterologous peptide or polypeptide. In certain embodiments, the fusion protein retains the biological activity of the C10orf54 or anti-C10orf54 antibody. In certain embodiments, the fusion protein comprises a C10orf54 antibody VH domain, VL domain, VH CDR (one, two or three VH CDRs), and/or VL CDR (one, two or three VL CDRs), wherein the fusion protein binds to a C10orf54 epitope.

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The term "host" as used herein refers to an animal, such as a mammal (e.g., a human).

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

"Humanized" forms of nonhuman (e.g., murine) antibodies are chimeric antibodies that include human immunoglobulins (recipient antibody) in which the native CDR residues are replaced by residues from the corresponding CDR of a nonhuman species (donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable domains, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., *Nature,* 321:522-525 (1986); Riechmann et al., *Nature,* 332:323-329 (1988); and Presta, *Curr. Op. Struct. Biol.,* 2:593-596 (1992); Carter et al., *Proc. Natl. Acad. Sci. USA* 89:4285-4289 (1992); and U.S. Pat. Nos. 6,800,738 (issued Oct. 5, 2004), 6,719,971 (issued Sep. 27, 2005), 6,639,055 (issued Oct. 28, 2003), 6,407,213 (issued Jun. 18, 2002), and 6,054,297 (issued Apr. 25, 2000).

An antibody that "inhibits the growth of and/or kills cells expressing C10orf54" or a "growth inhibitory" or "cytotoxic" antibody is one which results in measurable growth inhibition and/or killing of cells expressing or overexpressing the appropriate C10orf54 polypeptide. In some embodiments, such antibodies can inhibit the growth of and/or kill cells expressing C10orf54. Such cells include regulatory T cells (e.g., a CD4+ Foxp3+ regulatory T cells), a myeloid-derived suppressor cells (e.g., a CD11 b+ or CD11 bhigh myeloid-derived suppressor cells) and/or a suppressive dendritic cells (e.g., a CD11 b+ or CD11 bhigh dendritic cells). In a specific embodiment, antibodies inhibit the growth of and/or kill a cancer cell, a pre-cancerous cell, or a cell comprising a tumor. Certain growth inhibitory anti-C10orf54 antibodies inhibit growth of and/or kill C10orf54-expressing cells by greater than 20%, such as from about 20% to about 50%, or by greater than 50% (e.g., from about 50% to about 100%) as compared to the appropriate control, the control typically being cells not treated with the antibody being tested. In one embodiment, growth inhibition and/or killing can be measured at an antibody concentration of about 0.1 to 30 g/ml or about 0.5 nM to 200 nM in cell culture, where the growth inhibition is determined 1-10 days after exposure of the tumor cells to the antibody. Growth inhibition and/or killing of cells in vivo can be determined in various ways such as is described below. In the context of inhibiting a cancer cell or a cell comprising a tumor, the antibody is growth inhibitory or kills in vivo if administration of the anti-C10orf54 antibody at about 1 g/kg to about 100 mg/kg body weight results in reduction in tumor size or tumor cell proliferation within about 5 days to 3 months from the first administration of the antibody, such as within about 5 to 30 days.

As used herein, the term "in combination" in the context of the administration of other therapies refers to the use of more than one therapy. The use of the term "in combination" does not restrict the order in which therapies are administered to a subject with an infection. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a C10orf54-mediated disease. Any additional therapy can be administered in any order with the other additional therapies. In certain embodiments, the antibodies can be administered in combination with one or more therapies (e.g., therapies that are not the antibodies that are currently administered to prevent, treat, manage, and/or ameliorate a C10orf54-mediated disease. Non-limiting examples of therapies that can be administered in combination with an antibody include analgesic agents, anesthetic agents, antibiotics, or immunomodulatory agents or any other agent listed in the *U.S. Pharmacopoeia* and/or *Physician's Desk Reference*.

An antibody that "induces cell death" is one that causes a viable cell to become nonviable. The cell is of a cell type that specifically expresses or overexpresses a C10orf54 polypeptide. The cell may be cancerous or a normal cell of the particular cell type, such as a regulatory T cell. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (e.g., in the absence of complement) and in the absence of immune effector cells. To determine whether the antibody is able to induce cell death, loss of membrane integrity as evaluated by uptake of propidium iodide (PI), trypan blue (see Moore et al. *Cytotechnology* 17:1-11 (1995)). In some embodiments, cell death-inducing antibodies are those which induce PI uptake in the PI uptake assay in C10orf54 expressing cells.

An "isolated" antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). In certain embodiments, when the antibody is recombinantly produced, it is substantially free of culture medium, e.g., culture medium represents less than about 20%, 10%, or 5% of the volume of the protein preparation. In certain embodiments, when the antibody is produced by chemical synthesis, it is substantially free of chemical precursors or other chemicals, e.g., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 1951), such as 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In a specific embodiment, antibodies provided herein are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody provided herein is isolated or purified.

The term "leaving group," as used herein, refers to any group that leaves in the course of a chemical reaction involving the group as described herein and includes but is not limited to halogen, sulfonates (brosylate, mesylate, tosylate triflate etc. . . . ), p-nitrobenzoate and phosphonate groups, for example.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region.

The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

A "linker" (noted as L or $L^1$, $L^2$ and $L^3$) is a molecule with two reactive termini, one for conjugation to an antibody or to another linker and the other for conjugation to a cytotoxin. The antibody conjugation reactive terminus of the linker is typically a site that is capable of conjugation to the antibody through a cysteine thiol or lysine amine group on the antibody, and so is typically a thiol-reactive group such as a double bond (as in maleimide) or a leaving group such as a chloro, bromo or iodo or an R-sulfanyl group or sulfonyl group, or an amine-reactive group such as a carboxyl group or as defined herein; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. In one embodiment, when the term "linker" is used in describing the linker in conjugated form, one or both of the reactive termini will be absent (such as the leaving group of the thiol-reactive group) or incomplete (such as the being only the carbonyl of the carboxylic acid) because of the formation of the bonds between the linker and/or the cytotoxin. The linkers disclosed herein may be cleavable under normal physiological and/or intracellular conditions, or may remain stable (e.g., uncleaved or non-cleavable) under those same conditions. Examples of cleavable linkers are linkers which contain dipeptide moieties, where the peptide bond connecting the two peptides has the potential to be selectively cleaved by lysosomal proteases (e.g., cathepsin-B). Valine-citruline (Val-Cit) is a dipeptide moiety commonly used in cleavable linkers.

As used herein, the terms "manage," "managing," and "management" refer to the beneficial effects that a subject derives from a therapy (e.g., a prophylactic or therapeutic agent), which does not result in a cure of the disease. In certain embodiments, a subject is administered one or more therapies (e.g., prophylactic or therapeutic agents, such as an antibody provided herein) to "manage" a C10orf54-mediated disease, one or more symptoms thereof, so as to prevent the progression or worsening of the disease.

The term "monoclonal antibody" refers to an antibody obtained from a population of homogenous or substantially homogeneous antibodies, and each monoclonal antibody will typically recognize a single epitope on the antigen. In specific embodiments, a "monoclonal antibody," as used herein, is an antibody produced by a single hybridoma or other cell, wherein the antibody binds to only a C10orf54 epitope as determined, e.g., by ELISA or other antigen-binding or competitive binding assay known in the art. The term "monoclonal" is not limited to any particular method for making the antibody. For example, monoclonal antibodies provided herein may be made by the hybridoma method as described in Kohler et al.; Nature, 256:495 (1975) or may be isolated from phage libraries using the techniques. Other methods for the preparation of clonal cell lines and of monoclonal antibodies expressed thereby are well known in the art (see, for example, Chapter 11 in: *Short Protocols in Molecular Biology*, (2002) 5th Ed., Ausubel et al., eds., John Wiley and Sons, New York). Other exemplary methods of producing other monoclonal antibodies are provided in the Examples herein.

The term "native" when used in connection with biological materials such as nucleic acid molecules, polypeptides, host cells, and the like, refers to those which are found in nature and not manipulated by a human being.

The term "pharmaceutically acceptable" as used herein means being approved by a regulatory agency of the Federal or a state government, or listed in the U.S.

Pharmacopeia, European Pharmacopeia or other generally recognized Pharmacopeia for use in animals, and more particularly in humans.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., see, for example, Chapter 11 in: *Short Protocols in Molecular Biology*, (2002) 5th Ed., Ausubel et al., eds., John Wiley and Sons, New York).

As used herein, the term "polynucleotide," "nucleotide," nucleic acid" "nucleic acid molecule" and other similar terms are used interchangeable and include DNA, RNA, mRNA and the like.

A "pre-cancerous cell" refers to a cell that has an abnormal appearance such as a difference in size or shape in comparison to cells of the surrounding tissue or normal cells of its cell type, but are not invasive. The appearance of pre-cancerous cells can be suggestive of an increased cancer risk. Pre-cancerous cells expressing C10orf54 can be identified using methods disclosed herein, which can include analyzing a sample of cells from a patient.

As used herein, the terms "prevent," "preventing," and "prevention" refer to the total or partial inhibition of the development, recurrence, onset or spread of a C10orf54-mediated disease and/or symptom related thereto, resulting from the administration of a therapy or combination of therapies provided herein (e.g., a combination of prophylactic or therapeutic agents, such as an antibody provided herein).

As used herein, the term "prophylactic agent" refers to any agent that can totally or partially inhibit the development, recurrence, onset or spread of a C10orf54-mediated disease and/or symptom related thereto in a subject. In certain embodiments, the term "prophylactic agent" refers to an anti-C10orf54 antibody provided herein. In certain other embodiments, the term "prophylactic agent" refers to an agent other than an anti-C10orf54 antibody provided herein. In certain embodiments, a prophylactic agent is an agent which is known to be useful to or has been or is currently being used to prevent a C10orf54-mediated disease and/or a symptom related thereto or impede the onset, development, progression and/or severity of a C10orf54-mediated disease and/or a symptom related thereto. In specific embodiments, the prophylactic agent is a humanized anti-C10orf54 antibody, such as a humanized anti-C10orf54 monoclonal antibody.

In certain embodiments, a "prophylactically effective serum titer" is the serum titer in a subject, preferably a human, that totally or partially inhibits the development, recurrence, onset or spread of a C10orf54-mediated disease and/or symptom related thereto in the subject.

The term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see e.g., Taylor, L. D. et al. (1992) *Nucl. Acids Res.* 20:6287-6295) or antibodies prepared, expressed, created or isolated by any other means that involves splicing of immunoglobulin gene sequences to other DNA sequences. Such recombinant antibodies can have variable and constant regions derived from human germline immunoglobulin sequences (See Kabat, E. A. et al. (1991) *Sequences of Proteins of Immunological Interest*, Fifth Edition, U.S. Department of Health and Human Services, NIH Publication No. 91-3242). In certain embodiments, however, such recombinant antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "serum titer" as used herein refers to an average serum titer in a population of least 10, such as at least 20, or at least 40 subjects, up to about 100, 1000 or more.

As used herein, the term "side effects" encompasses unwanted and adverse effects of a therapy (e.g., a prophylactic or therapeutic agent). Unwanted effects are not necessarily adverse. An adverse effect from a therapy (e.g., a prophylactic or therapeutic agent) might be harmful or uncomfortable or risky. Examples of side effects include, diarrhea, cough, gastroenteritis, wheezing, nausea, vomiting, anorexia, abdominal cramping, fever, pain, loss of body weight, dehydration, alopecia, dyspenea, insomnia, dizziness, mucositis, nerve and muscle effects, fatigue, dry mouth, and loss of appetite, rashes or swellings at the site of administration, flu-like symptoms such as fever, chills and fatigue, digestive tract problems and allergic reactions. Additional undesired effects experienced by patients are numerous and known in the art. Many are described in the *Physician's Desk Reference* ($67^{th}$ ed., 2013).

As used herein, the terms "subject" and "patient" are used interchangeably. As used herein, in certain embodiments, a subject is a mammal, such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a C10orf54-mediated disease. In another embodiment, the subject is a mammal (e.g., a human) at risk of developing a C10orf54-mediated disease.

As used herein "substantially all" refers to refers to at least about 60%, at least about 70%, at least about 75%, at least about 80%, at least about 85%, at least about 90%, at least about 95%, at least about 98%, at least about 99%, or about 100%.

As used herein, the term "therapeutic agent" refers to any agent that can be used in treating, preventing or alleviating a disease, disorder or condition, including in the treatment, prevention or alleviation of one or more symptoms of a C10orf54-mediated disease, disorder, or condition and/or a symptom related thereto. In certain embodiments, a therapeutic agent refers to an antibody provided herein. In certain other embodiments, a therapeutic agent refers to an agent other than an antibody provided herein. In certain embodiments, a therapeutic agent is an agent which is known to be useful for, or has been or is currently being used for the treatment, prevention or alleviation of one or more symptoms of a C10orf54-mediated disease, disorder, condition, or a-symptom related thereto.

The combination of therapies (e.g., use of therapeutic agents) can be more effective than the additive effects of any two or more single therapy. For example, a synergistic effect of a combination of therapeutic agents permits the use of lower dosages of one or more of the agents and/or less frequent administration of the agents to a subject with a C10orf54-mediated disease. The ability to utilize lower dosages of therapeutic therapies and/or to administer the therapies less frequently reduces the toxicity associated with the administration of the therapies to a subject without reducing the efficacy of the therapies in the prevention, treatment or alleviation of one or more symptom of a C10orf54-mediated disease. In addition, a synergistic effect can result in improved efficacy of therapies in the prevention, treatment or alleviation of one or more symptom of a C10orf54-mediated disease. Finally, synergistic effect of a combination of therapies (e.g., therapeutic agents) may avoid or reduce adverse or unwanted side effects associated with the use of any single therapy.

The term "therapeutically effective amount" as used herein refers to the amount of a therapeutic agent (e.g., an antibody provided herein or any other therapeutic agent provided herein) that is sufficient to reduce and/or ameliorate the severity and/or duration of a given disease and/or a symptom related thereto. A therapeutically effective amount of a therapeutic agent can be an amount necessary for the reduction or amelioration of the advancement or progression of a given disease, reduction or amelioration of the recurrence, development or onset of a given disease, and/or to improve or enhance the prophylactic or therapeutic effect of another therapy (e.g., a therapy other than the administration of an antibody provided herein).

In certain embodiments, a "therapeutically effective serum titer" is the serum titer in a subject, preferably a human, that reduces the severity, the duration and/or the symptoms associated with a C10orf54-mediated disease in the subject.

As used herein, the term "therapy" refers to any protocol, method and/or agent that can be used in the prevention, management, treatment and/or amelioration of a C10orf54-mediated disease. In certain embodiments, the terms "therapies" and "therapy" refer to a biological therapy, supportive therapy, and/or other therapies useful in the prevention, management, treatment and/or amelioration of a C10orf54-mediated disease known to one of skill in the art such as medical personnel.

The term "thiol," as used herein, refers to the radical —SH.

As used herein, the terms "treat," "treatment" and "treating" refer to the reduction or amelioration of the progression, severity, and/or duration of a C10orf54-mediated disease resulting from the administration of one or more therapies (including, but not limited to, the administration of one or more therapeutic agents, such as an antibody provided herein). In specific embodiments, such terms refer to the reduction or inhibition of cancer or tumor formation. In other specific embodiments, such term refers to the reduction or amelioration of the progression, severity and/or duration of graft-versus-host disease. In yet other specific embodiments, such terms refer to the reduction or amelioration of the progression, severity, and/or duration of a disease that is responsive to immune modulation, such modulation resulting from increasing T cell activation, increasing T cell proliferation or increasing cytokine production.

"Tubulysin" includes both the natural products described as tubulysins, such as by Sasse et al. and other authors mentioned in the Description of the related art, and also the tubulysin analogs described in US Patent Application Publication No. US 2011/0021568 A1. Tubulysins disclosed in the present application are noted herein and may include the tubulysins of the formulae T3 and T4, and other tubulysins where the terminal N-methylpiperidine has been replaced by an unsubstituted piperidine, allowing amide bond formation with a linker.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. In specific embodiments, the variable region is a human variable region.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, MD. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc, according to Kabat) after heavy chain FR residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Unless stated otherwise herein, references to residue numbers in the variable domain of antibodies means residue numbering by the Kabat numbering system. Other numbering systems have been described, including, for example, by AbM, Chothia, Contact and IMGT. Various numbering systems are illustrated in FIGS. 16A and 16B.

The term "variant" when used in relation to C10orf54 or to an anti-C10orf54 antibody refers to a peptide or polypeptide comprising one or more (such as, for example, about 1 to about 25, about 1 to about 20, about 1 to about 15, about 1 to about 10, or about 1 to about 5) amino acid sequence substitutions, deletions, and/or additions as compared to a native or unmodified sequence. For example, a C10orf54 variant may result from one or more (such as, for example, about 1 to about 25, about 1 to about 20, about 1 to about 15, about 1 to about 10, or about 1 to about 5) changes to an amino acid sequence of native C10orf54. Also by way of example, a variant of an anti-C10orf54 antibody may result from one or more (such as, for example, about 1 to about 25, about 1 to about 20, about 1 to about 15, about 1 to about 10, or about 1 to about 5) changes to an amino acid sequence of a native or previously unmodified anti-C10orf54 antibody. Variants may be naturally occurring, such as allelic or splice variants, or may be artificially constructed. Polypeptide variants may be prepared from the corresponding nucleic acid molecules encoding the variants. In specific embodiments, the C10orf54 variant or anti-C10orf54 antibody variant at least retains C10orf54 or anti-C10orf54 antibody functional activity, respectively. In specific embodiments, an anti-C10orf54 antibody variant binds C10orf54 and/or is antagonistic to C10orf54 activity. In specific embodiments, an anti-C10orf54 antibody variant binds C10orf54 and/or is agonistic to C10orf54 activity. In certain embodiments, the variant is encoded by a single nucleotide polymorphism (SNP) variant of a nucleic acid molecule that encodes C10orf54 or anti-C10orf54 antibody VH or VL regions or subregions.

The term "vector" refers to a substance that is used to introduce a nucleic acid molecule into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecule is expressed in a sufficient amount to produce the desired product (e.g. an anti-C10orf54 antibody provided herein), and it is further understood that expression levels can be optimized to obtain sufficient expression using methods well known in the art.

BRIEF DESCRIPTION OF THE DRAWINGS

FIG. 2 shows FACS analysis of 23 primary AML-BM-MNC and 3 normal BM-MNC samples using anti-C10orf54 antibody 76E1.

FIGS. 3A and 3B show humanized sequences for murine monoclonal antibody 76E1 VH region. SEQ ID NOS: 1, 7, 8, 12-15 and 82 are depicted.

FIGS. 4A and 4B show humanized sequences for murine monoclonal antibody 141A VH region. SEQ ID NOS: 2, 7, 8, 16-19 and 82 are depicted.

FIGS. 5A and 5B show humanized sequences for murine monoclonal antibody 175A VH region. SEQ ID NOS: 3, 7, 8, 20-23 and 82 are depicted.

FIGS. 6A and 6B show humanized sequences for murine monoclonal antibody 76E1 VL region. SEQ ID NOS: 4, 9, 10, 24, 25 and 94 are depicted.

FIGS. 7A and 7B show humanized sequences for murine monoclonal antibody 141A VL region. SEQ ID NOS: 5, 10, 11, 26, 27 and 94 are depicted.

FIGS. 8A and 8B show humanized sequences for murine monoclonal antibody 175A VL region. SEQ ID NOS: 6, 9, 10, 28, 29 and 94 are depicted.

FIG. 9 shows pseudo-sequences of VH and VL domains of murine monoclonal antibodies 76E1, 141A and 175A (SEQ ID NOS: 1143-1148). CDRs are identified in bold.

FIG. 15 shows results of treatment with unconjugated and MMAF conjugated anti-C10orf54 antibodies in a tumor model using a C10orf54 expressing sarcoma line and parental sarcoma line.

FIGS. 16A and 16B shows a sequence alignment of the variable heavy chains and variable light chains of the anti-C10orf54 murine antibodies designated 76E1, 141 A and 175A (SEQ ID NOS:1-6). Boundaries of CDR's are indicated by Kabat, AbM, Chothia, Contact and IMGT numbering.

FIGS. 17A and 17B shows a sequence alignment of the variable heavy chains and variable light chains of exemplary humanized anti-C10orf54 antibodies designated hu76E1, hu141 A and hu175A (SEQ ID NOS: 1135-1137 for heavy chains; SEQ ID NOS: 1139-1141 for light chains) and the corresponding consensus sequences between hu76E1 and hu175A (SEQ ID NO: 1138 for the heavy chain; SEQ ID NO: 1142 for the light chain). Residues indicated just below that alignment indicate specific residues that can be varied at the above "X" position in the consensus sequence.

FIG. 18A to 18D show alignments of antibody VH and VL sequences disclosed herein by paratope group. SEQ ID NOS: 1271-1280 for VH and VL are depicted. SEQ ID NOS: 1291, 1306, 1441, 1918, 1440, 1368, 1442, 1919, 1385, 1405, 1446, 1920, 1443, 1458, 1446, 1921, 1473, 1445, 1447, 1922, 1444, 1508, 1448 and 1923 for consensus CDR sequences within paratope groups are also depicted.

FIG. 19 shows exemplary human germline sequences for humanization of anti-C10orf54 antibodies described herein.

FIGS. 20A and 20B show selected human VH and human VL sequences for humanization of anti-C10orf54 antibodies described herein. SEQ ID NOS: 7, 1902-1904, 1907, 1905, 1906, 1912, 1910, 11, 1909, 1913 (in order from top to bottom) for VH and VL sequences are depicted.

FIGS. 22A and 22B show humanized sequences for murine monoclonal antibody 26A VH and VL regions, respectively. SEQ ID NOS: 1902, 82, 1266, and 1529-1531 are depicted in FIG. 22A and SEQ ID NOS: 1910, 94, and 1532-1534 are depicted in FIG. 22B. Humanized VH designated h26AH1 and humanized VL designated h26AL1 are each "CDR-swap" constructs with no changes in the human framework. Subsequent sequences have altered amino acid residues. # indicates deamidation substitution: Q/S/A/D.

FIGS. 23A and 23B show humanized sequences for murine monoclonal antibody 128A VH and VL regions, respectively. SEQ ID NOS: 1902, 82, 1258, and 1535-1537 are depicted in FIG. 23A and SEQ ID NOS: 1907, 94, 1259, and 1538-1540 are depicted in FIG. 23B. Humanized VH designated h128AH1 and humanized VL designated h128AL1 are each "CDR-swap" constructs with no changes in the human framework. Subsequent sequences have altered amino acid residues. # indicates deamidation substitution: Q/S/A/D.

FIGS. 24A and 24B show humanized sequences for murine monoclonal antibody 124A VH and VL regions, respectively. SEQ ID NOS: 1902, 82, 1281, 1541, and 1542 are depicted in FIG. 24A and SEQ ID NOS: 1911, 94, 1282, 1546, and 1547 are depicted in FIG. 24B. Humanized VH designated h124AH1 and humanized VL designated h124AL1 are each "CDR-swap" constructs with no changes in the human framework. Subsequent sequences have altered amino acid residues. # indicates deamidation substitution: Q/S/A/D. @ indicates isoaspartate substitutions: Q/S/A.

FIGS. 25A and 25B show humanized sequences for murine monoclonal antibody 259A VH and VL regions, respectively. SEQ ID NOS: 1902, 82, 1275, and 1543-1545 are depicted in FIG. 25A and SEQ ID NOS: 1905, 94, 1276, 1548, and 1549 are depicted in FIG. 25B. Humanized VH designated h124AH1 and humanized VL designated h124AL1 are each "CDR-swap" constructs with no changes in the human framework. Subsequent sequences have altered amino acid residues. # indicates deamidation substitution: Q/S/A/D. @ indicates isoaspartate substitutions: E/S/A.

FIG. 26A shows the percentage of C10orf54 within Lin⁻/CD11 b⁺ MDSC subpopulations. FIG. 26B shows the copy number of C10orf54 for Lin⁻/CD11 b⁺ MDSC subpopulations. MDSC populations are referred to as: monocytic (CD14+/HLA⁻DR⁻), granulocytic (CD15⁺/HLA⁻DR⁻), and immature myeloid cells (CD15⁻/HLA⁻DR⁻).

FIGS. 30A to 30C show a comparison of naïve and pan T cell populations. 50,000 Tcells per well were grown in plates precoated with 5 ug/ml anti-CD3 antibody and various concentrations of C10orf54-Fc. Cells were co-stimulated further with various concentrations of anti-CD28 antibody (no anti-CD3 antibody was added to control wells (0 μg/ml αCD28). Values are the average of RLU/well (n=4). FIG. 30A shows pan T cells, 2 days upon stimulation. FIG. 30B shows naïve T cells, 2 days upon stimulation. FIG. 30C shows naïve T cells, 3 days upon stimulation.

DETAILED DESCRIPTION

Figure 1A:
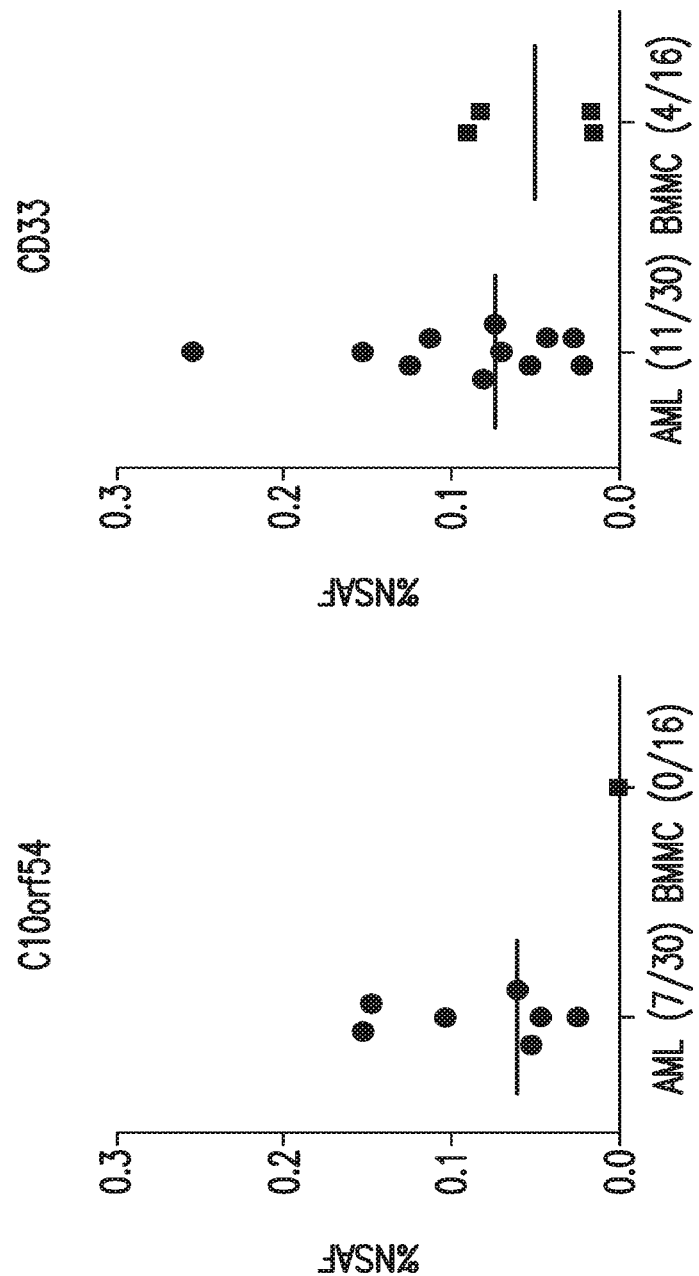
FIGS. 1A and 1B shows the protein expression level of C10orf54 that was identified and quantified by sTAg analysis in AML and BMMC samples and relevant control.

Provided herein are antibodies that bind to C10orf54, including a C10orf54 polypeptide, a C10orf54 polypeptide fragment, or a C10orf54 epitope. Such antibodies include humanized anti-C10orf54 antibodies. Also provided are antibodies (e.g., humanized anti-C10orf54 antibodies) that competitively block and anti-C10orf54 antibody provided herein from binding to a C10orf54 polypeptide. The anti-C10orf54 antibodies (e.g., humanized anti-C10orf54 antibodies) provided herein can also be conjugated or recombinantly fused to a diagnostic agent, detectable agent or therapeutic agent (e.g., antibody-drug conjugate). Further provided are compositions comprising an anti-C10orf54 antibody (e.g., a humanized anti-C10orf54 antibody). For example, a detectable agent may be a detectable probe.

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC10 (SEQ ID NO: 1251), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), and CC9 (SEQ ID NO: 1250).

In certain embodiments, the antibody provided herein binds a first group of C10orf54 proteins or chimeric proteins designated CC1 (SEQ ID NO: 1079), CC4 (SEQ ID NO: 1245), CC5 (SEQ ID NO: 1246), and CC8 (SEQ ID NO: 1249), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251). In some aspects, such an antibody does not comprise one or more CDR sequences selected from the group consisting of 30, 1099, 1104, 1105, 1110, 31, 1100, 1106, 1111, 1116, 32, 1101, 1107, 1112, 45, 1102, 1108, 1113, 40, 1103, 1114, 41, 1109, and 1115.

In certain embodiments, the antibody provided herein binds to a first group of C10orf54 proteins or chimeric proteins designated CC1 (SEQ ID NO: 1079), CC4 (SEQ ID NO: 1245), and CC5 (SEQ ID NO: 1246), and does not bind to a second group of C10orf54 proteins or chimeric proteins designated (SEQ ID NO: 1243), CC3 (SEQ ID NO: 1244), CC6 (SEQ ID NO: 1247), CC7 (SEQ ID NO: 1248), CC8 (SEQ ID NO: 1249), CC9 (SEQ ID NO: 1250), and CC10 (SEQ ID NO: 1251). In some aspects, such an antibody does not comprise one or more CDR sequences selected from the group consisting of 36, 1081, 1086, 1087, 1092, 37, 1082, 1088, 1093, 1098, 38, 1083, 1089, 1094, 45, 1084, 1090, 1095, 46, 1085, 1096, 47, 1091, and 1097.

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC9 (SEQ ID NO: 1250), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251). In some aspects, such an antibody does not comprise one or more CDR sequences selected from the group consisting of 33, 1117, 1122, 1123, 1128, 34, 1118, 1124, 1129, 1134, 35, 1119, 1125, 1130, 42, 1120, 1126, 1131, 43, 1121, 1132, 44, 1127, and 1133.

In certain embodiments, the antibody provided herein binds to a first group of C10orf54 proteins or chimeric proteins designated CC1 (SEQ ID NO: 1079), CC3 (SEQ ID NO: 1244), CC4 (SEQ ID NO: 1245), CC5 (SEQ ID NO: 1246), CC8 (SEQ ID NO: 1249), and CC9 (SEQ ID NO: 1250), and does not bind to a second group of C10orf54 proteins or chimeric proteins designated CC2 (SEQ ID NO: 1243), CC6 (SEQ ID NO: 1247), CC7 (SEQ ID NO: 1248), and CC10 (SEQ ID NO: 1251).

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC10 (SEQ ID NO: 1251), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251).

Also provided herein are isolated nucleic acid molecules encoding a VH chain, VL chain, VH domain, VL domain, VH CDR1, VH CDR2, VH CDR3, VL CDR1, VL CDR2, and/or VL CDR3 of anti-C10orf54 antibodies that bind to a C10orf54 polypeptide, a C10orf54 polypeptide fragment, or a C10orf54 epitope. Further provided are vectors and host cells comprising nucleic acid molecules encoding anti-C10orf54 antibodies that bind to a C10orf54 polypeptide, a C10orf54 polypeptide fragment, or a C10orf54 epitope. Also provided are methods of making antibodies that bind to a C10orf54 polypeptide, a C10orf54 polypeptide fragment, or a C10orf54 epitope.

Methods of using the anti-C10orf54 antibodies (e.g., humanized anti-C10orf54 antibodies) are provided. Methods include treating, preventing or alleviating a disease, disorder or condition, including one or more symptoms of a disease, disorder or condition, comprising administering a therapeutically effective amount of an anti-C10orf54 antibody, including an antibody-drug conjugate (ADC) comprising an anti-C10orf54 antibody, provided herein to a subject, thereby treating, preventing or alleviating the disease, disorder or condition, including one or more symptoms of the disease, disorder or condition. In some embodiments the anti-C10orf54 antibodies are humanized antibodies that bind to a C10orf54 polypeptide, a C10orf54 polypeptide fragment or a C10orf54 epitope. In one embodiment, the disease, disorder or condition is caused by or otherwise associated with C10orf54, including by or associated with C10orf54-expressing cells (e.g., tumor cells, myeloid-derived suppressor cells (MDSC), suppressive dendritic cells (suppressive DC), and/or regulatory T cells (T regs)). In certain embodiments, the disease is a cancer, such as a leukemia, bladder cancer, a skin cancer, a colon cancer, a breast cancer, a liver cancer, a kidney cancer, a lung cancer, a stomach cancer, a pancreas cancer, an esophagus cancer or a fibrosarcoma. In one embodiment, the leukemia is an acute myeloid leukemia (AML). In other embodiments, the disease is graft-versus-host disease (GVHD). Additional methods provided include using an anti-C10orf54 antibody with C10orf54 binding activity for C10orf54-expressing cells, provided herein, for example, as an unconjugated antibody or conjugated antibody (ADC), including to inhibit and/or kill the C10orf54-expressing cells (e.g., with anti-tumor activity to mediate an anti-tumor effect). In certain embodiments, the anti-C10orf54 antibodies, including ADCs comprising the anti-C10orf54 antibodies, provided herein inhibit C10orf54-mediated suppressor activity on T cells (e.g., to allow an effective anti-tumor immune response). In certain embodiments, the anti-C10orf54 antibodies provided herein directly kill C10orf54-expressing cells (e.g., C10orf54-bearing tumor cells, myeloid-derived suppressor cells (MDSC), suppressive dendritic cells (suppressive DC), and/or regulatory T cells (T regs)), for example, via antibody-dependent cellular cytotoxicity (ADCC) and/or complement-dependent cytotoxicity (CDC) In certain embodiments, antibody drug conjugates (ADCs) comprising anti-C10orf54 antibodies provided herein directly kill C10orf54-expressing cells including by binding to cells expressing C10orf54 (e.g., tumor cells, myeloid-derived suppressor cells (MDSC), suppressive dendritic cells (suppressive DC), and/or regulatory T cells (T regs)), for example, by allowing internalization of the cytotoxic drug. In any of the above embodiments, the anti-C10orf54 antibody can be a humanized anti-C10orf54 antibody provided herein that binds to a C10orf54 polypeptide, a C10orf54 polypeptide fragment or a C10orf54 epitope. In any of the above embodiments, the anti-C10orf54 antibody can be a humanized anti-C10orf54 antibody provided herein that binds to a C10orf54 polypeptide, a C10orf54 polypeptide fragment or a C10orf54 epitope.

Additional methods of using an anti-C10orf54 antibody are provided.

The methods include methods of inhibiting the growth of cells and/or killing cells having cell surface expression of C10orf54 comprising contacting the cells with an effective amount of an anti-C10orf54 antibody or antibody-drug conjugates provided herein. In one embodiment, the cell is a regulatory T cell (e.g., a CD4$^+$ Foxp3$^+$ regulatory T cell). In other embodiments, the cell is a myeloid-derived suppressor cell (e.g., a CD11 b$^+$ or CD11b$^{high}$ myeloid-derived suppressor cell) or a suppressive dendritic cell (e.g., a CD11 b$^+$ or CD11b$^{high}$ dendritic cell). In other embodiments, the cell is a cancerous or pre-cancerous cell. Additional methods provided include using an anti-C10orf54 antibody with C10orf54 binding activity for C10orf54-expressing cells provided herein, for example, as an unconjugated antibody or conjugated antibody (ADC) including to inhibit and/or kill C10orf54-expressing cells (e.g., with anti-tumor activity to mediate an anti-tumor effect). In certain embodiments, the anti-C10orf54 antibodies, including ADCs comprising the anti-C10orf54 antibodies, provided herein inhibit C10orf54-mediated suppressor activity on T cells (e.g., to allow an effective anti-tumor immune response). In certain embodiments, the anti-C10orf54 antibodies provided herein directly kill C10orf54-expressing cells (e.g., C10orf54-bearing tumor cells, myeloid-derived suppressor cells (MDSC), suppressive dendritic cells (suppressive DC), and/or regulatory T cells (T regs)), for example, via antibody-dependent cellular cytotoxicity (ADCC) and/or complement-dependent cytotoxicity (CDC) In certain embodiments, antibody drug conjugates (ADCs) comprising anti-C10orf54 antibodies provided herein directly kill C10orf54-expressing cells including by binding to cells expressing C10orf54 (e.g., tumor cells, myeloid-derived suppressor cells (MDSC), suppressive dendritic cells (suppressive DC), and/or regulatory T cells (T regs)), for example, by allowing internalization of the cytotoxic drug. In any of the above embodiments, the anti-C10orf54 antibody can be a humanized anti-C10orf54 antibody provided herein that binds to a C10orf54 polypeptide, a C10orf54 polypeptide fragment or a C10orf54 epitope.

The methods include methods of modulating an immune response in a subject comprising administering an effective amount of an anti-C10orf54 antibody (e.g., a humanized anti-C10orf54 antibody) provided herein to a subject. In one embodiment, the modulating comprises increasing T cell activation. In other embodiment, the modulating comprises increasing T cell proliferation. In another embodiment, the modulating comprises increasing cytokine production.

The methods include methods for detecting C10orf54 in a sample comprising contacting the sample with an anti-C10orf54 antibody (e.g., a humanized anti-C10orf54 antibody) provided herein, such as an antibody that comprises a detectible agent. In certain embodiments, the sample comprises a cell expressing C10orf54 on its surface.

The methods include methods of treating cancers comprising administering to a subject an anti-C10orf54 antibody or an antibody-drug conjugate (ADC) comprising an anti-C10orf54 (e.g., an ADC of the formula A-L-CTX, wherein A is the antibody, L is a linker, and CTX is a cytotoxic agent) in a therapeutically effective amount, including in an amount effective to kill a C10orf54-expressing cell (e.g., tumor cell, myeloid-derived suppressor cell (MDSC), suppressive dendritic cell (suppressive DC), and/or regulatory T cell (T reg)). In some embodiments the cancer is acute myeloid leukemia (AML). In any of the above embodiments, the anti-C10orf54 antibody can be a humanized anti-C10orf54 antibody provided herein that binds to a C10orf54 polypeptide, a C10orf54 polypeptide fragment or a C10orf54 epitope.

The methods include methods of killing C10orf54-expressing cells (e.g., tumor cells, myeloid-derived suppressor cells (MDSC), suppressive dendritic cells (suppressive DC), and/or regulatory T cells (T reg)) comprising contacting a C10orf54-expressing cell (e.g., tumor cell, myeloid-derived suppressor cell (MDSC), suppressive dendritic cell (suppressive DC), and/or regulatory T cell (T regs)) with an amount of an anti-C10orf54 antibody or an antibody-drug conjugate (ADC) comprising an anti-C10orf54 antibody (e.g., an ADC of the formula A-L-CTX, wherein A is the antibody, L is a linker, and CTX is a cytotoxic agent) effective to kill the cell (e.g., tumor cell, myeloid-derived suppressor cell (MDSC), suppressive dendritic cell (suppressive DC), and/or regulatory T cell (T reg)). In some embodiments, the tumor cell is an AML cell. In any of the above embodiments, the anti-C10orf54 antibody can be a humanized anti-C10orf54 antibody provided herein that binds to a C10orf54 polypeptide, a C10orf54 polypeptide fragment or a C10orf54 epitope.

In one embodiment, provided herein is a kit comprising an anti-C10orf54 antibody (e.g., a humanized anti-C10orf54 antibody) that binds to a C10orf54 polypeptide, a C10orf54 polypeptide fragment, or a C10orf54 epitope provided herein. In some embodiments, the kits comprise an anti-body-drug conjugate (ADC) wherein the antibody is an anti-C10orf54 antibody (e.g., a humanized anti-C10orf54 antibody).

ANTIBODIES

In some embodiments, provided herein are antibodies that bind to C10orf54, including a C10orf54 polypeptide, a C10orf54 polypeptide fragment or a C10orf54 epitope. In some embodiments the anti-C10orf54 antibodies are humanized antibodies that bind C10orf54, including to a C10orf54 polypeptide, a C10orf54 polypeptide fragment or a C10orf54 epitope.

In certain embodiments, the anti-C10orf54 antibody comprises a VH domain, VL domain, VH CDR1, VH CDR2, VH CDR3, VL CDR1, VL CDR2, and/or VL CDR3 of the murine monoclonal antibody 5B, 46A, 97A, 128A, 146C, 208A, 215A, 26A, 164A, 230A, 76E1, 53A, 259A, 33A, 39A, 124A, 175A, 321 D, 141 A, 51 A, 353A, or 305A as depicted in Table 2 and FIGS. 3-8, 22A, 22B, 23A, 23B, 24A, 24B, 25A, and 25B. Accordingly, in some aspects, the VH domain comprises the amino acid sequence of SEQ ID NO:1. In some embodiments, the VH domain comprises the amino acid sequence of SEQ ID NO:2. In some embodiments, the VH domain comprises the amino acid sequence of SEQ ID NO:3. In some embodiments, the VH domain comprises the amino acid sequence of SEQ ID NO:1252. In some embodiments, the VH domain comprises the amino acid sequence of SEQ ID NO:1254. In some embodiments, the VH domain comprises the amino acid sequence of SEQ ID NO:1256. In some embodiments, the VH domain comprises the amino acid sequence of SEQ ID NO:1258. In some embodiments, the VH domain comprises the amino acid sequence of SEQ ID NO:1260. In some embodiments, the VH domain comprises the amino acid sequence of SEQ ID NO:1262. In some embodiments, the VH domain comprises the amino acid sequence of SEQ ID NO:1266. In some embodiments, the VH domain comprises the amino acid sequence of SEQ ID NO:1268. In some embodiments, the VH domain comprises the amino acid sequence of SEQ ID NO:1271. In some embodiments, the VH domain comprises the amino acid sequence of SEQ ID NO:1273. In some embodiments, the VH domain comprises the amino acid sequence of SEQ ID NO:1375. In some embodiments, the VH domain comprises the amino acid sequence of SEQ ID NO:1277. In some embodiments, the VH domain comprises the amino acid sequence of SEQ ID NO:1279. In some embodiments, the VH domain comprises the amino acid sequence of SEQ ID NO:1281. In some embodiments, the VH domain comprises the amino acid sequence of SEQ ID NO:1283. In some embodiments, the VH domain comprises the amino acid sequence of SEQ ID NO:1285. In some embodiments, the VH domain comprises the amino acid sequence of SEQ ID NO:1287. In some embodiments, the VH domain comprises the amino acid sequence of SEQ ID NO:1289. In some embodiments, the VL domain comprises the amino acid sequence of SEQ ID NO:4. In some embodiments, the VL domain comprises the amino acid sequence of SEQ ID NO:5. In some embodiments, the VL domain comprises the amino acid sequence of SEQ ID NO:6. In some embodiments, the VL domain comprises the amino acid sequence of SEQ ID NO:1253. In some embodiments, the VL domain comprises the amino acid sequence of SEQ ID NO:1255. In some embodiments, the VL domain comprises the amino acid sequence of SEQ ID NO:1257. In some embodiments, the VL domain comprises the amino acid sequence of SEQ ID NO:1259. In some embodiments, the VL domain comprises the amino acid sequence of SEQ ID NO:1261. In some embodiments, the VL domain comprises the amino acid sequence of SEQ ID NO:1263. In some embodiments, the VL domain comprises the amino acid sequence of SEQ ID NO:1265. In some embodiments, the VL domain comprises the amino acid sequence of SEQ ID NO:1267. In some embodiments, the VL domain comprises the amino acid sequence of SEQ ID NO:1269. In some embodiments, the VL domain comprises the amino acid sequence of SEQ ID NO:1270. In some embodiments, the VL domain comprises the amino acid sequence of SEQ ID NO:1272. In some embodiments, the VL domain comprises the amino acid sequence of SEQ ID NO:1274. In some embodiments, the VL domain comprises the amino acid sequence of SEQ ID NO:1276. In some embodiments, the VL domain comprises the amino acid sequence of SEQ ID NO:1278. In some embodiments, the VL domain comprises the amino acid sequence of SEQ ID NO:1280. In some embodiments, the VL domain comprises the amino acid sequence of SEQ ID NO:1282. In some embodiments, the VL domain comprises the amino acid sequence of SEQ ID NO:1284. In some embodiments, the VL domain comprises the amino acid sequence of SEQ ID NO:1286. In some embodiments, the VL domain comprises the amino acid sequence of SEQ ID NO:1288. In some embodiments, the VL domain comprises the amino acid sequence of SEQ ID NO:1290.

TABLE 2

Murine Antibody Sequences

| Murine Antibody | VH Domain* | VL Domain* |
|---|---|---|
| 76E1 | EVQLLQSGPELEKPGASVKISCKASGYSFTGYNMNWVKQSNGKSLEWIGNIDPYYDYTSYNLKFKDKATLTVDKSSSTAYMQLKSLTSEDSAVYYCATSTMITPFDYWGQGTTLTVSS (SEQ ID NO: 1) | DVLMTQTPLSLPVSLGDQASISCRSSQSIVHSNGNTYLEWYLQKPGQSPKLLIYKVSNRFSGVPDRFSGSGSGTDFTLKINRVEAEDLGVYYCFQGSHVPWTFGGGTKLEIK (SEQ ID NO: 4) |
| 141A | QVQLQQSGAELMKPGASVKISCKATGYTFSRYWIEWVKQRPGHGLEWIG | QIVLSQSPAILSASPGEKVTMTCRASSSLSYMHWYQQKPGSSPKPWIYATSNLA |

TABLE 2-continued

Murine Antibody Sequences

| Murine Antibody | VH Domain* | VL Domain* |
|---|---|---|
| | EILPGSGSTNYNEKFKGKATFTADT SSNTAYMQLSSLTSEDSAVYYCAGE EVYDGYPWFGYWGQGTLVTVSA (SEQ ID NO: 2) | SGVPARFSGSGSGTSYSLTISRVEAED AATYYCQQWSSNPYTFGGGTKLEIK (SEQ ID NO: 5) |
| 175A | QVQLQQSGAELMKPGASVKISCKAT GYTFSTHWIEWVKQRPGHGLEWIG EILPGSGSTSYNEKFKGKATFTADT SSNTAYMQLSSLTSEDSAVYYCAR WLLYYYAMDYWGQGTSVTVSS (SEQ ID NO: 3) | DVLMTQTPLSLPVSLGDQASISCRSSQ SIVHSNGNTYLEWYLQKPGQSPKLLIY KLSNRFSGVPDRFSGSGSGTDFTLKIS RVEAEDLGVYYCFQGSHFPYTFGGGT KLEIK (SEQ ID NO: 6) |
| 5B | QVQLQQSGAELVRPGVSVKISCKG SGYTFTDYGMHWVKQSHAKSLEWI GIIDTYYGDATYNQKFKGKATMTVD KSSSTAYMELARLTSEDSAIYYCAR RAGNAMDYWGQGTSVTVSS (SEQ ID NO: 1252) | NIVMTQTPKFLLVSAGDRVTITCKASQS VSNDVAWYQQKPGQSPKLLIYYASNR YTGVPDRFTGSGYGTDFTFTISTVQAE DLAVYFCQQDYSSPRTFGGGTKLEIK (SEQ ID NO: 1253) |
| 46A | QVQLQQAGGELVRPGVSVKISCKG SGYTFTDYGMHWVKQSHAKSLEWI GIINTYYGDATYNQKFKGKATMTVD KSSSTAYMELARLTSEDSAIYYCAR RAGTAMDYWGQGTSVTVSS (SEQ ID NO: 1254) | SIVMTQTPKFLLVSAGDRVTITCKASQS VSNDVAWYQQKPGQSPKLLIYYASNR YTGVPDRFTGSGYGTDFTFTISTVQAE DLAVYFCQQDYGSPRTFGGGTKLEIK (SEQ ID NO: 1255) |
| 97A | QVQLQQSGAELVRPGVSVKISCKG SGYTFTDYGMHWVKQSHAKSLEWI GVIDTYYGDASNNQKFKGKATMTV DKSSSTAYMELARLTSEDSAIYYCA RRAGNAMDYWGQGTSVTVSS (SEQ ID NO: 1256) | SIVMTQTPKFLLVSAGDRVAITCKASQS VSNDVAWYQQKPGQSPKLLIYYASNR YTGVPDRFTGSGYGTDFTFTISTVQAE DLAVYFCQQDYGSPRTFGGGTKLEIK (SEQ ID NO: 1257) |
| 128A | QVQLQQSGAELVRPGVSVKISCKG SGYTFTDYGMHWVKQSHAKSLEWI GLIDTYYGDATYNHKFKGKATMTVD KSSRTAYMELARLTSEDSAIYYCAR RAGNAMDYWGQGTSVTASS (SEQ ID NO: 1258) | NIAMTQTPKFLLVSAGDRVTITCKASQS VSNDIAWYQQKPGQSPRLLIYYASNRY TGVPDRFTGSGYGTDFTFTISTVQAED LAVYFCQQDYSSPRTFGGGTKLEIK (SEQ ID NO: 1259) |
| 146C | QVQLQQSGAELVRPGVSVKISCKG SGYTFTDYGMHWVKQSHAKSLEWI GLIDTYYGDATYNHKFKGKATMTVD KSSRTAYMELARLTSEDSAIYYCAR RAGNAMDYWGQGTSVTASS (SEQ ID NO: 1260) | NIAMTQTPKFLLVSAGDRVTITCKASQS VSNDIAWYQQKPGQSPRLLIYYASNRY TGVPDRFTGSGYGTDFTFTISTVQAED LAVYFCQQDYSSPRTFGGGTKLEIK (SEQ ID NO: 1261) |
| 208A | QVQLQQSGAELVRPGVSVKISCKG SGYTFTDYGMHWVKQSHAKSLEWI GVIDTYYGDAGYNQKFKGKATMTV DKSSSTAYMELARLTSEDSAIYYCA RRAGNAMDYWGQGTSVTVSS (SEQ ID NO: 1262) | SIVMTQTPKFLLVSAGDRVTITCKASQS VSNDVAWYQQKPGQSPKLLIYYASNR YTGVPDRFTGSGYGTDFTFTISTVQAE DLAVYFCQQDYSSPRTFGGGTKLEIK (SEQ ID NO: 1263) |
| 215A | EVQLQQSGPELVKPGASMKISCKAS GFSFTGYTMNWVKQSHGKNLEWIG LISPYNGGTSYNQKFKGKATLTVDK SSSTAYMELLSLTSEDSAVYYCARR AYGYAMDYWGQGTSVTVSS (SEQ ID NO: 1264) | QIVLTQSPAIMSASPGEKVTMTCSASS SVSYMFWYQQKPGSSPRLLIYDTSNLA SGVPLRFSGSGSGTSYSLTISRMEAED AATYYCQQWSSYPFTFGSGTKLEIK (SEQ ID NO: 1265) |
| 26A | EVQLQQSGPELVKPGASMKISCKAS GFSFTGYTMNWVKQSHVKNLEWIG LISPYNGGTSYNQKFKGKATLTVDK SSSTAYMELLSLTSEDSAVYYCARR AYGYAMDYWGQGTSVTVSS (SEQ ID NO: 1266) | QIVLTQSPAIMSASPGEKVTMTCSASS SVSYMYWYQQKPGSSPRLLIYDTSNL ASGVPLRFSGSGSGTSYSLTISRMEAE DAATYYCQQWSSYPFTFGSGTKLEIK (SEQ ID NO: 1267) |
| 164A | EVQLQQSGPELEKPGASVKISCKAS GYSFTGYNMNWVKQSNGKSLEWIG NIDPYYGSASYNQKFKGKATLTVDK SSTTAYMQLKSLTSEDSAVYYCTRS NYGYYGYFDVWGAGTTVTVSS (SEQ ID NO: 1268) | NIMMTQSPSSLAVSAGEKVTMSCKSS QSVLYSSNQKNYLAWYQQKPGQSPK LLIYWASTRESGVPDRFTGSGSGTDFT LTISSVQAEDLAVYCHQFLSSYTFGG GTKLEMK (SEQ ID NO: 1269) |

TABLE 2-continued

Murine Antibody Sequences

| Murine Antibody | VH Domain* | VL Domain* |
|---|---|---|
| | | VL Sequence #2:<br>ENVLTQSPAIMAASPGEKVTMTCSASS<br>SVSSSNLHWYQQKSGTSTKFWIYRTS<br>NLASEVPAPFSGSGSGTSYSLTISSVE<br>AEDAATYYCQQWSGYPRTFGGGTKLE<br>IK<br>(SEQ ID NO: 1270) |
| 230A | EVQLQQSGPELEKPGASVKISCKAS<br>GYSFTGSNMNWVKQNNGKSLEWIG<br>NIDPYYGYTTYNQKFKGKATLTVDK<br>SSSTAYMQLKSLTSEDSAVYYCARD<br>YDYALGYFDVWGAGTTVTVSS<br>(SEQ ID NO: 1271) | DVVMTQTPLSLPVSLGDQASISCRSSQ<br>SLVHSNGNTYLHWYLQKPGQSPKLLIY<br>KVSNRFSGVPDRFSGSGSGTDFTLKIS<br>RVEAEDLGVYFCSQSTHVPYTFGGGT<br>KLEIK<br>(SEQ ID NO: 1272) |
| 53A | EVQLQQSGPELVKPGASVKMSCKA<br>SGYTFTSYFMHWVKQKPGQGLEWI<br>GYIYPYNDGTKYNEKFKGKATLTSD<br>KSSSTAYMELSSLTSEDSAVYYCAR<br>FDYDTLRYWGQGTTLTVSS<br>(SEQ ID NO: 1273) | DVVLTQTPLSLPVNIGDQASISCKSTKS<br>LLNSDGFTYLDWYLQKPGQSPQLLIYL<br>VSNRFSGVPDRFSGSGSGTDFTLKISR<br>VEAEDLGVYYCFQSNYFPWTFGGGTK<br>LEIK<br>(SEQ ID NO: 1274) |
| 259A | EVQLQQSGPELVKPGASVKMSCKA<br>SGYTFTSYFMHWVKQKPGQGLEWI<br>GYIYPYNDGTKYNEKFKGKATLTSD<br>KSSSTAYMDLSSLTSEDSAVYYCAR<br>FDYDTLRYWGQGTTLTVSS<br>(SEQ ID NO: 1275) | DVVLTQTPLSLPVNIGDQASISCKSTKS<br>LLNSDGFTYLDWYLQKPGQSPQLLIYLI<br>SNRFSGVPDRFSGSGSGTDFTLKISRV<br>EAEDLGVYYCFQSNYFPWTFGGGTKL<br>EIK<br>(SEQ ID NO: 1276) |
| 33A | QVQLQQSGAELMKPGASVKISCKAT<br>GYTFSSYWIEWVKQRPGHGLEWIG<br>EILPGSGSTSYNEKFKGKATFTADT<br>SSNTAYMQLSGLTSEDSAVYYCAR<br>WLLYYYAMVYWGQGTSVTVSS<br>(SEQ ID NO: 1277) | DVLMTQTPLSLPVSLGDQASISCRSSQ<br>SIVHSNGNTYLEWYLQKPGQSPKLLIY<br>KVSNRFSGVPDRFSGSGSGTDFTLKIS<br>RVEAEDLGVYYCFQGSHVPYTFGGGT<br>KLEIK<br>(SEQ ID NO: 1278) |
| 39A | QVQLQQSGAELMKPGASVKISCKAT<br>GYTFSSNWIEWVKQRPGHGLEWIG<br>EILPGSGSTSYNEKFKGKATFTADT<br>SSNTAYMQLSSLTSEDSAVYYCAR<br>WLLYYYAMDYWGQGTSVTVSS<br>(SEQ ID NO: 1279) | DVLMTQTPLSLPVSLGDPASISCRSSQ<br>SIVHNNGNTYLEWYLQKPGQSPKLLIY<br>KVSNRFSGVPDRFSGSGSGTDFTLKIS<br>RVEAEDLGVYYCFQGSHVPYTFGGGT<br>KLEIK<br>(SEQ ID NO: 1280) |
| 124A | QVQLQQSGAELMKPGASVKISCKAT<br>GYTFSSNWIEWVKQRPGHGLEWM<br>GEILPGSGSTSYNEKFKGKATFTAD<br>TSSNTAYMQLSSLTSEDSAVYYCAR<br>WLLYYYAMDFWGQGTSVTVSS<br>(SEQ ID NO: 1281) | DVLMTQTPLSLPVSLGDQASISCRSSQ<br>SIVHNNGNTYLEWYLQKPGQSPKLLIY<br>KVSNRFSGVPDRFSGSGSGTDFTLKIS<br>RVEAEDLGVYYCFQGSHVPYTFGGGT<br>KLEIK<br>(SEQ ID NO: 1282) |
| 321D | QVQLQQSGAELMKPGAAVKISCKAT<br>GYTFSSHWIEWVKQRPGHGLEWIG<br>EILPGSGSTDYNEKFKGKATFTADT<br>SSNTAYMQLSSLTSEDSAVYYCAR<br>WLLYYYAMDYWGQGTSVTVSS<br>(SEQ ID NO: 1283) | DVLMTQTPLSLPVSLGDQASISCRSSQ<br>SIVHSNGNTYLEWYLQKPGQSPKLLIY<br>KVSNRFSGVPDRFSGSGSGTDFTLKIT<br>RVEAEDLGVYYCFQGSHVPFTFGGGT<br>KLEIK<br>(SEQ ID NO: 1284) |
| 51A | QVQLQQSGAELMKPGASVKISCKAT<br>GYTFSRYWIEWVKQRPGHGLEWIG<br>EILPGSGSTNYNEKFKGKATFTADT<br>SSNTAYMQLSSLTSEDSAVYYCASE<br>EVYDGYPWFGYWGQGTLVTVSA<br>(SEQ ID NO: 1285) | QIVLSQSPAILSASPGEKVTMTCRASSS<br>LSYMHWYQQRPGSSPKPWIYATSNLA<br>SGVPARFSGSGSGTSYSLTISRVEAED<br>AATYYCQQWSSNPYTFGGGTKLEIK<br>(SEQ ID NO: 1286) |
| 353A | EVKLLESGGGLVQPGGSLKLSCAAS<br>GFDFSRYWMNWVRQAPGKGLEWI<br>GEINPDSSTINYTPSLKDKFIISRDNA<br>KNTLYLQMSKVRYEDTALYYCARPG<br>EIYYYGSYWFAYWGQGTLVTVSA<br>(SEQ ID NO: 1287) | DIVLTQSPASLAVSLGQRATISCRASES<br>VEYYGTSLMQWFQQKPGQPPKLLIYA<br>ASNVESRVPARFSGSGSGTDFSLNIHP<br>VEEDDIAMYFCQQSRKDPWTFGGGTK<br>LEIK<br>(SEQ ID NO: 1288) |

TABLE 2-continued

Murine Antibody Sequences

| Murine Antibody | VH Domain* | VL Domain* |
|---|---|---|
| 305A | DVQLQESGPGLVKPSQSLSLTCSVTGYSITSGYYWNWIRQFPGNKLEWMGYISYDGSNNYNPSLKNRISITRDTSKNQFFLKLNSVTTEDTATYYCARRHDYLSFAYWGQGTLVIVSA(SEQ ID NO: 1289) | DIVLTQSPASLAVSLGQRATISCKASQSVDYDGDSYMNWYQQKPGQPPKLLIYAASNLESGIPARFSGSGSGTDFTLNIHPVEEEDAATYYCQQSDEDPYTFGGGTKLEIK(SEQ ID NO: 1290) |

*Bold amino acid residues represent CDR sequences (CDR1 - first bolded sequence; CDR2 - second bolded sequence; CDR3 - third bolded sequence)

In certain embodiments, the anti-C10orf54 antibody comprises a VH FR1, VH FR2, VH FR3, VH FR4, VL FR1, VL FR2, VL FR3, and/or VL FR4 of a human germline immunoglobulin amino acid sequence or a variant thereof. For example, in some embodiments, the anti-C10orf54 antibody comprises a VH FR1, VH FR2, VH FR3, and/or VH FR4 depicted in a human germline sequence identified in Table 3.

Accordingly, in some embodiments, the anti-C10orf54 antibody comprises a VH FR1, VH FR2, VH FR3, and/or VH FR4 of the human germline IGHV1-18 (SEQ ID NO:7) and IGHJ4-01 (SEQ ID NO: 82). In some embodiments, the anti-C10orf54 antibody comprises a VH FR1, VH FR2, VH FR3, and/or VH FR4 of the human germline IGHV3-48 (SEQ ID NO:8) and IGHJ4-01 (SEQ ID NO: 82). In some embodiments, the anti-C10orf54 antibody comprises a VH FR1, VH FR2, VH FR3, and/or VH FR4 of the human germline IGHV1-46*01 (SEQ ID NO:1902) and IGHJ4-01 (SEQ ID NO: 82). In some embodiments, the anti-C10orf54 antibody comprises a VH FR1, VH FR2, VH FR3, and/or VH FR4 of the human germline IGHV3-74*01 (SEQ ID NO:1903) and IGHJ4-01 (SEQ ID NO: 82). In some embodiments, the anti-C10orf54 antibody comprises a VH FR1, VH FR2, VH FR3, and/or VH FR4 of the human germline IGHV4-61*01 (SEQ ID NO:1904) and IGHJ4-01 (SEQ ID NO: 82). In some embodiments, the anti-C10orf54 antibody comprises a VL FR1, VL FR2, VL FR3, and/or VL FR4 of the human germline IGKV2-28 (SEQ ID NO:9) and IGKJ2-1 (SEQ ID NO:94). In some embodiments, the anti-C10orf54 antibody comprises a VL FR1, VL FR2, VL FR3, and/or VL FR4 of the human germline IGKV1-39 (SEQ ID NO:10) and IGKJ2-1 (SEQ ID NO:94). In some embodiments, the anti-C10orf54 antibody comprises a VL FR1, VL FR2, VL FR3, and/or VL FR4 of the human germline IGKV3-(SEQ ID NO:10) and IGKJ2-1 (SEQ ID NO:94). In some embodiments, the anti-C10orf54 antibody comprises a VL FR1, VL FR2, VL FR3, and/or VL FR4 of the human germline IGHV1-46*01 (SEQ ID NO:1920) and IGKJ2-1 (SEQ ID NO:94). In some embodiments, the anti-C10orf54 antibody comprises a VL FR1, VL FR2, VL FR3, and/or VL FR4 of the human germline IGHV3-74*01 (SEQ ID NO:1903) and IGKJ2-1 (SEQ ID NO:94). In some embodiments, the anti-C10orf54 antibody comprises a VL FR1, VL FR2, VL FR3, and/or VL FR4 of the human germline IGHV4-61*01 (SEQ ID NO:1904) and IGKJ2-1 (SEQ ID NO:94). In some embodiments, the anti-C10orf54 antibody comprises a VL FR1, VL FR2, VL FR3, and/or VL FR4 of the human germline IGKV2-28*01 (SEQ ID NO:1905) and IGKJ2-1 (SEQ ID NO:94). In some embodiments, the anti-C10orf54 antibody comprises a VL FR1, VL FR2, VL FR3, and/or VL FR4 of the human germline IGKV2-29*02 (SEQ ID NO:1906) and IGKJ2-1 (SEQ ID NO:94). In some embodiments, the anti-C10orf54 antibody comprises a VL FR1, VL FR2, VL FR3, and/or VL FR4 of the human germline IGKV1-39*01 (SEQ ID NO:1907) and IGKJ2-1 (SEQ ID NO:94). In some embodiments, the anti-C10orf54 antibody comprises a VL FR1, VL FR2, VL FR3, and/or VL FR4 of the human germline IGKV3-20*01 (SEQ ID NO:1908) and IGKJ2-1 (SEQ ID NO:94). In some embodiments, the anti-C10orf54 antibody comprises a VL FR1, VL FR2, VL FR3, and/or VL FR4 of the human germline IGKV3D-20*01 (SEQ ID NO:1909) and IGKJ2-1 (SEQ ID NO:94). In some embodiments, the anti-C10orf54 antibody comprises a VL FR1, VL FR2, VL FR3, and/or VL FR4 of the human germline IGKV3-11*01 (SEQ ID NO:1910) and IGKJ2-1 (SEQ ID NO:94). In some embodiments, the anti-C10orf54 antibody comprises a VL FR1, VL FR2, VL FR3, and/or VL FR4 of the human germline IGKV2-30*01 (SEQ ID NO:1911) and IGKJ2-1 (SEQ ID NO:94). In some embodiments, the anti-C10orf54 antibody comprises a VL FR1, VL FR2, VL FR3, and/or VL FR4 of the human germline IGKV2-30*02 (SEQ ID NO:1912) and IGKJ2-1 (SEQ ID NO:94). In some embodiments, the anti-C10orf54 antibody comprises a VL FR1, VL FR2, VL FR3, and/or VL FR4 of the human germline IGKV4-1*01 (SEQ ID NO:1913) and IGKJ2-1 (SEQ ID NO:94).

TABLE 3

Human Germline Immunoglobulin Amino Acid Sequences

| Human Germline | Amino Acid Sequence | SEQ ID NO: |
|---|---|---|
| Heavy Chain | | |
| IMGT IGHV1-18 | QVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCAR | (SEQ ID NO: 7) |

TABLE 3-continued

Human Germline Immunoglobulin Amino Acid Sequences

| Human Germline | Amino Acid Sequence | SEQ ID NO: |
|---|---|---|
| IMGT IGHV3-48 | EVQLVESGGGLVQPGGSLRLSCAASGFTFSS YSMNWVRQAPGKGLEWVSYISSSSSTIYYAD SVKGRFTISRDNAKNSLYLQMNSLRAEDTAV YYCAR | (SEQ ID NO: 8) |
| IMGT IGHV1-46*01 | QVQLVQSGAEVKKPGASVKVSCKASGYTFT SYYMHWVRQAPGQGLEWMGIINPSGGSTSY AQKFQGRVTMTRDTSTSTVYMELSSLRSEDT AVYYCAR | (SEQ ID NO: 1902) |
| IMGT IGHV3-74*01 | EVQLVESGGGLVQPGGSLRLSCAASGFTFSS YWMHWVRQAPGKGLVWVSRINSDGSSTSY ADSVKGRFTISRDNAKNTLYLQMNSLRAEDT AVYYCAR | (SEQ ID NO: 1903) |
| IMGT IGHV4-61*01 | QVQLQESGPGLVKPSETLSLTCTVSGGSVSS GSYYWSWIRQPPGKGLEWIGYIYYSGSTNYN PSLKSRVTISVDTSKNQFSLKLSSVTAADTAV YYCAR | (SEQ ID NO: 1904) |
| Joining region IMGT IGHJ4-01 | YFDYWGQGTLVTVSS | (SEQ ID NO: 82) |

Light Chain

| | | |
|---|---|---|
| IMGT IGKV2-28 | DIVMTQSPLSLPVTPGEPASISCRSSQSLLHS NGYNYLDWYLQKPGQSPQLLIYLGSNRASG VPDRFSGSGSGTDFTLKISRVEAEDVGVYYC MQALQTP | (SEQ ID NO: 9) |
| IMGT IGKV2-28*01 | DIVMTQSPLSLPVTPGEPASISCRSSQSLLHS NGYNYLDWYLQKPGQSPQLLIYLGSNRASG VPDRFSGSGSGTDFTLKISRVEAEDVGVYYC MQALQTPP | (SEQ ID NO: 1905) |
| IMGT IGKV2-29*02 | DIVMTQTPLSLSVTPGQPASISCKSSQSLLHS DGKTYLYWYLQKPGQSPQLLIYEVSSRFSGV PDRFSGSGSGTDFTLKISRVEAEDVGVYYCM QGIHLPP | (SEQ ID NO: 1906) |
| IMGT IGKV1-39 | DIQMTQSPSSLSASVGDRVTITCRASQSISSY LNWYQQKPGKAPKLLIYAASSLQSGVPSRFS GSGSGTDFTLTISSLQPEDFATYYCQQSYST P | (SEQ ID NO: 10) |
| IMGT IGKV1-39*01 | DIQMTQSPSSLSASVGDRVTITCRASQSISSY LNWYQQKPGKAPKLLIYAASSLQSGVPSRFS GSGSGTDFTLTISSLQPEDFATYYCQQSYST PP | (SEQ ID NO: 1907) |
| IMGT IGKV3-20 | EIVLTQSPGTLSLSPGERATLSCRASQSVSSS YLAWYQQKPGQAPRLLIYGASSRATGIPDRF SGSGSGTDFTLTISRLEPEDFAVYYCQQYGS SP | (SEQ ID NO: 11) |
| IMGT IGKV3-20*01 | EIVLTQSPGTLSLSPGERATLSCRASQSVSSS YLAWYQQKPGQAPRLLIYGASSRATGIPDRF SGSGSGTDFTLTISRLEPEDFAVYYCQQYGS SPP | (SEQ ID NO: 1908) |
| IMGT IGKV3D-20*01 | EIVLTQSPATLSLSPGERATLSCGASQSVSSS YLAWYQQKPGLAPRLLIYDASSRATGIPDRFS GSGSGTDFTLTISRLEPEDFAVYYCQQYGSS PP | (SEQ ID NO: 1909) |
| IMGT IGKV3-11*01 | EIVLTQSPATLSLSPGERATLSCRASQSVSSY LAWYQQKPGQAPRLLIYDASNRATGIPARFS GSGSGTDFTLTISSLEPEDFAVYYCQQRSNW PP | (SEQ ID NO: 1910) |
| IMGT IGKV2-30*01 | DVVMTQSPLSLPVTLGQPASISCRSSQSLVY SDGNTYLNWFQQRPGQSPRRLIYKVSNRDS GVPDRFSGSGSGTDFTLKISRVEAEDVGVYY CMQGTHWPP | (SEQ ID NO: 1911) |

TABLE 3-continued

Human Germline Immunoglobulin Amino Acid Sequences

| Human Germline | Amino Acid Sequence | SEQ ID NO: |
|---|---|---|
| IMGT IGKV2-30*02 | DVVMTQSPLSLPVTLGQPASISCRSSQSLVH SDGNTYLNWFQQRPGQSPRRLIYKVSNRDS GVPDRFSGSGSGTDFTLKISRVEAEDVGVYY CMQGTHWPP | (SEQ ID NO: 1912) |
| IMGT IGKV4-1*01 | DIVMTQSPDSLAVSLGERATINCKSSQSVLYS SNNKNYLAWYQQKPGQPPKLLIYWASTRES GVPDRFSGSGSGTDFTLTISSLQAEDVAVYY CQQYYSTPP | (SEQ ID NO: 1913) |
| Joining region IMGT IGKJ2-01 | YTFGQGTKLEIK | (SEQ ID NO: 94) |

*Bold amino acid residues represent CDR sequences (CDR1 - first bolded sequence; CDR2 - second bolded sequence; CDR3 - third bolded sequence)

In certain embodiments, antibodies that bind to C10orf54 (e.g., C10orf54 polypeptide, C10orf54 polypeptide fragment, C10orf54 epitope) comprise a VH domain having an amino acid sequence identified in Table 4 or FIG. 3-8, 22A, 22B1, 23A, 23B1, 24A, 24B1, 25A or 25B and/or a VL domain having an amino acid sequence identified in Table 4 or FIG. 3-8, 22A, 22B1, 23A, 23B1, 24A, 24B1, 25A or 25B.

TABLE 4

Humanized Antibody Amino Acid Sequences of VH and VL Domains

| Murine Clone | Humanized VH Domains (SEQ ID NO:) | Humanized VL Domains (SEQ ID NO:) |
|---|---|---|
| 76E1 | QVQLVQSGAEVKKPGASVKVSCKA SGYSFTGYNMNWVRQAPGQGLEW MGNIDPYYDYTSYNLKFKDRVTMTT DTSTSTAYMELRSLRSDDTAVYYCA RSTMITPFDYWGQGTLVTVSS (SEQ ID NO: 12) | DIVMTQSPLSLPVTPGEPASISCRSSQS IVHSNGNTYLEWYLQKPGQSPQLLIYK VSNRFSGVPDRFSGSGSGTDFTLKISR VEAEDVGVYYCFQGSHVPWTFGQGTK LEIK (SEQ ID NO: 24) |
| | QVQLVQSGAEVKKPGASVKVSCKA SGYSFTGYNMNWVRQAPGQGLEW MGNIDPYYDYTSYAQKLQGRVTMT TDTSTSTAYMELRSLRSDDTAVYYC ARSTMITPFDYWGQGTLVTVSS (SEQ ID NO: 13) | DIQMTQSPSSLSASVGDRVTITCRSSQ SIVHSNGNTYLEWYQQKPGKAPKLLIY KVSNRFSGVPSRFSGSGSGTDFTLTIS SLQPEDFATYYCFQGSHVPWTFGQGT KLEIK (SEQ ID NO: 25) |
| | EVQLVESGGGLVQPGGSLRLSCAA SGYSFTGYNMNWVRQAPGKGLEW VSNIDPYYDYTSYNLKFKDRFTISRD NAKNSLYLQMNSLRAEDTAVYYCA RSTMITPFDYWGQGTLVTVSS (SEQ ID NO: 14) | |
| | EVQLVESGGGLVQPGGSLRLSCAA SGYSFTGYNMNWVRQAPGKGLEW VSNIDPYYDYTSYADSVKGRFTISRD NAKNSLYLQMNSLRAEDTAVYYCA RSTMITPFDYWGQGTLVTVSS (SEQ ID NO: 15) | |
| 141A | QVQLVQSGAEVKKPGASVKVSCKA SGYTFSRYWIEWVRQAPGQGLEW MGEILPGSGSTNYNEKFKGRVTMTT DTSTSTAYMELRSLRSDDTAVYYCA REEVYDGYPWFGYWGQGTLVTVS S (SEQ ID NO: 16) | EIVLTQSPGTLSLSPGERATLSCRASSS LSYMHWYQQKPGQAPRLLIYATSNLAS GIPDRFSGSGSGTDFTLTISRLEPEDFA VYYCQQWSSNPYTFGQGTKLEIK (SEQ ID NO: 26) |
| | QVQLVQSGAEVKKPGASVKVSCKA SGYTFSRYWIEWVRQAPGQGLEW MGEILPGSGSTNYAQKLQGRVTMT TDTSTSTAYMELRSLRSDDTAVYYC AREEVYDGYPWFGYWGQGTLVTV SS (SEQ ID NO: 17) | DIQMTQSPSSLSASVGDRVTITCRASS SLSYMHWYQQKPGKAPKLLIYATSNLA SGVPSRFSGSGSGTDFTLTISSLQPED FATYYCQQWSSNPYTFGQGTKLEIK (SEQ ID NO: 27) |

TABLE 4-continued

Humanized Antibody Amino Acid Sequences of VH and VL Domains

| Murine Clone | Humanized VH Domains (SEQ ID NO:) | Humanized VL Domains (SEQ ID NO:) |
|---|---|---|
| | EVQLVESGGGLVQPGGSLRLSCAA SGYTFSRYWIEWVRQAPGKGLEWV SEILPGSGSTNYNEKFKGRFTISRDN AKNSLYLQMNSLRAEDTAVYYCARE EVYDGYPWFGYWGQGTLVTVSS (SEQ ID NO: 18) | |
| | EVQLVESGGGLVQPGGSLRLSCAA SGYTFSRYWIEWVRQAPGKGLEWV SEILPGSGSTNYADSVKGRFTISRD NAKNSLYLQMNSLRAEDTAVYYCA REEVYDGYPWFGYWGQGTLVTVS S (SEQ ID NO: 19) | |
| 175A | QVQLVQSGAEVKKPGASVKVSCKA SGYTFSTHWIEWVRQAPGQGLEW MGEILPGSGSTSYNEKFKGRVTMTT DTSTSTAYMELRSLRSDDTAVYYCA RWLLYYYAMDYWGQGTLVTVSS (SEQ ID NO: 20) | DIVMTQSPLSLPVTPGEPASISCRSSQS IVHSNGNTYLEWYLQKPGQSPQLLIYK LSNRFSGVPDRFSGSGSGTDFTLKISR VEAEDVGVYYCFQGSHFPYTFGQGTK LEIK (SEQ ID NO: 28) |
| | QVQLVQSGAEVKKPGASVKVSCKA SGYTFSTHWIEWVRQAPGQGLEW MGEILPGSGSTSYAQKLQGRVTMTT DTSTSTAYMELRSLRSDDTAVYYCA RWLLYYYAMDYWGQGTLVTVSS (SEQ ID NO: 21) | DIQMTQSPSSLSASVGDRVTITCRSSQ SIVHSNGNTYLEWYQQKPGKAPKLLIY KLSNRFSGVPSRFSGSGSGTDFTLTIS SLQPEDFATYYCFQGSHFPYTFGQGT KLEIK (SEQ ID NO: 29) |
| | EVQLVESGGGLVQPGGSLRLSCAA SGYTFSTHWIEWVRQAPGKGLEWV SEILPGSGSTSYNEKFKGRFTISRDN AKNSLYLQMNSLRAEDTAVYYCAR WLLYYYAMDYWGQGTLVTVSS (SEQ ID NO: 22) | |
| | EVQLVESGGGLVQPGGSLRLSCAA SGYTFSTHWIEWVRQAPGKGLEWV SEILPGSGSTSYADSVKGRFTISRDN AKNSLYLQMNSLRAEDTAVYYCAR WLLYYYAMDYWGQGTLVTVSS (SEQ ID NO: 23) | |
| 26A | QVQLVQSGAEVKKPGASVKVSCKA SGFSFTGYTMNWVRQAPGQGLEW MGLISPYNGGTSYAQKFQGRVTMT RDTSTSTVYMELSSLRSEDTAVYYC ARRAYGYAMDYWGQGTLVTVSS (SEQ ID NO: 1529) | EIVLTQSPATLSLSPGERATLSCSASSS VSYMYWYQQKPGQAPRLLIYDTSNLA SGIPARFSGSGSGTDFTLTISSLEPEDF AVYYCQQWSSYPFTFGQGTKLEIK (SEQ ID NO: 1532) |
| | QVQLVQSGAEVKKPGASVKISCKAS GFSFTGYTMNWVRQAPGQGLEWIG LISPYNGGTSYAQKFQGRATLTVDT STSTAYMELSSLRSEDTAVYYCARR AYGYAMDWGQGTLVTVSS (SEQ ID NO: 1530) | EIVLTQSPATLSLSPGERVTMSCSASS SVSYMYWYQQKPGQAPRLLIYDTSNL ASGVPARFSGSGSGTDYTLTISSMEPE DFAVYYCQQWSSYPFTFGQGTKLEIK (SEQ ID NO: 1533) |
| | QVQLVQSGAEVKKPGASVKISCKAS GFSFTGYTMNWVRQAPGQGLEWIG LISPYNGGTSYAQKFQGRATLTVDK STSTAYMELSSLRSEDTAVYYCARR AYGYAMDYWGQGTLVTVSS (SEQ ID NO: 1531) | EIVLTQSPATMSASPGERVTMSCSASS SVSYMYWYQQKPGQAPRLLIYDTSNL ASGVPARFSGSGSGTDYTLTISSMEPE DFAVYYCQQWSSYPFTFGQGTKLEIK (SEQ ID NO: 1534) |
| 128A | QVQLVQSGAEVKKPGASVKVSCKA SGYTFTDYGMHWVRQAPGQGLEW MGLIDTYYGDATYAQKFQGRVTMT RDTSTSTVYMELSSLRSEDTAVYYC ARRAGNAMDYWGQGTLVTVSS (SEQ ID NO: 1535) | DIQMTQSPSSLSASVGDRVTITCKASQ SVSNDIAWYQQKPGKAPKLLIYYASNR YTGVPSRFSGSGSGTDFTLTISSLQPE DFATYYCQQDYSSPRTFGQGTKLEIK (SEQ ID NO: 1538) |

TABLE 4-continued

Humanized Antibody Amino Acid Sequences of VH and VL Domains

| Murine Clone | Humanized VH Domains (SEQ ID NO:) | Humanized VL Domains (SEQ ID NO:) |
|---|---|---|
| | QVQLVQSGAEVKKPGASVKISCKGS GYTFTDYGMHWVRQAPGQGLEWI GLIDTYYGDATYAQKFQGRATMTVD TSTSTAYMELSSLRSEDTAVYYCAR RAGNAMDYWGQGTLVTVSS (SEQ ID NO: 1536) | DIQMTQSPSSLSVSVGDRVTITCKASQ SVSNDIAQYQQKPGKAPKLLIYYASNR YTGVPSRFSGSGSGTDFTFTISSVQPE DFATYYCQQDYSSPRTFGQGTKLEIK (SEQ ID NO: 1539) |
| | QVQLVQSGAEVKKPGASVKISCKGS GYTFTDYGMHWVRQAPGQGLEWI GLIDTYYGDATYAQKFQGRATMTVD KSTSTAYMELSSLRSEDTAVYYCAR RAGNAMDYWGQGTLVTVSS (SEQ ID NO: 1537) | DIQMTQSPSSLSVSVGDRVTITCKASQ SVSNDIAWYQQKPGKAPKLLIYYASNR YTGVPSRFSGSGYGTDFTFTISSVQPE DFATYYCQQDYSSPRTFGQGTKLEIK (SEQ ID NO: 1540) |
| 124A | QVQLVQSGAEVKKPGASVKVSCKA SGYTFSSNWIEWVRQAPGQGLEW MGEILPGSGSTSYAQKFQGRVTMT RDTSTSTVYMELSSLRSEDTAVYYC ARWLLYYYAMDFWGQGTLVTVSS (SEQ ID NO: 1541) | DVVMTQSPLSLPVTLGQPASISCRSSQ SIVHNNGNTYLEWFQQRPGQSPRRLIY KVSNRFSGVPDRFSGSGSGTDFTLKIS RVEAEDVGVYYCFQGSHVPYTFGQGT KLEIK (SEQ ID NO: 1546) |
| | QVQLVQSGAEVKKPGASVKISCKAS GYTFSSNWIEWVRQAPGQGLEWM GEILPGSGSTSYAQKFQGRATFTAD TSTSTAYMELSSLRSEDTAVYYCAR WLLYYYAMDFWGQGTLVTVSS (SEQ ID NO: 1542) | DVVMTQSPLSLPVTLGQPASISCRSSQ SIVHNNGNTYLEWYQQRPGQSPRLLIY KVSNRFSGVPDRFSGSGSGTDFTLKIS RVEAEDLGVYYCFQGSHVPYTFGQGT KLEIK (SEQ ID NO: 1547) |
| 259A | QVQLVQSGAEVKKPGASVKVSCKA SGYTFTSYFMHWVRQAPGQGLEW MGYIYPYNDGTKYAQKFQGRVTMT RDTSTSTVYMELSSLRSEDTAVYYC ARFDYDTLRYWGQGTLVTVSS (SEQ ID NO: 1543) | DIVMTQSPLSLPVTPGEPASISCKSTKS LLNSDGFTYLDWYLQKPGQSPQLLIYLI SNRFSGVPDRFSGSGSGTDFTLKISRV EAEDVGVYYCFQSNYFPWTFGQGTKL EIK (SEQ ID NO: 1548) |
| | QVQLVQSGAEVKKPGASVKMSCKA SGYTFTSYFMHWVRQAPGQGLEWI GYIYPYNDGTKYAQKFQGRATLTSD TSTSTAYMELSSLRSEDTAVYYCAR FDYDTLRYWGQGTLLTVSS (SEQ ID NO: 1544) | DIVLTQSPLSLPVTPGEPASISCKSTKS LLNSDGFTYLDWYLQKPGQSPQLLIYLI SNRFSGVPDRFSGSGSGTDFTLKISRV EAEDLGVYYCFQSNYFPWTFGQGTKL EIK (SEQ ID NO: 1549) |
| | QVQLVQSGAEVKKPGASVKMSCKA SGYTFTSYFMHWVRQAPGQGLEWI GYIYPYNDGTKYAQKFQGRATLTSD KSTSTAYMELSSLRSEDTAVYYCAR FDYDTLRYWGQGTLLTVSS (SEQ ID NO: 1545) | |

Accordingly, in some embodiments, antibodies that bind to C10orf54 (e.g., C10orf54 polypeptide, C10orf54 polypeptide fragment, C10orf54 epitope) comprise a VH domain having the amino acid sequence of SEQ ID NOS:20, 21, 22, 23, 1529-1531, 1535-1537, or 1541-1545 and/or a VL domain having the amino acid sequence of SEQ ID NO:28, 29, 1532-1534, 1538-1540, or 1546-1549. In one embodiment, an antibody that binds to C10orf54 (e.g., C10orf54 polypeptide, C10orf54 polypeptide fragment, C10orf54 epitope) comprises a VH domain having the amino acid sequence of SEQ ID NO:20 and/or a VL domain having the amino acid sequence of SEQ ID NO:28. In one aspect an antibody that binds to C10orf54 (e.g., C10orf54 polypeptide, C10orf54 polypeptide fragment, C10orf54 epitope) comprises a VH domain having the amino acid sequence of SEQ ID NO:21 and/or a VL domain having the amino acid sequence of SEQ ID NO:28. In one aspect an antibody that binds to C10orf54 (e.g., C10orf54 polypeptide, C10orf54 polypeptide fragment, C10orf54 epitope) comprises a VH domain having the amino acid sequence of SEQ ID NO:22 and/or a VL domain having the amino acid sequence of SEQ ID NO:28. In one aspect an antibody that binds to C10orf54 (e.g., C10orf54 polypeptide, C10orf54 polypeptide fragment, C10orf54 epitope) comprises a VH domain having the amino acid sequence of SEQ ID NO:23 and/or a VL domain having the amino acid sequence of SEQ ID NO:28. In one aspect an antibody that binds to C10orf54 (e.g., C10orf54 polypeptide, C10orf54 polypeptide fragment, C10orf54 epitope) comprises a VH domain having the amino acid sequence of SEQ ID NO:20 and/or a VL domain having the amino acid sequence of SEQ ID NO:29. In one aspect an antibody that binds to C10orf54 (e.g., C10orf54 polypeptide, C10orf54 polypeptide fragment, C10orf54 epitope) comprises a VH domain having the amino acid sequence of SEQ ID NO:21 and/or a VL domain having the amino acid sequence of SEQ ID NO:29. In one aspect an antibody that binds to C10orf54 (e.g., C10orf54 polypeptide, C10orf54 polypeptide fragment, C10orf54 epitope) comprises a VH domain having the amino acid sequence of SEQ ID NO:22 and/or a VL domain having the amino acid sequence of SEQ ID NO:29. In one aspect an antibody that binds to C10orf54 (e.g., C10orf54 polypeptide, C10orf54 polypeptide fragment, C10orf54 epitope) comprises a VH domain having the amino acid sequence of SEQ ID NO:23 and/or a VL domain having the amino acid sequence of SEQ ID NO:29.

In some embodiments, antibodies that bind to C10orf54 (e.g., C10orf54 polypeptide, C10orf54 polypeptide fragment, C10orf54 epitope) comprise a VH domain having the amino acid sequence of SEQ ID NOS:12, 13, 14 or 15 and/or a VL domain having the amino acid sequence of SEQ ID NO:24 or 25. Accordingly, in one aspect an antibody that binds to C10orf54 (e.g., C10orf54 polypeptide, C10orf54 polypeptide fragment, C10orf54 epitope) comprises a VH domain having the amino acid sequence of SEQ ID NO:12 and/or a VL domain having the amino acid sequence of SEQ ID NO:24. In one aspect an antibody that binds to C10orf54 (e.g., C10orf54 polypeptide, C10orf54 polypeptide fragment, C10orf54 epitope) comprises a VH domain having the amino acid sequence of SEQ ID NO:13 and/or a VL domain having the amino acid sequence of SEQ ID NO:24. In one aspect an antibody that binds to C10orf54 (e.g., C10orf54 polypeptide, C10orf54 polypeptide fragment, C10orf54 epitope) comprises a VH domain having the amino acid sequence of SEQ ID NO:14 and/or a VL domain having the amino acid sequence of SEQ ID NO:24. In one aspect an antibody that binds to C10orf54 (e.g., C10orf54 polypeptide, C10orf54 polypeptide fragment, C10orf54 epitope) comprises a VH domain having the amino acid sequence of SEQ ID NO:15 and/or a VL domain having the amino acid sequence of SEQ ID NO:24. In one aspect an antibody that binds to C10orf54 (e.g., C10orf54 polypeptide, C10orf54 polypeptide fragment, C10orf54 epitope) comprises a VH domain having the amino acid sequence of SEQ ID NO:12 and/or a VL domain having the amino acid sequence of SEQ ID NO:25. In one aspect an antibody that binds to C10orf54 (e.g., C10orf54 polypeptide, C10orf54 polypeptide fragment, C10orf54 epitope) comprises a VH domain having the amino acid sequence of SEQ ID NO:13 and/or a VL domain having the amino acid sequence of SEQ ID NO:25. In one aspect an antibody that binds to C10orf54 (e.g., C10orf54 polypeptide, C10orf54 polypeptide fragment, C10orf54 epitope) comprises a VH domain having the amino acid sequence of SEQ ID NO:14 and/or a VL domain having the amino acid sequence of SEQ ID NO:25. In one aspect an antibody that binds to C10orf54 (e.g., C10orf54 polypeptide, C10orf54 polypeptide fragment, C10orf54 epitope) comprises a VH domain having the amino acid sequence of SEQ ID NO:15 and/or a VL domain having the amino acid sequence of SEQ ID NO:25.

In some embodiments, antibodies that bind to C10orf54 (e.g., C10orf54 polypeptide, C10orf54 polypeptide fragment, C10orf54 epitope) comprise a VH domain having the amino acid sequence of SEQ ID NOS:16, 17, 18 or 19 and/or a VL domain having the amino acid sequence of SEQ ID NO:26 or 27. Accordingly, in one aspect an antibody that binds to C10orf54 (e.g., C10orf54 polypeptide, C10orf54 polypeptide fragment, C10orf54 epitope) comprises a VH domain having the amino acid sequence of SEQ ID NO:16 and/or a VL domain having the amino acid sequence of SEQ ID NO:26. In one aspect an antibody that binds to C10orf54 (e.g., C10orf54 polypeptide, C10orf54 polypeptide fragment, C10orf54 epitope) comprises a VH domain having the amino acid sequence of SEQ ID NO:17 and/or a VL domain having the amino acid sequence of SEQ ID NO:26. In one aspect an antibody that binds to C10orf54 (e.g., C10orf54 polypeptide, C10orf54 polypeptide fragment, C10orf54 epitope) comprises a VH domain having the amino acid sequence of SEQ ID NO:18 and/or a VL domain having the amino acid sequence of SEQ ID NO:26. In one aspect an antibody that binds to C10orf54 (e.g., C10orf54 polypeptide, C10orf54 polypeptide fragment, C10orf54 epitope) comprises a VH domain having the amino acid sequence of SEQ ID NO:19 and/or a VL domain having the amino acid sequence of SEQ ID NO:26. In one aspect an antibody that binds to C10orf54 (e.g., C10orf54 polypeptide, C10orf54 polypeptide fragment, C10orf54 epitope) comprises a VH domain having the amino acid sequence of SEQ ID NO:16 and/or a VL domain having the amino acid sequence of SEQ ID NO:27. In one aspect an antibody that binds to C10orf54 (e.g., C10orf54 polypeptide, C10orf54 polypeptide fragment, C10orf54 epitope) comprises a VH domain having the amino acid sequence of SEQ ID NO:17 and/or a VL domain having the amino acid sequence of SEQ ID NO:27. In one aspect an antibody that binds to C10orf54 (e.g., C10orf54 polypeptide, C10orf54 polypeptide fragment, C10orf54 epitope) comprises a VH domain having the amino acid sequence of SEQ ID NO:18 and/or a VL domain having the amino acid sequence of SEQ ID NO:27. In one aspect an antibody that binds to C10orf54 (e.g., C10orf54 polypeptide, C10orf54 polypeptide fragment, C10orf54 epitope) comprises a VH domain having the amino acid sequence of SEQ ID NO:19 and/or a VL domain having the amino acid sequence of SEQ ID NO:27.

In certain embodiments, antibodies provided herein that bind to a C10orf54 epitope comprise a VH region having a VH CDR1, VH CDR2, and/or VH CDR3, that have an amino acid sequence identified in Tables 5-11 or Tables 12-33 below; and/or a VL region having VL CDR1, VL CDR 2 and/or VL CDR3 that have an amino acid sequence identified in Tables 5-11 or Tables 12-33 below.

TABLE 5

Amino Acid Sequences derived from Murine 175A Antibody.

175A HUMANIZED ANTIBODY SEQUENCE: HEAVY CHAIN 175A-huVH1a Variable Region

QVQLVQSGAEVKKPGASVKVSCKASGYTFSTHWIEWVRQAPGQGLEWMGEILPGSGSTS
YNEKFKGRVTMTTDTSTSTAYMELRSLRSDDTAVYYCARWLLYYYAMDYWGQGTLVTVS
S (SEQ ID NO: 20)

175A-huVH1a VH FR1

QVQLVQSGAEVKKPGASVKVSCKAS (SEQ ID NO: 51)

QVQLVQSGAEVKKPGASVKISCKAS (SEQ ID NO: 105)

TABLE 5-continued

Amino Acid Sequences derived from Murine 175A Antibody.

175A-huVH1a VH CDR1

GYTFSTHWIE (SEQ ID NO: 36)

175A-huVH1a VH FR2

WVRQAPGQGLEWMG (SEQ ID NO: 52)

WVRQAPGQGLEWIG (SEQ ID NO: 106)

175A-huVH1a VH CDR2

EILPGSGSTSYNEKFKG (SEQ ID NO: 37)

EILPGSGSTSYQEKFKG (SEQ ID NO: 101)

EILPGSGSTSYSEKFKG (SEQ ID NO: 102)

EILPGSGSTSYDEKFKG (SEQ ID NO: 103)

EILPGSGSTSYAEKFKG (SEQ ID NO: 104)

175A-huVH1a VH FR3

RVTMTTDTSTSTAYMELRSLRSDDTAVYYCAR (SEQ ID NO: 53)

RATMTTDTSTSTAYMELRSLRSDDTAVYYCAR (SEQ ID NO: 107)

RVTFTTDTSTSTAYMELRSLRSDDTAVYYCAR (SEQ ID NO: 108)

RVTMTADTSTSTAYMELRSLRSDDTAVYYCAR (SEQ ID NO: 109)

RATFTTDTSTSTAYMELRSLRSDDTAVYYCAR (SEQ ID NO: 110)

RVTFTADTSTSTAYMELRSLRSDDTAVYYCAR (SEQ ID NO: 111)

RATMTADTSTSTAYMELRSLRSDDTAVYYCAR (SEQ ID NO: 112)

RATFTADTSTSTAYMELRSLRSDDTAVYYCAR (SEQ ID NO: 113)

175A-huVH1a VH CDR3

WLLYYYAMDY (SEQ ID NO: 38)

175A-huVH1a VH FR4

WGQGTLVTVSS (SEQ ID NO: 54)

175A-huVH1b Variable Region

QVQLVQSGAEVKKPGASVKVSCKASGYTFSTHWIEWVRQAPGQGLEWMGEILPGSGSTS
YAQKLQGRVTMTTDTSTSTAYMELRSLRSDDTAVYYCARWLLYYYAMDYWGQGTLVTVS
S (SEQ ID NO: 21)

175A-huVH1b VH FR1

QVQLVQSGAEVKKPGASVKVSCKAS (SEQ ID NO: 51)

QVQLVQSGAEVKKPGASVKISCKAS (SEQ ID NO: 105)

175A-huVH1b VH CDR1

GYTFSTHWIE (SEQ ID NO: 36)

175A-huVH1b VH FR2

WVRQAPGQGLEWMG (SEQ ID NO: 52)

WVRQAPGQGLEWIG (SEQ ID NO: 106)

175A-huVH1b VH CDR2*

EILPGSGSTSYAQKLQG (SEQ ID NO: 50)

EILPGSGSTSYAQKFQG (SEQ ID NO: 114)

TABLE 5-continued

Amino Acid Sequences derived from Murine 175A Antibody.

175A-huVH1b VH FR3

RVTMTTDTSTSTAYMELRSLRSDDTAVYYCAR (SEQ ID NO: 53)

RATMTTDTSTSTAYMELRSLRSDDTAVYYCAR (SEQ ID NO: 107)

RVTFTTDTSTSTAYMELRSLRSDDTAVYYCAR (SEQ ID NO: 108)

RVTMTADTSTSTAYMELRSLRSDDTAVYYCAR (SEQ ID NO: 109)

RATFTTDTSTSTAYMELRSLRSDDTAVYYCAR (SEQ ID NO: 110)

RVTFTADTSTSTAYMELRSLRSDDTAVYYCAR (SEQ ID NO: 111)

RATMTADTSTSTAYMELRSLRSDDTAVYYCAR (SEQ ID NO: 112)

RATFTADTSTSTAYMELRSLRSDDTAVYYCAR (SEQ ID NO: 113)

175A-huVH1b VH CDR3

WLLYYYAMDY (SEQ ID NO: 38)

175A-huVH1b VH FR4

WGQGTLVTVSS (SEQ ID NO: 54)

175A-huVH3a Variable Region

EVQLVESGGGLVQPGGSLRLSCAASGYTFSTHWIEWVRQAPGKGLEWVSEILPGSGSTSY
NEKFKGRFTISRDNAKNSLYLQMNSLRAEDTAVYYCARWLLYYYAMDYWGQGTLVTVSS
(SEQ ID NO: 22)

175A-huVH3a VH FR1

EVQLVESGGGLVQPGGSLRLSCAAS (SEQ ID NO: 55)

EVQLVQSGGGLVQPGGSLRLSCAAS (SEQ ID NO: 115)

EVQLVESGGGLVQPGGSVRLSCAAS (SEQ ID NO: 116)

EVQLVESGGGLVQPGGSLRISCAAS (SEQ ID NO: 117)

EVQLVQSGGGLVQPGGSVRLSCAAS (SEQ ID NO: 118)

EVQLVESGGGLVQPGGSVRISCAAS (SEQ ID NO: 119)

EVQLVQSGGGLVQPGGSLRISCAAS (SEQ ID NO: 120)

EVQLVQSGGGLVQPGGSVRISCAAS (SEQ ID NO: 121)

175A-huVH3a VH CDR1

GYTFSTHWIE (SEQ ID NO: 36)

175A-huVH3a VH FR2

WVRQAPGKGLEWVS (SEQ ID NO: 56)

WVRQAPGKGLEWIS (SEQ ID NO: 122)

WVRQAPGKGLEWVG (SEQ ID NO: 123)

WVRQAPGKGLEWIG (SEQ ID NO: 124)

175A-huVH3a VH CDR2

EILPGSGSTSYNEKFKG (SEQ ID NO: 37)

EILPGSGSTSYQEKFKG (SEQ ID NO: 101)

EILPGSGSTSYSEKFKG (SEQ ID NO: 102)

EILPGSGSTSYDEKFKG (SEQ ID NO: 103)

EILPGSGSTSYAEKFKG (SEQ ID NO: 104)

TABLE 5-continued

Amino Acid Sequences derived from Murine 175A Antibody.

175A-huVH3a VH FR3

RFTISRDNAKNSLYLQMNSLRAEDTAVYYCAR (SEQ ID NO: 57)

RATISRDNAKNSLYLQMNSLRAEDTAVYYCAR (SEQ ID NO: 125)

RFTFSRDNAKNSLYLQMNSLRAEDTAVYYCAR (SEQ ID NO: 126)

RFTISADNAKNSLYLQMNSLRAEDTAVYYCAR (SEQ ID NO: 127)

RFTISRDTAKNSLYLQMNSLRAEDTAVYYCAR (SEQ ID NO: 128)

RFTISRDNAKNSAYLQMNSLRAEDTAVYYCAR (SEQ ID NO: 129)

RFTISRDNAKNSLYMQMNSLRAEDTAVYYCAR (SEQ ID NO: 130)

RFTISRDNAKNSLYLQLNSLRAEDTAVYYCAR (SEQ ID NO: 131)

RATFSRDNAKNSLYLQMNSLRAEDTAVYYCAR (SEQ ID NO: 132)

RATISADNAKNSLYLQMNSLRAEDTAVYYCAR (SEQ ID NO: 133)

RATISRDTAKNSLYLQMNSLRAEDTAVYYCAR (SEQ ID NO: 134)

RATISRDNAKNSAYLQMNSLRAEDTAVYYCAR (SEQ ID NO: 135)

RATISRDNAKNSLYMQMNSLRAEDTAVYYCAR (SEQ ID NO: 136)

RATISRDNAKNSLYLQLNSLRAEDTAVYYCAR (SEQ ID NO: 137)

RFTFSADNAKNSLYLQMNSLRAEDTAVYYCAR (SEQ ID NO: 138)

RFTFSRDTAKNSLYLQMNSLRAEDTAVYYCAR (SEQ ID NO: 139)

RFTFSRDNAKNSAYLQMNSLRAEDTAVYYCAR (SEQ ID NO: 140)

RFTFSRDNAKNSLYMQMNSLRAEDTAVYYCAR (SEQ ID NO: 141)

RFTFSRDNAKNSLYLQLNSLRAEDTAVYYCAR (SEQ ID NO: 142)

RFTISADTAKNSLYLQMNSLRAEDTAVYYCAR (SEQ ID NO: 143)

RFTISADNAKNSAYLQMNSLRAEDTAVYYCAR (SEQ ID NO: 144)

RFTISADNAKNSLYMQMNSLRAEDTAVYYCAR (SEQ ID NO: 145)

RFTISADNAKNSLYLQLNSLRAEDTAVYYCAR (SEQ ID NO: 146)

RFTISRDTAKNSAYLQMNSLRAEDTAVYYCAR (SEQ ID NO: 147)

RFTISRDTAKNSLYMQMNSLRAEDTAVYYCAR (SEQ ID NO: 148)

RFTISRDTAKNSLYLQLNSLRAEDTAVYYCAR (SEQ ID NO: 149)

RFTISRDNAKNSAYMQMNSLRAEDTAVYYCAR (SEQ ID NO: 150)

RFTISRDNAKNSAYLQLNSLRAEDTAVYYCAR (SEQ ID NO: 151)

RFTISRDNAKNSLYMQLNSLRAEDTAVYYCAR (SEQ ID NO: 152)

RATFSADNAKNSLYLQMNSLRAEDTAVYYCAR (SEQ ID NO: 153)

RATFSRDTAKNSLYLQMNSLRAEDTAVYYCAR (SEQ ID NO: 154)

RATFSRDNAKNSAYLQMNSLRAEDTAVYYCAR (SEQ ID NO: 155)

RATFSRDNAKNSLYMQMNSLRAEDTAVYYCAR (SEQ ID NO: 156)

RATFSRDNAKNSLYLQLNSLRAEDTAVYYCAR (SEQ ID NO: 157)

RATISADTAKNSLYLQMNSLRAEDTAVYYCAR (SEQ ID NO: 158)

RATISADNAKNSAYLQMNSLRAEDTAVYYCAR (SEQ ID NO: 159)

RATISADNAKNSLYMQMNSLRAEDTAVYYCAR (SEQ ID NO: 160)

RATISADNAKNSLYLQLNSLRAEDTAVYYCAR (SEQ ID NO: 161)

TABLE 5-continued

Amino Acid Sequences derived from Murine 175A Antibody.

RATISRDTAKNSAYLQMNSLRAEDTAVYYCAR (SEQ ID NO: 162)

RATISRDTAKNSLYMQMNSLRAEDTAVYYCAR (SEQ ID NO: 163)

RATISRDTAKNSLYLQLNSLRAEDTAVYYCAR (SEQ ID NO: 164)

RATISRDNAKNSAYMQMNSLRAEDTAVYYCAR (SEQ ID NO: 165)

RATISRDNAKNSAYLQLNSLRAEDTAVYYCAR (SEQ ID NO: 166)

RATISRDNAKNSLYMQLNSLRAEDTAVYYCAR (SEQ ID NO: 167)

RFTFSADTAKNSLYLQMNSLRAEDTAVYYCAR (SEQ ID NO: 168)

RFTFSADNAKNSAYLQMNSLRAEDTAVYYCAR (SEQ ID NO: 169)

RFTFSADNAKNSLYMQMNSLRAEDTAVYYCAR (SEQ ID NO: 170)

RFTFSADNAKNSLYLQLNSLRAEDTAVYYCAR (SEQ ID NO: 171)

RFTFSRDTAKNSAYLQMNSLRAEDTAVYYCAR (SEQ ID NO: 172)

RFTFSRDTAKNSLYMQMNSLRAEDTAVYYCAR (SEQ ID NO: 173)

RFTFSRDTAKNSLYLQLNSLRAEDTAVYYCAR (SEQ ID NO: 174)

RFTFSRDNAKNSAYMQMNSLRAEDTAVYYCAR (SEQ ID NO: 175)

RFTFSRDNAKNSAYLQLNSLRAEDTAVYYCAR (SEQ ID NO: 176)

RFTFSRDNAKNSLYMQLNSLRAEDTAVYYCAR (SEQ ID NO: 177)

RFTISADTAKNSAYLQMNSLRAEDTAVYYCAR (SEQ ID NO: 178)

RFTISADTAKNSLYMQMNSLRAEDTAVYYCAR (SEQ ID NO: 179)

RFTISADTAKNSLYLQLNSLRAEDTAVYYCAR (SEQ ID NO: 180)

RFTISADNAKNSAYMQMNSLRAEDTAVYYCAR (SEQ ID NO: 181)

RFTISADNAKNSAYLQLNSLRAEDTAVYYCAR (SEQ ID NO: 182)

RFTISADNAKNSLYMQLNSLRAEDTAVYYCAR (SEQ ID NO: 183)

RFTISRDTAKNSAYMQMNSLRAEDTAVYYCAR (SEQ ID NO: 184)

RFTISRDTAKNSAYLQLNSLRAEDTAVYYCAR (SEQ ID NO: 185)

RFTISRDTAKNSLYMQLNSLRAEDTAVYYCAR (SEQ ID NO: 186)

RFTISRDNAKNSAYMQLNSLRAEDTAVYYCAR (SEQ ID NO: 187)

RATFSADTAKNSLYLQMNSLRAEDTAVYYCAR (SEQ ID NO: 188)

RATFSADNAKNSAYLQMNSLRAEDTAVYYCAR (SEQ ID NO: 189)

RATFSADNAKNSLYMQMNSLRAEDTAVYYCAR (SEQ ID NO: 190)

RATFSADNAKNSLYLQLNSLRAEDTAVYYCAR (SEQ ID NO: 191)

RATFSRDTAKNSAYLQMNSLRAEDTAVYYCAR (SEQ ID NO: 192)

RATFSRDTAKNSLYMQMNSLRAEDTAVYYCAR (SEQ ID NO: 193)

RATFSRDTAKNSLYLQLNSLRAEDTAVYYCAR (SEQ ID NO: 194)

RATFSRDNAKNSAYMQMNSLRAEDTAVYYCAR (SEQ ID NO: 195)

RATFSRDNAKNSAYLQLNSLRAEDTAVYYCAR (SEQ ID NO: 196)

RATFSRDNAKNSLYMQLNSLRAEDTAVYYCAR (SEQ ID NO: 197)

RATISADTAKNALYLQMNSLRAEDTAVYYCAR (SEQ ID NO: 198)

RATISADTAKNSLYMQMNSLRAEDTAVYYCAR (SEQ ID NO: 199)

RATISADTAKNSLYLQLNSLRAEDTAVYYCAR (SEQ ID NO: 200)

TABLE 5-continued

Amino Acid Sequences derived from Murine 175A Antibody.

RATISADNAKNSAYMQMNSLRAEDTAVYYCAR (SEQ ID NO: 201)

RATISADNAKNSAYLQLNSLRAEDTAVYYCAR (SEQ ID NO: 202)

RATISADNAKNSLYMQLNSLRAEDTAVYYCAR (SEQ ID NO: 203)

RATISRDTAKNSAYMQMNSLRAEDTAVYYCAR (SEQ ID NO: 204)

RATISRDTAKNSAYLQLNSLRAEDTAVYYCAR (SEQ ID NO: 205)

RATISRDTAKNSLYMQLNSLRAEDTAVYYCAR (SEQ ID NO: 206)

RATISRDNAKNSAYMQLNSLRAEDTAVYYCAR (SEQ ID NO: 207)

RFTFSADTAKNSAYLQMNSLRAEDTAVYYCAR (SEQ ID NO: 208)

RFTFSADTAKNSLYMQMNSLRAEDTAVYYCAR (SEQ ID NO: 209)

RFTFSADTAKNSLYLQLNSLRAEDTAVYYCAR (SEQ ID NO: 210)

RFTFSADNAKNSAYMQMNSLRAEDTAVYYCAR (SEQ ID NO: 211)

RFTFSADNAKNSAYLQLNSLRAEDTAVYYCAR (SEQ ID NO: 212)

RFTFSADNAKNSLYMQLNSLRAEDTAVYYCAR (SEQ ID NO: 213)

RFTFSRDTAKNSAYMQMNSLRAEDTAVYYCAR (SEQ ID NO: 214)

RFTFSRDTAKNSAYLQLNSLRAEDTAVYYCAR (SEQ ID NO: 215)

RFTFSRDTAKNSLYMQLNSLRAEDTAVYYCAR (SEQ ID NO: 216)

RFTFSRDNAKNSAYMQMNSLRAEDTAVYYCAR (SEQ ID NO: 217)

RFTISADTAKNSAYMQMNSLRAEDTAVYYCAR (SEQ ID NO: 218)

RFTISADTAKNSAYLQLNSLRAEDTAVYYCAR (SEQ ID NO: 219)

RFTISADTAKNSLYMQLNSLRAEDTAVYYCAR (SEQ ID NO: 220)

RFTISADNAKNSAYMQLNSLRAEDTAVYYCAR (SEQ ID NO: 221)

RFTISRDTAKNSAYMQLNSLRAEDTAVYYCAR (SEQ ID NO: 222)

RATFSADTAKNSAYLQMNSLRAEDTAVYYCAR (SEQ ID NO: 223)

RATFSADTAKNSLYMQMNSLRAEDTAVYYCAR (SEQ ID NO: 224)

RATFSADTAKNSLYLQLNSLRAEDTAVYYCAR (SEQ ID NO: 225)

RATFSADNAKNSAYMQMNSLRAEDTAVYYCAR (SEQ ID NO: 226)

RATFSADNAKNSAYLQLNSLRAEDTAVYYCAR (SEQ ID NO: 227)

RATFSADNAKNSLYMQLNSLRAEDTAVYYCAR (SEQ ID NO: 228)

RATFSRDTAKNSAYMQMNSLRAEDTAVYYCAR (SEQ ID NO: 229)

RATFSRDTAKNSAYLQLNSLRAEDTAVYYCAR (SEQ ID NO: 230)

RATFSRDTAKNSLYMQLNSLRAEDTAVYYCAR (SEQ ID NO: 231)

RATFSRDNAKNSAYMQLNSLRAEDTAVYYCAR (SEQ ID NO: 232)

RATISADTAKNALYMQMNSLRAEDTAVYYCAR (SEQ ID NO: 233)

RATISADTAKNALYLQLNSLRAEDTAVYYCAR (SEQ ID NO: 234)

RATISADTAKNSLYMQLNSLRAEDTAVYYCAR (SEQ ID NO: 235)

RATISADNAKNSAYMQLNSLRAEDTAVYYCAR (SEQ ID NO: 236)

RATISRDTAKNSAYMQLNSLRAEDTAVYYCAR (SEQ ID NO: 237)

RFTFSADTAKNSAYMQMNSLRAEDTAVYYCAR (SEQ ID NO: 238)

RFTFSADTAKNSAYLQLNSLRAEDTAVYYCAR (SEQ ID NO: 239)

TABLE 5-continued

Amino Acid Sequences derived from Murine 175A Antibody.

RFTFSADTAKNSLYMQLNSLRAEDTAVYYCAR (SEQ ID NO: 240)

RFTFSADNAKNSAYMQLNSLRAEDTAVYYCAR (SEQ ID NO: 241)

RFTFSRDTAKNSAYMQLNSLRAEDTAVYYCAR (SEQ ID NO: 242)

RFTISADTAKNSAYMQ**LNSLRAEDTAVYYCAR (SEQ ID NO: 243)

RATFSADTAKNSAY**MQMNSLRAEDTAVYYCAR (SEQ ID NO: 244)

RATFSADTAKNSAYLQLNSLRAEDTAVYYCAR (SEQ ID NO: 245)

RATFSADTAKNSLYMQLNSLRAEDTAVYYCAR (SEQ ID NO: 246)

RATFSADNAKNSAYMQLNSLRAEDTAVYYCAR (SEQ ID NO: 247)

RATFSRDTAKNSAYMQLNSLRAEDTAVYYCAR (SEQ ID NO: 248)

RATISADTAKNALYMQLNSLRAEDTAVYYCAR (SEQ ID NO: 249)

RFTFSADTAKNSAYMQ**LNSLRAEDTAVYYCAR (SEQ ID NO: 250)

RATFSADTAKNSAYMQ**LNSLRAEDTAVYYCAR (SEQ ID NO: 251)

175A-huVH3a VH CDR3

WLLYYYAMDY (SEQ ID NO: 38)

175A-huVH3a VH FR4

WGQGTLVTVSS (SEQ ID NO: 54)

175A-huVH3b Variable Region

EVQLVESGGGLVQPGGSLRLSCAASGYTFSTHWIEWVRQAPGKGLEWVSEILPGSGSTSY
ADSVKGRFTISRDNAKNSLYLQMNSLRAEDTAVYYCARWLLYYYAMDYWGQGTLVTVSS
(SEQ ID NO: 23)

175A-huVH3b VH FR1

EVQLVESGGGLVQPGGSLRLSCAAS (SEQ ID NO: 55)

EVQLVQSGGGLVQPGGSLRLSCAAS (SEQ ID NO: 115)

EVQLVESGGGLVQPGGSVRLSCAAS (SEQ ID NO: 116)

EVQLVESGGGLVQPGGSLRISCAAS (SEQ ID NO: 117)

EVQLVQSGGGLVQPGGSVRLSCAAS (SEQ ID NO: 118)

EVQLVESGGGLVQPGGSVRISCAAS (SEQ ID NO: 119)

EVQLVQSGGGLVQPGGSLRISCAAS (SEQ ID NO: 120)

EVQLVQSGGGLVQPGGSVRISCAAS (SEQ ID NO: 121)

175A-huVH3b VH CDR1

GYTFSTHWIE (SEQ ID NO: 36)

175A-huVH3b VH FR2

WVRQAPGKGLEWVS (SEQ ID NO: 56)

WVRQAPGKGLEWIS (SEQ ID NO: 122)

WVRQAPGKGLEWVG (SEQ ID NO: 123)

WVRQAPGKGLEWIG (SEQ ID NO: 124)

175A-huVH3b VH CDR2*

EILPGSGSTSYADSVKG (SEQ ID NO: 99)

EILPGSGSTSYADSFKG (SEQ ID NO: 100)

TABLE 5-continued

Amino Acid Sequences derived from Murine 175A Antibody.

175A-huVH3b VH FR3

RFTISRDNAKNSLYLQMNSLRAEDTAVYYCAR (SEQ ID NO: 57)

RATISRDNAKNSLYLQMNSLRAEDTAVYYCAR (SEQ ID NO: 125)

RFTFSRDNAKNSLYLQMNSLRAEDTAVYYCAR (SEQ ID NO: 126)

RFTISADNAKNSLYLQMNSLRAEDTAVYYCAR (SEQ ID NO: 127)

RFTISRDTAKNSLYLQMNSLRAEDTAVYYCAR (SEQ ID NO: 128)

RFTISRDNAKNSAYLQMNSLRAEDTAVYYCAR (SEQ ID NO: 129)

RFTISRDNAKNSLYMQMNSLRAEDTAVYYCAR (SEQ ID NO: 130)

RFTISRDNAKNSLYLQLNSLRAEDTAVYYCAR (SEQ ID NO: 131)

RATFSRDNAKNSLYLQMNSLRAEDTAVYYCAR (SEQ ID NO: 132)

RATISADNAKNSLYLQMNSLRAEDTAVYYCAR (SEQ ID NO: 133)

RATISRDTAKNSLYLQMNSLRAEDTAVYYCAR (SEQ ID NO: 134)

RATISRDNAKNSAYLQMNSLRAEDTAVYYCAR (SEQ ID NO: 135)

RATISRDNAKNSLYMQMNSLRAEDTAVYYCAR (SEQ ID NO: 136)

RATISRDNAKNSLYLQLNSLRAEDTAVYYCAR (SEQ ID NO: 137)

RFTFSADNAKNSLYLQMNSLRAEDTAVYYCAR (SEQ ID NO: 138)

RFTFSRDTAKNSLYLQMNSLRAEDTAVYYCAR (SEQ ID NO: 139)

RFTFSRDNAKNSAYLQMNSLRAEDTAVYYCAR (SEQ ID NO: 140)

RFTFSRDNAKNSLYMQMNSLRAEDTAVYYCAR (SEQ ID NO: 141)

RFTFSRDNAKNSLYLQLNSLRAEDTAVYYCAR (SEQ ID NO: 142)

RFTISADT**AKNSLYLQMNSLRAEDTAVYYCAR (SEQ ID NO: 143)

RFTISADNAKNSAYLQMNSLRAEDTAVYYCAR (SEQ ID NO: 144)

RFTISADNAKNSLYMQMNSLRAEDTAVYYCAR (SEQ ID NO: 145)

RFTISADNAKNSLYLQLNSLRAEDTAVYYCAR (SEQ ID NO: 146)

RFTISRDTAKNSAYLQMNSLRAEDTAVYYCAR (SEQ ID NO: 147)

RFTISRDTAKNSLYMQMNSLRAEDTAVYYCAR (SEQ ID NO: 148)

RFTISRDTAKNSLYLQLNSLRAEDTAVYYCAR (SEQ ID NO: 149)

RFTISRDNAKNSAYMQMNSLRAEDTAVYYCAR (SEQ ID NO: 150)

RFTISRDNAKNSAYLQLNSLRAEDTAVYYCAR (SEQ ID NO: 151)

RFTISRDNAKNSLYMQLNSLRAEDTAVYYCAR (SEQ ID NO: 152)

RATFSADNAKNSLYLQMNSLRAEDTAVYYCAR (SEQ ID NO: 153)

RATFSRDTAKNSLYLQMNSLRAEDTAVYYCAR (SEQ ID NO: 154)

RATFSRDNAKNSAYLQMNSLRAEDTAVYYCAR (SEQ ID NO: 155)

RATFSRDNAKNSLYMQMNSLRAEDTAVYYCAR (SEQ ID NO: 156)

RATFSRDNAKNSLYLQLNSLRAEDTAVYYCAR (SEQ ID NO: 157)

RATISADTAKNSLYLQMNSLRAEDTAVYYCAR (SEQ ID NO: 158)

RATISADNAKNSAYLQMNSLRAEDTAVYYCAR (SEQ ID NO: 159)

RATISADNAKNSLYMQMNSLRAEDTAVYYCAR (SEQ ID NO: 160)

RATISADNAKNSLYLQLNSLRAEDTAVYYCAR (SEQ ID NO: 161)

TABLE 5-continued

Amino Acid Sequences derived from Murine 175A Antibody.

RATISRDTAKNSAYLQMNSLRAEDTAVYYCAR (SEQ ID NO: 162)

RATISRDTAKNSLYMQMNSLRAEDTAVYYCAR (SEQ ID NO: 163)

RATISRDTAKNSLYLQLNSLRAEDTAVYYCAR (SEQ ID NO: 164)

RATISRDNAKNSAYMQMNSLRAEDTAVYYCAR (SEQ ID NO: 165)

RATISRDNAKNSAYLQLNSLRAEDTAVYYCAR (SEQ ID NO: 166)

RATISRDNAKNSLYMQLNSLRAEDTAVYYCAR (SEQ ID NO: 167)

RFTFSADTAKNSLYLQMNSLRAEDTAVYYCAR (SEQ ID NO: 168)

RFTFSADNAKNSAYLQMNSLRAEDTAVYYCAR (SEQ ID NO: 169)

RFTFSADNAKNSLYMQMNSLRAEDTAVYYCAR (SEQ ID NO: 170)

RFTFSADNAKNSLYLQLNSLRAEDTAVYYCAR (SEQ ID NO: 171)

RFTFSRDTAKNSAYLQMNSLRAEDTAVYYCAR (SEQ ID NO: 172)

RFTFSRDTAKNSLYMQMNSLRAEDTAVYYCAR (SEQ ID NO: 173)

RFTFSRDTAKNSLYLQLNSLRAEDTAVYYCAR (SEQ ID NO: 174)

RFTFSRDNAKNSAYMQMNSLRAEDTAVYYCAR (SEQ ID NO: 175)

RFTFSRDNAKNSAYLQLNSLRAEDTAVYYCAR (SEQ ID NO: 176)

RFTFSRDNAKNSLYMQLNSLRAEDTAVYYCAR (SEQ ID NO: 177)

RFTISADTAKNSAYLQMNSLRAEDTAVYYCAR (SEQ ID NO: 178)

RFTISADTAKNSLYMQMNSLRAEDTAVYYCAR (SEQ ID NO: 179)

RFTISADTAKNSLYLQLNSLRAEDTAVYYCAR (SEQ ID NO: 180)

RFTISADNAKNSAYMQMNSLRAEDTAVYYCAR (SEQ ID NO: 181)

RFTISADNAKNSAYLQLNSLRAEDTAVYYCAR (SEQ ID NO: 182)

RFTISADNAKNSLYMQLNSLRAEDTAVYYCAR (SEQ ID NO: 183)

RFTISRDTAKNSAYMQMNSLRAEDTAVYYCAR (SEQ ID NO: 184)

RFTISRDTAKNSAYLQLNSLRAEDTAVYYCAR (SEQ ID NO: 185)

RFTISRDTAKNSLYMQLNSLRAEDTAVYYCAR (SEQ ID NO: 186)

RFTISRDNAKNSAYMQLNSLRAEDTAVYYCAR (SEQ ID NO: 187)

RATFSADTAKNSLYLQMNSLRAEDTAVYYCAR (SEQ ID NO: 188)

RATFSADNAKNSAYLQMNSLRAEDTAVYYCAR (SEQ ID NO: 189)

RATFSADNAKNSLYMQMNSLRAEDTAVYYCAR (SEQ ID NO: 190)

RATFSADNAKNSLYLQLNSLRAEDTAVYYCAR (SEQ ID NO: 191)

RATFSRDTAKNSAYLQMNSLRAEDTAVYYCAR (SEQ ID NO: 192)

RATFSRDTAKNSLYMQMNSLRAEDTAVYYCAR (SEQ ID NO: 193)

RATFSRDTAKNSLYLQLNSLRAEDTAVYYCAR (SEQ ID NO: 194)

RATFSRDNAKNSAYMQMNSLRAEDTAVYYCAR (SEQ ID NO: 195)

RATFSRDNAKNSAYLQLNSLRAEDTAVYYCAR (SEQ ID NO: 196)

RATFSRDNAKNSLYMQLNSLRAEDTAVYYCAR (SEQ ID NO: 197)

RATISADTAKNALYLQMNSLRAEDTAVYYCAR (SEQ ID NO: 198)

RATISADTAKNSLYMQMNSLRAEDTAVYYCAR (SEQ ID NO: 199)

RATISADTAKNSLYLQLNSLRAEDTAVYYCAR (SEQ ID NO: 200)

TABLE 5-continued

Amino Acid Sequences derived from Murine 175A Antibody.

RATISADNAKNSAYMQMNSLRAEDTAVYYCAR (SEQ ID NO: 201)

RATISADNAKNSAYLQLNSLRAEDTAVYYCAR (SEQ ID NO: 202)

RATISADNAKNSLYMQLNSLRAEDTAVYYCAR (SEQ ID NO: 203)

RATISRDTAKNSAYMQMNSLRAEDTAVYYCAR (SEQ ID NO: 204)

RATISRDTAKNSAYLQLNSLRAEDTAVYYCAR (SEQ ID NO: 205)

RATISRDTAKNSLYMQLNSLRAEDTAVYYCAR (SEQ ID NO: 206)

RATISRDNAKNSAYMQLNSLRAEDTAVYYCAR (SEQ ID NO: 207)

RFTFSADTAKNSAYLQMNSLRAEDTAVYYCAR (SEQ ID NO: 208)

RFTFSADTAKNSLYMQMNSLRAEDTAVYYCAR (SEQ ID NO: 209)

RFTFSADTAKNSLYLQLNSLRAEDTAVYYCAR (SEQ ID NO: 210)

RFTFSADNAKNSAYMQMNSLRAEDTAVYYCAR (SEQ ID NO: 211)

RFTFSADNAKNSAYLQLNSLRAEDTAVYYCAR (SEQ ID NO: 212)

RFTFSADNAKNSLYMQLNSLRAEDTAVYYCAR (SEQ ID NO: 213)

RFTFSRDTAKNSAYMQMNSLRAEDTAVYYCAR (SEQ ID NO: 214)

RFTFSRDTAKNSAYLQLNSLRAEDTAVYYCAR (SEQ ID NO: 215)

RFTFSRDTAKNSLYMQLNSLRAEDTAVYYCAR (SEQ ID NO: 216)

RFTFSRDNAKNSAYMQLNSLRAEDTAVYYCAR (SEQ ID NO: 217)

RFTISADTAKNSAYMQMNSLRAEDTAVYYCAR (SEQ ID NO: 218)

RFTISADTAKNSAYLQLNSLRAEDTAVYYCAR (SEQ ID NO: 219)

RFTISADTAKNSLYMQLNSLRAEDTAVYYCAR (SEQ ID NO: 220)

RFTISADNAKNSAYMQLNSLRAEDTAVYYCAR (SEQ ID NO: 221)

RFTISRDTAKNSAYMQLNSLRAEDTAVYYCAR (SEQ ID NO: 222)

RATFSADTAKNSAYLQMNSLRAEDTAVYYCAR (SEQ ID NO: 223)

RATFSADTAKNSLYMQMNSLRAEDTAVYYCAR (SEQ ID NO: 224)

RATFSADTAKNSLYLQLNSLRAEDTAVYYCAR (SEQ ID NO: 225)

RATFSADNAKNSAYMQMNSLRAEDTAVYYCAR (SEQ ID NO: 226)

RATFSADNAKNSAYLQLNSLRAEDTAVYYCAR (SEQ ID NO: 227)

RATFSADNAKNSLYMQLNSLRAEDTAVYYCAR (SEQ ID NO: 228)

RATFSRDTAKNSAYMQMNSLRAEDTAVYYCAR (SEQ ID NO: 229)

RATFSRDTAKNSAYLQLNSLRAEDTAVYYCAR (SEQ ID NO: 230)

RATFSRDTAKNSLYMQLNSLRAEDTAVYYCAR (SEQ ID NO: 231)

RATFSRDNAKNSAYMQLNSLRAEDTAVYYCAR (SEQ ID NO: 232)

RATISADTAKNALYMQMNSLRAEDTAVYYCAR (SEQ ID NO: 233)

RATISADTAKNALYLQLNSLRAEDTAVYYCAR (SEQ ID NO: 234)

RATISADTAKNSLYMQLNSLRAEDTAVYYCAR (SEQ ID NO: 235)

RATISADNAKNSAYMQLNSLRAEDTAVYYCAR (SEQ ID NO: 236)

RATISRDTAKNSAYMQLNSLRAEDTAVYYCAR (SEQ ID NO: 237)

RFTFSADTAKNSAYMQMNSLRAEDTAVYYCAR (SEQ ID NO: 238)

RFTFSADTAKNSAYLQLNSLRAEDTAVYYCAR (SEQ ID NO: 239)

TABLE 5-continued

Amino Acid Sequences derived from Murine 175A Antibody.

RFTFSADTAKNSLYMQLNSLRAEDTAVYYCAR (SEQ ID NO: 240)

RFTFSADNAKNSAYMQLNSLRAEDTAVYYCAR (SEQ ID NO: 241)

RFTFSRDTAKNSAYMQLNSLRAEDTAVYYCAR (SEQ ID NO: 242)

RFTISADTAKNSAYMQLNSLRAEDTAVYYCAR (SEQ ID NO: 243)

RATFSADTAKNSAYMQMNSLRAEDTAVYYCAR (SEQ ID NO: 244)

RATFSADTAKNSAYLQLNSLRAEDTAVYYCAR (SEQ ID NO: 245)

RATFSADTAKNSLYMQLNSLRAEDTAVYYCAR (SEQ ID NO: 246)

RATFSADNAKNSAYMQLNSLRAEDTAVYYCAR (SEQ ID NO: 247)

RATFSRDTAKNSAYMQLNSLRAEDTAVYYCAR (SEQ ID NO: 248)

RATISADTAKNALYMQLNSLRAEDTAVYYCAR (SEQ ID NO: 249)

RFTFSADTAKNSAYMQLNSLRAEDTAVYYCAR (SEQ ID NO: 250)

RATFSADTAKNSAYMQLNSLRAEDTAVYYCAR (SEQ ID NO: 251)

175A-huVH3b VH CDR3

WLLYYYAMDY (SEQ ID NO: 38)

175A-huVH3b VH FR4

WGQGTLVTVSS (SEQ ID NO: 54)

175A HUMANIZED ANTIBODY SEQUENCE: LIGHT CHAIN 175A-huVK2 Variable Region

DIVMTQSPLSLPVTPGEPASISCRSSQSIVHSNGNTYLEWYLQKPGQSPQLLIYKLSNRFSG
VPDRFSGSGSGTDFTLKISRVEAEDVGVYYCFQGSHFPYTFGQGTKLEIK
(SEQ ID NO: 28)

175A-huVK2 VL FR1

DIVMTQSPLSLPVTPGEPASISC (SEQ ID NO: 75)

DVVMTQSPLSLPVTPGEPASISC (SEQ ID NO: 252)

175A-huVK2 VL CDR1

RSSQSIVHSNGNTYLE (SEQ ID NO: 45)

RSSQSIVHSQGNTYLE (SEQ ID NO: 253)

RSSQSIVHSSGNTYLE (SEQ ID NO: 254)

RSSQSIVHSAGNTYLE (SEQ ID NO: 255)

RSSQSIVHSNGQTYLE (SEQ ID NO: 256)

RSSQSIVHSNGSTYLE (SEQ ID NO: 257)

RSSQSIVHSNGATYLE (SEQ ID NO: 258)

RSSQSIVHSNGDTYLE (SEQ ID NO: 259)

RSSQSIVHSQGQTYLE (SEQ ID NO: 260)

RSSQSIVHSQGSTYLE (SEQ ID NO: 261)

RSSQSIVHSQGATYLE (SEQ ID NO: 262)

RSSQSIVHSQGDTYLE (SEQ ID NO: 263)

RSSQSIVHSSGQTYLE (SEQ ID NO: 264)

RSSQSIVHSSGSTYLE (SEQ ID NO: 265)

RSSQSIVHSSGATYLE (SEQ ID NO: 266)

TABLE 5-continued

Amino Acid Sequences derived from Murine 175A Antibody.

RSSQSIVHSSGDTYLE (SEQ ID NO: 267)

RSSQSIVHSAGQTYLE (SEQ ID NO: 268)

RSSQSIVHSAGSTYLE (SEQ ID NO: 269)

RSSQSIVHSAGATYLE (SEQ ID NO: 270)

RSSQSIVHSAGDTYLE (SEQ ID NO: 271)

175A-huVK2 VL FR2

WYLQKPGQSPQLLIY (SEQ ID NO: 76)

175A-huVK2 VL CDR2

KLSNRFS (SEQ ID NO: 46)

KLSQRFS (SEQ ID NO: 272)

KLSSRFS (SEQ ID NO: 273)

KLSARFS (SEQ ID NO: 274)

KLSDRFS (SEQ ID NO: 275)

175A-huVK2 VL FR3

GVPDRFSGSGSGTDFTLKISRVEAEDVGVYYC (SEQ ID NO: 77)

GVPDRFSGSGSGTDFTLKISRVEAEDLGVYYC (SEQ ID NO: 276)

175A-huVK2 VL CDR3

FQGSHFPYT (SEQ ID NO: 47)

175A-huVK2 VL FR4

FGQGTKLEIK (SEQ ID NO: 78)

175A-huVK1 Variable Region

DIQMTQSPSSLSASVGDRVTITCRSSQSIVHSNGNTYLEWYQQKPGKAPKLLIYKLSNRFS
GVPSRFSGSGSGTDFTLTISSLQPEDFATYYCFQGSHFPYTFGQGTKLEIK
(SEQ ID NO: 29)

175A-huVK1 VL FR1

DIQMTQSPSSLSASVGDRVTITC (SEQ ID NO: 79)

DVQMTQSPSSLSASVGDRVTITC (SEQ ID NO: 277)

DIQMTQSPSSLSVSVGDRVTITC (SEQ ID NO: 278)

DIQMTQSPSSLSASVGDRATITC (SEQ ID NO: 279)

DVQMTQSPSSLSVSVGDRVTITC (SEQ ID NO: 280)

DVQMTQSPSSLSASVGDRATITC (SEQ ID NO: 281)

DIQMTQSPSSLSVSVGDRATITC (SEQ ID NO: 282)

DVQMTQSPSSLSVSVGDRATITC (SEQ ID NO: 283)

175A-huVK1 VL CDR1

RSSQSIVHSNGNTYLE (SEQ ID NO: 45)

RSSQSIVHSQGNTYLE (SEQ ID NO: 253)

RSSQSIVHSSGNTYLE (SEQ ID NO: 254)

RSSQSIVHSAGNTYLE (SEQ ID NO: 255)

RSSQSIVHSNGQTYLE (SEQ ID NO: 256)

RSSQSIVHSNGSTYLE (SEQ ID NO: 257)

TABLE 5-continued

Amino Acid Sequences derived from Murine 175A Antibody.

RSSQSIVHSNGATYLE (SEQ ID NO: 258)

RSSQSIVHSNGDTYLE (SEQ ID NO: 259)

RSSQSIVHSQGQTYLE (SEQ ID NO: 260)

RSSQSIVHSQGSTYLE (SEQ ID NO: 261)

RSSQSIVHSQGATYLE (SEQ ID NO: 262)

RSSQSIVHSQGDTYLE (SEQ ID NO: 263)

RSSQSIVHSSGQTYLE (SEQ ID NO: 264)

RSSQSIVHSSGSTYLE (SEQ ID NO: 265)

RSSQSIVHSSGATYLE (SEQ ID NO: 266)

RSSQSIVHSSGDTYLE (SEQ ID NO: 267)

RSSQSIVHSAGQTYLE (SEQ ID NO: 268)

RSSQSIVHSAGSTYLE (SEQ ID NO: 269)

RSSQSIVHSAGATYLE (SEQ ID NO: 270)

RSSQSIVHSAGDTYLE (SEQ ID NO: 271)

175A-huVK1 VL FR2

WYQQKPGKAPKLLIY (SEQ ID NO: 80)

WYQQKPGKSPKLLIY (SEQ ID NO: 284)

175A-huVK1 VL CDR2

KLSNRFS (SEQ ID NO: 46)

KLSQRFS (SEQ ID NO: 272)

KLSSRFS (SEQ ID NO: 273)

KLSARFS (SEQ ID NO: 274)

KLSDRFS (SEQ ID NO: 275)

175A-huVK1 VL FR3

GVPSRFSGSGSGTDFTLTISSLQPEDFATYYC (SEQ ID NO: 81)

GVPSRFSGSGSGTDFTLTISSVQPEDFATYYC (SEQ ID NO: 285)

GVPSRFSGSGSGTDFTLTISSLQPEDLATYYC (SEQ ID NO: 286)

GVPSRFSGSGSGTDFTLTISSLQPEDFGTYYC (SEQ ID NO: 287)

GVPSRFSGSGSGTDFTLTISSVQPEDLATYYC (SEQ ID NO: 288)

GVPSRFSGSGSGTDFTLTISSVQPEDFGTYYC (SEQ ID NO: 289)

GVPSRFSGSGSGTDFTLTISSLQPEDLGTYYC (SEQ ID NO: 290)

GVPSRFSGSGSGTDFTLTISSVQPEDLGTYYC (SEQ ID NO: 291)

TABLE 5-continued

Amino Acid Sequences derived from Murine 175A Antibody.

175A-huVK1 VL CDR3

FQGSHFPYT (SEQ ID NO: 47)

175A-huVK1 VL FR4

FGQGTKLEIK (SEQ ID NO: 78)

*Amino acid position numbering as in Kabat.

TABLE 6

Amino Acid Sequences derived from Murine 76E1 Antibody.

76E1 HUMANIZED ANTIBODY SEQUENCE: HEAVY CHAIN

76E1-huVH1a Variable Region

QVQLVQSGAEVKKPGASVKVSCKASGYSFTGYNMNWVRQAPGQGLEWMGNIDPYYDYT
SYNLKFKDRVTMTTDTSTSTAYMELRSLRSDDTAVYYCARSTMITPFDYWGQGTLVTVSS
(SEQ ID NO: 12)

76E1-huVH1a VH FR1

QVQLVQSGAEVKKPGASVKVSCKAS (SEQ ID NO: 51)

QVQLVQSGAEVKKPGASVKISCKAS (SEQ ID NO: 105)

76E1-huVH1a VH CDR1

GYSFTGYNMN (SEQ ID NO: 30)

GYSFTGYQMN (SEQ ID NO: 59)

GYSFTGYSMN (SEQ ID NO: 60)

GYSFTGYDMN (SEQ ID NO: 61)

GYSFTGYAMN (SEQ ID NO: 62)

76E1-huVH1a VH FR2

WVRQAPGQGLEWMG (SEQ ID NO: 52)

WVRQAPGQSLEWMG (SEQ ID NO: 63)

WVRQAPGQGLEWIG (SEQ ID NO: 106)

WVRQAPGQSLEWIG (SEQ ID NO: 64)

76E1-huVH1a VH CDR2

NIDPYYDYTSYNLKFKD (SEQ ID NO: 31)

NIEPYYDYTSYNLKFKD (SEQ ID NO: 65)

NISPYYDYTSYNLKFKD (SEQ ID NO: 66)

NIAPYYDYTSYNLKFKD (SEQ ID NO: 67)

NIDPYYDYTSYQLKFKD (SEQ ID NO: 68)

NIDPYYDYTSYSLKFKD (SEQ ID NO: 69)

NIDPYYDYTSYDLKFKD (SEQ ID NO: 70)

NIDPYYDYTSYALKFKD (SEQ ID NO: 71)

NIEPYYDYTSYQLKFKD (SEQ ID NO: 72)

NIEPYYDYTSYSLKFKD (SEQ ID NO: 73)

NIEPYYDYTSYDLKFKD (SEQ ID NO: 74)

NIEPYYDYTSYALKFKD (SEQ ID NO: 83)

TABLE 6-continued

Amino Acid Sequences derived from Murine 76E1 Antibody.

NISPYYDYTSYQLKFKD (SEQ ID NO: 84)

NISPYYDYTSYSLKFKD (SEQ ID NO: 85)

NISPYYDYTSYDLKFKD (SEQ ID NO: 86)

NISPYYDYTSYALKFKD (SEQ ID NO: 87)

NIAPYYDYTSYQLKFKD (SEQ ID NO: 88)

NIAPYYDYTSYSLKFKD (SEQ ID NO: 89)

NIAPYYDYTSYDLKFKD (SEQ ID NO: 90)

NIAPYYDYTSYALKFKD (SEQ ID NO: 95)

76E1-huVH1a VH FR3

RVTMTTDTSTSTAYMELRSLRSDDTAVYYCAR (SEQ ID NO: 53)

RATMTTDTSTSTAYMELRSLRSDDTAVYYCAR (SEQ ID NO: 107)

RVTLTTDTSTSTAYMELRSLRSDDTAVYYCAR (SEQ ID NO: 96)

RVTMTVDTSTSTAYMELRSLRSDDTAVYYCAR (SEQ ID NO: 97)

RVTMTTDKSTSTAYMELRSLRSDDTAVYYCAR (SEQ ID NO: 98)

RVTMTTDTSTSTAYMELRSLRSDDTAVYYCAT (SEQ ID NO: 292)

RATLTTDTSTSTAYMELRSLRSDDTAVYYCAR (SEQ ID NO: 293)

RATMTVDTSTSTAYMELRSLRSDDTAVYYCAR (SEQ ID NO: 294)

RATMTTDKSTSTAYMELRSLRSDDTAVYYCAR (SEQ ID NO: 295)

RATMTTDTSTSTAYMELRSLRSDDTAVYYCAT (SEQ ID NO: 296)

RVTLTVDTSTSTAYMELRSLRSDDTAVYYCAR (SEQ ID NO: 297)

RVTLTTDKSTSTAYMELRSLRSDDTAVYYCAR (SEQ ID NO: 298)

RVTLTTDTSTSTAYMELRSLRSDDTAVYYCAT (SEQ ID NO: 299)

RVTMTVDKSTSTAYMELRSLRSDDTAVYYCAR (SEQ ID NO: 300)

RVTMTVDTSTSTAYMELRSLRSDDTAVYYCAT (SEQ ID NO: 301)

RVTMTTDKSTSTAYMELRSLRSDDTAVYYCAT (SEQ ID NO: 302)

RATLTVDTSTSTAYMELRSLRSDDTAVYYCAR (SEQ ID NO: 303)

RATLTTDKSTSTAYMELRSLRSDDTAVYYCAR (SEQ ID NO: 304)

RATLTTDTSTSTAYMELRSLRSDDTAVYYCAT (SEQ ID NO: 305)

RATMTVDKSTSTAYMELRSLRSDDTAVYYCAR (SEQ ID NO: 306)

RATMTVDTSTSTAYMELRSLRSDDTAVYYCAT (SEQ ID NO: 307)

RATMTTDKSTSTAYMELRSLRSDDTAVYYCAT (SEQ ID NO: 308)

RVTLTVDKSTSTAYMELRSLRSDDTAVYYCAR (SEQ ID NO: 309)

RVTLTVDTSTSTAYMELRSLRSDDTAVYYCAT (SEQ ID NO: 310)

RVTLTTDKSTSTAYMELRSLRSDDTAVYYCAT (SEQ ID NO: 311)

RVTMTVDKSTSTAYMELRSLRSDDTAVYYCAT (SEQ ID NO: 312)

RATLTVDKSTSTAYMELRSLRSDDTAVYYCAR (SEQ ID NO: 313)

RATLTVDTSTSTAYMELRSLRSDDTAVYYCAT (SEQ ID NO: 314)

RATLTTDKSTSTAYMELRSLRSDDTAVYYCAT (SEQ ID NO: 315)

RATMTVDKSTSTAYMELRSLRSDDTAVYYCAT (SEQ ID NO: 316)

TABLE 6-continued

Amino Acid Sequences derived from Murine 76E1 Antibody.

RVTLTVDKSTSTAYMELRSLRSDDTAVYYCAT (SEQ ID NO: 317)

RATLTVDKSTSTAYMELRSLRSDDTAVYYCAT (SEQ ID NO: 318)

76E1-huVH1a VH CDR3

STMITPFDY (SEQ ID NO: 32)

STLITPFDY (SEQ ID NO: 319)

76E1-huVH1a VH FR4

WGQGTLVTVSS (SEQ ID NO: 54)

WGQGTLLTVSS (SEQ ID NO: 320)

76E1-huVH1b Variable Region

QVQLVQSGAEVKKPGASVKVSCKASGYSFTGYNMNWVRQAPGQGLEWMGNIDPYYDYT
SYAQKLQGRVTMTTDTSTSTAYMELRSLRSDDTAVYYCARSTMITPFDYWGQGTLVTVSS
(SEQ ID NO: 13)

76E1-huVH1b VH FR1

QVQLVQSGAEVKKPGASVKVSCKAS (SEQ ID NO: 51)

QVQLVQSGAEVKKPGASVKISCKAS (SEQ ID NO: 105)

76E1-huVH1b VH CDR1

GYSFTGYNMN (SEQ ID NO: 30)

GYSFTGYQMN (SEQ ID NO: 59)

GYSFTGYSMN (SEQ ID NO: 60)

GYSFTGYDMN (SEQ ID NO: 61)

GYSFTGYAMN (SEQ ID NO: 62)

76E1-huVH1b VH FR2

WVRQAPGQGLEWMG (SEQ ID NO: 52)

WVRQAPGQSLEWMG (SEQ ID NO: 63)

WVRQAPGQGLEWIG (SEQ ID NO: 106)

WVRQAPGQSLEWIG (SEQ ID NO: 64)

76E1-huVH1b VH CDR2*

NIDPYYDYTSYAQKLQG (SEQ ID NO: 321)

NIDPYYDYTSYAQKFQG (SEQ ID NO: 322)

76E1-huVH1b VH FR3

RVTMTTDTSTSTAYMELRSLRSDDTAVYYCAR (SEQ ID NO: 53)

RATMTTDTSTSTAYMELRSLRSDDTAVYYCAR (SEQ ID NO: 107)

RVTLTTDTSTSTAYMELRSLRSDDTAVYYCAR (SEQ ID NO: 96)

RVTMTVDTSTSTAYMELRSLRSDDTAVYYCAR (SEQ ID NO: 97)

RVTMTTDKSTSTAYMELRSLRSDDTAVYYCAR (SEQ ID NO: 98)

RVTMTTDTSTSTAYMELRSLRSDDTAVYYCAT (SEQ ID NO: 292)

RATLTTDTSTSTAYMELRSLRSDDTAVYYCAR (SEQ ID NO: 293)

RATMTVDTSTSTAYMELRSLRSDDTAVYYCAR (SEQ ID NO: 294)

RATMTTDKSTSTAYMELRSLRSDDTAVYYCAR (SEQ ID NO: 295)

TABLE 6-continued

Amino Acid Sequences derived from Murine 76E1 Antibody.

RATMTTDTSTSTAYMELRSLRSDDTAVYYCAT (SEQ ID NO: 296)

RVTLTVDTSTSTAYMELRSLRSDDTAVYYCAR (SEQ ID NO: 297)

RVTLTTDKSTSTAYMELRSLRSDDTAVYYCAR (SEQ ID NO: 298)

RVTLTTDTSTSTAYMELRSLRSDDTAVYYCAT (SEQ ID NO: 299)

RVTMTVDKSTSTAYMELRSLRSDDTAVYYCAR (SEQ ID NO: 300)

RVTMTVDTSTSTAYMELRSLRSDDTAVYYCAT (SEQ ID NO: 301)

RVTMTTDKSTSTAYMELRSLRSDDTAVYYCAT (SEQ ID NO: 302)

RATLTVDTSTSTAYMELRSLRSDDTAVYYCAR (SEQ ID NO: 303)

RATLTTDKSTSTAYMELRSLRSDDTAVYYCAR (SEQ ID NO: 304)

RATLTTDTSTSTAYMELRSLRSDDTAVYYCAT (SEQ ID NO: 305)

RATMTVDKSTSTAYMELRSLRSDDTAVYYCAR (SEQ ID NO: 306)

RATMTVDTSTSTAYMELRSLRSDDTAVYYCAT (SEQ ID NO: 307)

RATMTTDKSTSTAYMELRSLRSDDTAVYYCAT (SEQ ID NO: 308)

RVTLTVDKSTSTAYMELRSLRSDDTAVYYCAR (SEQ ID NO: 309)

RVTLTVDTSTSTAYMELRSLRSDDTAVYYCAT (SEQ ID NO: 310)

RVTLTTDKSTSTAYMELRSLRSDDTAVYYCAT (SEQ ID NO: 311)

RVTMTVDKSTSTAYMELRSLRSDDTAVYYCAT (SEQ ID NO: 312)

RATLTVDKSTSTAYMELRSLRSDDTAVYYCAR (SEQ ID NO: 313)

RATLTVDTSTSTAYMELRSLRSDDTAVYYCAT (SEQ ID NO: 314)

RATLTTDKSTSTAYMELRSLRSDDTAVYYCAT (SEQ ID NO: 315)

RATMTVDKSTSTAYMELRSLRSDDTAVYYCAT (SEQ ID NO: 316)

RVTLTVDKSTSTAYMELRSLRSDDTAVYYCAT (SEQ ID NO: 317)

RATLTVDKSTSTAYMELRSLRSDDTAVYYCAT (SEQ ID NO: 318)

76E1-huVH1b VH CDR3

STMITPFDY (SEQ ID NO: 32)

STLITPFDY (SEQ ID NO: 319)

76E1-huVH1b VH FR4

WGQGTLVTVSS (SEQ ID NO: 54)

WGQGTLLTVSS (SEQ ID NO: 320)

76E1-huVH3a Variable Region

EVQLVESGGGLVQPGGSLRLSCAASGYSFTGYNMNWVRQAPGKGLEWVSNIDPYYDTS
YNLKFKDRFTISRDNAKNSLYLQMNSLRAEDTAVYYCARSTMITPFDYWGQGTLVTVSS
(SEQ ID NO: 14)

76E1-huVH3a VH FR1

EVQLVESGGGLVQPGGSLRLSCAAS (SEQ ID NO: 55)

EVQLVQSGGGLVQPGGSLRLSCAAS (SEQ ID NO: 115)

EVQLVESGGGLVQPGGSVRLSCAAS (SEQ ID NO: 116)

EVQLVESGGGLVQPGGSLRISCAAS (SEQ ID NO: 117)

EVQLVQSGGGLVQPGGSVRLSCAAS (SEQ ID NO: 118)

EVQLVESGGGLVQPGGSVRISCAAS (SEQ ID NO: 119)

TABLE 6-continued

Amino Acid Sequences derived from Murine 76E1 Antibody.

EVQLVQSGGGLVQPGGSLRISCAAS (SEQ ID NO: 120)

EVQLVQSGGGLVQPGGSVRISCAAS (SEQ ID NO: 121)

76E1-huVH3a VH CDR1

GYSFTGYNMN (SEQ ID NO: 30)

GYSFTGYQMN (SEQ ID NO: 59)

GYSFTGYSMN (SEQ ID NO: 60)

GYSFTGYDMN (SEQ ID NO: 61)

GYSFTGYAMN (SEQ ID NO: 62)

76E1-huVH3a VH FR2

WVRQAPGKGLEWVS (SEQ ID NO: 56)

WVRQAPGKSLEWVS (SEQ ID NO: 323)

WVRQAPGKGLEWIS (SEQ ID NO: 122)

WVRQAPGKGLEWVG (SEQ ID NO: 123)

WVRQAPGKSLEWIS (SEQ ID NO: 324)

WVRQAPGKSLEWVG (SEQ ID NO: 325)

WVRQAPGKGLEWIG (SEQ ID NO: 124)

WVRQAPGKSLEWIG (SEQ ID NO: 326)

76E1-huVH3a VH CDR2

NIDPYYDYTSYNLKFKD (SEQ ID NO: 31)

NIEPYYDYTSYNLKFKD (SEQ ID NO: 65)

NISPYYDYTSYNLKFKD (SEQ ID NO: 66)

NIAPYYDYTSYNLKFKD (SEQ ID NO: 67)

NIDPYYDYTSYQLKFKD (SEQ ID NO: 68)

NIDPYYDYTSYSLKFKD (SEQ ID NO: 69)

NIDPYYDYTSYDLKFKD (SEQ ID NO: 70)

NIDPYYDYTSYALKFKD (SEQ ID NO: 71)

NIEPYYDYTSYQLKFKD (SEQ ID NO: 72)

NIEPYYDYTSYSLKFKD (SEQ ID NO: 73)

NIEPYYDYTSYDLKFKD (SEQ ID NO: 74)

NIEPYYDYTSYALKFKD (SEQ ID NO: 83)

NISPYYDYTSYQLKFKD (SEQ ID NO: 84)

NISPYYDYTSYSLKFKD (SEQ ID NO: 85)

NISPYYDYTSYDLKFKD (SEQ ID NO: 86)

NISPYYDYTSYALKFKD (SEQ ID NO: 87)

NIAPYYDYTSYQLKFKD (SEQ ID NO: 88)

NIAPYYDYTSYSLKFKD (SEQ ID NO: 89)

NIAPYYDYTSYDLKFKD (SEQ ID NO: 90)

NIAPYYDYTSYALKFKD (SEQ ID NO: 95)

TABLE 6-continued

Amino Acid Sequences derived from Murine 76E1 Antibody.

76E1-huVH3a VH FR3

RFTISRDNAKNSLYLQMNSLRAEDTAVYYCAR (SEQ ID NO: 57)

RATISRDNAKNSLYLQMNSLRAEDTAVYYCAR (SEQ ID NO: 327)

RFTLSRDNAKNSLYLQMNSLRAEDTAVYYCAR (SEQ ID NO: 328)

RFTISVDNAKNSLYLQMNSLRAEDTAVYYCAR (SEQ ID NO: 329)

RFTISRDKAKNSLYLQMNSLRAEDTAVYYCAR (SEQ ID NO: 330)

RFTISRDNAKSSLYLQMNSLRAEDTAVYYCAR (SEQ ID NO: 331)

RFTISRDNAKNSAYLQMNSLRAEDTAVYYCAR (SEQ ID NO: 332)

RFTISRDNAKNSLYMQMNSLRAEDTAVYYCAR (SEQ ID NO: 333)

RFTISRDNAKNSLYLQLNSLRAEDTAVYYCAR (SEQ ID NO: 334)

RFTISRDNAKNSLYLQMNSLRAEDTAVYYCAT (SEQ ID NO: 335)

RATLSRDNAKNSLYLQMNSLRAEDTAVYYCAR (SEQ ID NO: 336)

RATISVDNAKNSLYLQMNSLRAEDTAVYYCAR (SEQ ID NO: 337)

RATISRDKAKNSLYLQMNSLRAEDTAVYYCAR (SEQ ID NO: 338)

RATISRDNAKSSLYLQMNSLRAEDTAVYYCAR (SEQ ID NO: 339)

RATISRDNAKNSAYLQMNSLRAEDTAVYYCAR (SEQ ID NO: 340)

RATISRDNAKNSLYMQMNSLRAEDTAVYYCAR (SEQ ID NO: 341)

RATISRDNAKNSLYLQLNSLRAEDTAVYYCAR (SEQ ID NO: 342)

RATISRDNAKNSLYLQMNSLRAEDTAVYYCAT (SEQ ID NO: 343)

RFTLSVDNAKNSLYLQMNSLRAEDTAVYYCAR (SEQ ID NO: 344)

RFTLSRDKAKNSLYLQMNSLRAEDTAVYYCAR (SEQ ID NO: 345)

RFTLSRDNAKSSLYLQMNSLRAEDTAVYYCAR (SEQ ID NO: 346)

RFTLSRDNAKNSAYLQMNSLRAEDTAVYYCAR (SEQ ID NO: 347)

RFTLSRDNAKNSLYMQMNSLRAEDTAVYYCAR (SEQ ID NO: 348)

RFTLSRDNAKNSLYLQLNSLRAEDTAVYYCAR (SEQ ID NO: 349)

RFTLSRDNAKNSLYLQMNSLRAEDTAVYYCAT (SEQ ID NO: 350)

RFTISVDKAKNSLYLQMNSLRAEDTAVYYCAR (SEQ ID NO: 351)

RFTISVDNAKSSLYLQMNSLRAEDTAVYYCAR (SEQ ID NO: 352)

RFTISVDNAKNSAYLQMNSLRAEDTAVYYCAR (SEQ ID NO: 353)

RFTISVDNAKNSLYMQMNSLRAEDTAVYYCAR (SEQ ID NO: 354)

RFTISVDNAKNSLYLQLNSLRAEDTAVYYCAR (SEQ ID NO: 355)

RFTISVDNAKNSLYLQMNSLRAEDTAVYYCAT (SEQ ID NO: 356)

RFTISRDKAKSSLYLQMNSLRAEDTAVYYCAR (SEQ ID NO: 357)

RFTISRDKAKNSAYLQMNSLRAEDTAVYYCAR (SEQ ID NO: 358)

RFTISRDKAKNSLYMQMNSLRAEDTAVYYCAR (SEQ ID NO: 359)

RFTISRDKAKNSLYLQLNSLRAEDTAVYYCAR (SEQ ID NO: 360)

RFTISRDKAKNSLYLQMNSLRAEDTAVYYCAT (SEQ ID NO: 361)

RFTISRDNAKSSA**YLQMNSLRAEDTAVYYCAR (SEQ ID NO: 362)

RFTISRDNAKSSLYMQMNSLRAEDTAVYYCAR (SEQ ID NO: 363)

TABLE 6-continued

Amino Acid Sequences derived from Murine 76E1 Antibody.

RFTISRDNAKSSLYLQLNSLRAEDTAVYYCAR (SEQ ID NO: 364)

RFTISRDNAKSSLYLQMNSLRAEDTAVYYCAT (SEQ ID NO: 365)

RFTISRDNAKNSAYMQMNSLRAEDTAVYYCAR (SEQ ID NO: 366)

RFTISRDNAKNSAYLQLNSLRAEDTAVYYCAR (SEQ ID NO: 367)

RFTISRDNAKNSAYLQMNSLRAEDTAVYYCAT (SEQ ID NO: 368)

RFTISRDNAKNSLYMQLNSLRAEDTAVYYCAR (SEQ ID NO: 369)

RFTISRDNAKNSLYMQMNSLRAEDTAVYYCAT (SEQ ID NO: 370)

RFTISRDNAKNSLYLQLNSLRAEDTAVYYCAT (SEQ ID NO: 371)

RATLSVDNAKNSLYLQMNSLRAEDTAVYYCAR (SEQ ID NO: 372)

RATLSRDKAKNSLYLQMNSLRAEDTAVYYCAR (SEQ ID NO: 373)

RATLSRDNAKSSLYLQMNSLRAEDTAVYYCAR (SEQ ID NO: 374)

RATLSRDNAKNSAYLQMNSLRAEDTAVYYCAR (SEQ ID NO: 375)

RATLSRDNAKNSLYMQMNSLRAEDTAVYYCAR (SEQ ID NO: 376)

RATLSRDNAKNSLYLQLNSLRAEDTAVYYCAR (SEQ ID NO: 377)

RATLSRDNAKNSLYLQMNSLRAEDTAVYYCAT (SEQ ID NO: 378)

RATISVDKAKNSLYLQMNSLRAEDTAVYYCAR (SEQ ID NO: 379)

RATISVDNAKSSLYLQMNSLRAEDTAVYYCAR (SEQ ID NO: 380)

RATISVDNAKNSAYLQMNSLRAEDTAVYYCAR (SEQ ID NO: 381)

RATISVDNAKNSLYMQMNSLRAEDTAVYYCAR (SEQ ID NO: 382)

RATISVDNAKNSLYLQLNSLRAEDTAVYYCAR (SEQ ID NO: 383)

RATISVDNAKNSLYLQMNSLRAEDTAVYYCAT (SEQ ID NO: 384)

RATISRDKAKSSLYLQMNSLRAEDTAVYYCAR (SEQ ID NO: 385)

RATISRDKAKNSAYLQMNSLRAEDTAVYYCAR (SEQ ID NO: 386)

RATISRDKAKNSLYMQMNSLRAEDTAVYYCAR (SEQ ID NO: 387)

RATISRDKAKNSLYLQLNSLRAEDTAVYYCAR (SEQ ID NO: 388)

RATISRDKAKNSLYLQMNSLRAEDTAVYYCAT (SEQ ID NO: 389)

RATISRDNAKSSAYLQMNSLRAEDTAVYYCAR (SEQ ID NO: 390)

RATISRDNAKSSLYMQMNSLRAEDTAVYYCAR (SEQ ID NO: 391)

RATISRDNAKSSLYLQLNSLRAEDTAVYYCAR (SEQ ID NO: 392)

RATISRDNAKSSLYLQMNSLRAEDTAVYYCAT (SEQ ID NO: 393)

RATISRDNAKNSAYMQMNSLRAEDTAVYYCAR (SEQ ID NO: 394)

RATISRDNAKNSAYLQLNSLRAEDTAVYYCAR (SEQ ID NO: 395)

RATISRDNAKNSAYLQMNSLRAEDTAVYYCAT (SEQ ID NO: 396)

RATISRDNAKNSLYMQLNSLRAEDTAVYYCAR (SEQ ID NO: 397)

RATISRDNAKNSLYMQMNSLRAEDTAVYYCAT (SEQ ID NO: 398)

RATISRDNAKNSLYLQLNSLRAEDTAVYYCAT (SEQ ID NO: 399)

RFTLSVDKAKNSLYLQMNSLRAEDTAVYYCAR (SEQ ID NO: 400)

RFTLSVDNAKSSLYLQMNSLRAEDTAVYYCAR (SEQ ID NO: 401)

RFTLSVDNAKNSAYLQMNSLRAEDTAVYYCAR (SEQ ID NO: 402)

TABLE 6-continued

Amino Acid Sequences derived from Murine 76E1 Antibody.

RFTLSVDNAKNSLYMQMNSLRAEDTAVYYCAR (SEQ ID NO: 403)

RFTLSVDNAKNSLYLQLNSLRAEDTAVYYCAR (SEQ ID NO: 404)

RFTLSVDNAKNSLYLQMNSLRAEDTAVYYCAT (SEQ ID NO: 405)

RFTLSRDKASNSLYLQMNSLRAEDTAVYYCAR (SEQ ID NO: 406)

RFTLSRDKAKNSAYLQMNSLRAEDTAVYYCAR (SEQ ID NO: 407)

RFTLSRDKAKNSLYMQMNSLRAEDTAVYYCAR (SEQ ID NO: 408)

RFTLSRDKAKNSLYLQLNSLRAEDTAVYYCAR (SEQ ID NO: 409)

RFTLSRDKAKNSLYLQMNSLRAEDTAVYYCAT (SEQ ID NO: 410)

RFTLSRDNAKSSAYLQMNSLRAEDTAVYYCAR (SEQ ID NO: 411)

RFTLSRDNAKSSLYMQMNSLRAEDTAVYYCAR (SEQ ID NO: 412)

RFTLSRDNAKSSLYLQLNSLRAEDTAVYYCAR (SEQ ID NO: 413)

RFTLSRDNAKSSLYLQMNSLRAEDTAVYYCAT (SEQ ID NO: 414)

RFTLSRDNAKNSAYMQMNSLRAEDTAVYYCAR (SEQ ID NO: 415)

RFTLSRDNAKNSAYLQLNSLRAEDTAVYYCAR (SEQ ID NO: 416)

RFTLSRDNAKNSAYLQMNSLRAEDTAVYYCAT (SEQ ID NO: 417)

RFTLSRDNAKNSLYMQLNSLRAEDTAVYYCAR (SEQ ID NO: 418)

RFTLSRDNAKNSLYMQMNSLRAEDTAVYYCAT (SEQ ID NO: 419)

RFTLSRDNAKNSLYLQLNSLRAEDTAVYYCAT (SEQ ID NO: 420)

RFTISVDKAKSSLYLQMNSLRAEDTAVYYCAR (SEQ ID NO: 421)

RFTISVDKAKNSAYLQMNSLRAEDTAVYYCAR (SEQ ID NO: 422)

RFTISVDKAKNSLYMQMNSLRAEDTAVYYCAR (SEQ ID NO: 423)

RFTISVDKAKNSLYLQLNSLRAEDTAVYYCAR (SEQ ID NO: 424)

RFTISVDKAKNSLYLQMNSLRAEDTAVYYCAT (SEQ ID NO: 425)

RFTISVDNAKSSAYLQMNSLRAEDTAVYYCAR (SEQ ID NO: 426)

RFTISVDNAKSSLYMQMNSLRAEDTAVYYCAR (SEQ ID NO: 427)

RFTISVDNAKSSLYLQLNSLRAEDTAVYYCAR (SEQ ID NO: 428)

RFTISVDNAKSSLYLQMNSLRAEDTAVYYCAT (SEQ ID NO: 429)

RFTISVDNAKNSAYMQMNSLRAEDTAVYYCAR (SEQ ID NO: 430)

RFTISVDNAKNSAYLQLNSLRAEDTAVYYCAR (SEQ ID NO: 431)

RFTISVDNAKNSAYLQMNSLRAEDTAVYYCAT (SEQ ID NO: 432)

RFTISVDNAKNSLYMQLNSLRAEDTAVYYCAR (SEQ ID NO: 433)

RFTISVDNAKNSLYMQMNSLRAEDTAVYYCAT (SEQ ID NO: 434)

RFTISVDNAKNSLYLQLNSLRAEDTAVYYCAT (SEQ ID NO: 435)

RFTISRDKAKSSAYLQMNSLRAEDTAVYYCAR (SEQ ID NO: 436)

RFTISRDKAKSSLYMQMNSLRAEDTAVYYCAR (SEQ ID NO: 437)

RFTISRDKAKSSLYLQLNSLRAEDTAVYYCAR (SEQ ID NO: 438)

RFTISRDKAKSSLYLQMNSLRAEDTAVYYCAT (SEQ ID NO: 439)

RFTISRDKAKNSAYMQMNSLRAEDTAVYYCAR (SEQ ID NO: 440)

RFTISRDKAKNSAYLQLNSLRAEDTAVYYCAR (SEQ ID NO: 441)

TABLE 6-continued

Amino Acid Sequences derived from Murine 76E1 Antibody.

RFTISRDKAKNSAYLQMNSLRAEDTAVYYCAT (SEQ ID NO: 442)

RFTISRDKAKNSLYMQLNSLRAEDTAVYYCAR (SEQ ID NO: 443)

RFTISRDKAKNSLYMQMNSLRAEDTAVYYCAT (SEQ ID NO: 444)

RFTISRDKAKNSLYLQLNSLRAEDTAVYYCAT (SEQ ID NO: 445)

RFTISRDNAKSSAYMQMNSLRAEDTAVYYCAR (SEQ ID NO: 446)

RFTISRDNAKSSAYLQLNSLRAEDTAVYYCAR (SEQ ID NO: 447)

RFTISRDNAKSSAYLQMNSLRAEDTAVYYCAT (SEQ ID NO: 448)

RFTISRDNAKSSLYMQLNSLRAEDTAVYYCAR (SEQ ID NO: 449)

RFTISRDNAKSSLYMQMNSLRAEDTAVYYCAT (SEQ ID NO: 450)

RFTISRDNAKSSLYLQLNSLRAEDTAVYYCAT (SEQ ID NO: 451)

RFTISRDNAKNSAYMQLNSLRAEDTAVYYCAR (SEQ ID NO: 452)

RFTISRDNAKNSAYMQMNSLRAEDTAVYYCAT (SEQ ID NO: 453)

RFTISRDNAKNSAYLQLNSLRAEDTAVYYCAT (SEQ ID NO: 454)

RFTISRDNAKNSLYMQLNSLRAEDTAVYYCAT (SEQ ID NO: 455)

RATLSVDKAKNSLYLQMNSLRAEDTAVYYCAR (SEQ ID NO: 456)

RATLSVDNAKSSLYLQMNSLRAEDTAVYYCAR (SEQ ID NO: 457)

RATLSVDNAKNSAYLQMNSLRAEDTAVYYCAR (SEQ ID NO: 458)

RATLSVDNAKNSLYMQMNSLRAEDTAVYYCAR (SEQ ID NO: 459)

RATLSVDNAKNSLYLQLNSLRAEDTAVYYCAR (SEQ ID NO: 460)

RATLSVDNAKNSLYLQMNSLRAEDTAVYYCAT (SEQ ID NO: 461)

RATLSRDKAKSSLYLQMNSLRAEDTAVYYCAR (SEQ ID NO: 462)

RATLSRDKAKNSAYLQMNSLRAEDTAVYYCAR (SEQ ID NO: 463)

RATLSRDKAKNSLYMQMNSLRAEDTAVYYCAR (SEQ ID NO: 464)

RATLSRDKAKNSLYLQLNSLRAEDTAVYYCAR (SEQ ID NO: 465)

RATLSRDKAKNSLYLQMNSLRAEDTAVYYCAT (SEQ ID NO: 466)

RATLSRDNAKSSAYLQMNSLRAEDTAVYYCAR (SEQ ID NO: 467)

RATLSRDNAKSSLYMQMNSLRAEDTAVYYCAR (SEQ ID NO: 468)

RATLSRDNAKSSLYLQLNSLRAEDTAVYYCAR (SEQ ID NO: 469)

RATLSRDNAKSSLYLQMNSLRAEDTAVYYCAT (SEQ ID NO: 470)

RATLSRDNAKNSAYMQMNSLRAEDTAVYYCAR (SEQ ID NO: 471)

RATLSRDNAKNSAYLQLNSLRAEDTAVYYCAR (SEQ ID NO: 472)

RATLSRDNAKNSAYLQMNSLRAEDTAVYYCAT (SEQ ID NO: 473)

RATLSRDNAKNSLYMQLNSLRAEDTAVYYCAR (SEQ ID NO: 474)

RATLSRDNAKNSLYMQMNSLRAEDTAVYYCAT (SEQ ID NO: 475)

RATLSRDNAKNSLYLQLNSLRAEDTAVYYCAT (SEQ ID NO: 476)

RATISVDKAKSSLYLQMNSLRAEDTAVYYCAR (SEQ ID NO: 477)

RATISVDKAKNSAYLQMNSLRAEDTAVYYCAR (SEQ ID NO: 478)

RATISVDKAKNSLYMQMNSLRAEDTAVYYCAR (SEQ ID NO: 479)

RATISVDKAKNSLYLQLNSLRAEDTAVYYCAR (SEQ ID NO: 480)

TABLE 6-continued

Amino Acid Sequences derived from Murine 76E1 Antibody.

RATISVDKAKNSLYLQMNSLRAEDTAVYYCAT (SEQ ID NO: 481)

RATISVDNAKSSAYLQMNSLRAEDTAVYYCAR (SEQ ID NO: 482)

RATISVDNAKSSLYMQMNSLRAEDTAVYYCAR (SEQ ID NO: 483)

RATISVDNAKSSLYLQLNSLRAEDTAVYYCAR (SEQ ID NO: 484)

RATISVDNAKSSLYLQMNSLRAEDTAVYYCAT (SEQ ID NO: 485)

RATISVDNAKNSAYMQMNSLRAEDTAVYYCAR (SEQ ID NO: 486)

RATISVDNAKNSAYLQLNSLRAEDTAVYYCAR (SEQ ID NO: 487)

RATISVDNAKNSAYLQMNSLRAEDTAVYYCAT (SEQ ID NO: 488)

RATISVDNAKNSLYMQLNSLRAEDTAVYYCAR (SEQ ID NO: 489)

RATISVDNAKNSLYMQMNSLRAEDTAVYYCAT (SEQ ID NO: 490)

RATISVDNAKNSLYLQLNSLRAEDTAVYYCAT (SEQ ID NO: 491)

RATISRDKAKSSAYLQMNSLRAEDTAVYYCAR (SEQ ID NO: 492)

RATISRDKAKSSLYMQMNSLRAEDTAVYYCAR (SEQ ID NO: 493)

RATISRDKAKSSLYLQLNSLRAEDTAVYYCAR (SEQ ID NO: 494)

RATISRDKAKSSLYLQMNSLRAEDTAVYYCAT (SEQ ID NO: 495)

RATISRDKAKNSAYMQMNSLRAEDTAVYYCAR (SEQ ID NO: 496)

RATISRDKAKNSAYLQLNSLRAEDTAVYYCAR (SEQ ID NO: 497)

RATISRDKAKNSAYLQMNSLRAEDTAVYYCAT (SEQ ID NO: 498)

RATISRDKAKNSLYMQLNSLRAEDTAVYYCAR (SEQ ID NO: 499)

RATISRDKAKNSLYMQMNSLRAEDTAVYYCAT (SEQ ID NO: 500)

RATISRDKAKNSLYLQLNSLRAEDTAVYYCAT (SEQ ID NO: 501)

RATISRDNAKSSAYMQMNSLRAEDTAVYYCAR (SEQ ID NO: 502)

RATISRDNAKSSAYLQLNSLRAEDTAVYYCAR (SEQ ID NO: 503)

RATISRDNAKSSAYLQMNSLRAEDTAVYYCAT (SEQ ID NO: 504)

RATISRDNAKSSLYMQLNSLRAEDTAVYYCAR (SEQ ID NO: 505)

RATISRDNAKSSLYMQMNSLRAEDTAVYYCAT (SEQ ID NO: 506)

RATISRDNAKSSLYLQLNSLRAEDTAVYYCAT (SEQ ID NO: 507)

RATISRDNAKNSAYMQLNSLRAEDTAVYYCAR (SEQ ID NO: 508)

RATISRDNAKNSAYMQMNSLRAEDTAVYYCAT (SEQ ID NO: 509)

RATISRDNAKNSAYLQLNSLRAEDTAVYYCAT (SEQ ID NO: 510)

RATISRDNAKNSLYMQLNSLRAEDTAVYYCAT (SEQ ID NO: 511)

RFTLSVDKAKSSLYLQMNSLRAEDTAVYYCAR (SEQ ID NO: 512)

RFTLSVDKAKNSAYLQMNSLRAEDTAVYYCAR (SEQ ID NO: 513)

RFTLSVDKAKNSLYMQMNSLRAEDTAVYYCAR (SEQ ID NO: 514)

RFTLSVDKAKNSLYLQLNSLRAEDTAVYYCAR (SEQ ID NO: 515)

RFTLSVDKAKNSLYLQMNSLRAEDTAVYYCAT (SEQ ID NO: 516)

RFTLSVDNAKSSAYLQMNSLRAEDTAVYYCAR (SEQ ID NO: 517)

RFTLSVDNAKSSLYMQMNSLRAEDTAVYYCAR (SEQ ID NO: 518)

RFTLSVDNAKSSLYLQLNSLRAEDTAVYYCAR (SEQ ID NO: 519)

TABLE 6-continued

Amino Acid Sequences derived from Murine 76E1 Antibody.

RFTLSVDNAKSSLYLQMNSLRAEDTAVYYCAT (SEQ ID NO: 520)

RFTLSVDNAKNSAYMQMNSLRAEDTAVYYCAR (SEQ ID NO: 521)

RFTLSVDNAKNSAYLQLNSLRAEDTAVYYCAR (SEQ ID NO: 522)

RFTLSVDNAKNSAYLQMNSLRAEDTAVYYCAT (SEQ ID NO: 523)

RFTLSVDNAKNSLYMQLNSLRAEDTAVYYCAR (SEQ ID NO: 524)

RFTLSVDNAKNSLYMQMNSLRAEDTAVYYCAT (SEQ ID NO: 525)

RFTLSVDNAKNSLYLQLNSLRAEDTAVYYCAT (SEQ ID NO: 526)

RFTLSRDKASNSAYLQMNSLRAEDTAVYYCAR (SEQ ID NO: 527)

RFTLSRDKASNSLYMQMNSLRAEDTAVYYCAR (SEQ ID NO: 528)

RFTLSRDKASNSLYLQLNSLRAEDTAVYYCAR (SEQ ID NO: 529)

RFTLSRDKASNSLYLQMNSLRAEDTAVYYCAT (SEQ ID NO: 530)

RFTLSRDKAKNSAYMQMNSLRAEDTAVYYCAR (SEQ ID NO: 531)

RFTLSRDKAKNSAYLQLNSLRAEDTAVYYCAR (SEQ ID NO: 532)

RFTLSRDKAKNSAYLQMNSLRAEDTAVYYCAT (SEQ ID NO: 533)

RFTLSRDKAKNSLYMQLNSLRAEDTAVYYCAR (SEQ ID NO: 534)

RFTLSRDKAKNSLYMQMNSLRAEDTAVYYCAT (SEQ ID NO: 535)

RFTLSRDKAKNSLYLQLNSLRAEDTAVYYCAT (SEQ ID NO: 536)

RFTLSRDNAKSSAYMQMNSLRAEDTAVYYCAR (SEQ ID NO: 537)

RFTLSRDNAKSSAYLQLNSLRAEDTAVYYCAR (SEQ ID NO: 538)

RFTLSRDNAKSSAYLQMNSLRAEDTAVYYCAT (SEQ ID NO: 539)

RFTLSRDNAKSSLYMQLNSLRAEDTAVYYCAR (SEQ ID NO: 540)

RFTLSRDNAKSSLYMQMNSLRAEDTAVYYCAT (SEQ ID NO: 541)

RFTLSRDNAKSSLYLQLNSLRAEDTAVYYCAT (SEQ ID NO: 542)

RFTLSRDNAKNSAYMQLNSLRAEDTAVYYCAR (SEQ ID NO: 543)

RFTLSRDNAKNSAYMQMNSLRAEDTAVYYCAT (SEQ ID NO: 544)

RFTLSRDNAKNSAYLQLNSLRAEDTAVYYCAT (SEQ ID NO: 545)

RFTLSRDNAKNSLYMQLNSLRAEDTAVYYCAT (SEQ ID NO: 546)

RFTISVDKAKSSAYLQMNSLRAEDTAVYYCAR (SEQ ID NO: 547)

RFTISVDKAKSSLYMQMNSLRAEDTAVYYCAR (SEQ ID NO: 548)

RFTISVDKAKSSLYLQLNSLRAEDTAVYYCAR (SEQ ID NO: 549)

RFTISVDKAKSSLYLQMNSLRAEDTAVYYCAT (SEQ ID NO: 550)

RFTISVDKAKNSAYMQMNSLRAEDTAVYYCAR (SEQ ID NO: 551)

RFTISVDKAKNSAYLQLNSLRAEDTAVYYCAR (SEQ ID NO: 552)

RFTISVDKAKNSAYLQMNSLRAEDTAVYYCAT (SEQ ID NO: 553)

RFTISVDKAKNSLYMQLNSLRAEDTAVYYCAR (SEQ ID NO: 554)

RFTISVDKAKNSLYMQMNSLRAEDTAVYYCAT (SEQ ID NO: 555)

RFTISVDKAKNSLYLQLNSLRAEDTAVYYCAT (SEQ ID NO: 556)

RFTISVDNAKSSAYLQLNSLRAEDTAVYYCAR (SEQ ID NO: 557)

RFTISVDNAKSSAYLQMNSLRAEDTAVYYCAT (SEQ ID NO: 558)

TABLE 6-continued

Amino Acid Sequences derived from Murine 76E1 Antibody.

RFTISVDNAKSSLYMQLNSLRAEDTAVYYCAR (SEQ ID NO: 559)

RFTISVDNAKSSLYMQMNSLRAEDTAVYYCAT (SEQ ID NO: 560)

RFTISVDNAKSSLYLQLNSLRAEDTAVYYCAT (SEQ ID NO: 561)

RFTISVDNAKNSAYMQLNSLRAEDTAVYYCAR (SEQ ID NO: 562)

RFTISVDNAKNSAYMQMNSLRAEDTAVYYCAT (SEQ ID NO: 563)

RFTISVDNAKNSAYLQLNSLRAEDTAVYYCAT (SEQ ID NO: 564)

RFTISVDNAKNSLYMQLNSLRAEDTAVYYCAT (SEQ ID NO: 565)

RFTISRDKAKSSAYMQMNSLRAEDTAVYYCAR (SEQ ID NO: 566)

RFTISRDKAKSSAYLQLNSLRAEDTAVYYCAR (SEQ ID NO: 567)

RFTISRDKAKSSAYLQMNSLRAEDTAVYYCAT (SEQ ID NO: 568)

RFTISRDKAKSSLYMQLNSLRAEDTAVYYCAR (SEQ ID NO: 569)

RFTISRDKAKSSLYMQMNSLRAEDTAVYYCAT (SEQ ID NO: 570)

RFTISRDKAKSSLYLQLNSLRAEDTAVYYCAT (SEQ ID NO: 571)

RFTISRDKAKNSAYMQLNSLRAEDTAVYYCAR (SEQ ID NO: 572)

RFTISRDKAKNSAYMQMNSLRAEDTAVYYCAT (SEQ ID NO: 573)

RFTISRDKAKNSAYLQLNSLRAEDTAVYYCAT (SEQ ID NO: 574)

RFTISRDKAKNSLYMQLNSLRAEDTAVYYCAT (SEQ ID NO: 575)

RFTISRDNAKSSAYMQLNSLRAEDTAVYYCAR (SEQ ID NO: 576)

RFTISRDNAKSSAYMQMNSLRAEDTAVYYCAT (SEQ ID NO: 577)

RFTISRDNAKSSAYLQLNSLRAEDTAVYYCAT (SEQ ID NO: 578)

RFTISRDNAKSSLYMQLNSLRAEDTAVYYCAT (SEQ ID NO: 579)

RFTISRDNAKNSAYMQLNSLRAEDTAVYYCAT (SEQ ID NO: 580)

RATLSVDKAS NSLYLQMNSLRAEDTAVYYCAR (SEQ ID NO: 581)

RATLSVDKAKNSAYLQMNSLRAEDTAVYYCAR (SEQ ID NO: 582)

RATLSVDKAKNSLYMQMNSLRAEDTAVYYCAR (SEQ ID NO: 583)

RATLSVDKAKNSLYLQLNSLRAEDTAVYYCAR (SEQ ID NO: 584)

RATLSVDKAKNSLYLQMNSLRAEDTAVYYCAT (SEQ ID NO: 585)

RATLSVDNAKSSAYLQMNSLRAEDTAVYYCAR (SEQ ID NO: 586)

RATLSVDNAKSSLYMQMNSLRAEDTAVYYCAR (SEQ ID NO: 587)

RATLSVDNAKSSLYLQLNSLRAEDTAVYYCAR (SEQ ID NO: 588)

RATLSVDNAKSSLYLQMNSLRAEDTAVYYCAT (SEQ ID NO: 589)

RATLSVDNAKNSAYMQMNSLRAEDTAVYYCAR (SEQ ID NO: 590)

RATLSVDNAKNSAYLQLNSLRAEDTAVYYCAR (SEQ ID NO: 591)

RATLSVDNAKNSAYLQMNSLRAEDTAVYYCAT (SEQ ID NO: 592)

RATLSVDNAKNSLYMQLNSLRAEDTAVYYCAR (SEQ ID NO: 593)

RATLSVDNAKNSLYMQMNSLRAEDTAVYYCAT (SEQ ID NO: 594)

RATLSVDNAKNSLYLQLNSLRAEDTAVYYCAT (SEQ ID NO: 595)

RATLSRDKAKSSAYLQMNSLRAEDTAVYYCAR (SEQ ID NO: 596)

RATLSRDKAKSSLYMQMNSLRAEDTAVYYCAR (SEQ ID NO: 597)

TABLE 6-continued

Amino Acid Sequences derived from Murine 76E1 Antibody.

RATLSRDKAKSSLYLQLNSLRAEDTAVYYCAR (SEQ ID NO: 598)

RATLSRDKAKSSLYLQMNSLRAEDTAVYYCAT (SEQ ID NO: 599)

RATLSRDKAKNSAYMQMNSLRAEDTAVYYCAR (SEQ ID NO: 600)

RATLSRDKAKNSAYLQLNSLRAEDTAVYYCAR (SEQ ID NO: 601)

RATLSRDKAKNSAYLQMNSLRAEDTAVYYCAT (SEQ ID NO: 602)

RATLSRDKAKNSLYMQLNSLRAEDTAVYYCAR (SEQ ID NO: 603)

RATLSRDKAKNSLYMQMNSLRAEDTAVYYCAT (SEQ ID NO: 604)

RATLSRDKAKNSLYLQLNSLRAEDTAVYYCAT (SEQ ID NO: 605)

RATLSRDNAKSSAYMQMNSLRAEDTAVYYCAR (SEQ ID NO: 606)

RATLSRDNAKSSAYLQLNSLRAEDTAVYYCAR (SEQ ID NO: 607)

RATLSRDNAKSSAYLQMNSLRAEDTAVYYCAT (SEQ ID NO: 608)

RATLSRDNAKSSLYMQLNSLRAEDTAVYYCAR (SEQ ID NO: 609)

RATLSRDNAKSSLYMQMNSLRAEDTAVYYCAT (SEQ ID NO: 610)

RATLSRDNAKSSLYLQLNSLRAEDTAVYYCAT (SEQ ID NO: 611)

RATLSRDNAKNSAYMQLNSLRAEDTAVYYCAR (SEQ ID NO: 612)

RATLSRDNAKNSAYMQMNSLRAEDTAVYYCAT (SEQ ID NO: 613)

RATLSRDNAKNSAYLQLNSLRAEDTAVYYCAT (SEQ ID NO: 614)

RATLSRDNAKNSLYMQLNSLRAEDTAVYYCAT (SEQ ID NO: 615)

RATISVDKAKSSAYLQMNSLRAEDTAVYYCAR (SEQ ID NO: 616)

RATISVDKAKSSLYMQMNSLRAEDTAVYYCAR (SEQ ID NO: 617)

RATISVDKAKSSLYLQLNSLRAEDTAVYYCAR (SEQ ID NO: 618)

RATISVDKAKSSLYLQMNSLRAEDTAVYYCAT (SEQ ID NO: 619)

RATISVDKAKNSAYMQMNSLRAEDTAVYYCAR (SEQ ID NO: 620)

RATISVDKAKNSAYLQLNSLRAEDTAVYYCAR (SEQ ID NO: 621)

RATISVDKAKNSAYLQMNSLRAEDTAVYYCAT (SEQ ID NO: 622)

RATISVDKAKNSLYMQLNSLRAEDTAVYYCAR (SEQ ID NO: 623)

RATISVDKAKNSLYMQMNSLRAEDTAVYYCAT (SEQ ID NO: 624)

RATISVDKAKNSLYLQLNSLRAEDTAVYYCAT (SEQ ID NO: 625)

RATISVDNAKSSAYMQMNSLRAEDTAVYYCAR (SEQ ID NO: 626)

RATISVDNAKSSAYLQLNSLRAEDTAVYYCAR (SEQ ID NO: 627)

RATISVDNAKSSAYLQMNSLRAEDTAVYYCAT (SEQ ID NO: 628)

RATISVDNAKSSLYMQLNSLRAEDTAVYYCAR (SEQ ID NO: 629)

RATISVDNAKSSLYMQMNSLRAEDTAVYYCAT (SEQ ID NO: 630)

RATISVDNAKSSLYLQLNSLRAEDTAVYYCAT (SEQ ID NO: 631)

RATISVDNAKNSAYMQLNSLRAEDTAVYYCAR (SEQ ID NO: 632)

RATISVDNAKNSAYMQMNSLRAEDTAVYYCAT (SEQ ID NO: 633)

RATISVDNAKNSAYLQLNSLRAEDTAVYYCAT (SEQ ID NO: 634)

RATISVDNAKNSLYMQLNSLRAEDTAVYYCAT (SEQ ID NO: 635)

RATISRDKAKSSAYMQMNSLRAEDTAVYYCAR (SEQ ID NO: 636)

TABLE 6-continued

Amino Acid Sequences derived from Murine 76E1 Antibody.

RATISRDKAKSSAYLQLNSLRAEDTAVYYCAR (SEQ ID NO: 637)

RATISRDKAKSSAYLQMNSLRAEDTAVYYCAT (SEQ ID NO: 638)

RATISRDKAKSSLYMQLNSLRAEDTAVYYCAR (SEQ ID NO: 639)

RATISRDKAKSSLYMQMNSLRAEDTAVYYCAT (SEQ ID NO: 640)

RATISRDKAKSSLYLQLNSLRAEDTAVYYCAT (SEQ ID NO: 641)

RATISRDKAKNSAYMQLNSLRAEDTAVYYCAR (SEQ ID NO: 642)

RATISRDKAKNSAYMQMNSLRAEDTAVYYCAT (SEQ ID NO: 643)

RATISRDKAKNSAYLQLNSLRAEDTAVYYCAT (SEQ ID NO: 644)

RATISRDKAKNSLYMQLNSLRAEDTAVYYCAT (SEQ ID NO: 645)

RATISRDNAKSSAYMQLNSLRAEDTAVYYCAR (SEQ ID NO: 646)

RATISRDNAKSSAYMQMNSLRAEDTAVYYCAT (SEQ ID NO: 647)

RATISRDNAKSSAYLQLNSLRAEDTAVYYCAT (SEQ ID NO: 648)

RATISRDNAKSSLYMQMNSLRAEDTAVYYCAT (SEQ ID NO: 649)

RATISRDNAKNSAYMQMNSLRAEDTAVYYCAT (SEQ ID NO: 650)

RFTLSVDKAKSSAYLQMNSLRAEDTAVYYCAR (SEQ ID NO: 651)

RFTLSVDKAKSSLYMQMNSLRAEDTAVYYCAR (SEQ ID NO: 652)

RFTLSVDKAKSSLYLQLNSLRAEDTAVYYCAR (SEQ ID NO: 653)

RFTLSVDKAKSSLYLQMNSLRAEDTAVYYCAT (SEQ ID NO: 654)

RFTLSVDKAKNSAYMQMNSLRAEDTAVYYCAR (SEQ ID NO: 655)

RFTLSVDKAKNSAYLQLNSLRAEDTAVYYCAR (SEQ ID NO: 656)

RFTLSVDKAKNSAYLQMNSLRAEDTAVYYCAT (SEQ ID NO: 657)

RFTLSVDKAKNSLYMQLNSLRAEDTAVYYCAR (SEQ ID NO: 658)

RFTLSVDKAKNSLYMQMNSLRAEDTAVYYCAT (SEQ ID NO: 659)

RFTLSVDKAKNSLYLQLNSLRAEDTAVYYCAT (SEQ ID NO: 660)

RFTLSVDNAKSSAYMQMNSLRAEDTAVYYCAR (SEQ ID NO: 661)

RFTLSVDNAKSSAYLQMNSLRAEDTAVYYCAR (SEQ ID NO: 662)

RFTLSVDNAKSSAYLQMNSLRAEDTAVYYCAT (SEQ ID NO: 663)

RFTLSVDNAKSSLYMQLNSLRAEDTAVYYCAR (SEQ ID NO: 664)

RFTLSVDNAKSSLYMQMNSLRAEDTAVYYCAT (SEQ ID NO: 665)

RFTLSVDNAKSSLYLQLNSLRAEDTAVYYCAT (SEQ ID NO: 666)

RFTLSVDNAKNSAYMQMNSLRAEDTAVYYCAR (SEQ ID NO: 667)

RFTLSVDNAKNSAYMQMNSLRAEDTAVYYCAT (SEQ ID NO: 668)

RFTLSVDNAKNSAYLQLNSLRAEDTAVYYCAT (SEQ ID NO: 669)

RFTLSVDNAKNSLYMQMNSLRAEDTAVYYCAT (SEQ ID NO: 670)

RFTLSRDKASNSAYMQMNSLRAEDTAVYYCAR (SEQ ID NO: 671)

RFTLSRDKASNSAYLQLNSLRAEDTAVYYCAR (SEQ ID NO: 672)

RFTLSRDKASNSAYLQMNSLRAEDTAVYYCAT (SEQ ID NO: 673)

RFTLSRDKASNSLYMQLNSLRAEDTAVYYCAR (SEQ ID NO: 674)

RFTLSRDKASNSLYMQMNSLRAEDTAVYYCAT (SEQ ID NO: 675)

TABLE 6-continued

Amino Acid Sequences derived from Murine 76E1 Antibody.

RFTLSRDKASNSLYLQLNSLRAEDTAVYYCAT (SEQ ID NO: 676)

RFTLSRDKAKNSAYMQLNSLRAEDTAVYYCAR (SEQ ID NO: 677)

RFTLSRDKAKNSAYMQMNSLRAEDTAVYYCAT (SEQ ID NO: 678)

RFTLSRDKAKNSAYLQLNSLRAEDTAVYYCAT (SEQ ID NO: 679)

RFTLSRDKAKNSLYMQLNSLRAEDTAVYYCAT (SEQ ID NO: 680)

RFTLSRDNAKSSAYMQLNSLRAEDTAVYYCAR (SEQ ID NO: 681)

RFTLSRDNAKSSAYMQMNSLRAEDTAVYYCAT (SEQ ID NO: 682)

RFTLSRDNAKSSAYLQLNSLRAEDTAVYYCAT (SEQ ID NO: 683)

RFTLSRDNAKSSLYMQLNSLRAEDTAVYYCAT (SEQ ID NO: 684)

RFTLSRDNAKNSAYMQLNSLRAEDTAVYYCAT (SEQ ID NO: 685)

RFTISVDKAKSSAYMQMNSLRAEDTAVYYCAR (SEQ ID NO: 686)

RFTISVDKAKSSAYLQLNSLRAEDTAVYYCAR (SEQ ID NO: 687)

RFTISVDKAKSSAYLQMNSLRAEDTAVYYCAT (SEQ ID NO: 688)

RFTISVDKAKSSLYMQLNSLRAEDTAVYYCAR (SEQ ID NO: 689)

RFTISVDKAKSSLYMQMNSLRAEDTAVYYCAT (SEQ ID NO: 690)

RFTISVDKAKSSLYLQLNSLRAEDTAVYYCAT (SEQ ID NO: 691)

RFTISVDKAKNSAYMQLNSLRAEDTAVYYCAR (SEQ ID NO: 692)

RFTISVDKAKNSAYMQMNSLRAEDTAVYYCAT (SEQ ID NO: 693)

RFTISVDKAKNSAYLQLNSLRAEDTAVYYCAT (SEQ ID NO: 694)

RFTISVDKAKNSLYMQLNSLRAEDTAVYYCAT (SEQ ID NO: 695)

RFTISVDNAKSSAYLQLNSLRAEDTAVYYCAT (SEQ ID NO: 696)

RFTISVDNAKSSLYMQLNSLRAEDTAVYYCAT (SEQ ID NO: 697)

RFTISVDNAKNSAYMQLNSLRAEDTAVYYCAT (SEQ ID NO: 698)

RFTISRDKAKSSAYMQLNSLRAEDTAVYYCAR (SEQ ID NO: 699)

RFTISRDKAKSSAYMQMNSLRAEDTAVYYCAT (SEQ ID NO: 700)

RFTISRDKAKSSAYLQLNSLRAEDTAVYYCAT (SEQ ID NO: 701)

RFTISRDKAKSSLYMQLNSLRAEDTAVYYCAT (SEQ ID NO: 702)

RFTISRDKAKNSAYMQLNSLRAEDTAVYYCAT (SEQ ID NO: 703)

RFTISRDNAKSSAYMQLNSLRAEDTAVYYCAT (SEQ ID NO: 704)

RATLSVDKASNSAYLQMNSLRAEDTAVYYCAR (SEQ ID NO: 705)

RATLSVDKASNSLYMQMNSLRAEDTAVYYCAR (SEQ ID NO: 706)

RATLSVDKASNSLYLQLNSLRAEDTAVYYCAR (SEQ ID NO: 707)

RATLSVDKASNSLYLQMNSLRAEDTAVYYCAT (SEQ ID NO: 708)

RATLSVDKAKNSAYMQMNSLRAEDTAVYYCAR (SEQ ID NO: 709)

RATLSVDKAKNSAYLQLNSLRAEDTAVYYCAR (SEQ ID NO: 710)

RATLSVDKAKNSAYLQMNSLRAEDTAVYYCAT (SEQ ID NO: 711)

RATLSVDKAKNSLYMQLNSLRAEDTAVYYCAR (SEQ ID NO: 712)

RATLSVDKAKNSLYMQMNSLRAEDTAVYYCAT (SEQ ID NO: 713)

RATLSVDKAKNSLYLQLNSLRAEDTAVYYCAT (SEQ ID NO: 714)

TABLE 6-continued

Amino Acid Sequences derived from Murine 76E1 Antibody.

RATLSVDNAKSSAYMQMNSLRAEDTAVYYCAR (SEQ ID NO: 715)

RATLSVDNAKSSAYLQLNSLRAEDTAVYYCAR (SEQ ID NO: 716)

RATLSVDNAKSSAYLQMNSLRAEDTAVYYCAT (SEQ ID NO: 717)

RATLSVDNAKSSLYMQLNSLRAEDTAVYYCAR (SEQ ID NO: 718)

RATLSVDNAKSSLYMQMNSLRAEDTAVYYCAT (SEQ ID NO: 719)

RATLSVDNAKSSLYLQLNSLRAEDTAVYYCAT (SEQ ID NO: 720)

RATLSVDNAKNSAYMQLNSLRAEDTAVYYCAR (SEQ ID NO: 721)

RATLSVDNAKNSAYMQMNSLRAEDTAVYYCAT (SEQ ID NO: 722)

RATLSVDNAKNSAYLQLNSLRAEDTAVYYCAT (SEQ ID NO: 723)

RATLSVDNAKNSLYMQLNSLRAEDTAVYYCAT (SEQ ID NO: 724)

RATLSRDKAKSSAYMQMNSLRAEDTAVYYCAR (SEQ ID NO: 725)

RATLSRDKAKSSAYLQLNSLRAEDTAVYYCAR (SEQ ID NO: 726)

RATLSRDKAKSSAYLQMNSLRAEDTAVYYCAT (SEQ ID NO: 727)

RATLSRDKAKSSLYMQLNSLRAEDTAVYYCAR (SEQ ID NO: 728)

RATLSRDKAKSSLYMQMNSLRAEDTAVYYCAT (SEQ ID NO: 729)

RATLSRDKAKSSLYLQLNSLRAEDTAVYYCAT (SEQ ID NO: 730)

RATLSRDKAKNSAYMQMNSLRAEDTAVYYCAR (SEQ ID NO: 731)

RATLSRDKAKNSAYMQMNSLRAEDTAVYYCAT (SEQ ID NO: 732)

RATLSRDKAKNSAYLQLNSLRAEDTAVYYCAT (SEQ ID NO: 733)

RATLSRDKAKNSLYMQLNSLRAEDTAVYYCAT (SEQ ID NO: 734)

RATLSRDNAKSSAYMQLNSLRAEDTAVYYCAR (SEQ ID NO: 735)

RATLSRDNAKSSAYMQMNSLRAEDTAVYYCAT (SEQ ID NO: 736)

RATLSRDNAKSSAYLQLNSLRAEDTAVYYCAT (SEQ ID NO: 737)

RATLSRDNAKSSLYMQLNSLRAEDTAVYYCAT (SEQ ID NO: 738)

RATLSRDNAKNSAYMQLNSLRAEDTAVYYCAT (SEQ ID NO: 739)

RATISVDKAKSSAYMQMNSLRAEDTAVYYCAR (SEQ ID NO: 740)

RATISVDKAKSSAYLQLNSLRAEDTAVYYCAR (SEQ ID NO: 741)

RATISVDKAKSSAYLQMNSLRAEDTAVYYCAT (SEQ ID NO: 742)

RATISVDKAKSSLYMQLNSLRAEDTAVYYCAR (SEQ ID NO: 743)

RATISVDKAKSSLYMQMNSLRAEDTAVYYCAT (SEQ ID NO: 744)

RATISVDKAKSSLYLQLNSLRAEDTAVYYCAT (SEQ ID NO: 745)

RATISVDKAKNSAYMQLNSLRAEDTAVYYCAR (SEQ ID NO: 746)

RATISVDKAKNSAYMQMNSLRAEDTAVYYCAT (SEQ ID NO: 747)

RATISVDKAKNSAYLQLNSLRAEDTAVYYCAT (SEQ ID NO: 748)

RATISVDKAKNSLYMQLNSLRAEDTAVYYCAT (SEQ ID NO: 749)

RATISVDNAKSSAYMQLNSLRAEDTAVYYCAR (SEQ ID NO: 750)

RATISVDNAKSSAYMQMNSLRAEDTAVYYCAT (SEQ ID NO: 751)

RATISVDNAKSSAYLQLNSLRAEDTAVYYCAT (SEQ ID NO: 752)

RATISVDNAKSSLYMQLNSLRAEDTAVYYCAT (SEQ ID NO: 753)

TABLE 6-continued

Amino Acid Sequences derived from Murine 76E1 Antibody.

RATISVDNAKNSAYMQLNSLRAEDTAVYYCAT (SEQ ID NO: 754)

RATISRDKAKSSAYMQLNSLRAEDTAVYYCAR (SEQ ID NO: 755)

RATISRDKAKSSAYMQMNSLRAEDTAVYYCAT (SEQ ID NO: 756)

RATISRDKAKSSAYLQLNSLRAEDTAVYYCAT (SEQ ID NO: 757)

RATISRDKAKSSLYMQLNSLRAEDTAVYYCAT (SEQ ID NO: 758)

RATISRDKAKNSAYMQLNSLRAEDTAVYYCAT (SEQ ID NO: 759)

RATISRDNAKSSAYMQLNSLRAEDTAVYYCAT (SEQ ID NO: 760)

RFTLSVDKAKSSAYMQMNSLRAEDTAVYYCAR (SEQ ID NO: 761)

RFTLSVDKAKSSAYLQLNSLRAEDTAVYYCAR (SEQ ID NO: 762)

RFTLSVDKAKSSAYLQMNSLRAEDTAVYYCAT (SEQ ID NO: 763)

RFTLSVDKAKSSLYMQLNSLRAEDTAVYYCAR (SEQ ID NO: 764)

RFTLSVDKAKSSLYMQMNSLRAEDTAVYYCAT (SEQ ID NO: 765)

RFTLSVDKAKSSLYLQLNSLRAEDTAVYYCAT (SEQ ID NO: 766)

RFTLSVDKAKNSAYMQLNSLRAEDTAVYYCAR (SEQ ID NO: 767)

RFTLSVDKAKNSAYMQMNSLRAEDTAVYYCAT (SEQ ID NO: 768)

RFTLSVDKAKNSAYLQLNSLRAEDTAVYYCAT (SEQ ID NO: 769)

RFTLSVDKAKNSLYMQLNSLRAEDTAVYYCAT (SEQ ID NO: 770)

RFTLSVDNAKSSAYMQLNSLRAEDTAVYYCAR (SEQ ID NO: 771)

RFTLSVDNAKSSAYMQMNSLRAEDTAVYYCAT (SEQ ID NO: 772)

RFTLSVDNAKSSAYLQLNSLRAEDTAVYYCAT (SEQ ID NO: 773)

RFTLSVDNAKSSLYMQLNSLRAEDTAVYYCAT (SEQ ID NO: 774)

RFTLSVDNAKNSAYMQLNSLRAEDTAVYYCAT (SEQ ID NO: 775)

RFTLSRDKASNSAYMQLNSLRAEDTAVYYCAR (SEQ ID NO: 776)

RFTLSRDKASNSAYMQMNSLRAEDTAVYYCAT (SEQ ID NO: 777)

RFTLSRDKASNSAYLQLNSLRAEDTAVYYCAT (SEQ ID NO: 778)

RFTLSRDKASNSLYMQLNSLRAEDTAVYYCAT (SEQ ID NO: 779)

RFTLSRDKAKNSAYMQLNSLRAEDTAVYYCAT (SEQ ID NO: 780)

RFTLSRDNAKSSAYMQLNSLRAEDTAVYYCAT (SEQ ID NO: 781)

RFTISVDKAKSSAYMQLNSLRAEDTAVYYCAR (SEQ ID NO: 782)

RFTISVDKAKSSAYMQMNSLRAEDTAVYYCAT (SEQ ID NO: 783)

RFTISVDKAKSSAYLQLNSLRAEDTAVYYCAT (SEQ ID NO: 784)

RFTISVDKAKSSLYMQLNSLRAEDTAVYYCAT (SEQ ID NO: 785)

RFTISVDKAKNSAYMQLNSLRAEDTAVYYCAT (SEQ ID NO: 786)

RFTISRDKAKSSAYMQLNSLRAEDTAVYYCAT (SEQ ID NO: 787)

RATLSVDKASNSAYMQMNSLRAEDTAVYYCAR (SEQ ID NO: 788)

RATLSVDKASNSAYLQLNSLRAEDTAVYYCAR (SEQ ID NO: 789)

RATLSVDKASNSAYLQMNSLRAEDTAVYYCAT (SEQ ID NO: 790)

RATLSVDKASNSLYMQLNSLRAEDTAVYYCAR (SEQ ID NO: 791)

RATLSVDKASNSLYMQMNSLRAEDTAVYYCAT (SEQ ID NO: 792)

TABLE 6-continued

Amino Acid Sequences derived from Murine 76E1 Antibody.

RATLSVDKASNSLYLQLNSLRAEDTAVYYCAT (SEQ ID NO: 793)

RATLSVDKAKNSAYMQLNSLRAEDTAVYYCAR (SEQ ID NO: 794)

RATLSVDKAKNSAYMQMNSLRAEDTAVYYCAT (SEQ ID NO: 795)

RATLSVDKAKNSAYLQLNSLRAEDTAVYYCAT (SEQ ID NO: 796)

RATLSVDKAKNSLYMQLNSLRAEDTAVYYCAT (SEQ ID NO: 797)

RATLSVDNAKSSAYMQLNSLRAEDTAVYYCAR (SEQ ID NO: 798)

RATLSVDNAKSSAYMQMNSLRAEDTAVYYCAT (SEQ ID NO: 799)

RATLSVDNAKSSAYLQLNSLRAEDTAVYYCAT (SEQ ID NO: 800)

RATLSVDNAKSSLYMQLNSLRAEDTAVYYCAT (SEQ ID NO: 801)

RATLSVDNAKNSAYMQLNSLRAEDTAVYYCAT (SEQ ID NO: 802)

RATLSRDKAKSSAYMQLNSLRAEDTAVYYCAR (SEQ ID NO: 803)

RATLSRDKAKSSAYMQMNSLRAEDTAVYYCAT (SEQ ID NO: 804)

RATLSRDKAKSSAYLQLNSLRAEDTAVYYCAT (SEQ ID NO: 805)

RATLSRDKAKSSLYMQLNSLRAEDTAVYYCAT (SEQ ID NO: 806)

RATLSRDKAKNSAYMQLNSLRAEDTAVYYCAT (SEQ ID NO: 807)

RATLSRDNAKSSAYMQLNSLRAEDTAVYYCAT (SEQ ID NO: 808)

RATISVDKAKSSAYMQLNSLRAEDTAVYYCAR (SEQ ID NO: 809)

RATISVDKAKSSAYMQMNSLRAEDTAVYYCAT (SEQ ID NO: 810)

RATISVDKAKSSAYLQLNSLRAEDTAVYYCAT (SEQ ID NO: 811)

RATISVDKAKSSLYMQLNSLRAEDTAVYYCAT (SEQ ID NO: 812)

RATISVDKAKNSAYMQLNSLRAEDTAVYYCAT (SEQ ID NO: 813)

RATISVDNAKSSAYMQLNSLRAEDTAVYYCAT (SEQ ID NO: 814)

RATISRDKAKSSAYMQLNSLRAEDTAVYYCAT (SEQ ID NO: 815)

RFTLSVDKAKSSAYMQLNSLRAEDTAVYYCAR (SEQ ID NO: 816)

RFTLSVDKAKSSAYMQMNSLRAEDTAVYYCAT (SEQ ID NO: 817)

RFTLSVDKAKSSAYLQLNSLRAEDTAVYYCAT (SEQ ID NO: 818)

RFTLSVDKAKSSLYMQLNSLRAEDTAVYYCAT (SEQ ID NO: 819)

RFTLSVDKAKNSAYMQLNSLRAEDTAVYYCAT (SEQ ID NO: 820)

RFTLSVDNAKSSAYMQLNSLRAEDTAVYYCAT (SEQ ID NO: 821)

RFTLSRDKASNSAYMQLNSLRAEDTAVYYCAT (SEQ ID NO: 822)

RFTISVDKAKSSAYMQLNSLRAEDTAVYYCAT (SEQ ID NO: 823)

RATLSVDKASNSAYMQLNSLRAEDTAVYYCAR (SEQ ID NO: 824)

RATLSVDKASNSAYMQMNSLRAEDTAVYYCAT (SEQ ID NO: 825)

RATLSVDKASNSAYLQLNSLRAEDTAVYYCAT (SEQ ID NO: 826)

RATLSVDKASNSLYMQLNSLRAEDTAVYYCAT (SEQ ID NO: 827)

RATLSVDKAKNSAYMQLNSLRAEDTAVYYCAT (SEQ ID NO: 828)

RATLSVDNAKSSAYMQLNSLRAEDTAVYYCAT (SEQ ID NO: 829)

RATLSRDKAKSSAYMQLNSLRAEDTAVYYCAT (SEQ ID NO: 830)

RATISVDKAKSSAYMQLNSLRAEDTAVYYCAT (SEQ ID NO: 831)

TABLE 6-continued

Amino Acid Sequences derived from Murine 76E1 Antibody.

RFTLSVDKAKSSAYMQLNSLRAEDTAVYYCAT (SEQ ID NO: 832)

RATLSVDKASNSAYMQLNSLRAEDTAVYYCAT (SEQ ID NO: 833)

76E1-huVH3a VH CDR3

STMITPFDY (SEQ ID NO: 32)

STLITPFDY (SEQ ID NO: 319)

76E1-huVH3a VH FR4

WGQGTLVTVSS (SEQ ID NO: 54)

WGQGTLLTVSS (SEQ ID NO: 320)

76E1-huVH3b Variable Region

EVQLVESGGGLVQPGGSLRLSCAASGYSFTGYNMNWVRQAPGKGLEWVSNIDPYYDTS
YADSVKGRFTISRDNAKNSLYLQMNSLRAEDTAVYYCARSTMITPFDYWGQGTLVTVSS
(SEQ ID NO: 15)

76E1-huVH3b VH FR1

EVQLVESGGGLVQPGGSLRLSCAAS (SEQ ID NO: 55)

EVQLVQSGGGLVQPGGSLRLSCAAS (SEQ ID NO: 115)

EVQLVESGGGLVQPGGSVRLSCAAS (SEQ ID NO: 116)

EVQLVESGGGLVQPGGSLRISCAAS (SEQ ID NO: 117)

EVQLVQSGGGLVQPGGSVRLSCAAS (SEQ ID NO: 118)

EVQLVESGGGLVQPGGSVRISCAAS (SEQ ID NO: 119)

EVQLVQSGGGLVQPGGSLRISCAAS (SEQ ID NO: 120)

EVQLVQSGGGLVQPGGSVRISCAAS (SEQ ID NO: 121)

76E1-huVH3b VH CDR1

GYSFTGYNMN (SEQ ID NO: 30)

GYSFTGYQMN (SEQ ID NO: 59)

GYSFTGYSMN (SEQ ID NO: 60)

GYSFTGYDMN (SEQ ID NO: 61)

GYSFTGYAMN (SEQ ID NO: 62)

76E1-huVH3b VH FR2

WVRQAPGKGLEWVS (SEQ ID NO: 56)

WVRQAPGKSLEWVS (SEQ ID NO: 323)

WVRQAPGKGLEWIS (SEQ ID NO: 122)

WVRQAPGKGLEWVG (SEQ ID NO: 123)

WVRQAPGKSLEWIS (SEQ ID NO: 324)

WVRQAPGKSLEWVG (SEQ ID NO: 325)

WVRQAPGKGLEWIG (SEQ ID NO: 124)

WVRQAPGKSLEWIG (SEQ ID NO: 326)

76E1-huVH3b VH CDR2*

NIDPYYDYTSYADSVKG (SEQ ID NO: 835)

NIEPYYDYTSYADSVKG (SEQ ID NO: 836)

NISPYYDYTSYADSVKG (SEQ ID NO: 837)

TABLE 6-continued

Amino Acid Sequences derived from Murine 76E1 Antibody.

NIAPYYDYTSYADSVKG (SEQ ID NO: 838)

NIDPYYDYTSYADSVKG (SEQ ID NO: 839)

NIEPYYDYTSYADSVKG (SEQ ID NO: 840)

NISPYYDYTSYADSVKG (SEQ ID NO: 841)

NIAPYYDYTSYADSVKG (SEQ ID NO: 842)

76E1-huVH3b VH FR3

RFTISRDNAKNSLYLQMNSLRAEDTAVYYCAR (SEQ ID NO: 57)

RATISRDNAKNSLYLQMNSLRAEDTAVYYCAR (SEQ ID NO: 327)

RFTLSRDNAKNSLYLQMNSLRAEDTAVYYCAR (SEQ ID NO: 328)

RFTISVDNAKNSLYLQMNSLRAEDTAVYYCAR (SEQ ID NO: 329)

RFTISRDKAKNSLYLQMNSLRAEDTAVYYCAR (SEQ ID NO: 330)

RFTISRDNAKSSLYLQMNSLRAEDTAVYYCAR (SEQ ID NO: 331)

RFTISRDNAKNSAYLQMNSLRAEDTAVYYCAR (SEQ ID NO: 332)

RFTISRDNAKNSLYMQMNSLRAEDTAVYYCAR (SEQ ID NO: 333)

RFTISRDNAKNSLYLQLNSLRAEDTAVYYCAR (SEQ ID NO: 334)

RFTISRDNAKNSLYLQMNSLRAEDTAVYYCAT (SEQ ID NO: 335)

RATLSRDNAKNSLYLQMNSLRAEDTAVYYCAR (SEQ ID NO: 336)

RATISVDNAKNSLYLQMNSLRAEDTAVYYCAR (SEQ ID NO: 337)

RATISRDKAKNSLYLQMNSLRAEDTAVYYCAR (SEQ ID NO: 338)

RATISRDNAKSSLYLQMNSLRAEDTAVYYCAR (SEQ ID NO: 339)

RATISRDNAKNSAYLQMNSLRAEDTAVYYCAR (SEQ ID NO: 340)

RATISRDNAKNSLYMQMNSLRAEDTAVYYCAR (SEQ ID NO: 341)

RATISRDNAKNSLYLQLNSLRAEDTAVYYCAR (SEQ ID NO: 342)

RATISRDNAKNSLYLQMNSLRAEDTAVYYCAT (SEQ ID NO: 343)

RFTLSVDNAKNSLYLQMNSLRAEDTAVYYCAR (SEQ ID NO: 344)

RFTLSRDKAKNSLYLQMNSLRAEDTAVYYCAR (SEQ ID NO: 345)

RFTLSRDNAKSSLYLQMNSLRAEDTAVYYCAR (SEQ ID NO: 346)

RFTLSRDNAKNSAYLQMNSLRAEDTAVYYCAR (SEQ ID NO: 347)

RFTLSRDNAKNSLYMQMNSLRAEDTAVYYCAR (SEQ ID NO: 348)

RFTLSRDNAKNSLYLQLNSLRAEDTAVYYCAR (SEQ ID NO: 349)

RFTLSRDNAKNSLYLQMNSLRAEDTAVYYCAT (SEQ ID NO: 350)

RFTISVDKAKNSLYLQMNSLRAEDTAVYYCAR (SEQ ID NO: 351)

RFTISVDNAKSSLYLQMNSLRAEDTAVYYCAR (SEQ ID NO: 352)

RFTISVDNAKNSAYLQMNSLRAEDTAVYYCAR (SEQ ID NO: 353)

RFTISVDNAKNSLYMQMNSLRAEDTAVYYCAR (SEQ ID NO: 354)

RFTISVDNAKNSLYLQLNSLRAEDTAVYYCAR (SEQ ID NO: 355)

RFTISVDNAKNSLYLQMNSLRAEDTAVYYCAT (SEQ ID NO: 356)

RFTISRDKAKSSLYLQMNSLRAEDTAVYYCAR (SEQ ID NO: 357)

RFTISRDKAKNSAYLQMNSLRAEDTAVYYCAR (SEQ ID NO: 358)

TABLE 6-continued

Amino Acid Sequences derived from Murine 76E1 Antibody.

RFTISRDKAKNSLYMQMNSLRAEDTAVYYCAR (SEQ ID NO: 359)

RFTISRDKAKNSLYLQLNSLRAEDTAVYYCAR (SEQ ID NO: 360)

RFTISRDKAKNSLYLQMNSLRAEDTAVYYCAT (SEQ ID NO: 361)

RFTISRDNAKSSAYLQMNSLRAEDTAVYYCAR (SEQ ID NO: 362)

RFTISRDNAKSSLYMQMNSLRAEDTAVYYCAR (SEQ ID NO: 363)

RFTISRDNAKSSLYLQLNSLRAEDTAVYYCAR (SEQ ID NO: 364)

RFTISRDNAKSSLYLQMNSLRAEDTAVYYCAT (SEQ ID NO: 365)

RFTISRDNAKNSAYMQMNSLRAEDTAVYYCAR (SEQ ID NO: 366)

RFTISRDNAKNSAYLQLNSLRAEDTAVYYCAR (SEQ ID NO: 367)

RFTISRDNAKNSAYLQMNSLRAEDTAVYYCAT (SEQ ID NO: 368)

RFTISRDNAKNSLYMQLNSLRAEDTAVYYCAR (SEQ ID NO: 369)

RFTISRDNAKNSLYMQMNSLRAEDTAVYYCAT (SEQ ID NO: 370)

RFTISRDNAKNSLYLQLNSLRAEDTAVYYCAT (SEQ ID NO: 371)

RATLSVDNAKNSLYLQMNSLRAEDTAVYYCAR (SEQ ID NO: 372)

RATLSRDKAKNSLYLQMNSLRAEDTAVYYCAR (SEQ ID NO: 373)

RATLSRDNAKSSLYLQMNSLRAEDTAVYYCAR (SEQ ID NO: 374)

RATLSRDNAKNSAYLQMNSLRAEDTAVYYCAR (SEQ ID NO: 375)

RATLSRDNAKNSLYMQMNSLRAEDTAVYYCAR (SEQ ID NO: 376)

RATLSRDNAKNSLYLQLNSLRAEDTAVYYCAR (SEQ ID NO: 377)

RATLSRDNAKNSLYLQMNSLRAEDTAVYYCAT (SEQ ID NO: 378)

RATISVDKAKNSLYLQMNSLRAEDTAVYYCAR (SEQ ID NO: 379)

RATISVDNAKSSLYLQMNSLRAEDTAVYYCAR (SEQ ID NO: 380)

RATISVDNAKNSAYLQMNSLRAEDTAVYYCAR (SEQ ID NO: 381)

RATISVDNAKNSLYMQMNSLRAEDTAVYYCAR (SEQ ID NO: 382)

RATISVDNAKNSLYLQLNSLRAEDTAVYYCAR (SEQ ID NO: 383)

RATISVDNAKNSLYLQMNSLRAEDTAVYYCAT (SEQ ID NO: 384)

RATISRDKAKSSLYLQMNSLRAEDTAVYYCAR (SEQ ID NO: 385)

RATISRDKAKNSAYLQMNSLRAEDTAVYYCAR (SEQ ID NO: 386)

RATISRDKAKNSLYMQMNSLRAEDTAVYYCAR (SEQ ID NO: 387)

RATISRDKAKNSLYLQLNSLRAEDTAVYYCAR (SEQ ID NO: 388)

RATISRDKAKNSLYLQMNSLRAEDTAVYYCAT (SEQ ID NO: 389)

RATISRDNAKSSAYLQMNSLRAEDTAVYYCAR (SEQ ID NO: 390)

RATISRDNAKSSLYMQMNSLRAEDTAVYYCAR (SEQ ID NO: 391)

RATISRDNAKSSLYLQLNSLRAEDTAVYYCAR (SEQ ID NO: 392)

RATISRDNAKSSLYLQMNSLRAEDTAVYYCAT (SEQ ID NO: 393)

RATISRDNAKNSAYMQMNSLRAEDTAVYYCAR (SEQ ID NO: 394)

RATISRDNAKNSAYLQLNSLRAEDTAVYYCAR (SEQ ID NO: 395)

RATISRDNAKNSAYLQMNSLRAEDTAVYYCAT (SEQ ID NO: 396)

RATISRDNAKNSLYMQLNSLRAEDTAVYYCAR (SEQ ID NO: 397)

TABLE 6-continued

Amino Acid Sequences derived from Murine 76E1 Antibody.

RATISRDNAKNSLYMQMNSLRAEDTAVYYCAT (SEQ ID NO: 398)

RATISRDNAKNSLYLQLNSLRAEDTAVYYCAT (SEQ ID NO: 399)

RFTLSVDKAKNSLYLQMNSLRAEDTAVYYCAR (SEQ ID NO: 400)

RFTLSVDNAKSSLYLQMNSLRAEDTAVYYCAR (SEQ ID NO: 401)

RFTLSVDNAKNSAYLQMNSLRAEDTAVYYCAR (SEQ ID NO: 402)

RFTLSVDNAKNSLYMQMNSLRAEDTAVYYCAR (SEQ ID NO: 403)

RFTLSVDNAKNSLYLQLNSLRAEDTAVYYCAR (SEQ ID NO: 404)

RFTLSVDNAKNSLYLQMNSLRAEDTAVYYCAT (SEQ ID NO: 405)

RFTLSRDKASNSLYLQMNSLRAEDTAVYYCAR (SEQ ID NO: 406)

RFTLSRDKAKNSAYLQMNSLRAEDTAVYYCAR (SEQ ID NO: 407)

RFTLSRDKAKNSLYMQMNSLRAEDTAVYYCAR (SEQ ID NO: 408)

RFTLSRDKAKNSLYLQLNSLRAEDTAVYYCAR (SEQ ID NO: 409)

RFTLSRDKAKNSLYLQMNSLRAEDTAVYYCAT (SEQ ID NO: 410)

RFTLSRDNAKSSAYLQMNSLRAEDTAVYYCAR (SEQ ID NO: 411)

RFTLSRDNAKSSLYMQMNSLRAEDTAVYYCAR (SEQ ID NO: 412)

RFTLSRDNAKSSLYLQLNSLRAEDTAVYYCAR (SEQ ID NO: 413)

RFTLSRDNAKSSLYLQMNSLRAEDTAVYYCAT (SEQ ID NO: 414)

RFTLSRDNAKNSAYMQMNSLRAEDTAVYYCAR (SEQ ID NO: 415)

RFTLSRDNAKNSAYLQLNSLRAEDTAVYYCAR (SEQ ID NO: 416)

RFTLSRDNAKNSAYLQMNSLRAEDTAVYYCAT (SEQ ID NO: 417)

RFTLSRDNAKNSLYMQLNSLRAEDTAVYYCAR (SEQ ID NO: 418)

RFTLSRDNAKNSLYMQMNSLRAEDTAVYYCAT (SEQ ID NO: 419)

RFTLSRDNAKNSLYLQLNSLRAEDTAVYYCAT (SEQ ID NO: 420)

RFTISVDKAKSSLYLQMNSLRAEDTAVYYCAR (SEQ ID NO: 421)

RFTISVDKAKNSAYLQMNSLRAEDTAVYYCAR (SEQ ID NO: 422)

RFTISVDKAKNSLYMQMNSLRAEDTAVYYCAR (SEQ ID NO: 423)

RFTISVDKAKNSLYLQLNSLRAEDTAVYYCAR (SEQ ID NO: 424)

RFTISVDKAKNSLYLQMNSLRAEDTAVYYCAT (SEQ ID NO: 425)

RFTISVDNAKSSAYLQMNSLRAEDTAVYYCAR (SEQ ID NO: 426)

RFTISVDNAKSSLYMQMNSLRAEDTAVYYCAR (SEQ ID NO: 427)

RFTISVDNAKSSLYLQLNSLRAEDTAVYYCAR (SEQ ID NO: 428)

RFTISVDNAKSSLYLQMNSLRAEDTAVYYCAT (SEQ ID NO: 429)

RFTISVDNAKNSAYMQMNSLRAEDTAVYYCAR (SEQ ID NO: 430)

RFTISVDNAKNSAYLQLNSLRAEDTAVYYCAR (SEQ ID NO: 431)

RFTISVDNAKNSAYLQMNSLRAEDTAVYYCAT (SEQ ID NO: 432)

RFTISVDNAKNSLYMQLNSLRAEDTAVYYCAR (SEQ ID NO: 433)

RFTISVDNAKNSLYMQMNSLRAEDTAVYYCAT (SEQ ID NO: 434)

RFTISVDNAKNSLYLQLNSLRAEDTAVYYCAT (SEQ ID NO: 435)

RFTISRDKAKSSAYLQMNSLRAEDTAVYYCAR (SEQ ID NO: 436)

TABLE 6-continued

Amino Acid Sequences derived from Murine 76E1 Antibody.

RFTISRDKAKSSLYMQMNSLRAEDTAVYYCAR (SEQ ID NO: 437)

RFTISRDKAKSSLYLQLNSLRAEDTAVYYCAR (SEQ ID NO: 438)

RFTISRDKAKSSLYLQMNSLRAEDTAVYYCAT (SEQ ID NO: 439)

RFTISRDKAKNSAYMQMNSLRAEDTAVYYCAR (SEQ ID NO: 440)

RFTISRDKAKNSAYLQLNSLRAEDTAVYYCAR (SEQ ID NO: 441)

RFTISRDKAKNSAYLQMNSLRAEDTAVYYCAT (SEQ ID NO: 442)

RFTISRDKAKNSLYMQLNSLRAEDTAVYYCAR (SEQ ID NO: 443)

RFTISRDKAKNSLYMQMNSLRAEDTAVYYCAT (SEQ ID NO: 444)

RFTISRDKAKNSLYLQLNSLRAEDTAVYYCAT (SEQ ID NO: 445)

RFTISRDNAKSSAYMQMNSLRAEDTAVYYCAR (SEQ ID NO: 446)

RFTISRDNAKSSAYLQLNSLRAEDTAVYYCAR (SEQ ID NO: 447)

RFTISRDNAKSSAYLQMNSLRAEDTAVYYCAT (SEQ ID NO: 448)

RFTISRDNAKSSLYMQLNSLRAEDTAVYYCAR (SEQ ID NO: 449)

RFTISRDNAKSSLYMQMNSLRAEDTAVYYCAT (SEQ ID NO: 450)

RFTISRDNAKSSLYLQLNSLRAEDTAVYYCAT (SEQ ID NO: 451)

RFTISRDNAKNSAYMQLNSLRAEDTAVYYCAR (SEQ ID NO: 452)

RFTISRDNAKNSAYMQMNSLRAEDTAVYYCAT (SEQ ID NO: 453)

RFTISRDNAKNSAYLQLNSLRAEDTAVYYCAT (SEQ ID NO: 454)

RFTISRDNAKNSLYMQLNSLRAEDTAVYYCAT (SEQ ID NO: 455)

RATLSVDKAKNSLYLQMNSLRAEDTAVYYCAR (SEQ ID NO: 456)

RATLSVDNAKSSLYLQMNSLRAEDTAVYYCAR (SEQ ID NO: 457)

RATLSVDNAKNSAYLQMNSLRAEDTAVYYCAR (SEQ ID NO: 458)

RATLSVDNAKNSLYMQMNSLRAEDTAVYYCAR (SEQ ID NO: 459)

RATLSVDNAKNSLYLQLNSLRAEDTAVYYCAR (SEQ ID NO: 460)

RATLSVDNAKNSLYLQMNSLRAEDTAVYYCAT (SEQ ID NO: 461)

RATLSRDKAKSSLYLQMNSLRAEDTAVYYCAR (SEQ ID NO: 462)

RATLSRDKAKNSAYLQMNSLRAEDTAVYYCAR (SEQ ID NO: 463)

RATLSRDKAKNSLYMQMNSLRAEDTAVYYCAR (SEQ ID NO: 464)

RATLSRDKAKNSLYLQLNSLRAEDTAVYYCAR (SEQ ID NO: 465)

RATLSRDKAKNSLYLQMNSLRAEDTAVYYCAT (SEQ ID NO: 466)

RATLSRDNAKSSAYLQMNSLRAEDTAVYYCAR (SEQ ID NO: 467)

RATLSRDNAKSSLYMQMNSLRAEDTAVYYCAR (SEQ ID NO: 468)

RATLSRDNAKSSLYLQLNSLRAEDTAVYYCAR (SEQ ID NO: 469)

RATLSRDNAKSSLYLQMNSLRAEDTAVYYCAT (SEQ ID NO: 470)

RATLSRDNAKNSAYMQMNSLRAEDTAVYYCAR (SEQ ID NO: 471)

RATLSRDNAKNSAYLQLNSLRAEDTAVYYCAR (SEQ ID NO: 472)

RATLSRDNAKNSAYLQMNSLRAEDTAVYYCAT (SEQ ID NO: 473)

RATLSRDNAKNSLYMQLNSLRAEDTAVYYCAR (SEQ ID NO: 474)

RATLSRDNAKNSLYMQMNSLRAEDTAVYYCAT (SEQ ID NO: 475)

TABLE 6-continued

Amino Acid Sequences derived from Murine 76E1 Antibody.

RATLSRDNAKNSLYLQLNSLRAEDTAVYYCAT (SEQ ID NO: 476)

RATISVDKAKSSLYLQMNSLRAEDTAVYYCAR (SEQ ID NO: 477)

RATISVDKAKNSAYLQMNSLRAEDTAVYYCAR (SEQ ID NO: 478)

RATISVDKAKNSLYMQMNSLRAEDTAVYYCAR (SEQ ID NO: 479)

RATISVDKAKNSLYLQLNSLRAEDTAVYYCAR (SEQ ID NO: 480)

RATISVDKAKNSLYLQMNSLRAEDTAVYYCAT (SEQ ID NO: 481)

RATISVDNAKSSAYLQMNSLRAEDTAVYYCAR (SEQ ID NO: 482)

RATISVDNAKSSLYMQMNSLRAEDTAVYYCAR (SEQ ID NO: 483)

RATISVDNAKSSLYLQLNSLRAEDTAVYYCAR (SEQ ID NO: 484)

RATISVDNAKSSLYLQMNSLRAEDTAVYYCAT (SEQ ID NO: 485)

RATISVDNAKNSAYMQMNSLRAEDTAVYYCAR (SEQ ID NO: 486)

RATISVDNAKNSAYLQLNSLRAEDTAVYYCAR (SEQ ID NO: 487)

RATISVDNAKNSAYLQMNSLRAEDTAVYYCAT (SEQ ID NO: 488)

RATISVDNAKNSLYMQLNSLRAEDTAVYYCAR (SEQ ID NO: 489)

RATISVDNAKNSLYMQMNSLRAEDTAVYYCAT (SEQ ID NO: 490)

RATISVDNAKNSLYLQLNSLRAEDTAVYYCAT (SEQ ID NO: 491)

RATISRDKAKSAYLQMNSLRAEDTAVYYCAR (SEQ ID NO: 492)

RATISRDKAKSSLYMQMNSLRAEDTAVYYCAR (SEQ ID NO: 493)

RATISRDKAKSSLYLQLNSLRAEDTAVYYCAR (SEQ ID NO: 494)

RATISRDKAKSSLYLQMNSLRAEDTAVYYCAT (SEQ ID NO: 495)

RATISRDKAKNSAYMQMNSLRAEDTAVYYCAR (SEQ ID NO: 496)

RATISRDKAKNSAYLQLNSLRAEDTAVYYCAR (SEQ ID NO: 497)

RATISRDKAKNSAYLQMNSLRAEDTAVYYCAT (SEQ ID NO: 498)

RATISRDKAKNSLYMQLNSLRAEDTAVYYCAR (SEQ ID NO: 499)

RATISRDKAKNSLYMQMNSLRAEDTAVYYCAT (SEQ ID NO: 500)

RATISRDKAKNSLYLQLNSLRAEDTAVYYCAT (SEQ ID NO: 501)

RATISRDNAKSSAYMQMNSLRAEDTAVYYCAR (SEQ ID NO: 502)

RATISRDNAKSSAYLQLNSLRAEDTAVYYCAR (SEQ ID NO: 503)

RATISRDNAKSSAYLQMNSLRAEDTAVYYCAT (SEQ ID NO: 504)

RATISRDNAKSSLYMQLNSLRAEDTAVYYCAR (SEQ ID NO: 505)

RATISRDNAKSSLYMQMNSLRAEDTAVYYCAT (SEQ ID NO: 506)

RATISRDNAKSSLYLQLNSLRAEDTAVYYCAT (SEQ ID NO: 507)

RATISRDNAKNSAYMQLNSLRAEDTAVYYCAR (SEQ ID NO: 508)

RATISRDNAKNSAYMQMNSLRAEDTAVYYCAT (SEQ ID NO: 509)

RATISRDNAKNSAYLQLNSLRAEDTAVYYCAT (SEQ ID NO: 510)

RATISRDNAKNSLYMQLNSLRAEDTAVYYCAT (SEQ ID NO: 511)

RFTLSVDKAKSSLYLQMNSLRAEDTAVYYCAR (SEQ ID NO: 512)

RFTLSVDKAKNSAYLQMNSLRAEDTAVYYCAR (SEQ ID NO: 513)

RFTLSVDKAKNSLYMQMNSLRAEDTAVYYCAR (SEQ ID NO: 514)

TABLE 6-continued

Amino Acid Sequences derived from Murine 76E1 Antibody.

RFTLSVDKAKNSLYLQLNSLRAEDTAVYYCAR (SEQ ID NO: 515)

RFTLSVDKAKNSLYLQMNSLRAEDTAVYYCAT (SEQ ID NO: 516)

RFTLSVDNAKSSAYLQMNSLRAEDTAVYYCAR (SEQ ID NO: 517)

RFTLSVDNAKSSLYMQMNSLRAEDTAVYYCAR (SEQ ID NO: 518)

RFTLSVDNAKSSLYLQLNSLRAEDTAVYYCAR (SEQ ID NO: 519)

RFTLSVDNAKSSLYLQMNSLRAEDTAVYYCAT (SEQ ID NO: 520)

RFTLSVDNAKNSAYMQMNSLRAEDTAVYYCAR (SEQ ID NO: 521)

RFTLSVDNAKNSAYLQLNSLRAEDTAVYYCAR (SEQ ID NO: 522)

RFTLSVDNAKNSAYLQMNSLRAEDTAVYYCAT (SEQ ID NO: 523)

RFTLSVDNAKNSLYMQLNSLRAEDTAVYYCAR (SEQ ID NO: 524)

RFTLSVDNAKNSLYMQMNSLRAEDTAVYYCAT (SEQ ID NO: 525)

RFTLSVDNAKNSLYLQLNSLRAEDTAVYYCAT (SEQ ID NO: 526)

RFTLSRDKASNSAYLQMNSLRAEDTAVYYCAR (SEQ ID NO: 527)

RFTLSRDKASNSLYMQMNSLRAEDTAVYYCAR (SEQ ID NO: 528)

RFTLSRDKASNSLYLQLNSLRAEDTAVYYCAR (SEQ ID NO: 529)

RFTLSRDKASNSLYLQMNSLRAEDTAVYYCAT (SEQ ID NO: 530)

RFTLSRDKAKNSAYMQMNSLRAEDTAVYYCAR (SEQ ID NO: 531)

RFTLSRDKAKNSAYLQLNSLRAEDTAVYYCAR (SEQ ID NO: 532)

RFTLSRDKAKNSAYLQMNSLRAEDTAVYYCAT (SEQ ID NO: 533)

RFTLSRDKAKNSLYMQLNSLRAEDTAVYYCAR (SEQ ID NO: 534)

RFTLSRDKAKNSLYMQMNSLRAEDTAVYYCAT (SEQ ID NO: 535)

RFTLSRDKAKNSLYLQLNSLRAEDTAVYYCAT (SEQ ID NO: 536)

RFTLSRDNAKSSAYMQMNSLRAEDTAVYYCAR (SEQ ID NO: 537)

RFTLSRDNAKSSAYLQLNSLRAEDTAVYYCAR (SEQ ID NO: 538)

RFTLSRDNAKSSAYLQMNSLRAEDTAVYYCAT (SEQ ID NO: 539)

RFTLSRDNAKSSLYMQLNSLRAEDTAVYYCAR (SEQ ID NO: 540)

RFTLSRDNAKSSLYMQMNSLRAEDTAVYYCAT (SEQ ID NO: 541)

RFTLSRDNAKSSLYLQLNSLRAEDTAVYYCAT (SEQ ID NO: 542)

RFTLSRDNAKNSAYMQLNSLRAEDTAVYYCAR (SEQ ID NO: 543)

RFTLSRDNAKNSAYMQMNSLRAEDTAVYYCAT (SEQ ID NO: 544)

RFTLSRDNAKNSAYLQLNSLRAEDTAVYYCAT (SEQ ID NO: 545)

RFTLSRDNAKNSLYMQLNSLRAEDTAVYYCAT (SEQ ID NO: 546)

RFTISVDKAKSSAYLQMNSLRAEDTAVYYCAR (SEQ ID NO: 547)

RFTISVDKAKSSLYMQMNSLRAEDTAVYYCAR (SEQ ID NO: 548)

RFTISVDKAKSSLYLQLNSLRAEDTAVYYCAR (SEQ ID NO: 549)

RFTISVDKAKSSLYLQMNSLRAEDTAVYYCAT (SEQ ID NO: 550)

RFTISVDKAKNSAYMQMNSLRAEDTAVYYCAR (SEQ ID NO: 551)

RFTISVDKAKNSAYLQLNSLRAEDTAVYYCAR (SEQ ID NO: 552)

RFTISVDKAKNSAYLQMNSLRAEDTAVYYCAT (SEQ ID NO: 553)

TABLE 6-continued

Amino Acid Sequences derived from Murine 76E1 Antibody.

RFTISVDKAKNSLYMQLNSLRAEDTAVYYCAR (SEQ ID NO: 554)

RFTISVDKAKNSLYMQMNSLRAEDTAVYYCAT (SEQ ID NO: 555)

RFTISVDKAKNSLYLQLNSLRAEDTAVYYCAT (SEQ ID NO: 556)

RFTISVDNAKSSAYLQLNSLRAEDTAVYYCAR (SEQ ID NO: 557)

RFTISVDNAKSSAYLQMNSLRAEDTAVYYCAT (SEQ ID NO: 558)

RFTISVDNAKSSLYMQLNSLRAEDTAVYYCAR (SEQ ID NO: 559)

RFTISVDNAKSSLYMQMNSLRAEDTAVYYCAT (SEQ ID NO: 560)

RFTISVDNAKSSLYLQLNSLRAEDTAVYYCAT (SEQ ID NO: 561)

RFTISVDNAKNSAYMQLNSLRAEDTAVYYCAR (SEQ ID NO: 562)

RFTISVDNAKNSAYMQMNSLRAEDTAVYYCAT (SEQ ID NO: 563)

RFTISVDNAKNSAYLQLNSLRAEDTAVYYCAT (SEQ ID NO: 564)

RFTISVDNAKNSLYMQLNSLRAEDTAVYYCAT (SEQ ID NO: 565)

RFTISRDKAKSSAYMQMNSLRAEDTAVYYCAR (SEQ ID NO: 566)

RFTISRDKAKSSAYLQLNSLRAEDTAVYYCAR (SEQ ID NO: 567)

RFTISRDKAKSSAYLQMNSLRAEDTAVYYCAT (SEQ ID NO: 568)

RFTISRDKAKSSLYMQLNSLRAEDTAVYYCAR (SEQ ID NO: 569)

RFTISRDKAKSSLYMQMNSLRAEDTAVYYCAT (SEQ ID NO: 570)

RFTISRDKAKSSLYLQLNSLRAEDTAVYYCAT (SEQ ID NO: 571)

RFTISRDKAKNSAYMQLNSLRAEDTAVYYCAR (SEQ ID NO: 572)

RFTISRDKAKNSAYMQMNSLRAEDTAVYYCAT (SEQ ID NO: 573)

RFTISRDKAKNSAYLQLNSLRAEDTAVYYCAT (SEQ ID NO: 574)

RFTISRDKAKNSLYMQLNSLRAEDTAVYYCAT (SEQ ID NO: 575)

RFTISRDNAKSSAYMQLNSLRAEDTAVYYCAR (SEQ ID NO: 576)

RFTISRDNAKSSAYMQMNSLRAEDTAVYYCAT (SEQ ID NO: 577)

RFTISRDNAKSSAYLQLNSLRAEDTAVYYCAT (SEQ ID NO: 578)

RFTISRDNAKSSLYMQLNSLRAEDTAVYYCAT (SEQ ID NO: 579)

RFTISRDNAKNSAYMQLNSLRAEDTAVYYCAT (SEQ ID NO: 580)

RATLSVDKASNSLYLQMNSLRAEDTAVYYCAR (SEQ ID NO: 581)

RATLSVDKAKNSAYLQMNSLRAEDTAVYYCAR (SEQ ID NO: 582)

RATLSVDKAKNSLYMQMNSLRAEDTAVYYCAR (SEQ ID NO: 583)

RATLSVDKAKNSLYLQLNSLRAEDTAVYYCAR (SEQ ID NO: 584)

RATLSVDKAKNSLYLQMNSLRAEDTAVYYCAT (SEQ ID NO: 585)

RATLSVDNAKSSAYLQMNSLRAEDTAVYYCAR (SEQ ID NO: 586)

RATLSVDNAKSSLYMQMNSLRAEDTAVYYCAR (SEQ ID NO: 587)

RATLSVDNAKSSLYLQLNSLRAEDTAVYYCAR (SEQ ID NO: 588)

RATLSVDNAKSSLYLQMNSLRAEDTAVYYCAT (SEQ ID NO: 589)

RATLSVDNAKNSAYMQMNSLRAEDTAVYYCAR (SEQ ID NO: 590)

RATLSVDNAKNSAYLQLNSLRAEDTAVYYCAR (SEQ ID NO: 591)

RATLSVDNAKNSAYLQMNSLRAEDTAVYYCAT (SEQ ID NO: 592)

TABLE 6-continued

Amino Acid Sequences derived from Murine 76E1 Antibody.

RATLSVDNAKNSLYMQLNSLRAEDTAVYYCAR (SEQ ID NO: 593)

RATLSVDNAKNSLYMQMNSLRAEDTAVYYCAT (SEQ ID NO: 594)

RATLSVDNAKNSLYLQLNSLRAEDTAVYYCAT (SEQ ID NO: 595)

RATLSRDKAKSSAYLQMNSLRAEDTAVYYCAR (SEQ ID NO: 596)

RATLSRDKAKSSLYMQMNSLRAEDTAVYYCAR (SEQ ID NO: 597)

RATLSRDKAKSSLYLQLNSLRAEDTAVYYCAR (SEQ ID NO: 598)

RATLSRDKAKSSLYLQMNSLRAEDTAVYYCAT (SEQ ID NO: 599)

RATLSRDKAKNSAYMQMNSLRAEDTAVYYCAR (SEQ ID NO: 600)

RATLSRDKAKNSAYLQLNSLRAEDTAVYYCAR (SEQ ID NO: 601)

RATLSRDKAKNSAYLQMNSLRAEDTAVYYCAT (SEQ ID NO: 602)

RATLSRDKAKNSLYMQLNSLRAEDTAVYYCAR (SEQ ID NO: 603)

RATLSRDKAKNSLYMQMNSLRAEDTAVYYCAT (SEQ ID NO: 604)

RATLSRDKAKNSLYLQLNSLRAEDTAVYYCAT (SEQ ID NO: 605)

RATLSRDNAKSSAYMQMNSLRAEDTAVYYCAR (SEQ ID NO: 606)

RATLSRDNAKSSAYLQLNSLRAEDTAVYYCAR (SEQ ID NO: 607)

RATLSRDNAKSSAYLQMNSLRAEDTAVYYCAT (SEQ ID NO: 608)

RATLSRDNAKSSLYMQLNSLRAEDTAVYYCAR (SEQ ID NO: 609)

RATLSRDNAKSSLYMQMNSLRAEDTAVYYCAT (SEQ ID NO: 610)

RATLSRDNAKSSLYLQLNSLRAEDTAVYYCAT (SEQ ID NO: 611)

RATLSRDNAKNSAYMQLNSLRAEDTAVYYCAR (SEQ ID NO: 612)

RATLSRDNAKNSAYMQMNSLRAEDTAVYYCAT (SEQ ID NO: 613)

RATLSRDNAKNSAYLQLNSLRAEDTAVYYCAT (SEQ ID NO: 614)

RATLSRDNAKNSLYMQLNSLRAEDTAVYYCAT (SEQ ID NO: 615)

RATISVDKAKSSAYLQMNSLRAEDTAVYYCAR (SEQ ID NO: 616)

RATISVDKAKSSLYMQMNSLRAEDTAVYYCAR (SEQ ID NO: 617)

RATISVDKAKSSLYLQLNSLRAEDTAVYYCAR (SEQ ID NO: 618)

RATISVDKAKSSLYLQMNSLRAEDTAVYYCAT (SEQ ID NO: 619)

RATISVDKAKNSAYMQMNSLRAEDTAVYYCAR (SEQ ID NO: 620)

RATISVDKAKNSAYLQMNSLRAEDTAVYYCAR (SEQ ID NO: 621)

RATISVDKAKNSAYLQMNSLRAEDTAVYYCAT (SEQ ID NO: 622)

RATISVDKAKNSLYMQLNSLRAEDTAVYYCAR (SEQ ID NO: 623)

RATISVDKAKNSLYMQMNSLRAEDTAVYYCAT (SEQ ID NO: 624)

RATISVDKAKNSLYLQLNSLRAEDTAVYYCAT (SEQ ID NO: 625)

RATISVDNAKSSAYMQMNSLRAEDTAVYYCAR (SEQ ID NO: 626)

RATISVDNAKSSAYLQMNSLRAEDTAVYYCAR (SEQ ID NO: 627)

RATISVDNAKSSAYLQMNSLRAEDTAVYYCAT (SEQ ID NO: 628)

RATISVDNAKSSLYMQMNSLRAEDTAVYYCAR (SEQ ID NO: 629)

RATISVDNAKSSLYMQMNSLRAEDTAVYYCAT (SEQ ID NO: 630)

RATISVDNAKSSLYLQLNSLRAEDTAVYYCAT (SEQ ID NO: 631)

TABLE 6-continued

Amino Acid Sequences derived from Murine 76E1 Antibody.

RATISVDNAKNSAYMQLNSLRAEDTAVYYCAR (SEQ ID NO: 632)

RATISVDNAKNSAYMQMNSLRAEDTAVYYCAT (SEQ ID NO: 633)

RATISVDNAKNSAYLQLNSLRAEDTAVYYCAT (SEQ ID NO: 634)

RATISVDNAKNSLYMQLNSLRAEDTAVYYCAT (SEQ ID NO: 635)

RATISRDKAKSSAYMQMNSLRAEDTAVYYCAR (SEQ ID NO: 636)

RATISRDKAKSSAYLQLNSLRAEDTAVYYCAR (SEQ ID NO: 637)

RATISRDKAKSSAYLQMNSLRAEDTAVYYCAT (SEQ ID NO: 638)

RATISRDKAKSSLYMQLNSLRAEDTAVYYCAR (SEQ ID NO: 639)

RATISRDKAKSSLYMQMNSLRAEDTAVYYCAT (SEQ ID NO: 640)

RATISRDKAKSSLYLQLNSLRAEDTAVYYCAT (SEQ ID NO: 641)

RATISRDKAKNSAYMQLNSLRAEDTAVYYCAR (SEQ ID NO: 642)

RATISRDKAKNSAYMQMNSLRAEDTAVYYCAT (SEQ ID NO: 643)

RATISRDKAKNSAYLQLNSLRAEDTAVYYCAT (SEQ ID NO: 644)

RATISRDKAKNSLYMQLNSLRAEDTAVYYCAT (SEQ ID NO: 645)

RATISRDNAKSSAYMQLNSLRAEDTAVYYCAR (SEQ ID NO: 646)

RATISRDNAKSSAYMQMNSLRAEDTAVYYCAT (SEQ ID NO: 647)

RATISRDNAKSSAYLQLNSLRAEDTAVYYCAT (SEQ ID NO: 648)

RATISRDNAKSSLYMQLNSLRAEDTAVYYCAT (SEQ ID NO: 649)

RATISRDNAKNSAYMQLNSLRAEDTAVYYCAT (SEQ ID NO: 650)

RFTLSVDKAKSSAYLQMNSLRAEDTAVYYCAR (SEQ ID NO: 651)

RFTLSVDKAKSSLYMQMNSLRAEDTAVYYCAR (SEQ ID NO: 652)

RFTLSVDKAKSSLYLQLNSLRAEDTAVYYCAR (SEQ ID NO: 653)

RFTLSVDKAKSSLYLQMNSLRAEDTAVYYCAT (SEQ ID NO: 654)

RFTLSVDKAKNSAYMQMNSLRAEDTAVYYCAR (SEQ ID NO: 655)

RFTLSVDKAKNSAYLQLNSLRAEDTAVYYCAR (SEQ ID NO: 656)

RFTLSVDKAKNSAYLQMNSLRAEDTAVYYCAT (SEQ ID NO: 657)

RFTLSVDKAKNSLYMQLNSLRAEDTAVYYCAR (SEQ ID NO: 658)

RFTLSVDKAKNSLYMQMNSLRAEDTAVYYCAT (SEQ ID NO: 659)

RFTLSVDKAKNSLYLQLNSLRAEDTAVYYCAT (SEQ ID NO: 660)

RFTLSVDNAKSSAYMQMNSLRAEDTAVYYCAR (SEQ ID NO: 661)

RFTLSVDNAKSSAYLQLNSLRAEDTAVYYCAR (SEQ ID NO: 662)

RFTLSVDNAKSSAYLQLNSLRAEDTAVYYCAT (SEQ ID NO: 663)

RFTLSVDNAKSSLYMQLNSLRAEDTAVYYCAR (SEQ ID NO: 664)

RFTLSVDNAKSSLYMQLNSLRAEDTAVYYCAT (SEQ ID NO: 665)

RFTLSVDNAKSSLYLQLNSLRAEDTAVYYCAT (SEQ ID NO: 666)

RFTLSVDNAKNSAYMQLNSLRAEDTAVYYCAR (SEQ ID NO: 667)

RFTLSVDNAKNSAYMQMNSLRAEDTAVYYCAT (SEQ ID NO: 668)

RFTLSVDNAKNSAYLQLNSLRAEDTAVYYCAT (SEQ ID NO: 669)

RFTLSVDNAKNSLYMQLNSLRAEDTAVYYCAT (SEQ ID NO: 670)

TABLE 6-continued

Amino Acid Sequences derived from Murine 76E1 Antibody.

RFTLSRDKASNSAYMQMNSLRAEDTAVYYCAR (SEQ ID NO: 671)

RFTLSRDKASNSAYLLQNSLRAEDTAVYYCAR (SEQ ID NO: 672)

RFTLSRDKASNSAYLQMNSLRAEDTAVYYCAT (SEQ ID NO: 673)

RFTLSRDKASNSLYMQLNSLRAEDTAVYYCAR (SEQ ID NO: 674)

RFTLSRDKASNSLYMQMNSLRAEDTAVYYCAT (SEQ ID NO: 675)

RFTLSRDKASNSLYLQLNSLRAEDTAVYYCAT (SEQ ID NO: 676)

RFTLSRDKAKNSAYMQLNSLRAEDTAVYYCAR (SEQ ID NO: 677)

RFTLSRDKAKNSAYMQMNSLRAEDTAVYYCAT (SEQ ID NO: 678)

RFTLSRDKAKNSAYLQLNSLRAEDTAVYYCAT (SEQ ID NO: 679)

RFTLSRDKAKNSLYMQLNSLRAEDTAVYYCAT (SEQ ID NO: 680)

RFTLSRDNAKSSAYMQLNSLRAEDTAVYYCAR (SEQ ID NO: 681)

RFTLSRDNAKSSAYMQMNSLRAEDTAVYYCAT (SEQ ID NO: 682)

RFTLSRDNAKSSAYLQLNSLRAEDTAVYYCAT (SEQ ID NO: 683)

RFTLSRDNAKSSLYMQMNSLRAEDTAVYYCAT (SEQ ID NO: 684)

RFTLSRDNAKNSAYMQLNSLRAEDTAVYYCAT (SEQ ID NO: 685)

RFTISVDKAKSSAYMQMNSLRAEDTAVYYCAR (SEQ ID NO: 686)

RFTISVDKAKSSAYLQLNSLRAEDTAVYYCAR (SEQ ID NO: 687)

RFTISVDKAKSSAYLQMNSLRAEDTAVYYCAT (SEQ ID NO: 688)

RFTISVDKAKSSLYMQMNSLRAEDTAVYYCAR (SEQ ID NO: 689)

RFTISVDKAKSSLYMQMNSLRAEDTAVYYCAT (SEQ ID NO: 690)

RFTISVDKAKSSLYLQLNSLRAEDTAVYYCAT (SEQ ID NO: 691)

RFTISVDKAKNSAYMQLNSLRAEDTAVYYCAR (SEQ ID NO: 692)

RFTISVDKAKNSAYMQMNSLRAEDTAVYYCAT (SEQ ID NO: 693)

RFTISVDKAKNSAYLQLNSLRAEDTAVYYCAT (SEQ ID NO: 694)

RFTISVDKAKNSLYMQLNSLRAEDTAVYYCAT (SEQ ID NO: 695)

RFTISVDNAKSSAYLQLNSLRAEDTAVYYCAT (SEQ ID NO: 696)

RFTISVDNAKSSLYMQMNSLRAEDTAVYYCAT (SEQ ID NO: 697)

RFTISVDNAKNSAYMQLNSLRAEDTAVYYCAT (SEQ ID NO: 698)

RFTISRDKAKSSAYMQLNSLRAEDTAVYYCAR (SEQ ID NO: 699)

RFTISRDKAKSSAYMQMNSLRAEDTAVYYCAT (SEQ ID NO: 700)

RFTISRDKAKSSAYLQLNSLRAEDTAVYYCAT (SEQ ID NO: 701)

RFTISRDKAKSSLYMQMNSLRAEDTAVYYCAT (SEQ ID NO: 702)

RFTISRDKAKNSAYMQLNSLRAEDTAVYYCAT (SEQ ID NO: 703)

RFTISRDNAKSSAYMQLNSLRAEDTAVYYCAT (SEQ ID NO: 704)

RATLSVDKASNSAYLQMNSLRAEDTAVYYCAR (SEQ ID NO: 705)

RATLSVDKASNSLYMQMNSLRAEDTAVYYCAR (SEQ ID NO: 706)

RATLSVDKASNSLYLQLNSLRAEDTAVYYCAR (SEQ ID NO: 707)

RATLSVDKASNSLYLQMNSLRAEDTAVYYCAT (SEQ ID NO: 708)

RATLSVDKAKNSAYMQMNSLRAEDTAVYYCAR (SEQ ID NO: 709)

TABLE 6-continued

Amino Acid Sequences derived from Murine 76E1 Antibody.

RATLSVDKAKNSAYLQLNSLRAEDTAVYYCAR (SEQ ID NO: 710)

RATLSVDKAKNSAYLQMNSLRAEDTAVYYCAT (SEQ ID NO: 711)

RATLSVDKAKNSLYMQLNSLRAEDTAVYYCAR (SEQ ID NO: 712)

RATLSVDKAKNSLYMQMNSLRAEDTAVYYCAT (SEQ ID NO: 713)

RATLSVDKAKNSLYLQLNSLRAEDTAVYYCAT (SEQ ID NO: 714)

RATLSVDNAKSSAYMQMNSLRAEDTAVYYCAR (SEQ ID NO: 715)

RATLSVDNAKSSAYLQLNSLRAEDTAVYYCAR (SEQ ID NO: 716)

RATLSVDNAKSSAYLQMNSLRAEDTAVYYCAT (SEQ ID NO: 717)

RATLSVDNAKSSLYMQLNSLRAEDTAVYYCAR (SEQ ID NO: 718)

RATLSVDNAKSSLYMQMNSLRAEDTAVYYCAT (SEQ ID NO: 719)

RATLSVDNAKSSLYLQLNSLRAEDTAVYYCAT (SEQ ID NO: 720)

RATLSVDNAKNSAYMQLNSLRAEDTAVYYCAR (SEQ ID NO: 721)

RATLSVDNAKNSAYMQMNSLRAEDTAVYYCAT (SEQ ID NO: 722)

RATLSVDNAKNSAYLQLNSLRAEDTAVYYCAT (SEQ ID NO: 723)

RATLSVDNAKNSLYMQLNSLRAEDTAVYYCAT (SEQ ID NO: 724)

RATLSRDKAKSSAYMQMNSLRAEDTAVYYCAR (SEQ ID NO: 725)

RATLSRDKAKSSAYLQLNSLRAEDTAVYYCAR (SEQ ID NO: 726)

RATLSRDKAKSSAYLQMNSLRAEDTAVYYCAT (SEQ ID NO: 727)

RATLSRDKAKSSLYMQLNSLRAEDTAVYYCAR (SEQ ID NO: 728)

RATLSRDKAKSSLYMQMNSLRAEDTAVYYCAT (SEQ ID NO: 729)

RATLSRDKAKSSLYLQLNSLRAEDTAVYYCAT (SEQ ID NO: 730)

RATLSRDKAKNSAYMQLNSLRAEDTAVYYCAR (SEQ ID NO: 731)

RATLSRDKAKNSAYMQMNSLRAEDTAVYYCAT (SEQ ID NO: 732)

RATLSRDKAKNSAYLQLNSLRAEDTAVYYCAT (SEQ ID NO: 733)

RATLSRDKAKNSLYMQLNSLRAEDTAVYYCAT (SEQ ID NO: 734)

RATLSRDNAKSSAYMQLNSLRAEDTAVYYCAR (SEQ ID NO: 735)

RATLSRDNAKSSAYMQMNSLRAEDTAVYYCAT (SEQ ID NO: 736)

RATLSRDNAKSSAYLQLNSLRAEDTAVYYCAT (SEQ ID NO: 737)

RATLSRDNAKSSLYMQLNSLRAEDTAVYYCAT (SEQ ID NO: 738)

RATLSRDNAKNSAYMQLNSLRAEDTAVYYCAT (SEQ ID NO: 739)

RATISVDKAKSSAYMQMNSLRAEDTAVYYCAR (SEQ ID NO: 740)

RATISVDKAKSSAYLQMNSLRAEDTAVYYCAR (SEQ ID NO: 741)

RATISVDKAKSSAYLQMNSLRAEDTAVYYCAT (SEQ ID NO: 742)

RATISVDKAKSSLYMQLNSLRAEDTAVYYCAR (SEQ ID NO: 743)

RATISVDKAKSSLYMQMNSLRAEDTAVYYCAT (SEQ ID NO: 744)

RATISVDKAKSSLYLQLNSLRAEDTAVYYCAT (SEQ ID NO: 745)

RATISVDKAKNSAYMQLNSLRAEDTAVYYCAR (SEQ ID NO: 746)

RATISVDKAKNSAYMQMNSLRAEDTAVYYCAT (SEQ ID NO: 747)

RATISVDKAKNSAYLQLNSLRAEDTAVYYCAT (SEQ ID NO: 748)

TABLE 6-continued

Amino Acid Sequences derived from Murine 76E1 Antibody.

RATISVDKAKNSLYMQLNSLRAEDTAVYYCAT (SEQ ID NO: 749)

RATISVDNAKSSAYMQLNSLRAEDTAVYYCAR (SEQ ID NO: 750)

RATISVDNAKSSAYMQMNSLRAEDTAVYYCAT (SEQ ID NO: 751)

RATISVDNAKSSAYLQLNSLRAEDTAVYYCAT (SEQ ID NO: 752)

RATISVDNAKSSLYMQLNSLRAEDTAVYYCAT (SEQ ID NO: 753)

RATISVDNAKNSAYMQLNSLRAEDTAVYYCAT (SEQ ID NO: 754)

RATISRDKAKSSAYMQLNSLRAEDTAVYYCAR (SEQ ID NO: 755)

RATISRDKAKSSAYMQMNSLRAEDTAVYYCAT (SEQ ID NO: 756)

RATISRDKAKSSAYLQLNSLRAEDTAVYYCAT (SEQ ID NO: 757)

RATISRDKAKSSLYMQLNSLRAEDTAVYYCAT (SEQ ID NO: 758)

RATISRDKAKNSAYMQLNSLRAEDTAVYYCAT (SEQ ID NO: 759)

RATISRDNAKSSAYMQLNSLRAEDTAVYYCAT (SEQ ID NO: 760)

RFTLSVDKAKSSAYMQMNSLRAEDTAVYYCAR (SEQ ID NO: 761)

RFTLSVDKAKSSAYLQLNSLRAEDTAVYYCAR (SEQ ID NO: 762)

RFTLSVDKAKSSAYLQMNSLRAEDTAVYYCAT (SEQ ID NO: 763)

RFTLSVDKAKSSLYMQLNSLRAEDTAVYYCAR (SEQ ID NO: 764)

RFTLSVDKAKSSLYMQMNSLRAEDTAVYYCAT (SEQ ID NO: 765)

RFTLSVDKAKSSLYLQLNSLRAEDTAVYYCAT (SEQ ID NO: 766)

RFTLSVDKAKNSAYMQLNSLRAEDTAVYYCAR (SEQ ID NO: 767)

RFTLSVDKAKNSAYMQMNSLRAEDTAVYYCAT (SEQ ID NO: 768)

RFTLSVDKAKNSAYLQLNSLRAEDTAVYYCAT (SEQ ID NO: 769)

RFTLSVDKAKNSLYMQLNSLRAEDTAVYYCAT (SEQ ID NO: 770)

RFTLSVDNAKSSAYMQLNSLRAEDTAVYYCAR (SEQ ID NO: 771)

RFTLSVDNAKSSAYMQMNSLRAEDTAVYYCAT (SEQ ID NO: 772)

RFTLSVDNAKSSAYLQLNSLRAEDTAVYYCAT (SEQ ID NO: 773)

RFTLSVDNAKSSLYMQLNSLRAEDTAVYYCAT (SEQ ID NO: 774)

RFTLSVDNAKNSAYMQLNSLRAEDTAVYYCAT (SEQ ID NO: 775)

RFTLSRDKASNSAYMQLNSLRAEDTAVYYCAR (SEQ ID NO: 776)

RFTLSRDKASNSAYMQMNSLRAEDTAVYYCAT (SEQ ID NO: 777)

RFTLSRDKASNSAYLQLNSLRAEDTAVYYCAT (SEQ ID NO: 778)

RFTLSRDKASNSLYMQLNSLRAEDTAVYYCAT (SEQ ID NO: 779)

RFTLSRDKAKNSAYMQLNSLRAEDTAVYYCAT (SEQ ID NO: 780)

RFTLSRDNAKSSAYMQLNSLRAEDTAVYYCAT (SEQ ID NO: 781)

RFTISVDKAKSSAYMQLNSLRAEDTAVYYCAR (SEQ ID NO: 782)

RFTISVDKAKSSAYMQMNSLRAEDTAVYYCAT (SEQ ID NO: 783)

RFTISVDKAKSSAYLQLNSLRAEDTAVYYCAT (SEQ ID NO: 784)

RFTISVDKAKSSLYMQLNSLRAEDTAVYYCAT (SEQ ID NO: 785)

RFTISVDKAKNSAYMQLNSLRAEDTAVYYCAT (SEQ ID NO: 786)

RFTISRDKAKSSAYMQLNSLRAEDTAVYYCAT (SEQ ID NO: 787)

TABLE 6-continued

Amino Acid Sequences derived from Murine 76E1 Antibody.

RATLSVDKASNSAYMQMNSLRAEDTAVYYCAR (SEQ ID NO: 788)

RATLSVDKASNSAYLQLNSLRAEDTAVYYCAR (SEQ ID NO: 789)

RATLSVDKASNSAYLQMNSLRAEDTAVYYCAT (SEQ ID NO: 790)

RATLSVDKASNSLYMQLNSLRAEDTAVYYCAR (SEQ ID NO: 791)

RATLSVDKASNSLYMQMNSLRAEDTAVYYCAT (SEQ ID NO: 792)

RATLSVDKASNSLYLQLNSLRAEDTAVYYCAT (SEQ ID NO: 793)

RATLSVDKAKNSAYMQLNSLRAEDTAVYYCAR (SEQ ID NO: 794)

RATLSVDKAKNSAYMQMNSLRAEDTAVYYCAT (SEQ ID NO: 795)

RATLSVDKAKNSAYLQLNSLRAEDTAVYYCAT (SEQ ID NO: 796)

RATLSVDKAKNSLYMQLNSLRAEDTAVYYCAT (SEQ ID NO: 797)

RATLSVDNAKSSAYMQLNSLRAEDTAVYYCAR (SEQ ID NO: 798)

RATLSVDNAKSSAYMQMNSLRAEDTAVYYCAT (SEQ ID NO: 799)

RATLSVDNAKSSAYLQLNSLRAEDTAVYYCAT (SEQ ID NO: 800)

RATLSVDNAKSSLYMQLNSLRAEDTAVYYCAT (SEQ ID NO: 801)

RATLSVDNAKNSAYMQLNSLRAEDTAVYYCAT (SEQ ID NO: 802)

RATLSRDKAKSSAYMQLNSLRAEDTAVYYCAR (SEQ ID NO: 803)

RATLSRDKAKSSAYMQMNSLRAEDTAVYYCAT (SEQ ID NO: 804)

RATLSRDKAKSSAYLQLNSLRAEDTAVYYCAT (SEQ ID NO: 805)

RATLSRDKAKSSLYMQLNSLRAEDTAVYYCAT (SEQ ID NO: 806)

RATLSRDKAKNSAYMQLNSLRAEDTAVYYCAT (SEQ ID NO: 807)

RATLSRDNAKSSAYMQLNSLRAEDTAVYYCAT (SEQ ID NO: 808)

RATISVDKAKSSAYMQLNSLRAEDTAVYYCAR (SEQ ID NO: 809)

RATISVDKAKSSAYMQMNSLRAEDTAVYYCAT (SEQ ID NO: 810)

RATISVDKAKSSAYLQLNSLRAEDTAVYYCAT (SEQ ID NO: 811)

RATISVDKAKSSLYMQLNSLRAEDTAVYYCAT (SEQ ID NO: 812)

RATISVDKAKNSAYMQLNSLRAEDTAVYYCAT (SEQ ID NO: 813)

RATISVDNAKSSAYMQLNSLRAEDTAVYYCAT (SEQ ID NO: 814)

RATISRDKAKSSAYMQLNSLRAEDTAVYYCAT (SEQ ID NO: 815)

RFTLSVDKAKSSAYMQLNSLRAEDTAVYYCAR (SEQ ID NO: 816)

RFTLSVDKAKSSAYMQMNSLRAEDTAVYYCAT (SEQ ID NO: 817)

RFTLSVDKAKSSAYLQLNSLRAEDTAVYYCAT (SEQ ID NO: 818)

RFTLSVDKAKSSLYMQLNSLRAEDTAVYYCAT (SEQ ID NO: 819)

RFTLSVDKAKNSAYMQLNSLRAEDTAVYYCAT (SEQ ID NO: 820)

RFTLSVDNAKSSAYMQLNSLRAEDTAVYYCAT (SEQ ID NO: 821)

RFTLSRDKASNSAYMQLNSLRAEDTAVYYCAT (SEQ ID NO: 822)

RFTISVDKAKSSAYMQLNSLRAEDTAVYYCAT (SEQ ID NO: 823)

RATLSVDKASNSAYMQLNSLRAEDTAVYYCAR (SEQ ID NO: 824)

RATLSVDKASNSAYMQMNSLRAEDTAVYYCAT (SEQ ID NO: 825)

RATLSVDKASNSAYLQLNSLRAEDTAVYYCAT (SEQ ID NO: 826)

TABLE 6-continued

Amino Acid Sequences derived from Murine 76E1 Antibody.

RATLSVDKASNSLYMQLNSLRAEDTAVYYCAT (SEQ ID NO: 827)

RATLSVDKAKNSAYMQLNSLRAEDTAVYYCAT (SEQ ID NO: 828)

RATLSVDNAKSSAYMQLNSLRAEDTAVYYCAT (SEQ ID NO: 829)

RATLSRDKAKSSAYMQLNSLRAEDTAVYYCAT (SEQ ID NO: 830)

RATLSVDKAKSSAYMQLNSLRAEDTAVYYCAT (SEQ ID NO: 831)

RFTLSVDKAKSSAYMQLNSLRAEDTAVYYCAT (SEQ ID NO: 832)

RATLSVDKASNSAYMQLNSLRAEDTAVYYCAT (SEQ ID NO: 833)

76E1-huVH3b VH CDR3

STMITPFDY (SEQ ID NO: 32)

STLITPFDY (SEQ ID NO: 319)

76E1-huVH3b VH FR4

WGQGTLVTVSS (SEQ ID NO: 54)

WGQGTLLTVSS (SEQ ID NO: 320)

76E1 HUMANIZED ANTIBODY SEQUENCE: LIGHT CHAIN

76E1-huVK2 Variable Region

DIVMTQSPLSLPVTPGEPASISCRSSQSIVHSNGNTYLEWYLQKPGQSPQLLIYKVSNRFSG
VPDRFSGSGSGTDFTLKISRVEAEDVGVYYCFQGSHVPWTFGQGTKLEIK
(SEQ ID NO: 24)

76E1-huVK2 VL FR1

DIVMTQSPLSLPVTPGEPASISC (SEQ ID NO: 75)

DVVMTQSPLSLPVTPGEPASISC (SEQ ID NO: 252)

76E1-huVK2 VL CDR1

RSSQSIVHSNGNTYLE (SEQ ID NO: 45)

RSSQSIVHSQGNTYLE (SEQ ID NO: 253)

RSSQSIVHSSGNTYLE (SEQ ID NO: 254)

RSSQSIVHSAGNTYLE (SEQ ID NO: 255)

RSSQSIVHSNGQTYLE (SEQ ID NO: 256)

RSSQSIVHSNGSTYLE (SEQ ID NO: 257)

RSSQSIVHSNGATYLE (SEQ ID NO: 258)

RSSQSIVHSNGDTYLE (SEQ ID NO: 259)

RSSQSIVHSQGQTYLE (SEQ ID NO: 260)

RSSQSIVHSQGSTYLE (SEQ ID NO: 261)

RSSQSIVHSQGATYLE (SEQ ID NO: 262)

RSSQSIVHSQGDTYLE (SEQ ID NO: 263)

RSSQSIVHSSGQTYLE (SEQ ID NO: 264)

RSSQSIVHSSGSTYLE (SEQ ID NO: 265)

RSSQSIVHSSGATYLE (SEQ ID NO: 266)

RSSQSIVHSSGDTYLE (SEQ ID NO: 267)

RSSQSIVHSAGQTYLE (SEQ ID NO: 268)

RSSQSIVHSAGSTYLE (SEQ ID NO: 269)

TABLE 6-continued

Amino Acid Sequences derived from Murine 76E1 Antibody.

RSSQSIVHSAGATYLE (SEQ ID NO: 270)

RSSQSIVHSAGDTYLE (SEQ ID NO: 271)

76E1-huVK2 VL FR2

WYLQKPGQSPQLLIY (SEQ ID NO: 76)

76E1-huVK2 VL CDR2

KVSNRFS (SEQ ID NO: 40)

KVSQRFS (SEQ ID NO: 843)

KVSSRFS (SEQ ID NO: 844)

KVSDRFS (SEQ ID NO: 845)

KVSARFS (SEQ ID NO: 846)

76E1-huVK2 VL FR3

GVPDRFSGSGSGTDFTLKISRVEAEDVGVYYC (SEQ ID NO: 77)

GVPDRFSGSGSGTDFTLKISRVEAEDLGVYYC (SEQ ID NO: 276)

76E1-huVK2 VL CDR3

FQGSHVPWT (SEQ ID NO: 41)

76E1-huVK2 VL FR4

FGQGTKLEIK (SEQ ID NO: 78)

76E1-huVK1 Variable Region

DIQMTQSPSSLSASVGDRVTITCRSSQSIVHSNGNTYLEWYQQKPGKAPKLLIYKVSNRFS
GVPSRFSGSGSGTDFTLTISSLQPEDFATYYCFQGSHVPWTFGQGTKLEIK
(SEQ ID NO: 25)

76E1-huVK1 VL FR1

DIQMTQSPSSLSASVGDRVTITC (SEQ ID NO: 79)

DVQMTQSPSSLSASVGDRVTITC (SEQ ID NO: 277)

DIQMTQSPSSLSVSVGDRVTITC (SEQ ID NO: 278)

DIQMTQSPSSLSASVGDRATITC (SEQ ID NO: 279)

DVQMTQSPSSLSVSVGDRVTITC (SEQ ID NO: 280)

DVQMTQSPSSLSASVGDRATITC (SEQ ID NO: 281)

DIQMTQSPSSLSVSVGDRATITC (SEQ ID NO: 282)

DVQMTQSPSSLSVSVGDRATITC (SEQ ID NO: 283)

76E1-huVK1 VL CDR1

RSSQSIVHSNGNTYLE (SEQ ID NO: 45)

RSSQSIVHSQGNTYLE (SEQ ID NO: 253)

RSSQSIVHSSGNTYLE (SEQ ID NO: 254)

RSSQSIVHSAGNTYLE (SEQ ID NO: 255)

RSSQSIVHSNGQTYLE (SEQ ID NO: 256)

RSSQSIVHSNGSTYLE (SEQ ID NO: 257)

RSSQSIVHSNGATYLE (SEQ ID NO: 258)

RSSQSIVHSNGDTYLE (SEQ ID NO: 259)

RSSQSIVHSQGQTYLE (SEQ ID NO: 260)

TABLE 6-continued

Amino Acid Sequences derived from Murine 76E1 Antibody.

RSSQSIVHSQGSTYLE (SEQ ID NO: 261)

RSSQSIVHSQGATYLE (SEQ ID NO: 262)

RSSQSIVHSQGDTYLE (SEQ ID NO: 263)

RSSQSIVHSSGQTYLE (SEQ ID NO: 264)

RSSQSIVHSSGSTYLE (SEQ ID NO: 265)

RSSQSIVHSSGATYLE (SEQ ID NO: 266)

RSSQSIVHSSGDTYLE (SEQ ID NO: 267)

RSSQSIVHSAGQTYLE (SEQ ID NO: 268)

RSSQSIVHSAGSTYLE (SEQ ID NO: 269)

RSSQSIVHSAGATYLE (SEQ ID NO: 270)

RSSQSIVHSAGDTYLE (SEQ ID NO: 271)

76E1-huVK1 VL FR2

VVYQQKPGKAPKLLIY (SEQ ID NO: 80)

VVYQQKPGKSPKLLIY (SEQ ID NO: 284)

76E1-huVK1 VL CDR2

KVSNRFS (SEQ ID NO: 40)

KVSQRFS (SEQ ID NO: 843)

KVSSRFS (SEQ ID NO: 844)

KVSDRFS (SEQ ID NO: 845)

KVSARFS (SEQ ID NO: 846)

76E1-huVK1 VL FR3

GVPSRFSGSGSGTDFTLTISSLQPEDFATYYC (SEQ ID NO: 81)

GVPSRFSGSGSGTDFTLTISSVQPEDFATYYC (SEQ ID NO: 285)

GVPSRFSGSGSGTDFTLTISSLQPEDLATYYC (SEQ ID NO: 286)

GVPSRFSGSGSGTDFTLTISSLQPEDFGTYYC (SEQ ID NO: 287)

GVPSRFSGSGSGTDFTLTISSVQPEDLATYYC (SEQ ID NO: 288)

GVPSRFSGSGSGTDFTLTISSVQPEDFGTYYC (SEQ ID NO: 289)

GVPSRFSGSGSGTDFTLTISSLQPEDLGTYYC (SEQ ID NO: 290)

GVPSRFSGSGSGTDFTLTISSVQPEDLGTYYC (SEQ ID NO: 291)

76E1-huVK1 VL CDR3

FQGSHVPWT (SEQ ID NO: 41)

76E1-huVK1 VL FR4

FGQGTKLEIK (SEQ ID NO: 78)

*Amino acid position numbering as in Kabat.

TABLE 7

Amino Acid Sequences derived from Murine 141A Antibody.

141A HUMANIZED ANTIBODY SEQUENCE: HEAVY CHAIN 141A-huVH1a Variable Region

QVQLVQSGAEVKKPGASVKVSCKASGYTFSRYWIEVWRQAPGQGLEWMG**EILPGSGST
NYNEKFKGRVTMTTDTSTSTAYMELRSLRSDDTAVYYCAREEVYDGYPWFGY**WGQGTLV
TVSS (SEQ ID NO: 16)

141A-huVH1a VH FR1

QVQLVQSGAEVKKPGASVKVSCKAS (SEQ ID NO: 51)

QVQLVQSGAEVMKPGASVKVSCKAS (SEQ ID NO: 39)

QVQLVQSGAEVKKPGASVKISCKAS (SEQ ID NO: 105)

QVQLVQSGAEVMKPGASVKISCKAS (SEQ ID NO: 58)

141A-huVH1a VH CDR1

GYTFSRYWIE (SEQ ID NO: 33)

141A-huVH1a VH FR2

WVRQAPGQGLEWMG (SEQ ID NO: 52)

WVRQAPGQGLEWIG (SEQ ID NO: 106)

141A-huVH1a VH CDR2

EILPGSGSTNYNEKFKG (SEQ ID NO: 34)

EILPGSGSTQYNEKFKG (SEQ ID NO: 847)

EILPGSGSTSYNEKFKG (SEQ ID NO: 848)

EILPGSGSTDYNEKFKG (SEQ ID NO: 849)

EILPGSGSTAYNEKFKG (SEQ ID NO: 850)

EILPGSGSTNYQEKFKG (SEQ ID NO: 851)

EILPGSGSTNYSEKFKG (SEQ ID NO: 852)

EILPGSGSTNYDEKFKG (SEQ ID NO: 853)

EILPGSGSTNYAEKFKG (SEQ ID NO: 854)

EILPGSGSTQYQEKFKG (SEQ ID NO: 855)

EILPGSGSTSYSEKFKG (SEQ ID NO: 856)

EILPGSGSTDYDEKFKG (SEQ ID NO: 857)

EILPGSGSTAYAEKFKG (SEQ ID NO: 858)

141A-huVH1a VH FR3

RVTMTTDTSTSTAYMELRSLRSDDTAVYYCAR (SEQ ID NO: 53)

RATMTTDTSTSTAYMELRSLRSDDTAVYYCAR (SEQ ID NO: 107)

RVTFTTDTSTSTAYMELRSLRSDDTAVYYCAR (SEQ ID NO: 108)

RVTMTADTSTSTAYMELRSLRSDDTAVYYCAR (SEQ ID NO: 109)

RVTMTTDTNTSTAYMELRSLRSDDTAVYYCAR (SEQ ID NO: 859)

RVTMTTDTSTSTAYMELRSLRSDDTAVYYCAG (SEQ ID NO: 860)

RATFTTDTSTSTAYMELRSLRSDDTAVYYCAR (SEQ ID NO: 110)

RATMTADTSTSTAYMELRSLRSDDTAVYYCAR (SEQ ID NO: 112)

RATMTTDTNTSTAYMELRSLRSDDTAVYYCAR (SEQ ID NO: 861)

RATMTTDTSTSTAYMELRSLRSDDTAVYYCAG (SEQ ID NO: 862)

TABLE 7-continued

Amino Acid Sequences derived from Murine 141A Antibody.

RVTFTADTSTSTAYMELRSLRSDDTAVYYCAR (SEQ ID NO: 111)

RVTFTTDTNSTAYMELRSLRSDDTAVYYCAR (SEQ ID NO: 863)

RVTFTTDTSTSTAYMELRSLRSDDTAVYYCAG (SEQ ID NO: 864)

RVTMTADTNSTAYMELRSLRSDDTAVYYCAR (SEQ ID NO: 865)

RVTMTADTSTSTAYMELRSLRSDDTAVYYCAG (SEQ ID NO: 866)

RVTMTTDTNSTAYMELRSLRSDDTAVYYCAG (SEQ ID NO: 867)

RATFTADTSTSTAYMELRSLRSDDTAVYYCAR (SEQ ID NO: 113)

RATFTTDTNSTAYMELRSLRSDDTAVYYCAR (SEQ ID NO: 868)

RATFTTDTSTSTAYMELRSLRSDDTAVYYCAG (SEQ ID NO: 869)

RATMTADTNSTAYMELRSLRSDDTAVYYCAR (SEQ ID NO: 870)

RATMTADTSTSTAYMELRSLRSDDTAVYYCAG (SEQ ID NO: 871)

RATMTTDTNSTAYMELRSLRSDDTAVYYCAG (SEQ ID NO: 872)

RVTFTADTNSTAYMELRSLRSDDTAVYYCAR (SEQ ID NO: 873)

RVTFTADTSTSTAYMELRSLRSDDTAVYYCAG (SEQ ID NO: 874)

RVTFTTDTNSTAYMELRSLRSDDTAVYYCAG (SEQ ID NO: 875)

RVTMTADTNSTAYMELRSLRSDDTAVYYCAG (SEQ ID NO: 876)

RATFTADTNSTAYMELRSLRSDDTAVYYCAR (SEQ ID NO: 877)

RATFTADTSTSTAYMELRSLRSDDTAVYYCAG (SEQ ID NO: 878)

RATFTTDTNSTAYMELRSLRSDDTAVYYCAG (SEQ ID NO: 879)

RATMTADTNSTAYMELRSLRSDDTAVYYCAG (SEQ ID NO: 880)

RVTFTADTNSTAYMELRSLRSDDTAVYYCAG (SEQ ID NO: 881)

RATFTADTNSTAYMELRSLRSDDTAVYYCAG (SEQ ID NO: 882)

141A-huVH1a VH CDR3

EEVYDGYPWFGY (SEQ ID NO: 35)

EEVYEGYPWFGY (SEQ ID NO: 883)

EEVYSGYPWFGY (SEQ ID NO: 884)

EEVYAGYPWFGY (SEQ ID NO: 885)

141A-huVH1a VH FR4

WGQGTLVTVSS (SEQ ID NO: 54)

141A-huVH1b Variable Region

QVQLVQSGAEVKKPGASVKVSCKASGYTFSRYWIEWVRQAPGQGLEWMGEILPGSGST NYAQKLQGRVTMTTDTSTSTAYMELRSLRSDDTAVYYCAREEVYDGYPWFGYWGQGTLV TVSS (SEQ ID NO: 17)

141A-huVH1b VH FR1

QVQLVQSGAEVKKPGASVKVSCKAS (SEQ ID NO: 51)

QVQLVQSGAEVMKPGASVKVSCKAS (SEQ ID NO: 39)

QVQLVQSGAEVKKPGASVKISCKAS (SEQ ID NO: 105)

QVQLVQSGAEVMKPGASVKISCKAS (SEQ ID NO: 58)

TABLE 7-continued

Amino Acid Sequences derived from Murine 141A Antibody.

141A-huVH1b VH CDR1

GYTFSRYWIE (SEQ ID NO: 33)

141A-huVH1b VH FR2

WVRQAPGQGLEWMG (SEQ ID NO: 52)

WVRQAPGQGLEWIG (SEQ ID NO: 106)

141A-huVH1b VH CDR2*

EILPGSGSTNYAQKLQG (SEQ ID NO: 49)

EILPGSGSTQYAQKLQG (SEQ ID NO: 886)

EILPGSGSTSYAQKLQG (SEQ ID NO: 887)

EILPGSGSTDYAQKLQG (SEQ ID NO: 888)

EILPGSGSTAYAQKLQG (SEQ ID NO: 889)

EILPGSGSTNYAQKFQG (SEQ ID NO: 890)

EILPGSGSTQYAQKFQG (SEQ ID NO: 891)

EILPGSGSTSYAQKFQG (SEQ ID NO: 892)

EILPGSGSTDYAQKFQG (SEQ ID NO: 893)

EILPGSGSTAYAQKFQG (SEQ ID NO: 894)

141A-huVH1b VH FR3

RVTMTTDTSTSTAYMELRSLRSDDTAVYYCAR (SEQ ID NO: 53)

RATMTTDTSTSTAYMELRSLRSDDTAVYYCAR (SEQ ID NO: 107)

RVTFTTDTSTSTAYMELRSLRSDDTAVYYCAR (SEQ ID NO: 108)

RVTMTADTSTSTAYMELRSLRSDDTAVYYCAR (SEQ ID NO: 109)

RVTMTTDTNTSTAYMELRSLRSDDTAVYYCAR (SEQ ID NO: 859)

RVTMTTDTSTSTAYMELRSLRSDDTAVYYCAG (SEQ ID NO: 860)

RATFTTDTSTSTAYMELRSLRSDDTAVYYCAR (SEQ ID NO: 110)

RATMTADTSTSTAYMELRSLRSDDTAVYYCAR (SEQ ID NO: 112)

RATMTTDTNTSTAYMELRSLRSDDTAVYYCAR (SEQ ID NO: 861)

RATMTTDTSTSTAYMELRSLRSDDTAVYYCAG (SEQ ID NO: 862)

RVTFTADTSTSTAYMELRSLRSDDTAVYYCAR (SEQ ID NO: 111)

RVTFTTDTNTSTAYMELRSLRSDDTAVYYCAR (SEQ ID NO: 863)

RVTFTTDTSTSTAYMELRSLRSDDTAVYYCAG (SEQ ID NO: 864)

RVTMTADTNTSTAYMELRSLRSDDTAVYYCAR (SEQ ID NO: 865)

RVTMTADTSTSTAYMELRSLRSDDTAVYYCAG (SEQ ID NO: 866)

RVTMTTDTNTSTAYMELRSLRSDDTAVYYCAG (SEQ ID NO: 867)

RATFTADTSTSTAYMELRSLRSDDTAVYYCAR (SEQ ID NO: 113)

RATFTTDTNTSTAYMELRSLRSDDTAVYYCAR (SEQ ID NO: 868)

RATFTTDTSTSTAYMELRSLRSDDTAVYYCAG (SEQ ID NO: 869)

RATMTADTNTSTAYMELRSLRSDDTAVYYCAR (SEQ ID NO: 870)

RATMTADTSTSTAYMELRSLRSDDTAVYYCAG (SEQ ID NO: 871)

RATMTTDTNTSTAYMELRSLRSDDTAVYYCAG (SEQ ID NO: 872)

TABLE 7-continued

Amino Acid Sequences derived from Murine 141A Antibody.

RVTFTADTNSTAYMELRSLRSDDTAVYYCAR (SEQ ID NO: 873)

RVTFTADTSTSTAYMELRSLRSDDTAVYYCAG (SEQ ID NO: 874)

RVTFTTDTNSTAYMELRSLRSDDTAVYYCAG (SEQ ID NO: 875)

RVTMTADTNSTAYMELRSLRSDDTAVYYCAG (SEQ ID NO: 876)

RATFTADTNSTAYMELRSLRSDDTAVYYCAR (SEQ ID NO: 877)

RATFTADTSTSTAYMELRSLRSDDTAVYYCAG (SEQ ID NO: 878)

RATFTTDTNSTAYMELRSLRSDDTAVYYCAG (SEQ ID NO: 879)

RATMTADTNSTAYMELRSLRSDDTAVYYCAG (SEQ ID NO: 880)

RVTFTADTNSTAYMELRSLRSDDTAVYYCAG (SEQ ID NO: 881)

RATFTADTNSTAYMELRSLRSDDTAVYYCAG (SEQ ID NO: 882)

141A-huVH1b VH CDR3

EEVYDGYPWFGY (SEQ ID NO: 35)

141A-huVH1b VH FR4

WGQGTLVTVSS (SEQ ID NO: 54)

141A-huVH3a Variable Region

EVQLVESGGGLVQPGGSLRLSCAASGYTFSRYWIEWVRQAPGKGLEWVSEILPGSGSTN YNEKFKGRFTISRDNAKNSLYLQMNSLRAEDTAVYYCAREEVYDGYPWFGYWGQGTLVT VSS (SEQ ID NO: 18)

141A-huVH3a VH FR1

EVQLVESGGGLVQPGGSLRLSCAAS (SEQ ID NO: 55)

EVQLVQSGGGLVQPGGSLRLSCAAS (SEQ ID NO: 115)

EVQLVESGGGLVQPGGSVRLSCAAS (SEQ ID NO: 116)

EVQLVESGGGLVQPGGSLRISCAAS (SEQ ID NO: 117)

EVQLVQSGGGLVQPGGSVRLSCAAS (SEQ ID NO: 118)

EVQLVESGGGLVQPGGSVRISCAAS (SEQ ID NO: 119)

EVQLVQSGGGLVQPGGSLRISCAAS (SEQ ID NO: 120)

EVQLVQSGGGLVQPGGSVRISCAAS (SEQ ID NO: 121)

EVQLVESGGGLMQPGGSLRLSCAAS (SEQ ID NO: 895)

EVQLVQSGGGLMQPGGSLRLSCAAS (SEQ ID NO: 896)

EVQLVESGGGLMQPGGSVRLSCAAS (SEQ ID NO: 897)

EVQLVESGGGLMQPGGSLRISCAAS (SEQ ID NO: 898)

EVQLVQSGGGLMQPGGSVRLSCAAS (SEQ ID NO: 899)

EVQLVQSGGGLMQPGGSLRISCAAS (SEQ ID NO: 900)

EVQLVESGGGLMQPGGSVRISCAAS (SEQ ID NO: 901)

EVQLVQSGGGLMQPGGSVRISCAAS (SEQ ID NO: 902)

141A-huVH3a VH CDR1

GYTFSRYWIE (SEQ ID NO: 33)

141A-huVH3a VH FR2

WVRQAPGKGLEWVS (SEQ ID NO: 56)

WVRQAPGKGLEWIS (SEQ ID NO: 122)

TABLE 7-continued

Amino Acid Sequences derived from Murine 141A Antibody.

WVRQAPGKGLEWVG (SEQ ID NO: 123)

WVRQAPGKGLEWIG (SEQ ID NO: 124)

141A-huVH3a VH CDR2

EILPGSGSTNYNEKFKG (SEQ ID NO: 34)

EILPGSGSTQYNEKFKG (SEQ ID NO: 847)

EILPGSGSTSYNEKFKG (SEQ ID NO: 848)

EILPGSGSTDYNEKFKG (SEQ ID NO: 849)

EILPGSGSTAYNEKFKG (SEQ ID NO: 850)

EILPGSGSTNYQEKFKG (SEQ ID NO: 851)

EILPGSGSTNYSEKFKG (SEQ ID NO: 852)

EILPGSGSTNYDEKFKG (SEQ ID NO: 853)

EILPGSGSTNYAEKFKG (SEQ ID NO: 854)

EILPGSGSTQYQEKFKG (SEQ ID NO: 855)

EILPGSGSTSYSEKFKG (SEQ ID NO: 856)

EILPGSGSTDYDEKFKG (SEQ ID NO: 857)

EILPGSGSTAYAEKFKG (SEQ ID NO: 858)

141A-huVH3a VH FR3

RFTISRDNAKNSLYLQMNSLRAEDTAVYYCAR (SEQ ID NO: 57)

RATISRDNAKNSLYLQMNSLRAEDTAVYYCAR (SEQ ID NO: 125)

RFTFSRDNAKNSLYLQMNSLRAEDTAVYYCAR (SEQ ID NO: 126)

RFTISADNAKNSLYLQMNSLRAEDTAVYYCAR (SEQ ID NO: 127)

RFTISRDTAKNSLYLQMNSLRAEDTAVYYCAR (SEQ ID NO: 128)

RFTISRDNAKNSAYLQMNSLRAEDTAVYYCAR (SEQ ID NO: 129)

RFTISRDNAKNSLYMQMNSLRAEDTAVYYCAR (SEQ ID NO: 130)

RFTISRDNAKNSLYLQLNSLRAEDTAVYYCAR (SEQ ID NO: 131)

RATFSRDNAKNSLYLQMNSLRAEDTAVYYCAR (SEQ ID NO: 132)

RATISADNAKNSLYLQMNSLRAEDTAVYYCAR (SEQ ID NO: 133)

RATISRDTAKNSLYLQMNSLRAEDTAVYYCAR (SEQ ID NO: 134)

RATISRDNAKNSAYLQMNSLRAEDTAVYYCAR (SEQ ID NO: 135)

RATISRDNAKNSLYMQMNSLRAEDTAVYYCAR (SEQ ID NO: 136)

RATISRDNAKNSLYLQLNSLRAEDTAVYYCAR (SEQ ID NO: 137)

RFTFSADNAKNSLYLQMNSLRAEDTAVYYCAR (SEQ ID NO: 138)

RFTFSRDTAKNSLYLQMNSLRAEDTAVYYCAR (SEQ ID NO: 139)

RFTFSRDNAKNSAYLQMNSLRAEDTAVYYCAR (SEQ ID NO: 140)

RFTFSRDNAKNSLYMQMNSLRAEDTAVYYCAR (SEQ ID NO: 141)

RFTFSRDNAKNSLYLQLNSLRAEDTAVYYCAR (SEQ ID NO: 142)

RFTISADT**AKNSLYLQMNSLRAEDTAVYYCAR (SEQ ID NO: 143)

RFTISADNAKNSAYLQMNSLRAEDTAVYYCAR (SEQ ID NO: 144)

RFTISADNAKNSLYMQMNSLRAEDTAVYYCAR (SEQ ID NO: 145)

TABLE 7-continued

Amino Acid Sequences derived from Murine 141A Antibody.

RFTISADNAKNSLYLQLNSLRAEDTAVYYCAR (SEQ ID NO: 146)

RFTISRDTAKNSAYLQMNSLRAEDTAVYYCAR (SEQ ID NO: 147)

RFTISRDTAKNSLYMQMNSLRAEDTAVYYCAR (SEQ ID NO: 148)

RFTISRDTAKNSLYLQLNSLRAEDTAVYYCAR (SEQ ID NO: 149)

RFTISRDNAKNSAYMQMNSLRAEDTAVYYCAR (SEQ ID NO: 150)

RFTISRDNAKNSAYLQLNSLRAEDTAVYYCAR (SEQ ID NO: 151)

RFTISRDNAKNSLYMQLNSLRAEDTAVYYCAR (SEQ ID NO: 152)

RATFSADNAKNSLYLQMNSLRAEDTAVYYCAR (SEQ ID NO: 153)

RATFSRDTAKNSLYLQMNSLRAEDTAVYYCAR (SEQ ID NO: 154)

RATFSRDNAKNSAYLQMNSLRAEDTAVYYCAR (SEQ ID NO: 155)

RATFSRDNAKNSLYMQMNSLRAEDTAVYYCAR (SEQ ID NO: 156)

RATFSRDNAKNSLYLQLNSLRAEDTAVYYCAR (SEQ ID NO: 157)

RATISADTAKNSLYLQMNSLRAEDTAVYYCAR (SEQ ID NO: 158)

RATISADNAKNSAYLQMNSLRAEDTAVYYCAR (SEQ ID NO: 159)

RATISADNAKNSLYMQMNSLRAEDTAVYYCAR (SEQ ID NO: 160)

RATISADNAKNSLYLQLNSLRAEDTAVYYCAR (SEQ ID NO: 161)

RATISRDTAKNSAYLQMNSLRAEDTAVYYCAR (SEQ ID NO: 162)

RATISRDTAKNSLYMQMNSLRAEDTAVYYCAR (SEQ ID NO: 163)

RATISRDTAKNSLYLQLNSLRAEDTAVYYCAR (SEQ ID NO: 164)

RATISRDNAKNSAYMQMNSLRAEDTAVYYCAR (SEQ ID NO: 165)

RATISRDNAKNSAYLQLNSLRAEDTAVYYCAR (SEQ ID NO: 166)

RATISRDNAKNSLYMQLNSLRAEDTAVYYCAR (SEQ ID NO: 167)

RFTFSADTAKNSLYLQMNSLRAEDTAVYYCAR (SEQ ID NO: 168)

RFTFSADNAKNSAYLQMNSLRAEDTAVYYCAR (SEQ ID NO: 169)

RFTFSADNAKNSLYMQMNSLRAEDTAVYYCAR (SEQ ID NO: 170)

RFTFSADNAKNSLYLQLNSLRAEDTAVYYCAR (SEQ ID NO: 171)

RFTFSRDTAKNSAYLQMNSLRAEDTAVYYCAR (SEQ ID NO: 172)

RFTFSRDTAKNSLYMQMNSLRAEDTAVYYCAR (SEQ ID NO: 173)

RFTFSRDTAKNSLYLQLNSLRAEDTAVYYCAR (SEQ ID NO: 174)

RFTFSRDNAKNSAYMQMNSLRAEDTAVYYCAR (SEQ ID NO: 175)

RFTFSRDNAKNSAYLQLNSLRAEDTAVYYCAR (SEQ ID NO: 176)

RFTFSRDNAKNSLYMQLNSLRAEDTAVYYCAR (SEQ ID NO: 177)

RFTISADTAKNSAYLQMNSLRAEDTAVYYCAR (SEQ ID NO: 178)

RFTISADTAKNSLYMQMNSLRAEDTAVYYCAR (SEQ ID NO: 179)

RFTISADTAKNSLYLQLNSLRAEDTAVYYCAR (SEQ ID NO: 180)

RFTISADNAKNSAYMQMNSLRAEDTAVYYCAR (SEQ ID NO: 181)

RFTISADNAKNSAYLQLNSLRAEDTAVYYCAR (SEQ ID NO: 182)

RFTISADNAKNSLYMQLNSLRAEDTAVYYCAR (SEQ ID NO: 183)

RFTISRDTAKNSAYMQMNSLRAEDTAVYYCAR (SEQ ID NO: 184)

TABLE 7-continued

Amino Acid Sequences derived from Murine 141A Antibody.

RFTISRDTAKNSAYLQLNSLRAEDTAVYYCAR (SEQ ID NO: 185)

RFTISRDTAKNSLYMQLNSLRAEDTAVYYCAR (SEQ ID NO: 186)

RFTISRDNAKNSAYMQLNSLRAEDTAVYYCAR (SEQ ID NO: 187)

RATFSADTAKNSLYLQMNSLRAEDTAVYYCAR (SEQ ID NO: 188)

RATFSADNAKNSAYLQMNSLRAEDTAVYYCAR (SEQ ID NO: 189)

RATFSADNAKNSLYMQMNSLRAEDTAVYYCAR (SEQ ID NO: 190)

RATFSADNAKNSLYLQLNSLRAEDTAVYYCAR (SEQ ID NO: 191)

RATFSRDTAKNSAYLQMNSLRAEDTAVYYCAR (SEQ ID NO: 192)

RATFSRDTAKNSLYMQMNSLRAEDTAVYYCAR (SEQ ID NO: 193)

RATFSRDTAKNSLYLQLNSLRAEDTAVYYCAR (SEQ ID NO: 194)

RATFSRDNAKNSAYMQMNSLRAEDTAVYYCAR (SEQ ID NO: 195)

RATFSRDNAKNSAYLQLNSLRAEDTAVYYCAR (SEQ ID NO: 196)

RATFSRDNAKNSLYMQLNSLRAEDTAVYYCAR (SEQ ID NO: 197)

RATISADTAKNALYLQMNSLRAEDTAVYYCAR (SEQ ID NO: 198)

RATISADTAKNSLYMQMNSLRAEDTAVYYCAR (SEQ ID NO: 199)

RATISADTAKNSLYLQLNSLRAEDTAVYYCAR (SEQ ID NO: 200)

RATISADNAKNSAYMQMNSLRAEDTAVYYCAR (SEQ ID NO: 201)

RATISADNAKNSAYLQLNSLRAEDTAVYYCAR (SEQ ID NO: 202)

RATISADNAKNSLYMQLNSLRAEDTAVYYCAR (SEQ ID NO: 203)

RATISRDTAKNSAYMQMNSLRAEDTAVYYCAR (SEQ ID NO: 204)

RATISRDTAKNSAYLQLNSLRAEDTAVYYCAR (SEQ ID NO: 205)

RATISRDTAKNSLYMQLNSLRAEDTAVYYCAR (SEQ ID NO: 206)

RATISRDNAKNSAYMQLNSLRAEDTAVYYCAR (SEQ ID NO: 207)

RFTFSADTAKNSAYLQMNSLRAEDTAVYYCAR (SEQ ID NO: 208)

RFTFSADTAKNSLYMQMNSLRAEDTAVYYCAR (SEQ ID NO: 209)

RFTFSADTAKNSLYLQLNSLRAEDTAVYYCAR (SEQ ID NO: 210)

RFTFSADNAKNSAYMQMNSLRAEDTAVYYCAR (SEQ ID NO: 211)

RFTFSADNAKNSAYLQLNSLRAEDTAVYYCAR (SEQ ID NO: 212)

RFTFSADNAKNSLYMQLNSLRAEDTAVYYCAR (SEQ ID NO: 213)

RFTFSRDTAKNSAYMQMNSLRAEDTAVYYCAR (SEQ ID NO: 214)

RFTFSRDTAKNSAYLQLNSLRAEDTAVYYCAR (SEQ ID NO: 215)

RFTFSRDTAKNSLYMQLNSLRAEDTAVYYCAR (SEQ ID NO: 216)

RFTFSRDNAKNSAYMQLNSLRAEDTAVYYCAR (SEQ ID NO: 217)

RFTISADTAKNSAYMQMNSLRAEDTAVYYCAR (SEQ ID NO: 218)

RFTISADTAKNSAYLQLNSLRAEDTAVYYCAR (SEQ ID NO: 219)

RFTISADTAKNSLYMQLNSLRAEDTAVYYCAR (SEQ ID NO: 220)

RFTISADNAKNSAYMQLNSLRAEDTAVYYCAR (SEQ ID NO: 221)

RFTISRDTAKNSAYMQLNSLRAEDTAVYYCAR (SEQ ID NO: 222)

RATFSADTAKNSAYLQMNSLRAEDTAVYYCAR (SEQ ID NO: 223)

TABLE 7-continued

Amino Acid Sequences derived from Murine 141A Antibody.

RATFSADTAKNSLYMQMNSLRAEDTAVYYCAR (SEQ ID NO: 224)

RATFSADTAKNSLYLQLNSLRAEDTAVYYCAR (SEQ ID NO: 225)

RATFSADNAKNSAYMQMNSLRAEDTAVYYCAR (SEQ ID NO: 226)

RATFSADNAKNSAYLQLNSLRAEDTAVYYCAR (SEQ ID NO: 227)

RATFSADNAKNSLYMQLNSLRAEDTAVYYCAR (SEQ ID NO: 228)

RATFSRDTAKNSAYMQMNSLRAEDTAVYYCAR (SEQ ID NO: 229)

RATFSRDTAKNSAYLQLNSLRAEDTAVYYCAR (SEQ ID NO: 230)

RATFSRDTAKNSLYMQLNSLRAEDTAVYYCAR (SEQ ID NO: 231)

RATFSRDNAKNSAYMQLNSLRAEDTAVYYCAR (SEQ ID NO: 232)

RATISADTAKNALYMQMNSLRAEDTAVYYCAR (SEQ ID NO: 233)

RATISADTAKNALYLQLNSLRAEDTAVYYCAR (SEQ ID NO: 234)

RATISADTAKNSLYMQLNSLRAEDTAVYYCAR (SEQ ID NO: 235)

RATISADNAKNSAYMQLNSLRAEDTAVYYCAR (SEQ ID NO: 236)

RATISRDTAKNSAYMQLNSLRAEDTAVYYCAR (SEQ ID NO: 237)

RFTFSADTAKNSAYMQMNSLRAEDTAVYYCAR (SEQ ID NO: 238)

RFTFSADTAKNSAYLQLNSLRAEDTAVYYCAR (SEQ ID NO: 239)

RFTFSADTAKNSLYMQLNSLRAEDTAVYYCAR (SEQ ID NO: 240)

RFTFSADNAKNSAYMQLNSLRAEDTAVYYCAR (SEQ ID NO: 241)

RFTFSRDTAKNSAYMQLNSLRAEDTAVYYCAR (SEQ ID NO: 242)

RFTISADTAKNSAYMQLNSLRAEDTAVYYCAR (SEQ ID NO: 243)

RATFSADTAKNSAYMQMNSLRAEDTAVYYCAR (SEQ ID NO: 244)

RATFSADTAKNSAYLQLNSLRAEDTAVYYCAR (SEQ ID NO: 245)

RATFSADTAKNSLYMQLNSLRAEDTAVYYCAR (SEQ ID NO: 246)

RATFSADNAKNSAYMQLNSLRAEDTAVYYCAR (SEQ ID NO: 247)

RATFSRDTAKNSAYMQLNSLRAEDTAVYYCAR (SEQ ID NO: 248)

RATISADTAKNALYMQLNSLRAEDTAVYYCAR (SEQ ID NO: 249)

RFTFSADTAKNSAYMQLNSLRAEDTAVYYCAR (SEQ ID NO: 250)

RATFSADTAKNSAYMQLNSLRAEDTAVYYCAR (SEQ ID NO: 251)

RFTISRDNAKNSLYLQMNSLRAEDTAVYYCAG (SEQ ID NO: 903)

RATISRDNAKNSLYLQMNSLRAEDTAVYYCAG (SEQ ID NO: 904)

RFTFSRDNAKNSLYLQMNSLRAEDTAVYYCAG (SEQ ID NO: 905)

RFTISADNAKNSLYLQMNSLRAEDTAVYYCAG (SEQ ID NO: 906)

RFTISRDTAKNSLYLQMNSLRAEDTAVYYCAG (SEQ ID NO: 907)

RFTISRDNAKNAYLQMNSLRAEDTAVYYCAG (SEQ ID NO: 908)

RFTISRDNAKNSLYMQMNSLRAEDTAVYYCAG (SEQ ID NO: 909)

RFTISRDNAKNSLYLLNSLRAEDTAVYYCAG (SEQ ID NO: 910)

RATF SRDNAKNSLYLQMNSLRAEDTAVYYCAG (SEQ ID NO: 911)

RATISADNAKNSLYLQMNSLRAEDTAVYYCAG (SEQ ID NO: 912)

RATISRDTAKNSLYLQMNSLRAEDTAVYYCAG (SEQ ID NO: 913)

TABLE 7-continued

Amino Acid Sequences derived from Murine 141A Antibody.

RATISRDNAKNSAYLQMNSLRAEDTAVYYCAG (SEQ ID NO: 914)

RATISRDNAKNSLYMQMNSLRAEDTAVYYCAG (SEQ ID NO: 915)

RATISRDNAKNSLYLQLNSLRAEDTAVYYCAG (SEQ ID NO: 916)

RFTFSADNAKNSLYLQMNSLRAEDTAVYYCAG (SEQ ID NO: 917)

RFTFSRDTAKNSLYLQMNSLRAEDTAVYYCAG (SEQ ID NO: 918)

RFTFSRDNAKNSAYLQMNSLRAEDTAVYYCAG (SEQ ID NO: 919)

RFTFSRDNAKNSLYMQMNSLRAEDTAVYYCAG (SEQ ID NO: 920)

RFTFSRDNAKNSLYLQLNSLRAEDTAVYYCAG (SEQ ID NO: 921)

RFTISADTAKNSLYLQMNSLRAEDTAVYYCAG (SEQ ID NO: 922)

RFTISADNAKNSAYLQMNSLRAEDTAVYYCAG (SEQ ID NO: 923)

RFTISADNAKNSLYMQMNSLRAEDTAVYYCAG (SEQ ID NO: 924)

RFTISADNAKNSLYLQLNSLRAEDTAVYYCAG (SEQ ID NO: 925)

RFTISRDTAKNSAYLQMNSLRAEDTAVYYCAG (SEQ ID NO: 926)

RFTISRDTAKNSLYMQMNSLRAEDTAVYYCAG (SEQ ID NO: 927)

RFTISRDTAKNSLYLQLNSLRAEDTAVYYCAG (SEQ ID NO: 928)

RFTISRDNAKNSAYMQMNSLRAEDTAVYYCAG (SEQ ID NO: 929)

RFTISRDNAKNSAYLQLNSLRAEDTAVYYCAG (SEQ ID NO: 930)

RFTISRDNAKNSLYMQLNSLRAEDTAVYYCAG (SEQ ID NO: 931)

RATFSADNAKNSLYLQMNSLRAEDTAVYYCAG (SEQ ID NO: 932)

RATFSRDTAKNSLYLQMNSLRAEDTAVYYCAG (SEQ ID NO: 933)

RATFSRDNAKNSAYLQMNSLRAEDTAVYYCAG (SEQ ID NO: 934)

RATFSRDNAKNSLYMQMNSLRAEDTAVYYCAG (SEQ ID NO: 935)

RATFSRDNAKNSLYLQLNSLRAEDTAVYYCAG (SEQ ID NO: 936)

RATISADTAKNSLYLQMNSLRAEDTAVYYCAG (SEQ ID NO: 937)

RATISADNAKNSAYLQMNSLRAEDTAVYYCAG (SEQ ID NO: 938)

RATISADNAKNSLYMQMNSLRAEDTAVYYCAG (SEQ ID NO: 939)

RATISADNAKNSLYLQLNSLRAEDTAVYYCAG (SEQ ID NO: 940)

RATISRDTAKNSAYLQMNSLRAEDTAVYYCAG (SEQ ID NO: 941)

RATISRDTAKNSLYMQMNSLRAEDTAVYYCAG (SEQ ID NO: 942)

RATISRDTAKNSLYLQLNSLRAEDTAVYYCAG (SEQ ID NO: 943)

RATISRDNAKNSAYMQMNSLRAEDTAVYYCAG (SEQ ID NO: 944)

RATISRDNAKNSAYLQLNSLRAEDTAVYYCAG (SEQ ID NO: 945)

RATISRDNAKNSLYMQLNSLRAEDTAVYYCAG (SEQ ID NO: 946)

RFTFSADTAKNSLYLQMNSLRAEDTAVYYCAG (SEQ ID NO: 947)

RFTFSADNAKNSAYLQMNSLRAEDTAVYYCAG (SEQ ID NO: 948)

RFTFSADNAKNSLYMQMNSLRAEDTAVYYCAG (SEQ ID NO: 949)

RFTFSADNAKNSLYLQLNSLRAEDTAVYYCAG (SEQ ID NO: 950)

RFTFSRDTAKNSAYLQMNSLRAEDTAVYYCAG (SEQ ID NO: 951)

RFTFSRDTAKNSLYMQMNSLRAEDTAVYYCAG (SEQ ID NO: 952)

TABLE 7-continued

Amino Acid Sequences derived from Murine 141A Antibody.

RFTFSRDTAKNSLYLQLNSLRAEDTAVYYCAG (SEQ ID NO: 953)

RFTFSRDNAKNSAYMQMNSLRAEDTAVYYCAG (SEQ ID NO: 954)

RFTFSRDNAKNSAYLQLNSLRAEDTAVYYCAG (SEQ ID NO: 955)

RFTFSRDNAKNSLYMQLNSLRAEDTAVYYCAG (SEQ ID NO: 956)

RFTISADTAKNSAYLQMNSLRAEDTAVYYCAG (SEQ ID NO: 957)

RFTISADTAKNSLYMQMNSLRAEDTAVYYCAG (SEQ ID NO: 958)

RFTISADTAKNSLYLQLNSLRAEDTAVYYCAG (SEQ ID NO: 959)

RFTISADNAKNSAYMQMNSLRAEDTAVYYCAG (SEQ ID NO: 960)

RFTISADNAKNSAYLQLNSLRAEDTAVYYCAG (SEQ ID NO: 961)

RFTISADNAKNSLYMQLNSLRAEDTAVYYCAG (SEQ ID NO: 962)

RFTISRDTAKNSAYMQMNSLRAEDTAVYYCAG (SEQ ID NO: 963)

RFTISRDTAKNSAYLQLNSLRAEDTAVYYCAG (SEQ ID NO: 964)

RFTISRDTAKNSLYMQLNSLRAEDTAVYYCAG (SEQ ID NO: 965)

RFTISRDNAKNSAYMQLNSLRAEDTAVYYCAG (SEQ ID NO: 966)

RATFSADTAKNSLYLQMNSLRAEDTAVYYCAG (SEQ ID NO: 967)

RATFSADNAKNSAYLQMNSLRAEDTAVYYCAG (SEQ ID NO: 968)

RATFSADNAKNSLYMQMNSLRAEDTAVYYCAG (SEQ ID NO: 969)

RATFSADNAKNSLYLQLNSLRAEDTAVYYCAG (SEQ ID NO: 970)

RATFSRDTAKNSAYLQMNSLRAEDTAVYYCAG (SEQ ID NO: 971)

RATFSRDTAKNSLYMQMNSLRAEDTAVYYCAG (SEQ ID NO: 972)

RATFSRDTAKNSLYLQLNSLRAEDTAVYYCAG (SEQ ID NO: 973)

RATFSRDNAKNSAYMQMNSLRAEDTAVYYCAG (SEQ ID NO: 974)

RATFSRDNAKNSAYLQLNSLRAEDTAVYYCAG (SEQ ID NO: 975)

RATFSRDNAKNSLYMQLNSLRAEDTAVYYCAG (SEQ ID NO: 976)

RATISADTAKNALYLQMNSLRAEDTAVYYCAG (SEQ ID NO: 977)

RATISADTAKNSLYMQMNSLRAEDTAVYYCAG (SEQ ID NO: 978)

RATISADTAKNSLYLQLNSLRAEDTAVYYCAG (SEQ ID NO: 979)

RATISADNAKNSAYMQMNSLRAEDTAVYYCAG (SEQ ID NO: 980)

RATISADNAKNSAYLQLNSLRAEDTAVYYCAG (SEQ ID NO: 981)

RATISADNAKNSLYMQLNSLRAEDTAVYYCAG (SEQ ID NO: 982)

RATISRDTAKNSAYMQMNSLRAEDTAVYYCAG (SEQ ID NO: 983)

RATISRDTAKNSAYLQLNSLRAEDTAVYYCAG (SEQ ID NO: 984)

RATISRDTAKNSLYMQLNSLRAEDTAVYYCAG (SEQ ID NO: 985)

RATISRDNAKNSAYMQLNSLRAEDTAVYYCAG (SEQ ID NO: 986)

RFTFSADTAKNSAYLQMNSLRAEDTAVYYCAG (SEQ ID NO: 987)

RFTFSADTAKNSLYMQMNSLRAEDTAVYYCAG (SEQ ID NO: 988)

RFTFSADTAKNSLYLQLNSLRAEDTAVYYCAG (SEQ ID NO: 989)

RFTFSADNAKNSAYMQMNSLRAEDTAVYYCAG (SEQ ID NO: 990)

RFTFSADNAKNSAYLQLNSLRAEDTAVYYCAG (SEQ ID NO: 991)

TABLE 7-continued

Amino Acid Sequences derived from Murine 141A Antibody.

RFTFSADNAKNSLYMQLNSLRAEDTAVYYCAG (SEQ ID NO: 992)

RFTFSRDTAKNSAYMQMNSLRAEDTAVYYCAG (SEQ ID NO: 993)

RFTFSRDTAKNSAYLQLNSLRAEDTAVYYCAG (SEQ ID NO: 994)

RFTFSRDTAKNSLYMQLNSLRAEDTAVYYCAG (SEQ ID NO: 995)

RFTFSRDNAKNSAYMQLNSLRAEDTAVYYCAG (SEQ ID NO: 996)

RFTISADTAKNSAYMQMNSLRAEDTAVYYCAG (SEQ ID NO: 997)

RFTISADTAKNSAYLQLNSLRAEDTAVYYCAG (SEQ ID NO: 998)

RFTISADTAKNSLYMQLNSLRAEDTAVYYCAG (SEQ ID NO: 999)

RFTISADNAKNSAYMQLNSLRAEDTAVYYCAG (SEQ ID NO: 1000)

RFTISRDTAKNSAYMQLNSLRAEDTAVYYCAG (SEQ ID NO: 1001)

RATFSADTAKNSAYLQMNSLRAEDTAVYYCAG (SEQ ID NO: 1002)

RATFSADTAKNSLYMQMNSLRAEDTAVYYCAG (SEQ ID NO: 1003)

RATFSADTAKNSLYLQLNSLRAEDTAVYYCAG (SEQ ID NO: 1004)

RATFSADNAKNSAYMQMNSLRAEDTAVYYCAG (SEQ ID NO: 1005)

RATFSADNAKNSAYLQLNSLRAEDTAVYYCAG (SEQ ID NO: 1006)

RATFSADNAKNSLYMQLNSLRAEDTAVYYCAG (SEQ ID NO: 1007)

RATFSRDTAKNSAYMQMNSLRAEDTAVYYCAG (SEQ ID NO: 1008)

RATFSRDTAKNSAYLQLNSLRAEDTAVYYCAG (SEQ ID NO: 1009)

RATFSRDTAKNSLYMQLNSLRAEDTAVYYCAG (SEQ ID NO: 1010)

RATFSRDNAKNSAYMQLNSLRAEDTAVYYCAG (SEQ ID NO: 1011)

RATISADTAKNALYMQMNSLRAEDTAVYYCAG (SEQ ID NO: 1012)

RATISADTAKNALYLQLNSLRAEDTAVYYCAG (SEQ ID NO: 1013)

RATISADTAKNSLYMQLNSLRAEDTAVYYCAG (SEQ ID NO: 1014)

RATISADNAKNSAYMQLNSLRAEDTAVYYCAG (SEQ ID NO: 1015)

RATISRDTAKNSAYMQLNSLRAEDTAVYYCAG (SEQ ID NO: 1016)

RFTFSADTAKNSAYMQMNSLRAEDTAVYYCAG (SEQ ID NO: 1017)

RFTFSADTAKNSAYLQLNSLRAEDTAVYYCAG (SEQ ID NO: 1018)

RFTFSADTAKNSLYMQLNSLRAEDTAVYYCAG (SEQ ID NO: 1019)

RFTFSADNAKNSAYMQLNSLRAEDTAVYYCAG (SEQ ID NO: 1020)

RFTFSRDTAKNSAYMQLNSLRAEDTAVYYCAG (SEQ ID NO: 1021)

RFTISADTAKNSAYMQLNSLRAEDTAVYYCAG (SEQ ID NO: 1022)

RATFSADTAKNSAYMQMNSLRAEDTAVYYCAG (SEQ ID NO: 1023)

RATFSADTAKNSAYLQLNSLRAEDTAVYYCAG (SEQ ID NO: 1024)

RATFSADTAKNSLYMQLNSLRAEDTAVYYCAG (SEQ ID NO: 1025)

RATFSADNAKNSAYMQLNSLRAEDTAVYYCAG (SEQ ID NO: 1026)

RATFSRDTAKNSAYMQLNSLRAEDTAVYYCAG (SEQ ID NO: 1027)

RATISADTAKNALYMQLNSLRAEDTAVYYCAG (SEQ ID NO: 1028)

RFTFSADTAKNSAYMQLNSLRAEDTAVYYCAG (SEQ ID NO: 1029)

RATFSADTAKNSAYMQLNSLRAEDTAVYYCAG (SEQ ID NO: 1030)

TABLE 7-continued

Amino Acid Sequences derived from Murine 141A Antibody.

141A-huVH3a VH CDR3

EEVYDGYPWFGY (SEQ ID NO: 35)

EEVYEGYPWFGY (SEQ ID NO: 883)

EEVYSGYPWFGY (SEQ ID NO: 884)

EEVYAGYPWFGY (SEQ ID NO: 885)

141A-huVH3a VH FR4

WGQGTLVTVSS (SEQ ID NO: 54)

141A-huVH3b Variable Region

EVQLVESGGGLVQPGGSLRLSCAASGYTFSRYWIEWVRQAPGKGLEWVSEILPGSGSTN YADSVKGRFTISRDNAKNSLYLQMNSLRAEDTAVYYCAREEVYDGYPWFGYWGQGTLVT VSS (SEQ ID NO: 19)

141A-huVH3b VH FR1

EVQLVESGGGLVQPGGSLRLSCAAS (SEQ ID NO: 55)

EVQLVQSGGGLVQPGGSLRLSCAAS (SEQ ID NO: 115)

EVQLVESGGGLVQPGGSVRLSCAAS (SEQ ID NO: 116)

EVQLVESGGGLVQPGGSLRISCAAS (SEQ ID NO: 117)

EVQLVQSGGGLVQPGGSVRLSCAAS (SEQ ID NO: 118)

EVQLVESGGGLVQPGGSVRISCAAS (SEQ ID NO: 119)

EVQLVQSGGGLVQPGGSLRISCAAS (SEQ ID NO: 120)

EVQLVQSGGGLVQPGGSVRISCAAS (SEQ ID NO: 121)

EVQLVESGGGLMQPGGSLRLSCAAS (SEQ ID NO: 895)

EVQLVQSGGGLMQPGGSLRLSCAAS (SEQ ID NO: 896)

EVQLVESGGGLMQPGGSVRLSCAAS (SEQ ID NO: 897)

EVQLVESGGGLMQPGGSLRISCAAS (SEQ ID NO: 898)

EVQLVQSGGGLMQPGGSVRLSCAAS (SEQ ID NO: 899)

EVQLVQSGGGLMQPGGSLRISCAAS (SEQ ID NO: 900)

EVQLVESGGGLMQPGGSVRISCAAS (SEQ ID NO: 901)

EVQLVQSGGGLMQPGGSVRISCAAS (SEQ ID NO: 902)

141A-huVH3b VH CDR1

GTFSRYWIE (SEQ ID NO: 33)

141A-huVH3b VH FR2

WVRQAPGKGLEWVS (SEQ ID NO: 56)

WVRQAPGKGLEWIS (SEQ ID NO: 122)

WVRQAPGKGLEWVG (SEQ ID NO: 123)

WVRQAPGKGLEWIG (SEQ ID NO: 124)

141A-huVH3b VH CDR2*

EILPGSGSTNYADSVKG (SEQ ID NO: 1070)

EILPGSGSTQYADSVKG (SEQ ID NO: 1071)

EILPGSGSTSYADSVKG (SEQ ID NO: 99)

EILPGSGSTDYADSVKG (SEQ ID NO: 1072)

TABLE 7-continued

Amino Acid Sequences derived from Murine 141A Antibody.

EILPGSGSTAYADSVKG (SEQ ID NO: 1073)

EILPGSGSTNYADSFKG (SEQ ID NO: 1074)

EILPGSGSTQYADSFKG (SEQ ID NO: 1075)

EILPGSGSTSYADSFKG (SEQ ID NO: 1076)

EILPGSGSTDYADSFKG (SEQ ID NO: 1077)

EILPGSGSTAYADSFKG (SEQ ID NO: 1078)

141A-huVH3b VH FR3

RFTISRDNAKNSLYLQMNSLRAEDTAVYYCAR (SEQ ID NO: 57)

RATISRDNAKNSLYLQMNSLRAEDTAVYYCAR (SEQ ID NO: 125)

RFTFSRDNAKNSLYLQMNSLRAEDTAVYYCAR (SEQ ID NO: 126)

RFTISADNAKNSLYLQMNSLRAEDTAVYYCAR (SEQ ID NO: 127)

RFTISRDTAKNSLYLQMNSLRAEDTAVYYCAR (SEQ ID NO: 128)

RFTISRDNAKNSAYLQMNSLRAEDTAVYYCAR (SEQ ID NO: 129)

RFTISRDNAKNSLYMQMNSLRAEDTAVYYCAR (SEQ ID NO: 130)

RFTISRDNAKNSLYLQLNSLRAEDTAVYYCAR (SEQ ID NO: 131)

RATFSRDNAKNSLYLQMNSLRAEDTAVYYCAR (SEQ ID NO: 132)

RATISADNAKNSLYLQMNSLRAEDTAVYYCAR (SEQ ID NO: 133)

RATISRDTAKNSLYLQMNSLRAEDTAVYYCAR (SEQ ID NO: 134)

RATISRDNAKNSAYLQMNSLRAEDTAVYYCAR (SEQ ID NO: 135)

RATISRDNAKNSLYMQMNSLRAEDTAVYYCAR (SEQ ID NO: 136)

RATISRDNAKNSLYLQLNSLRAEDTAVYYCAR (SEQ ID NO: 137)

RFTFSADNAKNSLYLQMNSLRAEDTAVYYCAR (SEQ ID NO: 138)

RFTFSRDTAKNSLYLQMNSLRAEDTAVYYCAR (SEQ ID NO: 139)

RFTFSRDNAKNSAYLQMNSLRAEDTAVYYCAR (SEQ ID NO: 140)

RFTFSRDNAKNSLYMQMNSLRAEDTAVYYCAR (SEQ ID NO: 141)

RFTFSRDNAKNSLYLQLNSLRAEDTAVYYCAR (SEQ ID NO: 142)

RFTISADTAKNSLYLQMNSLRAEDTAVYYCAR (SEQ ID NO: 143)

RFTISADNAKNSAYLQMNSLRAEDTAVYYCAR (SEQ ID NO: 144)

RFTISADNAKNSLYMQMNSLRAEDTAVYYCAR (SEQ ID NO: 145)

RFTISADNAKNSLYLQLNSLRAEDTAVYYCAR (SEQ ID NO: 146)

RFTISRDTAKNSAYLQMNSLRAEDTAVYYCAR (SEQ ID NO: 147)

RFTISRDTAKNSLYMQMNSLRAEDTAVYYCAR (SEQ ID NO: 148)

RFTISRDTAKNSLYLQLNSLRAEDTAVYYCAR (SEQ ID NO: 149)

RFTISRDNAKNSAYMQMNSLRAEDTAVYYCAR (SEQ ID NO: 150)

RFTISRDNAKNSAYLQLNSLRAEDTAVYYCAR (SEQ ID NO: 151)

RFTISRDNAKNSLYMQLNSLRAEDTAVYYCAR (SEQ ID NO: 152)

RATFSADNAKNSLYLQMNSLRAEDTAVYYCAR (SEQ ID NO: 153)

RATFSRDTAKNSLYLQMNSLRAEDTAVYYCAR (SEQ ID NO: 154)

RATFSRDNAKNSAYLQMNSLRAEDTAVYYCAR (SEQ ID NO: 155)

TABLE 7-continued

Amino Acid Sequences derived from Murine 141A Antibody.

RATFSRDNAKNSLYMQMNSLRAEDTAVYYCAR (SEQ ID NO: 156)

RATFSRDNAKNSLYLQLNSLRAEDTAVYYCAR (SEQ ID NO: 157)

RATISADTAKNSLYLQMNSLRAEDTAVYYCAR (SEQ ID NO: 158)

RATISADNAKNSAYLQMNSLRAEDTAVYYCAR (SEQ ID NO: 159)

RATISADNAKNSLYMQMNSLRAEDTAVYYCAR (SEQ ID NO: 160)

RATISADNAKNSLYLQLNSLRAEDTAVYYCAR (SEQ ID NO: 161)

RATISRDTAKNSAYLQMNSLRAEDTAVYYCAR (SEQ ID NO: 162)

RATISRDTAKNSLYMQMNSLRAEDTAVYYCAR (SEQ ID NO: 163)

RATISRDTAKNSLYLQLNSLRAEDTAVYYCAR (SEQ ID NO: 164)

RATISRDNAKNSAYMQMNSLRAEDTAVYYCAR (SEQ ID NO: 165)

RATISRDNAKNSAYLQLNSLRAEDTAVYYCAR (SEQ ID NO: 166)

RATISRDNAKNSLYMQLNSLRAEDTAVYYCAR (SEQ ID NO: 167)

RFTFSADTAKNSLYLQMNSLRAEDTAVYYCAR (SEQ ID NO: 168)

RFTFSADNAKNSAYLQMNSLRAEDTAVYYCAR (SEQ ID NO: 169)

RFTFSADNAKNSLYMQMNSLRAEDTAVYYCAR (SEQ ID NO: 170)

RFTFSADNAKNSLYLQLNSLRAEDTAVYYCAR (SEQ ID NO: 171)

RFTFSRDTAKNSAYLQMNSLRAEDTAVYYCAR (SEQ ID NO: 172)

RFTFSRDTAKNSLYMQMNSLRAEDTAVYYCAR (SEQ ID NO: 173)

RFTFSRDTAKNSLYLQLNSLRAEDTAVYYCAR (SEQ ID NO: 174)

RFTFSRDNAKNSAYMQMNSLRAEDTAVYYCAR (SEQ ID NO: 175)

RFTFSRDNAKNSAYLQLNSLRAEDTAVYYCAR (SEQ ID NO: 176)

RFTFSRDNAKNSLYMQLNSLRAEDTAVYYCAR (SEQ ID NO: 177)

RFTISADTAKNSAYLQMNSLRAEDTAVYYCAR (SEQ ID NO: 178)

RFTISADTAKNSLYMQMNSLRAEDTAVYYCAR (SEQ ID NO: 179)

RFTISADTAKNSLYLQLNSLRAEDTAVYYCAR (SEQ ID NO: 180)

RFTISADNAKNSAYMQMNSLRAEDTAVYYCAR (SEQ ID NO: 181)

RFTISADNAKNSAYLQLNSLRAEDTAVYYCAR (SEQ ID NO: 182)

RFTISADNAKNSLYMQLNSLRAEDTAVYYCAR (SEQ ID NO: 183)

RFTISRDTAKNSAYMQMNSLRAEDTAVYYCAR (SEQ ID NO: 184)

RFTISRDTAKNSAYLQLNSLRAEDTAVYYCAR (SEQ ID NO: 185)

RFTISRDTAKNSLYMQLNSLRAEDTAVYYCAR (SEQ ID NO: 186)

RFTISRDNAKNSAYMQLNSLRAEDTAVYYCAR (SEQ ID NO: 187)

RATFSADTAKNSLYLQMNSLRAEDTAVYYCAR (SEQ ID NO: 188)

RATFSADNAKNSAYLQMNSLRAEDTAVYYCAR (SEQ ID NO: 189)

RATFSADNAKNSLYMQMNSLRAEDTAVYYCAR (SEQ ID NO: 190)

RATFSADNAKNSLYLQLNSLRAEDTAVYYCAR (SEQ ID NO: 191)

RATFSRDTAKNSAYLQMNSLRAEDTAVYYCAR (SEQ ID NO: 192)

RATFSRDTAKNSLYMQMNSLRAEDTAVYYCAR (SEQ ID NO: 193)

RATFSRDTAKNSLYLQLNSLRAEDTAVYYCAR (SEQ ID NO: 194)

TABLE 7-continued

Amino Acid Sequences derived from Murine 141A Antibody.

RATFSRDNAKNSAYMQMNSLRAEDTAVYYCAR (SEQ ID NO: 195)

RATFSRDNAKNSAYLQLNSLRAEDTAVYYCAR (SEQ ID NO: 196)

RATFSRDNAKNSLYMQLNSLRAEDTAVYYCAR (SEQ ID NO: 197)

RATISADTAKNALYLQMNSLRAEDTAVYYCAR (SEQ ID NO: 198)

RATISADTAKNSLYM**QMNSLRAEDTAVYYCAR (SEQ ID NO: 199)

RATISADTAKNSLYLQLNSLRAEDTAVYYCAR (SEQ ID NO: 200)

RATISADNAKNSAYMQMNSLRAEDTAVYYCAR (SEQ ID NO: 201)

RATISADNAKNSAYLQLNSLRAEDTAVYYCAR (SEQ ID NO: 202)

RATISADNAKNSLYMQLNSLRAEDTAVYYCAR (SEQ ID NO: 203)

RATISRDTAKNSAYM**QMNSLRAEDTAVYYCAR (SEQ ID NO: 204)

RATISRDTAKNSAYLQLNSLRAEDTAVYYCAR (SEQ ID NO: 205)

RATISRDTAKNSLYM**QLNSLRAEDTAVYYCAR (SEQ ID NO: 206)

RATISRDNAKNSAYMQLNSLRAEDTAVYYCAR (SEQ ID NO: 207)

RFTFSADTAKNSAYLQMNSLRAEDTAVYYCAR (SEQ ID NO: 208)

RFTFSADTAKNSLYM**QMNSLRAEDTAVYYCAR (SEQ ID NO: 209)

RFTFSADTAKNSLYLQLNSLRAEDTAVYYCAR (SEQ ID NO: 210)

RFTFSADNAKNSAYMQMNSLRAEDTAVYYCAR (SEQ ID NO: 211)

RFTFSADNAKNSAYLQLNSLRAEDTAVYYCAR (SEQ ID NO: 212)

RFTFSADNAKNSLYMQLNSLRAEDTAVYYCAR (SEQ ID NO: 213)

RFTFSRDTAKNSAYM**QMNSLRAEDTAVYYCAR (SEQ ID NO: 214)

RFTFSRDTAKNSAYLQLNSLRAEDTAVYYCAR (SEQ ID NO: 215)

RFTFSRDTAKNSLYM**QLNSLRAEDTAVYYCAR (SEQ ID NO: 216)

RFTFSRDNAKNSAYMQLNSLRAEDTAVYYCAR (SEQ ID NO: 217)

RFTISADTAKNSAYM**QMNSLRAEDTAVYYCAR (SEQ ID NO: 218)

RFTISADTAKNSAYLQLNSLRAEDTAVYYCAR (SEQ ID NO: 219)

RFTISADTAKNSLYM**QLNSLRAEDTAVYYCAR (SEQ ID NO: 220)

RFTISADNAKNSAYMQLNSLRAEDTAVYYCAR (SEQ ID NO: 221)

RFTISRDTAKNSAYM**QLNSLRAEDTAVYYCAR (SEQ ID NO: 222)

RATFSADTAKNSAYLQMNSLRAEDTAVYYCAR (SEQ ID NO: 223)

RATFSADTAKNSLYM**QMNSLRAEDTAVYYCAR (SEQ ID NO: 224)

RATFSADTAKNSLYLQLNSLRAEDTAVYYCAR (SEQ ID NO: 225)

RATFSADNAKNSAYMQMNSLRAEDTAVYYCAR (SEQ ID NO: 226)

RATFSADNAKNSAYLQLNSLRAEDTAVYYCAR (SEQ ID NO: 227)

RATFSADNAKNSLYMQLNSLRAEDTAVYYCAR (SEQ ID NO: 228)

RATFSRDTAKNSAYM**QMNSLRAEDTAVYYCAR (SEQ ID NO: 229)

RATFSRDTAKNSAYLQLNSLRAEDTAVYYCAR (SEQ ID NO: 230)

RATFSRDTAKNSLYM**QLNSLRAEDTAVYYCAR (SEQ ID NO: 231)

RATFSRDNAKNSAYMQLNSLRAEDTAVYYCAR (SEQ ID NO: 232)

RATISADTAKNALYM**QMNSLRAEDTAVYYCAR (SEQ ID NO: 233)

TABLE 7-continued

Amino Acid Sequences derived from Murine 141A Antibody.

RATISADTAKNALYLQLNSLRAEDTAVYYCAR (SEQ ID NO: 234)

RATISADTAKNSLYMQLNSLRAEDTAVYYCAR (SEQ ID NO: 235)

RATISADNAKNSAYMQLNSLRAEDTAVYYCAR (SEQ ID NO: 236)

RATISRDTAKNSAYMQLNSLRAEDTAVYYCAR (SEQ ID NO: 237)

RFTFSADTAKNSAYMQMNSLRAEDTAVYYCAR (SEQ ID NO: 238)

RFTFSADTAKNSAYLQLNSLRAEDTAVYYCAR (SEQ ID NO: 239)

RFTFSADTAKNSLYMQLNSLRAEDTAVYYCAR (SEQ ID NO: 240)

RFTFSADNAKNSAYMQLNSLRAEDTAVYYCAR (SEQ ID NO: 241)

RFTFSRDTAKNSAYMQLNSLRAEDTAVYYCAR (SEQ ID NO: 242)

RFTISADTAKNSAYMQLNSLRAEDTAVYYCAR (SEQ ID NO: 243)

RATFSADTAKNSAYMQMNSLRAEDTAVYYCAR (SEQ ID NO: 244)

RATFSADTAKNSAYLQLNSLRAEDTAVYYCAR (SEQ ID NO: 245)

RATFSADTAKNSLYMQLNSLRAEDTAVYYCAR (SEQ ID NO: 246)

RATFSADNAKNSAYMQLNSLRAEDTAVYYCAR (SEQ ID NO: 247)

RATFSRDTAKNSAYMQLNSLRAEDTAVYYCAR (SEQ ID NO: 248)

RATISADTAKNALYMQLNSLRAEDTAVYYCAR (SEQ ID NO: 249)

RFTFSADTAKNSAYMQLNSLRAEDTAVYYCAR (SEQ ID NO: 250)

RATFSADTAKNSAYMQLNSLRAEDTAVYYCAR (SEQ ID NO: 251)

RFTISRDNAKNSLYLQMNSLRAEDTAVYYCAG (SEQ ID NO: 903)

RATISRDNAKNSLYLQMNSLRAEDTAVYYCAG (SEQ ID NO: 904)

RFTFSRDNAKNSLYLQMNSLRAEDTAVYYCAG (SEQ ID NO: 905)

RFTISADNAKNSLYLQMNSLRAEDTAVYYCAG (SEQ ID NO: 906)

RFTISRDTAKNSLYLQMNSLRAEDTAVYYCAG (SEQ ID NO: 907)

RFTISRDNAKNSAYLQMNSLRAEDTAVYYCAG (SEQ ID NO: 908)

RFTISRDNAKNSLYMQMNSLRAEDTAVYYCAG (SEQ ID NO: 909)

RFTISRDNAKNSLYLQLNSLRAEDTAVYYCAG (SEQ ID NO: 910)

RATFSRDNAKNSLYLQMNSLRAEDTAVYYCAG (SEQ ID NO: 911)

RATISADNAKNSLYLQMNSLRAEDTAVYYCAG (SEQ ID NO: 912)

RATISRDTAKNSLYLQMNSLRAEDTAVYYCAG (SEQ ID NO: 913)

RATISRDNAKNSAYLQMNSLRAEDTAVYYCAG (SEQ ID NO: 914)

RATISRDNAKNSLYMQMNSLRAEDTAVYYCAG (SEQ ID NO: 915)

RATISRDNAKNSLYLQLNSLRAEDTAVYYCAG (SEQ ID NO: 916)

RFTFSADNAKNSLYLQMNSLRAEDTAVYYCAG (SEQ ID NO: 917)

RFTFSRDTAKNSLYLQMNSLRAEDTAVYYCAG (SEQ ID NO: 918)

RFTFSRDNAKNSAYLQMNSLRAEDTAVYYCAG (SEQ ID NO: 919)

RFTFSRDNAKNSLYMQMNSLRAEDTAVYYCAG (SEQ ID NO: 920)

RFTFSRDNAKNSLYLQLNSLRAEDTAVYYCAG (SEQ ID NO: 921)

RFTISADTAKNSLYLQMNSLRAEDTAVYYCAG (SEQ ID NO: 922)

RFTISADNAKNSAYLQMNSLRAEDTAVYYCAG (SEQ ID NO: 923)

TABLE 7-continued

Amino Acid Sequences derived from Murine 141A Antibody.

RFTISADNAKNSLYMQMNSLRAEDTAVYYCAG (SEQ ID NO: 924)

RFTISADNAKNSLYLQLNSLRAEDTAVYYCAG (SEQ ID NO: 925)

RFTISRDTAKNSAYLQMNSLRAEDTAVYYCAG (SEQ ID NO: 926)

RFTISRDTAKNSLYMQMNSLRAEDTAVYYCAG (SEQ ID NO: 927)

RFTISRDTAKNSLYLQLNSLRAEDTAVYYCAG (SEQ ID NO: 928)

RFTISRDNAKNSAYMQMNSLRAEDTAVYYCAG (SEQ ID NO: 929)

RFTISRDNAKNSAYLQLNSLRAEDTAVYYCAG (SEQ ID NO: 930)

RFTISRDNAKNSLYMQLNSLRAEDTAVYYCAG (SEQ ID NO: 931)

RATFSADNAKNSLYLQMNSLRAEDTAVYYCAG (SEQ ID NO: 932)

RATFSRDTAKNSLYLQMNSLRAEDTAVYYCAG (SEQ ID NO: 933)

RATFSRDNAKNSAYLQMNSLRAEDTAVYYCAG (SEQ ID NO: 934)

RATFSRDNAKNSLYMQMNSLRAEDTAVYYCAG (SEQ ID NO: 935)

RATFSRDNAKNSLYLQLNSLRAEDTAVYYCAG (SEQ ID NO: 936)

RATISADTAKNSLYLQMNSLRAEDTAVYYCAG** (SEQ ID NO: 937)

RATISADNAKNSAYLQMNSLRAEDTAVYYCAG (SEQ ID NO: 938)

RATISADNAKNSLYMQMNSLRAEDTAVYYCAG (SEQ ID NO: 939)

RATISADNAKNSLYLQLNSLRAEDTAVYYCAG (SEQ ID NO: 940)

RATISRDTAKNSAYLQMNSLRAEDTAVYYCAG (SEQ ID NO: 941)

RATISRDTAKNSLYMQMNSLRAEDTAVYYCAG (SEQ ID NO: 942)

RATISRDTAKNSLYLQLNSLRAEDTAVYYCAG (SEQ ID NO: 943)

RATISRDNAKNSAYMQMNSLRAEDTAVYYCAG (SEQ ID NO: 944)

RATISRDNAKNSAYLQLNSLRAEDTAVYYCAG (SEQ ID NO: 945)

RATISRDNAKNSLYMQLNSLRAEDTAVYYCAG (SEQ ID NO: 946)

RFTFSADTAKNSLYLQMNSLRAEDTAVYYCAG** (SEQ ID NO: 947)

RFTFSADNAKNSAYLQMNSLRAEDTAVYYCAG (SEQ ID NO: 948)

RFTFSADNAKNSLYMQMNSLRAEDTAVYYCAG (SEQ ID NO: 949)

RFTFSADNAKNSLYLQLNSLRAEDTAVYYCAG (SEQ ID NO: 950)

RFTFSRDTAKNSAYLQMNSLRAEDTAVYYCAG (SEQ ID NO: 951)

RFTFSRDTAKNSLYMQMNSLRAEDTAVYYCAG (SEQ ID NO: 952)

RFTFSRDTAKNSLYLQLNSLRAEDTAVYYCAG (SEQ ID NO: 953)

RFTFSRDNAKNSAYMQMNSLRAEDTAVYYCAG (SEQ ID NO: 954)

RFTFSRDNAKNSAYLQLNSLRAEDTAVYYCAG (SEQ ID NO: 955)

RFTFSRDNAKNSLYMQLNSLRAEDTAVYYCAG (SEQ ID NO: 956)

RFTISADTAKNSAYLQMNSLRAEDTAVYYCAG** (SEQ ID NO: 957)

RFTISADTAKNSLYMQMNSLRAEDTAVYYCAG** (SEQ ID NO: 958)

RFTISADTAKNSLYLQLNSLRAEDTAVYYCAG** (SEQ ID NO: 959)

RFTISADNAKNSAYMQMNSLRAEDTAVYYCAG (SEQ ID NO: 960)

RFTISADNAKNSAYLQLNSLRAEDTAVYYCAG (SEQ ID NO: 961)

RFTISADNAKNSLYMQLNSLRAEDTAVYYCAG (SEQ ID NO: 962)

TABLE 7-continued

Amino Acid Sequences derived from Murine 141A Antibody.

RFTISRDTAKNSAYMQMNSLRAEDTAVYYCAG (SEQ ID NO: 963)

RFTISRDTAKNSAYLQLNSLRAEDTAVYYCAG (SEQ ID NO: 964)

RFTISRDTAKNSLYMQLNSLRAEDTAVYYCAG (SEQ ID NO: 965)

RFTISRDNAKNSAYMQLNSLRAEDTAVYYCAG (SEQ ID NO: 966)

RATFSADTAKNSLYLQMNSLRAEDTAVYYCAG (SEQ ID NO: 967)

RATFSADNAKNSAYLQMNSLRAEDTAVYYCAG (SEQ ID NO: 968)

RATFSADNAKNSLYMQMNSLRAEDTAVYYCAG (SEQ ID NO: 969)

RATFSADNAKNSLYLQLNSLRAEDTAVYYCAG (SEQ ID NO: 970)

RATFSRDTAKNSAYLQMNSLRAEDTAVYYCAG (SEQ ID NO: 971)

RATFSRDTAKNSLYMQMNSLRAEDTAVYYCAG (SEQ ID NO: 972)

RATFSRDTAKNSLYLQLNSLRAEDTAVYYCAG (SEQ ID NO: 973)

RATFSRDNAKNSAYMQMNSLRAEDTAVYYCAG (SEQ ID NO: 974)

RATFSRDNAKNSAYLQLNSLRAEDTAVYYCAG (SEQ ID NO: 975)

RATFSRDNAKNSLYMQLNSLRAEDTAVYYCAG (SEQ ID NO: 976)

RATISADTAKNALYLQMNSLRAEDTAVYYCAG (SEQ ID NO: 977)

RATISADTAKNSLYMQMNSLRAEDTAVYYCAG (SEQ ID NO: 978)

RATISADTAKNSLYLQLNSLRAEDTAVYYCAG (SEQ ID NO: 979)

RATISADNAKNSAYMQMNSLRAEDTAVYYCAG (SEQ ID NO: 980)

RATISADNAKNSAYLQLNSLRAEDTAVYYCAG (SEQ ID NO: 981)

RATISADNAKNSLYMQLNSLRAEDTAVYYCAG (SEQ ID NO: 982)

RATISRDTAKNSAYMQMNSLRAEDTAVYYCAG (SEQ ID NO: 983)

RATISRDTAKNSAYLQLNSLRAEDTAVYYCAG (SEQ ID NO: 984)

RATISRDTAKNSLYMQLNSLRAEDTAVYYCAG (SEQ ID NO: 985)

RATISRDNAKNSAYMQLNSLRAEDTAVYYCAG (SEQ ID NO: 986)

RFTFSADTAKNSAYLQMNSLRAEDTAVYYCAG (SEQ ID NO: 987)

RFTFSADTAKNSLYMQMNSLRAEDTAVYYCAG (SEQ ID NO: 988)

RFTFSADTAKNSLYLQLNSLRAEDTAVYYCAG (SEQ ID NO: 989)

RFTFSADNAKNSAYMQMNSLRAEDTAVYYCAG (SEQ ID NO: 990)

RFTFSADNAKNSAYLQLNSLRAEDTAVYYCAG (SEQ ID NO: 991)

RFTFSADNAKNSLYMQLNSLRAEDTAVYYCAG (SEQ ID NO: 992)

RFTFSRDTAKNSAYMQMNSLRAEDTAVYYCAG (SEQ ID NO: 993)

RFTFSRDTAKNSAYLQLNSLRAEDTAVYYCAG (SEQ ID NO: 994)

RFTFSRDTAKNSLYMQLNSLRAEDTAVYYCAG (SEQ ID NO: 995)

RFTFSRDNAKNSAYMQLNSLRAEDTAVYYCAG (SEQ ID NO: 996)

RFTISADTAKNSAYMQMNSLRAEDTAVYYCAG (SEQ ID NO: 997)

RFTISADTAKNSAYLQLNSLRAEDTAVYYCAG (SEQ ID NO: 998)

RFTISADTAKNSLYMQMNSLRAEDTAVYYCAG (SEQ ID NO: 999)

RFTISADNAKNSAYMQLNSLRAEDTAVYYCAG (SEQ ID NO: 1000)

RFTISRDTAKNSAYMQLNSLRAEDTAVYYCAG (SEQ ID NO: 1001)

TABLE 7-continued

Amino Acid Sequences derived from Murine 141A Antibody.

RATFSTAKNSAYLQMNSLRAEDTAVYYCAG (SEQ ID NO: 1002)

RATFSTAKNSLYMQMNSLRAEDTAVYYCAG (SEQ ID NO: 1003)

RATFSTAKNSLYLQLNSLRAEDTAVYYCAG (SEQ ID NO: 1004)

RATFSADNAKNSAYMQMNSLRAEDTAVYYCAG (SEQ ID NO: 1005)

RATFSADNAKNSAYLQLNSLRAEDTAVYYCAG (SEQ ID NO: 1006)

RATFSADNAKNSLYMQLNSLRAEDTAVYYCAG (SEQ ID NO: 1007)

RATFSRTAKNSAYMQMNSLRAEDTAVYYCAG (SEQ ID NO: 1008)

RATFSRTAKNSAYLQLNSLRAEDTAVYYCAG (SEQ ID NO: 1009)

RATFSRTAKNSLYMQLNSLRAEDTAVYYCAG (SEQ ID NO: 1010)

RATFSRDNAKNSAYMQLNSLRAEDTAVYYCAG (SEQ ID NO: 1011)

RATISTAKNALYMQMNSLRAEDTAVYYCAG (SEQ ID NO: 1012)

RATISTAKNALYLQLNSLRAEDTAVYYCAG (SEQ ID NO: 1013)

RATISTAKNSLYMQLNSLRAEDTAVYYCAG (SEQ ID NO: 1014)

RATISADNAKNSAYMQLNSLRAEDTAVYYCAG (SEQ ID NO: 1015)

RATISRTAKNSAYMQLNSLRAEDTAVYYCAG (SEQ ID NO: 1016)

RFTSTAKNSAYMQMNSLRAEDTAVYYCAG (SEQ ID NO: 1017)

RFTSTAKNSAYLQLNSLRAEDTAVYYCAG (SEQ ID NO: 1018)

RFTSTAKNSLYMQLNSLRAEDTAVYYCAG (SEQ ID NO: 1019)

RFTSADNAKNSAYMQLNSLRAEDTAVYYCAG (SEQ ID NO: 1020)

RFTSRTAKNSAYMQLNSLRAEDTAVYYCAG (SEQ ID NO: 1021)

RFTISTAKNSAYMQLNSLRAEDTAVYYCAG (SEQ ID NO: 1022)

RATFSTAKNSAYMQMNSLRAEDTAVYYCAG (SEQ ID NO: 1023)

RATFSTAKNSAYLQLNSLRAEDTAVYYCAG (SEQ ID NO: 1024)

RATFSTAKNSLYMQLNSLRAEDTAVYYCAG (SEQ ID NO: 1025)

RATFSADNAKNSAYMQLNSLRAEDTAVYYCAG (SEQ ID NO: 1026)

RATFSRTAKNSAYMQLNSLRAEDTAVYYCAG (SEQ ID NO: 1027)

RATISTAKNALYMQLNSLRAEDTAVYYCAG (SEQ ID NO: 1028)

RFTSTAKNSAYMQLNSLRAEDTAVYYCAG (SEQ ID NO: 1029)

RATFSTAKNSAYMQLNSLRAEDTAVYYCAG (SEQ ID NO: 1030)

141A-huVH3b VH CDR3

EEVYDGYPWFGY (SEQ ID NO: 35)

EEVYEGYPWFGY (SEQ ID NO: 883)

EEVYSGYPWFGY (SEQ ID NO: 884)

EEVYAGYPWFGY (SEQ ID NO: 885)

TABLE 7-continued

Amino Acid Sequences derived from Murine 141A Antibody.

141A-huVH3b VH FR4

WGQGTLVTVSS (SEQ ID NO: 54)

141A HUMANIZED ANTIBODY SEQUENCE: LIGHT CHAIN 141A-huVK3 Variable Region

EIVLTQSPGTLSLSPGERATLSCRASSSLSYMHWYQQKPGQAPRLLIYATSNLASGIPDRF
SGSGSGTDFTLTISRLEPEDFAVYYCQQWSSNPYTFGQGTKLEIK (SEQ ID NO: 26)

141A-huVK3 VL FR1

EIVLTQSPGTLSLSPGERATLSC (SEQ ID NO: 91)

EIVLTQSPGTLSASPGERATLSC (SEQ ID NO: 1031)

EIVLTQSPGTLSLSPGERVTLSC (SEQ ID NO: 1032)

EIVLTQSPGTLSLSPGERATMSC (SEQ ID NO: 1033)

EIVLTQSPGTLSASPGERVTLSC (SEQ ID NO: 1034)

EIVLTQSPGTLSASPGERATMSC (SEQ ID NO: 1035)

EIVLTQSPGTLSLSPGERVTMSC (SEQ ID NO: 1036)

EIVLTQSPGTLSASPGERVTMSC (SEQ ID NO: 1037)

141A-huVK3 VL CDR1

RASSSLSYMH (SEQ ID NO: 42)

141A-huVK3 VL FR2

WYQQKPGQAPRLLIY (SEQ ID NO: 92)

WYQQKPGQSPRLLIY (SEQ ID NO: 1038)

WYQQKPGQAPRPLIY (SEQ ID NO: 1039)

WYQQKPGQAPRLWIY (SEQ ID NO: 1040)

WYQQKPGQSPRPLIY (SEQ ID NO: 1041)

WYQQKPGQSPRLWIY (SEQ ID NO: 1042)

WYQQKPGQAPRPWIY (SEQ ID NO: 1043)

WYQQKPGQSPRPWIY (SEQ ID NO: 1044)

141A-huVK3 VL CDR2

ATSNLAS (SEQ ID NO: 43)

ATSQLAS (SEQ ID NO: 1045)

ATSSLAS (SEQ ID NO: 1046)

ATSDLAS (SEQ ID NO: 1047)

ATSALAS (SEQ ID NO: 1048)

141A-huVK3 VL FR3

GIPDRFSGSGSGTDFTLTISRLEPEDFAVYYC (SEQ ID NO: 93)

GVPDRFSGSGSGTDFTLTISRLEPEDFAVYYC (SEQ ID NO: 1049)

GIPDRFSGSGSGTDYTLTISRLEPEDFAVYYC (SEQ ID NO: 1050)

GIPDRFSGSGSGTDFTLTISRVEPEDFAVYYC (SEQ ID NO: 1051)

GVPDRFSGSGSGTDYTLTISRLEPEDFAVYYC (SEQ ID NO: 1052)

GVPDRFSGSGSGTDFTLTISRVEPEDFAVYYC (SEQ ID NO: 1053)

TABLE 7-continued

Amino Acid Sequences derived from Murine 141A Antibody.

GIPDRFSGSGSGTDYTLTISRVEPEDFAVYYC (SEQ ID NO: 1054)

GVPDRFSGSGSGTDYTLTISRVEPEDFAVYYC (SEQ ID NO: 1055)

141A-huVK3 VL CDR3

QQWSSNPYT (SEQ ID NO: 44)

QQWSSQPYT (SEQ ID NO: 1056)

QQWSSSPYT (SEQ ID NO: 1057)

QQWSSAPYT (SEQ ID NO: 1058)

141A-huVK3 VL FR4

FGQGTKLEIK (SEQ ID NO: 78)

141A-huVK1 Variable Region

DIQMTQSPSSLSASVGDRVTITCRASSSLSYMHWYQQKPGKAPKLLIYATSNLASGVPSR
FSGSGSGTDFTLTISSLQPEDFATYYCQQWSSNPYTFGQGTKLEIK (SEQ ID NO: 27)

141A-huVK1 VL FR1

DIQMTQSPSSLSASVGDRVTITC (SEQ ID NO: 79)

DIQLTQSPSSLSASVGDRVTITC (SEQ ID NO: 1059)

DIQMTQSPSSLSASVGDRVTMTC (SEQ ID NO: 1060)

DIQLTQSPSSLSASVGDRVTMTC (SEQ ID NO: 1061)

141A-huVK1 VL CDR1

RASSSLSYMH (SEQ ID NO: 42)

141A-huVK1 VL FR2

WYQQKPGKAPKLLIY (SEQ ID NO: 80)

WYQQKPGKSPKLLIY (SEQ ID NO: 284)

WYQQKPGKAPKPLIY (SEQ ID NO: 1062)

WYQQKPGKAPKLWIY (SEQ ID NO: 1063)

WYQQKPGKSPKPLIY (SEQ ID NO: 1064)

WYQQKPGKSPKLWIY (SEQ ID NO: 1065)

WYQQKPGKAPKPWIY (SEQ ID NO: 1066)

WYQQKPGKSPKPWIY (SEQ ID NO: 1067)

141A-huVK1 VL CDR2

ATSNLAS (SEQ ID NO: 43)

ATSQLAS (SEQ ID NO: 1045)

ATSSLAS (SEQ ID NO: 1046)

ATSDLAS (SEQ ID NO: 1047)

ATSALAS (SEQ ID NO: 1048)

141A-huVK1 VL FR3

GVPSRFSGSGSGTDFTLTISSLQPEDFATYYC (SEQ ID NO: 81)

GVPSRFSGSGSGTDYTLTISSLQPEDFATYYC (SEQ ID NO: 1068)

GVPSRFSGSGSGTDFTLTISSVQPEDFATYYC (SEQ ID NO: 285)

GVPSRFSGSGSGTDYTLTISSVQPEDFATYYC (SEQ ID NO: 1069)

TABLE 7-continued

Amino Acid Sequences derived from Murine 141A Antibody.

141A-huVK1 VL CDR3

QQWSSNPYT (SEQ ID NO: 44)

QQWSSQPYT (SEQ ID NO: 1056)

QQWSSSPYT (SEQ ID NO: 1057)

QQWSSAPYT (SEQ ID NO: 1058)

141A-huVK1 VL FR4

FGQGTKLEIK (SEQ ID NO: 78)

*Amino acid position numbering as in Kabat.

TABLE 8

Amino Acid Sequences derived from Murine 26A Antibody.

26A HUMANIZED ANTIBODY SEQUENCE: HEAVY CHAIN h26AH1 Variable Region

QVQLVQSGAEVKKPGASVKVSCKASGFSFTGYTMNWVRQAPGQGLEWMGLISPYNGGTS
YAQKFQGRVTMTRDTSTSTVYMELSSLRSEDTAVYYCARRAYGYAMDYWGQGTLVTVSS
(SEQ ID NO: 1529)

h26A VH FR1

QVQLVQSGAEVKKPGASVKVSCKAS (SEQ ID NO: 51)

QVQLVQSGAEVVKPGASVKVSCKAS (SEQ ID NO: 1550)

QVQLVQSGAEVKKPGASMKVSCKAS (SEQ ID NO: 1551)

QVQLVQSGAEVKKPGASVKISCKAS (SEQ ID NO: 105)

QVQLVQSGAEVVKPGASMKVSCKAS (SEQ ID NO: 1552)

QVQLVQSGAEVVKPGASVKISCKAS (SEQ ID NO: 1553)

QVQLVQSGAEVKKPGASMKISCKAS (SEQ ID NO: 1554)

QVQLVQSGAEVVKPGASMKISCKAS (SEQ ID NO: 1555)

h26A VH CDR1

GFSFTGYTMN (SEQ ID NO: 1296)

h26A VH FR2

WVRQAPGQGLEWMG (SEQ ID NO: 52)

WVRQAPGQGLEWIG (SEQ ID NO: 106)

h26A VH CDR2

LISPYNGGTS (SEQ ID NO: 1358)

LISPYQGGTS (SEQ ID NO: 1556)

LISPYSGGTS (SEQ ID NO: 1557)

LISPYAGGTS (SEQ ID NO: 1558)

LISPYDGGTS (SEQ ID NO: 1559)

h26A VH FR3

YAQKFQGRVTMTRDTSTSTVYMELSSLRSEDTAVYYCAR (SEQ ID NO: 1560)

YNQKFQGRVTMTRDTSTSTVYMELSSLRSEDTAVYYCAR (SEQ ID NO: 1561)

YAQKFQGRATMTRDTSTSTVYMELSSLRSEDTAVYYCAR (SEQ ID NO: 1562)

TABLE 8-continued

Amino Acid Sequences derived from Murine 26A Antibody.

YAQKFQGRVTLTRDTSTSTVYMELSSLRSEDTAVYYCAR (SEQ ID NO: 1563)

YAQKFQGRVTMTVDTSTSTVYMELSSLRSEDTAVYYCAR (SEQ ID NO: 1564)

YAQKFQGRVTMTRDKSTSTVYMELSSLRSEDTAVYYCAR (SEQ ID NO: 1565)

YAQKFQGRVTMTRDTSTSTAYMELSSLRSEDTAVYYCAR (SEQ ID NO: 1566)

YNQKFQGRATMTRDTSTSTVYMELSSLRSEDTAVYYCAR (SEQ ID NO: 1567)

YNQKFQGRVTLTRDTSTSTVYMELSSLRSEDTAVYYCAR (SEQ ID NO: 1568)

YNQKFQGRVTMTVDTSTSTVYMELSSLRSEDTAVYYCAR (SEQ ID NO: 1569)

YNQKFQGRVTMTRDKSTSTVYMELSSLRSEDTAVYYCAR (SEQ ID NO: 1570)

YNQKFQGRVTMTRDTSTSTAYMELSSLRSEDTAVYYCAR (SEQ ID NO: 1571)

YAQKFQGRATL**TRDTSTSTVYMELSSLRSEDTAVYYCAR (SEQ ID NO: 1572)

YAQKFQGRATMTVDTSTSTVYMELSSLRSEDTAVYYCAR (SEQ ID NO: 1573)

YAQKFQGRATMTRDKSTSTVYMELSSLRSEDTAVYYCAR (SEQ ID NO: 1574)

YAQKFQGRATMTRDTSTSTAYMELSSLRSEDTAVYYCAR (SEQ ID NO: 1575)

YAQKFQGRVTLTVDTSTSTVYMELSSLRSEDTAVYYCAR (SEQ ID NO: 1576)

YAQKFQGRVTLTRDKSTSTVYMELSSLRSEDTAVYYCAR (SEQ ID NO: 1577)

YAQKFQGRVTLTRDTSTSTAYMELSSLRSEDTAVYYCAR (SEQ ID NO: 1578)

YAQKFQGRVTMTVDKSTSTVYMELSSLRSEDTAVYYCAR (SEQ ID NO: 1579)

YAQKFQGRVTMTVDTSTSTAYMELSSLRSEDTAVYYCAR (SEQ ID NO: 1580)

YAQKFQGRVTMTRDKSTSTAYMELSSLRSEDTAVYYCAR (SEQ ID NO: 1581)

YNQKFQGRATL**TRDTSTSTVYMELSSLRSEDTAVYYCAR (SEQ ID NO: 1582)

YNQKFQGRATMTVDTSTSTVYMELSSLRSEDTAVYYCAR (SEQ ID NO: 1583)

YNQKFQGRATMTRDKSTSTVYMELSSLRSEDTAVYYCAR (SEQ ID NO: 1584)

YNQKFQGRATMTRDTSTSTAYMELSSLRSEDTAVYYCAR (SEQ ID NO: 1585)

YNQKFQGRVTLTVDTSTSTVYMELSSLRSEDTAVYYCAR (SEQ ID NO: 1586)

YNQKFQGRVTLTRDKSTSTVYMELSSLRSEDTAVYYCAR (SEQ ID NO: 1587)

YNQKFQGRVTLTRDTSTSTAYMELSSLRSEDTAVYYCAR (SEQ ID NO: 1588)

YNQKFQGRVTMTVDKSTSTVYMELSSLRSEDTAVYYCAR (SEQ ID NO: 1589)

YNQKFQGRVTMTVDTSTSTAYMELSSLRSEDTAVYYCAR (SEQ ID NO: 1590)

YNQKFQGRVTMTRDKSTSTAYMELSSLRSEDTAVYYCAR (SEQ ID NO: 1591)

YAQKFQGRATLTV**DTSTSTVYMELSSLRSEDTAVYYCAR (SEQ ID NO: 1592)

YAQKFQGRATLTRDK**STSTVYMELSSLRSEDTAVYYCAR (SEQ ID NO: 1593)

YAQKFQGRATLTRDTSTSTA**YMELSSLRSEDTAVYYCAR (SEQ ID NO: 1594)

YAQKFQGRATMTVDKSTSTVYMELSSLRSEDTAVYYCAR (SEQ ID NO: 1595)

YAQKFQGRATMTVDTSTSTAYMELSSLRSEDTAVYYCAR (SEQ ID NO: 1596)

YAQKFQGRATMTRDKSTSTAYMELSSLRSEDTAVYYCAR (SEQ ID NO: 1597)

YAQKFQGRVTLTVDKSTSTVYMELSSLRSEDTAVYYCAR (SEQ ID NO: 1598)

YAQKFQGRVTLTVDTSTSTAYMELSSLRSEDTAVYYCAR (SEQ ID NO: 1599)

YAQKFQGRVTMTVDKSTSTAYMELSSLRSEDTAVYYCAR (SEQ ID NO: 1600)

YNQKFQGRATLTV**DTSTSTVYMELSSLRSEDTAVYYCAR (SEQ ID NO: 1601)

TABLE 8-continued

Amino Acid Sequences derived from Murine 26A Antibody.

YN̲QKFQGRATL̲TRDKSTSTVYMELSSLRSEDTAVYYCAR (SEQ ID NO: 1602)

YN̲QKFQGRATL̲TRDTSTSTAYMELSSLRSEDTAVYYCAR (SEQ ID NO: 1603)

YN̲QKFQGRVTLTV̲D̲KSTSTVYMELSSLRSEDTAVYYCAR (SEQ ID NO: 1604)

YN̲QKFQGRVTLTV̲DTSTSTAYMELSSLRSEDTAVYYCAR (SEQ ID NO: 1605)

YN̲QKFQGRVTMTV̲D̲KSTSTAYMELSSLRSEDTAVYYCAR (SEQ ID NO: 1606)

YAQKFQGRATL̲V̲D̲KSTSTVYMELSSLRSEDTAVYYCAR (SEQ ID NO: 1607)

YAQKFQGRATL̲V̲DTSTSTAYMELSSLRSEDTAVYYCAR (SEQ ID NO: 1608)

YAQKFQGRATMT̲V̲D̲KSTSTAYMELSSLRSEDTAVYYCAR (SEQ ID NO: 1609)

YAQKFQGRVTLTV̲D̲KSTSTAYMELSSLRSEDTAVYYCAR (SEQ ID NO: 1610)

YN̲QKFQGRATL̲V̲D̲KSTSTVYMELSSLRSEDTAVYYCAR (SEQ ID NO: 1611)

YN̲QKFQGRATL̲V̲DTSTSTAYMELSSLRSEDTAVYYCAR (SEQ ID NO: 1612)

YAQKFQGRATL̲V̲D̲KSTSTAYMELSSLRSEDTAVYYCAR (SEQ ID NO: 1613)

YN̲QKFQGRATL̲V̲D̲KSTSTAYMELSSLRSEDTAVYYCAR (SEQ ID NO: 1614)

h26A VH CDR3

RAYGYAMDY (SEQ ID NO: 1393)

h26A VH FR4

WGQGTLVTVSS (SEQ ID NO: 54)

26A HUMANIZED ANTIBODY SEQUENCE: LIGHT CHAIN h26AL1 Variable Region

EIVLTQSPATLSLSPGERATLSCSASSSVSYMYWYQQKPGQAPRLLIYDTSNLASGIPARFS GSGSGTDFTLTISSLEPEDFAVYYCQQWSSYPFTFGQGTKLEIK (SEQ ID NO: 1532)

h26A VL FR1

EIVLTQSPATLSLSPGERATLSC (SEQ ID NO: 1615)

EIVLTQSPATMSLSPGERATLSC (SEQ ID NO: 1616)

EIVLTQSPATLSASPGERATLSC (SEQ ID NO: 1617)

EIVLTQSPATLSLSPGERVTLSC (SEQ ID NO: 1618)

EIVLTQSPATLSLSPGERATMSC (SEQ ID NO: 1619)

EIVLTQSPATMSASPGERATLSC (SEQ ID NO: 1620)

EIVLTQSPATMSLSPGERVTLSC (SEQ ID NO: 1621)

EIVLTQSPATMSLSPGERATMSC (SEQ ID NO: 1622)

EIVLTQSPATLSASPGERVTLSC (SEQ ID NO: 1623)

EIVLTQSPATLSASPGERATMSC (SEQ ID NO: 1624)

EIVLTQSPATLSLSPGERVTMSC (SEQ ID NO: 1625)

EIVLTQSPATMSASPGERVTLSC (SEQ ID NO: 1626)

EIVLTQSPATMSASPGERATMSC (SEQ ID NO: 1627)

EIVLTQSPATLSASPGERVTMSC (SEQ ID NO: 1628)

EIVLTQSPATMSASPGERVTMSC (SEQ ID NO: 1629)

TABLE 8-continued

Amino Acid Sequences derived from Murine 26A Antibody.

h26A VL CDR1

SASSSVSYMY (SEQ ID NO: 1435)

h26A VL FR2

WYQQKPGQAPRLLIY (SEQ ID NO: 92)

h26A VL CDR2

DTSNLAS (SEQ ID NO: 1476)

DTSQLAS (SEQ ID NO: 1630)

DTSSLAS (SEQ ID NO: 1631)

DTSALAS (SEQ ID NO: 1632)

DTSDLAS (SEQ ID NO: 1633)

h26A VL FR3

GIPARFSGSGSGTDFTLTISSLEPEDFAVYYC (SEQ ID NO: 1634)

GVPARFSGSGSGTDFTLTISSLEPEDFAVYYC (SEQ ID NO: 1635)

GIPARFSGSGSGTDYTLTISSLEPEDFAVYYC (SEQ ID NO: 1636)

GIPARFSGSGSGTDFTLTISSMEPEDFAVYYC (SEQ ID NO: 1637)

GIPARFSGSGSGTDFTLTISSLEPEDAAVYYC (SEQ ID NO: 1638)

GVPARFSGSGSGTDYTLTISSLEPEDFAVYYC (SEQ ID NO: 1639)

GVPARFSGSGSGTDFTLTISSMEPEDFAVYYC (SEQ ID NO: 1640)

GVPARFSGSGSGTDFTLTISSLEPEDAAVYYC (SEQ ID NO: 1641)

GIPARFSGSGSGTDYTLTISSMEPEDFAVYYC (SEQ ID NO: 1642)

GIPARFSGSGSGTDYTLTISSLEPEDAAVYYC (SEQ ID NO: 1643)

GIPARFSGSGSGTDFTLTISSMEPEDAAVYYC (SEQ ID NO: 1644)

GVPARFSGSGSGTDYTLTISSMEPEDFAVYYC (SEQ ID NO: 1645)

GVPARFSGSGSGTDYTLTISSLEPEDAAVYYC (SEQ ID NO: 1646)

GIPARFSGSGSGTDYTLTISSMEPEDAAVYYC (SEQ ID NO: 1647)

GVPARFSGSGSGTDYTLTISSMEPEDAAVYYC (SEQ ID NO: 1648)

h26A VL CDR3

QQWSSYPFT (SEQ ID NO: 1499)

h26A VL FR4

FGQGTKLEIK (SEQ ID NO: 78)

TABLE 9

Amino Acid Sequences derived from Murine 128A Antibody.

128A HUMANIZED ANTIBODY SEQUENCE: HEAVY CHAIN h128AH1 Variable Region

QVQLVQSGAEVKKPGASVKVSCKASGYTFTDYGMHWVRQAPGQGLEWMGLIDTYYGDAT
YAQKFQGRVTMTRDTSTSTVYMELSSLRSEDTAVYYCARRAGNAMDYWGQGTLVTVSS
(SEQ ID NO: 1535)

TABLE 9-continued

Amino Acid Sequences derived from Murine 128A Antibody.

h128A VH FR1

QVQLVQSGAEVKKPGASVKVSCKAS (SEQ ID NO: 51)

QVQLVQSGAEVVKPGASVKVSCKAS (SEQ ID NO: 1550)

QVQLVQSGAEVKKPGASVKISCKAS (SEQ ID NO: 105)

QVQLVQSGAEVKKPGASVKVSCKGS (SEQ ID NO: 1649)

QVQLVQSGAEVVKPGASVKISCKAS (SEQ ID NO: 1553)

QVQLVQSGAEVVKPGASVKVSCKGS (SEQ ID NO: 1650)

QVQLVQSGAEVKKPGASVKISCKGS (SEQ ID NO: 1651)

QVQLVQSGAEVVKPGASVKISCKGS (SEQ ID NO: 1652)

h128A VH CDR1

GYTFTDYGMH (SEQ ID NO: 1291)

h128A VH FR2

WVRQAPGQGLEWMG (SEQ ID NO: 52)

WVRQAPGQGLEWIG (SEQ ID NO: 106)

h128A VH CDR2

LIDTYYGDAT (SEQ ID NO: 1350)

h128A VH FR3

YAQKFQGRVTMTRDTSTSTVYMELSSLRSEDTAVYYCAR (SEQ ID NO: 1560)

YNQKFQGRVTMTRDTSTSTVYMELSSLRSEDTAVYYCAR (SEQ ID NO: 1561)

YAQKFQGRATMTRDTSTSTVYMELSSLRSEDTAVYYCAR (SEQ ID NO: 1562)

YAQKFQGRVTMTVDTSTSTVYMELSSLRSEDTAVYYCAR (SEQ ID NO: 1564)

YAQKFQGRVTMTRDKSTSTVYMELSSLRSEDTAVYYCAR (SEQ ID NO: 1565)

YAQKFQGRVTMTRDTSTSTAYMELSSLRSEDTAVYYCAR (SEQ ID NO: 1566)

YAQKFQGRVTMTRDTSTSTVYMELSSLRSEDTAIYYCAR (SEQ ID NO: 1653)

YNQKFQGRATMTRDTSTSTVYMELSSLRSEDTAVYYCAR (SEQ ID NO: 1567)

YNQKFQGRVTMTVDTSTSTVYMELSSLRSEDTAVYYCAR (SEQ ID NO: 1569)

YNQKFQGRVTMTRDKSTSTVYMELSSLRSEDTAVYYCAR (SEQ ID NO: 1570)

YNQKFQGRVTMTRDTSTSTAYMELSSLRSEDTAVYYCAR (SEQ ID NO: 1571)

YNQKFQGRVTMTRDTSTSTVYMELSSLRSEDTAIYYCAR (SEQ ID NO: 1654)

YAQKFQGRATMTVDTSTSTVYMELSSLRSEDTAVYYCAR (SEQ ID NO: 1573)

YAQKFQGRATMTRDKSTSTVYMELSSLRSEDTAVYYCAR (SEQ ID NO: 1574)

YAQKFQGRATMTRDTSTSTAYMELSSLRSEDTAVYYCAR (SEQ ID NO: 1575)

YAQKFQGRATMTRDTSTSTVYMELSSLRSEDTAIYYCAR (SEQ ID NO: 1655)

YAQKFQGRVTMTVDKSTSTVYMELSSLRSEDTAVYYCAR (SEQ ID NO: 1579)

YAQKFQGRVTMTVDTSTSTAYMELSSLRSEDTAVYYCAR (SEQ ID NO: 1580)

YAQKFQGRVTMTVDTSTSTVYMELSSLRSEDTAIYYCAR (SEQ ID NO: 1656)

YAQKFQGRVTMTRDKSTSTAYMELSSLRSEDTAVYYCAR (SEQ ID NO: 1581)

YAQKFQGRVTMTRDKSTSTVYMELSSLRSEDTAIYYCAR (SEQ ID NO: 1657)

YAQKFQGRVTMTRDTSTSTAYMELSSLRSEDTAIYYCAR (SEQ ID NO: 1658)

TABLE 9-continued

Amino Acid Sequences derived from Murine 128A Antibody.

YNQKFQGRATMTVDTSTSTVYMELSSLRSEDTAVYYCAR (SEQ ID NO: 1583)

YNQKFQGRATMTRDKSTSTVYMELSSLRSEDTAVYYCAR (SEQ ID NO: 1584)

YNQKFQGRATMTRDTSTSTAYMELSSLRSEDTAVYYCAR (SEQ ID NO: 1585)

YNQKFQGRATMTRDTSTSTVYMELSSLRSEDTAIYYCAR (SEQ ID NO: 1659)

YNQKFQGRVTMTVDKSTSTVYMELSSLRSEDTAVYYCAR (SEQ ID NO: 1589)

YNQKFQGRVTMTVDTSTSTAYMELSSLRSEDTAVYYCAR (SEQ ID NO: 1590)

YNQKFQGRVTMTVDTSTSTVYMELSSLRSEDTAIYYCAR (SEQ ID NO: 1660)

YNQKFQGRVTMTRDKSTSTAYMELSSLRSEDTAVYYCAR (SEQ ID NO: 1591)

YNQKFQGRVTMTRDKSTSTVYMELSSLRSEDTAIYYCAR (SEQ ID NO: 1661)

YNQKFQGRVTMTRDTSTSTAYMELSSLRSEDTAIYYCAR (SEQ ID NO: 1662)

YAQKFQGRATMTVDKSTSTVYMELSSLRSEDTAVYYCAR (SEQ ID NO: 1595)

YAQKFQGRATMTVDTSTSTAYMELSSLRSEDTAVYYCAR (SEQ ID NO: 1596)

YAQKFQGRATMTVDTSTSTVYMELSSLRSEDTAIYYCAR (SEQ ID NO: 1663)

YAQKFQGRATMTRDKSTSTAYMELSSLRSEDTAVYYCAR (SEQ ID NO: 1597)

YAQKFQGRATMTRDKSTSTVYMELSSLRSEDTAIYYCAR (SEQ ID NO: 1664)

YAQKFQGRATMTRDTSTSTAYMELSSLRSEDTAIYYCAR (SEQ ID NO: 1665)

YAQKFQGRVTMTVDKSTSTAYMELSSLRSEDTAVYYCAR (SEQ ID NO: 1600)

YAQKFQGRVTMTVDKSTSTVYMELSSLRSEDTAIYYCAR (SEQ ID NO: 1666)

YAQKFQGRVTMTRDKSTSTAYMELSSLRSEDTAIYYCAR (SEQ ID NO: 1667)

YNQKFQGRATMTVDKSTSTVYMELSSLRSEDTAVYYCAR (SEQ ID NO: 1668)

YNQKFQGRATMTVDTSTSTAYMELSSLRSEDTAVYYCAR (SEQ ID NO: 1669)

YNQKFQGRATMTVDTSTSTVYMELSSLRSEDTAIYYCAR (SEQ ID NO: 1670)

YNQKFQGRVTMTVDKSTSTAYMELSSLRSEDTAVYYCAR (SEQ ID NO: 1606)

YNQKFQGRVTMTVDKSTSTVYMELSSLRSEDTAIYYCAR (SEQ ID NO: 1671)

YNQKFQGRVTMTRDKSTSTAYMELSSLRSEDTAIYYCAR (SEQ ID NO: 1672)

YAQKFQGRATMTVDKSTSTAYMELSSLRSEDTAVYYCAR (SEQ ID NO: 1609)

YAQKFQGRATMTVDKSTSTVYMELSSLRSEDTAIYYCAR (SEQ ID NO: 1673)

YAQKFQGRATMTRDKSTSTAYMELSSLRSEDTAIYYCAR (SEQ ID NO: 1674)

YAQKFQGRVTMTVDKSTSTAYMELSSLRSEDTAIYYCAR (SEQ ID NO: 1675)

YNQKFQGRATMTVDKSTSTAYMELSSLRSEDTAVYYCAR (SEQ ID NO: 1676)

YNQKFQGRATMTVDKSTSTVYMELSSLRSEDTAAYYCAR (SEQ ID NO: 1677)

YAQKFQGRATMTVDKSTSTAYMELSSLRSEDTAAYYCAR (SEQ ID NO: 1678)

YNQKFQGRATMTVDKSTSTAYMELSSLRSEDTAAYYCAR (SEQ ID NO: 1679)

TABLE 9-continued

Amino Acid Sequences derived from Murine 128A Antibody.

h128A VH CDR3

RAGNAMDY (SEQ ID NO: 1385)

h128A VH FR4

WGQGTLVTVSS (SEQ ID NO: 54)

WGQGTLVTASS (SEQ ID NO: 1680)

128A HUMANIZED ANTIBODY SEQUENCE: LIGHT CHAIN h128AL1 Variable Region

DIQMTQSPSSLSASVGDRVTITCKASQSVSNDIAWYQQKPGKAPKLLIYYASNRYTGVPSR
FSGSGSGTDFTLTISSLQPEDFATYYCQQDYSSPRTFGQGTKLEIK (SEQ ID NO: 1538)

h128A VL FR1

DIQMTQSPSSLSASVGDRVTITC (SEQ ID NO: 79)

DIQMTQSPSSLSVSVGDRVTITC (SEQ ID NO: 278)

h128A VL CDR1

KASQSVSNDIA (SEQ ID NO: 1429)

KASQSVSQDIA (SEQ ID NO: 1681)

KASQSVSSDIA (SEQ ID NO: 1682)

KASQSVSADIA (SEQ ID NO: 1683)

KASQSVSDDIA (SEQ ID NO: 1684)

h128A VL FR2

WYQQKPGKAPKLLIY (SEQ ID NO: 80)

WYQQKPGKSPKLLIY (SEQ ID NO: 284)

h128A VL CDR2

YASNRYT (SEQ ID NO: 1473)

YASQRYT (SEQ ID NO: 1685)

YASSRYT (SEQ ID NO: 1686)

YASARYT (SEQ ID NO: 1687)

YASDRYT (SEQ ID NO: 1688)

h128A VL FR3

GVPSRFSGSGSGTDFTLTISSLQPEDFATYYC (SEQ ID NO: 81)

GVPSRFSGSYGTDFTLTISSLQPEDFATYYC (SEQ ID NO: 1689)

GVPSRFSGSGSGTDFTFTISSLQPEDFATYYC (SEQ ID NO: 1690)

GVPSRFSGSGSGTDFTLTISSVQPEDFATYYC (SEQ ID NO: 285)

GVPSRFSGSGSGTDFTLTISSLQPEDLATYYC (SEQ ID NO: 286)

GVPSRFSGSGSGTDFTLTISSLQPEDFATYFC (SEQ ID NO: 1691)

GVPSRFSGSYGTDFTFTISSLQPEDFATYYC (SEQ ID NO: 1692)

GVPSRFSGSYGTDFTLTISSVQPEDFATYYC (SEQ ID NO: 1693)

GVPSRFSGSYGTDFTLTISSLQPEDLATYYC (SEQ ID NO: 1694)

GVPSRFSGSYGTDFTLTISSLQPEDFATYFC (SEQ ID NO: 1695)

GVPSRFSGSGSGTDFTFTISSVQPEDFATYYC (SEQ ID NO: 1696)

TABLE 9-continued

Amino Acid Sequences derived from Murine 128A Antibody.

GVPSRFSGSGSGTDFTFTISSLQPEDLATYYC (SEQ ID NO: 1697)

GVPSRFSGSGSGTDFTFTISSLQPEDFATYFC (SEQ ID NO: 1698)

GVPSRFSGSGSGTDFTLTISSVQPEDLATYYC (SEQ ID NO: 288)

GVPSRFSGSGSGTDFTLTISSVQPEDFATYFC (SEQ ID NO: 1699)

GVPSRFSGSGSGTDFTLTISSLQPEDLATYFC (SEQ ID NO: 1700)

GVPSRFSGSGYGTDFTFTISSVQPEDFATYYC (SEQ ID NO: 1701)

GVPSRFSGSGYGTDFTFTISSLQPEDFATYYC (SEQ ID NO: 1702)

GVPSRFSGSGYGTDFTFTISSLQPEDFATYFC (SEQ ID NO: 1703)

GVPSRFSGSGYGTDFTLTISSVQPEDLATYYC (SEQ ID NO: 1704)

GVPSRFSGSGYGTDFTLTISSVQPEDFATYFC (SEQ ID NO: 1705)

GVPSRFSGSGYGTDFTLTISSLQPEDLATYFC (SEQ ID NO: 1706)

GVPSRFSGSGSGTDFTFTISSVQPEDLATYYC (SEQ ID NO: 1707)

GVPSRFSGSGSGTDFTFTISSVQPEDFATYFC (SEQ ID NO: 1708)

GVPSRFSGSGSGTDFTLTISSVQPEDLATYFC (SEQ ID NO: 1709)

GVPSRFSGSGYGTDFTFTISSVQPEDLATYYC (SEQ ID NO: 1710)

GVPSRFSGSGYGTDFTFTISSVQPEDFATYFC (SEQ ID NO: 1711)

GVPSRFSGSGYGTDFTLTISSVQPEDLATYFC (SEQ ID NO: 1712)

GVPSRFSGSGSGTDFTFTISSVQPEDLATYFC (SEQ ID NO: 1713)

GVPSRFSGSGYGTDFTFTISSVQPEDLATYFC (SEQ ID NO: 1714)

h128A VL CDR3

QQDYSSPRT (SEQ ID NO: 1493)

h128A VL FR4

FGQGTKLEIK (SEQ ID NO: 78)

TABLE 10

Amino Acid Sequences derived from Murine 124A Antibody.

124A HUMANIZED ANTIBODY SEQUENCE: HEAVY CHAIN h124AH1 Variable Region

QVQLVQSGAEVKKPGASVKVSCKASGYTFSSNWIEWVRQAPGQGLEWMGEILPGSGSTSYAQKFQGRVTMTRDTSTSTVYMELSSLRSEDTAVYYCARWLLYYYAMDFWGQGTLVTVSS (SEQ ID NO: 1541)

h124A VH FR1

QVQLVQSGAEVKKPGASVKVSCKAS (SEQ ID NO: 51)

QVQLVQSGAEVMKPGASVKVSCKAS (SEQ ID NO: 39)

QVQLVQSGAEVKKPGASIKVSCKAS (SEQ ID NO: 1715)

QVQLVQSGAEVMKPGASIKVSCKAS (SEQ ID NO: 1716)

h124A VH CDR1

GYTFSSNWIE (SEQ ID NO: 1316)

GYTFSSQWIE (SEQ ID NO: 1717)

GYTFSSSWIE (SEQ ID NO: 1718)

TABLE 10-continued

Amino Acid Sequences derived from Murine 124A Antibody.

GYTFSSAWIE (SEQ ID NO: 1719)

GYTFSSDWIE (SEQ ID NO: 1720)

h124A VH FR2

WVRQAPGQGLEWMG (SEQ ID NO: 52)

h124A VH CDR2

EILPGSGSTS (SEQ ID NO: 1098)

h124A VH FR3

YAQKFQGRVTMTRDTSTSTVYMELSSLRSEDTAVYYCAR (SEQ ID NO: 1560)

YNQKFQGRVTMTRDTSTSTVYMELSSLRSEDTAVYYCAR (SEQ ID NO: 1561)

YAQKFQGRATMTRDTSTSTVYMELSSLRSEDTAVYYCAR (SEQ ID NO: 1562)

YAQKFQGRVTFTRDTSTSTVYMELSSLRSEDTAVYYCAR (SEQ ID NO: 1721)

YAQKFQGRVTMTADTSTSTVYMELSSLRSEDTAVYYCAR (SEQ ID NO: 1722)

YAQKFQGRVTMTRDTSTSTAYMELSSLRSEDTAVYYCAR (SEQ ID NO: 1566)

YNQKFQGRATMTRDTSTSTVYMELSSLRSEDTAVYYCAR (SEQ ID NO: 1567)

YNQKFQGRVTFTRDTSTSTVYMELSSLRSEDTAVYYCAR (SEQ ID NO: 1723)

YNQKFQGRVTMTADTSTSTVYMELSSLRSEDTAVYYCAR (SEQ ID NO: 1724)

YNQKFQGRVTMTRDTSTSTAYMELSSLRSEDTAVYYCAR (SEQ ID NO: 1571)

YAQKFQGRATFTRDTSTSTVYMELSSLRSEDTAVYYCAR (SEQ ID NO: 1725)

YAQKFQGRATMTADTSTSTVYMELSSLRSEDTAVYYCAR (SEQ ID NO: 1726)

YAQKFQGRATMTRDTSTSTAYMELSSLRSEDTAVYYCAR (SEQ ID NO: 1575)

YAQKFQGRVTFT ADTSTSTVYMELSSLRSEDTAVYYCAR (SEQ ID NO: 1727)

YAQKFQGRVTFTRDTSTSTAYMELSSLRSEDTAVYYCAR (SEQ ID NO: 1728)

YAQKFQGRVTMTADTSTSTAYMELSSLRSEDTAVYYCAR (SEQ ID NO: 1729)

YNQKFQGRATFTRDTSTSTVYMELSSLRSEDTAVYYCAR (SEQ ID NO: 1730)

YNQKFQGRATMTADTSTSTVYMELSSLRSEDTAVYYCAR (SEQ ID NO: 1731)

YNQKFQGRATMTRDTSTSTAYMELSSLRSEDTAVYYCAR (SEQ ID NO: 1585)

YNQKFQGRVTFT ADTSTSTVYMELSSLRSEDTAVYYCAR (SEQ ID NO: 1732)

YNQKFQGRVTFTRDTSTSTAYMELSSLRSEDTAVYYCAR (SEQ ID NO: 1733)

YNQKFQGRVTMTADTSTSTAYMELSSLRSEDTAVYYCAR (SEQ ID NO: 1734)

YAQKFQGRATFT ADTSTSTVYMELSSLRSEDTAVYYCAR (SEQ ID NO: 1735)

YAQKFQGRATFTRDTSTSTAYMELSSLRSEDTAVYYCAR (SEQ ID NO: 1736)

YAQKFQGRATMTADTSTSTAYMELSSLRSEDTAVYYCAR (SEQ ID NO: 1737)

YAQKFQGRVTFT ADTSTSTAYMELSSLRSEDTAVYYCAR (SEQ ID NO: 1738)

YNQKFQGRATFT ADTSTSTVYMELSSLRSEDTAVYYCAR (SEQ ID NO: 1739)

YNQKFQGRATFTRDTSTSTAYMELSSLRSEDTAVYYCAR (SEQ ID NO: 1740)

YNQKFQGRATMTADTSTSTAYMELSSLRSEDTAVYYCAR (SEQ ID NO: 1741)

YNQKFQGRATFT ADTSTSTAYMELSSLRSEDTAVYYCAR (SEQ ID NO: 1742)

TABLE 10-continued

Amino Acid Sequences derived from Murine 124A Antibody.

h124A VH CDR3

WLLYYYAMDF (SEQ ID NO: 1413)

h124A VH FR4

WGQGTLVTVSS (SEQ ID NO: 54)

124A HUMANIZED ANTIBODY SEQUENCE: LIGHT CHAIN h124AL1 Variable Region

DVVMTQSPLSLPVTLGQPASISCRSSQSIVHNNGNTYLEWFQQRPGQSPRRLIYKVSNRFS
GVPDRFSGSGSGTDFTLKISRVEAEDVGVYYCFQGSHVPYTFGQGTKLEIK
(SEQ ID NO: 1546)

h124A VL FR1

DVVMTQSPLSLPVTLGQPASISC (SEQ ID NO: 1743)

h124A VL CDR1

RSSQSIVHNNGNTYLE (SEQ ID NO: 1462)

RSSQSIVHQNGNTYLE (SEQ ID NO: 1744)

RSSQSIVHSNGNTYLE (SEQ ID NO: 45)

RSSQSIVHANGNTYLE (SEQ ID NO: 1745)

RSSQSIVHDNGNTYLE (SEQ ID NO: 1746)

RSSQSIVHNQGNTYLE (SEQ ID NO: 1747)

RSSQSIVHNSGNTYLE (SEQ ID NO: 1748)

RSSQSIVHNAGNTYLE (SEQ ID NO: 1749)

RSSQSIVHNNGQTYLE (SEQ ID NO: 1750)

RSSQSIVHNNGSTYLE (SEQ ID NO: 1751)

RSSQSIVHNNGATYLE (SEQ ID NO: 1752)

RSSQSIVHNNGDTYLE (SEQ ID NO: 1753)

RSSQSIVHQQGNTYLE (SEQ ID NO: 1754)

RSSQSIVHQSGNTYLE (SEQ ID NO: 1755)

RSSQSIVHQAGNTYLE (SEQ ID NO: 1756)

RSSQSIVHQNGQTYLE (SEQ ID NO: 1757)

RSSQSIVHQNGSTYLE (SEQ ID NO: 1758)

RSSQSIVHQNGATYLE (SEQ ID NO: 1759)

RSSQSIVHQNGDTYLE (SEQ ID NO: 1760)

RSSQSIVHSQGNTYLE (SEQ ID NO: 253)

RSSQSIVHSSGNTYLE (SEQ ID NO: 254)

RSSQSIVHSAGNTYLE (SEQ ID NO: 255)

RSSQSIVHSNGQTYLE (SEQ ID NO: 256)

RSSQSIVHSNGSTYLE (SEQ ID NO: 257)

RSSQSIVHSNGATYLE (SEQ ID NO: 258)

RSSQSIVHSNGDTYLE (SEQ ID NO: 259)

RSSQSIVHAQGNTYLE (SEQ ID NO: 1761)

RSSQSIVHASGNTYLE (SEQ ID NO: 1762)

TABLE 10-continued

Amino Acid Sequences derived from Murine 124A Antibody.

RSSQSIVHAAGNTYLE (SEQ ID NO: 1763)

RSSQSIVHANGQTYLE (SEQ ID NO: 1764)

RSSQSIVHANGSTYLE (SEQ ID NO: 1765)

RSSQSIVHANGATYLE (SEQ ID NO: 1766)

RSSQSIVHANGDTYLE (SEQ ID NO: 1767)

RSSQSIVHDQGNTYLE (SEQ ID NO: 1768)

RSSQSIVHDSGNTYLE (SEQ ID NO: 1769)

RSSQSIVHDAGNTYLE (SEQ ID NO: 1770)

RSSQSIVHDNGQTYLE (SEQ ID NO: 1771)

RSSQSIVHDNGSTYLE (SEQ ID NO: 1772)

RSSQSIVHDNGATYLE (SEQ ID NO: 1773)

RSSQSIVHDNGDTYLE (SEQ ID NO: 1774)

RSSQSIVHNQGQTYLE (SEQ ID NO: 1775)

RSSQSIVHNQGSTYLE (SEQ ID NO: 1776)

RSSQSIVHNQGATYLE (SEQ ID NO: 1777)

RSSQSIVHNQGDTYLE (SEQ ID NO: 1778)

RSSQSIVHNSGQTYLE (SEQ ID NO: 1779)

RSSQSIVHNSGSTYLE (SEQ ID NO: 1780)

RSSQSIVHNSGATYLE (SEQ ID NO: 1781)

RSSQSIVHNSGDTYLE (SEQ ID NO: 1782)

RSSQSIVHNAGQTYLE (SEQ ID NO: 1783)

RSSQSIVHNAGSTYLE (SEQ ID NO: 1784)

RSSQSIVHNAGATYLE (SEQ ID NO: 1785)

RSSQSIVHNAGDTYLE (SEQ ID NO: 1786)

RSSQSIVHQQGQTYLE (SEQ ID NO: 1787)

RSSQSIVHSQGQTYLE (SEQ ID NO: 260)

RSSQSIVHAQGQTYLE (SEQ ID NO: 1788)

RSSQSIVHDQGQTYLE (SEQ ID NO: 1789)

RSSQSIVHQSGQTYLE (SEQ ID NO: 1790)

RSSQSIVHQAGQTYLE (SEQ ID NO: 1791)

RSSQSIVHSSGQTYLE (SEQ ID NO: 264)

RSSQSIVHSAGQTYLE (SEQ ID NO: 268)

RSSQSIVHASGQTYLE (SEQ ID NO: 1792)

RSSQSIVHAAGQTYLE (SEQ ID NO: 1793)

RSSQSIVHDSGQTYLE (SEQ ID NO: 1794)

RSSQSIVHDAGQTYLE (SEQ ID NO: 1795)

RSSQSIVHQQGSTYLE (SEQ ID NO: 1796)

RSSQSIVHSQGSTYLE (SEQ ID NO: 261)

RSSQSIVHAQGSTYLE (SEQ ID NO: 1797)

TABLE 10-continued

Amino Acid Sequences derived from Murine 124A Antibody.

RSSQSIVHDQGSTYLE (SEQ ID NO: 1798)

RSSQSIVHQSGSTYLE (SEQ ID NO: 1799)

RSSQSIVHQAGSTYLE (SEQ ID NO: 1800)

RSSQSIVHSSGSTYLE (SEQ ID NO: 265)

RSSQSIVHSAGSTYLE (SEQ ID NO: 269)

RSSQSIVHASGSTYLE (SEQ ID NO: 1801)

RSSQSIVHAAGSTYLE (SEQ ID NO: 1802)

RSSQSIVHDSGSTYLE (SEQ ID NO: 1803)

RSSQSIVHDAGSTYLE (SEQ ID NO: 1804)

RSSQSIVHQQGATYLE (SEQ ID NO: 1805)

RSSQSIVHSQGATYLE (SEQ ID NO: 262)

RSSQSIVHAQGATYLE (SEQ ID NO: 1806)

RSSQSIVHDQGATYLE (SEQ ID NO: 1807)

RSSQSIVHQSGATYLE (SEQ ID NO: 1808)

RSSQSIVHQAGATYLE (SEQ ID NO: 1809)

RSSQSIVHSSGATYLE (SEQ ID NO: 266)

RSSQSIVHSAGATYLE (SEQ ID NO: 270)

RSSQSIVHASGATYLE (SEQ ID NO: 1810)

RSSQSIVHAAGATYLE (SEQ ID NO: 1811)

RSSQSIVHDSGATYLE (SEQ ID NO: 1812)

RSSQSIVHDAGATYLE (SEQ ID NO: 1813)

RSSQSIVHQQGDTYLE (SEQ ID NO: 1814)

RSSQSIVHSQGDTYLE (SEQ ID NO: 263)

RSSQSIVHAQGDTYLE (SEQ ID NO: 1815)

RSSQSIVHDQGDTYLE (SEQ ID NO: 1816)

RSSQSIVHQSGDTYLE (SEQ ID NO: 1817)

RSSQSIVHQAGDTYLE (SEQ ID NO: 1818)

RSSQSIVHSSGDTYLE (SEQ ID NO: 267)

RSSQSIVHSAGDTYLE (SEQ ID NO: 271)

RSSQSIVHASGDTYLE (SEQ ID NO: 1819)

RSSQSIVHAAGDTYLE (SEQ ID NO: 1820)

RSSQSIVHDSGDTYLE (SEQ ID NO: 1821)

RSSQSIVHDAGDTYLE (SEQ ID NO: 1822)

h124A VL FR2

WFQQRPGQSPRRLIY (SEQ ID NO: 1823)

WYQQRPGQSPRRLIY (SEQ ID NO: 1824)

WFQQRPGQSPRLLIY (SEQ ID NO: 1825)

WYQQRPGQSPRLLIY (SEQ ID NO: 1826)

TABLE 10-continued

Amino Acid Sequences derived from Murine 124A Antibody.

h124A VL CDR2

KVSNRFS (SEQ ID NO: 40)

KVSQRFS (SEQ ID NO: 843)

KVSSRFS (SEQ ID NO: 844)

KVSARFS (SEQ ID NO: 846)

KVSDRFS (SEQ ID NO: 845)

h124A VL FR3

GVPDRFSGSGSGTDFTLKISRVEAEDVGVYYC (SEQ ID NO: 77)

GVPDRFSGSGSGTDFTLKISRVEAEDLGVYYC (SEQ ID NO: 276)

h124A VL CDR3

FQGSHVPYT (SEQ ID NO: 1511)

h124A VL FR4

FGQGTKLEIK (SEQ ID NO: 78)

TABLE 11

Amino Acid Sequences derived from Murine 259A Antibody.

259A HUMANIZED ANTIBODY SEQUENCE: HEAVY CHAIN h259AH1 Variable Region

QVQLVQSGAEVKKPGASVKVSCKASGYTFTSYFMHWVRQAPGQGLEWMG**YIYPYNDGT
KYAQKFQGRVTMTRDTSTSTVYMELSSLRSEDTAVYYCARFDYDTLRY**WGQGTLVTVS
S (SEQ ID NO: 1543)

h259A VH FR1

QVQLVQSGAEVKKPGASVKVSCKAS (SEQ ID NO: 51)

QVQLVQSGAEVVKPGASVKVSCKAS (SEQ ID NO: 1550)

QVQLVQSGAEVKKPGASVKMSCKAS (SEQ ID NO: 1827)

QVQLVQSGAEVVKPGASVKMSCKAS (SEQ ID NO: 1828)

h259A VH CDR1

GYTFTSYFMH (SEQ ID NO: 1306)

h259A VH FR2

WVRQAPGQGLEWMG (SEQ ID NO: 52)

WVRQAPGQGLEWIG (SEQ ID NO: 106)

h259A VH CDR2

YIYPYNDGTK (SEQ ID NO: 1372)

YIYPYQDGTK (SEQ ID NO: 1829)

YIYPYSDGTK (SEQ ID NO: 1830)

YIYPYADGTK (SEQ ID NO: 1831)

YIYPYDDGTK (SEQ ID NO: 1832)

YIYPYNEGTK (SEQ ID NO: 1833)

YIYPYNSGTK (SEQ ID NO: 1834)

TABLE 11-continued

Amino Acid Sequences derived from Murine 259A Antibody.

YIYPYNAGTK (SEQ ID NO: 1835)

YIYPYQEGTK (SEQ ID NO: 1836)

YIYPYQSGTK (SEQ ID NO: 1837)

YIYPYQAGTK (SEQ ID NO: 1838)

YIYPYSEGTK (SEQ ID NO: 1839)

YIYPYSSGTK (SEQ ID NO: 1840)

YIYPYSAGTK (SEQ ID NO: 1841)

YIYPYAEGTK (SEQ ID NO: 1842)

YIYPYASGTK (SEQ ID NO: 1843)

YIYPYAAGTK (SEQ ID NO: 1844)

YIYPYDEGTK (SEQ ID NO: 1845)

YIYPYDSGTK (SEQ ID NO: 1846)

YIYPYDAGTK (SEQ ID NO: 1847)

h259A VH FR3

YAQKFQGRVTMTRDTSTSTVYMELSSLRSEDTAVYYCAR (SEQ ID NO: 1560)

YNQKFQGRVTMTRDTSTSTVYMELSSLRSEDTAVYYCAR (SEQ ID NO: 1561)

YAQKFQGRATMTRDTSTSTVYMELSSLRSEDTAVYYCAR (SEQ ID NO: 1562)

YAQKFQGRVTLTRDTSTSTVYMELSSLRSEDTAVYYCAR (SEQ ID NO: 1563)

YAQKFQGRVTMTFDTSTSTVYMELSSLRSEDTAVYYCAR (SEQ ID NO: 1848)

YAQKFQGRVTMTRDKSTSTVYMELSSLRSEDTAVYYCAR (SEQ ID NO: 1565)

YAQKFQGRVTMTRDTSTSTAYMELSSLRSEDTAVYYCAR (SEQ ID NO: 1566)

YNQKFQGRATMTRDTSTSTVYMELSSLRSEDTAVYYCAR (SEQ ID NO: 1567)

YNQKFQGRVTLTRDTSTSTVYMELSSLRSEDTAVYYCAR (SEQ ID NO: 1568)

YNQKFQGRVTMTFDTSTSTVYMELSSLRSEDTAVYYCAR (SEQ ID NO: 1849)

YNQKFQGRVTMTRDKSTSTVYMELSSLRSEDTAVYYCAR (SEQ ID NO: 1570)

YNQKFQGRVTMTRDTSTSTAYMELSSLRSEDTAVYYCAR (SEQ ID NO: 1571)

YAQKFQGRATLTRDTSTSTVYMELSSLRSEDTAVYYCAR (SEQ ID NO: 1572)

YAQKFQGRATMTFDTSTSTVYMELSSLRSEDTAVYYCAR (SEQ ID NO: 1850)

YAQKFQGRATMTRDKSTSTVYMELSSLRSEDTAVYYCAR (SEQ ID NO: 1574)

YAQKFQGRATMTRDTSTSTAYMELSSLRSEDTAVYYCAR (SEQ ID NO: 1575)

YAQKFQGRVTLTFDTSTSTVYMELSSLRSEDTAVYYCAR (SEQ ID NO: 1851)

YAQKFQGRVTLTRDKSTSTVYMELSSLRSEDTAVYYCAR (SEQ ID NO: 1577)

YAQKFQGRVTLTRDTSTSTAYMELSSLRSEDTAVYYCAR (SEQ ID NO: 1578)

YAQKFQGRVTMTFDKSTSTVYMELSSLRSEDTAVYYCAR (SEQ ID NO: 1852)

YAQKFQGRVTMTFDTSTSTAYMELSSLRSEDTAVYYCAR (SEQ ID NO: 1853)

YAQKFQGRVTMTRDKSTSTAYMELSSLRSEDTAVYYCAR (SEQ ID NO: 1581)

YNQKFQGRATLTRDTSTSTVYMELSSLRSEDTAVYYCAR (SEQ ID NO: 1582)

YNQKFQGRATMTFDTSTSTVYMELSSLRSEDTAVYYCAR (SEQ ID NO: 1854)

YNQKFQGRATMTRDKSTSTVYMELSSLRSEDTAVYYCAR (SEQ ID NO: 1584)

TABLE 11-continued

Amino Acid Sequences derived from Murine 259A Antibody.

YNQKFQGRATMTRDTSTSTAYMELSSLRSEDTAVYYCAR (SEQ ID NO: 1585)

YNQKFQGRVTLTFDTSTSTVYMELSSLRSEDTAVYYCAR (SEQ ID NO: 1855)

YNQKFQGRVTLTRDKSTSTVYMELSSLRSEDTAVYYCAR (SEQ ID NO: 1587)

YNQKFQGRVTLTRDTSTSTAYMELSSLRSEDTAVYYCAR (SEQ ID NO: 1588)

YNQKFQGRVTMTFDKSTSTVYMELSSLRSEDTAVYYCAR (SEQ ID NO: 1856)

YNQKFQGRVTMTFDTSTSTAYMELSSLRSEDTAVYYCAR (SEQ ID NO: 1857)

YNQKFQGRVTMTRDKSTSTAYMELSSLRSEDTAVYYCAR (SEQ ID NO: 1591)

YAQKFQGRATLTFDTSTSTVYMELSSLRSEDTAVYYCAR (SEQ ID NO: 1858)

YAQKFQGRATLTRDKSTSTVYMELSSLRSEDTAVYYCAR (SEQ ID NO: 1593)

YAQKFQGRATLTRDTSTSTAYMELSSLRSEDTAVYYCAR (SEQ ID NO: 1594)

YAQKFQGRATMTFDKSTSTVYMELSSLRSEDTAVYYCAR (SEQ ID NO: 1859)

YAQKFQGRATMTFDTSTSTAYMELSSLRSEDTAVYYCAR (SEQ ID NO: 1860)

YAQKFQGRATMTRDKSTSTAYMELSSLRSEDTAVYYCAR (SEQ ID NO: 1597)

YAQKFQGRVTLTFDKSTSTVYMELSSLRSEDTAVYYCAR (SEQ ID NO: 1861)

YAQKFQGRVTLTFDTSTSTAYMELSSLRSEDTAVYYCAR (SEQ ID NO: 1862)

YAQKFQGRVTMTFDKSTSTAYMELSSLRSEDTAVYYCAR (SEQ ID NO: 1863)

YNQKFQGRATLTFDTSTSTVYMELSSLRSEDTAVYYCAR (SEQ ID NO: 1864)

YNQKFQGRATLTRDKSTSTVYMELSSLRSEDTAVYYCAR (SEQ ID NO: 1602)

YNQKFQGRATLTRDTSTSTAYMELSSLRSEDTAVYYCAR (SEQ ID NO: 1603)

YNQKFQGRVTLTFDKSTSTVYMELSSLRSEDTAVYYCAR (SEQ ID NO: 1865)

YNQKFQGRVTLTFDTSTSTAYMELSSLRSEDTAVYYCAR (SEQ ID NO: 1866)

YNQKFQGRVTMTFDKSTSTAYMELSSLRSEDTAVYYCAR (SEQ ID NO: 1867)

YAQKFQGRATLTFDKSTSTVYMELSSLRSEDTAVYYCAR (SEQ ID NO: 1868)

YAQKFQGRATLTFDTSTSTAYMELSSLRSEDTAVYYCAR (SEQ ID NO: 1869)

YAQKFQGRATMTFDKSTSTAYMELSSLRSEDTAVYYCAR (SEQ ID NO: 1870)

YAQKFQGRVTLTFDKSTSTAYMELSSLRSEDTAVYYCAR (SEQ ID NO: 1871)

YNQKFQGRATLTFDKSTSTVYMELSSLRSEDTAVYYCAR (SEQ ID NO: 1872)

YNQKFQGRATLTFDTSTSTAYMELSSLRSEDTAVYYCAR (SEQ ID NO: 1873)

YAQKFQGRATLTFDKSTSTAYMELSSLRSEDTAVYYCAR (SEQ ID NO: 1874)

YNQKFQGRATLTFDKSTSTAYMELSSLRSEDTAVYYCAR (SEQ ID NO: 1875)

h259A VH CDR3

FDYDTLRY (SEQ ID NO: 1405)

h259A VH FR4

WGQGTLVTVSS (SEQ ID NO: 54)

WGQGTLLTVSS (SEQ ID NO: 320)

259A HUMANIZED ANTIBODY SEQUENCE: LIGHT CHAIN h259AL1 Variable Region

DIVMTQSPLSLPVTPGEPASISCKSTKSLLNSDGFTYLDWYLQKPGQSPQLLIY**LISN
RFSGVPDRFSGSGSGTDFTLKISRVEAEDVGVYYCFQSNYFPWT**FGQGTKLEIK
(SEQ ID NO: 1548)

TABLE 11-continued

Amino Acid Sequences derived from Murine 259A Antibody.

h259A VL FR1

DIVMTQSPLSLPVTPGEPASISC (SEQ ID NO: 75)

DVVMTQSPLSLPVTPGEPASISC (SEQ ID NO: 252)

DIVLTQSPLSLPVTPGEPASISC (SEQ ID NO: 1876)

DVVLTQSPLSLPVTPGEPASISC (SEQ ID NO: 1877)

h259A VL CDR1

KSTKSLLNSDGFTYLD (SEQ ID NO: 1458)

KSTKSLLQSDGFTYLD (SEQ ID NO: 1878)

KSTKSLLSSDGFTYLD (SEQ ID NO: 1879)

KSTKSLLASDGFTYLD (SEQ ID NO: 1880)

KSTKSLLDSDGFTYLD (SEQ ID NO: 1881)

KSTKSLLNSEGFTYLD (SEQ ID NO: 1882)

KSTKSLLNSSGFTYLD (SEQ ID NO: 1883)

KSTKSLLNSAGFTYLD (SEQ ID NO: 1884)

KSTKSLLQSEGFTYLD (SEQ ID NO: 1885)

KSTKSLLQSSGFTYLD (SEQ ID NO: 1886)

KSTKSLLQSAGFTYLD (SEQ ID NO: 1887)

KSTKSLLSSEGFTYLD (SEQ ID NO: 1888)

KSTKSLLSSSGFTYLD (SEQ ID NO: 1889)

KSTKSLLSSAGFTYLD (SEQ ID NO: 1890)

KSTKSLLASEGFTYLD (SEQ ID NO: 1891)

KSTKSLLASSGFTYLD (SEQ ID NO: 1892)

KSTKSLLASAGFTYLD (SEQ ID NO: 1893)

KSTKSLLDSEGFTYLD (SEQ ID NO: 1894)

KSTKSLLDSSGFTYLD (SEQ ID NO: 1895)

KSTKSLLDSAGFTYLD (SEQ ID NO: 1896)

h259A VL FR2

WYLQKPGQSPQLLIY (SEQ ID NO: 76)

h259A VL CDR2

LISNRFS (SEQ ID NO: 1485)

LISQRFS (SEQ ID NO: 1897)

LISSRFS (SEQ ID NO: 1898)

LISARFS (SEQ ID NO: 1899)

LISDRFS (SEQ ID NO: 1900)

h259A VL FR3

GVPDRFSGSGSGTDFTLKISRVEAEDVGVYYC (SEQ ID NO: 77)

GVPDRFSGSGSGTDFTLKISRVEAEDVGLYYC (SEQ ID NO: 1901)

TABLE 11-continued

Amino Acid Sequences derived from Murine 259A Antibody.

h259A VL CDR3

FQSNYFPWT (SEQ ID NO: 1508)

h259A VL FR4

FGQGTKLEIK (SEQ ID NO: 78)

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:36; (2) a VH CDR2 having an amino acid sequence of SEQ ID NO:37; and (3) a VH CDR3 having an amino acid sequence of SEQ ID NO:38. In certain embodiments, the antibody further comprises a VL region comprising: (1) a VL CDR1 having an amino acid sequence of SEQ ID NO:45; (2) a VL CDR2 having an amino acid sequence of SEQ ID NO:46; and (3) a VL CDR3 having an amino acid sequence of SEQ ID NO:47. In other embodiments, the antibody further comprises a VL region having the amino acid sequence of SEQ ID NO:6. In another embodiment, the antibody further comprises a VL region having the amino acid sequence of SEQ ID NO:28. In yet other embodiments, the antibody further comprises a VL region having the amino acid sequence of SEQ ID NO:29. In some embodiments, the antibody comprises (a) a VH region comprising: (1) a VH CDR1 having an amino acid sequence of SEQ ID NO:36; (2) a VH CDR2 having an amino acid sequence of SEQ ID NO:37; and (3) a VH CDR3 having an amino acid sequence of SEQ ID NO:38; and (b) a VL region comprising: (1) a VL CDR1 having an amino acid sequence of SEQ ID NO:45; (2) a VL CDR2 having an amino acid sequence of SEQ ID NO:46; and (3) a VL CDR3 having an amino acid sequence of SEQ ID NO:47. To the extent an antibody provided herein is the to "bind to a C10orf54 epitope", it is envisioned those antibodies also bind to a C10orf54 polypeptide, polypeptide fragment, or antigen thereof.

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:36; (2) a VH CDR2 having an amino acid sequence of SEQ ID NO:50; and (3) a VH CDR3 having an amino acid sequence of SEQ ID NO:38. In certain embodiments, the antibody further comprises a VL region comprising: (1) a VL CDR1 having an amino acid sequence of SEQ ID NO:45; (2) a VL CDR2 having an amino acid sequence of SEQ ID NO:46; and (3) a VL CDR3 having an amino acid sequence of SEQ ID NO:47. In other embodiments, the antibody further comprises a VL region having the amino acid sequence of SEQ ID NO:6. In another embodiment, the antibody further comprises a VL region having the amino acid sequence of SEQ ID NO:28. In yet other embodiments, the antibody further comprises a VL region having the amino acid sequence of SEQ ID NO:29. In some embodiments, the antibody comprises: (a) a VH region comprising: (1) a VH CDR1 having an amino acid sequence of SEQ ID NO:36; (2) a VH CDR2 having an amino acid sequence of SEQ ID NO:50; and (3) a VH CDR3 having an amino acid sequence of SEQ ID NO:38; and (b) a VL region comprising: (1) a VL CDR1 having an amino acid sequence of SEQ ID NO:45; (2) a VL CDR2 having an amino acid sequence of SEQ ID NO:46; and (3) a VL CDR3 having an amino acid sequence of SEQ ID NO:47.

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:36; (2) a VH CDR2 having an amino acid sequence of SEQ ID NO:99; and (3) a VH CDR3 having an amino acid sequence of SEQ ID NO:38. In certain embodiments, the antibody further comprises a VL region comprising: (1) a VL CDR1 having an amino acid sequence of SEQ ID NO:45; (2) a VL CDR2 having an amino acid sequence of SEQ ID NO:46; and (3) a VL CDR3 having an amino acid sequence of SEQ ID NO:47. In other embodiments, the antibody further comprises a VL region having the amino acid sequence of SEQ ID NO:6. In another embodiment, the antibody further comprises a VL region having the amino acid sequence of SEQ ID NO:28. In yet other embodiments, the antibody further comprises a VL region having the amino acid sequence of SEQ ID NO:29. In some embodiments, the antibody comprises: (a) a VH region comprising: (1) a VH CDR1 having an amino acid sequence of SEQ ID NO:36; (2) a VH CDR2 having an amino acid sequence of SEQ ID NO:99; and (3) a VH CDR3 having an amino acid sequence of SEQ ID NO:38; and (b) a VL region comprising: (1) a VL CDR1 having an amino acid sequence of SEQ ID NO:45; (2) a VL CDR2 having an amino acid sequence of SEQ ID NO:46; and (3) a VL CDR3 having an amino acid sequence of SEQ ID NO:47.

In another embodiment, an antibody that binds to C10orf54 (e.g., C10orf54 polypeptide, C10orf54 polypeptide fragment, C10orf54 epitope) comprises: a VL region comprising: (1) a VL CDR1 having an amino acid sequence of SEQ ID NO:45; (2) a VL CDR2 having an amino acid sequence of SEQ ID NO:46; and (3) a VL CDR3 having an amino acid sequence of SEQ ID NO:47. In some embodiments, the antibody further comprises a VH region having the amino acid sequence of SEQ ID NO:20. In another embodiment, the antibody further comprises a VH region having the amino acid sequence of SEQ ID NO:21. In other embodiments, the antibody further comprises a VH region having the amino acid sequence of SEQ ID NO:22. In other embodiments, the antibody further comprises a VH region having the amino acid sequence of SEQ ID NO:23.

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:30; (2) a VH CDR2 having an amino acid sequence of SEQ ID NO:31; and (3) a VH CDR3 having an amino acid sequence of SEQ ID NO:32. In some embodiments, the antibody further comprises a VL region comprising: (1) a VL CDR1 having an amino acid sequence of SEQ ID NO:45; (2) a VL CDR2 having an amino acid sequence of SEQ ID NO:40; and (3) a VL CDR3 having an amino acid sequence of SEQ ID NO:41. In other embodiments, the antibody further comprises a VL region having the amino acid sequence of SEQ ID NO:24. In another embodiment, the antibody further comprises a VL region having the amino acid sequence of SEQ ID NO:25. In one embodiment, the antibody comprises: (a) a VH region comprising: (1) a VH CDR1 having an amino acid sequence of SEQ ID NO:30; (2) a VH CDR2 having an amino acid sequence of SEQ ID NO:31; and (3) a VH CDR3 having an amino acid sequence of SEQ ID NO:32; and (b) a VL region comprising: (1) a VL CDR1 having an amino acid sequence of SEQ ID NO:45; (2) a VL CDR2 having an amino acid sequence of SEQ ID NO:40; and (3) a VL CDR3 having an amino acid sequence of SEQ ID NO:41.

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:30; (2) a VH CDR2 having an amino acid sequence of SEQ ID NO:321; and (3) a VH CDR3 having an amino acid sequence of SEQ ID NO:32. In some embodiments, the antibody further comprises a VL region comprising: (1) a VL CDR1 having an amino acid sequence of SEQ ID NO:45; (2) a VL CDR2 having an amino acid sequence of SEQ ID NO:40; and (3) a VL CDR3 having an amino acid sequence of SEQ ID NO:41. In other embodiments, the antibody further comprises a VL region having the amino acid sequence of SEQ ID NO:24. In another embodiment, the antibody further comprises a VL region having the amino acid sequence of SEQ ID NO:25. In one embodiment, the antibody comprises: (a) a VH region comprising: (1) a VH CDR1 having an amino acid sequence of SEQ ID NO:30; (2) a VH CDR2 having an amino acid sequence of SEQ ID NO:321; and (3) a VH CDR3 having an amino acid sequence of SEQ ID NO:32; and (b) a VL region comprising: (1) a VL CDR1 having an amino acid sequence of SEQ ID NO:45; (2) a VL CDR2 having an amino acid sequence of SEQ ID NO:40; and (3) a VL CDR3 having an amino acid sequence of SEQ ID NO:41.

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:30; (2) a VH CDR2 having an amino acid sequence of SEQ ID NO:835; and (3) a VH CDR3 having an amino acid sequence of SEQ ID NO:32. In some embodiments, the antibody further comprises a VL region comprising: (1) a VL CDR1 having an amino acid sequence of SEQ ID NO:45; (2) a VL CDR2 having an amino acid sequence of SEQ ID NO:40; and (3) a VL CDR3 having an amino acid sequence of SEQ ID NO:41. In other embodiments, the antibody further comprises a VL region having the amino acid sequence of SEQ ID NO:24. In another embodiment, the antibody further comprises a VL region having the amino acid sequence of SEQ ID NO:25. In one embodiment, the antibody comprises: (a) a VH region comprising: (1) a VH CDR1 having an amino acid sequence of SEQ ID NO:30; (2) a VH CDR2 having an amino acid sequence of SEQ ID NO:835; and (3) a VH CDR3 having an amino acid sequence of SEQ ID NO:32; and (b) a VL region comprising: (1) a VL CDR1 having an amino acid sequence of SEQ ID NO:45; (2) a VL CDR2 having an amino acid sequence of SEQ ID NO:40; and (3) a VL CDR3 having an amino acid sequence of SEQ ID NO:41.

In some embodiments, an antibody that binds to C10orf54 (e.g., C10orf54 polypeptide, C10orf54 polypeptide fragment, C10orf54 epitope) comprises: a VL region comprising: (1) a VL CDR1 having an amino acid sequence of SEQ ID NO:45; (2) a VL CDR2 having an amino acid sequence of SEQ ID NO:40; and (3) a VL CDR3 having an amino acid sequence of SEQ ID NO:41. In some embodiments, the antibody further comprises a VH region having the amino acid sequence of SEQ ID NO:12. In another embodiment, the antibody further comprises a VH region having the amino acid sequence of SEQ ID NO:13. In other embodiments, the antibody further comprises a VH region having the amino acid sequence of SEQ ID NO:14. In other embodiments, the antibody further comprises a VH region having the amino acid sequence of SEQ ID NO:15.

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:33; (2) a VH CDR2 having an amino acid sequence of SEQ ID NO:34; and (3) a VH CDR3 having an amino acid sequence of SEQ ID NO:35. In some embodiments, the antibody further comprises a VL region comprising: (1) a VL CDR1 having an amino acid sequence of SEQ ID NO:42; (2) a VL CDR2 having an amino acid sequence of SEQ ID NO:43; and (3) a VL CDR3 having an amino acid sequence of SEQ ID NO:44. In other embodiments, the antibody further comprises a VL region having the amino acid sequence of SEQ ID NO:26. In another embodiment, the antibody further comprises a VL region having the amino acid sequence of SEQ ID NO:27. In one embodiment, the antibody comprises: (a) a VH region comprising: (1) a VH CDR1 having an amino acid sequence of SEQ ID NO:33; (2) a VH CDR2 having an amino acid sequence of SEQ ID NO:34; and (3) a VH CDR3 having an amino acid sequence of SEQ ID NO:35; and (b) a VL region comprising: (1) a VL CDR1 having an amino acid sequence of SEQ ID NO:42; (2) a VL CDR2 having an amino acid sequence of SEQ ID NO:43; and (3) a VL CDR3 having an amino acid sequence of SEQ ID NO:44.

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:33; (2) a VH CDR2 having an amino acid sequence of SEQ ID NO:49; and (3) a VH CDR3 having an amino acid sequence of SEQ ID NO:35. In some embodiments, the antibody further comprises a VL region comprising: (1) a VL CDR1 having an amino acid sequence of SEQ ID NO:42; (2) a VL CDR2 having an amino acid sequence of SEQ ID NO:43; and (3) a VL CDR3 having an amino acid sequence of SEQ ID NO:44. In other embodiments, the antibody further comprises a VL region having the amino acid sequence of SEQ ID NO:26. In another embodiment, the antibody further comprises a VL region having the amino acid sequence of SEQ ID NO:27. In one embodiment, the antibody comprises: (a) a VH region comprising: (1) a VH CDR1 having an amino acid sequence of SEQ ID NO:33; (2) a VH CDR2 having an amino acid sequence of SEQ ID NO:49; and (3) a VH CDR3 having an amino acid sequence of SEQ ID NO:35; and (b) a VL region comprising: (1) a VL CDR1 having an amino acid sequence of SEQ ID NO:42; (2) a VL CDR2 having an amino acid sequence of SEQ ID NO:43; and (3) a VL CDR3 having an amino acid sequence of SEQ ID NO:44.

In one embodiment, an antibody that binds to C10orf54 (e.g., C10orf54 polypeptide, C10orf54 polypeptide fragment, C10orf54 epitope) comprises: (a) a VH region comprising: (1) a VH CDR1 having an amino acid sequence of SEQ ID NO:33; (2) a VH CDR2 having an amino acid sequence of SEQ ID NO:1070; and (3) a VH CDR3 having an amino acid sequence of SEQ ID NO:35. In some embodiments, the antibody further comprises a VL region comprising: (1) a VL CDR1 having an amino acid sequence of SEQ ID NO:42; (2) a VL CDR2 having an amino acid sequence of SEQ ID NO:43; and (3) a VL CDR3 having an amino acid sequence of SEQ ID NO:44. In other embodiments, the antibody further comprises a VL region having the amino acid sequence of SEQ ID NO:26. In another embodiment, the antibody further comprises a VL region having the amino acid sequence of SEQ ID NO:27. In one embodiment, the antibody comprises: (a) a VH region comprising: (1) a VH CDR1 having an amino acid sequence of SEQ ID NO:33; (2) a VH CDR2 having an amino acid sequence of SEQ ID NO:1070; and (3) a VH CDR3 having an amino acid sequence of SEQ ID NO:35; and (b) a VL region comprising: (1) a VL CDR1 having an amino acid sequence of SEQ ID NO:42; (2) a VL CDR2 having an amino acid sequence of SEQ ID NO:43; and (3) a VL CDR3 having an amino acid sequence of SEQ ID NO:44.

As will be understood by a person skilled in the art, the boundaries between the CDRs and framework sequences for any of the VH regions and VL regions described herein can be determined using any one of the well-known methods in the art, including IMGT, Kabat, Chothia, Contact, AbM or Kabat plus Chothia (e.g., "Exemplary" as described herein). Accordingly, any anti-C10orf54 antibody having one or more CDR or framework sequence as described herein includes a CDR or framework amino acid sequence as determined using IMGT, Kabat, Chothia, Contact, AbM or Kabat plus Chothis. For instance, exemplary CDR sequences for both VH and VL regions that can be included in an anti-C10orf54 antibody of the disclosure are depicted in Tables 12-33 (see also, e.g., Tables 5-11).

TABLE 12

Antibody 5B-CDR Sequences

| | | Exemplary* | IMGT | Kabat | Chothia | Contact | AbM |
|---|---|---|---|---|---|---|---|
| VH CDR Seq. | VH CDR1 | GYTFTDYGMH (SEQ ID NO: 1291) | GYTFTDYG (SEQ ID NO: 1292) | DYGMH (SEQ ID NO: 1293) | GYTFTDY (SEQ ID NO: 1294) | TDYGMH (SEQ ID NO: 1295) | GYTFTDYGMH (SEQ ID NO: 1291) |
| | VH CDR2 | IIDTYYGDATY NQKFKG (SEQ ID NO: 1336) | IDTYYGDA (SEQ ID NO: 1337) | IIDTYYGDATY NQKFKG (SEQ ID NO: 1336) | TYYG (SEQ ID NO: 1338) | WIGIIDTYYGD AT (SEQ ID NO: 1339) | IIDTYYGDAT (SEQ ID NO: 1340) |
| | VH CDR3 | RAGNAMDY (SEQ ID NO: 1385) | ARRAGNAMDY (SEQ ID NO: 1386) | RAGNAMDY (SEQ ID NO: 1385) | AGNAMD (SEQ ID NO: 1387) | ARRAGNAMD (SEQ ID NO: 1388) | RAGNAMDY (SEQ ID NO: 1385) |
| VL CDR Seq. | VL CDR1 | KASQSVSNDVA (SEQ ID NO: 1425) | QSVSND (SEQ ID NO: 1426) | KASQSVSNDVA (SEQ ID NO: 1425) | SQSVSND (SEQ ID NO: 1427) | SNDVAWY (SEQ ID NO: 1428) | KASQSVSNDVA (SEQ ID NO: 1425) |
| | VL CDR2 | YASNRYT (SEQ ID NO: 1473) | YAS (SEQ ID NO: 1474) | YASNRYT (SEQ ID NO: 1473) | YAS (SEQ ID NO: 1474) | LLIYYASNRY (SEQ ID NO: 1475) | YASNRYT (SEQ ID NO: 1473) |
| | VL CDR3 | QQDYSSPRT (SEQ ID NO: 1493) | QQDYSSPRT (SEQ ID NO: 1493) | QQDYSSPRT (SEQ ID NO: 1493) | DYSSPR (SEQ ID NO: 1494) | QQDYSSPR (SEQ ID NO: 1495) | QQDYSSPRT (SEQ ID NO: 1493) |

VH Sequence:
QVQLQQSGAELVRPGVSVKISCKGSGYTFTDYGMHWVKQSHAKSLEWIGIIDTYYGDATYNQKFKGKATMTVDKSSSTA
YMELARLTSEDSAIYYCARRAGNAMDYWGQGTSVTVSS (SEQ ID NO: 1252)

VL Sequence:
NIVMTQTPKFLLVSAGDRVTITCKASQSVSNDVAWYQQKPGQSPKLLIYYASNRYTGVPDRFTGSGYGTDFTFTISTVQ
AEDLAVYFCQQDYSSPRTFGGGTKLEIK (SEQ ID NO: 1253)

*Exemplary CDR sequences encompass amino acids as determined by Kabat plus Chothia.

TABLE 13

Antibody 46A CDR Sequences

| | | Exemplary* | IMGT | Kabat | Chothia | Contact | AbM |
|---|---|---|---|---|---|---|---|
| VH CDR Seq. | VH CDR1 | GYTFTDYGMH (SEQ ID NO: 1291) | GYTFTDYG (SEQ ID NO: 1292) | DYGMH (SEQ ID NO: 1293) | GYTFTDY (SEQ ID NO: 1294) | TDYGMH (SEQ ID NO: 1295) | GYTFTDYGMH (SEQ ID NO: 1291) |
| | VH CDR2 | IINTYYGDATY NQKFKG (SEQ ID NO: 1341) | INTYYGDA (SEQ ID NO: 1342) | IINTYYGDATY NQKFKG (SEQ ID NO: 1341) | TYYG (SEQ ID NO: 1338) | WIGIINTYYGD AT (SEQ ID NO: 1343) | IINTYYGDAT (SEQ ID NO: 1344) |

TABLE 13-continued

Antibody 46A CDR Sequences

| | | Exemplary* | IMGT | Kabat | Chothia | Contact | AbM |
|---|---|---|---|---|---|---|---|
| | VH CDR3 | RAGTAMDY (SEQ ID NO: 1389) | ARRAGTAMDY (SEQ ID NO: 1390) | RAGTAMDY (SEQ ID NO: 1389) | AGTAMD (SEQ ID NO: 1391) | ARRAGTAMD (SEQ ID NO: 1392) | RAGTAMDY (SEQ ID NO: 1389) |
| VL CDR Seq. | VL CDR1 | KASQSVSNDVA (SEQ ID NO: 1425) | QSVSND (SEQ ID NO: 1426) | KASQSVSNDVA (SEQ ID NO: 1425) | SQSVSND (SEQ ID NO: 1427) | SNDVAWY (SEQ ID NO: 1428) | KASQSVSNDVA (SEQ ID NO: 1425) |
| | VL CDR2 | YASNRYT (SEQ ID NO: 1473) | YAS (SEQ ID NO: 1474) | YASNRYT (SEQ ID NO: 1473) | YAS (SEQ ID NO: 1474) | LLIYYASNRY (SEQ ID NO: 1475) | YASNRYT (SEQ ID NO: 1473) |
| | VL CDR3 | QQDYGSPRT (SEQ ID NO: 1496) | QQDYGSPRT (SEQ ID NO: 1496) | QQDYGSPRT (SEQ ID NO: 1496) | DYGSPR (SEQ ID NO: 1497) | QQDYGSPR (SEQ ID NO: 1498) | QQDYGSPRT (SEQ ID NO: 1496) |

VH Sequence:
QVQLQQAGGELVRPGVSVKISCKGSGYTFTDYGMHWVKQSHAKSLEWIGIINTYYGDATYNQFKGKATMTVDKSSSTA
YMELARLTSEDSAIYYCARRAGTAMDYWGQGTSVTVSS (SEQ ID NO: 1254)

VL Sequence:
SIVMTQTPKFLLVSAGDRVTITCKASQSVSNDVAWYQQKPGQSPKLLIYYASNRYTGVPDRFTGSGYGTDFTFTISTVQ
AEDLAVYFCQQDYGSPRTFGGGTKLEIK (SEQ ID NO: 1255)

*Exemplary CDR sequences encompass amino acids as determined by Kabat plus Chothia.

TABLE 14

Antibody 97A CDR Sequences

| | | Exemplary* | IMGT | Kabat | Chothia | Contact | AbM |
|---|---|---|---|---|---|---|---|
| VH CDR Seq. | VH CDR1 | GYTFTDYGMH (SEQ ID NO: 1291) | GYTFTDYG (SEQ ID NO: 1292) | DYGMH (SEQ ID NO: 1293) | GYTFTDY (SEQ ID NO: 1294) | TDYGMH (SEQ ID NO: 1295) | GYTFTDYGMH (SEQ ID NO: 1291) |
| | VH CDR2 | VIDTYYGDASNNQKFKG (SEQ ID NO: 1345) | IDTYYGDA (SEQ ID NO: 1337) | VIDTYYGDASNNQKFKG (SEQ ID NO: 1345) | TYYG (SEQ ID NO: 1338) | WIGVIDTYYGDAS (SEQ ID NO: 1346) | VIDTYYGDAS (SEQ ID NO: 1347) |
| | VH CDR3 | RAGNAMDY (SEQ ID NO: 1385) | ARRAGNAMDY (SEQ ID NO: 1386) | RAGNAMDY (SEQ ID NO: 1385) | AGNAMD (SEQ ID NO: 1387) | ARRAGNAMD (SEQ ID NO: 1388) | RAGNAMDY (SEQ ID NO: 1385) |
| VL CDR Seq. | VL CDR1 | KASQSVSNDVA (SEQ ID NO: 1425) | QSVSND (SEQ ID NO: 1426) | KASQSVSNDVA (SEQ ID NO: 1425) | SQSVSND (SEQ ID NO: 1427) | SNDVAWY (SEQ ID NO: 1428) | KASQSVSNDVA (SEQ ID NO: 1425) |
| | VL CDR2 | YASNRYT (SEQ ID NO: 1473) | YAS (SEQ ID NO: 1474) | YASNRYT (SEQ ID NO: 1473) | YAS (SEQ ID NO: 1474) | LLIYYASNRY (SEQ ID NO: 1475) | YASNRYT (SEQ ID NO: 1473) |
| | VL CDR3 | QQDYGSPRT (SEQ ID NO: 1496) | QQDYGSPRT (SEQ ID NO: 1496) | QQDYGSPRT (SEQ ID NO: 1496) | DYGSPR (SEQ ID NO: 1497) | QQDYGSPR (SEQ ID NO: 1498) | QQDYGSPRT (SEQ ID NO: 1496) |

VH Sequence:
QVQLQQSGAELVRPGVSVKISCKGSGYTFTDYGMHWVKQSHAKSLEWIGVIDTYYGDASNNQKFKGKATMTVDKSSSTA
YMELARLTSEDSAIYYCARRAGNAMDYWGQGTSVTVSS (SEQ ID NO: 1256)

VL Sequence:
SIVMTQTPKFLLVSAGDRVAITCKASQSVSNDVAWYQQKPGQSPKLLIYYASNRYTGVPDRFTGSGYGTDFTFTISTVQ
AEDLAVYFCQQDYGSPRTFGGGTKLEIK (SEQ ID NO: 1257)

*Exemplary CDR sequences encompass amino acids as determined by Kabat plus Chothia.

TABLE 15

Antibody 128A-CDR Sequences

|   |   | Exemplary* | IMGT | Kabat | Chothia | Contact | AbM |
|---|---|---|---|---|---|---|---|
| VH CDR Seq. | VH CDR1 | GYTFTDYGMH (SEQ ID NO: 1291) | GYTFTDYG (SEQ ID NO: 1292) | DYGMH (SEQ ID NO: 1293) | GYTFTDY (SEQ ID NO: 1294) | TDYGMH (SEQ ID NO: 1295) | GYTFTDYGMH (SEQ ID NO: 1291) |
|   | VH CDR2 | LIDTYYGDATY NHKFKG (SEQ ID NO: 1348) | IDTYYGDA (SEQ ID NO: 1337) | LIDTYYGDATY NHKFKG (SEQ ID NO: 1348) | TYYG (SEQ ID NO: 1338) | WIGLIDTYYGD AT (SEQ ID NO: 1349) | LIDTYYGDAT (SEQ ID NO: 1350) |
|   | VH CDR3 | RAGNAMDY (SEQ ID NO: 1385) | ARRAGNAMDY (SEQ ID NO: 1386) | RAGNAMDY (SEQ ID NO: 1385) | AGNAMD (SEQ ID NO: 1387) | ARRAGNAMD (SEQ ID NO: 1388) | RAGNAMDY (SEQ ID NO: 1385) |
| VL CDR Seq. | VL CDR1 | KASQSVSNDIA (SEQ ID NO: 1429) | QSVSND (SEQ ID NO: 1426) | KASQSVSNDIA (SEQ ID NO: 1429) | SQSVSND (SEQ ID NO: 1427) | SNDIAWY (SEQ ID NO: 1430) | KASQSVSNDIA (SEQ ID NO: 1429) |
|   | VL CDR2 | YASNRYT (SEQ ID NO: 1473) | YAS (SEQ ID NO: 1474) | YASNRYT (SEQ ID NO: 1473) | YAS (SEQ ID NO: 1474) | LLIYYASNRY (SEQ ID NO: 1475) | YASNRYT (SEQ ID NO: 1473) |
|   | VL CDR3 | QQDYSSPRT (SEQ ID NO: 1493) | QQDYSSPRT (SEQ ID NO: 1493) | QQDYSSPRT (SEQ ID NO: 1493) | DYSSPR (SEQ ID NO: 1494) | QQDYSSPR (SEQ ID NO: 1495) | QQDYSSPRT (SEQ ID NO: 1493) |

VH Sequence:
QVQLQQSGAELVRPGVSVKISCKGSGYTFTDYGMHWVKQSHAKSLEWIGLIDTYYGDATYNHKFKGKATMTVDKSSRTA
YMELARLTSEDSAIYYCARRAGNAMDYWGQGTSVTASS (SEQ ID NO: 1258)

VL Sequence:
NIAMTQTPKFLLVSAGDRVTITCKASQSVSNDIAWYQQKPGQSPRLLIYYASNRYTGVPDRFTGSGYGTDFTFTISTVQ
AEDLAVYFCQQDYSSPRTFGGGTKLEIK (SEQ ID NO: 1259)

*Exemplary CDR sequences encompass amino acids as determined by Kabat plus Chothia.

TABLE 16

Antibody 146C-CDR Sequences

|   |   | Exemplary* | IMGT | Kabat | Chothia | Contact | AbM |
|---|---|---|---|---|---|---|---|
| VH CDR Seq. | VH CDR1 | GYTFTDYGMH (SEQ ID NO: 1291) | GYTFTDYG (SEQ ID NO: 1292) | DYGMH (SEQ ID NO: 1293) | GYTFTDY (SEQ ID NO: 1294) | TDYGMH (SEQ ID NO: 1295) | GYTFTDYGMH (SEQ ID NO: 1291) |
|   | VH CDR2 | LIDTYYGDATY NHKFKG (SEQ ID NO: 1348) | IDTYYGDA (SEQ ID NO: 1337) | LIDTYYGDATY NHKFKG (SEQ ID NO: 1348) | TYYG (SEQ ID NO: 1338) | WIGLIDTYYGD AT (SEQ ID NO: 1349) | LIDTYYGDAT (SEQ ID NO: 1350) |
|   | VH CDR3 | RAGNAMDY (SEQ ID NO: 1385) | ARRAGNAMDY (SEQ ID NO: 1386) | RAGNAMDY (SEQ ID NO: 1385) | AGNAMD (SEQ ID NO: 1387) | ARRAGNAMD (SEQ ID NO: 1388) | RAGNAMDY (SEQ ID NO: 1385) |
| VL CDR Seq. | VL CDR1 | KASQSVSNDIA (SEQ ID NO: 1429) | QSVSND (SEQ ID NO: 1426) | KASQSVSNDIA (SEQ ID NO: 1429) | SQSVSND (SEQ ID NO: 1427) | SNDIAWY (SEQ ID NO: 1430) | KASQSVSNDIA (SEQ ID NO: 1429) |
|   | VL CDR2 | YASNRYT (SEQ ID NO: 1473) | YAS (SEQ ID NO: 1474) | YASNRYT (SEQ ID NO: 1473) | YAS (SEQ ID NO: 1474) | LLIYYASNRY (SEQ ID NO: 1475) | YASNRYT (SEQ ID NO: 1473) |
|   | VL CDR3 | QQDYSSPRT (SEQ ID NO: 1493) | QQDYSSPRT (SEQ ID NO: 1493) | QQDYSSPRT (SEQ ID NO: 1493) | DYSSPR (SEQ ID NO: 1494) | QQDYSSPR (SEQ ID NO: 1495) | QQDYSSPRT (SEQ ID NO: 1493) |

TABLE 16-continued

Antibody 146C-CDR Sequences

| Exemplary* | IMGT | Kabat | Chothia | Contact | AbM |
|---|---|---|---|---|---|

VH Sequence:
QVQLQQSGAELVRPGVSVKISCKGSGYTFTDYGMHWVKQSHAKSLEWIGLIDTYYGDATYNHKFKGKATMTVDKSSRTA
YMELARLTSEDSAIYYCARRAGNAMDYWGQGTSVTASS (SEQ ID NO: 1260)

VL Sequence:
NIAMTQTPKFLLVSAGDRVTITCKASQSVSNDIAWYQQKPGQSPRLLIYYASNRYTGVPDRFTGSGYGTDFTFTISTVQ
AEDLAVYFCQQDYSSPRTFGGGTKLEIK (SEQ ID NO: 1261)

*Exemplary CDR sequences encompass amino acids as determined by Kabat plus Chothia.

TABLE 17

Antibody 208A-CDR Sequences

| | | Exemplary* | IMGT | Kabat | Chothia | Contact | AbM |
|---|---|---|---|---|---|---|---|
| VH CDR Seq. | VH CDR1 | GYTFTDYGMH (SEQ ID NO: 1291) | GYTFTDYG (SEQ ID NO: 1292) | DYGMH (SEQ ID NO: 1293) | GYTFTDY (SEQ ID NO: 1294) | TDYGMH (SEQ ID NO: 1295) | GYTFTDYGMH (SEQ ID NO: 1291) |
| | VH CDR2 | VIDTYYGDAGY NQKFKG (SEQ ID NO: 1351) | IDTYYGDA (SEQ ID NO: 1337) | VIDTYYGDAGY NQKFKG (SEQ ID NO: 1351) | TYYG (SEQ ID NO: 1338) | WIGVIDTYYGD AG (SEQ ID NO: 1352) | VIDTYYGDAG (SEQ ID NO: 1353) |
| | VH CDR3 | RAGNAMDY (SEQ ID NO: 1385) | ARRAGNAMDY (SEQ ID NO: 1386) | RAGNAMDY (SEQ ID NO: 1385) | AGNAMD (SEQ ID NO: 1387) | ARRAGNAMD (SEQ ID NO: 1388) | RAGNAMDY (SEQ ID NO: 1385) |
| VL CDR Seq. | VL CDR1 | KASQSVSNDVA (SEQ ID NO: 1425) | QSVSND (SEQ ID NO: 1426) | KASQSVSNDVA (SEQ ID NO: 1425) | SQSVSND (SEQ ID NO: 1427) | SNDVAWY (SEQ ID NO: 1428) | KASQSVSNDVA (SEQ ID NO: 1425) |
| | VL CDR2 | YASNRYT (SEQ ID NO: 1473) | YAS (SEQ ID NO: 1474) | YASNRYT (SEQ ID NO: 1473) | YAS (SEQ ID NO: 1474) | LLIYYASNRY (SEQ ID NO: 1475) | YASNRYT (SEQ ID NO: 1473) |
| | VL CDR3 | QQDYSSPRT (SEQ ID NO: 1493) | QQDYSSPRT (SEQ ID NO: 1493) | QQDYSSPRT (SEQ ID NO: 1493) | DYSSPR (SEQ ID NO: 1494) | QQDYSSPR (SEQ ID NO: 1495) | QQDYSSPRT (SEQ ID NO: 1493) |

VH Sequence:
QVQLQQSGAELVRPGVSVKISCKGSGYTFTDYGMHWVKQSHAKSLEWIGVIDTYYGDAGYNQKFKGKATMTVDKSSSTA
YMELARLTSEDSAIYYCARRAGNAMDYWGQGTSVTVSS (SEQ ID NO: 1262)

VL Sequence:
SIVMTQTPKFLLVSAGDRVTITCKASQSVSNDVAWYQQKPGQSPKLLIYYASNRYTGVPDRFTGSGYGTDFTFTISTVQ
AEDLAVYFCQQDYSSPRTFGGGTKLEIK (SEQ ID NO: 1263)

*Exemplary CDR sequences encompass amino acids as determined by Kabat plus Chothia.

TABLE 18

Antibody 215A-CDR Sequences

| | | Exemplary* | IMGT | Kabat | Chothia | Contact | AbM |
|---|---|---|---|---|---|---|---|
| VH CDR Seq. | VH CDR1 | GFSFTGYTMN (SEQ ID NO: 1296) | GFSFTGYT (SEQ ID NO: 1297) | GYTMN (SEQ ID NO: 1298) | GFSFTGY (SEQ ID NO: 1299) | TGYTMN (SEQ ID NO: 1300) | GFSFTGYTMN (SEQ ID NO: 1296) |
| | VH CDR2 | LISPYNGGTSY NQKFKG (SEQ ID NO: 1354) | ISPYNGGT (SEQ ID NO: 1355) | LISPYNGGTSY NQKFKG (SEQ ID NO: 1354) | PYNG (SEQ ID NO: 1356) | WIGLISPYNGG TS (SEQ ID NO: 1357) | LISPYNGGTS (SEQ ID NO: 1358) |
| | VH CDR3 | RAYGYAMDY (SEQ ID NO: 1393) | ARRAYGYAMDY (SEQ ID NO: 1394) | RAYGYAMDY (SEQ ID NO: 1393) | AYGYAMD (SEQ ID NO: 1395) | ARRAYGYAMD (SEQ ID NO: 1396) | RAYGYAMDY (SEQ ID NO: 1393) |

TABLE 18-continued

Antibody 215A-CDR Sequences

| | | Exemplary* | IMGT | Kabat | Chothia | Contact | AbM |
|---|---|---|---|---|---|---|---|
| VL CDR Seq. | VL CDR1 | SASSSVSYMF (SEQ ID NO: 1431) | SSVSY (SEQ ID NO: 1432) | SASSSVSYMF (SEQ ID NO: 1431) | SSSVSY (SEQ ID NO: 1433) | SYMFWY (SEQ ID NO: 1434) | SASSSVSYMF (SEQ ID NO: 1431) |
| | VL CDR2 | DTSNLAS (SEQ ID NO: 1476) | DTS (SEQ ID NO: 1477) | DTSNLAS (SEQ ID NO: 1476) | DTS (SEQ ID NO: 1477) | LLIYDTSNLA (SEQ ID NO: 1478) | DTSNLAS (SEQ ID NO: 1476) |
| | VL CDR3 | QQWSSYPFT (SEQ ID NO: 1499) | QQWSSYPFT (SEQ ID NO: 1499) | QQWSSYPFT (SEQ ID NO: 1499) | WSSYPF (SEQ ID NO: 1500) | QQWSSYPF (SEQ ID NO: 1501) | QQWSSYPFT (SEQ ID NO: 1499) |

VH Sequence:
EVQLQQSGPELVKPGASMKISCKASGFSFTGYTMNWVKQSHGKNLEWIGLISPYNGGTSYNQKFKGKATLTVDKSSSTA
YMELLSLTSEDSAVYYCARRAYGYAMDYWGQGTSVTVSS (SEQ ID NO: 1264)

VL Sequence:
QIVLTQSPAIMSASPGEKVTMTCSASSSVSYMFWYQQKPGSSPRLLIYDTSNLASGVPLRFSGSGSGTSYSLTISRMEA
EDAATYYCQQWSSYPFTFGSGTKLEIK (SEQ ID NO: 1265)

*Exemplary CDR sequences encompass amino acids as determined by Kabat plus Chothia.

TABLE 19

Antibody 26A-CDR Sequences

| | | Exemplary* | IMGT | Kabat | Chothia | Contact | AbM |
|---|---|---|---|---|---|---|---|
| VH CDR Seq. | VH CDR1 | GFSFTGYTMN (SEQ ID NO: 1296) | GFSFTGYT (SEQ ID NO: 1297) | GYTMN (SEQ ID NO: 1298) | GFSFTGY (SEQ ID NO: 1299) | TGYTMN (SEQ ID NO: 1300) | GFSFTGYTMN (SEQ ID NO: 1296) |
| | VH CDR2 | LISPYNGGTSYNQKFKG (SEQ ID NO: 1354) | ISPYNGGT (SEQ ID NO: 1355) | LISPYNGGTSYNQKFKG (SEQ ID NO: 1354) | PYNG (SEQ ID NO: 1356) | WIGLISPYNGGTS (SEQ ID NO: 1357) | LISPYNGGTS (SEQ ID NO: 1358) |
| | VH CDR3 | RAYGYAMDY (SEQ ID NO: 1393) | ARRAYGYAMDY (SEQ ID NO: 1394) | RAYGYAMDY (SEQ ID NO: 1393) | AYGYAMD (SEQ ID NO: 1395) | ARRAYGYAMD (SEQ ID NO: 1396) | RAYGYAMDY (SEQ ID NO: 1393) |
| VL CDR Seq. | VL CDR1 | SASSSVSYMY (SEQ ID NO: 1435) | SSVSY (SEQ ID NO: 1432) | SASSSVSYMY (SEQ ID NO: 1435) | SSSVSY (SEQ ID NO: 1433) | SYMYWY (SEQ ID NO: 1436) | SASSSVSYMY (SEQ ID NO: 1435) |
| | VL CDR2 | DTSNLAS (SEQ ID NO: 1476) | DTS (SEQ ID NO: 1477) | DTSNLAS (SEQ ID NO: 1476) | DTS (SEQ ID NO: 1477) | LLIYDTSNLA (SEQ ID NO: 1478) | DTSNLAS (SEQ ID NO: 1476) |
| | VL CDR3 | QQWSSYPFT (SEQ ID NO: 1499) | QQWSSYPFT (SEQ ID NO: 1499) | QQWSSYPFT (SEQ ID NO: 1499) | WSSYPF (SEQ ID NO: 1500) | QQWSSYPF (SEQ ID NO: 1501) | QQWSSYPFT (SEQ ID NO: 1499) |

VH Sequence:

EVQLQQSGPELVKPGASMKISCKASGFSFTGYTMNWVKQSHVKNLEWIGLISPYNGGTSYNQKFKGKATLTVD
KSSSTAYMELLSLTSEDSAVYYCARRAYGYAMDYWGQGTSVTVSS (SEQ ID NO: 1266)

VL Sequence:

QIVLTQSPAIMSASPGEKVTMTCSASSSVSYMYWYQQKPGSSPRLLIYDTSNLASGVPLRFSGSGSGTSYSLT
ISRMEAEDAATYYCQQWSSYPFTFGSGTKLEIK (SEQ ID NO: 1267)

*Exemplary CDR sequences encompass amino acids as determined by Kabat plus Chothia.

TABLE 20

Antibody 164A-CDR Sequences

| | | Exemplary* | IMGT | Kabat | Chothia | Contact | AbM |
|---|---|---|---|---|---|---|---|
| VH CDR Seq. | VH CDR1 | GYSFTGYNMN (SEQ ID NO: 30) | GYSFTGYN (SEQ ID NO: 1099 | GYNMN (SEQ ID NO: 1104) | GYSFTGY (SEQ ID NO: 1105) | TGYNMN (SEQ ID NO: 1110) | GYSFTGYNMN (SEQ ID NO: 30) |
| | VH CDR2 | NIDPYYGSASYNQKFKG (SEQ ID NO: 1359) | IDPYYGSA (SEQ ID NO: 1360) | NIDPYYGSASYNQKFKG (SEQ ID NO: 1359) | PYYG (SEQ ID NO: 1361) | WIGNIDPYYGSAS (SEQ ID NO: 1362) | NIDPYYGSAS (SEQ ID NO: 1363) |
| | VH CDR3 | SNYGYYGYFDV (SEQ ID NO: 1397) | TRSNYGYYGYFDV (SEQ ID NO: 1398) | SNYGYYGYFDV (SEQ ID NO: 1397) | NYGYYGYFD (SEQ ID NO: 1399) | TRSNYGYYGYFD (SEQ ID NO: 1400) | SNYGYYGYFDV (SEQ ID NO: 1397) |
| VL CDR Seq. #1 | VL CDR1 | KSSQSVLYSSNQKNYLA (SEQ ID NO: 1437) | QSVLYSSNQKNY (SEQ ID NO: 1438) | KSSQSVLYSSNQKNYLA (SEQ ID NO: 1437) | SQSVLYSSNQKNY (SEQ ID NO: 1439) | LYSSNQKNYLAWY (SEQ ID NO: 1450) | KSSQSVLYSSNQKNYLA (SEQ ID NO: 1437) |
| | VL CDR2 | WASTRES (SEQ ID NO: 1526) | WAS (SEQ ID NO: 1527) | WASTRES (SEQ ID NO: 1526) | WAS (SEQ ID NO: 157) | LLIYWASTRE (SEQ ID NO: 1528) | WASTRES (SEQ ID NO: 1526) |
| | VL CDR3 | HQFLSSYT (SEQ ID NO: 1523) | HQFLSSYT (SEQ ID NO: 1523) | HQFLSSYT (SEQ ID NO: 1523) | FLSSY (SEQ ID NO: 1524) | HQFLSSY (SEQ ID NO: 1525) | HQFLSSYT (SEQ ID NO: 1523) |
| VL CDR Seq. #2 | VL CDR1 | SASSSVSSSNLH (SEQ ID NO: 1451) | SSVSSSN (SEQ ID NO: 1452) | SASSSVSSSNLH (SEQ ID NO: 1451) | SSSVSSSN (SEQ ID NO: 1453) | SSSNLHWY (SEQ ID NO: 1915) | SASSSVSSSNLH (SEQ ID NO: 1451) |
| | VL CDR2 | RTSNLAS (SEQ ID NO: 1479) | RTS (SEQ ID NO: 1480) | RTSNLAS (SEQ ID NO: 1479) | RTS (SEQ ID NO: 1480) | FWIYRTSNLA (SEQ ID NO: 1481) | RTSNLAS (SEQ ID NO: 1479) |
| | VL CDR3 | QQWSGYPRT (SEQ ID NO: 1502) | QQWSGYPRT (SEQ ID NO: 1502) | QQWSGYPRT (SEQ ID NO: 1502) | WSGYPR (SEQ ID NO: 1503) | QQWSGYPR (SEQ ID NO: 1504) | QQWSGYPRT (SEQ ID NO: 1502) |

VH Sequence:

EVQLQQSGPELEKPGASVKISCKASGYSFTGYNMNWVKQSNGKSLEWIGNIDPYYGSASYNQKFKGKATLTVD
KSSTTAYMQLKSLTSEDSAVYYCTRSNYGYYGYFDVWGAGTTVTVSS (SEQ ID NO: 1268)

VL Sequence #1:

NIMMTQSPSSLAVSAGEKVTMSCKSSQSVLYSSNQKNYLAWYQQKPGQSPKLLIYWASTRESGVPDRFTGSGS
GTDFTLTISSVQAEDLAVYYCHQFLSSYTFGGGTKLEMK (SEQ ID NO: 1269)

VL Sequence #2:

ENVLTQSPAIMAASPGEKVTMTCSASSSVSSSNLHWYQQKSGTSTKFWIYRTSNLASEVPAPFSGSGSGTSYS
LTISSVEAEDAATYYCQQWSGYPRTFGGGTKLEIK (SEQ ID NO: 1270)

*Exemplary CDR sequences encompass amino acids as determined by Kabat plus Chothia.

TABLE 21

Antibody 230A-CDR Sequences

| | | Exemplary* | IMGT | Kabat | Chothia | Contact | AbM |
|---|---|---|---|---|---|---|---|
| VH CDR Seq. | VH CDR1 | GYSFTGSNMN (SEQ ID NO: 1301) | GYSFTGSN (SEQ ID NO: 1302) | GSNMN (SEQ ID NO: 1303) | GYSFTGS (SEQ ID NO: 1304) | TGSNMN (SEQ ID NO: 1305) | GYSFTGSNMN (SEQ ID NO: 1301) |
| | VH CDR2 | NIDPYYGYTTYNQKFKG (SEQ ID NO: 1364) | IDPYYGYT (SEQ ID NO: 1365) | NIDPYYGYTTYNQKFKG (SEQ ID NO: 1364) | PYYG (SEQ ID NO: 1361) | WIGNIDPYYGYTT (SEQ ID NO: 1366) | NIDPYYGYTT (SEQ ID NO: 1367) |

TABLE 21-continued

Antibody 230A-CDR Sequences

|  |  | Exemplary* | IMGT | Kabat | Chothia | Contact | AbM |
|---|---|---|---|---|---|---|---|
|  | VH CDR3 | DYDYALGYFDV (SEQ ID NO: 1401) | ARDYDYALGYFDV (SEQ ID NO: 1402) | DYDYALGYFDV (SEQ ID NO: 1401) | YDYALGYFD (SEQ ID NO: 1403) | ARDYDYALGYFD (SEQ ID NO: 1404) | DYDYALGYFDV (SEQ ID NO: 1401) |
| VL CDR Seq. | VL CDR1 | RSSQSLVHSNGNTYLH (SEQ ID NO: 1454) | QSLVHSNGNTY (SEQ ID NO: 1455) | RSSQSLVHSNGNTYLH (SEQ ID NO: 1454) | SQSLVHSNGNTY (SEQ ID NO: 1456) | VHSNGNTYLHW (SEQ ID NO: 1457) | RSSQSLVHSNGNTYLH (SEQ ID NO: 1454) |
|  | VL CDR2 | KVSNRFS (SEQ ID NO: 40) | KVS (SEQ ID NO: 1103) | KVSNRFS (SEQ ID NO: 40) | KVS (SEQ ID NO: 1103) | LLIYKVSNRF (SEQ ID NO: 1114) | KVSNRFS (SEQ ID NO: 40) |
|  | VL CDR3 | SQSTHVPYT (SEQ ID NO: 1505) | SQSTHVPYT (SEQ ID NO: 1505) | SQSTHVPYT (SEQ ID NO: 1505) | STHVPY (SEQ ID NO: 1506) | SQSTHVPY (SEQ ID NO: 1507) | SQSTHVPYT (SEQ ID NO: 1505) |

VH Sequence:

EVQLQQSGPELEKPGASVKISCKASGYSFTGSNMNWVKQNNGKSLEWIGNIDPYYGYTTYNQKFKGKATLTVD
KSSSTAYMQLKSLTSEDSAVYYCARDYDYALGYFDVWGAGTTVTVSS (SEQ ID NO: 1271)

VL Sequence:

DVVMTQTPLSLPVSLGDQASISCRSSQSLVHSNGNTYLHWYLQKPGQSPKLLIYKVSNRFSGVPDRFSGSGSG
TDFTLKISRVEAEDLGVYFCSQSTHVPYTFGGGTKLEIK (SEQ ID NO: 1272)

*Exemplary CDR sequences encompass amino acids as determined by Kabat plus Chothia.

TABLE 22

Antibody 76E1-CDR Sequences

|  |  | Exemplary* | IMGT | Kabat | Chothia | Contact | AbM |
|---|---|---|---|---|---|---|---|
| VH CDR Seq. | VH CDR1 | GYSFTGYNMN (SEQ ID NO. 30) | GYSFTGYN (SEQ ID NO. 1099) | GYNMN (SEQ ID NO. 1104) | GYSFTGY (SEQ ID NO. 1105) | TGYNMN (SEQ ID NO. 1110) | GYSFTGYNMN (SEQ ID NO. 30) |
|  | VH CDR2 | NIDPYYDYTSYNLKFKD (SEQ ID NO. 31) | IDPYYDYT (SEQ ID NO. 1100) | NIDPYYDYTSYNLKFKD (SEQ ID NO. 31) | PYYD (SEQ ID NO. 1106) | WIGNIDPYYDYTS (SEQ ID NO. 1111) | NIDPYYDYTS (SEQ ID NO. 1116) |
|  | VH CDR3 | STMITPFDY (SEQ ID NO. 32) | ATSTMITPFDY (SEQ ID NO. 1101) | STMITPFDY (SEQ ID NO. 32) | TMITPFD (SEQ ID NO. 1107) | ATSTMITPFD (SEQ ID NO. 1112) | STMITPFDY (SEQ ID NO. 32) |
| VL CDR Seq. | VL CDR1 | RSSQSIVHSNGNTYLE (SEQ ID NO. 45) | QSIVHSNGNTY (SEQ ID NO. 1102) | RSSQSIVHSNGNTYLE (SEQ ID NO. 45) | SQSIVHSNGNTY (SEQ ID NO. 1108) | VHSNGNTYLEW (SEQ ID NO. 1113) | RSSQSIVHSNGNTYLE (SEQ ID NO. 45) |
|  | VL CDR2 | KVSNRFS (SEQ ID NO. 40) | KVS (SEQ ID NO. 1103) | KVSNRFS (SEQ ID NO. 40) | KVS (SEQ ID NO. 1103) | LLIYKVSNRF (SEQ ID NO. 1114) | KVSNRFS (SEQ ID NO. 40) |
|  | VL CDR3 | FQGSHVPWT (SEQ ID NO. 41) | FQGSHVPWT (SEQ ID NO. 41) | FQGSHVPWT (SEQ ID NO. 41) | GSHVPW (SEQ ID NO. 1109) | FQGSHVPW (SEQ ID NO. 1115) | FQGSHVPWT (SEQ ID NO. 41) |

VH Sequence:

EVQLLQSGPELEKPGASVKISCKASGYSFTGYNMNWVKQSNGKSLEWIGNIDPYYDYTSYNLKFKDKATLTVD
KSSSTAYMQLKSLTSEDSAVYYCATSTMITPFDYWGQGTTLTVSS (SEQ ID NO: 1)

VL Sequence:

DVLMTQTPLSLPVSLGDQASISCRSSQSIVHSNGNTYLEWYLQKPGQSPKLLIYKVSNRFSGVPDRFSGSGSG
TDFTLKINRVEAEDLGVYYCFQGSHVPWTFGGGTKLEIK (SEQ ID NO: 4)

*Exemplary CDR sequences encompass amino acids as determined by Kabat plus Chothia.

TABLE 23

Antibody 53A-CDR Sequences

| | | Exemplary* | IMGT | Kabat | Chothia | Contact | AbM |
|---|---|---|---|---|---|---|---|
| VH CDR Seq. | VH CDR1 | GYTFTSYFMH (SEQ ID NO: 1306) | GYTFTSYF (SEQ ID NO: 1307) | SYFMH (SEQ ID NO: 1308) | GYTFTSY (SEQ ID NO: 1309) | TSYFMH (SEQ ID NO: 1310) | GYTFTSYFMH (SEQ ID NO: 1306) |
| | VH CDR2 | YIYPYNDGTKYNEKFKG (SEQ ID NO: 1368) | IYPYNDGT (SEQ ID NO: 1369) | YIYPYNDGTKYNEKFKG (SEQ ID NO: 1368) | PYND (SEQ ID NO: 1370) | WIGYIYPYNDGTK (SEQ ID NO: 1371) | YIYPYNDGTK (SEQ ID NO: 1372) |
| | VH CDR3 | FDYDTLRY (SEQ ID NO: 1405) | ARFDYDTLRY (SEQ ID NO: 1406) | FDYDTLRY (SEQ ID NO: 1405) | DYDTLR (SEQ ID NO: 1407) | ARFDYDTLR (SEQ ID NO: 1408) | FDYDTLRY (SEQ ID NO: 1405) |
| VL CDR Seq. | VL CDR1 | KSTKSLLNSDGFTYLD (SEQ ID NO: 1458) | KSLLNSDGFTY (SEQ ID NO: 1459) | KSTKSLLNSDGFTYLD (SEQ ID NO: 1458) | TKSLLNSDGFTY (SEQ ID NO: 1460) | LNSDGFTYLDW (SEQ ID NO: 1461) | KSTKSLLNSDGFTYLD (SEQ ID NO: 1458) |
| | VL CDR2 | LVSNRFS (SEQ ID NO: 1482) | LVS (SEQ ID NO: 1483) | LVSNRFS (SEQ ID NO: 1482) | LVS (SEQ ID NO: 1483) | LLIYLVSNRF (SEQ ID NO: 1484) | LVSNRFS (SEQ ID NO: 1482) |
| | VL CDR3 | FQSNYFPWT (SEQ ID NO: 1508) | FQSNYFPWT (SEQ ID NO: 1508) | FQSNYFPWT (SEQ ID NO: 1508) | SNYFPW (SEQ ID NO: 1509) | FQSNYFPW (SEQ ID NO: 1510) | FQSNYFPWT (SEQ ID NO: 1508) |

VH Sequence:

EVQLQQSGPELVKPGASVKMSCKASGYTFTSYFMHWVKQKPGQGLEWIGYIYPYNDGTKYNEKFKGKATLTSD
KSSSTAYMELSSLTSEDSAVYYCARFDYDTLRYWGQGTTLTVSS (SEQ ID NO: 1273)

VL Sequence:

DVVLTQTPLSLPVNIGDQASISCKSTKSLLNSDGFTYLDWYLQKPGQSPQLLIYLVSNRFSGVPDRFSGSGSG
TDFTLKISRVEAEDLGVYYCFQSNYFPWTFGGGTKLEIK (SEQ ID NO: 1274)

*Exemplary CDR sequences encompass amino acids as determined by Kabat plus Chothia.

TABLE 24

Antibody 259A-CDR Sequences

| | | Exemplary* | IMGT | Kabat | Chothia | Contact | AbM |
|---|---|---|---|---|---|---|---|
| VH CDR Seq. | VH CDR1 | GYTFTSYFMH (SEQ ID NO: 1306) | GYTFTSYF (SEQ ID NO: 1307) | SYFMH (SEQ ID NO: 1308) | GYTFTSY (SEQ ID NO: 1309) | TSYFMH (SEQ ID NO: 1310) | GYTFTSYFMH (SEQ ID NO: 1306) |
| | VH CDR2 | YIYPYNDGTKYNEKFKG (SEQ ID NO: 1368) | IYPYNDGT (SEQ ID NO: 1369) | YIYPYNDGTKYNEKFKG (SEQ ID NO: 1368) | PYND (SEQ ID NO: 1370) | WIGYIYPYNDGTK (SEQ ID NO: 1371) | YIYPYNDGTK (SEQ ID NO: 1372) |
| | VH CDR3 | FDYDTLRY (SEQ ID NO: 1405) | ARFDYDTLRY (SEQ ID NO: 1406) | FDYDTLRY (SEQ ID NO: 1405) | DYDTLR (SEQ ID NO: 1407) | ARFDYDTLR (SEQ ID NO: 1408) | FDYDTLRY (SEQ ID NO: 1405) |
| VL CDR Seq. | VL CDR1 | KSTKSLLNSDGFTYLD (SEQ ID NO: 1458) | KSLLNSDGFTY (SEQ ID NO: 1459) | KSTKSLLNSDGFTYLD (SEQ ID NO: 1458) | TKSLLNSDGFTY (SEQ ID NO: 1460) | LNSDGFTYLDW (SEQ ID NO: 1461) | KSTKSLLNSDGFTYLD (SEQ ID NO: 1458) |
| | VL CDR2 | LISNRFS (SEQ ID NO: 1485) | LIS (SEQ ID NO: 1486) | LISNRFS (SEQ ID NO: 1485) | LIS (SEQ ID NO: 1486) | LLIYLISNRF (SEQ ID NO: 1487) | LISNRFS (SEQ ID NO: 1485) |
| | VL CDR3 | FQSNYFPWT (SEQ ID NO: 1508) | FQSNYFPWT (SEQ ID NO: 1508) | FQSNYFPWT (SEQ ID NO: 1508) | SNYFPW (SEQ ID NO: 1509) | FQSNYFPW (SEQ ID NO: 1510) | FQSNYFPWT (SEQ ID NO: 1508) |

TABLE 24-continued

Antibody 259A-CDR Sequences

| | Exemplary* | IMGT | Kabat | Chothia | Contact | AbM |
|---|---|---|---|---|---|---|

VH Sequence:

EVQLQQSGPELVKPGASVKMSCKASGYTFTSYFMHWVKQKPGQGLEWIGYIYPYNDGTKYNEKFKGKATLTSD
KSSSTAYMDLSSLTSEDSAVYYCARFDYDTLRYWGQGTTLTVSS (SEQ ID NO: 1275)

VL Sequence:

DVVLTQTPLSLPVNIGDQASISCKSTKSLLNSDGFTYLDWYLQKPGQSPQLLIYLISNRFSGVPDRFSGSGSG
TDFTLKISRVEAEDLGVYYCFQSNYFPWTFGGGTKLEIK (SEQ ID NO: 1276)

*Exemplary CDR sequences encompass amino acids as determined by Kabat plus Chothia.

TABLE 25

Antibody 33A-CDR Sequences

| | | Exemplary* | IMGT | Kabat | Chothia | Contact | AbM |
|---|---|---|---|---|---|---|---|
| VH CDR Seq. | VH CDR1 | GYTFSSYWIE (SEQ ID NO: 1311) | GYTFSSYW (SEQ ID NO: 1312) | SYWIE (SEQ ID NO: 1313) | GYTFSSY (SEQ ID NO: 1314) | SSYWIE (SEQ ID NO: 1315) | GYTFSSYWIE (SEQ ID NO: 1311) |
| | VH CDR2 | EILPGSGSTSYNEKFKG (SEQ ID NO: 37) | ILPGSGST (SEQ ID NO: 1082) | EILPGSGSTSYNEKFKG (SEQ ID NO: 37) | PGSG (SEQ ID NO: 1088) | WIGEILPGSGSTS (SEQ ID NO: 1093) | EILPGSGSTS (SEQ ID NO: 1098) |
| | VH CDR3 | WLLYYYAMVY (SEQ ID NO: 1409) | ARWLLYYYAMVY (SEQ ID NO: 1410) | WLLYYYAMVY (SEQ ID NO: 1409) | LLYYYAMV (SEQ ID NO: 1411) | ARWLLYYYAMV (SEQ ID NO: 1412) | WLLYYYAMVY (SEQ ID NO: 1409) |
| VL CDR Seq. | VL CDR1 | RSSQSIVHSNGNTYLE (SEQ ID NO: 45) | QSIVHSNGNTY (SEQ ID NO: 1102) | RSSQSIVHSNGNTYLE (SEQ ID NO: 45) | SQSIVHSNGNTY (SEQ ID NO: 1108) | VHSNGNTYLEW (SEQ ID NO: 1113) | RSSQSIVHSNGNTYLE (SEQ ID NO: 45) |
| | VL CDR2 | KVSNRFS (SEQ ID NO: 40) | KVS (SEQ ID NO: 1103) | KVSNRFS (SEQ ID NO: 40) | KVS (SEQ ID NO: 1103) | LLIYKVSNRF (SEQ ID NO: 1114) | KVSNRFS (SEQ ID NO: 40) |
| | VL CDR3 | FQGSHVPYT (SEQ ID NO: 1511) | FQGSHVPYT (SEQ ID NO: 1511) | FQGSHVPYT (SEQ ID NO: 1511) | GSHVPY (SEQ ID NO: 1512) | FQGSHVPY (SEQ ID NO: 1513) | FQGSHVPYT (SEQ ID NO: 1511) |

VH Sequence:

QVQLQQSGAELMKPGASVKISCKATGYTFSSYWIEWVKQRPGHGLEWIGEILPGSGSTSYNEKFKGKATFTAD
TSSNTAYMQLSGLTSEDSAVYYCARWLLYYYAMVYWGQGTSVTVSS (SEQ ID NO: 1277)

VL Sequence:

DVLMTQTPLSLPVSLGDQASISCRSSQSIVHSNGNTYLEWYLQKPGQSPKLLIYKVSNRFSGVPDRFSGSGSG
TDFTLKISRVEAEDLGVYYCFQGSHVPYTFGGGTKLEIK (SEQ ID NO: 1278)

*Exemplary CDR sequences encompass amino acids as determined by Kabat plus Chothia.

TABLE 26

Antibody 39A-CDR Sequences

| | | Exemplary* | IMGT | Kabat | Chothia | Contact | AbM |
|---|---|---|---|---|---|---|---|
| VH CDR Seq. | VH CDR1 | GYTFSSNWIE (SEQ ID NO: 1316) | GYTFSSNW (SEQ ID NO: 1317) | SNWIE (SEQ ID NO: 1318) | GYTFSSN (SEQ ID NO: 1319) | SSNWIE (SEQ ID NO: 1320) | GYTFSSNWIE (SEQ ID NO: 1316) |

TABLE 26-continued

Antibody 39A-CDR Sequences

| | | Exemplary* | IMGT | Kabat | Chothia | Contact | AbM |
|---|---|---|---|---|---|---|---|
| | VH CDR2 | EILPGSGSTSYNEKFKG (SEQ ID NO: 37) | ILPGSGST (SEQ ID NO: 1082) | EILPGSGSTSYNEKFKG (SEQ ID NO: 37) | PGSG (SEQ ID NO: 1088) | WIGEILPGSGSTS (SEQ ID NO: 1093) | EILPGSGSTS (SEQ ID NO: 1098) |
| | VH CDR3 | WLLYYYAMDY (SEQ ID NO: 38) | ARWLLYYYAMDY (SEQ ID NO: 1083) | WLLYYYAMDY (SEQ ID NO: 38) | LLYYYAMD (SEQ ID NO: 1089) | ARWLLYYYAMD (SEQ ID NO: 1094) | WLLYYYAMDY (SEQ ID NO: 38) |
| VL CDR Seq. | VL CDR1 | RSSQSIVHNNGNTYLE (SEQ ID NO: 1462) | QSIVHNNGNTY (SEQ ID NO: 1463) | RSSQSIVHNNGNTYLE (SEQ ID NO: 1462) | SQSIVHNNGNTY (SEQ ID NO: 1464) | VHNNGNTYLEW (SEQ ID NO: 1465) | RSSQSIVHNNGNTYLE (SEQ ID NO: 1462) |
| | VL CDR2 | KVSNRFS (SEQ ID NO: 40) | KVS (SEQ ID NO: 1103) | KVSNRFS (SEQ ID NO: 40) | KVS (SEQ ID NO: 1103) | LLIYKVSNRF (SEQ ID NO: 1114) | KVSNRFS (SEQ ID NO: 40) |
| | VL CDR3 | FQGSHVPYT (SEQ ID NO: 1511) | FQGSHVPYT (SEQ ID NO: 1511) | FQGSHVPYT (SEQ ID NO: 1511) | GSHVPY (SEQ ID NO: 1512) | FQGSHVPY (SEQ ID NO: 1513) | FQGSHVPYT (SEQ ID NO: 1511) |

VH Sequence:

QVQLQQSGAELMKPGASVKISCKATGYTFSSNWIEWVKQRPGHGLEWIGEILPGSGSTSYNEKFKGKATFTAD
TSSNTAYMQLSSLTSEDSAVYYCARWLLYYYAMDYWGQGTSVTVSS (SEQ ID NO: 1279)

VL Sequence:

DVLMTQTPLSLPVSLGDPASISCRSSQSIVHNNGNTYLEWYLQKPGQSPKLLIYKVSNRFSGVPDRFSGSGSG
TDFTLKISRVEAEDLGVYYCFQGSHVPYTFGGGTKLEIK (SEQ ID NO: 1280)

*Exemplary CDR sequences encompass amino acids as determined by Kabat plus Chothia.

TABLE 27

Antibody 124A-CDR Sequences

| | | Exemplary* | IMGT | Kabat | Chothia | Contact | AbM |
|---|---|---|---|---|---|---|---|
| VH CDR Seq. | VH CDR1 | GYTFSSNWIE (SEQ ID NO: 1316) | GYTFSSNW (SEQ ID NO: 1317) | SNWIE (SEQ ID NO: 1318) | GYTFSSN (SEQ ID NO: 1319) | SSNWIE (SEQ ID NO: 1320) | GYTFSSNWIE (SEQ ID NO: 1316) |
| | VH CDR2 | EILPGSGSTSYNEKFKG (SEQ ID NO: 37) | ILPGSGST (SEQ ID NO: 1082) | EILPGSGSTSYNEKFKG (SEQ ID NO: 37) | PGSG (SEQ ID NO: 1088) | WMGEILPGSGSTS (SEQ ID NO: 1917) | EILPGSGSTS (SEQ ID NO: 1098) |
| | VH CDR3 | WLLYYYAMDF (SEQ ID NO: 1413) | ARWLLYYYAMDF (SEQ ID NO: 1414) | WLLYYYAMDF (SEQ ID NO: 1413) | LLYYYAMD (SEQ ID NO: 1089) | ARWLLYYYAMD (SEQ ID NO: 1094) | WLLYYYAMDF (SEQ ID NO: 1413) |
| VL CDR Seq. | VL CDR1 | RSSQSIVHNNGNTYLE (SEQ ID NO: 1462) | QSIVHNNGNTY (SEQ ID NO: 1463) | RSSQSIVHNNGNTYLE (SEQ ID NO: 1462) | SQSIVHNNGNTY (SEQ ID NO: 1464) | VHNNGNTYLEW (SEQ ID NO: 1465) | RSSQSIVHNNGNTYLE (SEQ ID NO: 1462) |
| | VL CDR2 | KVSNRFS (SEQ ID NO: 40) | KVS (SEQ ID NO: 1103) | KVSNRFS (SEQ ID NO: 40) | KVS (SEQ ID NO: 1103) | LLIYKVSNRF (SEQ ID NO: 1114) | KVSNRFS (SEQ ID NO: 40) |
| | VL CDR3 | FQGSHVPYT (SEQ ID NO: 1511) | FQGSHVPYT (SEQ ID NO: 1511) | FQGSHVPYT (SEQ ID NO: 1511) | GSHVPY (SEQ ID NO: 1512) | FQGSHVPY (SEQ ID NO: 1513) | FQGSHVPYT (SEQ ID NO: 1511) |

VH Sequence:

QVQLQQSGAELMKPGASVKISCKATGYTFSSNWIEWVKQRPGHGLEWMGEILPGSGSTSYNEKFKGKATFTAD
TSSNTAYMQLSSLTSEDSAVYYCARWLLYYYAMDFWGQGTSVTVSS (SEQ ID NO: 1281)

TABLE 27-continued

Antibody 124A-CDR Sequences

| | Exemplary* | IMGT | Kabat | Chothia | Contact | AbM |
|---|---|---|---|---|---|---|

VL Sequence:

DVLMTQTPLSLPVSLGDQASISCRSSQSIVHNNGNTYLEWYLQKPGQSPKLLIYKVSNRFSGVPDRFSGSGSG
TDFTLKISRVEAEDLGVYYCFQGSHVPYTFGGGTKLEIK (SEQ ID NO: 1282)

*Exemplary CDR sequences encompass amino acids as determined by Kabat plus Chothia.

TABLE 28

Antibody 175A-CDR Sequences

| | | Exemplary* | IMGT | Kabat | Chothia | Contact | AbM |
|---|---|---|---|---|---|---|---|
| VH CDR Seq. | VH CDR1 | GYTFSTHWIE (SEQ ID NO. 36) | GYTFSTHW (SEQ ID NO. 1081) | THWIE (SEQ ID NO. 1086) | GYTFSTH (SEQ ID NO. 1087) | STHWIE (SEQ ID NO. 1092) | GYTFSTHWIE (SEQ ID NO. 36) |
| | VH CDR2 | EILPGSGSTSYNEKFKG (SEQ ID NO. 37) | ILPGSGST (SEQ ID NO. 1082) | EILPGSGSTSYNEKFKG (SEQ ID NO. 37) | PGSG (SEQ ID NO. 1088) | WIGEILPGSGSTS (SEQ ID NO. 1093) | EILPGSGSTS (SEQ ID NO. 1098) |
| | VH CDR3 | WLLYYYAMDY (SEQ ID NO. 38) | ARWLLYYYAMDY (SEQ ID NO. 1083) | WLLYYYAMDY (SEQ ID NO. 38) | LLYYYAMD (SEQ ID NO. 1089) | ARWLLYYYAMDY (SEQ ID NO. 1094) | WLLYYYAMDY (SEQ ID NO. 38) |
| VL CDR Seq. | VL CDR1 | RSSQSIVHSNGNTYLE (SEQ ID NO. 45) | QSIVHSNGNTY (SEQ ID NO. 1084) | RSSQSIVHSNGNTYLE (SEQ ID NO. 45) | SQSIVHSNGNTY (SEQ ID NO. 1090) | VHSNGNTYLEW (SEQ ID NO. 1095) | RSSQSIVHSNGNTYLE (SEQ ID NO. 45) |
| | VL CDR2 | KLSNRFS (SEQ ID NO. 46) | KLS (SEQ ID NO. 1085) | KLSNRFS (SEQ ID NO. 46) | KLS (SEQ ID NO. 1085) | LLIYKLSNRF (SEQ ID NO. 1096) | KLSNRFS (SEQ ID NO. 46) |
| | VL CDR3 | FQGSHFPYT (SEQ ID NO. 47) | FQGSHFPYT (SEQ ID NO. 47) | FQGSHFPYT (SEQ ID NO. 47) | GSHFPY (SEQ ID NO. 1091) | FQGSHFPY (SEQ ID NO. 1097) | FQGSHFPYT (SEQ ID NO. 47) |

VH Sequence:

QVQLQQSGAELMKPGASVKISCKATGYTFSTHWIEWVKQRPGHGLEWIGEILPGSGSTSYNEKFKGKATFTAD
TSSNTAYMQLSSLTSEDSAVYYCARWLLYYYAMDYWGQGTSVTVSS (SEQ ID NO: 3)

VL Sequence:

DVLMTQTPLSLPVSLGDQASISCRSSQSIVHSNGNTYLEWYLQKPGQSPKLLIYKLSNRFSGVPDRFSGSGSG
TDFTLKISRVEAEDLGVYYCFQGSHFPYTFGGGTKLEIK (SEQ ID NO: 6)

*Exemplary CDR sequences encompass amino acids as determined by Kabat plus Chothia.

TABLE 29

Antibody 321D-CDR Sequences

| | | Exemplary* | IMGT | Kabat | Chothia | Contact | AbM |
|---|---|---|---|---|---|---|---|
| VH CDR Seq. | VH CDR1 | GYTFSSHWIE (SEQ ID NO: 1321) | GYTFSSHW (SEQ ID NO: 1322) | SHWIE (SEQ ID NO: 1323) | GYTFSSH (SEQ ID NO: 1324) | SSHWIE (SEQ ID NO: 1325) | GYTFSSHWIE (SEQ ID NO: 1321) |
| | VH CDR2 | EILPGSGSTDYNEKFKG (SEQ ID NO: 849) | ILPGSGST (SEQ ID NO: 1082) | EILPGSGSTDYNEKFKG (SEQ ID NO: 849) | PGSG (SEQ ID NO: 1088) | WIGEILPGSGSTD (SEQ ID NO: 1373) | EILPGSGSTD (SEQ ID NO: 1374) |

TABLE 29-continued

Antibody 321D-CDR Sequences

|  |  | Exemplary* | IMGT | Kabat | Chothia | Contact | AbM |
|---|---|---|---|---|---|---|---|
|  | VH CDR3 | WLLYYYAMDY (SEQ ID NO: 38) | ARWLLYYYAMDY (SEQ ID NO: 1083) | WLLYYYAMDY (SEQ ID NO: 38) | LLYYYAMD (SEQ ID NO: 1089) | ARWLLYYYAMD (SEQ ID NO: 1094) | WLLYYYAMDY (SEQ ID NO: 38) |
| VL CDR Seq. | VL CDR1 | RSSQSIVHSNGNTYLE (SEQ ID NO: 45) | QSIVHSNGNTY (SEQ ID NO: 1102) | RSSQSIVHSNGNTYLE (SEQ ID NO: 45) | SQSIVHSNGNTY (SEQ ID NO: 1108) | VHSNGNTYLEW (SEQ ID NO: 1113) | RSSQSIVHSNGNTYLE (SEQ ID NO: 45) |
|  | VL CDR2 | KVSNRFS (SEQ ID NO: 40) | KVS (SEQ ID NO: 1103) | KVSNRFS (SEQ ID NO: 40) | KVS (SEQ ID NO: 1103) | LLIYKVSNRF (SEQ ID NO: 1114) | KVSNRFS (SEQ ID NO: 40) |
|  | VL CDR3 | FQGSHVPFT (SEQ ID NO: 1514) | FQGSHVPFT (SEQ ID NO: 1514) | FQGSHVPFT (SEQ ID NO: 1514) | GSHVPF (SEQ ID NO: 1515) | FQGSHVPF (SEQ ID NO: 1516) | FQGSHVPFT (SEQ ID NO: 1514) |

VH Sequence:

QVQLQQSGAELMKPGAAVKISCKATGYTFSSHWIEWVKQRPGHGLEWIGEILPGSGSTDYNEKFKGKATFTAD
TSSNTAYMQLSSLTSEDSAVYYCARWLLYYYAMDYWGQGTSVTVSS (SEQ ID NO: 1283)

VL Sequence:

DVLMTQTPLSLPVSLGDQASISCRSSQSIVHSNGNTYLEWYLQKPGQSPKLLIYKVSNRFSGVPDRFSGSGSG
TDFTLKITRVEAEDLGVYYCFQGSHVPFTFGGGTKLEIK (SEQ ID NO: 1284)

*Exemplary CDR sequences encompass amino acids as determined by Kabat plus Chothia.

TABLE 30

Antibody 141A-CDR Sequences

|  |  | Exemplary* | IMGT | Kabat | Chothia | Contact | AbM |
|---|---|---|---|---|---|---|---|
| VH CDR Seq. | VH CDR1 | GYTFSRYWIE (SEQ ID NO. 33) | GYTFSRYW (SEQ ID NO. 1117) | RYWIE (SEQ ID NO. 1122) | GYTFSRY (SEQ ID NO. 1123) | SRYWIE (SEQ ID NO. 1128) | GYTFSRYWIE (SEQ ID NO. 33) |
|  | VH CDR2 | EILPGSGSTNYNEKFKG (SEQ ID NO. 34) | ILPGSGST (SEQ ID NO. 1118) | EILPGSGSTNYNEKFKG (SEQ ID NO. 34) | PGSG (SEQ ID NO. 1124) | WIGEILPGSGSTN (SEQ ID NO. 1129) | EILPGSGSTN (SEQ ID NO. 1134) |
|  | VH CDR3 | EEVYDGYPWFGY (SEQ ID NO. 35) | AGEEVYDGYPWFGY (SEQ ID NO. 1119) | EEVYDGYPWFGY (SEQ ID NO. 35) | EVYDGYPWFG (SEQ ID NO. 1125) | AGEEVYDGYPWFG (SEQ ID NO. 1130) | EEVYDGYPWFGY (SEQ ID NO. 35) |
| VL CDR Seq. | VL CDR1 | RASSSLSYMH (SEQ ID NO. 42) | SSLSY (SEQ ID NO. 1120) | RASSSLSYMH (SEQ ID NO. 42) | SSSLSY (SEQ ID NO. 1126) | SYMHWY (SEQ ID NO. 1131) | RASSSLSYMH (SEQ ID NO. 42) |
|  | VL CDR2 | ATSNLAS (SEQ ID NO. 43) | ATS (SEQ ID NO. 1121) | ATSNLAS (SEQ ID NO. 43) | ATS (SEQ ID NO. 1121) | PWIYATSNLA (SEQ ID NO. 1132) | ATSNLAS (SEQ ID NO. 43) |
|  | VL CDR3 | QQWSSNPYT (SEQ ID NO. 44) | QQWSSNPYT (SEQ ID NO. 44) | QQWSSNPYT (SEQ ID NO. 44) | WSSNPY (SEQ ID NO. 1127) | QQWSSNPY (SEQ ID NO. 1133) | QQWSSNPYT (SEQ ID NO. 44) |

VH Sequence:

QVQLQQSGAELMKPGASVKISCKATGYTFSRYWIEWVKQRPGHGLEWIGEILPGSGSTNYNEKFKGKATFTAD
TSSNTAYMQLSSLTSEDSAVYYCAGEEVYDGYPWFGYWGQGTLVTVSA (SEQ ID NO: 2)

VL Sequence:

QIVLSQSPAILSASPGEKVTMTCRASSSLSYMHWYQQKPGSSPKPWIYATSNLASGVPARFSGSGSGTSYSLT
ISRVEAEDAATYYCQQWSSNPYTFGGGTKLEIK (SEQ ID NO: 5)

*Exemplary CDR sequences encompass amino acids as determined by Kabat plus Chothia.

TABLE 31

Antibody 51A-CDR Sequences

| | | Exemplary* | IMGT | Kabat | Chothia | Contact | AbM |
|---|---|---|---|---|---|---|---|
| VH CDR Seq. | VH CDR1 | GYTFSRYWIE (SEQ ID NO: 33) | GYTFSRYW (SEQ ID NO: 1117) | RYWIE (SEQ ID NO: 1122) | GYTFSRY (SEQ ID NO: 1123) | SRYWIE (SEQ ID NO: 1128) | GYTFSRYWIE (SEQ ID NO: 33) |
| | VH CDR2 | EILPGSGSTNYNEKFKG (SEQ ID NO: 34) | ILPGSGST (SEQ ID NO: 1082) | EILPGSGSTNYNEKFKG (SEQ ID NO: 34) | PGSG (SEQ ID NO: 1088) | WIGEILPGSGSTN (SEQ ID NO: 1129) | EILPGSGSTN (SEQ ID NO: 1134) |
| | VH CDR3 | EEVYDGYPWFGY (SEQ ID NO: 35) | ASEEVYDGYPWFGY (SEQ ID NO: 1415) | EEVYDGYPWFGY (SEQ ID NO: 35) | EVYDGYPWFG (SEQ ID NO: 1125) | ASEEVYDGYPWFG (SEQ ID NO: 1416) | EEVYDGYPWFGY (SEQ ID NO: 35) |
| VL CDR Seq. | VL CDR1 | RASSSLSYMH (SEQ ID NO: 42) | SSLSY (SEQ ID NO: 1120) | RASSSLSYMH (SEQ ID NO: 42) | SSSLSY (SEQ ID NO: 1126) | SYMHWY (SEQ ID NO: 1131) | RASSSLSYMH (SEQ ID NO: 42) |
| | VL CDR2 | ATSNLAS (SEQ ID NO: 43) | ATS (SEQ ID NO: 1121) | ATSNLAS (SEQ ID NO: 43) | ATS (SEQ ID NO: 1121) | PWIYATSNLA (SEQ ID NO: 1132) | ATSNLAS (SEQ ID NO: 43) |
| | VL CDR3 | QQWSSNPYT (SEQ ID NO: 44) | QQWSSNPYT (SEQ ID NO: 44) | QQWSSNPYT (SEQ ID NO: 44) | WSSNPY (SEQ ID NO: 1127) | QQWSSNPY (SEQ ID NO: 1133) | QQWSSNPYT (SEQ ID NO: 44) |

VH Sequence:

QVQLQQSGAELMKPGASVKISCKATGYTFSRYWIEWVKQRPGHGLEWIGEILPGSGSTNYNEKFKGKATFTAD
TSSNTAYMQLSSLTSEDSAVYYCASEEVYDGYPWFGYWGQGTLVTVSA (SEQ ID NO: 1285)

VL Sequence:

QIVLSQSPAILSASPGEKVTMTCRASSSLSYMHWYQQRPGSSPKPWIYATSNLASGVPARFSGSGSGTSYSLT
ISRVEAEDAATYYCQQWSSNPYTFGGGTKLEIK (SEQ ID NO: 1286)

*Exemplary CDR sequences encompass amino acids as determined by Kabat plus Chothia.

TABLE 32

Antibody 353A-CDR Sequences

| | | Exemplary* | IMGT | Kabat | Chothia | Contact | AbM |
|---|---|---|---|---|---|---|---|
| VH CDR Seq. | VH CDR1 | GFDFSRYWMN (SEQ ID NO: 1326) | GFDFSRYW (SEQ ID NO: 1327) | RYWMN (SEQ ID NO: 1328) | GFDFSRY (SEQ ID NO: 1329) | SRYWMN (SEQ ID NO: 1330) | GFDFSRYWMN (SEQ ID NO: 1326) |
| | VH CDR2 | EINPDSSTINYTPSLKD (SEQ ID NO: 1375) | INPDSSTI (SEQ ID NO: 1376) | EINPDSSTINYTPSLKD (SEQ ID NO: 1375) | PDSS (SEQ ID NO: 1377) | WIGEINPDSSTIN (SEQ ID NO: 1378) | EINPDSSTIN (SEQ ID NO: 1379) |
| | VH CDR3 | PGEIYYYGSYWFAY (SEQ ID NO: 1417) | ARPGEIYYYGSYWFAY (SEQ ID NO: 1418) | PGEIYYYGSYWFAY (SEQ ID NO: 1417) | GEIYYYGSYWFA (SEQ ID NO: 1419) | ARPGEIYYYGSYWFA (SEQ ID NO: 1420) | PGEIYYYGSYWFAY (SEQ ID NO: 1417) |
| VL CDR Seq. | VL CDR1 | RASESVEYYGTSLMQ (SEQ ID NO: 1466) | ESVEYYGTSLMQ (SEQ ID NO: 1467) | RASESVEYYGTSLMQ (SEQ ID NO: 1466) | SESVEYYGTSL (SEQ ID NO: 1468) | EYYGTSLMQWF (SEQ ID NO: 1468) | RASESVEYYGTSLMQ (SEQ ID NO: 1466) |
| | VL CDR2 | AASNVES (SEQ ID NO: 1488) | AAS (SEQ ID NO: 1489) | AASNVES (SEQ ID NO: 1488) | AAS (SEQ ID NO: 1489) | LLIYAASNVE (SEQ ID NO: 1490) | AASNVES (SEQ ID NO: 1488) |
| | VL CDR3 | QQSRKDPWT (SEQ ID NO: 1517) | QQSRKDPWT (SEQ ID NO: 1517) | QQSRKDPWT (SEQ ID NO: 1517) | SRKDPW (SEQ ID NO: 1518) | QQSRKDPW (SEQ ID NO: 1519) | QQSRKDPWT (SEQ ID NO: 1517) |

TABLE 32-continued

Antibody 353A-CDR Sequences

| | Exemplary* | IMGT | Kabat | Chothia | Contact | AbM |
|---|---|---|---|---|---|---|

VH Sequence:

EVKLLESGGGLVQPGGSLKLSCAASGFDFSRYWMNWVRQAPGKGLEWIGEINPDSSTINYTPSLKDKFIISRD
NAKNTLYLQMSKVRYEDTALYYCARPGEIYYYGSYWFAYWGQGTLVTVSA (SEQ ID NO: 1287)

VL Sequence:

DIVLTQSPASLAVSLGQRATISCRASESVEYYGTSLMQWFQQKPGQPPKLLIYAASNVESRVPARFSGSGSGT
DFSLNIHPVEEDDIAMYFCQQSRKDPWTFGGGTKLEIK (SEQ ID NO: 1288)

*Exemplary CDR sequences encompass amino acids as determined by Kabat plus Chothia.

TABLE 33

Antibody 305A-CDR Sequences

| | | Exemplary* | IMGT | Kabat | Chothia | Contact | AbM |
|---|---|---|---|---|---|---|---|
| VH CDR Seq. | VH CDR1 | GYSITSGYYWN (SEQ ID NO: 1331) | GYSITSGYY (SEQ ID NO: 1332) | SGYYWN (SEQ ID NO: 1333) | GYSITSGY (SEQ ID NO: 1334) | TSGYYWN (SEQ ID NO: 1335) | GYSITSGYYWN (SEQ ID NO: 1331) |
| | VH CDR2 | YISYDGSNNYN PSLKN (SEQ ID NO: 1380) | ISYDGSN (SEQ ID NO: 1381) | YISYDGSNNYN PSLKN (SEQ ID NO: 1380) | YDG (SEQ ID NO: 1382) | WMGYISYDGSN N (SEQ ID NO: 1383) | YISYDGSNN (SEQ ID NO: 1384) |
| | VH CDR3 | RHDYLSFAY (SEQ ID NO: 1421) | ARRHDYLSFAY (SEQ ID NO: 1422) | RHDYLSFAY (SEQ ID NO: 1421) | HDYLSFA (SEQ ID NO: 1423) | ARRHDYLSFA (SEQ ID NO: 1424) | RHDYLSFAY (SEQ ID NO: 1421) |
| VL CDR Seq. | VL CDR1 | KASQSVDYDGD SYMN (SEQ ID NO:1469) | QSVDYDGDSY (SEQ ID NO: 1470) | KASQSVDYDGD SYMN (SEQ ID NO: 1469) | SQSVDYDGDSY (SEQ ID NO: 1471) | DYDGDSYMNWY (SEQ ID NO: 1472) | KASQSVDYDGD SYMN (SEQ ID NO: 1469) |
| | VL CDR2 | AASNLES (SEQ ID NO: 1491) | AAS (SEQ ID NO: 1488) | AASNLES (SEQ ID NO: 1491) | AAS (SEQ ID NO: 1488) | LLIYAASNLE (SEQ ID NO: 1492) | AASNLES (SEQ ID NO: 1491) |
| | VL CDR3 | QQSDEDPYT (SEQ ID NO: 1520) | QQSDEDPYT (SEQ ID NO: 1520) | QQSDEDPYT (SEQ ID NO: 1520) | SDEDPY (SEQ ID NO: 1521) | QQSDEDPY (SEQ ID NO: 1522) | QQSDEDPYT (SEQ ID NO: 1520) |

VH Sequence:

DVQLQESGPGLVKPSQSLSLTCSVTGYSITSGYYWNWIRQFPGNKLEWMGYISYDGSNNYNPSLKNRISITRD
TSKNQFFLKLNSVTTEDTATYYCARRHDYLSFAYWGQGTLVIVSA (SEQ ID NO: 1289)

VL Sequence:

DIVLTQSPASLAVSLGQRATISCKASQSVDYDGDSYMNWYQQKPGQPPKLLIYAASNLESGIPARFSGSGSGT
DFTLNIHPVEEEDAATYYCQQSDEDPYTFGGGTKLEIK (SEQ ID NO: 1290)

*Exemplary CDR sequences encompass amino acids as determined by Kabat plus Chothia.

In certain embodiments, an antibody that binds to C10orf54 (e.g., C10orf54 polypeptide, C10orf54 polypeptide fragment, C10orf54 epitope) comprises: a VH region comprising: (1) a VH CDR1 having an amino acid sequence selected from the group consisting of SEQ ID NOS: 30, 33, 36, 1081, 1086, 1087, 1092, 1099, 1104, 1105, 1110, 1117, 1122, 1123, 1128, 1291-1335, and 1717-1720; (2) a VH CDR2 having an amino acid sequence selected from the group consisting of SEQ ID NOS: 31, 34, 37, 849, 1082, 1088, 1092, 1093, 1098, 1100, 1106, 1111, 1118, 1124, 1129, 1134, 1161, 1336-1344, 1348-1384, 1556-1559, 1829-1847, and 1917; and (3) a VH CDR3 having an amino acid sequence selected from the group consisting of SEQ ID NOS: 32, 35, 38, 1083, 1089, 1094, 1101, 1107, 1112, 1119, 1125, 1130, and 1385-1424.

In certain embodiments, an antibody that binds to C10orf54 (e.g., C10orf54 polypeptide, C10orf54 polypeptide fragment, C10orf54 epitope) comprises: a VL region comprising: (1) a VL CDR1 having an amino acid sequence selected from the group consisting of SEQ ID NOS: 42, 45, 253-271, 1084, 1090, 1095, 1102, 1108, 1113, 1120, 1126, 1131, 1425-1472, 1681-1684, 1744-1822, 1878-1896, and 1915; (2) a VL CDR2 having an amino acid sequence selected from the group consisting of SEQ ID NOS: 40, 43, 46, 157, 843-846, 1085, 1096, 1103, 1114, 1121, 1132, 1473-1492, 1526-1528, 1630-1633, 1685-1688, and 1898-

1900; and (3) a VL CDR3 having an amino acid sequence selected from the group consisting of SEQ ID NOS: 41, 44, 47, 1091, 1097, 1109, 1115, 1127, 1133, and 1493-1525.

In certain embodiments, the antibody comprises (a) a VH region comprising: (1) a VH CDR1 having an amino acid sequence selected from the group consisting of SEQ ID NOS: 30, 33, 36, 1081, 1086, 1087, 1092, 1099, 1104, 1105, 1110, 1117, 1122, 1123, 1128, 1291-1335, and 1717-1720; (2) a VH CDR2 having an amino acid sequence selected from the group consisting of SEQ ID NOS: 31, 34, 37, 849, 1082, 1088, 1092, 1093, 1098, 1100, 1106, 1111, 1118, 1124, 1129, 1134, 1161, 1336-1344, 1348-1384, 1556-1559, 1829-1847, and 1917; and (3) a VH CDR3 having an amino acid sequence selected from the group consisting of SEQ ID NOS: 32, 35, 38, 1083, 1089, 1094, 1101, 1107, 1112, 1119, 1125, 1130, and 1385-1424; and (b) a VL region comprising: (1) a VL CDR1 having an amino acid sequence selected from the group consisting of SEQ ID NOS: 42, 45, 253-271, 1084, 1090, 1095, 1102, 1108, 1113, 1120, 1126, 1131, 1425-1472, 1681-1684, 1744-1822, 1878-1896, and 1915; (2) a VL CDR2 having an amino acid sequence selected from the group consisting of SEQ ID NOS: 40, 43, 46, 157, 843-846, 1085, 1096, 1103, 1114, 1121, 1132, 1473-1492, 1526-1528, 1630-1633, 1685-1688, and 1898-1900; and (3) a VL CDR3 having an amino acid sequence selected from the group consisting of SEQ ID NOS: 41, 44, 47, 1091, 1097, 1109, 1115, 1127, 1133, and 1493-1525.

To the extent an antibody provided herein is the to "bind to a C10orf54 epitope", it is envisioned those antibodies also bind to a C10orf54 polypeptide, polypeptide fragment, or antigen thereof.

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC10 (SEQ ID NO: 1251), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), and CC9 (SEQ ID NO: 1250). In some aspects, the antibody comprises: (a) a heavy chain variable (VH) region comprising: (1) a VH CDR1 having an amino acid sequence selected from the group consisting of SEQ ID NOS: 30, 1099, 1104, 1105, 1110, 1291-1305, 1311-1315, and 1321-1325; (2) a VH CDR2 having an amino acid sequence selected from the group consisting of SEQ ID NOS: 37, 849, 1082, 1088, 1093, 1098, 1336-1344, 1348-1367, 1373, 1374, and 1556-1559; and (3) a VH CDR3 having an amino acid sequence selected from the group consisting of SEQ ID NOS: 38, 1083, 1089, 1094, 1385-1404, and 1409-1412; and/or (b) a light chain variable (VL) region comprising: (1) a VL CDR1 having an amino acid sequence selected from the group consisting of SEQ ID NOS: 45, 1102, 1108, 1113, 1425-1430, 1432-1457, 1681-1684, and 1915; (2) a VL CDR2 having an amino acid sequence selected from the group consisting of SEQ ID NOS: 40, 157, 1103, 1114, 1473-1481, 1526-1528, 1630-1633, and 1685-1688; and (3) a VL CDR3 having an amino acid sequence selected from the group consisting of SEQ ID NOS: 1493-1507, 1511-1516, and 1523-1525. In some aspects, the antibody comprises: (a) a VH region comprising: (1) a VH CDR1 having an amino acid sequence of SEQ ID NO: 1291, 1292, 1293, 1294, or 1295; (2) a VH CDR2 having an amino acid sequence of SEQ ID NO: 1336, 1337, 1338, 1339, or 1340; and (3) a VH CDR3 having an amino acid sequence of SEQ ID NO: 1385, 1386, 1387, or 1388; and (b) a VL region comprising: (1) a VL CDR1 having an amino acid sequence of SEQ ID NO: 1425, 1426, 1427, or 1428; (2) a VL CDR2 having an amino acid sequence of SEQ ID NO: 1473, 1474, or 1475; and (3) a VL CDR3 having an amino acid sequence of SEQ ID NO: 1493, 1494, or 1495. In some aspects, the antibody comprises: (a) a VH region comprising: (1) a VH CDR1 having an amino acid sequence of SEQ ID NO: 1291, 1292, 1293, 1294, or 1295; (2) a VH CDR2 having an amino acid sequence of SEQ ID NO: 1341, 1342, 1338, 1343, or 1344; and (3) a VH CDR3 having an amino acid sequence of SEQ ID NO: 1389, 1390, 1391, or 1392; and (b) a VL region comprising: (1) a VL CDR1 having an amino acid sequence of SEQ ID NO: 1425, 1426, 1427, or 1428; (2) a VL CDR2 having an amino acid sequence of SEQ ID NO: 1473, 1474, or 1475; and (3) a VL CDR3 having an amino acid sequence of SEQ ID NO: 1496, 1497, or 1498. In some aspects, the antibody comprises: (a) a VH region comprising: (1) a VH CDR1 having an amino acid sequence of SEQ ID NO: 1291, 1292, 1293, 1294, or 1295; (2) a VH CDR2 having an amino acid sequence of SEQ ID NO: 1348, 1337, 1338, 1349, or 1350; and (3) a VH CDR3 having an amino acid sequence of SEQ ID NO: 1385, 1386, 1387, or 1388; and (b) a VL region comprising: (1) a VL CDR1 having an amino acid sequence of SEQ ID NO: 1429, 1426, 1427, 1430, 1681, 1682, 1683, or 1684; (2) a VL CDR2 having an amino acid sequence of SEQ ID NO: 1473, 1474, 1475, 1685, 1686, 1687, or 1688; and (3) a VL CDR3 having an amino acid sequence of SEQ ID NO: 1493, 1494, or 1495. In some aspects, the antibody comprises: (a) a VH region comprising: (1) a VH CDR1 having an amino acid sequence of SEQ ID NO: 1291, 1292, 1293, 1294, or 1295; (2) a VH CDR2 having an amino acid sequence of SEQ ID NO: 1348, 1337, 1338, 1349, or 1350; and (3) a VH CDR3 having an amino acid sequence of SEQ ID NO: 1385, 1386, 1387, or 1388; and (b) a VL region comprising: (1) a VL CDR1 having an amino acid sequence of SEQ ID NO: 1429, 1426, 1427, or 1430; (2) a VL CDR2 having an amino acid sequence of SEQ ID NO: 1473, 1474, or 1475; and (3) a VL CDR3 having an amino acid sequence of SEQ ID NO: 1493, 1494, or 1495. In some aspects, the antibody comprises: (a) a VH region comprising: (1) a VH CDR1 having an amino acid sequence of SEQ ID NO: 1291, 1292, 1293, 1294, or 1295; (2) a VH CDR2 having an amino acid sequence of SEQ ID NO: 1351, 1337, 1338, 1352, or 1353; and (3) a VH CDR3 having an amino acid sequence of SEQ ID NO: 1385, 1386, 1387, or 1388; and (b) a VL region comprising: (1) a VL CDR1 having an amino acid sequence of SEQ ID NO: 1425, 1426, 1427, or 1428; (2) a VL CDR2 having an amino acid sequence of SEQ ID NO: 1473, 1474, or 1475; and (3) a VL CDR3 having an amino acid sequence of SEQ ID NO: 1493, 1494, or 1495. In some aspects, the antibody comprises: (a) a VH region comprising: (1) a VH CDR1 having an amino acid sequence of SEQ ID NO: 30, 1099, 1104, 1105, or 1110; (2) a VH CDR2 having an amino acid sequence of SEQ ID NO: 1359, 1360, 1361, 1362, or 1363; and (3) a VH CDR3 having an amino acid sequence of SEQ ID NO: 1397, 1398, 1399, or 1400; and (b) a VL region comprising: (1) a VL CDR1 having an amino acid sequence of SEQ ID NO: 1437, 1451, 1438, 1452, 1451 1439, 1453, 1450, or 1915; (2) a VL CDR2 having an amino acid sequence of SEQ ID NO: 1526, 1479, 1527, 1480, 157, 1528, or 1481; and (3) a VL CDR3 having an amino acid sequence of SEQ ID NO: 1523, 1502, 1524, 1503, 1525, or 1504. In some aspects, the antibody comprises: (a) a VH region comprising: (1) a VH CDR1 having an amino acid sequence of SEQ ID NO: 1301, 1302, 1303, 1304, or 1305; (2) a VH CDR2 having an amino acid sequence of SEQ ID NO: 1364, 1365, 1361, 1366, or 1367; and (3) a VH CDR3 having an amino acid sequence of SEQ ID NO: 1401, 1402, 1403, or 1404; and (b) a VL region comprising: (1) a VL CDR1 having an amino acid sequence of SEQ ID NO: 1454, 1455, 1456, or 1457; (2) a VL CDR2 having an amino acid sequence of SEQ ID NO: 40, 1103, or 1114; and (3) a VL CDR3 having an amino acid sequence of SEQ ID NO: 1505, 1506, or 1507. In some aspects, the antibody comprises: (a) a VH region comprising: (1) a VH CDR1 having an amino acid sequence of SEQ ID NO: 1311, 1312, 1313, 1314, or 1315; (2) a VH CDR2 having an amino acid sequence of SEQ ID NO: 37, 1082, 1088, 1093, or 1098; and (3) a VH CDR3 having an amino acid sequence of SEQ ID NO: 1409, 1410, 1411, or 1412; and (b) a VL region comprising: (1) a VL CDR1 having an amino acid sequence of SEQ ID NO: 45, 1102, 1108, or 1113; (2) a VL CDR2 having an amino acid sequence of SEQ ID NO: 40, 1103, or 1114; and (3) a VL CDR3 having an amino acid sequence of SEQ ID NO: 1511, 1512, or 1513. In some aspects, the antibody comprises: (a) a VH region comprising: (1) a VH CDR1 having an amino acid sequence of SEQ ID NO: 1321, 1322, 1323, 1324, or 1325; (2) a VH CDR2 having an amino acid sequence of SEQ ID NO: 849, 1082, 1088, 1373, or 1374; and (3) a VH CDR3 having an amino acid sequence of SEQ ID NO: 38, 1083, 1089, or 1094; and (b) a VL region comprising: (1) a VL CDR1 having an amino acid sequence of SEQ ID NO: 45, 1102, 1108, or 1113; (2) a VL CDR2 having an amino acid sequence of SEQ ID NO: 40, 1103, or 1114; and (3) a VL CDR3 having an amino acid sequence of SEQ ID NO: 1514, 1515, or 1516.

In certain embodiments, the antibody provided herein binds a first group of C10orf54 proteins or chimeric proteins designated CC1 (SEQ ID NO: 1079), CC4 (SEQ ID NO: 1245), CC5 (SEQ ID NO: 1246), and CC8 (SEQ ID NO: 1249), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251). In some aspected, such an antibody does not comprise one or more CDR sequences selected from the group consisting of 30, 1099, 1104, 1105, 1110, 31, 1100, 1106, 1111, 1116, 32, 1101, 1107, 1112, 45, 1102, 1108, 1113, 40, 1103, 1114, 41, 1109, and 1115. In some aspects, the antibody comprises: (a) a heavy chain variable (VH) region comprising: (1) a VH CDR1 having an amino acid sequence selected from the group consisting of SEQ ID NOS: 30, 1099, 1110, 1104, 1105, 1296-1300, 1306-1310, 1316-1320, and 1717-1720; (2) a VH CDR2 having an amino acid sequence selected from the group consisting of SEQ ID NOS: 31, 37, 1082, 1088, 1092, 1098, 1100, 1106, 1111, 1116, 1354-1358, 1368-1372, 1829-1847, and 1917; and (3) a VH CDR3 having an amino acid sequence selected from the group consisting of SEQ ID NOS: 32, 38, 1083, 1089, 1094, 1101, 1107, 1112, 1393-1396, 1405-1408, 1413, 1414; and/or (b) a light chain variable (VL) region comprising: (1) a VL CDR1 having an amino acid sequence selected from the group consisting of SEQ ID NOS: 45, 253-271, 1102, 1108, 1113, 1431-1434, 1458-1465, 1744-1822, 1878-1896; (2) a VL CDR2 having an amino acid sequence selected from the group consisting of SEQ ID NOS: 40, 843-846, 1103, 1114, 1476-1478, 1482-1487, 1898-1900; and (3) a VL CDR3 having an amino acid sequence selected from the group consisting of SEQ ID NOS: 41, 1109, 1115, 1499-1501, 1508-1513. In some aspects, the antibody comprises: (a) a VH region comprising: (1) a VH CDR1 having an amino acid sequence of SEQ ID NO: 1296, 1297, 1298, 1299, or 1300; (2) a VH CDR2 having an amino acid sequence of SEQ ID NO: 1354, 1355, 1356, 1357, or 1358; and (3) a VH CDR3 having an amino acid sequence of SEQ ID NO: 1393, 1394, 1395, or 1396; and (b) a VL region comprising: (1) a VL CDR1 having an amino acid sequence of SEQ ID NO: 1431, 1432, 1433, or 1434; (2) a VL CDR2 having an amino acid sequence of SEQ ID NO: 1476, 1477, or 1478; and (3) a VL CDR3 having an amino acid sequence of SEQ ID NO: 1499, 1500, or 1501. In some aspects, the antibody comprises: (a) a VH region comprising: (1) a VH CDR1 having an amino acid sequence of SEQ ID NO: 1306, 1307, 1308, 1309, or 1310; (2) a VH CDR2 having an amino acid sequence of SEQ ID NO: 1368, 1369, 1370, 1371, or 1372; and (3) a VH CDR3 having an amino acid sequence of SEQ ID NO: 1405, 1406, 1407, or 1408; and (b) a VL region comprising: (1) a VL CDR1 having an amino acid sequence of SEQ ID NO: 1458, 1459, 1460, or 1461; (2) a VL CDR2 having an amino acid sequence of SEQ ID NO: 1482, 1483, or 1484; and (3) a VL CDR3 having an amino acid sequence of SEQ ID NO: 1508, 1509, or 1510. In some aspects, the antibody comprises: (a) a VH region comprising: (1) a VH CDR1 having an amino acid sequence of SEQ ID NO: 1306, 1307, 1308, 1309, or 1310; (2) a VH CDR2 having an amino acid sequence of SEQ ID NO: 1368, 1369, 1370, 1371, 1372, 1829, 1830, 1831, 1832, 1833, 1834, 1835, 1836, 1837, 1838, 1839, 1840, 1841, 1842, 1843, 1844, 1845, 1846, or 1847; and (3) a VH CDR3 having an amino acid sequence of SEQ ID NO: 1405, 1406, 1407, or 1408; and (b) a VL region comprising: (1) a VL CDR1 having an amino acid sequence of SEQ ID NO: 1458, 1459, 1460, 1461, 1878, 1879, 1880, 1881, 1882, 1883, 1884, 1885, 1886, 1887, 1888, 1889, 1890, 1891, 1892, 1893, 1894, 1895, or 1896; (2) a VL CDR2 having an amino acid sequence of SEQ ID NO: 1485, 1486, 1487, 1897, 1898, 1899, or 1900; and (3) a VL CDR3 having an amino acid sequence of SEQ ID NO: 1508, 1509, or 1510. In some aspects, the antibody comprises: (a) a VH region comprising: (1) a VH CDR1 having an amino acid sequence of SEQ ID NO: 1316, 1317, 1318, 1319, or 1320; (2) a VH CDR2 having an amino acid sequence of SEQ ID NO: 37, 1082, 1088, 1092, or 1098; and (3) a VH CDR3 having an amino acid sequence of SEQ ID NO: 38, 1083, 1089, or 1094; and (b) a VL region comprising: (1) a VL CDR1 having an amino acid sequence of SEQ ID NO: 1462, 1463, 1464, or 1465; (2) a VL CDR2 having an amino acid sequence of SEQ ID NO: 40, 1103, or 1114; and (3) a VL CDR3 having an amino acid sequence of SEQ ID NO: 1511, 1512, or 1513. In some aspects, the antibody comprises: (a) a VH region comprising: (1) a VH CDR1 having an amino acid sequence of SEQ ID NO: 1316, 1317, 1318, 1319, 1320, 1717, 1718, 1719, or 1720; (2) a VH CDR2 having an amino acid sequence of SEQ ID NO: 37, 1082, 1088, 1917, or 1098; and (3) a VH CDR3 having an amino acid sequence of SEQ ID NO: 1413, 1414, 1089, or 1094; and (b) a VL region comprising: (1) a VL CDR1 having an amino acid sequence of SEQ ID NO: 1462, 1463, 1464, 1465, 1744, 45, 1745, 1746, 1747, 1748, 1749, 1750, 1751, 1752, 1753, 1754, 1755, 1756, 1757, 1758, 1759, 1760, 253, 254, 255, 256, 257, 258, 259, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 260, 1788, 1789, 1790, 1791, 264, 268, 1792, 1793, 1794, 1795, 1796,261, 1797, 1798, 1799, 1800, 265, 269, 1801, 1802, 1803, 1804, 1805, 262, 1806, 1807, 1808, 1809, 266, 270, 1810, 1811, 1812, 1813, 1814,263, 1815, 1816, 1817, 1818, 267, 271, 1819, 1820, 1821, or 1822; (2) a VL CDR2 having an amino acid sequence of SEQ ID NO: 40, 1103, 1114, 843, 844, 846, or 845; and (3) a VL CDR3 having an amino acid sequence of SEQ ID NO: 1511, 1512, or 1513.

In certain embodiments, the antibody provided herein binds to a first group of C10orf54 proteins or chimeric proteins designated CC1 (SEQ ID NO: 1079), CC4 (SEQ ID NO: 1245), and CC5 (SEQ ID NO: 1246), and does not bind to a second group of C10orf54 proteins or chimeric proteins designated (SEQ ID NO: 1243), CC3 (SEQ ID NO: 1244), CC6 (SEQ ID NO: 1247), CC7 (SEQ ID NO: 1248), CC8 (SEQ ID NO: 1249), CC9 (SEQ ID NO: 1250), and CC10 (SEQ ID NO: 1251). In some aspects, such an antibody does not comprise one or more CDR sequences selected from the group consisting of 36, 1081, 1086, 1087, 1092, 37, 1082, 1088, 1093, 1098, 38, 1083, 1089, 1094, 45, 1084, 1090, 1095, 46, 1085, 1096, 47, 1091, and 1097.

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC9 (SEQ ID NO: 1250), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251). In some aspects, such an antibody does not comprise one or more CDR sequences selected from the group consisting of 33, 1117, 1122, 1123, 1128, 34, 1118, 1124, 1129, 1134, 35, 1119, 1125, 1130, 42, 1120, 1126, 1131, 43, 1121, 1132, 44, 1127, and 1133. In some aspects, the antibody comprises: (a) a heavy chain variable (VH) region comprising: (1) a VH CDR1 having an amino acid sequence selected from the group consisting of SEQ ID NOS: 33, 1117, 1122, 1123, and 1128; (2) a VH CDR2 having an amino acid sequence selected from the group consisting of SEQ ID NOS: 34, 1082, 1088, 1118, 1124, 1129, and 1134; and (3) a VH CDR3 having an amino acid sequence selected from the group consisting of SEQ ID NOS: 35, 1119, 1125, 1130, 1415, and 1416; and/or (b) a light chain variable (VL) region comprising: (1) a VL CDR1 having an amino acid sequence selected from the group consisting of SEQ ID NOS: 42, 1120, 1126, and 1131; (2) a VL CDR2 having an amino acid sequence selected from the group consisting of SEQ ID NOS: 43, 1121, and 1132; and (3) a VL CDR3 having an amino acid sequence selected from the group consisting of SEQ ID NOS: 44, 1127, and 1133. In some aspects, the antibody comprises: (a) a VH region comprising: (1) a VH CDR1 having an amino acid sequence of SEQ ID NO: 33, 1117, 1122, 1123, or 1128; (2) a VH CDR2 having an amino acid sequence of SEQ ID NO: 34, 1082, 1088, 1129, or 1134; and (3) a VH CDR3 having an amino acid sequence of SEQ ID NO: 35, 1415, 1125, or 1416; and/or (b) a VL region comprising: (1) a VL CDR1 having an amino acid sequence of SEQ ID NO: 42, 1120, 1126, or 1131; (2) a VL CDR2 having an amino acid sequence of SEQ ID NO: 43, 1121, or 1132; and (3) a VL CDR3 having an amino acid sequence of SEQ ID NO: 44, 1127, or 1133.

In certain embodiments, the antibody provided herein binds to a first group of C10orf54 proteins or chimeric proteins designated CC1 (SEQ ID NO: 1079), CC3 (SEQ ID NO: 1244), CC4 (SEQ ID NO: 1245), CC5 (SEQ ID NO: 1246), CC8 (SEQ ID NO: 1249), and CC9 (SEQ ID NO: 1250), and does not bind to a second group of C10orf54 proteins or chimeric proteins designated CC2 (SEQ ID NO: 1243), CC6 (SEQ ID NO: 1247), CC7 (SEQ ID NO: 1248), and CC10 (SEQ ID NO: 1251). In some aspects, the antibody comprises: (a) a VH region comprising: (1) a VH CDR1 having an amino acid sequence of SEQ ID NO: 1326, 1327, 1328, 1329, or 1330; (2) a VH CDR2 having an amino acid sequence of SEQ ID NO: 1375, 1376, 1377, 1378, or 1379; and (3) a VH CDR3 having an amino acid sequence of SEQ ID NO: 1417, 1418, 1419, or 1420; and/or (b) a VL region comprising: (1) a VL CDR1 having an amino acid sequence of SEQ ID NO: 1466, 1467, or 1468; (2) a VL CDR2 having an amino acid sequence of SEQ ID NO: 1488, 1489, or 1490; and (3) a VL CDR3 having an amino acid sequence of SEQ ID NO: 1517, 1518, or 1519.

In certain embodiments, the antibody provided herein binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC10 (SEQ ID NO: 1251), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), CC9 (SEQ ID NO: 1250), and CC10 (SEQ ID NO: 1251). In some aspects, the antibody comprises: (a) a VH region comprising: (1) a VH CDR1 having an amino acid sequence of SEQ ID NO: 1331, 1332, 1333, 1334, or 1335; (2) a VH CDR2 having an amino acid sequence of SEQ ID NO: 1380, 1381, 1382, 1383, or 1384; and (3) a VH CDR3 having an amino acid sequence of SEQ ID NO: 1421, 1422, 1423, or 1424; and/or (b) a VL region comprising: (1) a VL CDR1 having an amino acid sequence of SEQ ID NO: 1469, 1470, 1471, or 1472; (2) a VL CDR2 having an amino acid sequence of SEQ ID NO: 1491, 1488, or 1492; and (3) a VL CDR3 having an amino acid sequence of SEQ ID NO: 1520, 1521, or 1522.

In accordance with the amino acid sequences disclosed in Tables 12-33, in some embodiments, an antibody that binds to a C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 36, 1081, 1086, 1087, 1092, 30, 1099, 1104, 1105, 1110, 33, 1117, 1122, 1123, 1128 or 1291-1335; (2) a VH CDR2 having an amino acid sequence of SEQ ID NO: 37, 1082, 1088, 1093, 1098, 31, 1100, 1106, 1111, 1116, 34, 1118, 1124, 1129, 1134 or 1336-1384; and/or (3) a VH CDR3 having an amino acid sequence of SEQ ID NO: 38, 1083, 1089, 1094, 32, 1101, 1107, 1112, 35, 1119, 1125, 1130 or 1385-1424. In certain embodiments, an antibody that binds to C10orf54 (e.g., C10orf54 polypeptide, C10orf54 polypeptide fragment, C10orf54 epitope) comprises a VL region comprising: (1) a VL CDR1 having an amino acid sequence of SEQ ID NO: 45, 1084, 1090, 1095, 1102, 1108, 1113, 42, 1120, 1126, 1131 or 1425-1472; (2) a VL CDR2 having an amino acid sequence of SEQ ID NO: 46, 1085, 1096, 40, 1103, 1114, 43, 1121 and 1132; and/or (3) a VL CDR3 having an amino acid sequence of SEQ ID NO: 47, 1091, 1097, 41, 1109, 1115, 44, 1127, 1133 or 1493-1525. In some embodiments, the antibody comprises: (a) a VH region comprising: (1) a VH CDR1 having an amino acid sequence of SEQ ID NO: 36, 1081, 1086, 1087, 1092, 30, 1099, 1104, 1105, 1110, 33, 1117, 1122, 1123, 1128 or 1291-1335; (2) a VH CDR2 having an amino acid sequence of SEQ ID NO: 37, 1082, 1088, 1093, 1098, 31, 1100, 1106, 1111, 1116, 34, 1118, 1124, 1129, 1134 or 1336-1384; and/or (3) a VH CDR3 having an amino acid sequence of SEQ ID NO: 38, 1083, 1089, 1094, 32, 1101, 1107, 1112, 35, 1119, 1125, 1130 or 1385-1424; and (b) a VL region comprising: (1) a VL CDR1 having an amino acid sequence of SEQ ID NO: 45, 1084, 1090, 1095, 1102, 1108, 1113, 42, 1120, 1126, 1131 or 1425-1472; (2) a VL CDR2 having an amino acid sequence of SEQ ID NO: 46, 1085, 1096, 40, 1103, 1114, 43, 1121, 1132, 1473-1492 or 1526-

1528; and/or (3) a VL CDR3 having an amino acid sequence of SEQ ID NO: 47, 1091, 1097, 41, 1109, 1115, 44, 1127, 1133 or 1493-1525.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1081; (2) a VH CDR2 having an amino acid sequence of SEQ ID NO: 1082; and (3) a VH CDR3 having an amino acid sequence of SEQ ID NO: 1083. In some embodiments, the antibody further comprises a VL region comprising: (1) a VL CDR1 having an amino acid sequence of SEQ ID NO: 1084; (2) a VL CDR2 having an amino acid sequence of SEQ ID NO: 1085; and (3) a VL CDR3 having an amino acid sequence of SEQ ID NO: 47. In one embodiment, the antibody comprises: (a) a VH region comprising: (1) a VH CDR1 having an amino acid sequence of SEQ ID NO: 1081; (2) a VH CDR2 having an amino acid sequence of SEQ ID NO: 1082; and (3) a VH CDR3 having an amino acid sequence of SEQ ID NO: 1083; and (b) a VL region comprising: (1) a VL CDR1 having an amino acid sequence of SEQ ID NO: 1084; (2) a VL CDR2 having an amino acid sequence of SEQ ID NO: 1085; and (3) a VL CDR3 having an amino acid sequence of SEQ ID NO: 47.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1086; (2) a VH CDR2 having an amino acid sequence of SEQ ID NO: 37; and (3) a VH CDR3 having an amino acid sequence of SEQ ID NO: 38. In some embodiments, the antibody further comprises a VL region comprising: (1) a VL CDR1 having an amino acid sequence of SEQ ID NO: 45; (2) a VL CDR2 having an amino acid sequence of SEQ ID NO: 46; and (3) a VL CDR3 having an amino acid sequence of SEQ ID NO: 47. In one embodiment, the antibody comprises: (a) a VH region comprising: (1) a VH CDR1 having an amino acid sequence of SEQ ID NO: 1086; (2) a VH CDR2 having an amino acid sequence of SEQ ID NO: 37; and (3) a VH CDR3 having an amino acid sequence of SEQ ID NO: 38; and (b) a VL region comprising: (1) a VL CDR1 having an amino acid sequence of SEQ ID NO: 45; (2) a VL CDR2 having an amino acid sequence of SEQ ID NO: 46; and (3) a VL CDR3 having an amino acid sequence of SEQ ID NO: 47.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1087; (2) a VH CDR2 having an amino acid sequence of SEQ ID NO: 1088; and (3) a VH CDR3 having an amino acid sequence of SEQ ID NO: 1089. In some embodiments, the antibody further comprises a VL region comprising: (1) a VL CDR1 having an amino acid sequence of SEQ ID NO: 1090; (2) a VL CDR2 having an amino acid sequence of SEQ ID NO: 1085; and (3) a VL CDR3 having an amino acid sequence of SEQ ID NO: 1091. In one embodiment, the antibody comprises: (a) a VH region comprising: (1) a VH CDR1 having an amino acid sequence of SEQ ID NO: 1087; (2) a VH CDR2 having an amino acid sequence of SEQ ID NO: 1088; and (3) a VH CDR3 having an amino acid sequence of SEQ ID NO: 1089; and (b) a VL region comprising: (1) a VL CDR1 having an amino acid sequence of SEQ ID NO: 1090; (2) a VL CDR2 having an amino acid sequence of SEQ ID NO: 1085; and (3) a VL CDR3 having an amino acid sequence of SEQ ID NO: 1091.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1092; (2) a VH CDR2 having an amino acid sequence of SEQ ID NO: 1093; and (3) a VH CDR3 having an amino acid sequence of SEQ ID NO: 1094. In some embodiments, the antibody further comprises a VL region comprising: (1) a VL CDR1 having an amino acid sequence of SEQ ID NO: 1095; (2) a VL CDR2 having an amino acid sequence of SEQ ID NO: 1096; and (3) a VL CDR3 having an amino acid sequence of SEQ ID NO: 1097. In one embodiment, the antibody comprises: (a) a VH region comprising: (1) a VH CDR1 having an amino acid sequence of SEQ ID NO: 1092; (2) a VH CDR2 having an amino acid sequence of SEQ ID NO: 1093; and (3) a VH CDR3 having an amino acid sequence of SEQ ID NO: 1094; and (b) a VL region comprising: (1) a VL CDR1 having an amino acid sequence of SEQ ID NO: 1095; (2) a VL CDR2 having an amino acid sequence of SEQ ID NO: 1096; and (3) a VL CDR3 having an amino acid sequence of SEQ ID NO: 1097.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 36; (2) a VH CDR2 having an amino acid sequence of SEQ ID NO: 1098; and (3) a VH CDR3 having an amino acid sequence of SEQ ID NO: 38. In some embodiments, the antibody further comprises a VL region comprising: (1) a VL CDR1 having an amino acid sequence of SEQ ID NO: 45; (2) a VL CDR2 having an amino acid sequence of SEQ ID NO: 46; and (3) a VL CDR3 having an amino acid sequence of SEQ ID NO: 47. In one embodiment, the antibody comprises: (a) a VH region comprising: (1) a VH CDR1 having an amino acid sequence of SEQ ID NO: 36; (2) a VH CDR2 having an amino acid sequence of SEQ ID NO: 1098; and (3) a VH CDR3 having an amino acid sequence of SEQ ID NO: 38; and (b) a VL region comprising: (1) a VL CDR1 having an amino acid sequence of SEQ ID NO: 45; (2) a VL CDR2 having an amino acid sequence of SEQ ID NO: 46; and (3) a VL CDR3 having an amino acid sequence of SEQ ID NO: 47.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1099; (2) a VH CDR2 having an amino acid sequence of SEQ ID NO: 1100; and (3) a VH CDR3 having an amino acid sequence of SEQ ID NO: 1101. In some embodiments, the antibody further comprises a VL region comprising: (1) a VL CDR1 having an amino acid sequence of SEQ ID NO: 1102; (2) a VL CDR2 having an amino acid sequence of SEQ ID NO: 1103; and (3) a VL CDR3 having an amino acid sequence of SEQ ID NO: 41. In one embodiment, the antibody comprises: (a) a VH region comprising: (1) a VH CDR1 having an amino acid sequence of SEQ ID NO: 1099; (2) a VH CDR2 having an amino acid sequence of SEQ ID NO: 1100; and (3) a VH CDR3 having an amino acid sequence of SEQ ID NO: 1101; and (b) a VL region comprising: (1) a VL CDR1 having an amino acid sequence of SEQ ID NO: 1102; (2) a VL CDR2 having an amino acid sequence of SEQ ID NO: 1103; and (3) a VL CDR3 having an amino acid sequence of SEQ ID NO: 41.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1104; (2) a VH CDR2 having an amino acid sequence of SEQ ID NO: 31; and (3) a VH CDR3 having an amino acid sequence of SEQ ID NO: 32. In some embodiments, the antibody further comprises a VL region comprising: (1) a VL CDR1 having an amino acid sequence of SEQ ID NO: 45; (2) a VL CDR2 having an amino acid sequence of SEQ ID NO: 40; and (3) a VL CDR3 having an amino acid sequence of SEQ ID NO: 41. In one embodiment, the antibody comprises: (a) a VH region comprising: (1) a VH CDR1 having an amino acid sequence of SEQ ID NO: 1104; (2) a VH CDR2 having an amino acid sequence of SEQ ID NO: 31; and (3) a VH CDR3 having an amino acid sequence of SEQ ID NO: 32; and (b) a VL region comprising: (1) a VL CDR1 having an amino acid sequence of SEQ ID NO: 45; (2) a VL CDR2 having an amino acid sequence of SEQ ID NO: 40; and (3) a VL CDR3 having an amino acid sequence of SEQ ID NO: 41.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1105; (2) a VH CDR2 having an amino acid sequence of SEQ ID NO: 1106; and (3) a VH CDR3 having an amino acid sequence of SEQ ID NO: 1107. In some embodiments, the antibody further comprises a VL region comprising: (1) a VL CDR1 having an amino acid sequence of SEQ ID NO: 1108; (2) a VL CDR2 having an amino acid sequence of SEQ ID NO: 1103; and (3) a VL CDR3 having an amino acid sequence of SEQ ID NO: 1109. In one embodiment, the antibody comprises: (a) a VH region comprising: (1) a VH CDR1 having an amino acid sequence of SEQ ID NO: 1105; (2) a VH CDR2 having an amino acid sequence of SEQ ID NO: 1106; and (3) a VH CDR3 having an amino acid sequence of SEQ ID NO: 1107; and (b) a VL region comprising: (1) a VL CDR1 having an amino acid sequence of SEQ ID NO: 1108; (2) a VL CDR2 having an amino acid sequence of SEQ ID NO: 1103; and (3) a VL CDR3 having an amino acid sequence of SEQ ID NO: 1109.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1110; (2) a VH CDR2 having an amino acid sequence of SEQ ID NO: 1111; and (3) a VH CDR3 having an amino acid sequence of SEQ ID NO: 1112. In some embodiments, the antibody further comprises a VL region comprising: (1) a VL CDR1 having an amino acid sequence of SEQ ID NO: 1113; (2) a VL CDR2 having an amino acid sequence of SEQ ID NO: 1114; and (3) a VL CDR3 having an amino acid sequence of SEQ ID NO: 1115. In one embodiment, the antibody comprises: (a) a VH region comprising: (1) a VH CDR1 having an amino acid sequence of SEQ ID NO: 1110; (2) a VH CDR2 having an amino acid sequence of SEQ ID NO: 1111; and (3) a VH CDR3 having an amino acid sequence of SEQ ID NO: 1112; and (b) a VL region comprising: (1) a VL CDR1 having an amino acid sequence of SEQ ID NO: 1113; (2) a VL CDR2 having an amino acid sequence of SEQ ID NO: 1114; and (3) a VL CDR3 having an amino acid sequence of SEQ ID NO: 1115.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 30; (2) a VH CDR2 having an amino acid sequence of SEQ ID NO: 1116; and (3) a VH CDR3 having an amino acid sequence of SEQ ID NO: 32. In some embodiments, the antibody further comprises a VL region comprising: (1) a VL CDR1 having an amino acid sequence of SEQ ID NO: 45; (2) a VL CDR2 having an amino acid sequence of SEQ ID NO: 40; and (3) a VL CDR3 having an amino acid sequence of SEQ ID NO: 41. In one embodiment, the antibody comprises: (a) a VH region comprising: (1) a VH CDR1 having an amino acid sequence of SEQ ID NO: 30; (2) a VH CDR2 having an amino acid sequence of SEQ ID NO: 1116; and (3) a VH CDR3 having an amino acid sequence of SEQ ID NO: 32; and (b) a VL region comprising: (1) a VL CDR1 having an amino acid sequence of SEQ ID NO: 45; (2) a VL CDR2 having an amino acid sequence of SEQ ID NO: 40; and (3) a VL CDR3 having an amino acid sequence of SEQ ID NO: 41.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1117; (2) a VH CDR2 having an amino acid sequence of SEQ ID NO: 1118; and (3) a VH CDR3 having an amino acid sequence of SEQ ID NO: 1119. In some embodiments, the antibody further comprises a VL region comprising: (1) a VL CDR1 having an amino acid sequence of SEQ ID NO: 1120; (2) a VL CDR2 having an amino acid sequence of SEQ ID NO: 1121; and (3) a VL CDR3 having an amino acid sequence of SEQ ID NO: 44. In one embodiment, the antibody comprises: (a) a VH region comprising: (1) a VH CDR1 having an amino acid sequence of SEQ ID NO: 1117; (2) a VH CDR2 having an amino acid sequence of SEQ ID NO: 1118; and (3) a VH CDR3 having an amino acid sequence of SEQ ID NO: 1119; and (b) a VL region comprising: (1) a VL CDR1 having an amino acid sequence of SEQ ID NO: 1120; (2) a VL CDR2 having an amino acid sequence of SEQ ID NO: 1121; and (3) a VL CDR3 having an amino acid sequence of SEQ ID NO: 44.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1122; (2) a VH CDR2 having an amino acid sequence of SEQ ID NO: 34; and (3) a VH CDR3 having an amino acid sequence of SEQ ID NO: 35. In some embodiments, the antibody further comprises a VL region comprising: (1) a VL CDR1 having an amino acid sequence of SEQ ID NO: 42; (2) a VL CDR2 having an amino acid sequence of SEQ ID NO: 43; and (3) a VL CDR3 having an amino acid sequence of SEQ ID NO: 44. In one embodiment, the antibody comprises: (a) a VH region comprising: (1) a VH CDR1 having an amino acid sequence of SEQ ID NO: 1122; (2) a VH CDR2 having an amino acid sequence of SEQ ID NO: 34; and (3) a VH CDR3 having an amino acid sequence of SEQ ID NO: 35; and (b) a VL region comprising: (1) a VL CDR1 having an amino acid sequence of SEQ ID NO: 42; (2) a VL CDR2 having an amino acid sequence of SEQ ID NO: 43; and (3) a VL CDR3 having an amino acid sequence of SEQ ID NO: 44.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1123; (2) a VH CDR2 having an amino acid sequence of SEQ ID NO: 1124; and (3) a VH CDR3 having an amino acid sequence of SEQ ID NO: 1125. In some embodiments, the antibody further comprises a VL region comprising: (1) a VL CDR1 having an amino acid sequence of SEQ ID NO: 1126; (2) a VL CDR2 having an amino acid sequence of SEQ ID NO: 1121; and (3) a VL CDR3 having an amino acid sequence of SEQ ID NO: 1127. In one embodiment, the antibody comprises: (a) a VH region comprising: (1) a VH CDR1 having an amino acid sequence of SEQ ID NO: 1123; (2) a VH CDR2 having an amino acid sequence of SEQ ID NO: 1124; and (3) a VH CDR3 having an amino acid sequence of SEQ ID NO: 1125; and (b) a VL region comprising: (1) a VL CDR1 having an amino acid sequence of SEQ ID NO: 1126; (2) a VL CDR2 having an amino acid sequence of SEQ ID NO: 1121; and (3) a VL CDR3 having an amino acid sequence of SEQ ID NO: 1127.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 1128; (2) a VH CDR2 having an amino acid sequence of SEQ ID NO: 1129; and (3) a VH CDR3 having an amino acid sequence of SEQ ID NO: 1130. In some embodiments, the antibody further comprises a VL region comprising: (1) a VL CDR1 having an amino acid sequence of SEQ ID NO: 1131; (2) a VL CDR2 having an amino acid sequence of SEQ ID NO: 1132; and (3) a VL CDR3 having an amino acid sequence of SEQ ID NO: 1133. In one embodiment, the antibody comprises: (a) a VH region comprising: (1) a VH CDR1 having an amino acid sequence of SEQ ID NO: 1128; (2) a VH CDR2 having an amino acid sequence of SEQ ID NO: 1129; and (3) a VH CDR3 having an amino acid sequence of SEQ ID NO: 1130; and (b) a VL region comprising: (1) a VL CDR1 having an amino acid sequence of SEQ ID NO: 1131; (2) a VL CDR2 having an amino acid sequence of SEQ ID NO: 1132; and (3) a VL CDR3 having an amino acid sequence of SEQ ID NO: 1133.

In one embodiment, an antibody that binds to C10orf54 (e.g., C10orf54 polypeptide, C10orf54 polypeptide fragment, C10orf54 epitope) comprises a VH region comprising: (1) a VH CDR1 having an amino acid sequence of SEQ ID NO: 33; (2) a VH CDR2 having an amino acid sequence of SEQ ID NO: 1134; and (3) a VH CDR3 having an amino acid sequence of SEQ ID NO: 35. In some embodiments, the antibody further comprises a VL region comprising: (1) a VL CDR1 having an amino acid sequence of SEQ ID NO: 42; (2) a VL CDR2 having an amino acid sequence of SEQ ID NO: 43; and (3) a VL CDR3 having an amino acid sequence of SEQ ID NO: 44. In one embodiment, the antibody comprises: (a) a VH region comprising: (1) a VH CDR1 having an amino acid sequence of SEQ ID NO: 33; (2) a VH CDR2 having an amino acid sequence of SEQ ID NO: 1134; and (3) a VH CDR3 having an amino acid sequence of SEQ ID NO: 35; and (b) a VL region comprising: (1) a VL CDR1 having an amino acid sequence of SEQ ID NO: 42; (2) a VL CDR2 having an amino acid sequence of SEQ ID NO: 43; and (3) a VL CDR3 having an amino acid sequence of SEQ ID NO: 44.

In certain embodiments, a humanized anti-C10orf54 antibody that binds to C10orf54 (e.g., C10orf54 polypeptide, C10orf54 polypeptide fragment, C10orf54 epitope) comprises one or more consensus sequences derived from related antibodies as depicted in FIGS. 17A and 17B. As described herein, a "consensus sequence" refers to amino acid sequences having conserved amino acids common among a number of sequences and variable amino acids that vary within a given amino acid sequences. The CDR consensus sequences provided include CDRs corresponding to CDRH1, CDRH2, CDRH3, CDRL1, CDRL2 and/or CDRL3. Consensus sequences of CDRs of anti-C10orf54 antibodies are shown in FIGS. 17A and 17B. Accordingly, in some embodiments, a humanized anti-C10orf54 antibody comprises a VH region comprising: (1) a VH CDR1 having an amino acid sequence of GYTFSX$_1$X$_2$WIE (SEQ ID NO: 1149), wherein X$_1$ is a R or T and X$_2$ is a Y or H; (2) a VH CDR2 having an amino acid sequence of EILPGSGSTX$_1$YNEKFKG (SEQ ID NO: 1150), wherein X$_1$ is a N or S; and/or (3) a VH CDR3 having an amino acid sequence of xxxxxxxxxX$_1$X$_2$Y (SEQ ID NO: 1151), wherein x is any amino acid residue, X$_1$ is a M or F, and X$_2$ is G or D. In certain embodiments, a humanized anti-C10orf54 antibody comprises a VL region comprising: (1) a VL CDR1 having an amino acid sequence of RSSQ-SIVHSNGNTYLE (SEQ ID NO: 45); (2) a VL CDR2 having an amino acid sequence of KX$_1$SNRFS (SEQ ID NO: 1152), wherein X$_1$ is a V or L; and/or (3) a VL CDR3 having an amino acid sequence of FQGSHX$_1$PX$_2$T (SEQ ID NO: 1153), wherein X$_1$ is V or F and X$_2$ is a W or Y. In certain embodiments, a humanized anti-C10orf54 antibody comprises: (a) a VH region comprising: (1) a VH CDR1 having an amino acid sequence of GYTFSX$_1$X$_2$WIE (SEQ ID NO: 1149), wherein X$_1$ is a R or T and X$_2$ is a Y or H; (2) a VH CDR2 having an amino acid sequence of EILPGSGSTX$_1$YNEKFKG (SEQ ID NO: 1150), wherein X$_1$ is a N or S; and/or (3) a VH CDR3 having an amino acid sequence of xxxxxxxxxX$_1$X$_2$Y (SEQ ID NO: 1151), wherein x is any amino acid residue, X$_1$ is a M or F, and X$_2$ is G or D; and (b) a VL region comprising: (1) a VL CDR1 having an amino acid sequence of RSSQSIVHSNGNTYLE (SEQ ID NO: 45); (2) a VL CDR2 having an amino acid sequence of KX$_1$SNRFS (SEQ ID NO: 1152), wherein X$_1$ is a V or L; and/or (3) a VL CDR3 having an amino acid sequence of FQGSHX$_1$PX$_2$T (SEQ ID NO: 1153), wherein X$_1$ is V or F and X$_2$ is a W or Y.

In some embodiments, the antibodies provided herein comprise a VH region that comprises or consists of a VH domain. In other embodiments, the antibodies provided herein comprise a VH region that comprises or consists of a VH chain. In some embodiments, the antibodies provided herein comprise a VL region that comprises or consists of a VL domain. In other embodiments, the antibodies provided herein comprise a VL region that comprises or consists of a VL chain. In some embodiments, the antibodies provided herein have a combination of (i) a VH domain or VH chain; and/or (ii) a VL domain or VL chain.

In some embodiments, an antibody provided herein comprises or consists six CDRs, for example, VH CDR1, VH CDR2, VH CDR3, VL CDR1, VL CDR2, and/or VL CDR3 identified in Tables 5-33. In certain embodiments, an antibody provided herein can comprise less than six CDRs. In some embodiments, the antibody comprises or consists of one, two, three, four, or five CDRs selected from the group consisting of VH CDR1, VH CDR2, VH CDR3, VL CDR1, VL CDR2, and/or VL CDR3. In specific embodiments, the antibody comprises or consists of one, two, three, four, or five CDRs selected from the group consisting of VH CDR1, VH CDR2, VH CDR3, VL CDR1, VL CDR2, and/or VL CDR3 of the murine monoclonal antibody 5B, 46A, 97A, 128A, 146C, 208A, 215A, 26A, 164A, 230A, 76E1, 53A, 259A, 33A, 39A, 124A, 175A, 321D, 141A, 51A, 353A, or 305A described herein, or a humanized variant thereof, as identified in Tables 5-33. Accordingly, in some embodiments, the antibody comprises or consists of one, two, three four or five CDRs of anyone of the VH CDR1, VH CDR2, VH CDR3, VL CDR1, VL CDR2, and/or VL CDR3 identified in Tables 5-33.

In some embodiments, the antibodies provided herein comprise one or more (e.g. one, two or three) VH CDRs listed in Tables 5-33. In other embodiments, the antibodies provided herein comprise one or more (e.g., one, two or three) VL CDRs listed in Tables 5-33. In yet other embodiments, the antibodies provided herein comprise one or more (e.g., one, two or three) VH CDRs listed in Tables 5-33 and one or more VL CDRs listed in Tables 5-33. Accordingly, in certain embodiments, the antibodies comprise a VH CDR1 having the amino acid sequence of any one of SEQ ID NOS:36, 30, 59-62, 33, 1081, 1086, 1087, 1092, 1099, 1104, 1105, 1110, 1117, 1122, 1123, 1128, 1291-1335, 1291-1335, and 1717-1720. In another embodiment, the antibodies comprise a VH CDR2 having the amino acid sequence of any one of SEQ ID NOS: 37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847, and 1917. In another embodiment, the antibodies comprise a VH CDR3 having the amino acid sequence of any one of SEQ ID NOS: 38, 32, 319, 35, 883-885, 1083, 1089, 1094, 1101, 1107, 1112, 1119, 1125, 1130 and 1385-1424. In certain embodiments, the antibodies comprise a VH CDR1 and/or a VH CDR2 and/or a VH CDR3 independently selected from a VH CDR1, VH CDR2, VH CDR3 as depicted in any one of the VH regions depicted in Table 5-33. In certain embodiments, the antibodies comprise a VL CDR1 having the amino acid sequence of any one of SEQ ID NOS: 45, 253-271, 42, 1084, 1090, 1095, 1102, 1108, 1113, 1120, 1126, 1131, 1425-1472, 1681-1684, 1744-1822, 1878-1896, and 1915. In another embodiment, the antibodies comprise a VL CDR2 having the amino acid sequence of any one of SEQ ID NOS: 46, 272-275, 40, 843-846, 43, 1045-1048, 1085, 1096, 1103, 1114, 1121, 1132, 1473-1492, 1526-1528, 1630-1633, 1685-1688, and 1898-1900. In another embodiment, the antibodies comprise a VL CDR3 having the amino acid sequence of any one of SEQ ID NOS: 47, 41, 44, 1056-1058, 1091, 1097, 1109, 1115, 1127, 1133 and 1493-1525. In certain embodiments, the antibodies comprise a VL CDR1 and/or a VL CDR2 and/or a VL CDR3 independently selected from a VL CDR1, VL CDR2, VL CDR3 as depicted in any one of the VL regions depicted in Tables 5-33.

Also provided herein are antibodies comprising one or more VH CDRs and one or more (e.g., one, two or three) VL CDRs listed in Tables 5-33. In particular, provided herein is an antibody comprising a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720) and a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720) and a VL CDR2 (SEQ ID NOS: 46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720) and a VL CDR3 (SEQ ID NOS:47, 41, 44, 1056-1058, 1091, 1097, 1109, 1115, 1127, 1133 or 1493-1525); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917) and a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR2 (SEQ ID NOS:37, 101-104, 50,114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917) and a VL CDR3 (SEQ ID NOS:47, 41, 44, 1056-1058, 1091, 1097, 1109, 1115, 1127, 1133 or 1493-1525); a VH CDR3 (SEQ ID NOS:38, 32, 319, 35, 883-885, 1083, 1089, 1094, 1101, 1107, 1112, 1119, 1125, 1130 or 1385-1424) and a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915); a VH CDR3 (SEQ ID NOS:38, 32, 319, 35, 883-885, 1083, 1089, 1094, 1101, 1107, 1112, 1119, 1125, 1130 or 1385-1424) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR3 (SEQ ID NOS:38, 32, 319, 35, 883-885, 1083, 1089, 1094, 1101, 1107, 1112, 1119, 1125, 1130 or 1385-1424) and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917) and a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917) and a VL CDR3 (SEQ ID NOS:47, 41, 44, 1056-1058, 1091, 1097, 1109, 1115, 1127, 1133 or 1493-1525); a VH CDR2 (SEQ ID NOS:37, 101-104, 50,114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VH CDR3 (SEQ ID NOS:38, 32, 319, 35, 883-885, 1083, 1089, 1094, 1101, 1107, 1112, 1119, 1125, 1130 or 1385-1424) and a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915), a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VH CDR3 (SEQ ID NOS:38, 32, 319, 35, 883-885, 1083, 1089, 1094, 1101, 1107, 1112, 1119, 1125, 1130 or 1385-1424) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VH CDR3 (SEQ ID NOS:38, 32, 319, 35, 883-885, 1083, 1089, 1094, 1101, 1107, 1112, 1119, 1125, 1130 or 1385-1424) and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900) and a VL CDR3 (SEQ ID NOS:47, 41, 44, 1056-1058, 1091, 1097, 1109, 1115, 1127, 1133 or 1493-1525); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR3 (SEQ ID NOS:47, 41, 44, 1056-1058, 1091, 1097, 1109, 1115, 1127, 1133 or 1493-1525); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900) and a VL CDR3 (SEQ ID NOS:47, 41, 44, 1056-1058, 1091, 1097, 1109, 1115, 1127, 1133 or 1493-1525); a VH CDR3 (SEQ ID NOS:38, 32, 319, 35, 883-885, 1083, 1089, 1094, 1101, 1107, 1112, 1119, 1125, 1130 or 1385-1424), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR3 (SEQ ID NOS:38, 32, 319, 35, 883-885, 1083, 1089, 1094, 1101, 1107, 1112, 1119, 1125, 1130 or 1385-1424), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR3 (SEQ ID NOS:47, 41, 44, 1056-1058, 1091, 1097, 1109, 1115, 1127, 1133 or 1493-1525); a VH CDR3 (SEQ ID NOS:38, 32, 319, 35, 883-885, 1083, 1089, 1094, 1101, 1107, 1112, 1119, 1125, 1130 or 1385-1424), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900) and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VH CDR3 (SEQ ID NOS:38, 32, 319, 35, 883-885, 1083, 1089, 1094, 1101, 1107, 1112, 1119, 1125, 1130 or 1385-1424) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900) and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR3 (SEQ ID NOS:38, 32, 319, 35, 883-885, 1083, 1089, 1094, 1101, 1107, 1112, 1119, 1125, 1130 or 1385-1424), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR3 (SEQ ID NOS:38, 32, 319, 35, 883-885, 1083, 1089, 1094, 1101, 1107, 1112, 1119, 1125, 1130 or 1385-1424), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR3 (SEQ ID NOS:38, 32, 319, 35, 883-885, 1083, 1089, 1094, 1101, 1107, 1112, 1119, 1125, 1130 or 1385-1424), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900) and a VL CDR3 (SEQ ID NOS:47, 41, 44, 1056-1058, 1091, 1097, 1109, 1115, 1127, 1133 or 1493-1525); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VH CDR3 (SEQ ID NOS:38, 32, 319, 35, 883-885, 1083, 1089, 1094, 1101, 1107, 1112, 1119, 1125, 1130 or 1385-1424), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VH CDR3 (SEQ ID NOS:38, 32, 319, 35, 883-885, 1083, 1089, 1094, 1101, 1107, 1112, 1119, 1125, 1130 or 1385-1424), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915) and a VL CDR3 (SEQ ID NOS:47, 41, 44, 1056-1058, 1091, 1097, 1109, 1115, 1127, 1133 or 1493-1525); a VH CDR2 (SEQ ID NOS:37, 101-104, 50, 114, 99,100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VH CDR3 (SEQ ID NOS:38, 32, 319, 35, 883-885, 1083, 1089, 1094, 1101, 1107, 1112, 1119, 1125, 1130 or 1385-1424), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900) and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900), and a VL CDR3 (SEQ ID NOS:47, 41, 44, 1056-1058, 1091, 1097, 1109, 1115, 1127, 1133 or 1493-1525); a VH CDR1 (SEQ ID NOS:36, 30, 59-62, 33, 1081, 1086, 1087, 1092, 1099, 1104, 1105, 1110, 1117, 1122, 1123, 1128, 1291-1335, 1291-1335 or 1717-1720), a VH CDR3 (SEQ ID NOS:38, 32, 319, 35, 883-885, 1083, 1089, 1094, 1101, 1107, 1112, 1119, 1125, 1130 or 1385-1424), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900), and a VL CDR3 (SEQ ID NOS: 47, 41, 44, 1056-1058, 1091, 1097, 1109, 1115, 1127, 1133 or 1493-1525); a VH CDR2 (SEQ ID NOS:37, 101-104, 50, 114, 99, 100, 31, 65-74, 83-90, 95, 321, 322, 835-842, 34, 847-858, 49, 886-894, 1070-1078, 1082, 1088, 1093, 1098, 1100, 1106, 1111, 1116, 1118, 1124, 1129, 1134, 1336-1384, 1556-1559, 1829-1847 or 1917), a VH CDR3 (SEQ ID NOS:38, 32, 319, 35, 883-885, 1083, 1089, 1094, 1101, 1107, 1112, 1119, 1125, 1130 or 1385-1424), a VL CDR1 (SEQ ID NOS:45, 253-271, 42, 1084, 1090, 1095, 1102, 1108, 1113, 1120, 1126, 1131, 1425-1472, 1681-1684, 1744-1822, 1878-1896 or 1915), a VL CDR2 (SEQ ID NOS:46, 272-275, 40, 843-846, 43, 1045-1048, 1085, 1096, 1103, 1114, 1121, 1132, 1473-1492, 1526-1528, 1630-1633, 1685-1688 or 1898-1900), and a VL CDR3 (SEQ ID NOS:47, 41, 44, 1056-1058, 1091, 1097, 1109, 1115, 1127, 1133 or 1493-1525); or any combination thereof of the VH CDRs (SEQ ID NOS:36, 30, 59-62, 33, 37, 101-104, 50, 114, 99, 100, 31, 65-74, 83-90, 95, 321, 322, 835-842, 34, 847-858, 49, 886-894 1070-1078, 38, 32, 319, 35, 883-885, 1081, 1086, 1087, 1092, 1099, 1104, 1105, 1110, 1117, 1122, 1123, 1128, 1082, 1088, 1093, 1098, 1100, 1106, 1111, 1116, 1118, 1124, 1129, 1134, 1083, 1089, 1094, 1101, 1107, 1112, 1119, 1125 and 1130) and VL CDRs (SEQ ID NOS:45, 253-271, 42, 46, 272-275, 40, 843-846, 43, 1045-1048, 47, 41, 44, 1056-1058, 1084, 1090, 1095, 1102, 1108, 1113, 1120, 1126, 1131, 1085, 1096, 1103, 1114, 1121, 1132, 1091, 1097, 1109, 1115, 1127 and 1133) listed in Tables 5-33.

In certain embodiments, humanized anti-C10orf54 antibodies bind to a C10orf54 polypeptide, polypeptide fragment or epitope with an affinity comparable to that of one or more of the murine monoclonal antibodies designated 5B, 46A, 97A, 128A, 146C, 208A, 215A, 26A, 164A, 230A, 76E1, 53A, 259A, 33A, 39A, 124A, 175A, 321D, 141A, 51A, 353A, or 305A. The humanized anti-C10orf54 the antibodies can also comprise one, two, three or four human or humanized framework regions of the immunoglobulin heavy chain variable region and/or one, two, three or four human or humanized framework regions of the immunoglobulin light chain variable region. Also provided are heavy and/or light chain FR regions that contain one or more back-mutations in which a human FR residue is exchanged for the corresponding residue present in the parental murine heavy or light chain or another residue comparable residue. In some aspects, the amino acid sequences for CDR1, CDR2, and CDR3 of the heavy and light chains for some of the humanized anti-C10orf54 the antibodies can also include one or more mutations in which a CDR residue as identified in Tables 5-33. The amino acid sequences for FR1, FR2, FR3 and FR4 of the heavy and light chains that can be used for the humanized anti-C10orf54 the antibodies are identified in Tables 5-11 and FIGS. 3-9, 17 and 22-25.

In certain embodiments, a humanized antibody that binds to C10orf54 (e.g., C10orf54 polypeptide, C10orf54 polypeptide fragment, C10orf54 epitope) comprises a VH region that comprises: (1) a VH FR1 having an amino acid sequence selected from the group consisting of SEQ ID NOS:51, 105, 55, 115-121, 39, 58, 895-902, 1550-1555, 1649-1652, 1715, 1716, 1827, and 1828; (2) a VH FR2 having an amino acid sequence selected from the group consisting of SEQ ID NOS:52, 106, 56, 122-124, 63, 64, and 323-326; (3) a VH FR3 having an amino acid sequence selected from the group consisting of SEQ ID NOS:53, 107-113, 57, 125-251, 96-98, 292-318, 327-833, 53, 859-882, 903-1030, 1560-1614, 1653-1679, 1721-1742, and 1848-1875; and/or (4) a VH FR4 having an amino acid sequence of SEQ ID NO:54, 320, 168054, 320, 1680. Accordingly, in some embodiments, the humanized antibody comprises a VH region that includes a VH FR1 having an amino acid sequence selected from the group consisting of SEQ ID NOS:51, 105, 55, 115-121, 39, 58, 895-902, 1550-1555, 1649-1652, 1715, 1716, 1827, and 1828. In some embodiments, the humanized antibody comprises a VH region that includes a VH FR2 having an amino acid sequence selected from the group consisting of SEQ ID NOS:52, 106, 56, 122-124, 63, 64, and 323-326. In some embodiments, the humanized antibody comprises a VH region that includes a VH FR3 having an amino acid sequence selected from the group consisting of SEQ ID NOS:53, 107-113, 57, 125-251, 96-98, 292-318, 327-833, 53, 859-882, 903-1030, 1560-1614, 1653-1679, 1721-1742, and 1848-1875. In some embodiments, the humanized antibody comprises a VH region that includes a VH FR4 having an amino acid sequence of SEQ ID NO:54, 320, 168054, 320, 1680.

In certain embodiments, a humanized antibody that binds to C10orf54 (e.g., C10orf54 polypeptide, C10orf54 polypeptide fragment, C10orf54 epitope) comprises a VL region that comprises: (1) a VL FR1 having an amino acid sequence selected from the group consisting of SEQ ID NOS:75, 252, 79, 277-283, 91, 1031-1037, 1059-1061, 1615-1629, 1743, 1877, and 1878; (2) a VL FR2 having an amino acid sequence selected from the group consisting of SEQ ID NOS:76, 80, 284, 92, 1038-1044, 1062-1067, and 1823-1826; (3) a VL FR3 having an amino acid sequence selected from the group consisting of SEQ ID NOS:77, 276, 81, 285-291, 93, 1049-1055, 1068, 1069, 1689-1714, and 1901; and/or (4) a VL FR4 having an amino acid of SEQ ID NO:78. Accordingly, in some aspects, the humanized antibody comprises a VL region that includes a VL FR1 having an amino acid sequence selected from the group consisting of SEQ ID NOS:75, 252, 79, 277-283, 91, 1031-1037, 1059-1061, 1615-1629, 1743, 1877, and 1878. In some aspects, the humanized antibody comprises a VL region that includes a VL FR2 having an amino acid sequence selected from the group consisting of SEQ ID NOS:76, 80, 284, 92, 1038-1044, 1062-1067, and 1823-1826. In some aspects, the humanized antibody comprises a VL region that includes a VL FR3 having an amino acid sequence selected from the group consisting of SEQ ID NOS:77, 276, 81, 285-291, 93, 1049-1055, 1068, 1069, 1689-1714, and 1901. In some aspects, the humanized antibody comprises a VL region that includes a VL FR4 having an amino acid of SEQ ID NO:78.

In certain embodiments, a humanized antibody that binds to C10orf54 (e.g., C10orf54 polypeptide, C10orf54 polypeptide fragment, C10orf54 epitope) comprises a VH region and a VL region, wherein the VH region further comprises: (1) a VH FR1 having an amino acid sequence selected from the group consisting of SEQ ID NOS:51, 105, 55, 115-121, 39, 58, 895-902, 1550-1555, 1649-1652, 1715, 1716, 1827, and 1828; (2) a VH FR2 having an amino acid sequence selected from the group consisting of SEQ ID NOS:52, 106, 56, 122-124, 63, 64, and 323-326; (3) a VH FR3 having an amino acid sequence selected from the group consisting of SEQ ID NOS:53, 107-113, 57, 125-251, 96-98, 292-318, 327-833, 53, 859-882, 903-1030, 1560-1614, 1653-1679, 1721-1742, and 1848-1875; and/or (4) a VH FR4 having an amino acid sequence of SEQ ID NO:54, 320, 168054, 320, 1680; and wherein the VL region further comprises: (1) a VL FR1 having an amino acid sequence selected from the group consisting of SEQ ID NOS:75, 252, 79, 277-283, 91, 1031-1037, 1059-1061, 1615-1629, 1743, 1877, and 1878; (2) a VL FR2 having an amino acid sequence selected from the group consisting of SEQ ID NOS:76, 80, 284, 92, 1038-1044, 1062-1067, and 1823-1826; (3) a VL FR3 having an amino acid sequence selected from the group consisting of SEQ ID NOS:77, 276, 81, 285-291, 93, 1049-1055, 1068, 1069, 1689-1714, and 1901; and/or (4) a VL FR4 having an amino acid of SEQ ID NO:78.

Also provided herein are antibodies comprising one or more (e.g., one, two, three or four) VH FRs and one or more VL FRs listed in Tables 5-11. In particular, provided herein is an antibody comprising a VH FR1 (SEQ ID NOS:51, 105, 55, 115-121, 39, 58, 895-902, 1550-1555, 1649-1652, 1715, 1716, 1827 or 1828) and a VL FR1 (SEQ ID NOS:75, 252, 79, 277-283, 91, 1031-1037, 1059-1061, 1615-1629, 1743, 1877 or 18781037, 1059-1061, 1615-1629, 1743, 1877 or 1878); a VH FR1 (SEQ ID NOS:51, 105, 55, 115-121, 39, 58, 895-902, 1550-1555, 1649-1652, 1715, 1716, 1827 or 1828) and a VL FR2 (SEQ ID NOS:76, 80, 284, 92, 1038-1044, 1062-1067 or 1823-18261044, 1062-1067 or 1823-1826); a VH FR1 (SEQ ID NOS:51, 105, 55, 115-121, 39, 58, 895-902, 1550-1555, 1649-1652, 1715, 1716, 1827 or 1828) and a VL FR3 (SEQ ID NOS:77, 276, 81, 285-291, 93, 1049-1055, 1068, 1069, 1689-1714 or 19011068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828) and a VL FR4 (SEQ ID NO:78); a VH FR2 (SEQ ID NOS:52, 106, 56, 122-124, 63, 64 or 323-326) and a VL FR1 (SEQ ID NOS:75, 252, 79, 277-283, 91, 1031-1037, 1059-1061, 1615-1629, 1743, 1877 or 18781037, 1059-1061, 1615-1629, 1743, 1877 or 1878); a VH FR2 (SEQ ID NOS:52, 106, 56, 122-124, 63, 64 or 323-326) and a VL FR2 (SEQ ID NOS:76, 80, 284, 92, 1038-1044, 1062-1067 or 1823-18261044, 1062-1067 or 1823-1826); a VH FR2 (SEQ ID NOS:52, 106, 56, 122-124, 63, 64 or 323-326) and a VL FR3 (SEQ ID NOS:77, 276, 81, 285-291, 93, 1049-1055, 1068, 1069, 1689-1714 or 19011068, 1069, 1689-1714 or 1901); a VH FR2 (SEQ ID NOS:52, 106, 56, 122-124, 63, 64 or 323-326) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875882, 903-1030, 1560-1614, 1653-1679, 1721-1742 or 1848-1875) and a VH FR1 (SEQ ID NOS:51, 105, 55, 115-121, 39, 58, 895-902, 1550-1555, 1649-1652, 1715, 1716, 1827 or 1828); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875882, 903-1030, 1560-1614, 1653-1679, 1721-1742 or 1848-1875) and a VL FR2 (SEQ ID NOS:76, 80, 284, 92, 1038-1044, 1062-1067 or 1823-1826); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875882, 903-1030, 1560-1614, 1653-1679, 1721-1742 or 1848-1875) and a VL FR3 (SEQ ID NOS:77, 276, 81, 285-291, 93, 1049-1055, 1068, 1069, 1689-1714 or 1901); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875882, 903-1030, 1560-1614, 1653-1679, 1721-1742 or 1848-1875) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326) and a VL FR1 (SEQ ID NOS:75, 252, 79, 277-283, 91, 1031-1037, 1059-1061, 1615-1629, 1743, 1877 or 1878); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875) and a VL FR1 (SEQ ID NOS:75, 252, 79, 277-283, 91, 1031-1037, 1059-1061, 1615-1629, 1743, 1877 or 1878), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875) and a VL FR2 (SEQ ID NOS:76, 80, 284, 92, 1038-1044, 1062-1067 or 1823-1826); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VL FR2 (SEQ ID NOS:76, 80, 284, 92, 1038-1044, 1062-1067 or 1823-1826) and a VL FR4 (SEQ ID NO:78); a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR2 (SEQ ID NOS:52, 106, 56, 122-124, 63, 64 or 323-326), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VL FR2 (SEQ ID NOS:76, 80, 284, 92, 1038-1044, 1062-1067 or 1823-1826) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826) and a VL FR4 (SEQ ID NO:78); a VH FR4 (SEQ ID NO:54, 320, 168054, 320, 1680), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR4 (SEQ ID NO:54, 320, 1680), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR4 (SEQ ID NO:54, 320, 1680), a VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875) and a VL FR1 (SEQ ID NOS:75, 252, 79, 277-283, 91, 1031-1037, 1059-1061, 1615-1629, 1743, 1877 or 1878); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680) and a VL FR1 (SEQ ID NOS:75, 252, 79, 277-283, 91, 1031-1037, 1059-1061, 1615-1629, 1743, 1877 or 1878); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR1 (SEQ ID NOS:75, 252, 79, 277-283, 91, 1031-1037, 1059-1061, 1615-1629, 1743, 1877 or 1878); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR1 (SEQ ID NOS:75, 252, 79, 277-283, 91, 1031-1037, 1059-1061, 1615-1629, 1743, 1877 or 1878); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR2 (SEQ ID NOS:76, 80, 284, 92, 1038-1044, 1062-1067 or 1823-1826); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS: 75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS: 75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR2 (SEQ ID NOS:76, 80, 284, 92, 1038-1044, 1062-1067 or 1823-1826) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826) and a VL FR4 (SEQ ID NO:78); a VH FR2 (SEQ ID NOS:52, 106, 56, 122-124, 63, 64 or 323-326), a VH FR4 (SEQ ID NO:54, 320, 1680), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VH FR4 (SEQ ID NO:54, 320, 1680), a VL FR2 (SEQ ID NOS:76, 80, 284, 92, 1038-1044, 1062-1067 or 1823-1826) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VH FR4 (SEQ ID NO:54, 320, 1680), a VL FR3 (SEQ ID NOS:77, 276, 81, 285-291, 93, 1049-1055, 1068, 1069, 1689-1714 or 1901) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826) and a VL FR4 (SEQ ID NO:78); a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS: 75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901) and a VL FR4 (SEQ ID NO:78); a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826) and a VL FR4 (SEQ ID NO:78); a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901) and a VL FR4 (SEQ ID NO:78); a VH FR4 (SEQ ID NO:54, 320, 1680), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR1 (SEQ ID NOS:75, 252, 79, 277-283, 91, 1031-1037, 1059-1061, 1615-1629, 1743, 1877 or 1878); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR2 (SEQ ID NOS:76, 80, 284, 92, 1038-1044, 1062-1067 or 1823-1826) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901), and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR3 (SEQ ID NOS:77, 276, 81, 285-291, 93, 1049-1055, 1068, 1069, 1689-1714 or 1901); a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR4 (SEQ ID NO:78); a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901), and a VL FR4 (SEQ ID NO:78); a VH FR2 (SEQ ID NOS:52, 106, 56, 122-124, 63, 64 or 323-326), a VH FR4 (SEQ ID NO:54, 320, 1680), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR3 (SEQ ID NOS:77, 276, 81, 285-291, 93, 1049-1055, 1068, 1069, 1689-1714 or 1901); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR3 (SEQ ID NOS:77, 276, 81, 285-291, 93, 1049-1055, 1068, 1069, 1689-1714 or 1901), and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS: 75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), a VL FR3 (SEQ ID NOS:77, 276, 81, 285-291, 93, 1049-1055, 1068, 1069, 1689-1714 or 1901), and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR1 (SEQ ID NOS: 75, 252, 79, 277-283, 91, 1031-1037, 1059-1061, 1615-1629, 1743, 1877 or 1878) and a VL FR2 (SEQ ID NOS:76, 80, 284, 92, 1038-1044, 1062-1067 or 1823-1826); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR1 (SEQ ID NOS:75, 252, 79, 277-283, 91, 1031-1037, 1059-1061, 1615-1629, 1743, 1877 or 1878) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR1 (SEQ ID NOS: 75, 252, 79, 277-283, 91, 1031-1037, 1059-1061, 1615-1629, 1743, 1877 or 1878) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR2 (SEQ ID NOS: 76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR3 (SEQ ID NOS: 77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), a VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR1 (SEQ ID NOS: 75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826) and a VL FR3 (SEQ ID NOS:77, 276, 81, 285-291, 93, 1049-1055, 1068, 1069, 1689-1714 or 1901); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR1 (SEQ ID NOS:51, 105, 55, 115-121, 39, 58, 895-902, 1550-1555, 1649-1652, 1715, 1716, 1827 or 1828), a VH FR2 (SEQ ID NOS:52, 106, 56, 122-124, 63, 64 or 323-326), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); a VH FR2 (SEQ ID NOS:52, 106, 56, 122-124, 63, 64 or 323-326), a VH FR3 (SEQ ID NOS:53, 107-113, 57, 125-251, 96-98, 292-318, 327-833, 53, 859-882, 903-1030, 1560-1614, 1653-1679, 1721-1742 or 1848-1875), a VH FR4 (SEQ ID NO:54, 320, 1680), a VL FR1 (SEQ ID NOS:75, 252, 79, 277-283, 91, 1031-1037, 1059-1061, 1615-1629, 1743, 1877 or 1878), VL FR2 (SEQ ID NOS:76, 80, 284, 92, 1038-1044, 1062-1067 or 1823-1826), VL FR3 (SEQ ID NOS:77, 276, 81, 285-291, 93, 1049-1055, 1068, 1069, 1689-1714 or 1901) and a VL FR4 (SEQ ID NO:78); or any combination thereof of the VH FRs (SEQ ID NOS:51, 105, 55, 115-121, 39, 58, 895-902, 52, 106, 56, 122-124, 63, 64, 323-326, 53, 107-113, 57, 125-251, 96-98, 292-318, 327-833, 53, 859-882 903-1030, 54, 320, 1680) and VL FRs (SEQ ID NOS:75, 252, 79, 277-283, 91, 1031-1037, 1059-1061, 76, 80, 284, 92, 1038-1044, 1062-1067, 77, 276, 81, 285-291, 93, 1049-1055, 1068, 1069, or 78) listed in Tables 5-11.

In certain embodiments, a humanized antibody that binds to A group of C10orf54 proteins or chimeric proteins described herein comprises a VH region comprising: (1) a VH FR1 having an amino acid sequence selected from the group consisting of SEQ ID NOS: 51, 1550-1555, 105, and 1649-1652; (2) a VH FR2 having an amino acid sequence selected from the group consisting of SEQ ID NOS: 52 and 106; (3) a VH FR3 having an amino acid sequence selected from the group consisting of SEQ ID NOS: 1560-1614, and 1653-1679; and/or (4) a VH FR4 having an amino acid sequence selected from the group consisting of SEQ ID NOS: 54 and 1680. In certain embodiments, a humanized antibody that binds to A group of C10orf54 proteins or chimeric proteins described herein comprises a VL region comprising: (1) a VL FR1 having an amino acid sequence selected from the group consisting of SEQ ID NOS: 1615-1629, 79, and 278; (2) a VL FR2 having an amino acid sequence selected from the group consisting of SEQ ID NOS: 92, 80, and 284; (3) a VL FR3 having an amino acid sequence selected from the group consisting of SEQ ID NOS: 1634-1648, 81, 1689-1714, 285, 286, and 288; and/or (4) a VL FR4 having an amino acid of SEQ ID NO: 78. In certain embodiments, a humanized antibody that binds to A group of C10orf54 proteins or chimeric proteins described herein comprises a VH region and a VL region, wherein the VH region further comprises: (1) a VH FR1 having an amino acid sequence selected from the group consisting of SEQ ID NOS: 51, 1550-1555, 105, and 1649-1652; (2) a VH FR2 having an amino acid sequence selected from the group consisting of SEQ ID NOS: 52 and 106; (3) a VH FR3 having an amino acid sequence selected from the group consisting of SEQ ID NOS: 1560-1614, and 1653-1679; and/or (4) a VH FR4 having an amino acid sequence selected from the group consisting of SEQ ID NOS: 54 and 1680; and wherein the VL region further comprises: (1) a VL FR1 having an amino acid sequence selected from the group consisting of SEQ ID NOS: 1615-1629, 79, and 278; (2) a VL FR2 having an amino acid sequence selected from the group consisting of SEQ ID NOS: 92, 80, and 284; (3) a VL FR3 having an amino acid sequence selected from the group consisting of SEQ ID NOS: 1634-1648, 81, 1689-1714, 285, 286, and 288; and/or (4) a VL FR4 having an amino acid sequence of SEQ ID NO: 78.

In certain embodiments, a humanized antibody that binds to A group of C10orf54 proteins or chimeric proteins described herein comprises a VH region comprising: (1) a VH FR1 having an amino acid sequence selected from the group consisting of SEQ ID NOS: 51, 39, 1715, 1716, 1550, 1827, 1828, 105, 55, and 115-121; (2) a VH FR2 having an amino acid sequence selected from the group consisting of SEQ ID NOS: 52, 106, 63, 64, 56, 323-326, and 122-124; (3) a VH FR3 having an amino acid sequence selected from the group consisting of SEQ ID NOS: 1560, 1561, 1721-1742, 1566, 1567, 1571, 1575, 1585, 1562, 1563, 1848-1875, 1565-1568, 1570-1572, 1574, 1575, 1577, 1578, 1581, 1582, 1584, 1585, 1587, 1591, 1593, 1594, 1597, 1602, 1603, 53, 107, 96-98, 292-318, 57, and 327-833; and/or (4) a VH FR4 having an amino acid sequence selected from the group consisting of SEQ ID NOS: 54 and 320. In certain embodiments, a humanized antibody that binds to A group of C10orf54 proteins or chimeric proteins described herein comprises a VL region comprising: (1) a VL FR1 having an amino acid sequence selected from the group consisting of SEQ ID NOS: 1743, 75, 252, 1878, 1877, 79, and 277-283; (2) a VL FR2 having an amino acid sequence selected from the group consisting of SEQ ID NOS: 1823-1826, 76, 80, and 284; (3) a VL FR3 having an amino acid sequence selected from the group consisting of SEQ ID NOS: 77, 276, 1901, 81, and 285-291; and/or (4) a VL FR4 having an amino acid sequence of SEQ ID NO: 78. In certain embodiments, a humanized antibody that binds to A group of C10orf54 proteins or chimeric proteins described herein comprises a VH region and a VL region, wherein the VH region further comprises: (1) a VH FR1 having an amino acid sequence selected from the group consisting of SEQ ID NOS: 51, 39, 1715, 1716, 1550, 1827, 1828, 105, 55, and 115-121; (2) a VH FR2 having an amino acid sequence selected from the group consisting of SEQ ID NOS: 52, 106, 63, 64, 56, 323-326, and 122-124; (3) a VH FR3 having an amino acid sequence selected from the group consisting of SEQ ID NOS: 1560, 1561, 1721-1742, 1566, 1567, 1571, 1575, 1585, 1562, 1563, 1848-1875, 1565-1568, 1570-1572, 1574, 1575, 1577, 1578, 1581, 1582, 1584, 1585, 1587, 1591, 1593, 1594, 1597, 1602, 1603, 53, 107, 96-98, 292-318, 57, and 327-833; and/or (4) a VH FR4 having an amino acid sequence selected from the group consisting of SEQ ID NOS: 54 and 320; and wherein the VL region further comprises: (1) a VL FR1 having an amino acid sequence selected from the group consisting of SEQ ID NOS: 1743, 75, 252, 1878, 1877, 79, and 277-283; (2) a VL FR2 having an amino acid sequence selected from the group consisting of SEQ ID NOS: 1823-1826, 76, 80, and 284; (3) a VL FR3 having an amino acid sequence selected from the group consisting of SEQ ID NOS: 77, 276, 1901, 81, and 285-291; and/or (4) a VL FR4 having an amino acid sequence of SEQ ID NO: 78.

In certain embodiments, a humanized antibody that binds to A group of C10orf54 proteins or chimeric proteins described herein comprises a VH region comprising: (1) a VH FR1 having an amino acid sequence selected from the group consisting of SEQ ID NOS: 51, 39, 105, 58, 55, 115-121, and 895-902; (2) a VH FR2 having an amino acid sequence selected from the group consisting of SEQ ID NOS: 52, 106, 56, and 122-124; (3) a VH FR3 having an amino acid sequence selected from the group consisting of SEQ ID NOS: 53, 107-113, 859-882, 57, 125-251, and 903-1030; and/or (4) a VH FR4 having an amino acid sequence of SEQ ID NO: 54. In certain embodiments, a humanized antibody that binds to A group of C10orf54 proteins or chimeric proteins described herein comprises a VL region comprising: (1) a VL FR1 having an amino acid sequence selected from the group consisting of SEQ ID NOS: 91, 1031-1037, 79, and 1059-1061; (2) a VL FR2 having an amino acid sequence selected from the group consisting of SEQ ID NOS: 92, 1038-1044, 80, 284, and 1062-1067; (3) a VL FR3 having an amino acid sequence selected from the group consisting of SEQ ID NOS: 93, 1049-1055, 81, 1068, 285, and 1069; and/or (4) a VL FR4 having an amino acid sequence of SEQ ID NO: 78. In certain embodiments, a humanized antibody that binds to A group of C10orf54 proteins or chimeric proteins described herein comprises a VH region and a VL region, wherein the VH region further comprises: (1) a VH FR1 having an amino acid sequence selected from the group consisting of SEQ ID NOS: 51, 39, 105, 58, 55, 115-121, and 895-902; (2) a VH FR2 having an amino acid sequence selected from the group consisting of SEQ ID NOS: 52, 106, 56, and 122-124; (3) a VH FR3 having an amino acid sequence selected from the group consisting of SEQ ID NOS: 53, 107-113, 859-882, 57, 125-251, and 903-1030; and/or (4) a VH FR4 having an amino acid sequence of SEQ ID NO: 54; and wherein the VL region further comprises: (1) a VL FR1 having an amino acid sequence selected from the group consisting of SEQ ID NOS: 91, 1031-1037, 79, and 1059-1061; (2) a VL FR2 having an amino acid sequence selected from the group consisting of SEQ ID NOS: 92, 1038-1044, 80, 284, and 1062-1067; (3) a VL FR3 having an amino acid sequence selected from the group consisting of SEQ ID NOS: 93, 1049-1055, 81, 1068, 285, and 1069; and/or (4) a VL FR4 having an amino acid sequence of SEQ ID NO: 78.

In some embodiments, antibodies provided herein are antibodies that bind to C10orf54 (e.g., C10orf54 polypeptide, C10orf54 polypeptide fragment, C10orf54 epitope), and include antibodies comprising derivatives of the VH domains, VH CDRs, VL domains, and VL CDRs described herein that bind to C10orf54 (e.g., C10orf54 polypeptide, C10orf54 polypeptide fragment, C10orf54 epitope). Also provided herein are antibodies comprising derivatives of the murine monoclonal antibody 5B, 46A, 97A, 128A, 146C, 208A, 215A, 26A, 164A, 230A, 76E1, 53A, 259A, 33A, 39A, 124A, 175A, 321D, 141A, 51A, 353A, or 305A, wherein the antibodies bind to C10orf54 (e.g., C10orf54 polypeptide, C10orf54 polypeptide fragment, C10orf54 epitope). Standard techniques known to those of skill in the art can be used to introduce mutations in the nucleotide sequence encoding an antibody, or fragment thereof, provided herein, including, for example, site-directed mutagenesis and PCR-mediated mutagenesis which results in amino acid substitutions. In certain embodiments, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In one embodiment, an antibody that binds to C10orf54 (e.g., C10orf54 polypeptide, C10orf54 polypeptide fragment, C10orf54 epitope) comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the murine monoclonal antibody 5B, 46A, 97A, 128A, 146C, 208A, 215A, 26A, 164A, 230A, 76E1, 53A, 259A, 33A, 39A, 124A, 175A, 321 D, 141 A, 51 A, 353A, or 305A, or an antigen-binding fragment thereof, such as a VH domain or VL domain. In one embodiment, an antibody that binds to C10orf54 (e.g., C10orf54 polypeptide, C10orf54 polypeptide fragment, C10orf54 epitope) comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in SEQ ID NOS:12-29. In another embodiment, an antibody that binds to C10orf54 (e.g., C10orf54 polypeptide, C10orf54 polypeptide fragment, C10orf54 epitope) comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in Tables 5-33. In yet another embodiment, an antibody that binds to C10orf54 (e.g., C10orf54 polypeptide, C10orf54 polypeptide fragment, C10orf54 epitope) comprises a VH CDR and/or a VL CDR amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a VH CDR amino acid sequence depicted in Tables 5-33 and/or a VL CDR amino acid sequence depicted in Tables 5-33.

In certain embodiments, the antibodies used in accordance with the methods provided herein have a high affinity for a C10orf54 polypeptide, or polypeptide fragment or epitope thereof. In one embodiment, the antibodies used in accordance with the methods provided herein have a higher affinity for a C10orf54 antibody than known antibodies (e.g., commercially available monoclonal antibodies discussed elsewhere herein). In a specific embodiment, the antibodies used in accordance with the methods provided herein have a 2- to 10-fold (or more) higher affinity for a C10orf54 antigen than a known anti-C10orf54 antibody as assessed by techniques described herein or known to one of skill in the art (e.g., a BIAcore assay). In accordance with these embodiments, the affinity of the antibodies are, in one embodiment, assessed by a BIAcore assay.

In a specific embodiment, an antibody that binds C10orf54 (e.g., C10orf54 polypeptide, C10orf54 polypeptide fragment, C10orf54 epitope) comprises an amino acid sequence of a VH domain and/or an amino acid sequence a VL domain encoded by a nucleotide sequence that hybridizes to (1) the complement of a nucleotide sequence encoding any one of the VH and/or VL domains depicted in Tables 2 and 4-10 under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In another embodiment, an antibody that binds C10orf54 (e.g., C10orf54 polypeptide, C10orf54 polypeptide fragment, C10orf54 epitope) comprises an amino acid sequence of a VH CDR or an amino acid sequence of a VL CDR encoded by a nucleotide sequence that hybridizes to the complement of a nucleotide sequence encoding any one of the VH CDRs and/or VL CDRs depicted in Tables 2 and 4-10 under stringent conditions (e.g., hybridization to filter-bound DNA in 6×SSC at about 45° C. followed by one or more washes in 0.2×SSC/0.1% SDS at about 50-65° C.), under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3) In some embodiments, antibodies provided herein are chemically modified, e.g., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

Also provided herein are antibodies that bind to C10orf54 (e.g., C10orf54 polypeptide, C10orf54 polypeptide fragment, C10orf54 epitope) which comprises a framework region known to those of skill in the art (e.g., a human or non-human fragment). The framework region may, for example, be naturally occurring or consensus framework regions. In specific embodiments, the framework region of an antibody provided herein is human (see, e.g., Chothia et al., 1998, *J. Mol. Biol.* 278:457-479 for a listing of human framework regions, which is incorporated by reference herein in its entirety). See also Kabat et al. (1991) *Sequences of Proteins of Immunological Interest* (U.S. Department of Health and Human Services, Washington, D.C.) 5th ed.

Also provided herein are antibodies that bind to C10orf54 (e.g., C10orf54 polypeptide, C10orf54 polypeptide fragment, C10orf54 epitope), the antibodies comprising the amino acid sequence of one or more of the CDRs of the murine monoclonal antibody 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A, including those also provided in Tables 5-33, or humanized variants thereof (e.g., VH CDRs or VL CDRs of Tables 5-11), and human framework regions with one or more amino acid substitutions at one, two, three or more of the following residues: (a) rare framework residues that differ between the murine antibody framework (e.g., donor antibody framework) and the human antibody framework (e.g., acceptor antibody framework); (b) Venier zone residues when differing between donor antibody framework and acceptor antibody framework; (c) interchain packing residues at the VH/VL interface that differ between the donor antibody framework and the acceptor antibody framework; (d) canonical residues which differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the VH domain and the VL domain. In certain embodiments, antibodies that bind to a C10orf54 antigen comprising the human framework regions with one or more amino acid substitutions at one, two, three or more of the above-identified residues are antagonistic C10orf54 antibodies. In certain embodiments, antibodies that bind to a C10orf54 antigen comprising the human framework regions with one or more amino acid substitutions at one, two, three or more of the above-identified residues are agonistic C10orf54 antibodies.

Antibodies provided herein include, but are not limited to, synthetic antibodies, monoclonal antibodies, recombinantly produced antibodies, multispecific antibodies (including bispecific antibodies), human antibodies, humanized antibodies, camelized antibodies, chimeric antibodies, intrabodies, anti-idiotypic (anti-Id) antibodies, and functional fragments of any of the above. Non-limiting examples of functional fragments include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (sdFv), Fd fragments, Fv fragments, diabody, triabody, tetrabody and minibody.

In particular, antibodies provided herein include immunoglobulin molecules and immunologically active portions of immunoglobulin molecules, e.g., molecules that contain an antigen binding site that bind to C10orf54 (e.g., C10orf54 polypeptide, C10orf54 polypeptide fragment, C10orf54 epitope). The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

Variants and derivatives of antibodies include antibody functional fragments that retain the ability to bind to C10orf54 (e.g., C10orf54 polypeptide, C10orf54 polypeptide fragment, C10orf54 epitope). Exemplary functional fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')$_2$ (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in *The Pharmacology of Monoclonal Antibodies*, vol. 113, Rosenburg and Moore eds. Springer-Verlag, New York, pp. 269-315 (1994).

The antibodies provided herein may be monospecific, bispecific, trispecific or of greater multispecificity. Multispecific antibodies may be specific for different epitopes of a C10orf54 polypeptide or may be specific for both a C10orf54 polypeptide as well as for a heterologous epitope, such as a heterologous polypeptide or solid support material. In specific embodiments, the antibodies provided herein are monospecific for a given epitope of a C10orf54 polypeptide and do not bind to other epitopes.

Also provided herein are fusion proteins comprising an antibody provided herein that binds to a C10orf54 antigen and a heterologous polypeptide. In some embodiments, the heterologous polypeptide to which the antibody is fused is useful for targeting the antibody to cells having cell surface-expressed C10orf54.

Also provided herein are panels of antibodies that bind to a C10orf54 antigen. In specific embodiments, panels of antibodies have different association rate constants different dissociation rate constants, different affinities for C10orf54 antigen, and/or different specificities for a C10orf54 antigen. In some embodiments, the panels comprise or consist of about 10, about 25, about 50, about 75, about 100, about 125, about 150, about 175, about 200, about 250, about 300, about 350, about 400, about 450, about 500, about 550, about 600, about 650, about 700, about 750, about 800, about 850, about 900, about 950, or about 1000 antibodies or more. Panels of antibodies can be used, for example, in 96 well or 384 well plates, such as for assays such as ELISAs.

Antibody Conjugates and Fusion Proteins

In some embodiments, antibodies provided herein are conjugated or recombinantly fused to a diagnostic, detectable or therapeutic agent or any other molecule. The conjugated or recombinantly fused antibodies can be useful, e.g., for monitoring or prognosing the onset, development, progression and/or severity of a C10orf54-mediated disease as part of a clinical testing procedure, such as determining the efficacy of a particular therapy.

Such diagnosis and detection can accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; chemiluminescent material, such as but not limited to, an acridinium based compound or a HALOTAG; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

Also provided herein are antibodies that are conjugated or recombinantly fused to a therapeutic moiety (or one or more therapeutic moieties), as well as uses thereof. The antibody may be conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclophosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, auristatin F, monomethyl auristatin E, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885, 834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, an antibody provided herein may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

Also provided herein are antibodies that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90 or about 100 amino acids) to generate fusion proteins, as well as uses thereof. In particular, provided herein are fusion proteins comprising an antigen-binding fragment of an antibody provided herein (e.g., a Fab fragment, Fd fragment, Fv fragment, F(ab)$_2$ fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses C10orf54 or an C10orf54 receptor. For example, an antibody that binds to a cell surface receptor expressed by a particular cell type (e.g., an immune cell) may be fused or conjugated to a modified antibody provided herein.

A conjugated or fusion protein can comprise any antibody provided herein described herein and a heterologous polypeptide. In one embodiment, a conjugated or fusion protein provided herein comprises the VH or VL domain of any one of the murine monoclonal antibodies 5B, 46A, 97A, 128A, 146C, 208A, 215A, 26A, 164A, 230A, 76E1, 53A, 259A, 33A, 39A, 124A, 175A, 321 D, 141A, 51A, 353A, or 305A, as depicted in Table 2, and a heterologous polypeptide. In another embodiment, a conjugated or fusion protein provided herein comprises a VH domain having the amino acid sequence of any one of the VH domains depicted in Tables 5-33, and/or a VL domain having the amino acid sequence of any one of the VL domains depicted Tables 5-33, and a heterologous polypeptide. In another embodiment, a conjugated or fusion protein provided herein comprises one or more VH CDRs having the amino acid sequence of any one of the VH CDRs depicted in Tables 5-33, and a heterologous polypeptide. In another embodiment, a conjugated or fusion protein comprises one or more VL CDRs having the amino acid sequence of any one of the VL CDRs depicted in Tables 5-33, and a heterologous polypeptide. In another embodiment, a conjugated or fusion protein provided herein comprises at least one VH domain and at least one VL domain depicted in Tables 5-33, and a heterologous polypeptide. In yet another embodiment, a conjugated or fusion protein provided herein comprises at least one VH CDR and at least one VL CDR depicted in Tables 5-33, and a heterologous polypeptide.

In addition, an antibody provided herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$LU, $^{131}$Y, $^{131}$Ho, $^{131}$Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Moreover, antibodies provided herein can be fused to marker sequences, such as a peptide to facilitate purification. In specific embodiments, the marker amino acid sequence is a hexa-histidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992, which are incorporated herein by reference in their entireties.

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of antibodies provided herein (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding an antibody provided herein may be recombined with one or more components, motifs, sections, parts, domains, fragments, etc. of one or more heterologous molecules.

An antibody provided herein can also be conjugated to a second antibody to form an antibody heteroconjugate as described in U.S. Pat. No. 4,676,980, which is incorporated herein by reference in its entirety.

The therapeutic moiety or drug conjugated or recombinantly fused to an antibody provided herein that binds to a C10orf54 antigen should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody provided herein: the nature of the disease, the severity of the disease, and the condition of the subject.

Antibodies provided herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Antibody-Drug Conjugate (Adc)

In some embodiments, provided herein are antibody-drug conjugates, including an antibody-drug conjugate of the following formulas (Ia) and (Ib):

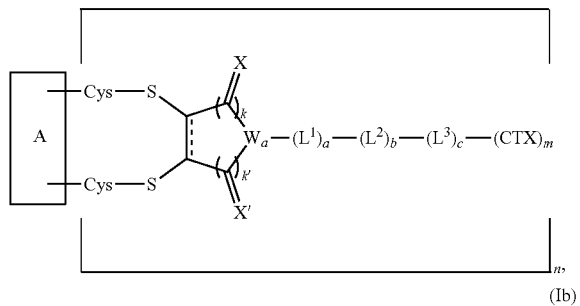

(Ia)

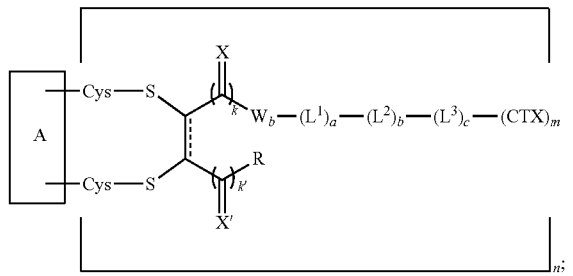

(Ib)

or a pharmaceutically acceptable salt thereof;
wherein:
A is an antibody or antibody fragment;
the two depicted cysteine residues are from an opened cysteine-cysteine disulfide bond in A;
each X and X is independently O, S, NH, or $NR^1$ wherein $R^1$ is $C_{1-6}$ alkyl;
$W_a$ is =N—, =CH—, =CHCH$_2$—, =C($R^2$)—, or =CHCH($R^2$)—; $W_b$—NH—, —N($R^1$)—, —CH$_2$—, —CH$_2$—NH—, —CH$_2$—N($R^1$)—, —CH$_2$CH$_2$—, —CH($R^2$)—, or —CH$_2$CH($R^2$)—; wherein $R^1$ and $R^2$ are independently $C_{1-6}$ alkyl;
CTX is a cytotoxin;
R is any chemical group; or R is absent;
each $L^1$, $L^2$ and $L^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —C(O)CH$_3$, —CN, —NH—, —NH$_2$, —O—, —OH, —NHCH$_3$, —N(CH$_3$)$_2$, and $C_{1-3}$ alkyl;
a, b and c are each independently an integer of 0, 1, 2 or 3, provided that at least one of a, b or c is 1;
each k and k' is independently an integer of 0 or 1;
each p is independently an integer of 1 to 14;
each q is independently an integer from 1 to 12;
each AA is independently an amino acid;
each r is 1 to 12;
m is an integer of 1 to 4;
n is an integer of 1 to 4; and
the ===== bond represents a single or a double bond.

In certain embodiments of the antibody-drug conjugate of formula (Ib), R is selected from the group consisting of W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, and W-$(L^1)_a$-$(L^2)_b$-$(L^3)_c$-Z, as defined herein. In certain embodiments, R is selected from the group consisting of W, $(L^1)_a$, $(L^2)_b$, $(L^3)_c$, and W-$(L^1)_a$-$(L^2)_b$-$(L^3)_c$. In certain embodiments, R is selected from the group consisting of Z, $(L^1)_a$-$(L^2)_b$-$(L^3)_c$-Z, and W-$(L^1)_a$-$(L^2)_b$-$(L^3)_c$-Z.

In certain embodiments of the antibody-drug conjugate of formula (Ia) or (Ib), n is an integer of 2 (e.g., two heavy chain-light chain interchain disulfide bonds). In certain embodiments, n is an integer of 3 (e.g., two heavy chain-light chain interchain disulfide bonds and one hinge heavy chain-heavy chain interchain disulfide bond). In certain embodiments, n is an integer of 4 (e.g., two heavy chain-light chain interchain disulfide bonds and two hinge heavy chain-heavy chain interchain disulfide bonds).

In certain embodiments of the antibody-drug conjugate of formula (Ib), R is a detectable probe. In certain embodiments, R is a fluorophore, chromophore, radiolabel, enzyme, ligand, antibody or antibody fragment. In certain embodiments, R is a ligand (e.g., a ligand specific for a receptor on a tumor cell, such as a prostate specific membrane antigen, or a virally infected cell, such as an HIV infected cell).

In certain embodiments of the antibody-drug conjugate of formula (Ib), R is bonded to the rest of the linker molecule via an amide, an N—($C_{1-6}$ alkyl)amide, a carbamate, an N—($C_{1-6}$ alkyl)carbamate, an amine, an N—($C_{1-6}$ alkyl) amine, an ether, a thioether, an urea, an N—($C_{1-6}$ alkyl)urea, or an N,N-di($C_{1-6}$ alkyl)urea bond.

In certain embodiments of the antibody-drug conjugate of formula (Ia) or (Ib), each $L^1$, $L^2$ and $L^3$ is independently selected from the group consisting of —NHC(O)—, —C(O)NH—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$, -(AA)$_r$-, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$alkyl, —C(O)CH$_3$, —CN, —NH—, —NH$_2$, —O—, —OH, —NHCH$_3$, —N(CH$_3$)$_2$, and C$_{1-3}$ alkyl; where a, b and c are each independently 0 or 1; and each p and r is independently 1, 2 or 3. In certain embodiments, one or more of the $L^1$, $L^2$ and $L^3$ is -(AA)$_r$-, wherein -(AA)$_r$- is ValCit (e.g., the first amino acid is Valine, the second amino acid is Citrulline, and r is 1). In certain embodiments, one or more of the $L^1$, $L^2$ and $L^3$ is -(AA)$_r$-, wherein -(AA)$_r$- is ValAla (e.g., the first amino acid is Valine, the second amino acid is Alanine, and r is 1). In certain embodiments, one or more of the $L^1$, $L^2$ and $L^3$ is phenylenyl substituted by —C(O)OH and —NH$_2$. In certain embodiments, one or more of the $L^1$, $L^2$ and $L^3$ is phenylenyl substituted by —C(O)O— and —NH—. In certain embodiments, one or more of the $L^1$, $L^2$ and $L^3$ is phenylenyl substituted by —OC(O)— and —NH—. In certain embodiments, one or more of the $L^1$, $L^2$ and $L^3$ is phenylenyl substituted by —O— and —NH—. In certain embodiments, one or more of the $L^1$, $L^2$ and $L^3$ is para aminobenzyl (PAB), which is optionally substituted with —C(O)O—, —OC(O)— or —O—. In certain embodiments, $L^1$ is —(CH$_2$)$_q$—, $L^2$ is absent, $L^3$ is absent, and the CTX is bonded to $(L^1)_a$-$(L^2)_b$-$(L^3)_c$ via an amide bond. In certain embodiments, $L^1$ is —(CH$_2$)$_q$—, $L^2$ is —(OCH$_2$CH$_2$)$_p$—, $L^3$ is absent, and the CTX is bonded to $(L^1)_a$-$(L^2)_b$-$(L^3)_c$ via an amide bond. In certain embodiments, $L^1$ is —(CH$_2$CH$_2$O)$_p$—, $L^2$ is —(CH$_2$)$_q$—, $L^3$ is absent, and the CTX is bonded to $(L^1)_a$-$(L^2)_b$-$(L^3)_c$ via an amide bond. In certain embodiments, each $L^1$ is independently selected from the group consisting of —(CH$_2$CH$_2$O)$_p$CH$_2$CH$_2$— and —CH$_2$CH$_2$—(CH$_2$CH$_2$O)$_p$—, $L^2$ is absent, $L^3$ is absent, and the CTX is bonded to $(L^1)_a$-$(L^2)_b$-$(L^3)_c$ via an amide bond. In certain embodiments, each $L^1$ is independently selected from the group consisting of —(CH$_2$)$_q$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, and —C(O)—, $L^2$ is Val-Cit, $L^3$ is PAB, and the CTX is bonded to $(L^1)_a$-$(L^2)_b$-$(L^3)_c$ via an amide bond. In certain embodiments, each $L^1$ is independently selected from the group consisting of —(CH$_2$)$_q$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, and —C(O)—, $L^2$ is Val-Cit, $L^3$ is PAB, and the CTX is bonded to $(L^1)_a$-$(L^2)_b$-$(L^3)_c$ via an amide bond. In certain embodiments, each $L^1$ is independently selected from the group consisting of —(CH$_2$)$_q$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, and —C(O)—, $L^2$ is Val-Ala, $L^3$ is PAB, and the CTX is bonded to $(L^1)_a$-$(L^2)_b$-$(L^3)_c$ via an amide bond.

In certain embodiments of the antibody-drug conjugate of formula (Ia) or (Ib), CTX is selected from a from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments of the antibody-drug conjugate of formula (Ia) or (Ib), the CTX is a chemotherapeutic agent. Those of ordinary skill in the art will be aware of appropriate chemotherapeutic agents as disclosed, for example, in Chu, E., DeVite, V. T., 2012, Physicians' Cancer Chemotherapy Drug Manual 2012 (Jones & Bartlett Learning Oncology), and similar documents.

In certain embodiments, the CTX may be any FDA-approved chemotherapeutic agent. In certain embodiments, the CTX may be any FDA-approved chemotherapeutic agent available for cancer treatment.

In certain embodiments, the CTX is selected from the group consisting of an alkylating agents, an anthracyclines, a cytoskeletal disruptors (taxanes), an epothilones, an histone deacetylase Inhibitor (HDAC), an inhibitor of Topoisomerase 1, an Inhibitor of Topoisomerase 1l, a kinase inhibitor, a monoclonal antibodies, a nucleotide analog, a peptide antibiotic, a platinum-based agent, a retinoids, a Vinca alkaloid or a derivative thereof, and radioisotope.

In certain embodiments, the CTX is selected from the group consisting of Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In certain embodiments, the CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments, the CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, the CTX is an auristatin, a calicheamicin, a maytansinoid, or a tubulysin.

In certain embodiments, the cytotoxin is a pyrrolobenzodiazepine (PBD), a calicheamicin, doxorubicin, camptothecin, duocarmycin, DM1, DM4, a maytansinoid, or a tubulysin. In certain embodiments, CTX is an auristatin, a PDB, calicheamicin, doxorubicin, camptothecin, duocarmycin, DM1, DM4, a maytansinoid, or a tubulysin.

In certain embodiments, CTX is an auristatin, such as monomethylauristatin F (MMAF) and monomethylauristatin E (MMAE). In certain embodiments, the cytotoxin is a PBD.

In certain embodiments, the CTX is MMAE, MMAF, a PDB, calicheamicin γ, mertansine, or tubulysin T2.

317
In certain embodiments, the CTX is MMAE or MMAF, the structures for which are provided below:
MMAF
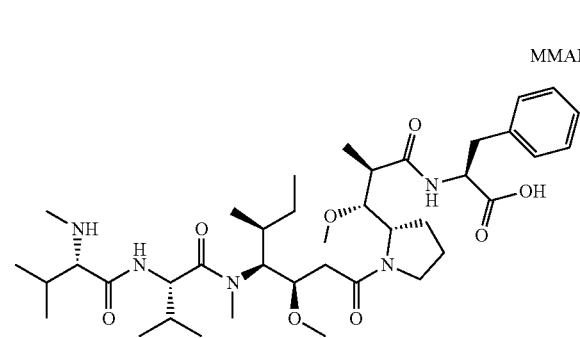
318
-continued
MMAE
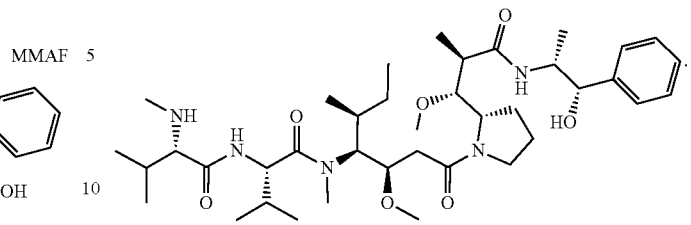
In certain embodiments, the CTX is a PDB, selected from the group consisting of:
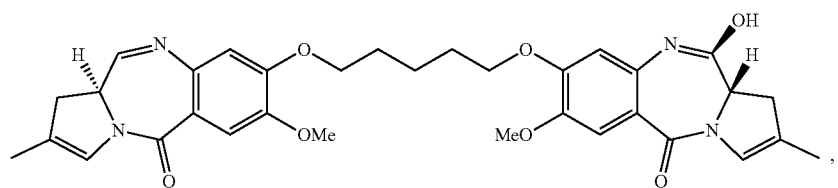
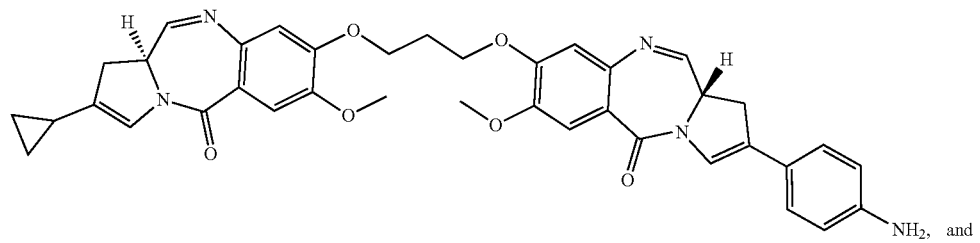
NH₂, and
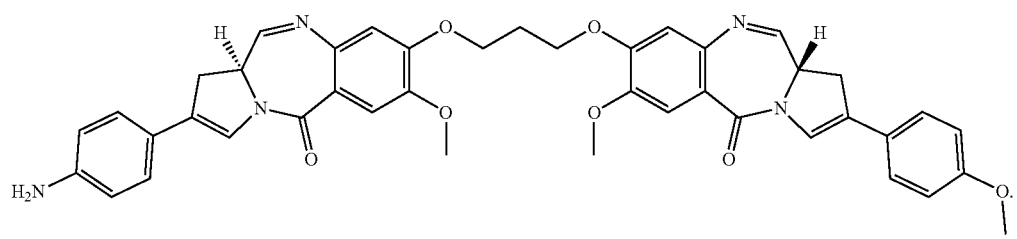

In certain embodiments, the CTX is tubulysin T2.

In certain embodiments, the CTX is tubulysin T3, or tubulysin T4, the structures for which are provided below:

T3

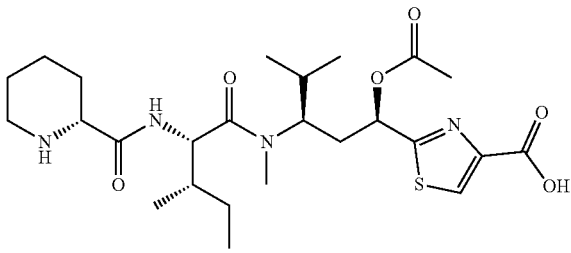

T4

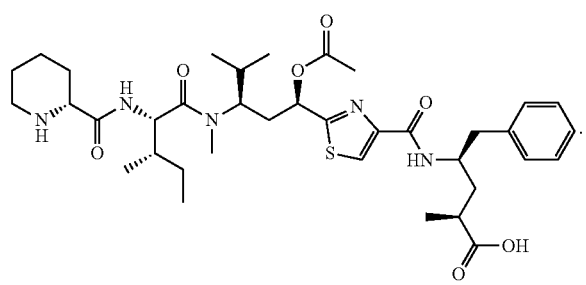

In some embodiments, provided herein are antibody-drug conjugates, including an antibody-drug conjugate of the following formula (Ic):

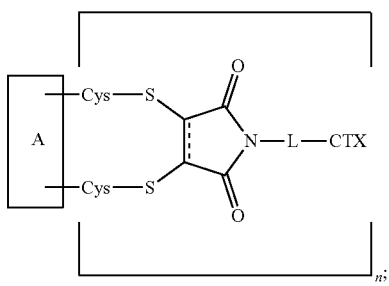
(Ic)

or pharmaceutically acceptable salt thereof,
wherein:
A is an anti-C10orf54 antibody, optionally a humanized anti-C10orf54 antibody;
the two depicted cysteine residues are from an opened cysteine-cysteine disulfide bond in A;
L is a cleavable or a noncleavable linker;
CTX is cytotoxin bonded to L by an amide bond, a carbamate bond, a disulfide bond, an ether bond, a thioether bond, or an ester bond;
the ===== bond represents a single or a double bond; and
n is an integer of 1 to 4.

In some embodiments, provided herein are antibody-drug conjugates, including an antibody-drug conjugate of the following formula (Ic1):

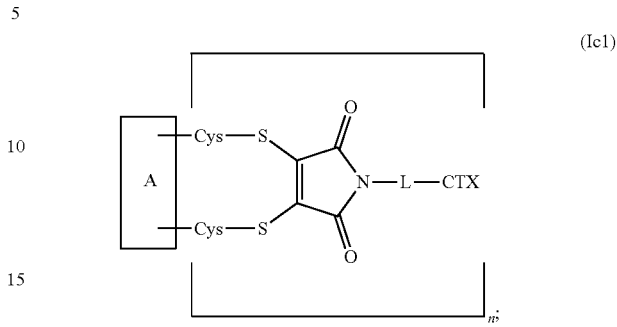
(Ic1)

or pharmaceutically acceptable salt thereof,
wherein:
A is an anti-C10orf54 antibody, optionally a humanized anti-C10orf54 antibody;
the two depicted cysteine residues are from an opened cysteine-cysteine disulfide bond in A;
L is a cleavable or a noncleavable linker;
CTX is cytotoxin bonded to L by an amide bond, a carbamate bond, a disulfide bond, an ether bond, a thioether bond, or an ester bond; and
n is an integer of 1 to 4.

In some embodiments, provided herein are antibody-drug conjugates, including an antibody-drug conjugate of the following formula (Ic2):

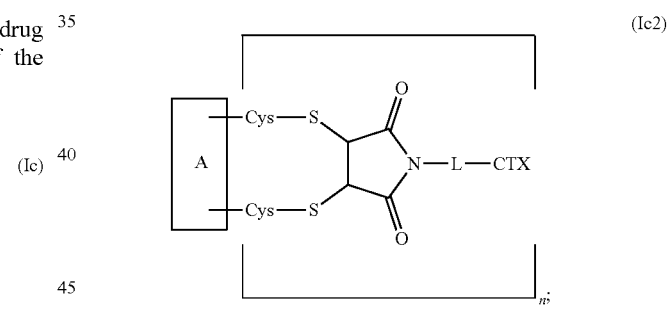
(Ic2)

or pharmaceutically acceptable salt thereof,
wherein:
A is an anti-C10orf54 antibody, optionally a humanized anti-C10orf54 antibody;
the two depicted cysteine residues are from an opened cysteine-cysteine disulfide bond in A;
L is a cleavable or a noncleavable linker;
CTX is cytotoxin bonded to L by an amide bond, a carbamate bond, a disulfide bond, an ether bond, a thioether bond, or an ester bond; and
n is an integer of 1 to 4.

In certain embodiments of the antibody-drug conjugate of the formula (Ic), (Ic1) or (Ic2), the opened cysteine-cysteine disulfide bond in A is an interchain disulfide bond. In certain embodiments, where the opened cysteine-cysteine disulfide bond in A is an interchain disulfide bond n is 4. (e.g., two heavy chain-light chain interchain disulfide bonds and two hinge heavy chain-heavy chain interchain disulfide bonds). In certain embodiments, where the opened cysteine-cysteine disulfide bond in A is an interchain disulfide bond n is 3 (e.g., two heavy chain-light chain interchain disulfide bonds and one hinge heavy chain-heavy chain interchain disulfide bond). In certain embodiments, where the opened cysteine-cysteine disulfide bond in A is an interchain disulfide bond n is 2 (e.g., two heavy chain-light chain interchain disulfide bonds).

In certain embodiments of the antibody-drug conjugate of the formula (Ic), (Ic1) or (Ic2), CTX is an auristatin, a pyrrolobenzodiazepine (PDB), calicheamicin, doxorubicin, camptothecin, duocarmycin, DM1, DM4, a maytansinoid, or a tubulysin, wherein CTX is bonded to L by an amide bond, a carbamate bond, a disulfide bond, an ether bond, a thio-ether bond, or an ester bond. In certain embodiments, CTX is an auristatin bonded to L by an amide bond or a carbamate bond. In certain embodiments, CTX is MMAF bonded to L by an amide bond. In certain embodiments, CTX is MMAE bonded to L by a carbamate bond. In certain embodiments, CTX is a PBD bonded to L by an amide bond or a carbamate bond.

In certain embodiments of the antibody-drug conjugate of the formula (Ic), (Ic1) or (Ic2), L is a noncleavable linker.

In certain embodiments of the antibody-drug conjugate of the formula (Ic), (Ic1) or (Ic2), L is:
—$(CH_2)_mC(O)$—,
—$(CH_2CH_2O)_p(CH_2CH_2)C(O)$—, or
—$(CH_2CH_2)(OCH_2CH_2)_pC(O)$—;
wherein m is an integer of 5 to 11, and p is an integer of 1 to 3.

In certain embodiments of the antibody-drug conjugate of the formula (Ic), (Ic1) or (Ic2), L is a cleavable linker.

In certain embodiments of the antibody-drug conjugate of the formula (Ic), (Ic1) or (Ic2), L is:
—$(CH_2)_mC(O)$-Val-Ala-PAB-C(O)—,
—$(CH_2)_mC(O)$-Val-Cit-PAB-C(O)—,
—$(CH_2CH_2O)_p(CH_2CH_2)C(O)$-Val-Ala-PAB-C(O)—,
—$(CH_2CH_2O)_p(CH_2CH_2)C(O)$-Val-Cit-PAB-C(O)—,
—$(CH_2CH_2)(OCH_2CH_2)_pC(O)$-Val-Ala-PAB-C(O)—, or
—$(CH_2CH_2)(OCH_2CH_2)_pC(O)$-Val-Cit-PAB-C(O)—;
wherein m is an integer of 5 to 11, and p is an integer of 1 to 3; and
wherein PAB has the following structure:

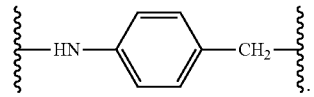 [SMILES: *Cc1ccc(N*)cc1]

In certain embodiments of the antibody-drug conjugate of the formula (Ic), (Ic1) or (Ic2), CTX is an auristatin. In certain embodiments, the CTX is MMAF. In certain embodiments the CTX is MMAE. In certain embodiments, the CTX is a PDB.

In certain embodiments of the antibody-drug conjugate of the formula (Ic), (Ic1) or (Ic2), n is 2, 3, or 4.

In certain embodiments of the antibody-drug conjugate of the formula (Ic), (Ic1) or (Ic2), CTX is MMAF, and L is —$(CH_2)_5C(O)$—. In certain embodiments, CTX is MMAE, and L is —$(CH_2)_5C(O)$-Val-Ala-PAB-O—C(O)—. In certain embodiments, CTX is a PBD, and L is —$(CH_2)_5C(O)$-Val-Ala-PAB-O—C(O)— or —$(CH_2)_5C(O)$-Val-Cit-PAB-O—C(O)—.

In certain embodiments, the antibody-drug conjugate is of the following formula:

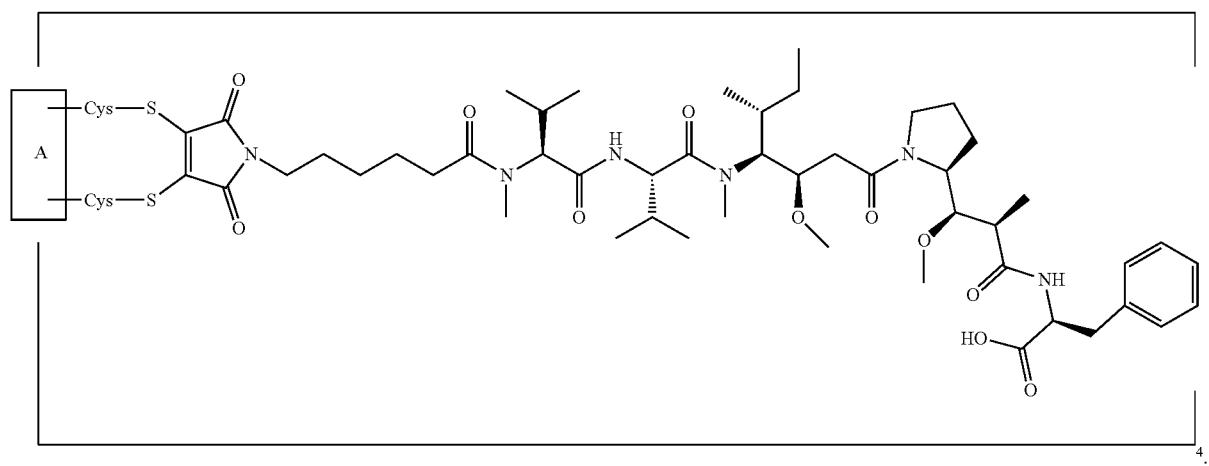

In certain embodiments, the antibody-drug conjugate is of the following formula:
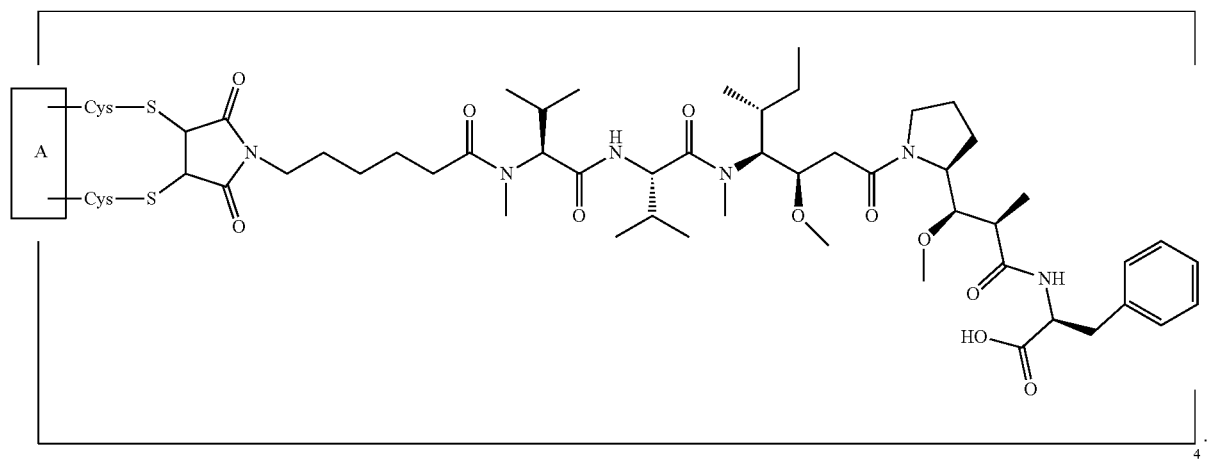
In certain embodiments, the antibody-drug conjugate is of the following formula:
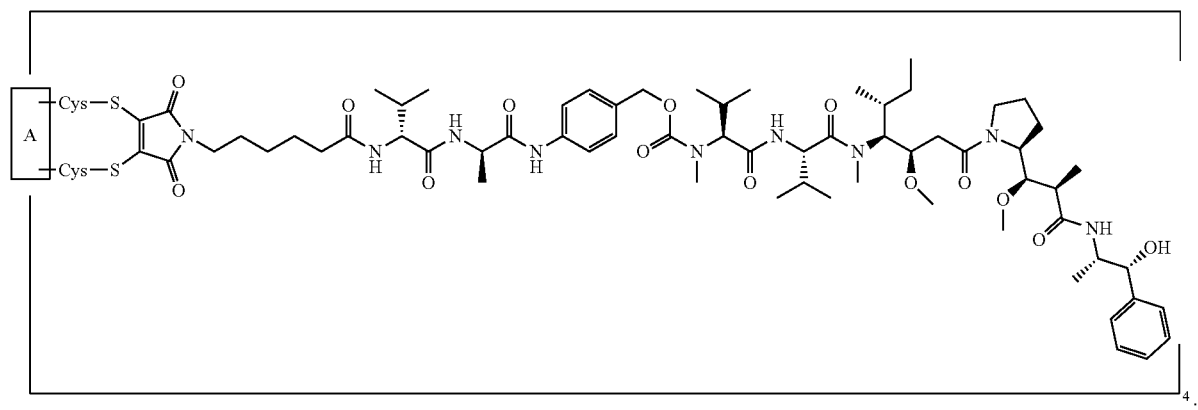
In certain embodiments, the antibody-drug conjugate is of the following formula:
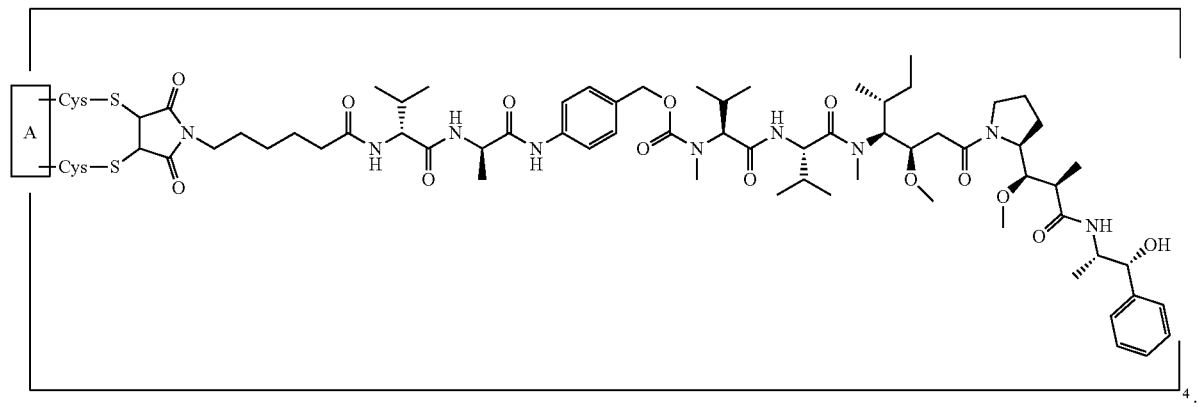

In certain embodiments, the antibody-drug conjugate is one of the following formulas:
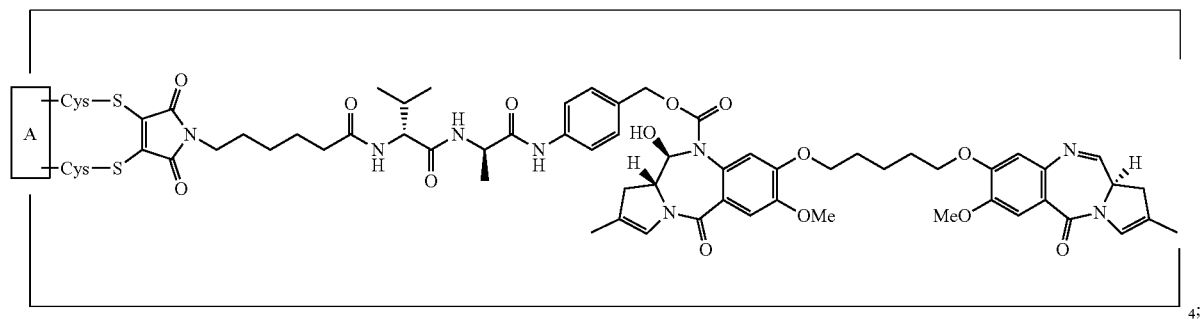
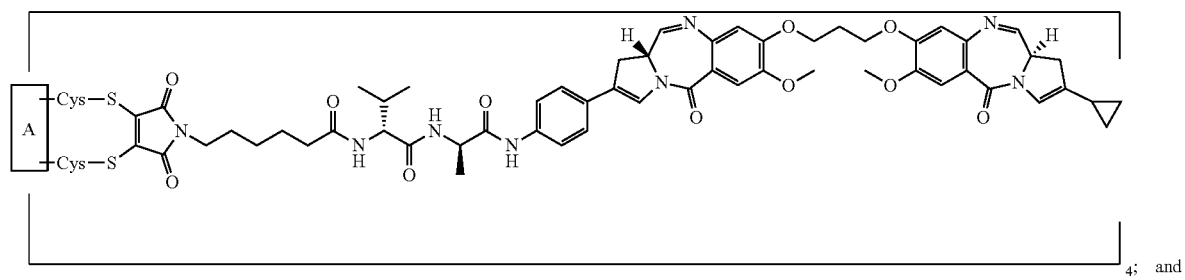
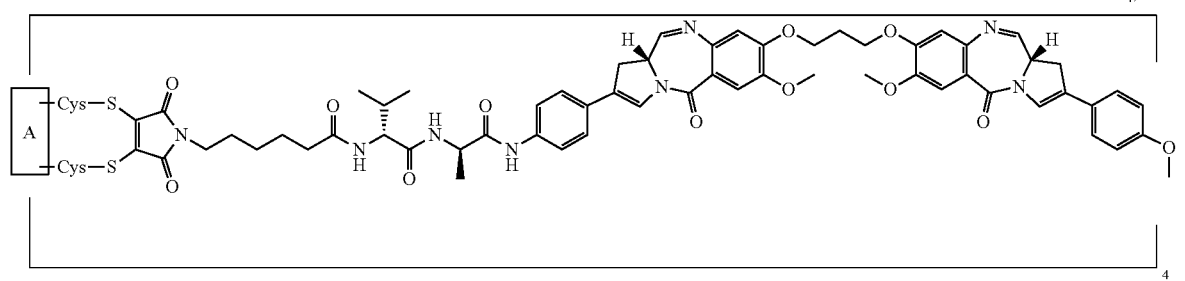
In certain embodiments, the antibody-drug conjugate is one of the following formulas:
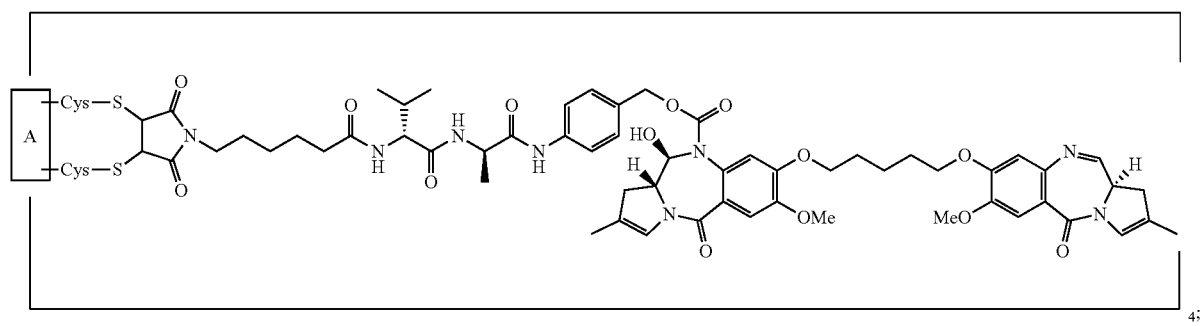
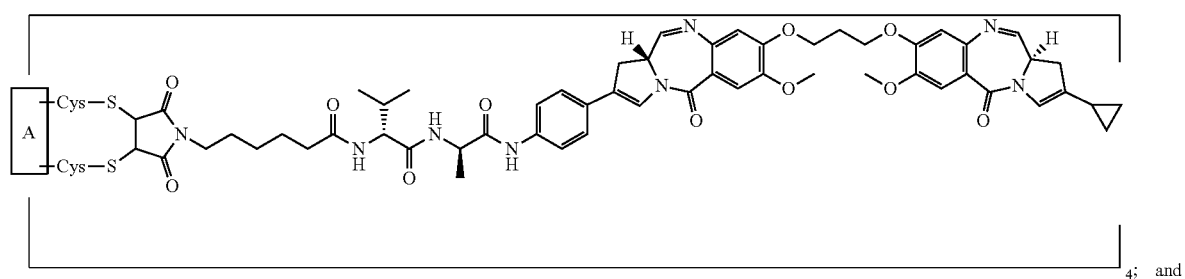

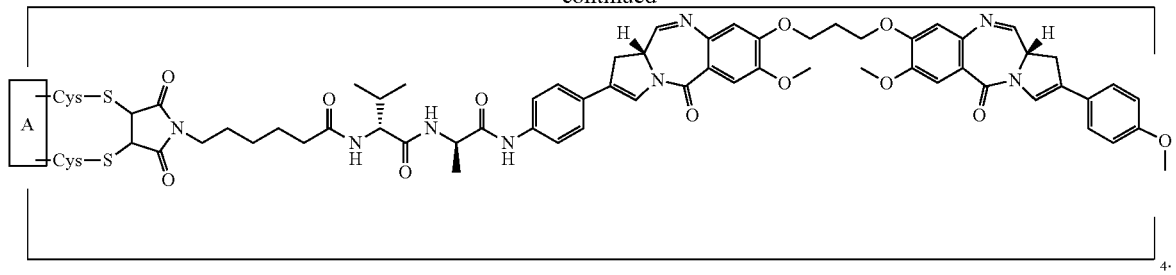

In some embodiments, provided herein is an antibody-drug conjugate of the following formula (Id):

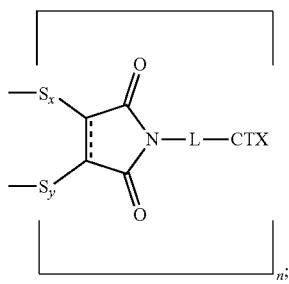

(Id)

wherein:

L is a cleavable or a noncleavable linker;

CTX is a cytotoxin bonded to L by an amide bond, a carbamate bond, a disulfide bond, an ether bond, a thioether bond, or an ester bond;

$S_x$ is a sulfur atom from a first cysteine residue, and $S_y$ is a sulfur atom from a second cysteine residue, wherein the first cysteine residue and the second cysteine residue are from different chains and/or from the same chain of a multi-chain antibody;

the ===== bond represents a single or a double bond; and n is an integer of 1 to 4.

In some embodiments, provided herein is an antibody-drug conjugate of the following formula (Id1):

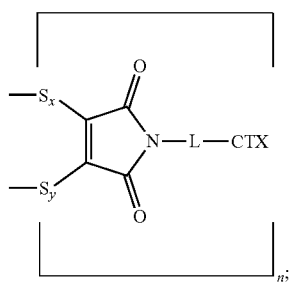

(Id1)

wherein:

L is a cleavable or a noncleavable linker;

CTX is a cytotoxin bonded to L by an amide bond, a carbamate bond, a disulfide bond, an ether bond, a thioether bond, or an ester bond;

$S_x$ is a sulfur atom from a first cysteine residue, and $S_y$ is a sulfur atom from a second cysteine residue, wherein the first cysteine residue and the second cysteine residue are from different chains and/or from the same chain of a multi-chain antibody; and n is an integer of 1 to 4.

In some embodiments, provided herein is an antibody-drug conjugate of the following formula (Id2):

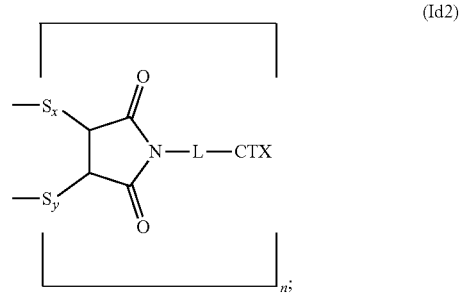

(Id2)

wherein:

L is a cleavable or a noncleavable linker;

CTX is a cytotoxin bonded to L by an amide bond, a carbamate bond, a disulfide bond, an ether bond, a thioether bond, or an ester bond;

$S_x$ is a sulfur atom from a first cysteine residue, and $S_y$ is a sulfur atom from a second cysteine residue, wherein the first cysteine residue and the second cysteine residue are from different chains and/or from the same chain of a multi-chain antibody; and n is an integer of 1 to 4.

In certain embodiments of the antibody-drug conjugate of the formula (Id), (Id1) or (Id2), CTX is an auristatin, a pyrrolobenzodiazepine (PDB), calicheamicin, doxorubicin, camptothecin, duocarmycin, DM1, DM4, a maytansinoid, or a tubulysin, wherein CTX is bonded to L by an amide bond, a carbamate bond, a disulfide bond, an ether bond, a thioether bond, or an ester bond. In certain embodiments, CTX is an auristatin bonded to L by an amide bond or a carbamate bond. In certain embodiments, CTX is MMAF bonded to L by an amide bond. In certain embodiments, CTX is MMAE bonded to L by a carbamate bond. In certain embodiments, CTX is a PBD bonded to L by an amide bond or a carbamate bond.

In certain embodiments of the antibody-drug conjugate of the formula (Id), (Id1) or (Id2), the multi-chain antibody comprises two heavy chains and two light chains.

In certain embodiments of the antibody-drug conjugate of the formula (Id), (Id1) or (Id2), the first cysteine residue is from a first heavy chain and the second cysteine residue is from a second heavy chain of the multi-chain antibody.

In certain embodiments of the antibody-drug conjugate of the formula (Id), (Id1) or (Id2), the first cysteine residue is from a heavy chain and the second cysteine residue is from a light chain of the multi-chain antibody.

In certain embodiments of the antibody-drug conjugate of the formula (Id), (Id1) or (Id2), the first and second cysteine residues are from the same heavy chain of the multi-chain antibody.

In certain embodiments of the antibody-drug conjugate of the formula (Id), (Id1) or (Id2), the multi-chain antibody is an anti-C10orf54 antibody, optionally a humanized anti-C10orf54 antibody.

In certain embodiments of the antibody-drug conjugate of the formula (Id), (Id1) or (Id2), the first cysteine residue is from a heavy chain and the second cysteine residue is from a light chain of the multi-chain antibody.

In certain embodiments of the antibody-drug conjugate of formula the formula (Id), (Id1) or (Id2), the first and second cysteine residues are from the same heavy chain of the multi-chain antibody.

In certain embodiments of the antibody-drug conjugate of formula (Id), the antibody-drug conjugate is of the following formula:

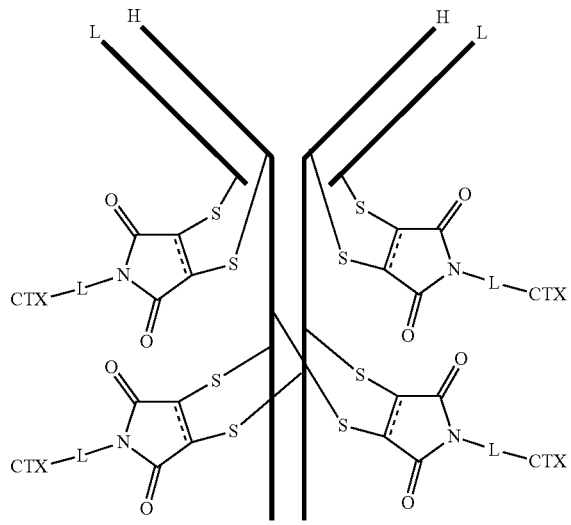

where each heavy chain of the multi-chain antibody is denoted by the letter H, and each light chain of the multi-chain antibody is denoted by the letter L; and the ===== bond represents a single or a double bond.

In certain embodiments of the antibody-drug conjugate of formula (Id), the antibody-drug conjugate is of the following formula:

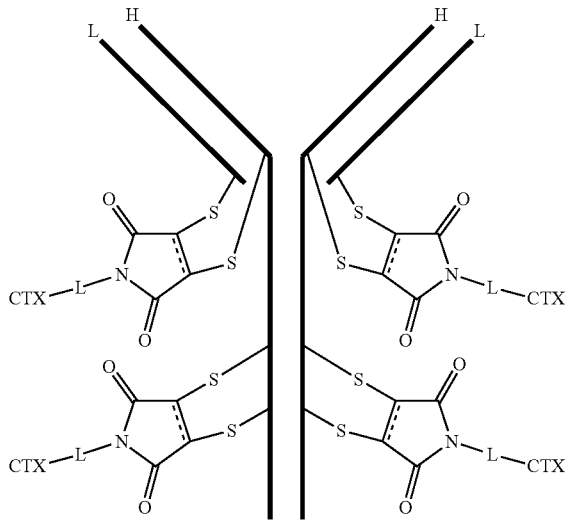

where each heavy chain of the multi-chain antibody is denoted by the letter H, and each light chain of the multi-chain antibody is denoted by the letter L; and the ===== bond represents a single or a double bond.

In certain embodiments of the antibody-drug conjugate of formula (Id1), the antibody-drug conjugate is of the following formula:

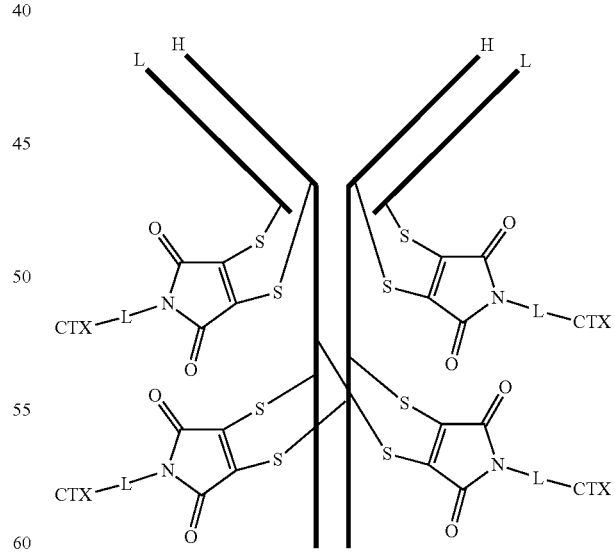

where each heavy chain of the multi-chain antibody is denoted by the letter H, and each light chain of the multi-chain antibody is denoted by the letter L.

In certain embodiments of the antibody-drug conjugate of formula (Id1), the antibody-drug conjugate is of the following formula:

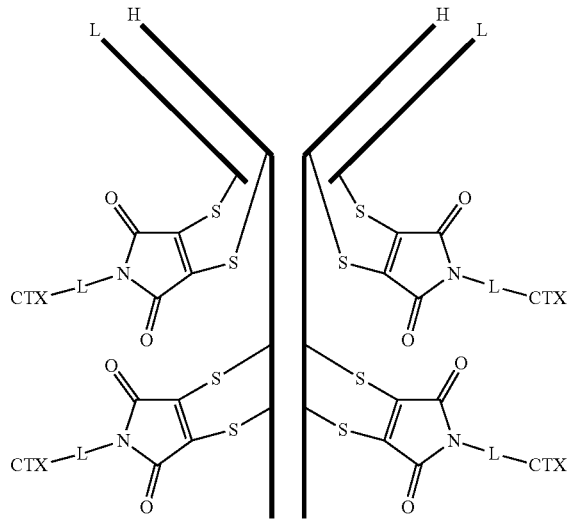

where each heavy chain of the multi-chain antibody is denoted by the letter H, and each light chain of the multi-chain antibody is denoted by the letter L.

In certain embodiments of the antibody-drug conjugate of formula (Id2), the antibody-drug conjugate is of the following formula:

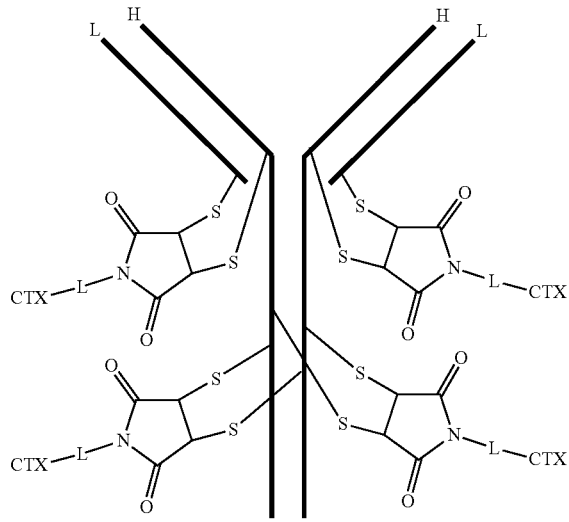

where each heavy chain of the multi-chain antibody is denoted by the letter H, and each light chain of the multi-chain antibody is denoted by the letter L.

In certain embodiments of the antibody-drug conjugate of formula (Id2), the antibody-drug conjugate is of the following formula:

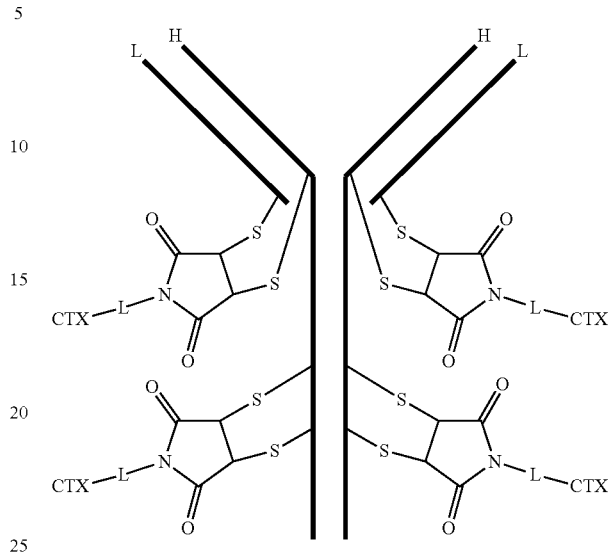

where each heavy chain of the multi-chain antibody is denoted by the letter H, and each light chain of the multi-chain antibody is denoted by the letter L.

In certain embodiments of the antibody-drug conjugate of the formula (Id), (Id1) or (Id2), the multi-chain antibody comprises mutations in one or more cysteines in the hinge regions of two heavy chains. In certain embodiments, the one or more cysteine residues are mutated to structurally related amino acids. In certain embodiments, the one or more cysteine residues are mutated to alanines.

In certain embodiments of the antibody-drug conjugate of formula (Id), wherein the multi-chain antibody comprises mutations in one or more cysteines in the hinge regions of two heavy chains, the antibody-drug conjugate is of the following formula:

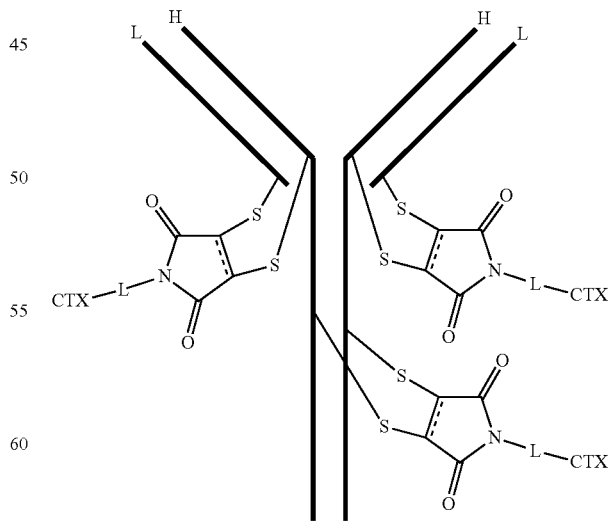

where each heavy chain of the multi-chain antibody is denoted by the letter H, and each light chain of the multi-chain antibody is denoted by the letter L; and the bond represents a single or a double bond. For the embodiments of the antibody-drug conjugate of formula (Id) depicted above, the ADC has a DAR=3 (three drugs per antibody). As described herein, such ADCs may be prepared, as described herein, by mutating one or more of the hinge cysteine residues of a human IgG1 (e.g., 1 hinge cysteine), IgG2 (e.g., 3 hinge cysteines), IgG3 (e.g., 10 hinge cysteines), or IgG4 (e.g., 1 hinge cysteine).

In certain embodiments of the antibody-drug conjugate of formula (Id), wherein the multi-chain antibody comprises mutations in one or more cysteines in the hinge regions of two heavy chains, the antibody-drug conjugate is of the following formula:

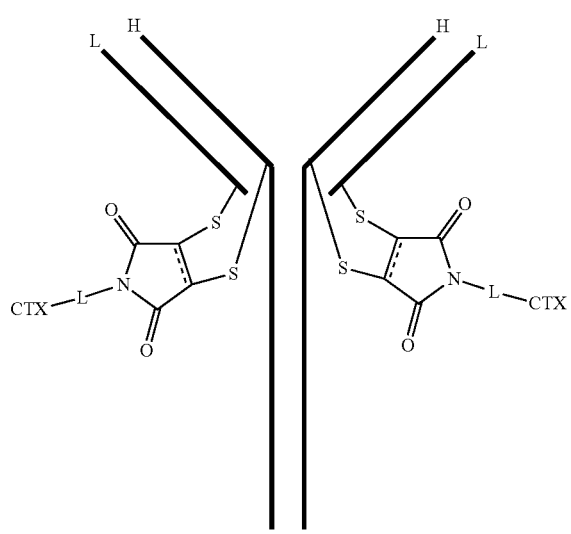

where each heavy chain of the multi-chain antibody is denoted by the letter H, and each light chain of the multi-chain antibody is denoted by the letter L; and the ===== bond represents a single or a double bond. For the embodiments of the antibody-drug conjugate of formula (Id) depicted above, the ADC has a DAR=2 (two drugs per antibody). As described herein, such ADCs may be prepared by mutating one or more of the hinge cysteine residues of a human IgG1 (e.g., 2 hinge cysteines), IgG2 (e.g., 4 hinge cysteines), IgG3 (e.g., 11 hinge cysteines), or IgG4 (e.g., 2 hinge cysteines). In certain embodiments of the antibody-drug conjugate of formula (Id), L is a noncleavable linker.

In certain embodiments of the antibody-drug conjugate of formula (Id1), wherein the multi-chain antibody comprises mutations in one or more cysteines in the hinge regions of two heavy chains, the antibody-drug conjugate is of the following formula:

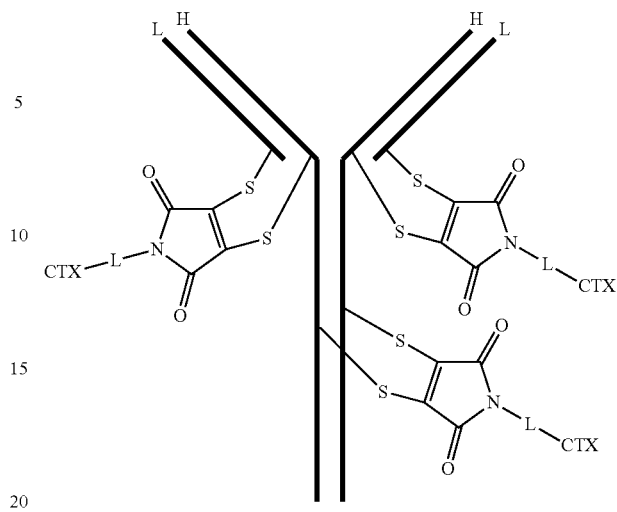

where each heavy chain of the multi-chain antibody is denoted by the letter H, and each light chain of the multi-chain antibody is denoted by the letter L. For the embodiments of the antibody-drug conjugate of formula (Id1) depicted above, the ADC has a DAR=3 (three drugs per antibody). As described herein, such ADCs may be prepared by mutating one or more of the hinge cysteine residues of a human IgG1 (e.g., 1 hinge cysteine), IgG2 (e.g., 3 hinge cysteines), IgG3 (e.g., 10 hinge cysteines), or IgG4 (e.g., 1 hinge cysteine).

In certain embodiments of the antibody-drug conjugate of formula (Id1), wherein the multi-chain antibody comprises mutations in one or more cysteines in the hinge regions of two heavy chains, the antibody-drug conjugate is of the following formula:

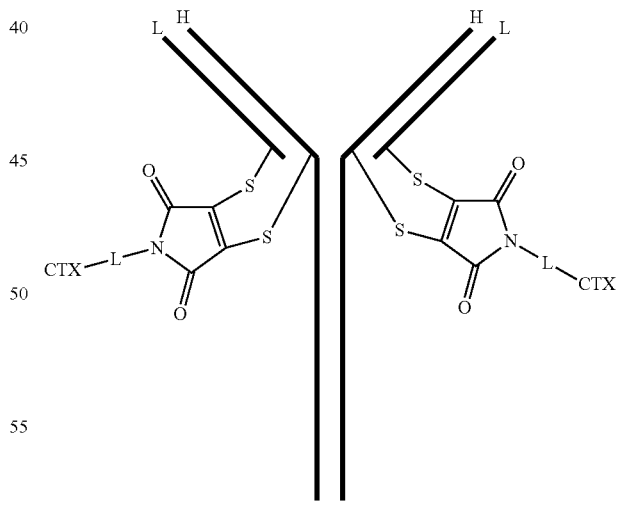

where each heavy chain of the multi-chain antibody is denoted by the letter H, and each light chain of the multi-chain antibody is denoted by the letter L. For the embodiments of the antibody-drug conjugate of formula (Id1) depicted above, the ADC has a DAR=2 (two drugs per antibody). As described herein, such ADCs may be prepared by mutating one or more of the hinge cysteine residues of a human IgG1 (e.g., 2 hinge cysteines), IgG2 (e.g., 4 hinge cysteines), IgG3 (e.g., 11 hinge cysteines), or IgG4 (e.g., 2 hinge cysteines). In certain embodiments of the antibody-drug conjugate of formula (Id1), L is a noncleavable linker.

In certain embodiments of the antibody-drug conjugate of formula (Id2), wherein the multi-chain antibody comprises mutations in one or more cysteines in the hinge regions of two heavy chains, the antibody-drug conjugate is of the following formula:

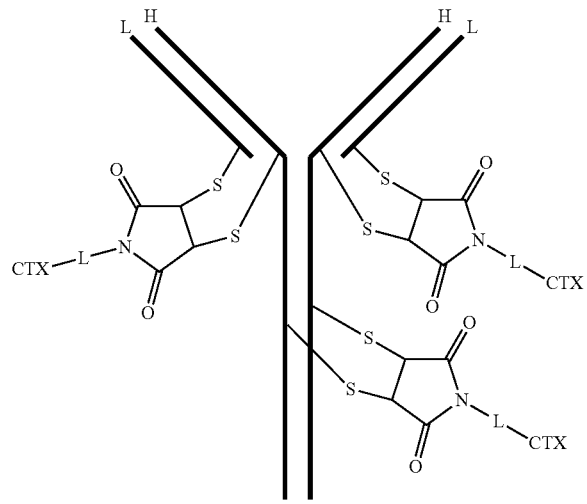

where each heavy chain of the multi-chain antibody is denoted by the letter H, and each light chain of the multi-chain antibody is denoted by the letter L. For the embodiments of the antibody-drug conjugate of formula (Id2) depicted above, the ADC has a DAR=3 (three drugs per antibody). As described herein, such ADCs may be prepared by mutating one or more of the hinge cysteine residues of a human IgG1 (e.g., 1 hinge cysteine), IgG2 (e.g., 3 hinge cysteines), IgG3 (e.g., 10 hinge cysteines), or IgG4 (e.g., 1 hinge cysteine).

In certain embodiments of the antibody-drug conjugate of formula (Id2), wherein the multi-chain antibody comprises mutations in one or more cysteines in the hinge regions of two heavy chains, the antibody-drug conjugate is of the following formula:

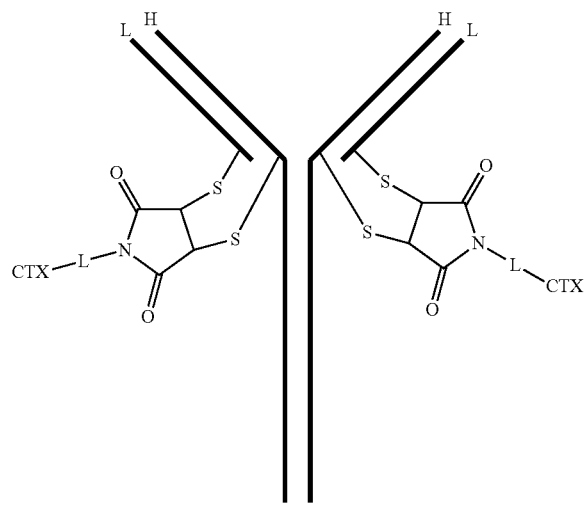

where each heavy chain of the multi-chain antibody is denoted by the letter H, and each light chain of the multi-chain antibody is denoted by the letter L. For the embodiments of the antibody-drug conjugate of formula (Id2) depicted above, the ADC has a DAR=2 (two drugs per antibody). As described herein, such ADCs may be prepared by mutating one or more of the hinge cysteine residues of a human IgG1 (e.g., 2 hinge cysteines), IgG2 (e.g., 4 hinge cysteines), IgG3 (e.g., 11 hinge cysteines), or IgG4 (e.g., 2 hinge cysteines). In certain embodiments of the antibody-drug conjugate of formula (Id2), L is a noncleavable linker.

In certain embodiments of the antibody-drug conjugate of the formula (Id), (Id1) or (Id2), L is:
—(CH$_2$)$_m$C(O)—,
—(CH$_2$CH$_2$O)$_p$(CH$_2$CH$_2$)C(O)—, or
—(CH$_2$CH$_2$)(OCH$_2$CH$_2$)$_p$C(O)—;
wherein m is an integer of 5 to 11, and p is an integer of 1 to 3.

In certain embodiments of the antibody-drug conjugate of the formula (Id), (Id1) or (Id2), L is a cleavable linker.

In certain embodiments of the antibody-drug conjugate of the formula (Id), (Id1) or (Id2), L is:
—(CH$_2$)$_m$C(O)-Val-Ala-PAB-C(O)—,
—(CH$_2$)$_m$C(O)-Val-Cit-PAB-C(O)—,
—(CH$_2$CH$_2$O)$_p$(CH$_2$CH$_2$)C(O)-Val-Ala-PAB-C(O)—,
—(CH$_2$CH$_2$O)$_p$(CH$_2$CH$_2$)C(O)-Val-Cit-PAB-C(O)—,
—(CH$_2$CH$_2$)(OCH$_2$CH$_2$)$_p$C(O)-Val-Ala-PAB-C(O)—, or
—(CH$_2$CH$_2$)(OCH$_2$CH$_2$)$_p$C(O)-Val-Cit-PAB-C(O)—;
wherein m is an integer of 5 to 11, and p is an integer of 1 to 3; and
wherein PAB has the following structure:

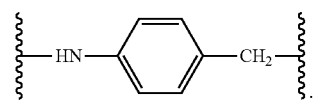

In certain embodiments of the antibody-drug conjugate of the formula (Id), (Id1) or (Id2), CTX is MMAF. In certain embodiments, the CTX is MMAE. In certain embodiments, the CTX is a PDB.

In certain embodiments of the antibody-drug conjugate of the formula (Id), (Id1) or (Id2), n is 2, 3, or 4.

In certain embodiments of the antibody-drug conjugate of the formula (Id), (Id1) or (Id2), CTX is MMAF, and L is —(CH$_2$)$_5$C(O)—. In certain embodiments, CTX is MMAE, and L is —(CH$_2$)$_5$C(O)-Val-Ala-PAB-O—C(O)—. In certain embodiments, CTX is a PBD, and L is —(CH$_2$)$_5$C(O)-Val-Ala-, —(CH$_2$)$_5$C(O)-Val-Cit-, —(CH$_2$)$_5$C(O)-Val-Ala-PAB-O—C(O)—, or —(CH$_2$)$_5$C(O)-Val-Cit-PAB-O—C(O)—.

Methods for Making Adcs

Methods for making ADCs include using the linker-cytotoxin conjugates and antibody hinge mutants.

An optional DAR (drugs-antibody ratio) is desirable for ADCs, including, for example, a DAR of 2, 3, or 4. For example, the following schemes illustrates general schemes for preparation of homogenous ADCs with DAR=2, 3, or 4, as disclosed herein, which may be made by the methods disclosed herein.

For example, for ADCs with IgG1 antibodies, one or both of the hinge cysteines may be mutated to another amino acid (e.g., alanine) to prepare ADC with a DAR of 3 or 2, respectively.

For example, for ADCs with IgG2 antibodies, two, three or four of the hinge cysteines may be mutated to another amino acid (e.g., alanine) to prepare ADC with a DAR of 4, 3 or 2, respectively.

For example, for ADCs with IgG3 antibodies, nine, ten or eleven of the hinge cysteines may be mutated to another amino acid (e.g., alanine) to prepare ADC with a DAR of 4, 3 or 2, respectively.

For another example, for ADCs with IgG4 antibodies, one or both of the hinge cysteines may be mutated to another amino acid (e.g., alanine) for prepare ADC with a DAR of 3 or 2, respectively.

Illustrative General Schemes for Preparation of ADCs with DAR=2 or 3:

A. Preparation of Hinge Mutants

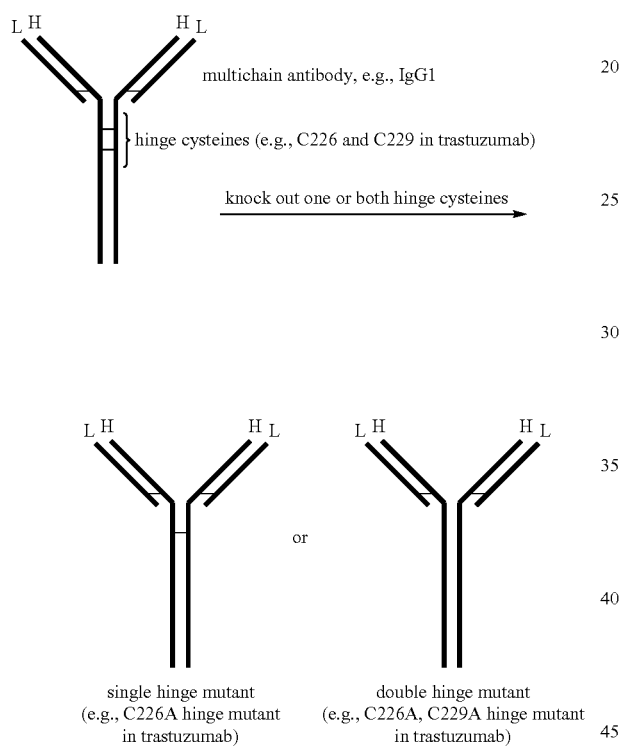

B. Conjugation

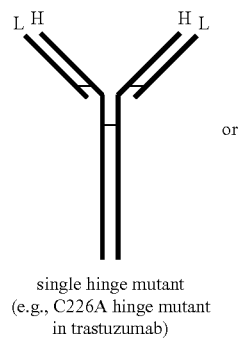

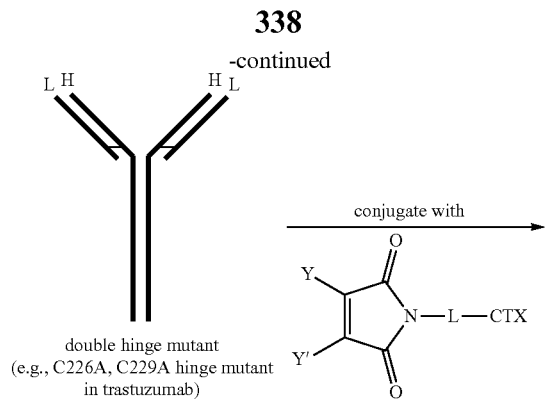

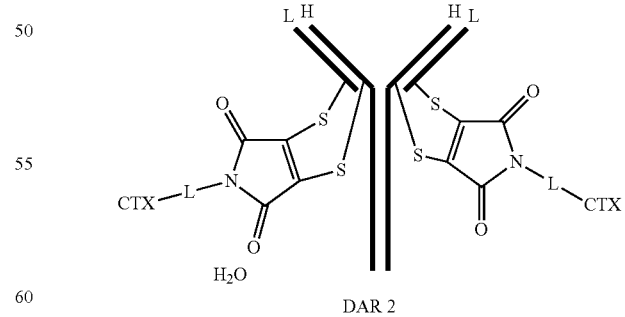

The hinge regions of the human IgG1 and IgG4 heavy chains contain two cysteine residues, whereas the hinge region of the human IgG3 heavy chains contains eleven cysteine residues, and the hinge region of the human IgG4 heavy chains contains four cysteine residues (see Table A).

TABLE A

Hinge sequences of human IgG1, IgG2, IgG3 and IgG4 antibodies

| Residue position | 216 | 217 | 218 | 219 | 220 | 221 | 222 | 223 | 224 | 225 | 226 | 227 | 228 | | | | | | | |
|---|---|---|---|---|---|---|---|---|---|---|---|---|---|---|---|---|---|---|---|---|
| Human IgG1 | E | P | K | S | C | D | K | T |   | H | T | C | P | P | | | | | | |
| Human IgG2 | E | R | K |   |   |   |   |   |   |   |   | C | C | V | E | C | P | P | | |
| Human IgG3 | E | L | K | T | P | L | G | D | T | T | H | T | C | P | R | C | P | (E | P | K | S | C | D | T | P |
| Human IgG4 | E | S | K | Y | G | P | P |   |   |   |   | C | P | S | | | | | | |

| | Residue position | 229 | 230 | 231 | 232 | 233 | 234 | 235 | 236 | 237 | 238 |
|---|---|---|---|---|---|---|---|---|---|---|---|
| | Human IG1 | C | P | A | P | E | L | L | G | G | P |
| | Human IG2 | C | P | A | P | P | V | A | G |   | P |
| | Human IG3 | P | P | C | P | R | C | P)₃ | A | P | E | L | L | G | G | P |
| | Human IG4 | C | P | A | P | E | F | L | G | G | P |

The amino acid sequence of the hinge region and the N terminus of the CH₂ domain are aligned against amino acids 216 to 238 of human IgG1 (Eu numbering; adapted from Burton D R (1985) Immunoglobulin G: functional sites. Mol Immunol 22: 161-206)

IgG hinge mutants were generated by mutating one or both cysteines in the hinge region to structurally related amino acids, for example, alanines. Hinge residues are numbered using human IgG1 Eu numbering (Burton D R (1985) Immunoglobulin G: functional sites. Mol Immunol 22: 161-206). Tables B-E provide the correspondence between the IMGT unique numbering for C-DOMAIN, the IMGT exon numbering, the Eu and Kabat numberings for human IgG1 (Table B), IgG2 (Table C), IgG3 (Table D) and IgG4 (Table E).

TABLE B

Human IgG1

| IMGT numbering for the hinge | IGHG1 amino acid translation J00228 | IMGT exon numbering | Eu numbering [1](4) | Kabat numbering [2](4) |
|---|---|---|---|---|
| 1 | (E) | 1 | 216 | 226 |
| 2 | P | 2 | 217 | 227 |
| 3 | K | 3 | 218 | 228 |
| 4 | S | 4 | 219 | 232 |
| 5 | C | 5 | 220 | 233 |
| 6 | D | 6 | 221 | 234 |
| 7 | K | 7 | 222 | 235 |
| 8 | T | 8 | 223 | 236 |
| 9 | H | 9 | 224 | 237 |
| 10 | T | 10 | 225 | 238 |
| 11 | C | 11 | 226 | 239 |
| 12 | P | 12 | 227 | 240 |
| 13 | P | 13 | 228 | 241 |

TABLE B-continued

Human IgG1

| IMGT numbering for the hinge | IGHG1 amino acid translation J00228 | IMGT exon numbering | Eu numbering [1](4) | Kabat numbering [2](4) |
|---|---|---|---|---|
| 14 | C | 14 | 229 | 242 |
| 15 | P | 15 | 230 | 243 |

TABLE C

Human IgG2

| IMGT numbering for the hinge | IGHG2 amino acid translation J00230 | IMGT exon numbering | Eu numbering [1](4) | Kabat numbering [2](4) |
|---|---|---|---|---|
| 1 | (E) | 1 | 216 | 226 |
| 2 | R | 2 | 217 | 227 |
| 3 | K | 3 | 218 | 228 |
| 4 | C | 4 | 219 | 232 |
| 5 | C | 5 | 220 | 233 |
| 6 | V | 6 | 222 | 235 |
| 7 | E | 7 | 224 | 237 |
| 8 | C | 8 | 226 | 239 |
| 9 | P | 9 | 227 | 240 |
| 10 | P | 10 | 228 | 241 |
| 11 | C | 11 | 229 | 242 |
| 12 | P | 12 | 230 | 243 |

TABLE D

Human IgG3

| IMGT numbering acid for the hinge | IGHG3 amino acid translation X03604 | IMGT exon number-ing | H1 Eu number-ing [1](4) | H1 Kabat number-ing [2](4) | IMGT numbering for the hinge | IGHG3 amino acid translation X03604 | IMGT exon number-ing | H2 Eu number-ing [1] | H2 Kabat number-ing [2] | H3 IMGT exon number-ing | H3 Eu number-ing [1] | H3 Kabat number-ing [2] | H4 IMGT exon number-ing | H4 Eu number-ing [1] | H4 Kabat number-ing [2] |
|---|---|---|---|---|---|---|---|---|---|---|---|---|---|---|---|
| 1 | (E) | 1 | 216 | 226 | 1 | (E) | 1 | — | 241C | 1 | — | 241R | 1 | — | 241GG |
| 2 | L | 2 | 217 | 227 | 2 | P | 2 | — | 241D | 2 | — | 241S | 2 | — | 241HH |
| 3 | K | 3 | 218 | 228 | 3 | K | 3 | — | 241E | 3 | — | 241T | 3 | — | 241II |
| 4 | T | 4 | — | 229 | 4 | S | 4 | — | 241F | 4 | — | 241U | 4 | — | 241JJ |
| 5 | P | 5 | — | 230 | 5 | C | 5 | — | 241G | 5 | — | 241V | 5 | — | 241KK |
| 6 | L | 6 | 219 | 232 | 6 | D | 6 | — | 241H | 6 | — | 241W | 6 | — | 241LL |
| 7 | G | 7 | 220 | 233 | 7 | T | 7 | — | 241I | 7 | — | 241X | 7 | — | 241MM |
| 8 | D | 8 | 221 | 234 | 8 | P | 8 | — | 241J | 8 | — | 241Y | 8 | — | 241NN |
| 9 | T | 9 | 222 | 235 | 9 | P | 9 | — | 241K | 9 | — | 241Z | 9 | — | 241OO |
| 10 | T | 10 | 223 | 236 | 10 | P | 10 | — | 241L | 10 | — | 241AA | 10 | — | 241PP |
| 11 | H | 11 | 224 | 237 | 11 | C | 11 | — | 241M | 11 | — | 241BB | 11 | — | 241QQ |
| 12 | T | 12 | 225 | 238 | 12 | P | 12 | — | 241N | 12 | — | 241CC | 12 | — | 241RR |
| 13 | C | 13 | 226 | 239 | 13 | R | 13 | — | 241O | 13 | — | 241DD | 13 | — | 241SS |
| 14 | P | 14 | 227 | 240 | 14 | C | 14 | — | 241P | 14 | — | 241EE | 14 | 229 | 242 |
| 15 | R | 15 | 228 | 241 | 15 | P | 15 | — | 241Q | 15 | — | 241FF | 15 | 230 | 243 |
| 16 | C | 16 | — | 241A | 16 | — | — | — | — | — | — | — | — | — | — |
| 17 | P | 17 | — | 241B | 17 | — | — | — | — | — | — | — | — | — | — |

TABLE E

Human IgG4

| IMGT numbering for the hinge | IGHG4 amino acid translation K01316 | IMGT exon numbering | Eu numbering [1] | Kabat numbering [2] |
|---|---|---|---|---|
| 1 | (E) | 1 | 216 | 226 |
| 2 | S | 2 | 217 | 227 |
| 3 | K | 3 | 218 | 228 |
| 4 | Y | 4 | — | 229 |
| 5 | G | 5 | — | 230 |
| 6 | P | 6 | 224 | 237 |
| 7 | P | 7 | 225 | 238 |
| 8 | C | 8 | 226 | 239 |
| 9 | P | 9 | 227 | 240 |
| 10 | S | 10 | 228 | 241 |
| 11 | C | 11 | 229 | 242 |
| 12 | P | 12 | 230 | 243 |

(1) J00228 corresponds to the IGHG1*01 allele (Alignment of alleles: Human IGHG1) and to a G1m1,17 chain (G1m allotypes). The Eu gamma1 chain is encoded by the IGHG1*03 allele (CH1 K120 > R, CH3 D12 > E and L14 > M) and is a G1m3 chain (G1m allotypes).
(2) The IGHG1, IGHG3 and IGHG4 CH2 exons encode 110 amino acids. The IGHG2 CH2 exon encodes 109 amino acids, due to a 3 nt deletion corresponding to codon 3 (position 1.4 in the IMGT unique numbering for C-DOMAINs).
(3) The last two amino acids of the IGHG CH3 exons belong to the CHS which encodes the heavy chain C-terminus found in the secreted immunoglobulins.
(4) In Kabat [2], Eu index from 219 to 221 should have been aligned with the Eu protein (pp. 671). As a consequence, Kabat positions 232, 233 and 234 correspond to Eu index positions 219, 220 and 221, respectively (pp. 670-678).
(5) MGT labels (concepts of description) are written in capital letters.

References:
[1] Edelman, G.M. et al., Proc. Natl. Acad. USA, 63, 78-85 (1969). PMID: 5257969
[2] Kabat, E.A. et al., Sequences of proteins of immunological interest. 5th Edition-US Department of Health and Human Services, NIH publication n° 91-3242, pp 662,680,689 (1991).

Linker-Cytotoxin Conjugates

In another aspect, provided herein for use with the antibodies described herein are linker-cytotoxin conjugates of the following formulas (IIa), (IIb) an (IIc):

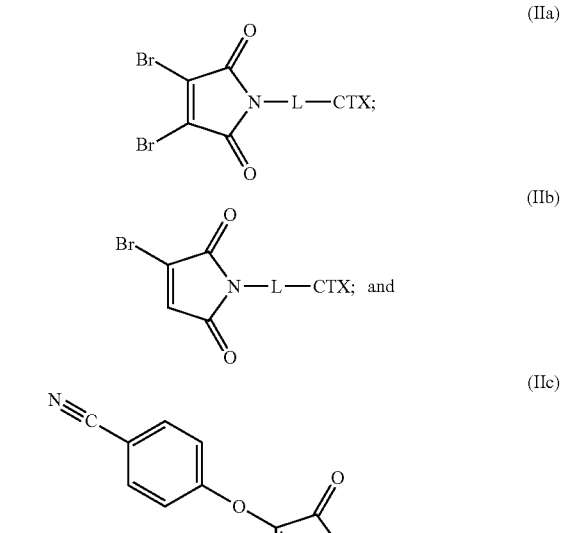

or an enantiomer, diasteriomer, or mixtures thereof;
wherein:
L is a cleavable or noncleavable linker; and
CTX is cytotoxin bonded to L by an amide bond or a carbamate bond.

In certain embodiments of the linker-cytotoxin conjugate of the formula (IIa), (IIb), or (IIc), L is a noncleavable linker.
In certain embodiments of the linker-cytotoxin conjugate of the formula (IIa), (IIb), or (IIc), L is:
—$(CH_2)_mC(O)$—,
—$(CH_2CH_2O)_p(CH_2CH_2)C(O)$—, or
—$(CH_2CH_2)(OCH_2CH_2)_pC(O)$—;
wherein m is an integer of 5 to 11, and p is an integer of 1 to 3.

In certain embodiments of the linker-cytotoxin conjugate of the formula (IIa), (IIb), or (IIc), L is a cleavable linker.

In certain embodiments of the linker-cytotoxin conjugate of the formula (IIa), (IIb), or (IIc), L is:
- —(CH$_2$)$_m$C(O)-Val-Ala-PAB-C(O)—,
- —(CH$_2$)$_m$C(O)-Val-Cit-PAB-C(O)—,
- —(CH$_2$CH$_2$O)$_p$(CH$_2$CH$_2$)C(O)-Val-Ala-PAB-C(O)—,
- —(CH$_2$CH$_2$O)$_p$(CH$_2$CH$_2$)C(O)-Val-Cit-PAB-C(O)—,
- —(CH$_2$CH$_2$)(OCH$_2$CH$_2$)$_p$C(O)-Val-Ala-PAB-C(O)—, or
- —(CH$_2$CH$_2$)(OCH$_2$CH$_2$)$_p$C(O)-Val-Cit-PAB-C(O)—;

wherein m is an integer of 5 to 11, and p is an integer of 1 to 3; and wherein PAB has the following structure:

$$\text{—HN—C}_6\text{H}_4\text{—CH}_2\text{—}$$

In certain embodiments of the linker-cytotoxin conjugate of the formula (IIa), (IIb), or (IIc), the CTX is an auristatin. In certain embodiments, the CTX is MMAF. In certain embodiments the CTX is MMAE. In certain embodiments, the CTX is a PBD. In certain embodiments, the CTX is a calicheamicin, doxorubicin, camptothecin, duocarmycin, DM1, DM4, a maytansinoid, or a tubulysin.

In certain embodiments of the linker-cytotoxin conjugate of formula (IIa), (IIb) or (IIc), where CTX is MMAE, L is a cleavable linker.

In certain embodiments of the linker-cytotoxin conjugate of formula (IIa), (IIb) or (IIc), where CTX is MMAE, L is —(CH$_2$)$_m$C(O)-Val-Aa-PAB-O—C(O)—, or —(CH$_2$)$_m$C(O)-Val-Cit-PAB-O—C(O)—, wherein m is an integer of 5 to 11.

In certain embodiments of the linker-cytotoxin conjugate of formula (IIa), (IIb) or (IIc), where CTX is MMAE, L is —(CH$_2$)$_5$C(O)-Val-Ala-PAB-O—C(O)—, or —(CH$_2$)$_5$C(O)-Val-Cit-PAB-O—C(O)—.

In certain embodiments of the linker-cytotoxin conjugate of formula (IIa), (IIb) or (IIc), where CTX is a PBD, L is a cleavable linker.

In certain embodiments of the linker-cytotoxin conjugate of formula (IIa), (IIb) or (IIc), where CTX is a PBD, L is —(CH$_2$)$_m$C(O)-Val-Aa-PAB-O—C(O)—, or —(CH$_2$)$_m$C(O)-Val-Cit-PAB-O—C(O)—, wherein m is an integer of 5 to 11.

In certain embodiments of the linker-cytotoxin conjugate of formula (IIa), (IIb) or (IIc), where CTX is a PBD, L is —(CH$_2$)$_5$C(O)-Val-Ala-PAB-O—C(O)—, or —(CH$_2$)$_5$C(O)-Val-Cit-PAB-O—C(O)—.

In certain embodiments, the linker-cytotoxin conjugate has the following structure:

In certain embodiments, the linker-cytotoxin conjugate has the following structure:

In certain embodiments, the linker-cytotoxin conjugate has the following structure:
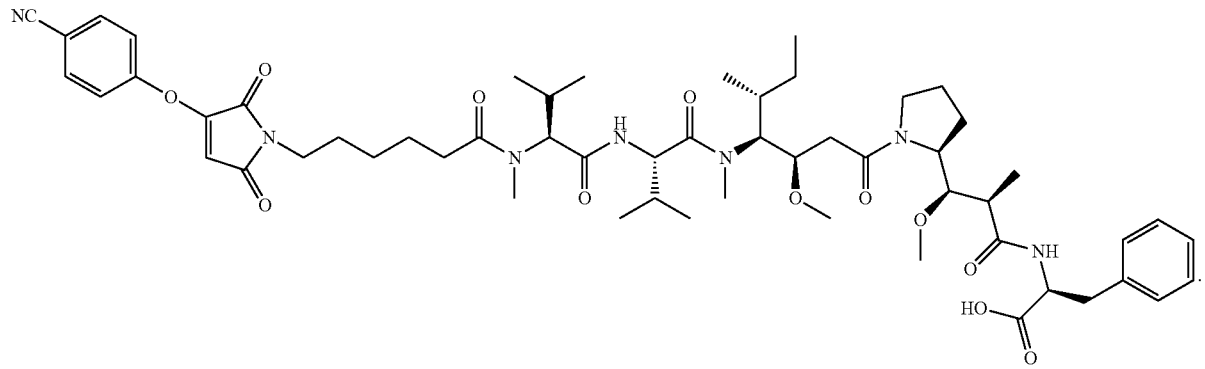 [SMILES: CC[C@@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCN1C(=O)C=C(Oc2ccc(C#N)cc2)C1=O)C(C)C]
In certain embodiments, the linker-cytotoxin conjugate has the following structure:
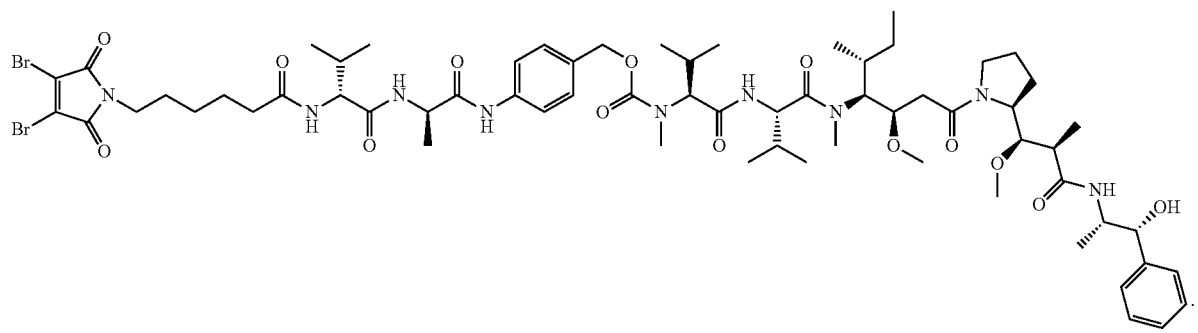 [SMILES: CC[C@@H](C)[C@@H]([C@@H](CC(=O)N1CCC[C@H]1[C@H](OC)[C@@H](C)C(=O)N[C@@H](C)[C@H](O)c1ccccc1)OC)N(C)C(=O)[C@@H](NC(=O)[C@H](C(C)C)N(C)C(=O)OCc1ccc(NC(=O)[C@@H](C)NC(=O)[C@H](NC(=O)CCCCCN2C(=O)C(Br)=C(Br)C2=O)C(C)C)cc1)C(C)C]
In certain embodiments, the linker-cytotoxin conjugate has the following structure:
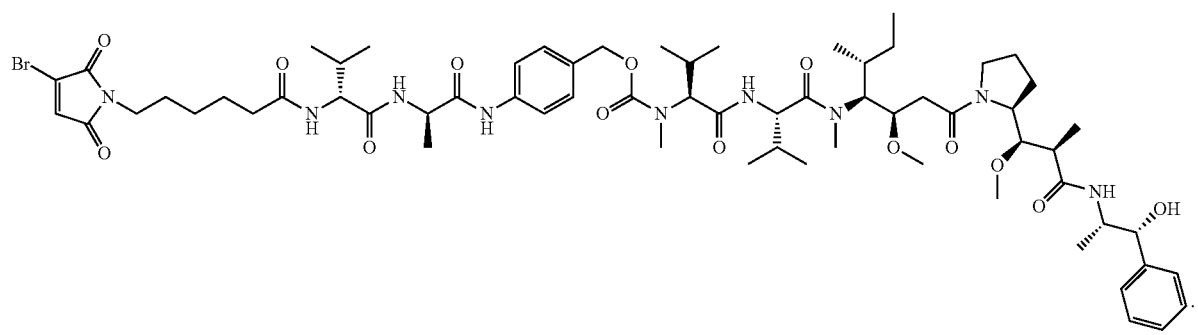 [SMILES: CC[C@@H](C)[C@@H]([C@@H](CC(=O)N1CCC[C@H]1[C@H](OC)[C@@H](C)C(=O)N[C@@H](C)[C@H](O)c1ccccc1)OC)N(C)C(=O)[C@@H](NC(=O)[C@H](C(C)C)N(C)C(=O)OCc1ccc(NC(=O)[C@@H](C)NC(=O)[C@H](NC(=O)CCCCCN2C(=O)C=C(Br)C2=O)C(C)C)cc1)C(C)C]

In certain embodiments, the linker-cytotoxin conjugate has the following structure:
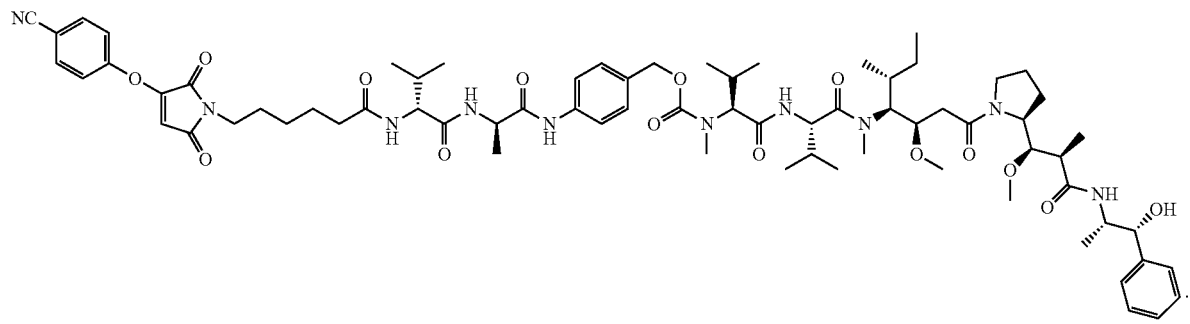 [SMILES: CC[C@@H](C)[C@@H]([C@@H](CC(=O)N1CCC[C@H]1[C@H](OC)[C@@H](C)C(=O)N[C@@H](C)[C@H](O)c1ccccc1)OC)N(C)C(=O)[C@@H](NC(=O)[C@H](C(C)C)N(C)C(=O)OCc1ccc(NC(=O)[C@@H](C)NC(=O)[C@H](NC(=O)CCCCCN2C(=O)C=C(Oc3ccc(C#N)cc3)C2=O)C(C)C)cc1)C(C)C]
In certain embodiments, the linker-cytotoxin conjugate has one of the following structures:
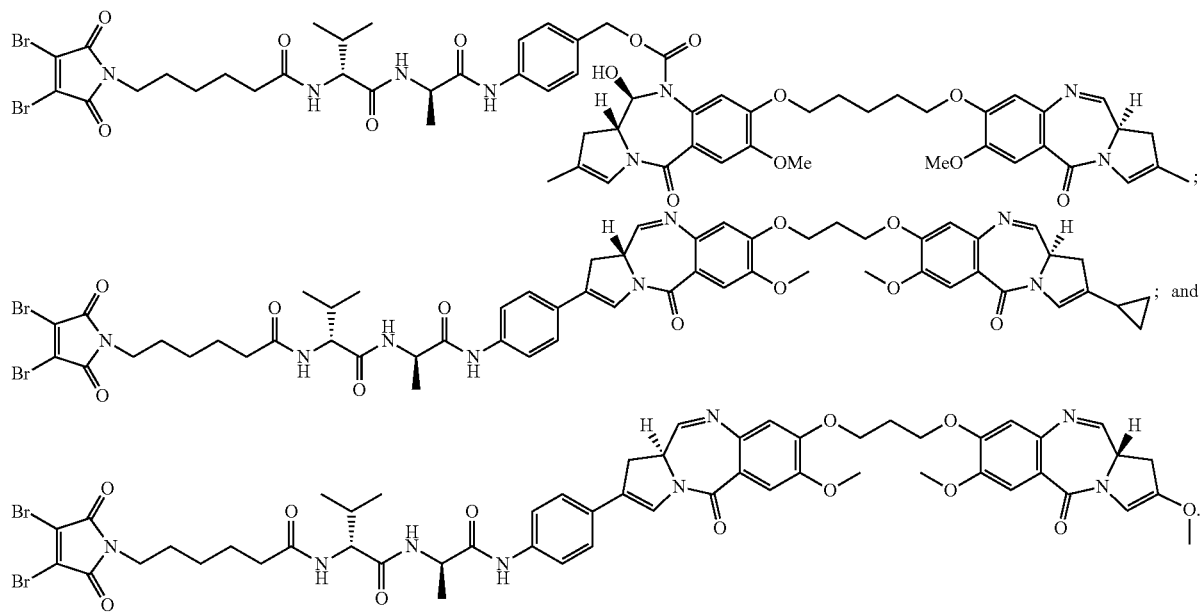
In certain embodiments, the linker-cytotoxin conjugate has one of the following structures:
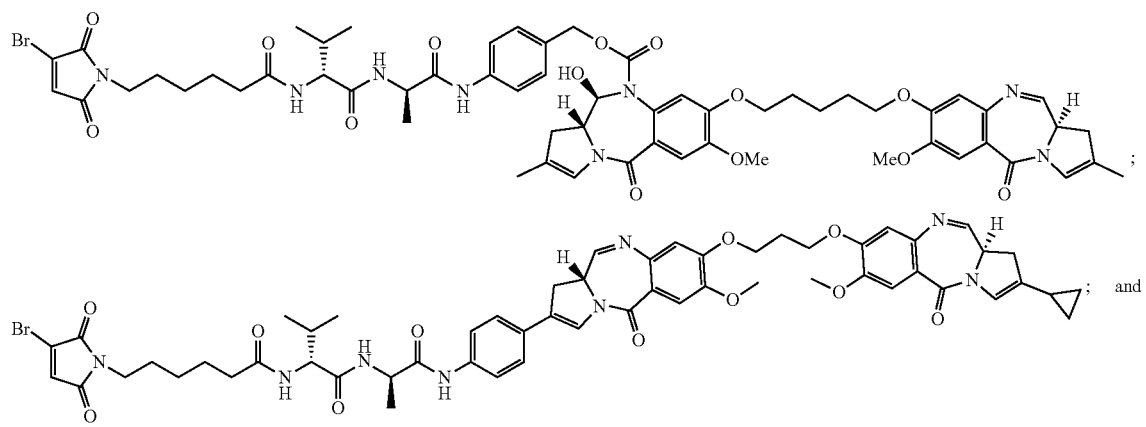

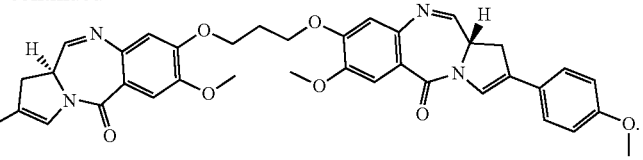

In certain embodiments, the linker-cytotoxin conjugate has one of the following structures:

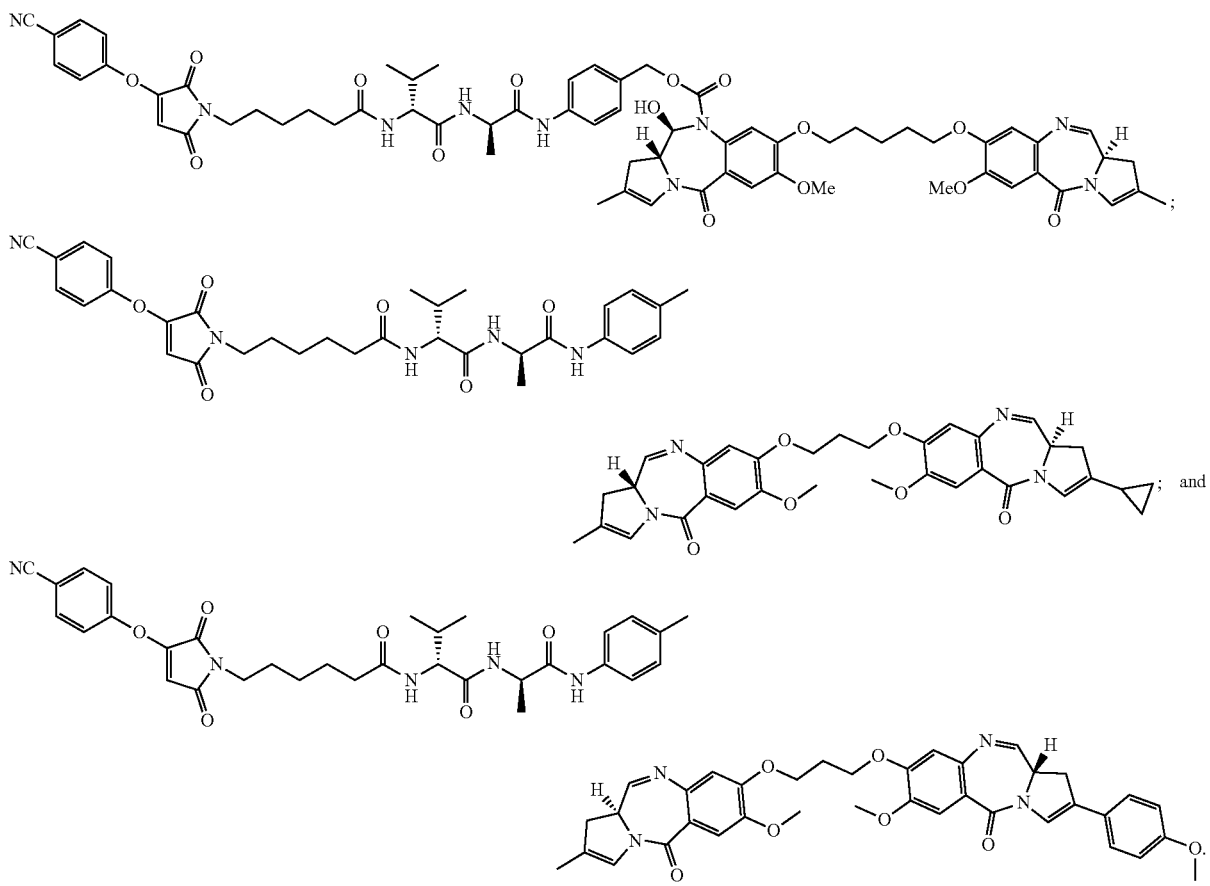

Pharmaceutical Compositions

Therapeutic formulations containing one or more of the antibodies provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, PA), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies provided herein can also, for example, be formulated in liposomes. Liposomes containing the molecule of interest are prepared by methods known in the art, such as described in Epstein et al. (1985) *Proc. Natl. Acad.*

Sci. USA 82:3688; Hwang et al. (1980) *Proc. Natl. Acad. Sci. USA* 77:4030; and U.S. Pat. Nos. 4,485,045 and 4,544,545. Liposomes with enhanced circulation time are disclosed in U.S. Pat. No. 5,013,556.

Particularly useful immunoliposomes can be generated by the reverse phase evaporation method with a lipid composition containing phosphatidylcholine, cholesterol and PEG-derivatized phosphatidylethanolamine (PEG-PE). Liposomes are extruded through filters of defined pore size to yield liposomes with the desired diameter. Fab' fragments of an antibody provided herein can be conjugated to the liposomes as described in Martin et al. (1982) *J. Biol. Chem.* 257:286-288 via a disulfide interchange reaction. A chemotherapeutic agent (such as Doxorubicin) is optionally contained within the liposome; See Gabizon et al., (1989) *J. National Cancer Inst.* 81(19):1484.

Formulations, such as those described herein, can also contain more than one active compound as necessary for the particular indication being treated. In certain embodiments, formulations comprise an antibody provided herein and one or more active compounds with complementary activities that do not adversely affect each other. Such molecules are suitably present in combination in amounts that are effective for the purpose intended. For example, an antibody provided herein can be combined with one or more other therapeutic agents. Such combined therapy can be administered to the patient serially or simultaneously or in sequence.

An antibody provided herein can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* (1990) Mack Publishing Co., Easton, PA.

The formulations to be used for in vivo administration can be sterile. This is readily accomplished by filtration through, e.g., sterile filtration membranes.

Sustained-release preparations can also be prepared. Suitable examples of sustained-release preparations include semipermeable matrices of solid hydrophobic polymers containing the polypeptide, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

In some embodiments, the pharmaceutical compositions provided herein contain therapeutically effective amounts of one or more of the antibodies provided herein, and optionally one or more additional prophylactic of therapeutic agents, in a pharmaceutically acceptable carrier. Such pharmaceutical compositions are useful in the prevention, treatment, or alleviation of one or more symptom of a C10orf54-mediated disease.

Pharmaceutical carriers suitable for administration of the compounds provided herein include any such carriers known to those skilled in the art to be suitable for the particular mode of administration.

In addition, the antibodies provided herein may be formulated as the sole pharmaceutically active ingredient in the composition or may be combined with other active ingredients (such as one or more other prophylactic or therapeutic agents).

The compositions can contain one or more antibodies provided herein. In one embodiment, the antibodies are formulated into suitable pharmaceutical preparations, such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the antibodies described above are formulated into pharmaceutical compositions using techniques and procedures well known in the art (see, e.g., Ansel (1985) *Introduction to Pharmaceutical Dosage Forms*, 4$^{th}$ Ed., p. 126).

In certain embodiments of the compositions, effective concentrations of one or more antibodies or derivatives thereof is (are) mixed with a suitable pharmaceutical carrier. In specific embodiments, concentrations of the compounds in the compositions are effective for delivery of an amount, upon administration, that treats, prevents, or ameliorates a C10orf54-mediated disease or symptom thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

In some embodiments, the antibody provided herein is included in the pharmaceutically acceptable carrier in an effective amount sufficient to exert a therapeutically useful effect in the absence of undesirable side effects on the patient treated. The therapeutically effective concentration can be determined empirically by testing the compounds in in vitro and in vivo systems using routine methods and then extrapolated therefrom for dosages for humans.

The concentration of antibody in the pharmaceutical composition will depend on, e.g., the physicochemical characteristics of the antibody, the dosage schedule, and amount administered as well as other factors known to those of skill in the art.

In one embodiment, a therapeutically effective dosage produces a serum concentration of antibody of from about 0.1 ng/ml to about 50-100 µg/ml. The pharmaceutical compositions, in another embodiment, provide a dosage of from about 0.001 mg to about 2000 mg of antibody per kilogram of body weight per day. Pharmaceutical dosage unit forms can be prepared to provide from about 0.01 mg, 0.1 mg or 1 mg to about 500 mg, 1000 mg or 2000 mg, and in one embodiment from about 10 mg to about 500 mg of the antibody and/or a combination of other optional essential ingredients per dosage unit form.

The antibody can be administered at once, or may be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

In some embodiments, the pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The antibody is, in one embodiment, formulated and administered in unit-dosage forms or multiple-dosage forms. "Unit-dose" forms as used herein refers to physically discrete units suitable for human and animal subjects and packaged individually as is known in the art. Each unit-dose contains a predetermined quantity of the antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A "multiple-dose" form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In specific embodiments, one or more anti-C10orf54 antibodies provided herein are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see *Remington's Pharmaceutical Sciences* (1990) Mack Publishing Co., Easton, PA.

Dosage forms or compositions containing antibody in the range of 0.005% to 100% with the balance made up from non-toxic carrier can be prepared. Methods for preparation of these compositions are known to those skilled in the art.

Oral pharmaceutical dosage forms are either solid, gel or liquid. The solid dosage forms include tablets, capsules, granules, and bulk powders. Types of oral tablets include compressed, chewable lozenges and tablets which may be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms. In certain embodiments, the formulations are capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The antibodies provided herein can be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The antibody can also be mixed with other active materials which do not impair the desired action, or with materials that supplement the desired action, such as antacids, H2 blockers, and diuretics. The active ingredient is an antibody or pharmaceutically acceptable derivative thereof as described herein. Higher concentrations, up to about 98% by weight of the active ingredient may be included.

In all embodiments, tablets and capsules formulations can be coated as known by those of skill in the art in order to modify or sustain dissolution of the active ingredient. Thus, for example, they may be coated with a conventional enterically digestible coating, such as phenylsalicylate, waxes and cellulose acetate phthalate.

In specific embodiments, the formulations are liquid dosage forms. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is, in one embodiment, encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/ vinyloxyethanol copolymer, that is insoluble in body fluids. The antibody diffuses through the outer polymeric membrane in a release rate controlling step. The amount of antibody contained in such parenteral compositions is highly dependent on the specific nature thereof, as well as the activity of the compound and the needs of the subject.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylceluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration can be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The antibody can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and may be empirically determined.

In other embodiments, the pharmaceutical formulations are lyophilized powders, which can be reconstituted for administration as solutions, emulsions and other mixtures. They may also be reconstituted and formulated as solids or gels.

The lyophilized powder is prepared by dissolving an antibody provided herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The antibodies provided herein can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts. Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010,715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration can be manufactured using the same pharmaceutically acceptable substance and by the same methods as for formulations for oral administration.

The antibodies and other compositions provided herein may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In one embodiment, liposomal suspensions, including tissue-targeted liposomes, such as tumor-targeted liposomes, may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Methods of Administration and Dosing

Also provided herein are compositions comprising one or more antibodies provided herein for use in the prevention, treatment and/or alleviation of one or more symptom of a disease, such as a C10orf54-mediated disease.

In certain embodiments, provided herein are compositions comprising one or more antibodies provided herein for use in the management, prevention, or treatment of a C10orf54-mediated disease and/or the alleviation of one or more symptom of a C10orf54-mediated disease. Exemplary C10orf54-mediated diseases include a cell proliferative disorder, cancer, tumor, and graft-versus-host disease (GVHD), or a symptom thereof.

In certain embodiments, provided herein are compositions comprising one or more antibodies provided herein for use in the prevention, treatment and/or alleviation of one or more symptom of an C10orf54-mediated disease, such as a cell proliferative disorder. A cell proliferative disorder can include cancer or tumor formation, or a symptom thereof. In certain embodiments, the cell proliferative disorder is associated with increased expression and/or activity of C10orf54. For example, in certain embodiments, the cell proliferative disorder is associated with increased expression of C10orf54 on the surface of a cancer cell. Examples of cell proliferative disorders to be treated, prevented, or symptoms of which can be alleviated by the antibodies provided herein include, but are not limited to, bladder, breast, colon, connective tissue, rectal, gastric, esophageal, lung, laryx, kidney, oral, ovarian, or prostate cancers, or sarcomas, melanomas, gliomas, lymphomas or leukemias, or metatases of any of these cancers. Exemplary cell proliferative disorders include, but are not limited to, a leukemia, either acute or chronic, a fibrosarcoma, and a bladder cancer.

Leukemias are cancers of the blood-forming tissues characterized by distorted proliferation and development of leukocytes and their precursors in the blood and bone marrow. Leukemias are typically classified as either chronic (slowly progressing) or acute (rapidly progressing). Leukemias can be further classified based upon the type of blood cell affected. For example, leukemia of lymphoid cells include lymphoid leukemia, lymphocytic leukemia or lymphoblastic leukemia, and leukemia of myeloid cells include myeloid leukemia, myelogenous leukemia, myeloblastic leukemia or granulocytic leukemia. The four of the main types of leukemias that can be treated, prevented or symptoms thereof alleviated by the methods provided herein include acute lymphoblastic leukemia (ALL), chronic lymphocytic leukemia (CLL), acute myelogenous leukemia (AML) and chronic myelobastic leukemia (CML).

In one aspect, provided herein are methods for preventing or treating a disease described herein by administering to a subject a therapeutically effective amount, respectively, of an anti-C10orf54 antibody described herein, or a composition thereof. In certain embodiments, a method for treating the disease comprises administering to subject a therapeutically effective amount of a pharmaceutical formulation comprising an anti-C10orf54 antibody and a pharmaceutically acceptable carrier or excipient. A method provided herein can also optionally include at least one additional therapeutic agent, such as those provided herein, either as a separate treatment or conjugated or recombinately fused to an anti-C10orf54 antibody provided herein.

In one embodiment, an anti-C10orf54 antibody provided herein can be used for targeting C10orf54 expressed by the cancer cells by contacting the antibody with C10orf54 to form an antibody-antigen complex such that a conjugated or recombinately fused agent described herein accesses the interior of the cell. In one embodiment, the bound antibody is internalized into the cancer cell expressing C10orf54.

In certain embodiments, provided herein are compositions comprising one or more antibodies provided herein for use in the prevention, treatment and/or alleviation of one or more symptom of an C10orf54-mediated disease, such as GVHD, or a symptom thereof. GVHD generally occurs following allogeneic or matched unrelated bone marrow transplants (BMT).

In some embodiments, the GVHD is acute GVHD. The symptoms of acute GVHD can happen quickly and can be mild or severe. In certain instances, acute GVHD develops within about three months after transplant, such as when blood counts recover after transplant. It certain instances, the acute GVHD affects the skin, gastrointestinal (GI) tract and/or liver. For example, in some patients, acute skin GVHD begins with a rash, for example, on the palms of the patient's hands, soles of the feet, or shoulders. However, the rash can become widespread, and may be itchy and painful and/or might blister and peel. Acute liver GVHD may affect normal functions of the liver, such as liver enzymes, and may in turn, cause jaundice. Acute liver GVHD may also cause the patient's abdomen to become swollen and painful if the liver becomes enlarged. Finally, symptoms of acute gut GVHD (or GVHD of the digestive system) can include diarrhea, mucus or blood in the stool, cramping or abdominal pain, indigestion, nausea and/or loss of appetite. Other general symptoms of acute GVHD can include anemia, low grade fever, and/or being more prone to infections. Any combination of these symptoms of acute GVHD may be prevented, treated, and/or alleviated using the compositions and methods provided herein.

In other embodiments, the GVHD is chronic GVHD. Chronic GVHD can occur from about three months to about a year or longer after transplant. Chronic GVHD can be mild or severe, and generally includes symptoms similar to those of acute GVHD. Chronic GVHD can affect the skin and digestive system, including the liver but can also involve other organs and the immune system (e.g., making the patient more prone to infections) and/or connective tissues. Symptoms of chronic skin GVHD include a rash, dry skin, tight skin, itchy skin, darkening of the color of the skin, thickening of the skin, and/or may affect hair (e.g., hair loss, turning gray) or nails (e.g., hard or brittle nails). Chronic gut GVHD can affect the digestive system, mouth, esophagus, lining of the stomach, and/or lining of the bowel, and symptoms can include diarrhea, dry or sore mouth, painful swallowing, low nutrient absorption by the stomach, bloating, stomach cramps. Chronic liver GVHD can cause damage and scarring of the liver (cirrhosis). Chronic GVHD of the eyes can affect the glands that make tears, causing eyes to become dry, burning and painful or difficult to tolerate bright light. Chronic lung GVHD can cause shortness of breath, wheezing, persistent cough, and/or being more prone to chest infections. Chronic GVHD affects tendons (e.g., inflammation) that connect muscle to bone causing difficulty straightening or bending your arms and legs. Any combination of these symptoms of chronic GVHD may be prevented, treated, and/or alleviated using the compositions and methods provided herein.

In certain embodiments, an antibody provided herein may be used in, for example, in vitro, ex vivo, and in vivo therapeutic methods. In some embodiments, provided herein are methods for inhibiting cell growth or proliferation, either in vivo or in vitro, the method comprising contacting a cell with an effective amount of a composition or an anti-C10orf54 antibody provided herein. In some embodiments, an antibody provided herein may be used in a method for inducing cell death. The method can comprise contacting a cell with an effective amount of a composition or an anti-C10orf54 antibody provided herein. The methods can be performed under conditions permissive for binding of the antibody to a C10orf54 polypeptide, polypeptide fragment or epitope, such as, but not limited to when the C10orf54 polypeptide is expressed on the surface of a cell. For inhibiting the cell growth or proliferation of a cell, the inhibition can include decreasing a cell's growth or proliferation by at least 10%, 20%, 30%, 40%, 50%, 60%, 70%, 80%, 90%, 95%, or 100%, and can include cell death. In certain embodiments, the cell is a cancer cell or a pre-cancerous cell. In certain embodiments, the cell is a bladder, breast, colon, connective tissue, rectal, gastric, esophageal, lung, laryx, kidney, oral, ovarian, or prostate cancer cell, or a sarcoma, melanoma, glioma, lymphoma or leukemia cell. In certain embodiments, the cell is an immune cell expressing a C10orf54 polypeptide, such as, but not limited to, a regulatory T cell (i.e. a suppressor T cell).

An anti-C10orf54 antibody can be administered to a human for therapeutic or prophylactic purposes. Moreover, an anti-C10orf54 antibody can be administered to a non-human mammal expressing C10orf54 with which the antibody cross-reacts (e.g., a primate, pig, rat, or mouse) for veterinary purposes or as an animal model of human disease. Regarding the latter, such animal models may be useful for evaluating the therapeutic or prophylactic efficacy of antibodies or immunoconjugates provided herein (e.g., testing of dosages and time courses of administration).

In certain embodiments, an antibody provided herein can be used in a method of modulating an immune response in a subject. Such methods can include administering an effective amount of the composition of comprising an antibody provided herein to a subject. In some aspects, the modulating can include (a) increasing T cell activation; (b) increasing T cell proliferation; and/or (c) increasing cytokine production. Methods for assaying the modulation of an immune response are well known to one of skill in the art, and it is understood that a skill artisan would be able to readily conduct such assays.

In a specific embodiment, a composition for use in the management, prevention, treatment and/or alleviation of one or more symptom of a C10orf54-mediated disease comprises an antibody as described herein. In another specific embodiment, a composition for use in the management, prevention, treatment and/or alleviation of one or more symptom of a C10orf54-mediated disease comprises an antigen-binding fragment, a fusion protein or an functional fragment of an antibody as described herein.

In another embodiment, a composition for use in the management, prevention, treatment and/or alleviation of one or more symptom of a C10orf54-mediated disease comprises one or more antibodies described herein.

As discussed in more detail elsewhere herein, a composition provided herein may be used either alone or in combination with other compounds or compositions. Moreover, the antibodies may further be recombinantly fused to a heterologous polypeptide at the N- or C-terminus or chemically conjugated (including covalently and non-covalently conjugations) to polypeptides or other compositions. For example, antibodies provided herein may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

Antibodies provided herein may be used, for example, to purify, detect, and target C10orf54 antigens, in both in vitro and in vivo diagnostic and therapeutic methods. For example, the modified antibodies have use in immunoassays for qualitatively and quantitatively measuring levels of C10orf54 in biological samples. See, e.g., Harlow et al., Antibodies: A Laboratory Manual, (Cold Spring Harbor Laboratory Press, 2nd ed. 1988) (incorporated by reference herein in its entirety).

Also provided herein are methods of managing, treating, preventing and/or ameliorating one or more symptom of a C10orf54-mediated disease by administrating to a subject of an effective amount of an antibody, or pharmaceutical composition comprising an antibody provided herein. In one aspect, an antibody is substantially purified (e.g., substantially free from substances that limit its effect or produce undesired side-effects). In specific embodiments, the antibody is a humanized monoclonal antibody. The subject administered a therapy can be a mammal such as non-primate (e.g., cows, pigs, horses, cats, dogs, rats etc.) or a primate (e.g., a monkey, such as a cynomolgous monkey, or a human). In a specific embodiment, the subject is a human. In another embodiment, the subject is a human with a C10orf54-mediated disease.

Various delivery systems are known and can be used to administer a prophylactic or therapeutic agent (e.g., an antibody provided herein), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., an antibody provided herein), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody provided herein), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition provided herein locally to the area in need of treatment. This may be achieved by, for example, and not by way of limitation, local infusion, by topical administration (e.g., by intranasal spray), by injection, or by means of an implant, the implant being of a porous, non-porous, or gelatinous material, including membranes, such as sialastic membranes, or fibers. In certain embodiments, when administering an antibody provided herein, care must be taken to use materials to which the antibody does not absorb.

In another embodiment, a therapeutic agent or composition provided herein can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a therapeutic agent or composition provided herein can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a therapeutic agent (e.g., an antibody provided herein) or a composition provided herein (see e.g., Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679, 377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In a specific embodiment, the polymer used in a sustained release formulation is inert, free of leachable impurities, stable on storage, sterile, and biodegradable. In yet another embodiment, a controlled or sustained release system can be placed in proximity of the therapeutic target, e.g., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more antibodies provided herein. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760.

In a specific embodiment, where the composition provided herein is a nucleic acid encoding a prophylactic or therapeutic agent (e.g., an antibody provided herein), the nucleic acid can be administered in vivo to promote expression of its encoded therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition comprises one, two or more antibodies provided herein. In another embodiment, a composition comprises one, two or more antibodies provided herein and a prophylactic or therapeutic agent other than an antibody provided herein. In certain embodiments, the agents are known to be useful for or have been or are currently used for the prevention, treatment and/or alleviation of one or more symptom of a C10orf54-mediated disease. In addition to prophylactic or therapeutic agents, the compositions provided herein may also comprise a carrier.

The compositions provided herein include bulk drug compositions useful in the manufacture of pharmaceutical compositions (e.g., compositions that are suitable for administration to a subject or patient) that can be used in the preparation of unit dosage forms. In a specific embodiment, a composition provided herein is a pharmaceutical composition. Such compositions comprise a prophylactically or therapeutically effective amount of one or more prophylactic or therapeutic agents (e.g., an antibody provided herein or other prophylactic or therapeutic agent), and a pharmaceutically acceptable carrier. In certain embodiments, the pharmaceutical compositions are formulated to be suitable for the route of administration to a subject.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, an antibody provided herein is packaged in a hermetically sealed container such as an ampoule or sachette indicating the quantity of antibody. In one embodiment, the antibody is supplied as a dry sterilized lyophilized powder or water free concentrate in a hermetically sealed container and can be reconstituted, e.g., with water or saline to the appropriate concentration for administration to a subject. In certain embodiments, the antibody is supplied as a dry sterile lyophilized powder in a hermetically sealed container at a unit dosage of at least 0.1 mg, at least 0.5 mg, at least 1 mg, at least 2 mg, or at least 3 mg, such as at least 5 mg, at least 10 mg, at least 15 mg, at least 25 mg, at least 30 mg, at least 35 mg, at least 45 mg, at least 50 mg, at least 60 mg, at least 75 mg, at least 80 mg, at least 85 mg, at least 90 mg, at least 95 mg, or at least 100 mg. The lyophilized antibody can be stored at between 2 and 8° C. in its original container and the antibody can be administered within 12 hours, such as within 6 hours, within 5 hours, within 3 hours, or within 1 hour after being reconstituted. In an alternative embodiment, an antibody is supplied in liquid form in a hermetically sealed container indicating the quantity and concentration of the antibody. In certain embodiments, the liquid form of the antibody is supplied in a hermetically sealed container at least 0.1 mg/ml, at least 0.5 mg/ml, or at least 1 mg/ml, such as at least 5 mg/ml, at least 10 mg/ml, at least 15 mg/ml, at least 25 mg/ml, at least 30 mg/ml, at least 40 mg/ml, at least 50 mg/ml, at least 60 mg/ml, at least 70 mg/ml, at least 80 mg/ml, at least 90 mg/ml, or at least 100 mg/ml.

The compositions provided herein can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a therapeutic agent (e.g., an antibody provided herein) or a composition provided herein that will be effective in the prevention, treatment and/or alleviation of one or more symptom of a C10orf54-mediated disease can be determined by standard clinical techniques.

Accordingly, a dosage of an antibody or a composition that results in a serum titer of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, such as at least 2 µg/ml, at least µg/ml, at least 10 µg/ml, at least 15 µg/ml, at least 20 µg/ml, at least 25 µg/ml, at least 30 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the prevention, treatment and/or alleviation of one or more symptom of a C10orf54-mediated disease. In addition, in vitro assays may optionally be employed to help identify optimal dosage ranges. The precise dose to be employed in the formulation will also depend on the route of administration, and the seriousness of a C10orf54-mediated disease, and should be decided according to the judgment of the practitioner and each patient's circumstances.

Effective doses may be extrapolated from dose-response curves derived from in vitro or animal model test systems.

For the antibodies provided herein, the dosage administered to a patient can be, in certain embodiments, 0.1 mg/kg to 100 mg/kg of the patient's body weight. In some embodiments, the dosage administered to the patient is about 1 mg/kg to about 75 mg/kg of the patient's body weight. In certain embodiments, the dosage administered to a patient is between 1 mg/kg and 20 mg/kg of the patient's body weight, such as 1 mg/kg to 5 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies provided herein may be reduced by enhancing uptake and tissue penetration of the antibodies by modifications such as, for example, lipidation.

In one embodiment, approximately 100 mg/kg or less, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less of an antibody provided herein is administered 5 times, 4 times, 3 times, 2 times or 1 time to prevent, treat or alleviate one or more symptom of a C10orf54-mediated disease. In some embodiments, an antibody provided herein is administered about 1-12 times, wherein the doses may be administered as necessary, e.g., weekly, biweekly, monthly, bimonthly, trimonthly, etc., as determined by a physician. In some embodiments, a lower dose (e.g., 1-15 mg/kg) can be administered more frequently (e.g., 3-6 times). In other embodiments, a higher dose (e.g., 25-100 mg/kg) can be administered less frequently (e.g., 1-3 times). However, as will be apparent to those in the art, other dosing amounts and schedules are easily determinable and within the scope of the disclosure.

In a specific embodiment, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, approximately 0.1 mg/kg or less of an antibody provided herein in a sustained release formulation is administered to a subject, such as a human, to prevent, treat and/or alleviate one or more symptom of a C10orf54-mediated disease. In another specific embodiment, an approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less bolus of an antibody provided herein not in a sustained release formulation is administered to a subject, such as a human, to prevent, treat and/or alleviate one or more symptom of a C10orf54-mediated disease, and after a certain period of time, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 5 mg/kg or less of an antibody provided herein in a sustained release is administered to the subject (e.g., intranasally or intramuscularly) one, two, three or four times. In accordance with this embodiment, a certain period of time can be 1 to 5 days, a week, two weeks, or a month.

In some embodiments, a single dose of an antibody provided herein is administered to a patient to prevent, treat and/or alleviate one or more symptom of a C10orf54-mediated disease two, three, four, five, six, seven, eight, nine, ten, eleven, twelve times, thirteen, fourteen, fifteen, sixteen, seventeen, eighteen, nineteen, twenty, twenty-one, twenty-two, twenty-three, twenty-four, twenty five, or twenty six at biweekly (e.g., about 14 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (e.g., each dose monthly dose may or may not be identical).

In another embodiment, a single dose of an antibody provided herein is administered to patient to prevent, treat and/or alleviate one or more symptom of a C10orf54-mediated disease two, three, four, five, six, seven, eight, nine, ten, eleven, or twelve times at about monthly (e.g., about 30 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (e.g., each dose monthly dose may or may not be identical).

In one embodiment, a single dose of an antibody provided herein is administered to a patient to treat, prevent and/or alleviate a symptom of a C10orf54-mediated disease two, three, four, five, or six times at about bi-monthly (e.g., about 60 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (e.g., each bi-monthly dose may or may not be identical).

In some embodiments, a single dose of an antibody provided herein is administered to a patient to treat, prevent and/or alleviate one or more symptom of a C10orf54-mediated disease two, three, or four times at about tri-monthly (e.g., about 120 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (e.g., each tri-monthly dose may or may not be identical).

In certain embodiments, the route of administration for a dose of an antibody provided herein to a patient is intranasal, intramuscular, intravenous, or a combination thereof, but other routes described herein are also acceptable. Each dose may or may not be administered by an identical route of administration. In some embodiments, an antibody provided herein may be administered via multiple routes of administration simultaneously or subsequently to other doses of the same or a different antibody provided herein.

In certain embodiments, antibodies provided herein are administered prophylactically or therapeutically to a subject. Antibodies can be prophylactically or therapeutically administered to a subject so as to prevent, lessen or alleviate a C10orf54-mediated disease or symptom thereof.

Diagnostic Use of Antibodies

Labeled antibodies provided herein and derivatives and analogs thereof, which bind to a C10orf54 antigen can be used for diagnostic purposes to detect, diagnose, or monitor a C10orf54-mediated disease. Also provided herein are methods for the detection of a C10orf54-mediated disease comprising: (a) assaying the expression of a C10orf54 antigen in cells or a tissue sample of a subject using one or more antibodies provided herein that bind to the C10orf54 antigen; and (b) comparing the level of the C10orf54 antigen with a control level, e.g., levels in normal tissue samples (e.g., from a patient not having a C10orf54-mediated disease, or from the same patient before disease onset), whereby an increase in the assayed level of C10orf54 antigen compared to the control level of the C10orf54 antigen is indicative of a C10orf54-mediated disease.

Also provided herein is a diagnostic assay for diagnosing a C10orf54-mediated disease comprising: (a) assaying for the level of a C10orf54 antigen in cells or a tissue sample of an individual using one or more antibodies provided herein that bind to a C10orf54 antigen; and (b) comparing the level of the C10orf54 antigen with a control level, e.g., levels in normal tissue samples, whereby an increase in the assayed C10orf54 antigen level compared to the control level of the C10orf54 antigen is indicative of a C10orf54-mediated disease. A more definitive diagnosis of a C10orf54-mediated disease may allow health professionals to employ preventative measures or aggressive treatment earlier thereby preventing the development or further progression of the C10orf54-mediated disease.

Antibodies provided herein can be used to assay C10orf54 antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

One aspect provided herein is the detection and diagnosis of a C10orf54-mediated disease in a human. In one embodiment, diagnosis comprises: a) administering (for example, parenterally, subcutaneously, or intraperitoneally) to a subject an effective amount of a labeled antibody that binds to a C10orf54 antigen; b) waiting for a time interval following the administering for permitting the labeled antibody to preferentially concentrate at sites in the subject where the C10orf54 antigen is expressed (and for unbound labeled molecule to be cleared to background level); c) determining background level; and d) detecting the labeled antibody in the subject, such that detection of labeled antibody above the background level indicates that the subject has a C10orf54-mediated disease. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

In one embodiment, monitoring of a C10orf54-mediated disease is carried out by repeating the method for diagnosing the a C10orf54-mediated disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods provided herein include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Methods of Producing Antibodies

Antibodies provided herein that bind to an antigen can be produced by any method known in the art for the synthesis of antibodies, in particular, by chemical synthesis or by recombinant expression techniques. The practice of the disclosure employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, NY; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Polyclonal antibodies that bind to an antigen can be produced by various procedures well-known in the art. For example, a human antigen can be administered to various host animals including, but not limited to, rabbits, mice, rats, etc. to induce the production of sera containing polyclonal antibodies specific for the human antigen.

Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981) (the references incorporated by reference in their entireties). The term "monoclonal antibody" as used herein is not limited to antibodies produced through hybridoma technology. Other exemplary methods of producing monoclonal antibodies are discussed elsewhere herein, such as e.g., use of the KM Mouse™. Additional exemplary methods of producing monoclonal antibodies are provided in the Examples herein.

Methods for producing and screening for specific antibodies using hybridoma technology are routine and well known in the art. Briefly, mice can be immunized with a C10orf54 antigen and once an immune response is detected, e.g., antibodies specific for C10orf54 antigen are detected in the mouse serum, the mouse spleen is harvested and splenocytes isolated. The splenocytes are then fused by well known techniques to any suitable myeloma cells, for example cells from cell line SP20 available from the ATCC©. Hybridomas are selected and cloned by limited dilution.

Additionally, a RIMMS (repetitive immunization multiple sites) technique can be used to immunize an animal (Kilptrack et al., 1997 Hybridoma 16:381-9, incorporated by reference in its entirety). The hybridoma clones are then assayed by methods known in the art for cells that secrete antibodies capable of binding a given polypeptide. Ascites fluid, which generally contains high levels of antibodies, can be generated by immunizing mice with positive hybridoma clones.

Accordingly, also provided herein are methods of generating antibodies by culturing a hybridoma cell secreting a modified antibody provided herein wherein, in certain embodiments, the hybridoma is generated by fusing splenocytes isolated from a mouse immunized with a C10orf54 antigen with myeloma cells and then screening the hybridomas resulting from the fusion for hybridoma clones that secrete an antibody able to bind to a C10orf54 antigen.

Antibody fragments which recognize specific C10orf54 antigens may be generated by any technique known to those of skill in the art. For example, Fab and F(ab')$_2$ fragments provided herein may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Further, the antibodies provided herein can also be generated using various phage display methods known in the art.

For example, antibodies can also be generated using various phage display methods. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies provided herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')$_2$ fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (the references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, human or chimeric antibodies can be used. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

In specific embodiments, human antibodies are produced. Human antibodies and/or fully human antibodies can be produced using any method known in the art, including the Examples provided herein. For example, transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of the polypeptide. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633, 425, 5,569,825, 5,661,016, 5,545,806, 5,814,318, and 5,939, 598, which are incorporated by reference herein in their entirety. Other methods are detailed in the Examples herein. In addition, companies such as Abgenix, Inc. (Freemont, CA) and Genpharm (San Jose, CA) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331, 415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fabc, Fv) in which all or substantially all of the CDR regions correspond to those of a non human immunoglobulin (e.g., donor antibody) and all or substantially all of the framework regions are those of a human immunoglobulin consensus sequence. In certain embodiments, a humanized antibody also comprises at least a portion of an immunoglobulin constant region (Fc), typically that of a human immunoglobulin.

Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. Examples of VL and VH constant domains that can be used in certain embodiments include, but are not limited to, C-kappa and C-gamma-1 (nG1 m) described in Johnson et al. (1997) J. Infect. Dis. 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, or greater than 95%. Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety. Often, framework residues in the framework regions will be substituted with the corresponding residue from the CDR donor antibody to alter (e.g., improve) antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that bind to a C10orf54 antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

Polynucleotides Encoding an Antibody

Also provided herein are polynucleotides comprising a nucleotide sequence encoding an antibody provided herein that binds to C10orf54 (e.g., C10orf54 polypeptide, C10orf54 polypeptide fragment, C10orf54 epitope). Also provided herein are polynucleotides that hybridize under high stringency, intermediate or lower stringency hybridization conditions, e.g., as defined supra, to polynucleotides that encode a antibody or modified antibody provided herein.

In certain embodiments, nucleic acid molecules provided herein comprise or consist of a nucleic acid sequence encoding a VH and/or VL amino acid sequence disclosed herein, or any combination thereof (e.g., as a nucleotide sequence encoding an antibody provided herein, such as a full-length antibody, heavy and/or light chain of an antibody, or a single chain antibody provided herein).

Recombinant Expression of an Antibody

Recombinant expression of an antibody provided herein (e.g., a full-length antibody, heavy and/or light chain of an antibody, or a single chain antibody provided herein) that binds to a C10orf54 antigen requires construction of an expression vector containing a polynucleotide that encodes the antibody. Once a polynucleotide encoding an antibody molecule, heavy or light chain of an antibody, or fragment thereof (such as that containing the heavy and/or light chain variable domain) has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Thus, also provided herein are replicable vectors comprising a nucleotide sequence encoding an antibody molecule provided herein, a heavy or light chain of an antibody, a heavy or light chain variable domain of an antibody or a fragment thereof, or a heavy or light chain CDR, operably linked to a promoter. Such vectors may include the nucleotide sequence encoding the constant region of the antibody molecule (see, e.g., International Publication Nos. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody provided herein. Thus, also provided herein are host cells containing a polynucleotide encoding an antibody provided herein or fragments thereof, or a heavy or light chain thereof, or fragment thereof, or a single chain antibody provided herein, operably linked to a heterologous promoter. In certain embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibodies provided herein (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody provided herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells, such as *Escherichia coli*, or eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In specific embodiments, antibodies provided herein are produced in CHO cells. In a specific embodiment, the expression of nucleotide sequences encoding antibodies provided herein which bind to a C10orf54 antigen is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells. In specific embodiments, fully human, monoclonal anti-C10orf54 antibodies provided herein are produced in mammalian cells, such as CHO cells.

For long-term, high-yield production of recombinant proteins, stable expression is useful, but not mandatory. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker.

Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors provided herein, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains may comprise cDNA or genomic DNA.

Once an antibody has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies provided herein may be fused to heterologous polypeptide sequences described herein or otherwise known in the art to facilitate purification.

Kits

Also provided herein is a pharmaceutical pack or kit comprising one or more containers filled with one or more of the ingredients of the pharmaceutical compositions provided herein, such as one or more antibodies provided herein. Optionally associated with such container(s) can be a notice in the form prescribed by a governmental agency regulating the manufacture, use or sale of pharmaceuticals or biological products, which notice reflects approval by the agency of manufacture, use or sale for human administration. In some embodiments, the kit comprises a package insert. The term "package insert" is used to refer to instructions customarily included in commercial packages of therapeutic products, that contain information about the indications, usage, dosage, administration, contraindications and/or warnings concerning the use of such therapeutic products, as well as instructions for use.

Also provided herein are kits that can be used in the above methods. In one embodiment, a kit comprises an antibody provided herein, such as an isolated antibody, in one or more containers. In a specific embodiment, the kits provided herein contain a substantially isolated C10orf54 antigen as a control. In certain embodiments, the kits provided herein further comprise a control antibody which does not react with the C10orf54 antigen. In another specific embodiment, the kits provided herein contain a means for detecting the binding of a modified antibody to a C10orf54 antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized C10orf54 antigen. The C10orf54 antigen provided in the kit may also be attached to a solid support. In a more specific embodiment the detecting means of the above described kit includes a solid support to which C10orf54 antigen is attached. Such a kit may also include a non-attached reporter-labeled anti-human antibody. In this embodiment, binding of the antibody to the C10orf54 antigen can be detected by binding of the reporter-labeled antibody.

The following examples are offered by way of illustration, and not by way of limitation.

EXAMPLES

Example 1—Identification of C10orf54 on the Surface of Acute Myelogenous Leukemia (AML) Tumor Cells A total of 14 fresh bone marrow mononuclear cells (BMMCs) from patients with AML were obtained from AllCells and additional 16 frozen patient samples were from Fred Hutchinson Cancer Research Center (FHCRC). As a control, 16 fresh BMMC samples from healthy donors were analyzed. To monitor the quality of individual AML samples, hematoxylin and eosin staining of AML blasts were performed or AML marker expression was monitored using flow cytometry/FACS analysis. Sample handling was optimized so as to maximally maintain cell viability during sample isolation. Optimal labeling times for AML samples were determined to allow for efficient labeling without compromise of cellular integrity.

Surface tagged antigen profiling (sTAg) was used to identify and quantitatively profile the repertoire of surface proteins on cells in the samples. The extracellular domains of proteins associated with the cell membranes of intact primary AML tumor cells were chemically tagged and then chromatographically enriched for tagged proteins using a solid-phase affinity resin. Eluted proteins were stored at −80° C. prior to mass spectrometry analysis as described below.

Proteins enriched by the sTAg method were identified and quantified using high-resolution, shotgun liquid chromatography tandem mass spectrometry (MS). A hybrid ThermoFisher LTQ ORBITRAP™ Velos mass spectrometer, which combines the sensitivity of a linear ion trap with the high-resolution and mass accuracy afforded by the revolutionary ORBITRAP™ mass analyzer (Olsen et al., Mol. Cell Proteomics 8:2759-2769, 2009) coupled to a nanoflow liquid chromatography apparatus was employed for shotgun-based, bottoms-up proteomics to determine the identities and quantitative abundance measurements of proteins in the AML cell surface enrichment fractions (Yates et al., Annu. Rev. Biomed. Eng. 11:49-79, 2009). Tryptic digests from enriched surface proteins were separated by hydrophobicity via online, nanoflow liquid chromatography as peptide masses and fragmentation patterns were recorded dynamically by the mass spectrometer. To determine peptide and protein identities, the raw MS data were processed using the SEQUEST algorithm executed on a fast-processing Sorcerer 2 platform (Lundgren et al., Curr. Protoc. Bioinformatics, Chapter 13: Unit 13.3, 2009), to determine best-fit matches between experimental fragmentation patterns and those determined in-silico from the human proteome. Resulting matches were statistically validated using the PEPTIDEPROHPHET™ (Keller et al., Anal. Chem. 74:5383-5392, 2002) and PROTEINPROPHET™ (Nesvizhskii et al., Anal. Chem. 75: 4646-4658, 2003) algorithms as implemented in SCAFFOLD Software (Proteome Software) to ensure the lowest possible false discovery rates (FDR) and thus inclusion of only robustly identified proteins in the candidate pool.

The relative quantitative levels of identified proteins in the sTAg samples were determined using the spectral counting method (reviewed in Neilson et al., Proteomics 11:535-553, 2011). Spectral counting is based on the empirical demonstration that the number of assigned (positively identified) spectra associated with peptides from each protein correlates strongly with that protein's relative abundance in the original mixture (Liu et al., Anal. Chem. 76:4193-4201, 2004). Spectral counts of identified peptides were obtained from the SCAFFOLD Software program that displays, sorts and filters the results of SEQUEST-searched mass spectrometry data. Raw spectral counts were transformed to percent Normalized Spectral Abundance Factor (% NSAF) values (Zybailov et al., J. Proteome Res. 5:2339-2347, 2006) to account for differences in protein length and variability in total protein concentration. Selected monoclonal antibodies were used to validate the proteomic measurements using quantitative FACS analysis as an independent, external confirmatory measure of the sTAg mass spectrometry-based proteomic profiling of the primary tumor cell surface expression (see, e.g., Example 2).

Figure 1B:
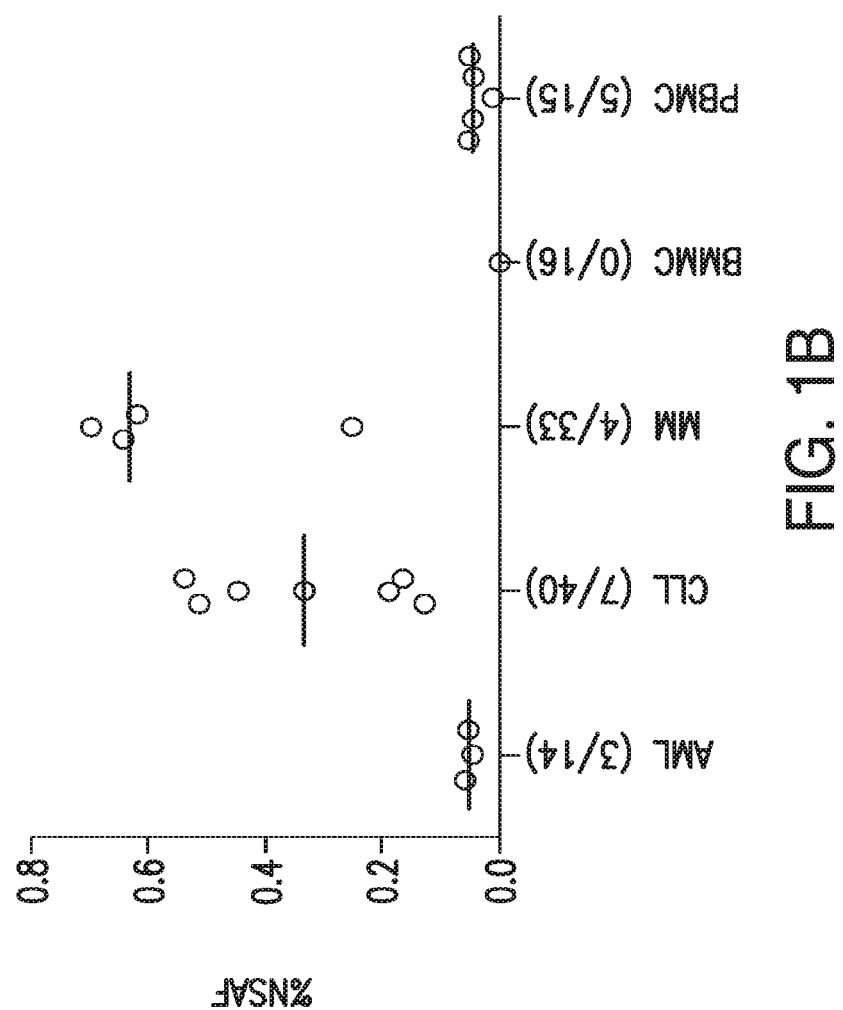

Using sTAg analysis, C10orf54 having the amino acid sequence of SEQ ID NO:1080 was identified as being present on the surface of AML tumor cells. As shown in FIG. 1A, the sTAg method identified C10orf54 in 7 of 30 primary AML samples with a median % NSAF of 0.06. In contrast, C10orf54 was not detected in any 16 BMMC samples from healthy donors. The AML benchmark, CD33, was identified in 11 of AML samples with a median % NSAF of 0.07, and four of 16 normal BMMC samples with a median % NSAF of 0.05. FIG. 1B, shows a subset of the sTAg samples shown in FIG. 1A. Based on this analysis, C10orf54 appears to be comparably expressed to CD33 in patient-derived AML specimens and expressed on a significant portion of AML patients relative to relevant normal controls.

Example 2—Expression of C10orf54

A. Expression in AML

Flow cytometry studies were conducted with 23 primary and 3 normal BM-MNC samples obtained as described in Example 1 using anti-C10orf54 antibodies to analyze the expression profile of C10orf54 in AML. Antibodies were labeled with AF647 or AF488-fluorochromes. Cells were counted and used at 500000 cells/stain, resuspended in FACS buffer: RPMI, 4% HIFBS, 0.02% NaN3. Antibodies were incubated for 15 minutes, at room temperature in the dark and then analyzed on a MACSQuant (Miltenyl Biotec, Auburn, CA) instrument. Data analysis was performed using the FLOWJO (TreeStar, Ashland, OR) software. Results of FACS analysis using anti-C10orf54 antibody 76E1 are shown in FIG. 2.

B. Expression in Normal Vs. Tumor Tissues

Tissue microarray (TMA) studies were conducted to determine the protein expression for C10orf54 in a variety of human normal and tumor tissues.

A variety of formalin fixed paraffin embedded tissues, including TMAs obtained from US Biomax (Rockville, MD) and Protein Biotechnologies (Ramona, CA), were used. Formalin fixed paraffin embedded sarcoma cells transfected with C10orf54, sarcoma parental cells and human placenta cells were used as positive and negative controls. An anti-C10orf54 antibody (Novus Biologicals (Littleton CO80120) Cat #NBP1-88967 C10orf54/B7-H5/PD-1H) was used at a dilution of 1:150 with citrate buffer pH6.0 for antigen retrieval.

The immunohistochemistry staining was performed using a Dako Autostainer (Dako North America, Carpenteria, CA93013) at room temperature with PBS washes between each step.

Normal tissue C10orf54 expression was primarily confined to immune cells in most normal tissues evaluated. C10orf54 positive blood vessels were observed in CNS tissues although at higher magnification, and C10orf54 expression appeared to be on perivascular cells (pericytes) and immune cells. Trophoblasts in the placenta were strongly positive for C10orf54. The only epithelial tissue where C10orf54 positive expression was observed was in the reactive tonsil. However, this positive expression may be due to the large numbers of positive lymphocytes trafficking through the epithelium. Negative tissues included kidney glomeruli, tubules and ducts, liver hepatocytes and sinusoids, lung alveoli and bronchi, pancreas islets and acini, heart muscle, prostate glands, ovary, colon crypts, stomach glands and epithelia, skin glands and epithelia, thymus, uterus, adrenal glands, skeletal muscle, CNS neurons, bladder epithelia, and large vessels.

Thus, in summary, the normal tissue TMA studies showed the strongest positive staining for placenta trophoblasts, with positive immune cells in small intestine (lamina propria), spleen, tonsil, ureter and lung.

The tumor tissue TMA studies surprisingly showed C10orf54 positive cells present in more than 99% of tumors having inflammation. These results are summarized in Table 34.

TABLE 34

| ORGAN | TUMOR TYPE | N No Inflammation | N Inflammation Present | INFLAMMATION/ C10orf54 POSITIVE CELLS |
|---|---|---|---|---|
| SKIN | Melanoma Primary | 31 | 9 | 9/9 |
| | Melanoma Metastatic | 9 | 5 | 5/5 |
| | Melanoma Benign | 23 | 0 | N/A* |
| | Squamous Cell | 0 | 2 | 2/2 |
| COLON | Adenocarcinoma | 1 | 9 | 9/9 |
| BREAST | Ductal | 5 | 4 | 4/4 |
| LIVER | Hepatocellular | 7 | 1 | 1/1 |
| BLADDER | Transitional Cell | 3 | 2 | 2/2 |
| KIDNEY | Clear Cell | 5 | 0 | N/A* |
| LUNG | Squamous Cell | 0 | 5 | 5/5 |
| | Adenocarcinoma | 2 | 2 | 2/2 |
| | Small Cell** | 0 | 1 | 0/1 |
| STOMACH | Adenocarcinoma | 2 | 2 | 2/2 |
| PANCREAS | Adenocarcinoma | 0 | 2 | 2/2 |
| ESOPHAGUS | Squamous Cell | 0 | 2 | 2/2 |

N/A*-not applicable as no inflammation present.
**Small cell lung cancer sample had inflammation that was negative for C10orf54.

Thus, in summary, C10orf54 expression in tumor tissue was localized within the inflammatory immune cells in many types of tumors.

C. Expression in Myeloid Derived Suppressor Cells (MDSC)

Flow cytometry studies were conducted as described below to determine C10orf54 expression levels in the MDSC sub-population (CD11 b$^+$ leukocytes) of purified human peripheral blood mononuclear cells (PBMCs) from healthy donors. Expression was assessed and quantified using labeled monoclonal antibody 76E1 in the following MDSC populations: monocytic (CD11 b$^+$/CD14$^+$/HLA-DR$^-$), granulocytic (CD11 b$^+$/CD15$^+$/HLA-DR$^-$), and immature myeloid cells (CD11 b$^+$/CD15$^-$/HLA-DR$^-$). The PBMC samples used in these experiments were obtained from ALLCELLS (Emeryville, CA).

The antibody clone 76E1 was labeled with ALEXA FLUOR® 647 dye. PBMC samples were prepared and labeled with LIVE/DEAD Yellow (LDY). 100 µl (1E6 cells) were added to the following: FcR Blocking Reagent, human; Lineage markers; CD11 b-PE; CD14-APC-Cy7; CD15-PerCP-Cy5.5; HLA-DR-PE-Cy7; and 1 µg of labeled 76E1-AF647 antibody. After incubation for 30 minutes at 4° C. in the dark, samples were washed and analyzed.

Median Fluorescence Intensities (MFI) was calculated for each sample on a MACSQuant Analyzer. In order to determine C10orf54 copy numbers, Quantum Simply Cellular anti-Mouse IgG kit (Bangs Laboratories, 815B) was used.

Figures 26A, 26B:
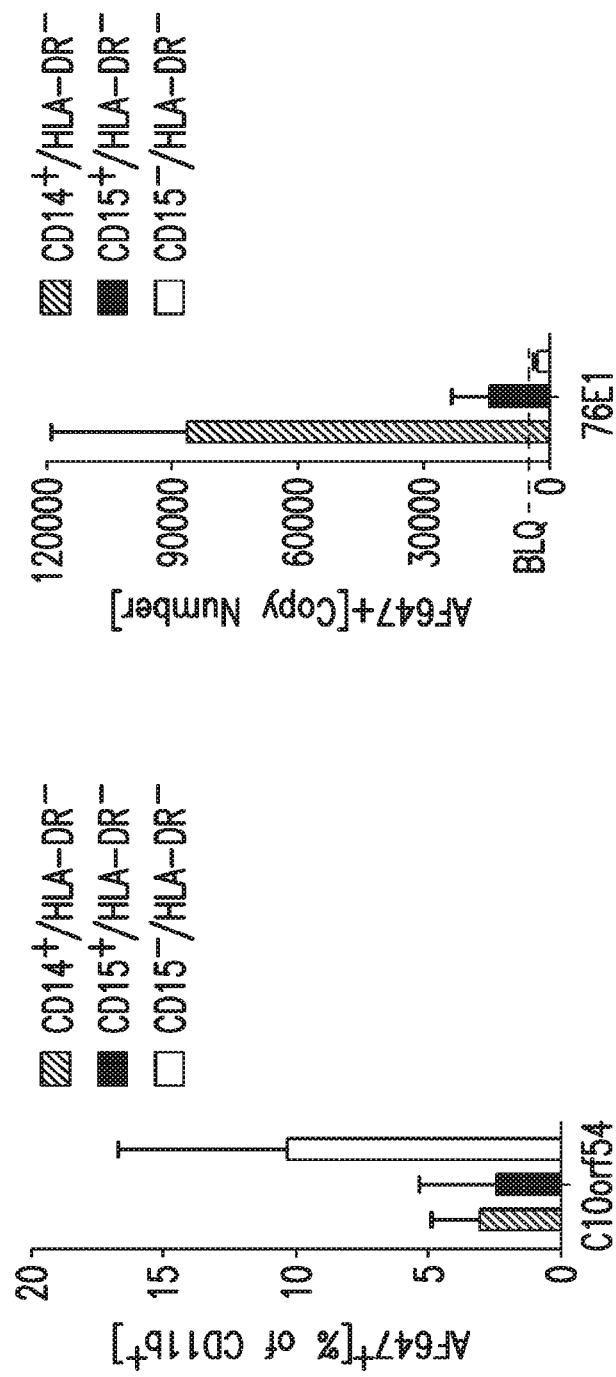
FIGS. 26A and 26B show C10orf54 expression in MDSC sub-populations.

The percentage of 76E1-AF-647$^+$ cells found within the three MDSC sub-populations are summarized in FIG. 26A. Similarly, the C10orf54 copy numbers for each MDSC subpopulation are summarized in FIG. 26B.

Using the above analysis, it was possible to identify both the Lin$^-$/CD11 b$^+$ leukocytes and MDSC subpopulations, which showed that the monocytic MDSC population exhibits the highest level of C10orf54 expression in healthy PBMC samples.

D. Expression in CD4$^+$/CD25$^+$ T-Cells

Flow cytometry studies were conducted as described above to determine C10orf54 expression levels in naïve CD4$^+$/CD25$^+$ T-cells found in human PBMCs. As described above, expression was assessed and quantified using labeled monoclonal antibody 76E1. The CD4$^+$/CD25$^+$ T-cells were isolated using the human CD4+/CD25+ Regulatory T Cell Isolation Kit (Miltenyi-Biotec, 130-091-301). Aliquots from each stage of the separation (PBMC, CD4+ T-cells, CD4+/CD25+ T-cells) were analyzed for C10orf54 expression. MFI values were quantified using the Quantum Simply Cellular anti-Mouse IgG Kit (Bangs Laboratories, 815B). Human PBMC samples were obtained from ALLCELLS to assess this methodology.

The above analysis showed that C10orf54 was minimally expressed in CD4$^+$/CD25$^+$ T-cells.

E. Expression in Human Melanoma

Immunohistochemistry (IHC) staining and immunofluorescence (IF) double staining studies were conducted as described below to determine C10orf54 expression in human melanoma tumor samples and to evaluate a large number of cell subtypes (macrophages, myeloid cells, T-cells and tumor cells).

Three distinct melanomas were evaluated: two soft tissue skin melanomas (M113044 and OD41239) and one metastatic melanoma to the lymph node (WD-12972). One sample of soft tissue melanoma (OD41239) was >90% tumor while the other soft tissue melanoma and the melanoma met to the lymph node (LN) had a large inflammatory response with fewer tumor cells present.

The antibodies used in this study are outlined in Table 35 below. Gp100, which is preferentially expressed at high levels in melanoma cells, was also stained in each melanoma tissue using IHC to determine the amount of tumor cells within the tissue samples and the extent of C10orf54 positive tumor cells.

TABLE 35

| Primary Antibody | Company | Host | Clone | Dilution | Antibody Cat# | Secondary Antibody | Secondary Cat#* |
|---|---|---|---|---|---|---|---|
| CD3 | Abcam | Rabbit | Pab | 1:400 | ab5690 | anti-Rabbit-Cy3 | 711-165-152 |
| CD68 | Spring Bioscience | Rabbit | SP251 | 1:100 | M5510 | anti-Rabbit-Cy3 | 711-165-152 |
| CD11b | BioLegend | Rat | M1/70 | 5 ug/ml | 101202 | anti-Rat-Cy3 | 712-165-150 |
| PD-L1 | Spring Bioscience | Rabbit | SP142 | 1:150 | M4420 | anti-Rabbit-Cy3 | 711-165-152 |
| gp100 | Abcam | Rabbit | EPR4864 | 1:100 | ab137062 | anti-Rabbit-Cy3 | 711-165-152 |
| VISTA | Abgent | Mouse | Pab | 3 ug/ml | H0064115-P01 | anti-mouse-488 | 715-545-150 |

*Jackson ImmunoResearch Laboratories Inc

For IF double staining, 8 µm frozen cryostat sections were fixed in 75% 200 proof Ethanol and 25% Acetone for 5 minutes. A cocktail of primary antibodies (2 different species diluted in Dako diluent cat #S3022; diluted according to Table 35) were added to the samples and incubated for 1 hour. Secondary antibodies were then added at a ratio of 1:200 and incubated 30 mins. Coverslips with Prolong Gold+DAPI (ThermoFisher cat #36935) were added and left to cure overnight. An Olympus BX52 upright fluorescent microscope was used to analyze the samples.

For IHC staining with gp100 antibody, 8 µm frozen cryostat sections were fixed in 75% 200 proof Ethanol and 25% Acetone for 5 minutes. Endogenous peroxidase was blocked by incubation with Bloxall (Vector cat #SP-6000)) for 5 minutes. Samples were further blocked using Avidin and Biotin blocking kit (BioLegend cat #SIG-31126) for 10 mins each and Protein Block (Dako cat #0909) for 30 mins. Primary gp100 antibody (abcam cat #ab137062; ratio of 1:100) was added and incubated for 1 hour. Secondary antibody biotin anti-rabbit (Vector cat #BA1000) was added at a ratio of 1:200 and incubated for 30 mins. Streptavidin-HRP staining was performed using VECTASTAIN Elite ABC kit (Vector Laboratories cat #PK6100) for 30 mins. DAB (Sigma cat #D4418) staining and Mayers hematoxylin counterstain (EMS cat #26043-05) were also performed.

The following summarizes the results of the above experiments:

Gp100: Almost all the tumor cells in all three melanoma tissue samples were C10orf54 negative.

CD3: M113044: A large number of T-cells were very weakly C10orf54 positive. ~30% cells were C10orf54 positive/CD3 negative. OD41239: Very few T-cells present and almost all CD3 positive cells were C10orf54 negative. WD-12972: A large numbers of T-cells present. Many were also weakly C10orf54 positive. T-cells within the tumor were mostly C10orf54 negative and there were many C10orf54 positive cells that were CD3 negative throughout the tumor tissue.

CD68: M113044: Most CD68 positive cells were C10orf54 negative. OD41239: A subset of CD68 positive cells was also C10orf54 positive. WD-12972: CD68 positive cells were predominantly C10orf54 negative although there were also some CD68 negative/C10orf54 positive cells.

CD11 b: Almost all CD11 b positive cells were also C10orf54 positive. However, there were C10orf54 positive cells that were CD11 b negative in all three melanoma tumors.

PD-L1: PD-L1 positive cells were also predominantly C10orf54 positive in all three tumors. Again, there was C10orf54 positive cells that were PD-L1 negative in all three melanomas.

In summary, nearly all the gp100 positive melanoma tumor cells were C10orf54 negative in all three melanoma samples. There was a large variability in the amount of inflammatory cell infiltrate within the 3 different melanoma sample tissues. However, almost all the CD11 b and PD-L1 positive cells in these melanomas were C10orf54 positive and most CD3 positive T-cells were either C10orf54 negative or very weakly C10orf54 positive.

F. Expression in Non-Small Cell Lung Carcinoma (NSCLC)

Flow cytometry studies were conducted as described below to determine C10orf54 expression levels in PBMCs from NSCLC patients. Expression was assessed and quantified using labeled monoclonal antibody 26A to assess the sub-populations of CD11 b, CD33, CD14 and CD15. Exemplary PBMC samples from a healthy patient and a clinically diagnosed NSCLC patient that were used in these studies were obtained from ALLCELLS (Emeryville, CA).

The antibody clone 26A was labeled with ALEXA FLUOR© 647 dye. PBMC samples were prepared. 100 µl (1E6 cells) were added to the following: FcR Blocking Reagent, human; Lineage markers; CD11 b-PE; CD14-APC-Cy7; CD15-PerCP-Cy5.5; HLA-DR-PE-Cy7; and 1 µg of labeled 26a-AF647 antibody. After incubation for 30 minutes at 4° C. in the dark, samples were washed, resuspended in DAPI working solution and analyzed.

Median Fluorescence Intensities (MFI) was calculated for each sample on a MACSQuant Analyzer. In order to determine C10orf54 copy numbers, Quantum Simply Cellular anti-Mouse IgG kit (Bangs Laboratories, 815B) was used.

Figure 27:
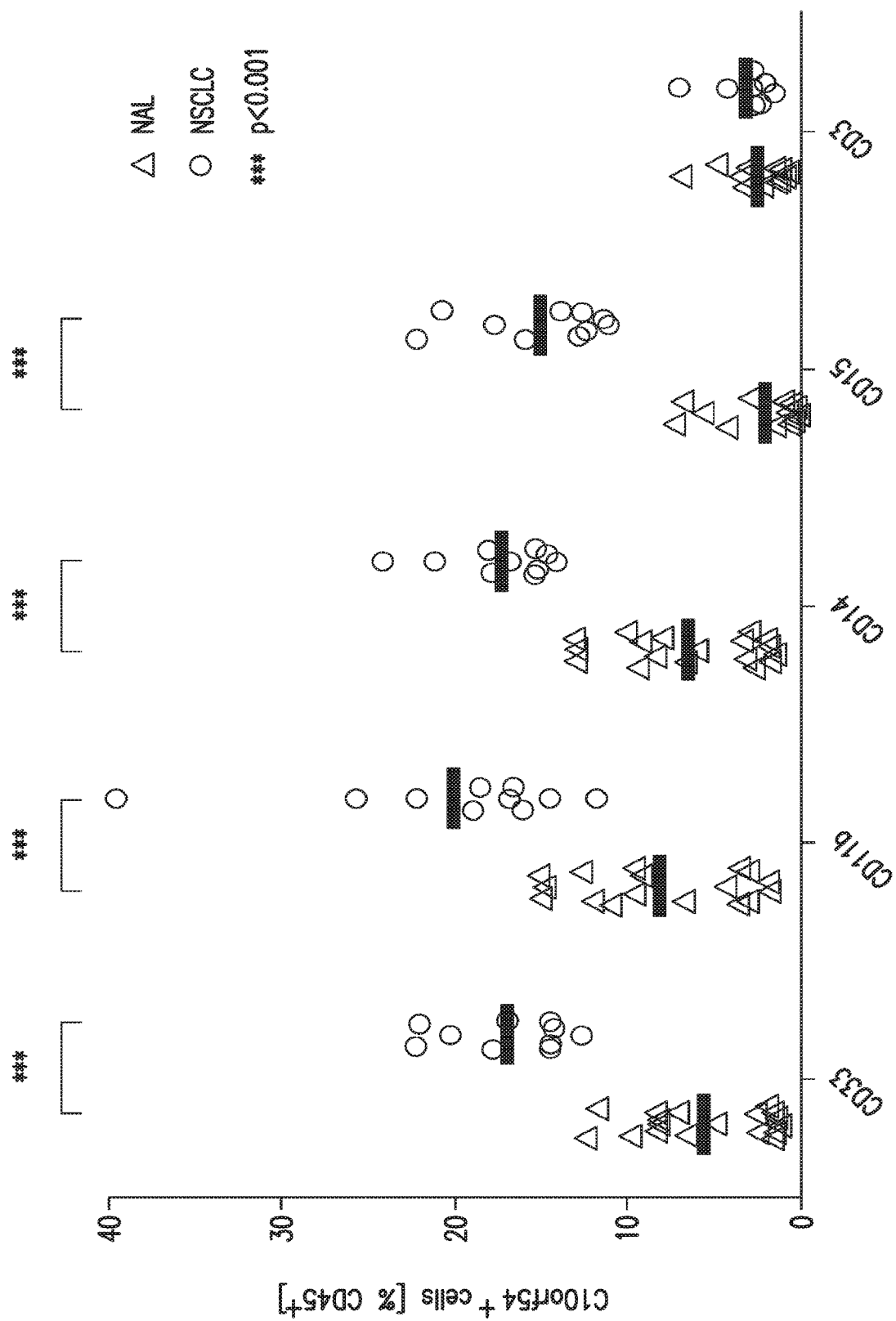
FIG. 27 shows a scatter plot of C10orf54 expression in PBMC subsets of NSCLC patients.

C10orf54 expression was elevated in the PBMC subpopulations from the NSCLC sample in comparison to the healthy sample as depicted in FIG. 27. These results are summarized in Table 36, which shows the C10orf54 copy numbers for expression within cell subsets.

TABLE 36

| Cell Subset | C10orf54 [Copy Numbers] | |
| --- | --- | --- |
| | Healthy | NSCLC |
| CD11b | 102611 | 141143 |
| CD33 | 97087 | 183352 |

TABLE 36-continued

| Cell Subset | C10orf54 [Copy Numbers] | |
| --- | --- | --- |
| | Healthy | NSCLC |
| CD14 | 102937 | 191727 |
| CD15 | 19388 | 60436 |

Additionally, tissue microarray (TMA) studies were conducted to determine the protein expression for C10orf54 in NSCLC.

A variety of formalin fixed paraffin embedded tissues, including TMAs obtained from US Biomax (Rockville, MD), were used. Formalin fixed paraffin embedded sarcoma cells transfected with C10orf54 and sarcoma parental cells were used as positive and negative controls. An anti-C10orf54 antibody (Novus Biologicals (Littleton C080120) Cat #NBP1-88967 C10orf54/B7-H5/PD-1H) was used at a dilution of 1:150 with citrate buffer pH6.0 for antigen retrieval.

The immunohistochemistry staining was performed using a Dako Autostainer (Dako North America, Carpenteria, CA93013) at room temperature with PBS washes between each step.

A TMA of a lung tumor having all types of NSCLC tumors revealed that all the NSCLC types had positive C10orf54 expression. However, the sample numbers in this TMA were relatively small, except for the squamous cell carcinomas (SCC), which showed a strong C10orf54 expression pattern.

The SCC subtype was further evaluated in four additional TMAs. Two TMAs had additional survival data. However, no correlation was observed when this data was plotted against percentage of C10orf54 positive cells. One TMA also provided EGFR expression data, but no correlation was observed when plotted against percentage of C10orf54 positive cells. In this TMA, the number of samples may have been too low to determine a true correlation. Pooled data for all four SCC TMAs was also evaluated. The samples were separated according to the degree of inflammation present in the cores assayed. When no inflammation is observed, no C10orf54 positive cells were detected. However, surprisingly, in specimens with either mild or marked inflammation, the majority of these samples had C10orf54 positive infiltrating cells. For example, in one SCC TMA, 17% showed now inflammation, 28% showed mild inflammation and 55% showed moderate-marked inflammation. Of the 28% that showed mild inflammation, 85% were C10orf54-positive, and of the 55% that showed moderate-marked inflammation, 92% were C10orf54-positive.

Thus, the above analyses indicate an increased C10orf54 population within each subset relative to the healthy donor. Similarly, the C10orf54 copy numbers are higher in the samples from the NSCLC patient in comparison to the healthy donor. Moreover, NSCLC with inflammation strongly correlated with C10orf54 expression.

Example 3—Preparation of Monoclonal Antibodies to C10orf54

Antibodies to C10orf54 were generated using the iTAb platform. In this system, a mouse tumor cell line is transduced to stably express the human protein and then implanted subcutaneously in syngeneic mice. The mice are treated with anti-CD8 antibody to remove the cell mediated rejection pathway while leaving the humoral immune response intact. Following this immunization, splenocytes are harvested, and are fused to an immortalized partner cell to generate hybridomas. Antibodies from these hybridomas are screened in multiple assays designed to identify a diverse panel of antibodies with good binding properties. The selected antibodies are then produced for in vivo testing as follows.

Murine sarcoma cell lines that express C10orf54 were prepared by virus infection of sarcoma cell lines. A PCR-amplified C10orf54 gene was cloned into a murine stem cell virus expression vector with a neomycin resistance gene and sequenced to confirm the identity. To prepare virus particles, HEK 293t cells with retroviral packaging proteins were transfected, in the presence of transfection reagent FUGENE HD (Roche), with the retroviral expression vector containing C10orf54. The virus particles collected from the supernatant of the culture media 48 hours after transfection were used to infect the sarcoma cells. After G418 selection, stable transfectants were pooled and then cloned by limiting dilution. Clones were then picked and expanded in the presence of antibiotics. Clones with the highest expression level of C10orf54 as measured by flow cytometry were expanded and banked. These cell lines were then used to immunize the syngeneic mice for antibody production and in the binding assays for antibody selection as follows.

For immunization, the mouse sarcoma cell line that expresses C10orf54 was implanted subcutaneously in 129s6/SvEv mice, which are syngeneic with the sarcoma line. Mice were boosted with the cell line three days prior to spleen harvest. Splenocytes were isolated as single cells and fused with SP2-MIL6 cells using PEG1500. Resulting hybridomas were plated in 384-well plates and allowed to grow for ten days.

Antibodies against C10orf54 were initially selected using a cell-based enzyme-linked immunosorbant assay (ELISA) to detect binding to C10orf54. For this assay, the C10orf54 expressing sarcoma cells were plated in 384-well plates one day prior to assay. Cells were then treated with hybridoma supernatants. Following incubation and wash, the presence of bound antibody was detected using a peroxidase-conjugated goat anti-mouse IgG antibody (Jackson ImmunResearch Laboratories) followed by a chemiluminescent substrate (ThermoScientific SuperSignal ELISA Pico Substrate). Hybridomas identified as positive in the initial screen were transferred to the wells of a 96-well plate. After growth, the supernatants were tested in a similar assay for confirmation.

The isotype of the antibodies was identified by ELISA by using isotype specific goat anti-mouse Fc antibodies. For this assay, C10orf54 expressing cells were plated in 384-well plates one day prior to assay. Cells were then treated with hybridoma supernatants. Following incubation and wash, cells were incubated with peroxidase-conjugated goat antibody specific for mouse IgG1 or IgG2a (Jackson ImmunResearch Laboratories), followed by a chemiluminescent substrate (ThermoScientific SuperSignal ELISA Pico Substrate).

Concentration of antibody in supernatants found to be positive for binding to the C10orf54 expressing cells was measured by ELISA. Supernatants were tested at four dilutions. For each antibody, the dilution that generated a value within the linear range of the standard curve was used to calculate the concentration of the antibody in the supernatant. Antibody concentration in the supernatants ranged in concentration from >1 µg/ml to <500 µg/ml, with approximately 300 supernatants >10 µg/ml. Twenty-two monoclonal antibodies were selected for their binding to C10orf54 and further analyzed in vitro and in vivo as described herein.

The sequences for the selected twenty-two monoclonal antibodies (5B, 46A, 97A, 128A, 146C, 208A, 215A, 26A, 164A, 230A, 76E1, 53A, 259A, 33A, 39A, 124A, 175A, 321D, 141A, 51A, 353A, 305A) are shown below.

The nucleic acid and amino acid sequences for the heavy chain and light chain variable regions of the antibody 5B are shown below:

5B Heavy Chain Variable Region with Signal Sequence (SEQ ID NO: 1154)
ATGGGTTGGAGCTGTATCATCTTCTTTCTGGTAGCAACAGCTACAGGTGTG

CACTCCCAGGTCCAGCTGCAGCAGTCTGGGGCTGAGCTGGTGAGGCCTGGG

GTCTCAGTGAAGATTTCCTGCAAGGGTTCTGGCTACACATTCACTGATTAT

GGTATGCACTGGGTGAAGCAGAGTCATGCAAAGAGTCTAGAGTGGATTGGA

ATTATTGATACTTACTATGGTGATGCTACCTACAACCAGAAGTTCAAGGGC

AAGGCCACGATGACTGTAGACAAATCCTCCAGCACAGCCTATATGGAACTT

GCCAGACTGACATCTGAGGATTCTGCCATCTATTACTGTGCAAGAAGGGCT

GGGAATGCTATGGACTACTGGGGTCAAGGAACCTCAGTCACCGTCTCCTCA (SEQ ID NO: 1155; Kabat CDRs are underlined; see also, Table 12)
MGWSCIIFFLVATATGVHSQVQLQQSGAELVRPGVSVKISCKGSGYTFTD<u>Y</u>

<u>GMHW</u>VKQSHAKSLEWIGI<u>IDTYYGDATYNQKFKG</u>KATMTVDKSSSTAYMEL

ARLTSEDSAIYYCAR<u>RAGNAMDY</u>WGQGTSVTVSS 5B light chain variable region with signal sequence
(SEQ ID NO: 1156)
ATGAAGTCACAGACCCAGGTCTTCGTATTTCTACTGCTCTGTGTGTCTGGT

GCTCATGGGAATATTGTGATGACCCAGACTCCCAAATTCCTGCTTGTATCA

GCAGGAGACAGGGTTACCATAACCTGCAAGGCCAGTCAGAGTGTGAGTAAT

GATGTAGCTTGGTACCAACAGAAGCCAGGGCAGTCTCCTAAACTGCTGATA

TACTATGCATCCAATCGCTACACTGGAGTCCCTGATCGCTTCACTGGCAGT

GGATATGGGACGGATTTCACTTTCACCATCAGCACTGTGCAGGCTGAAGAC

CTGGCAGTTTATTTCTGTCAGCAGGATTATAGCTCTCCTCGGACGTTCGGT

GGAGGCACCAAGCTGGAAATCAAA (SEQ ID NO: 1157; Kabat CDRs are underlined; see also, Table 12)
MKSQTQVFVFLLLCVSGAHGNIVMTQTPKFLLVSAGDRVTITC<u>KASQSVSN</u>

<u>DVAW</u>YQQKPGQSPKLLIY<u>YASNRYT</u>GVPDRFTGSGYGTDFTFTISTVQAED

LAVYFC<u>QQDYSSPRT</u>FGGGTKLEIK

The nucleic acid and amino acid sequences for the heavy chain and light chain variable regions of the antibody 46A are shown below:

46A Heavy Chain Variable Region with Signal Sequence (SEQ ID NO: 1158)
ATGGGTTGGAGCTGTATCGTCTTCTTTCTGGTAGCAACAGCTACAGGTGTG

CACTCCCAGGTCCAGCTGCAGCAGGCCGGGGGTGAGCTGGTGAGGCCTGGG

GTCTCAGTGAAGATTTCCTGCAAGGGTTCTGGCTACACATTCACTGATTAT

GGTATGCACTGGGTGAAGCAGAGTCATGCAAAGAGTCTAGAGTGGATTGGA

```
ATTATTAATACTTACTATGGGGATGCTACCTACAACCAGAAGTTCAAGGGC

AAGGCCACAATGACTGTAGACAAATCCTCCAGCACAGCCTATATGGAACTT

GCCAGACTGACATCTGAGGATTCTGCCATCTATTACTGTGCAAGAAGGGCT

GGGACTGCTATGGACTACTGGGGTCAAGGAACCTCAGTCACCGTCTCCTCA (SEQ ID NO :1159; Kabat CDRs are
             underlined; see also, Table 13)
MGWSCIVFFLVATATGVHSQVQLQQAGGELVRPGVSVKISCKGSGYTFTDY

GMHWVKQSHAKSLEWIGIINTYYGDATYNQKFKGKATMTVDKSSSTAYMEL

ARLTSEDSAIYYCARRAGTAMDYWGQGTSVTVSS 46A light chain variable region with signal
sequence
                              (SEQ ID NO: 1160)
ATGAAGTCACAGACCCAGGTCTTCGTATTTCTACTGCTCTGTGTCTGGT

GGTCATGGGAGTATTGTGATGACCCAGACTCCCAAATTCCTGCTTGTATCA

GCAGGAGACAGGGTTACCATAACCTGCAAGGCCAGTCAGAGTGTGAGTAAT

GATGTAGCTTGGTACCAACAGAAGCCAGGGCAGTCTCCTAAACTGCTGATA

TACTATGCATCCAATCGCTACACTGGAGTCCCTGATCGCTTCACTGGCAGT

GGATATGGGACGGATTTCACTTTCACCATCAGCACTGTGCAGGCTGAAGAC

CTGGCAGTTTATTTCTGTCAGCAGGATTATGGCTCTCCTCGGACGTTCGGT

GGAGGCACCAAGCTGGAAATCAAA (SEQ ID NO: 1161; Kabat CDRs are
             underlined; see also, Table 13)
MKSQTQVFVFLLLCVSGGHGSIVMTQTPKFLLVSAGDRVTITCKASQSVSN

DVAWYQQKPGQSPKLLIYYASNRYTGVPDRFTGSGYGTDFTFTISTVQAED

LAVYFCQQDYGSPRTFGGGTKLEIK
```

The nucleic acid and amino acid sequences for the heavy chain and light chain variable regions of the antibody 97A are shown below:

97A Heavy Chain Variable Region with Signal Sequence

```
                              (SEQ ID NO: 1162)
ATGGGTTGGAGCTGTATCATCTTCTTTCTGGTAGCAACAGCTACAGGTGTG

CACTCCCAGGTCCAGCTGCAGCAGTCTGGGGCTGAGCTGGTGAGGCCTGGG

GTCTCAGTGAAGATTTCCTGCAAGGGTTCTGGCTACACATTCACTGATTAT

GGTATGCACTGGGTGAAGCAGAGTCATGCAAAGAGTCTAGAGTGGATTGGA

GTTATTGATACTTACTATGGTGATGCTAGTAACAACCAGAAGTTCAAGGGC

AAGGCCACAATGACTGTAGACAAATCCTCCAGCACAGCCTATATGGAACTT

GCCAGACTGACATCTGAGGATTCTGCCATCTATTACTGTGCAAGAAGGGCT

GGGAATGCTATGGACTACTGGGGTCAAGGAACCTCAGTCACCGTCTCCTCA (SEQ ID NO: 1163; Kabat CDRs are
             underlined; see also, Table 14)
MGWSCIIFFLVATATGVHSQVQLQQSGAELVRPGVSVKISCKGSGYTFTDY

GMHWVKQSHAKSLEWIGVIDTYYGDASNNQKFKGKATMTVDKSSSTAYMEL

ARLTSEDSAIYYCARRAGNAMDYWGQGTSVTVSS 97A light chain variable region with signal
sequence
                              (SEQ ID NO: 1164)
ATGAAGTCACAGACCCAGGTCTTCGTATTTCTACTGCTCTGTGTCTGGT

GCTCATGGGAGTATTGTGATGACCCAGACTCCCAAATTCCTGCTTGTATCA

GCAGGAGACAGGGTTGCCATAACCTGCAAGGCCAGTCAGAGTGTGAGTAAT

GATGTAGCTTGGTACCAACAGAAGCCAGGGCAGTCTCCTAAACTGCTGATA

TACTATGCATCCAATCGCTACACTGGAGTCCCTGATCGCTTCACTGGCAGT

GGATATGGGACGGATTTCACTTTCACCATCAGCACTGTGCAGGCTGAAGAC

CTGGCAGTTTATTTCTGTCAGCAGGATTATGGCTCTCCTCGGACGTTCGGT

GGAGGCACCAAGCTGGAAATCAAA (SEQ ID NO: 1165; Kabat CDRs are
             underlined; see also, Table 14)
MKSQTQVFVFLLLCVSGAHGSIVMTQTPKFLLVSAGDRVAITCKASQSVSN

DVAWYQQKPGQSPKLLIYYASNRYTGVPDRFTGSGYGTDFTFTISTVQAED

LAVYFCQQDYGSPRTFGGGTKLEIK
```

The nucleic acid and amino acid sequences for the heavy chain and light chain variable regions of the antibody 128A are shown below:

128A Heavy Chain Variable Region with Signal Sequence

```
128A heavy chain variable region with signal
sequence
                              (SEQ ID NO: 1166)
ATGGGTTGGAGCTGTATCATCTTCTTTCTGGTAGCAACAGCTACAGGTGTG

CACTCCCAGGTCCAGCTGCAGCAGTCTGGGGCTGAGCTGGTGAGGCCTGGG

GTCTCAGTGAAGATTTCCTGCAAGGGTTCTGGCTACACATTCACTGATTAT

GGTATGCACTGGGTGAAGCAGAGTCATGCAAAGAGTCTAGAGTGGATTGGA

CTTATTGATACTTACTATGGTGATGCTACCTACAACCACAAATTCAAGGGC

AAGGCCACGATGACTGTAGACAAATCCTCCAGAACAGCCTATATGGAACTT

GCCAGACTGACATCTGAGGATTCTGCCATCTATTACTGTGCAAGAAGGGCT

GGGAATGCTATGGACTACTGGGGTCAAGGAACCTCAGTCACCGCCTCCTCA (SEQ ID NO: 1167; Kabat CDRs are
             underlined; see also, Table 15)
MGWSCIIFFLVATATGVHSQVQLQQSGAELVRPGVSVKISCKGSGYTFTDY

GMHWVKQSHAKSLEWIGLIDTYYGDATYNHKFKGKATMTVDKSSRTAYMEL

ARLTSEDSAIYYCARRAGNAMDYWGQGTSVTASS 128A light chain variable region with signal
sequence
                              (SEQ ID NO: 1168)
ATGAAGTCACAGACCCAGGTCTTCGTATTTCTACTGCTCTGTGTCTGGT

ACTCATGGGAATATTGCGATGACCCAGACTCCCAAATTCCTGCTTGTATCA

GCAGGAGACAGGGTTACCATAACCTGCAAGGCCAGTCAGAGTGTGAGTAAT

GATATAGCTTGGTACCAACAGAAGCCAGGACAGTCTCCTAGATTGCTGATA

TACTATGCATCCAATCGCTACACTGGAGTCCCTGATCGCTTCACTGGCAGT

GGATATGGGACGGATTTCACTTTCACCATCAGCACTGTGCAGGCTGAAGAC

CTGGCAGTTTATTTCTGTCAGCAGGATTATAGCTCTCCTCGGACGTTCGGT

GGAGGCACCAAGCTGGAAATCAAA (SEQ ID NO: 1169; Kabat CDRs are
             underlined; see also, Table 16)
MKSQTQVFVFLLLCVSGTHGNIAMTQTPKFLLVSAGDRVTITCKASQSVSN

DIAWYQQKPGQSPRLLIYYASNRYTGVPDRFTGSGYGTDFTFTISTVQAED

LAVYFCQQDYSSPRTFGGGTKLEIK
```

The nucleic acid and amino acid sequences for the heavy chain and light chain variable regions of the antibody 146C are shown below:

146C Heavy Chain Variable Region with Signal Sequence (SEQ ID NO: 1170)
ATGGGTTGGAGCTGTATCATCTTCTTTCTGGTAGCAACAGCTACAGGTGTG

CACTCCCAGGTCCAGCTGCAGCAGTCTGGGGCTGAGCTGGTGAGGCCTGGG

GTCTCAGTGAAGATTTCCTGCAAGGGTTCTGGCTACACATTCACTGATTAT

GGTATGCACTGGGTGAAGCAGAGTCATGCAAAGAGTCTAGAGTGGATTGGA

CTTATTGATACTTACTATGGTGATGCTACCTACAACCACAAATTCAAGGGC

AAGGCCACGATGACTGTAGACAAATCCTCCAGAACAGCCTATATGGAACTT

GCCAGACTGACATCTGAGGATTCTGCCATCTATTACTGTGCAAGAAGGGCT

GGGAATGCTATGGACTACTGGGGTCAAGGAACCTCAGTCACCGCCTCCTCA (SEQ ID NO: 1171; Kabat CDRs are underlined; see also, Table 16)
MGWSCIIFFLVATATGVHSQVQLQQSGAELVRPGVSVKISCKGSGYTFT<u>DY GMH</u>WVKQSHAKSLEWIG<u>LIDTYYGDATYNHKFKG</u>KATMTVDKSSRTAYMEL ARLTSEDSAIYYCAR<u>RAGNAMDY</u>WGQGTSVTASS 146C light chain variable region with signal sequence (SEQ ID NO: 1172)
ATGAAGTCACAGACCCAGGTCTTCGTATTTCTACTGCTCTGTGTGTCTGGT

ACTCATGGGAATATTGCGATGACCCAGACTCCCAAATTCCTGCTTGTATCA

GCAGGAGACAGGGTTACCATAACCTGCAAGGCCAGTCAGAGTGTGAGTAAT

GATATAGCTTGGTACCAACAGAAGCCAGGACAGTCTCCTAGATTGCTGATA

TACTATGCATCCAATCGCTACACTGGAGTCCCTGATCGCTTCACTGGCAGT

GGATATGGGACGGATTTCACTTTCACCATCAGCACTGTGCAGGCTGAAGAC

CTGGCAGTTTATTTCTGTCAGCAGGATTATAGCTCTCCTCGGACGTTCGGT

GGAGGCACCAAGCTGGAAATCAAA (SEQ ID NO: 1173; Kabat CDRs are underlined; see also, Table 16)
MKSQTQVFVFLLLCVSGTHGNIAMTQTPKFLLVSAGDRVTITC<u>KASQSVSN DIAW</u>YQQKPGQSPRLLIY<u>YASNRYT</u>GVPDRFTGSGYGTDFTFTISTVQAED LAVYFC<u>QQDYSSPRT</u>FGGGTKLEIK The nucleic acid and amino acid sequences for the heavy chain and light chain variable regions of the antibody 208A are shown below:

208A Heavy Chain Variable Region with Signal Sequence (SEQ ID NO: 1174)
ATGGGTTGGAGCTGTATCATCTTCTTTCTGGTAGCAACAGCTACAGGTGTG

CACTCCCAGGTCCAGCTGCAGCAGTCTGGGGCTGAGCTGGTGAGGCCTGGG

GTCTCAGTGAAGATTTCCTGCAAGGGTTCTGGCTACACATTCACTGATTAT

GGTATGCACTGGGTGAAGCAGAGTCATGCAAAGAGTCTAGAGTGGATTGGA

GTTATTGATACTTACTATGGTGATGCTGGCTACAACCAGAAGTTCAAGGGC

AAGGCCACAATGACTGTAGACAAATCCTCCAGCACAGCCTATATGGAACTT

GCCAGACTGACATCTGAGGATTCTGCCATCTATTACTGTGCAAGAAGGGCT

GGAAATGCTATGGACTACTGGGGTCAAGGAACCTCAGTCACCGTCTCCTCA (SEQ ID NO: 1175; Kabat CDRs are underlined; see also, Table 17)
MGWSCIIFFLVATATGVHSQVQLQQSGAELVRPGVSVKISCKGSGYTFT<u>DY GMH</u>WVKQSHAKSLEWIG<u>VIDTYYGDAGYNQKFKG</u>KATMTVDKSSSTAYMEL ARLTSEDSAIYYCAR<u>RAGNAMDY</u>WGQGTSVTVSS 208A light chain variable region with signal sequence (SEQ ID NO: 1176)
ATGAAGTCACAGACCCAGGTCTTCGTATTTCTACTGCTCTGTGTGTCTGGT

GCTCTTGGGAGTATTGTGATGACCCAGACTCCCAAATTCCTGCTTGTATCA

GCAGGAGACAGGGTCACCATAACCTGCAAGGCCAGTCAGAGTGTGAGTAAT

GATGTTGCTTGGTACCAACAGAAGCCAGGGCAGTCTCCTAAACTGCTGATA

TACTATGCATCCAATCGCTACACTGGAGTCCCTGATCGCTTCACTGGCAGT

GGATATGGGACGGATTTCACTTTCACCATCAGCACTGTGCAGGCTGAGGAC

CTGGCAGTTTATTTCTGTCAGCAGGATTATAGCTCTCCTCGGACGTTCGGT

GGAGGCACCAAGCTGGAAATCAAA (SEQ ID NO: 1177; Kabat CDRs are underlined; see also, Table 17)
MKSQTQVFVFLLLCVSGALGSIVMTQTPKFLLVSAGDRVTITC<u>KASQSVSN DVAW</u>YQQKPGQSPKLLIY<u>YASNRYT</u>GVPDRFTGSGYGTDFTFTISTVQAED LAVYFC<u>QQDYSSPRT</u>FGGGTKLEIK The nucleic acid and amino acid sequences for the heavy chain and light chain variable regions of the antibody 215A are shown below:

215A heavy chain variable region with signal sequence (SEQ ID NO: 1178)
ATGGGATGGAGCTGGATCTTTCTCTTCCTCCTGTCAGGAACTGCAGGTGTC

CACTCTGAGGTCCAGCTGCAGCAGTCTGGACCTGAGTTGGTGAAGCCTGGT

GCTTCAATGAAGATATCCTGCAAGGCTTCTGGTTTCTCTTTCACTGGCTAC

ACCATGAACTGGGTGAAGCAGAGCCATGGAAAGAACCTTGAGTGGATTGGA

CTTATTAGTCCTTACAATGGTGGTACTAGCTACAACCAGAAGTTCAAGGGC

AAGGCCACATTAACTGTAGATAAGTCATCCAGCACAGCCTACATGGAGCTC

CTCAGTCTGACATCTGAGGACTCTGCAGTCTATTACTGTGCAAGAAGGGCC

TACGGCTATGCTATGGACTACTGGGGTCAAGGAACCTCAGTCACCGTCTCC

TCA (SEQ ID NO: 1179; Kabat CDRs are underlined; see also, Table 18)
MGWSWIFLFLLSGTAGVHSEVQLQQSGPELVKPGASMKISCKASGFSFTG<u>Y TMN</u>WVKQSHGKNLEWIG<u>LISPYNGGTSYNQKFKG</u>KATLTVDKSSSTAYMEL LSLTSEDSAVYYCAR<u>RAYGYAMDY</u>WGQGTSVTVSS 215A light chain variable region with signal sequence (SEQ ID NO: 1180)
ATGGATTTTCAAGTGCAGATTTTCAGCTTCCTGCTAATCAGTGCCTCAGTC

ATACTGTCCAGAGGACAAATTGTTCTCACCCAGTCTCCAGCAATCATGTCT

GCATCTCCAGGGGAGAAGGTCACCATGACCTGCAGTGCCAGCTCAAGTGTA

AGTTACATGTTCTGGTACCAGCAGAAGCCAGGATCCTCCCCCAGACTCCTG

-continued

ATTTATGACACATCCAACCTGGCTTCTGGAGTCCCTCTTCGCTTCAGTGGC

AGTGGGTCTGGGACCTCTTACTCTCTCACAATCAGCCGAATGGAGGCTGAG

GATGCTGCCACTTATTACTGCCAGCAGTGGAGTAGTTACCCATTCACGTTC

GGCTCGGGGACAAAGTTGGAAATAAAA (SEQ ID NO: 1181; Kabat CDRs are underlined; see also, Table 18)
MDFQVQIFSFLLISASVILSRGQIVLTQSPAIMSASPGEKVTMTC<u>SASSSV
SYMF</u>WYQQKPGSSPRLLIY<u>DTSNLAS</u>GVPLRFSGSGSGTSYSLTISRMEAE
DAATYYC<u>QQWSSYPFT</u>FGSGTKLEIK The nucleic acid and amino acid sequences for the heavy chain and light chain variable regions of the antibody 26A are shown below:

26A Heavy Chain Variable Region with Signal Sequence 26A heavy chain variable region with signal sequence
(SEQ ID NO: 1182)
ATGGGATGGAGCTGGATCTTTCTCTTCCTCCTGTCAGGAACTGCAGGTGTC

CACTCTGAGGTCCAGCTGCAGCAGTCTGGACCTGAGCTGGTGAAGCCTGGT

GCTTCAATGAAGATATCCTGCAAGGCTTCTGGTTTCTCATTCACTGGCTAC

ACCATGAACTGGGTGAAGCAGAGCCATGTAAAGAACCTTGAGTGGATTGGA

CTTATTAGTCCTTACAATGGTGGTACTAGCTACAACCAGAAGTTCAAGGGC

AAGGCCACATTAACTGTAGACAAGTCATCCAGCACAGCCTACATGGAGCTC

CTCAGTCTGACATCTGAGGACTCTGCAGTCTATTACTGTGCAAGAAGGGCC

TACGGCTATGCTATGGACTACTGGGGTCAAGGAACCTCAGTCACCGTCTCC

TCA (SEQ ID NO: 1183; Kabat CDRs are underlined; see also, Table 19)
MGWSWIFLFLLSGTAGVHSEVQLQQSGPELVKPGASMKISCKASGFSFTG<u>Y
TMN</u>WVKQSHVKNLEWIG<u>LISPYNGGTSYNQKFKG</u>KATLTVDKSSSTAYMEL
LSLTSEDSAVYYCAR<u>RAYGYAMDY</u>WGQGTSVTVSS 26A light chain variable region with signal sequence
(SEQ ID NO: 1184)
ATGGATTTTCAAGTGCAGATTTTCAGCTTCCTGCTAATCAGTGCCTCAGTC

ATACTGTCCAGAGGACAAATTGTTCTCACCCAGTCTCCAGCAATCATGTCT

GCATCTCCAGGGGAGAAGGTCACCATGACCTGCAGTGCCAGCTCAAGTGTA

AGTTACATGTACTGGTACCAGCAGAAGCCAGGATCCTCCCCCAGACTCCTG

ATTTATGACACATCCAACCTGGCTTCTGGAGTCCCTCTTCGCTTCAGTGGC

AGTGGGTCTGGGACCTCTTACTCTCTCACAATCAGCCGAATGGAGGCTGAG

GATGCTGCCACTTATTACTGCCAGCAGTGGAGTAGTTACCCATTCACGTTC

GGCTCGGGGACAAAGTTGGAAATAAAA (SEQ ID NO: 1185; Kabat CDRs are underlined; see also, Table 19)
MDFQVQIFSFLLISASVILSRGQIVLTQSPAIMSASPGEKVTMTC<u>SASSSV
SYMY</u>WYQQKPGSSPRLLIY<u>DTSNLAS</u>GVPLRFSGSGSGTSYSLTISRMEAE
DAATYYC<u>QQWSSYPFT</u>FGSGTKLEIK The nucleic acid and amino acid sequences for the heavy chain and light chain variable regions of the antibody 164A are shown below:

164A heavy chain variable region with signal sequence
(SEQ ID NO: 1186)
ATGGGATGGACCTGGATCTTTATTTTAATCCTGTCAGTAACTACAGGTGTC

CACTCTGAGGTCCAGCTGCAGCAGTCTGGACCTGAGTTGGAGAAGCCTGGC

GCTTCAGTGAAGATATCCTGCAAGGCTTCTGGTTACTCATTCACTGGCTAC

AACATGAACTGGGTGAAGCAGAGCAATGGAAAGAGCCTTGAGTGGATTGGA

AATATTGATCCTTACTATGGTAGTGCTAGCTACAACCAGAAAATTCAAGGGC

AAGGCCACATTGACTGTAGACAAATCCTCCACCACAGCCTACATGCAGCTC

AAGAGCCTGACATCTGAAGACTCTGCAGTCTATTACTGTACAAGAAGTAAT

TATGGTTACTACGGGTACTTCGATGTCTGGGGCGCAGGGACCACGGTCACC

GTCTCCTCA (SEQ ID NO: 1187; Kabat CDRs are underlined; see also, Table 20)
MGWTWIFILILSVTTGVHSEVQLQQSGPELEKPGASVKISCKASGYSFTG<u>Y
NMN</u>WVKQSNGKSLEWIG<u>NIDPYYGSASYNQKFKG</u>KATLTVDKSSTTAYMQL
KSLTSEDSAVYYCTR<u>SNYGYYGYFDV</u>WGAGTTVTVSS 164A light chain variable region with signal sequence
(SEQ ID NO: 1188)
ATGGAATCACAGACTCAGGTCTTCCTCTCCCTGCTGCTCTGGGTATCTGGT

ACCTGTGGGAACATTATGATGACACAGTCGCCATCATCTCTGGCTGTGTCT

GCAGGAGAAAAGGTCACTATGAGCTGTAAGTCCAGTCAAAGTGTTTTATAC

AGTTCAAATCAGAAGAACTACTTGGCCTGGTACCAGCAGAAACCAGGGCAG

TCTCCTAAACTGCTGATCTATTGGGCATCCACTAGGGAATCTGGTGTCCCT

GATCGCTTCACAGGCAGTGGATCTGGGACAGATTTTACTCTTACTATCAGC

AGTGTACAAGCTGAAGACCTGGCAGTTTATTACTGTCATCAATTCCTCTCC

TCGTACACGTTCGGAGGGGGGACCAAGCTGGAAATGAAA (SEQ ID NO: 1189; Kabat CDRs are underlined; see also, Table 20)
MESQTQVFLSLLLWVSGTCGNIMMTQSPSSLAVSAGEKVTMSC<u>KSSQSVLY
SSNQKNYLA</u>WYQQKPGQSPKLLIY<u>WASTRES</u>GVPDRFTGSGSGTDFTLTIS
SVQAEDLAVYYC<u>HQFLSSYT</u>FGGGTKLEMK 164A light chain variable region number 2 with signal sequence
(SEQ ID NO: 1190)
ATGGATTTTCAGGTGCAGATTTTCAGCTTCCTGTTAATCAGTGTCTCAGTC

ATAATGTCCAGAGGAGAAAATGTGCTGACCCAGTCTCCAGCAATCATGGCT

GCATCTCCAGGGGAGAAGGTCACCATGACCTGCAGTGCCAGCTCAAGTGTA

AGTTCTAGTAACTTGCACTGGTACCAGCAGAAGTCAGGCACTTCTACCCAA

TTCTGGATTTATAGGACATCCAACCTGGCTTCAGAAGTCCCAGCTCCCTTC

AGTGGCAGTGGGTCTGGGACCTCTTACTCTCTTACAATCAGCAGCGTGGAG

GCCGAAGATGCTGCCACTTATTACTGCCAGCAGTGGAGTGGTTACCCACGG

ACGTTCGGTGGAGGCACCAAGCTGGAAATCAAA (SEQ ID NO: 1191; Kabat CDRs are underlined; see also, Table 20)
MDFQVQIFSFLLISVSVIMSRGENVLTQSPAIMAASPGEKVTMTC<u>SASSSV
SSSNLH</u>WYQQKSGTSTKFWIY<u>RTSNLAS</u>EVPAPFSGSGSGTSYSLTISSVE
AEDAATYYC<u>QQWSGYPRT</u>FGGGTKLEIK The nucleic acid and amino acid sequences for the heavy chain and light chain variable regions of the antibody 230A are shown below:

230A heavy chain variable region with signal sequence
(SEQ ID NO: 1191)
ATGGGATGGACCTGGATCTTTATTTTAATCCTGTCAGTAACTACAGGTGTC
CACTCTGAGGTCCAGCTGCAGCAGTCTGGACCTGAGCTGGAGAAGCCTGGC
GCTTCAGTGAAGATATCCTGCAAGGCTTCTGGTTACTCATTCACTGGCTCC
AACATGAACTGGGTGAAGCAGAACAATGGAAAGAGCCTTGAGTGGATTGGA
AATATTGATCCTTACTATGGTTATACTACCTACAACCAGAAGTTCAAGGGC
AAGGCCACATTGACTGTAGACAAATCCTCCAGCACAGCCTACATGCAGCTC
AAGAGCCTGACATCTGAGGACTCTGCAGTCTATTACTGTGCAAGAGACTAT
GATTACGCCCTCGGGTACTTCGATGTCTGGGGCGCAGGGACCACGGTCACC
GTCTCCTCA (SEQ ID NO: 1192; Kabat CDRs are underlined; see also, Table 21)
MGWTWIFILILSVTTGVHSEVQLQQSGPELEKPGASVKISCKASGYSFT<u>G
SNMN</u>WVKQNNGKSLEWIG<u>NIDPYYGYTTYNQKFKG</u>KATLTVDKSSSTAYMQ
LKSLTSEDSAVYYCAR<u>DYDYALGYFDV</u>WGAGTTVTVSS 230A light chain variable region with signal sequence
(SEQ ID NO: 1193)
ATGAAGTTGCCTGTTAGGCTGTTGGTGCTGATGTTCTGGATTCCTGCTTCC
AGCAGTGATGTTGTGATGACCCAAACTCCACTCTCCCTGCCTGTCAGTCTT
GGAGATCAAGCCTCCATCTCTTGCAGATCTAGTCAGAGCCTTGTACACAGT
AATGGAAACACCTATTTACATTGGTACCTGCAGAAGCCAGGCCAGTCTCCA
AAGCTCCTGATCTACAAAGTTTCCAACCGATTTTCTGGGGTCCCAGACAGG
TTCAGTGGCAGTGGATCAGGGACAGATTTCACACTCAAGATCAGCAGAGTG
GAGGCTGAGGATCTGGGAGTTTATTTCTGCTCTCAAAGTACACATGTTCCG
TACACGTTCGGAGGGGGGACCAAGCTGGAAATAAAA (SEQ ID NO: 1194; Kabat CDRs are underlined; see also, Table 21)
MKLPVRLLVLMFWIPASSSDVVMTQTPLSLPVSLGDQASISC<u>RSSQSLVHS
NGNTYLH</u>WYLQKPGQSPKWY<u>KVSNRFS</u>GVPDRFSGSGSGTDFTLKISRVEA
EDLGVYFC<u>SQSTHVPYT</u>FGGGTKLEIK The nucleic acid and amino acid sequences for the heavy chain and light chain variable regions of the antibody 76E1 are shown below:

76E1 heavy chain variable region with signal sequence
(SEQ ID NO: 1195)
ATGGGATGGACCTGGATCTTTATTTTAATCCTGTCAGTAACTACAGGTGTC
CACTCTGAGGTCCAGCTGCTGCAGTCTGGACCTGAGCTGGAGAAGCCTGGC
GCTTCAGTGAAGATATCCTGCAAGGCTTCTGGTTACTCATTCACTGGCTAC
AACATGAACTGGGTGAAGCAGAGCAATGGAAAGAGCCTTGAGTGGATTGGA
AATATTGATCCTTACTATGATTATACTAGTTACAACCTGAAGTTCAAGGAC
AAGGCCACATTGACTGTAGACAAATCCTCCAGCACAGCCTACATGCAGCTC
AAGAGCCTGACATCTGAGGACTCTGCAGTCTATTACTGTGCAACCTCTACT
ATGATTACTCCCTTTGACTACTGGGGCCAAGGCACCACTCTCACAGTCTCC
TCA (SEQ ID NO: 1196; Kabat CDRs are underlined; see also, Table 22)
MGWTWIFILILSVTTGVHSEVQLLQSGPELEKPGASVKISCKAS<u>GYSFTGY
NMN</u>WVKQSNGKSLEWIG<u>NIDPYYDYTSYNLKFKD</u>KATLTVDKSSSTAYMQL
KSLTSEDSAVYYCAT<u>STMITPFDY</u>WGQGTTLTVSS 76E1 light chain variable region with signal sequence
(SEQ ID NO: 1197)
ATGAAGTTGCCTGTTAGGCTGTTGGTGCTGATGTTCTGGATTCCTGCTTCC
AGCAGTGATGTTTGATGACCCAAACTCCACTCTCCCTGCCTGTCAGTCTT
GGAGATCAAGCCTCCATCTCTTGCAGATCTAGTCAGAGCATTGTACATAGT
AATGGAAACACCTATTTAGAATGGTACCTGCAGAAACCAGGCCAGTCTCCA
AAGCTCCTGATCTACAAAGTTTCCAACCGATTTTCTGGGGTCCCAGACAGG
TTCAGTGGCAGTGGATCAGGGACAGATTTCACACTCAAGATCAACAGAGTG
GAGGCTGAAGATCTGGGAGTTTATTACTGCTTTCAAGGTTCACATGTTCCG
TGGACGTTCGGTGGAGGCACCAAGCTGGAAATCAAA (SEQ ID NO: 1198; Kabat CDRs are underlined; see also, Table 22)
MKLPVRLLVLMFWIPASSSDVLMTQTPLSLPVSLGDQASISC<u>RSSQSIVHS
NGNTYLE</u>WYLQKPGQSPKLLIY<u>KVSNRFS</u>GVPDRFSGSGSGTDFTLKINRV
EAEDLGVYYC<u>FQGSHVPWT</u>FGGGTKLEIK The nucleic acid and amino acid sequences for the heavy chain and light chain variable regions of the antibody 53A are shown below:

53A heavy chain variable region with signal sequence
(SEQ ID NO: 1199)
ATGGAATGGAGTTGGATATTTCTCTTTCTCCTGTCAGGAACTGCAGGTGTC
CACTCTGAGGTCCAGCTGCAGCAGTCTGGACCTGAGCTGGTAAAGCCTGGG
GCTTCAGTGAAGATGTCCTGCAAGGCTTCTGGATACACATTCACTAGCTAT
TTTATGCACTGGGTGAAGCAGAAGCCTGGGCAGGGCCTTGAGTGGATTGGA
TATATTTATCCTTACAATGATGGTACTAAGTACAATGAGAAGTTCAAAGGC
AAGGCCACACTGACTTCAGACAAATCCTCCAGCACAGCCTACATGGAGCTC

AGCAGCCTGACCTCTGAGGACTCTGCGGTCTATTACTGTGCAAGATTTGAT

TACGACACCCTGCGATACTGGGGCCAAGGCACCACTCTCACAGTCTCCTCA (SEQ ID NO: 1200; Kabat CDRs are
underlined; see also, Table 23)
MEWSWIFLFLLSGTAGVHSEVQLQQSGPELVKPGASVKMSCKASGYTFT<u>SY FMH</u>WVKQPGQGLEWIG<u>YIYPYNDGTKYNEKFKG</u>KATLTSDKSSSTAYMEL SSLTSEDSAVYYCAR<u>FDYDTLRY</u>WGQGTTLTVSS 53A light chain variable region with signal
sequence
(SEQ ID NO: 1201)
ATGAAGCTGCCTGTTCTGCTAGTGGTGCTGCTATTGTTCACGAGTCCAGCC

TCAAGTAGTGATGTTGTTCTGACCCAAACTCCACTCTCTCTGCCTGTCAAT

ATTGGAGATCAAGCCTCTATCTCTTGCAAGTCTACTAAGAGTCTTCTGAAT

AGTGATGGATTCACTTATTTGGACTGGTACCTGCAGAAGCCAGGCCAGTCT

CCACAGCTCCTAATATATTTGGTTTCTAATCGATTTTCTGGAGTTCCAGAC

AGGTTCAGTGGCAGTGGGTCAGGAACAGATTTCACACTCAAGATCAGCAGA

GTGGAGGCTGAGGATTTGGGAGTTTATTATTGCTTCCAGAGTAACTATTTT

CCGTGGACGTTCGGTGGAGGCACCAAGCTGGAAATCAAA (SEQ ID NO: 1202; Kabat CDRs are
underlined; see also, Table 23)
MKLPVLLVVLLLFTSPASSSDVVLTQTPLSLPVNIGDQASISC<u>KSTKSLLN SDGFTYLDW</u>YLQKPGQSPQLLIY<u>LVSNRFS</u>GVPDRFSGSGSGTDFTLKISR VEAEDLGVYYC<u>FQSNYFPWT</u>FGGGTKLEIK The nucleic acid and amino acid sequences for the heavy chain and light chain variable regions of the antibody 259A are shown below:

259A heavy chain variable region with signal
sequence
(SEQ ID NO: 1203)
ATGGAATGGAGTTGGATATTTCTCTTTCTCCTGTCAGGAACTGCAGGTGTC

CACTCTGAGGTCCAGCTGCAGCAGTCTGGACCTGAGCTGGTAAAGCCTGGG

GCTTCAGTGAAGATGTCCTGCAAGGCTTCTGGATACACATTCACTAGCTAT

TTTATGCACTGGGTGAAGCAGAAGCCTGGGCAGGGCCTTGAGTGGATTGGA

TATATTTATCCTTACAATGATGGTACTAAGTACAATGAGAAGTTCAAAGGC

AAGGCCACACTGACTTCAGACAAATCCTCCAGCACAGCCTACATGGACCTC

AGCAGCCTGACCTCTGAAGACTCTGCGGTCTATTACTGTGCAAGATTTGAT

TACGACACCCTGCGATACTGGGGCCAAGGCACCACTCTCACAGTCTCCTCA (SEQ ID NO: 1204; Kabat CDRs are
underlined; see also, Table 24)
MEWSWIFLFLLSGTAGVHSEVQLQQSGPELVKPGASVKMSCKASGYTFT<u>SY FMH</u>WVKQPGQGLEWIG<u>YIYPYNDGTKYNEKFKG</u>KATLTSDKSSSTAYMDL SSLTSEDSAVYYCAR<u>FDYDTLRY</u>WGQGTTLTVSS 259A light chain variable region with signal
sequence
(SEQ ID NO: 1205)
ATGAAGCTGCCTGTTCTGCTAGTGGTGCTGCTATTGTTCACGAGTCCAGCC

TCAAGTAGTGATGTTGTTCTGACCCAAACTCCACTCTCTCTGCCTGTCAAT

ATTGGAGATCAAGCCTCTATCTCTTGCAAGTCTACTAAGAGTCTTCTGAAT

AGTGATGGATTCACTTATTTGGACTGGTACCTGCAGAAGCCAGGCCAGTCT

CCACAGCTCCTAATATATTTGATTTCTAATCGATTTTCTGGAGTTCCAGAC

AGGTTCAGTGGCAGTGGGTCAGGAACAGATTTCACACTCAAGATCAGCAGA

GTGGAGGCTGAGGATTTGGGAGTTTATTATTGCTTCCAGAGTAACTATTTT

CCGTGGACGTTCGGTGGAGGCACCAAGCTGGAAATCAAA (SEQ ID NO: 1206; Kabat CDRs are
underlined; see also, Table 24)
MKLPVLLVVLLLFTSPASSSDVVLTQTPLSLPVNIGDQASISC<u>KSTKSLLN SDGFTYLDW</u>YLQKPGQSPQLLIY<u>LISNRFS</u>GVPDRFSGSGSGTDFTLKISR VEAEDLGVYYC<u>FQSNYFPWT</u>FGGGTKLEIK The nucleic acid and amino acid sequences for the heavy chain and light chain variable regions of the antibody 33A are shown below:

33A heavy chain variable region with signal
sequence
(SEQ ID NO: 1207)
ATGGAATGGACCTGGGTCTTTCTCTTCCTCCTGTCAGTAACTGCAGGTGTC

CACTCCCAGGTTCAGCTGCAGCAGTCTGGAGCTGAGCTGATGAAGCCTGGG

GCCTCAGTGAAGATATCCTGCAAGGCTACTGGCTACACATTCAGTAGCTAC

TGGATAGAGTGGGTAAAGCAGAGGCCTGGACATGGCCTTGAGTGGATTGGA

GAGATTTTACCTGGAAGTGGTAGTACTAGCTACAATGAGAAGTTCAAGGGC

AAGGCCACATTCACTGCAGATACATCCTCCAACACAGCCTACATGCAACTC

AGCGGCCTGACATCTGAGGACTCTGCCGTCTATTACTGTGCAAGATGGTTA

CTATATTACTATGCTATGGTCTACTGGGGTCAAGGAACCTCAGTCACCGTC

TCCTCA (SEQ ID NO: 1208; Kabat CDRs are
underlined; see also, Table 25)
MEWTWVFLFLLSVTAGVHSQVQLQQSGAELMKPGASVKISCKATGYTFS<u>SY WIE</u>WVKQRPGHGLEWIG<u>EILPGSGSTSYNEKFKG</u>KATFTADTSSNTAYMQL SGLTSEDSAVYYCAR<u>WLLYYYAMVY</u>WGQGTSVTVSS 33A light chain variable region with signal
sequence
(SEQ ID NO: 1209)
ATGAAGTTGCCTGTTAGGCTGTTGGTGCTGATGTTCTGGATTCCTGCTTCC

AGCAGTGATGTTTTGATGACCCAAACTCCACTCTCCCTGCCTGTCAGTCTT

GGAGATCAAGCCTCCATCTCTTGCAGATCTAGTCAGAGCATTGTACATAGT

AATGGAAACACCTATTTAGAATGGTACCTGCAGAAACCAGGCCAGTCTCCA

AAGCTCCTGATCTACAAAGTTTCCAACCGATTTTCTGGGGTCCCAGACAGG

TTCAGTGGCAGTGGATCAGGGACAGATTTCACACTCAAGATCAGCAGAGTG

GAGGCTGAGGATCTGGGAGTTTATTACTGCTTTCAAGGTTCACATGTTCCG

TACACGTTCGGAGGGGGGACCAAGCTGGAAATAAAA (SEQ ID NO: 1210; Kabat CDRs are
underlined; see also, Table 25)
MKLPVRLLVLMFWIPASSSDVLMTQTPLSLPVSLGDQASISC<u>RSSQSIVHS NGNTYLEW</u>YLQKPGQSPKLLIY<u>KVSNRFS</u>GVPDRFSGSGSGTDFTLKISRV EAEDLGVYYC<u>FQGSHVPYT</u>FGGGTKLEIK The nucleic acid and amino acid sequences for the heavy chain and light chain variable regions of the antibody 39A are shown below:

39A heavy chain variable region with signal sequence
(SEQ ID NO: 1211)
ATGGAATGGACCTGGGTCTGTCTCTTCCTCCTGTCAGTAACTGCAGGTGTC
CACTCCCAGGTTCAGCTGCAGCAGTCTGGAGCTGAGCTGATGAAGCCTGGG
GCCTCAGTGAAGATATCCTGCAAGGCTACTGGCTACACATTCAGTAGTAAC
TGGATAGAGTGGGTAAAGCAGAGGCCTGGACATGGCCTTGAGTGGATTGGA
GAGATTTTACCTGGAAGTGGCAGTACTAGCTACAATGAGAAGTTCAAGGGC
AAGGCCACATTCACTGCAGATACATCCTCCAACACAGCCTACATGCAGCTC
AGCAGCCTGACATCTGAAGACTCTGCCGTCTATTACTGTGCAAGATGGTTA
CTATATTACTATGCTATGGACTACTGGGGTCAAGGAACCTCAGTCACCGTC
TCCTCA (SEQ ID NO: 1212; Kabat CDRs are underlined; see also, Table 26)
MEWTWVCLFLLSVTAGVHSQVQLQQSGAELMKPGASVKISCKATGYTFSSN
WIEWVKQRPGHGLEWIGEILPGSGSTSYNEKFKGKATFTADTSSNTAYMQL
SSLTSEDSAVYYCARWLLYYYAMDYWGQGTSVTVSS 39A light chain variable region with signal sequence
(SEQ ID NO: 1213)
ATGAAGTTGCCTGTTAGGCTGTTGGTGCTGATGTTCTGGATTCCTGCTTCC
AGCAGTGATGTTTTGATGACCCAAACTCCACTCTCCCTGCCTGTCAGTCTT
GGAGATCCAGCCTCCATCTCTTGCAGATCTAGTCAGAGCATTGTACATAAT
AATGGAAACACCTATTTAGAATGGTACCTGCAGAAACCAGGCCAGTCTCCA
AAGCTCCTGATCTACAAAGTTTCCAACCGATTTTCTGGGGTCCCAGACAGG
TTCAGTGGCAGTGGATCAGGGACAGATTTCACACTCAAGATCAGCAGAGTG
GAGGCTGAGGATCTGGGAGTTTATTACTGCTTTCAAGGTTCACATGTTCCG
TACACGTTCGGAGGGGGGACCAAGCTGGAAATAAAA (SEQ ID NO: 1214; Kabat CDRs are underlined; see also, Table 26)
MKLPVRLLVLMFWIPASSSDVLMTQTPLSLPVSLGDPASISCRSSQSIVHN
NGNTYLEWYLQKPGQSPKLLIYKVSNRFSGVPDRFSGSGSGTDFTLKISRV
EAEDLGVYYCFQGSHVPYTFGGGTKLEIK The nucleic acid and amino acid sequences for the heavy chain and light chain variable regions of the antibody 124A are shown below:

124A heavy chain variable region with signal sequence
(SEQ ID NO: 1215)
ATGGAATGGACCTGGGTCTTTCTCTTCCTCCTGTCAGTAACTGCAGGTGT
CCACTCCCAGGTTCAGCTGCAGCAGTCTGGAGCTGAGCTGATGAAGCCTG
GGGCCTCAGTGAAGATATCCTGCAAGGCTACTGGCTACACATTCAGTAGC
AACTGGATAGAGTGGGTAAAGCAGAGGCCTGGACATGGCCTTGAGTGGAT
GGGAGAGATTTTACCTGGAAGTGGCAGTACTAGCTACAATGAGAAGTTCA
AGGGCAAGGCCACATTCACTGCAGATACATCCTCCAACACAGCCTACATG
CAGCTCAGCAGCCTGACATCTGAAGACTCTGCCGTCTATTACTGTGCAAG
ATGGTTACTATATTACTATGCTATGGACTTCTGGGGTCAAGGAACCTCAG
TCACCGTCTCCTCA (SEQ ID NO: 1216; Kabat CDRs are underlined; see also, Table 27)
MEWTWVFLFLLSVTAGVHSQVQLQQSGAELMKPGASVKISCKATGYTF
SSNWIEWVKQRPGHGLEWMGEILPGSGSTSYNEKFKGKATFTADTSSNT
AYMQLSSLTSEDSAVYYCARWLLYYYAMDFWGQGTSVTVSS 124A light chain variable region with signal sequence
(SEQ ID NO: 1217)
ATGAAGTTGCCTGTTAGGCTGTTGGTGCTGATGTTCTGGATTCCTGCTTC
CAGCAGTGATGTTTTGATGACCCAAACTCCACTCTCCCTGCCTGTCAGTC
TTGGAGATCAAGCCTCCATCTCTTGCAGATCTAGTCAGAGCATTGTACAT
AATAATGGAAACACCTATTTAGAATGGTACCTGCAGAAACCAGGCCAGTC
TCCAAAGCTCCTGATCTACAAAGTTTCCAACCGATTTTCTGGGGTCCCAG
ACAGGTTCAGTGGCAGTGGATCAGGGACAGATTTCACACTCAAGATCAGC
AGAGTGGAGGCTGAGGATCTGGGAGTTTATTACTGCTTTCAAGGTTCACA
TGTTCCGTACACGTTCGGAGGGGGGACCAAGCTGGAAATAAAA (SEQ ID NO: 1218; Kabat CDRs are underlined; see also, Table 27)
MKLPVRLLVLMFWIPASSSDVLMTQTPLSLPVSLGDQASISCRSSQSIVH
NNGNTYLEWYLQKPGQSPKLLIYKVSNRFSGVPDRFSGSGSGTDFTLKI
SRVEAEDLGVYYCFQGSHVPYTFGGGTKLEIK The nucleic acid and amino acid sequences for the heavy chain and light chain variable regions of the antibody 175A are shown below:

175A heavy chain variable region with signal sequence
(SEQ ID NO: 1219)
ATGGAATGGACCTGGGTCTTTCTCTTCCTCCTGTCAGTAACTGCAGGTGTC
CACTCCCAGGTTCAGCTGCAGCAGTCTGGAGCTGAGCTGATGAAGCCTGGG
GCCTCAGTGAAGATATCCTGCAAGGCTACTGGCTACACATTCAGTACCCAC
TGGATAGAGTGGGTAAAGCAGAGGCCTGGACATGGCCTTGAGTGGATTGGA
GAGATTTTACCTGGAAGTGGTAGTACTAGCTACAATGAGAAGTTCAAGGGC
AAGGCCACATTCACTGCAGATACATCCTCCAACACAGCCTACATGCAACTC
AGCAGCCTGACATCTGAGGACTCTGCCGTCTATTACTGTGCAAGATGGTTA
CTATATTACTATGCTATGGACTACTGGGGTCAAGGAACCTCAGTCACCGTC
TCCTCA (SEQ ID NO: 1220; Kabat CDRs are underlined; see also, Table 28)
MEWTWVFLFLLSVTAGVHSQVQLQQSGAELMKPGASVKISCKATGYTFSTH
WIEWVKQRPGHGLEWIGEILPGSGSTSYNEKFKGKATFTADTSSNTAYMQL
SSLTSEDSAVYYCARWLLYYYAMDYWGQGTSVTVSS 175A light chain variable region with signal sequence (SEQ ID NO: 1221)
ATGAAGTTGCCTGTTAGGCTGTTGGTGCTGATGTTCTGGATTCCTGCTTCC

AGCAGTGATGTTTTGATGACCCAAACTCCACTCTCCCTGCCTGTCAGTCTT

GGAGATCAAGCCTCCATCTCTTGCAGATCTAGTCAGAGCATTGTACATAGT

AATGGAAACACCTATTTAGAATGGTACCTGCAGAAACCAGGCCAGTCTCCA

AAGCTCCTGATCTACAAACTTTCCAACCGATTTTCTGGGGTCCCAGACAGG

TTCAGTGGCAGTGGATCAGGGACAGATTTCACACTCAAGATCAGCAGAGTG

GAGGCTGAGGATCTGGGAGTTTATTACTGCTTTCAAGGTTCACATTTTCCG

TACACGTTCGGAGGGGGGACCAAGCTGGAAATAAAA (SEQ ID NO: 1222;
Kabat CDRs are underlined; see also, Table 28)
MKLPVRLLVLMFWIPASSSDVLMTQTPLSLPVSLGDQASISCRSSQSIVHS

NGNTYLEWYLQKPGQSPKLLIYKLSNRFSGVPDRFSGSGSGTDFTLKISRV

EAEDLGVYYCFQGSHFPYTFGGGTKLEIK

The nucleic acid and amino acid sequences for the heavy chain and light chain variable regions of the antibody 321 D are shown below:

321D heavy chain variable region with signal sequence (SEQ ID NO: 1223)
ATGGAATGGACCTGGGTCTTTCTCTTCCTCCTGTCAGTAACTGCAGGTGT

CCACTCCCAGGTTCAGCTGCAGCAGTCTGGAGCTGAGCTGATGAAGCCTG

GGGCCGCAGTGAAGATATCCTGCAAGGCTACTGGCTACACATTCAGTAGC

CACTGGATAGAGTGGGTAAAGCAGAGGCCTGGACATGGCCTTGAGTGGAT

TGGAGAGATTTTACCTGGAAGTGGTAGTACTGACTACAATGAGAAGTTCA

AGGGCAAGGCCACATTCACTGCAGATACATCCTCCAACACAGCCTACATG

CAACTCAGCAGCCTGACATCTGAGGACTCTGCCGTCTATTACTGTGCAAG

ATGGTTACTATATTACTATGCTATGGACTACTGGGGTCAAGGAACCTCAG

TCACCGTCTCCTCA (SEQ ID NO: 1224;
Kabat CDRs are underlined; see also, Table 29)
MEWTWVFLFLLSVTAGVHSQVQLQQSGAELMKPGAAVKISCKATGYTF

SSHWIEWVKQRPGHGLEWIGEILPGSGSTDYNEKFKGKATFTADTSSNTA

YMQLSSLTSEDSAVYYCARWLLYYYAMDYWGQGTSVTVSS 321D light chain variable region with signal sequence (SEQ ID NO: 1225)
ATGAAGTTGCCTGTTAGGCTGTTGGTGCTGATGTTCTGGATTCCTGCTTC

CAGCAGTGATGTTTTGATGACCCAAACTCCACTCTCCCTGCCTGTCAGTC

TTGGAGATCAAGCCTCCATCTCTTGCAGATCTAGTCAGAGCATTGTACAT

AGTAATGGAAACACCTATTTAGAATGGTACCTGCAGAAACCAGGCCAGTC

TCCAAAGCTCCTGATCTACAAAGTTTCCAACCGATTTTCTGGGGTCCCAG

ACAGGTTCAGTGGCAGTGGATCAGGGACAGATTTCACACTCAAGATCACC

AGAGTGGAGGCTGAGGATCTGGGAGTTTATTACTGCTTTCAAGGTTCACA

TGTTCCGTTCACGTTCGGAGGGGGGACCAAGCTGGAAATAAAA (SEQ ID NO: 1226;
Kabat CDRs are underlined; see also, Table 29)
MKLPVRLLVLMFWIPASSSDVLMTQTPLSLPVSLGDQASISCRSSQSIVH

SNGNTYLEWYLQKPGQSPKLLIYKVSNRFSGVPDRFSGSGSGTDFTLKI

TRVEAEDLGVYYCFQGSHVPFTFGGGTKLEIK

The nucleic acid and amino acid sequences for the heavy chain and light chain variable regions of the antibody 141A are shown below:

141A heavy chain variable region with signal sequence (SEQ ID NO: 1227)
ATGGAATGGACCTGGGTCTTTCTCTTCCTCCTGTCAGTAACTGCAGGTGT

CCACTCCCAGGTTCAGCTGCAGCAGTCTGGAGCTGAGCTGATGAAGCCTG

GGGCCTCAGTGAAGATATCCTGCAAGGCTACTGGCTACACATTCAGTAGG

TACTGGATAGAGTGGGTAAAGCAGAGGCCTGGACATGGCCTTGAGTGGAT

TGGAGAGATTTTACCTGGAAGTGGTAGTACTAACTACAATGAGAAGTTCA

AGGGCAAGGCCACATTCACTGCAGATACATCCTCCAACACAGCCTACATG

CAACTCAGCAGCCTGACATCTGAGGACTCTGCCGTCTATTACTGTGCAGG

AGAGGAAGTCTATGATGGTTACCCCTGGTTTGGTTACTGGGGCCAAGGGA

CTCTGGTCACTGTCTCTGCA (SEQ ID NO: 1228;
Kabat CDRs are underlined; see also, Table 30)
MEWTWVFLFLLSVTAGVHSQVQLQQSGAELMKPGASVKISCKATGYTFS

RYWIEWVKQRPGHGLEWIGEILPGSGSTNYNEKFKGKATFTADTSSNTAY

MQLSSLTSEDSAVYYCAGEEVYDGYPWFGYWGQGTLVTVSA 141A light chain variable region with signal sequence (SEQ ID NO: 1229)
ATGGATTTTCAAGTGCAGATTTTCAGCTTCCTGCTAATCAGTGCTTCAGT

CATAATGTCCAGAGGACAAATTGTTCTCTCCCAGTCTCCAGCAATCCTGT

CTGCATCTCCAGGGGAGAAGGTCACAATGACTTGCAGGGCCAGCTCAAGT

TTAAGTTACATGCACTGGTACCAGCAGAAGCCAGGATCCTCCCCCAAACC

CTGGATTTATGCCACATCCAACCTGGCTTCTGGAGTCCCTGCTCGCTTCA

GTGGCAGTGGGTCTGGGACCTCTTACTCTCTCACAATCAGCAGAGTGGAG

GCTGAAGATGCTGCCACTTATTACTGCCAGCAGTGGAGTAGTAACCCGTA

CACGTTCGGAGGGGGGACCAAGCTGGAAATAAAA (SEQ ID NO: 1230;
Kabat CDRs are underlined; see also, Table 30)
MDFQVQIFSFLLISASVIMSRGQIVLSQSPAILSASPGEKVTMTCRASSS

LSYMHWYQQKPGSSPKPWIYATSNLASGVPARFSGSGSGTSYSLTISRV

EAEDAATYYCQQWSSNPYTFGGGTKLEIK

The nucleic acid and amino acid sequences for the heavy chain and light chain variable regions of the antibody 51A are shown below:

51A heavy chain variable region with signal sequence
(SEQ ID NO: 1231)
ATGGAATGGACCTGGGTCTTTCTCTTCCTCCTGTCAGTAACTGCAGGTGT
CCACTCCCAGGTTCAGCTGCAGCAGTCTGGAGCTGAGCTGATGAAGCCTG
GGGCCTCAGTGAAGATATCCTGCAAGGCTACTGGCTACACATTCAGTAGG
TACTGGATAGAGTGGGTAAAGCAGAGGCCTGGACATGGCCTTGAGTGGAT
TGGAGAGATTTTACCTGGAAGTGGTAGTACTAACTACAATGAGAAGTTCA
AGGGCAAGGCCACATTCACTGCAGATACATCCTCCAACACAGCCTACATG
CAACTCAGCAGCCTGACATCTGAGGACTCTGCCGTCTATTACTGTGCAAG
CGAGGAAGTCTATGATGGTTACCCCTGGTTTGGTTACTGGGGCCAAGGGA
CTCTGGTCACTGTCTCTGCA (SEQ ID NO: 1232;
Kabat CDRs are underlined; see also, Table 31)
MEWTWVFLFLLSVTAGVHSQVQLQQSGAELMKPGASVKISCKATGYTF
SRYWIEWVKQRPGHGLEWIGEILPGSGSTNYNEKFKGKATFTADTSSNTA
YMQLSSLTSEDSAVYYCASEEVYDGYPWFGYWGQGTLVTVSA 51A light chain variable region with signal sequence
(SEQ ID NO: 1233)
ATGGATTTTCAAGTGCAGATTTTCAGCTTCCTGCTAATCAGTGCTTCAGT
CATAATGTCCAGAGGACAAATTGTTCTCTCCCAGTCTCCAGCAATCCTGT
CTGCATCTCCAGGGGAGAAGGTCACAATGACTTGCAGGGCCAGCTCAAGT
TTAAGTTACATGCACTGGTACCAGCAGAGGCCAGGATCCTCCCCCAAACC
CTGGATTTATGCCACATCCAACCTGGCTTCTGGAGTCCCTGCTCGCTTCA
GTGGCAGTGGGTCTGGGACCTCTTACTCTCTCACAATCAGCAGAGTGGAG
GCTGAAGATGCTGCCACTTATTACTGCCAGCAGTGGAGTAGTAACCCGTA
CACGTTCGGAGGGGGGACCAAGCTGGAAATAAAA (SEQ ID NO: 1234;
Kabat CDRs are underlined; see also, Table 31)
MDFQVQIFSFLLISASVIMSRGQIVLSQSPAILSASPGEKVTMTCRASSS
LSYMHWYQQRPGSSPKPWIYATSNLASGVPARFSGSGSGTSYSLTISRV
EAEDAATYYCQQWSSNPYTFGGGTKLEIK The nucleic acid and amino acid sequences for the heavy chain and light chain variable regions of the antibody 353A are shown below:

353A heavy chain variable region with signal sequence
(SEQ ID NO: 1235)
ATGGATTTTGGGCTGATTTTTTTTATTGTTGCTCTTTTAAAAGGGGTCCA
GTGTGAGGTGAAGCTTCTCGAGTCTGGAGGTGGCCTGGTGCAGCCTGGAG
GATCCCTGAAACTCTCCTGTGCAGCCTCAGGATTCGATTTTAGTAGATAC
TGGATGAATTGGGTCCGGCAGGCTCCAGGGAAAGGGCTAGAATGGATTGG
AGAAATTAATCCAGATAGCAGTACGATAAACTATACGCCATCTCTAAAGG
ATAAATTCATCATCTCCAGAGACAACGCCAAAAATACGCTGTACCTGCAA
ATGAGCAAAGTGAGATATGAGGACACAGCCCTTTATTACTGTGCAAGACC
GGGGGAAATTTATTACTACGGTAGTTACTGGTTTGCTTACTGGGGCCAAG
GGACTCTGGTCACTGTCTCTGCA (SEQ ID NO: 1236;
Kabat CDRs are underlined; see also, Table 32)
MDFGLIFFIVALLKGVQCEVKLLESGGGLVQPGGSLKLSCAASGFDFSRY
WMNWVRQAPGKGLEWIGEINPDSSTINYTPSLKDKFIISRDNAKNTLYLQ
MSKVRYEDTALYYCARPGEIYYYGSYWFAYWGQGTLVTVSA 353A light chain variable region with signal sequence
(SEQ ID NO: 1237)
ATGGAGTCAGACACACTCCTGCTATGGGTGCTGCTGCTCTGGGTTCCAGG
CTCCACTGGTGACATTGTGCTCACCCAATCTCCAGCTTCTTTGGCTGTGT
CTCTAGGGCAGAGAGCCACCATCTCCTGCAGAGCCAGTGAAAGTGTTGAA
TATTATGGCACAAGTTTAATGCAGTGGTTCCAACAGAAACCAGGACAGCC
ACCCAAACTCCTCATCTATGCTGCATCCAACGTAGAATCTAGGGTCCCTG
CCAGGTTTAGTGGCAGTGGGTCTGGGACAGACTTCAGCCTCAACATCCAT
CCTGTGGAGGAGGATGATATTGCAATGTATTTCTGTCAGCAAAGTAGGAA
GGATCCTTGGACATTCGGTGGAGGCACCAAGCTGGAAATCAAA (SEQ ID NO: 1238;
Kabat CDRs are underlined; see also, Table 32)
MESDTLLLWVLLLWVPGSTGDIVLTQSPASLAVSLGQRATISCRASESVE
YYGTSLMQWFQQKPGQPPKLLIYAASNVESRVPARFSGSGSGTDFSLNIH
PVEEDDIAMYFCQQSRKDPWTFGGGTKLEIK The nucleic acid and amino acid sequences for the heavy chain and light chain variable regions of the antibody 305A are shown below:

305A heavy chain variable region with signal sequence
(SEQ ID NO: 1239)
ATGAAAGTGTTGAGTCTGTTGTACCTGTTGACAGCCATTCCTGGTATCCT
GTCTGATGTACAGCTTCAGGAGTCAGGACCTGGCCTCGTGAAACCTTCTC
AGTCTCTGTCTCTCACCTGCTCTGTCACTGGCTACTCCATCACCAGTGGT
TATTACTGGAACTGGATCCGGCAGTTTCCAGGAAACAAACTGGAATGGAT
GGGCTACATAAGCTACGACGGTAGCAATAACTACAACCCATCTCTCAAAA
ATCGAATCTCCATCACTCGTGACACATCTAAGAACCAGTTTTTCCTGAAG
TTGAATTCTGTGACTACTGAGGACACAGCTACATATTACTGTGCAAGACG
GCATGATTACCTCTCCTTTGCTTACTGGGGCCAAGGGACTCTGGTCATTG
TCTCTGCA (SEQ ID NO: 1240;
Kabat CDRs are underlined; see also, Table 33)
MKVLSLLYLLTAIPGILSDVQLQESGPGLVKPSQSLSLTCSVTGYSITSG
YYWNWIRQFPGNKLEWMGYISYDGSNNYNPSLKNRISITRDTSKNQFFL
KLNSVTTEDTATYYCARRHDYLSFAYWGQGTLVIVSA -continued 305A light chain variable region with signal
sequence
(SEQ ID NO: 1241)
ATGGAGACAGACACAATCCTGCTATGGGTGCTGCTGCTCTGGGTTCCAGG

CTCCACTGGTGACATTGTGCTGACCCAATCTCCAGCTTCTTTGGCTGTGT

CTCTAGGGCAGAGGGCCACCATCTCCTGCAAGGCCAGCCAAAGTGTTGAT

TATGATGGTGATAGTTATATGAACTGGTACCAACAGAAACCAGGACAGCC

ACCCAAACTCCTCATCTATGCTGCATCCAATCTAGAATCTGGGATCCCAG

CCAGGTTTAGTGGCAGTGGGTCTGGGACAGACTTCACCCTCAACATCCAT

CCTGTGGAGGAGGAGGATGCTGCAACCTATTACTGTCAGCAAAGTGATGA

GGATCCGTACACGTTCGGAGGGGGGACCAAGCTGGAAATAAAA (SEQ ID NO: 1242;
Kabat CDRs are underlined; see also, Table 33)
METDTILLWVLLLWVPGSTGDIVLTQSPASLAVSLGQRATISC<u>KASQS</u>

<u>VDYDGDSYMN</u>WYQQKPGQPPKLLIY<u>AASNLES</u>GIPARFSGSGSGTDFTL

NIHPVEEEDAATYYC<u>QQSDEDPYT</u>FGGGTKLEIK

CDR sequences for the selected twenty-two monoclonal antibodies are provided in Tables 12-33 and are used for the preparation of humanized anti-C10orf54 antibodies.

Example 4—Binning and Epitope Mapping of Anti-C10orf54 Antibodies

Paratope diversity of the 22 anti-human C10orf54 antibodies the VH's and VK's was evaluated by analyzing the variable region sequences. An IMGT®/V-Quest search (IMGT®, the international ImMunoGeneTics information System®, founder and director: Marie-Paule Lefranc, Montpellier, France)) of each nucleotide sequence was conducted, and the germline gene sequence with the highest degree of identity with the query sequence was tabulated (Table 37). Antibodies with the same VH and VK germline gene sequences were placed in the same paratope group (Table 37).

TABLE 37

| Ab | Antibody Designation | VH | VK | Paratope Binning |
|---|---|---|---|---|
| 1 | 5B | IGHV1S137*01 | IGKV6-32*01 | 1 |
| 2 | 46A | IGHV1S137*01 | IGKV6-32*01 | 1 |
| 3 | 97A | IGHV1S137*01 | IGKV6-32*01 | 1 |
| 4 | 128A | IGHV1S137*01 | IGKV6-32*01 | 1 |
| 5 | 146C | IGHV1S137*01 | IGKV6-32*01 | 1 |
| 6 | 208A | IGHV1S137*01 | IGKV6-32*01 | 1 |
| 7 | 215A | IGHV1-26*01 | IGKV4-55*01 | 2 |
| 8 | 26A | IGHV1-18*01 | IGKV4-55*01 | 3 |
| 9 | 164A | IGHV1-39*01 | IGKV8-27*01/ IGKV4-81*01 | 4 |
| 10 | 230A | IGHV1-39*01 | IGKV1-110*01 | 5 |
| 11 | 76E1 | IGHV1-39*01 | IGKV1-117*01 | 6 |
| 12 | 53A | IGHV1-14*01 | IGKV1-99*01 | 7 |
| 13 | 259A | IGHV1-14*01 | IGKV1-99*01 | 7 |
| 14 | 33A | IGHV1-9*01 | IGKV1-117*01 | 8 |
| 15 | 39A | IGHV1-9*01 | IGKV1-117*01 | 8 |
| 16 | 124A | IGHV1-9*01 | IGKV1-117*01 | 8 |
| 17 | 175A | IGHV1-9*01 | IGKV1-117*01 | 8 |
| 18 | 321D | IGHV1-9*01 | IGKV1-117*01 | 8 |
| 19 | 141A | IGHV1-9*01 | IGKV4-72*01 | 9 |
| 20 | 51A | IGHV1-9*01 | IGKV4-72*01 | 9 |
| 21 | 353A | IGHV4-1*02 | IGKV3-1*01 | 10 |
| 22 | 305A | IGHV3-6*02 | IGKV3-4*01 | 11 |

To investigate epitope diversity of the anti-human C10orf54 antibodies, 293t cells were transfected with 1 of 10 different -C10orf54 expression constructs that co-express a fluorescent marker. The C10orf54 proteins and chimeric proteins encoded by the constructs used is shown in Table 38. Two days after transfection, cells were stripped from the tissue culture plate, stained with 2 μg/ml anti-human C10orf54 antibody, washed, stained with anti-mouse IgG-Fc ALEXA FLUOR© 647 polyclonal antibody, washed, and stained with the viability dye 4',6-Diamidino-2-Phenylindole, Dihydrochloride. Upon acquisition of 10,000 live events on a flow cytometer, live cells marked with the fluorescent marker were analyzed for the degree of staining by the anti-human C10orf54 antibody. When the median fluorescence intensity fold-change relative to an isotype control antibody was at least 20-fold, the antibody was considered to stain the C10orf54 expression construct in question. The results of these binning experiments and the description of the construct bins are shown in Table 39.

TABLE 38

| Construct Designation | C10orf54 Proteins and Chimeric Proteins Encoded by the Construct Description |
|---|---|
| CC1 | full length human |
| CC2 | full length mouse |
| CC3 | full length rat |
| CC4 | full length cynomolgus monkey (cyno) |
| CC5 | human IgV with mouse STALK* |
| CC6 | mouse IgV with human STALK* |
| CC7 | first half of IgV human and remainder (including loop) mouse* |
| CC8 | first half of IgV mouse and remainder (including loop) human* |
| CC9 | human with mouse loop* |
| CC10 | mouse with human loop* |

*Human IgV domain = aa33-169; Mouse IgV domain = aa33-168; Human loop = aa84-116; Mouse loop = aa84-116; Human Stalk = aa170-194; Mouse Stalk = aa169-192; Human Extracellular Domain (hECD) = aa33-194; Mouse Extracellular Domain (mECD) 33-192

The amino acid sequences for the C10orf54 proteins and chimeric proteins encoded by the expression constructs are shown below.

The amino acid sequence for the human C10orf54 protein encoded by the CC1 expression construct is shown below:

(SEQ ID NO: 1079; C10orf54 Construct 1 (CC1))
MGVPTALEAGSWRWGSLLFALFLAASLGPVAAFKVATPYSLYVCPEGQNVT

LTCRLLGPVDKGHDVTFYKTWYRSSRGEVQTCSERRPIRNLTFQDLHLHHG

GHQAANTSHDLAQRHGLESASDHHGNFSITMRNLTLLDSGLYCCLWEIRHH

HSEHRVHGAMELQVQTGKDAPSNCVVYPSSSQDSENITAAALATGACIVGI

LCLPLILLLVYKQRQAASNRRAQELVRMDSNIQGIENPGFEASPPAQGIPE

AKVRHPLSYVAQRQPSESGRHLLSEPSTPLSPPGPGDVFFPSLDPVPDSPN

FEVI

The amino acid sequence for the mouse C10orf54 protein encoded by the CC2 expression construct is shown below:

(SEQ ID NO: 1243; C10orf54 Construct 2 (CC2))
MGVPAVPEASSPRWGTLLLAIFLAASRGLVAAFKVTTPYSLYVCPEGQNAT

LTCRILGPVSKGHDVTIYKTWYLSSRGEVQMCKEHRPIRNFTLQHLQHHGS

HLKANASHDQPQKHGLELASDHHGNFSITLRNVTPRDSGLYCCLVIELKNH

```
HPEQRFYGSMELQVQAGKGSGSTCMASNEQDSDSITAAALATGACIVGILC
LPLILLLVYKQRQVASHRRAQELVRMDSSNTQGIENPGFETTPPFQGMPEA
KTRPPLSYVAQRQPSESGRYLLSDPSTPLSPPGPGDVFFPSLDPVPDSPNS
EAI
```

The amino acid sequence for the rat C10orf54 protein encoded by the CC3 expression construct is shown below:

```
(SEQ ID NO: 1244; C10orf54 Construct 3 (CC3))
MGVPTVPEASSLRWGTLLLTIFLAASRGLVAAIKVTTPYSLYVCPEGQNVT
LTCRILDSVSKGHDANFLKTWFLSSRGEVQVCKEHRPIRNFISHHQHHRSH
PAVNASHDQPQKHGLEIAYDNHGNFSITLHNVTLSDSGLYCCLVIEVKHHH
PERRLYGYMELQVQTGKGSASTCTAYPPNEQDSDSITAAALATGACIVGIL
CLPLILLLVYKQRQAASHRRAQELVRMDSNTQGIENPGYETTPPFQGMPEA
KTRPPLSYVAQRQPSESGRHLLSDPSTPLSPPGPGDVFFPSLDPVPD-
SPNS
EAI
```

The amino acid sequence for the cynomolgus C10orf54 protein encoded by the CC4 expression construct is shown below:

```
(SEQ ID NO: 1245; C10orf54 Construct 4 (CC4))
MGVPTAPEAGCWRWGSLLFALFLAASLGPVAAFKVATLYSLYVCPEGQNVT
LTCRVFGPVDKGHDVTFYKTWYRSSRGEVQTCSERRPIRNLTFQDLHLHHG
GHQAANTSHDLAQRHGLESASDHHGNFSITMRNLTLLDSGLYCCLVVEIRH
HHSEHRVHGAMELQVQTGKDAPSSCVAYPSSSQESENITAAALATGACIVG
ILCLPLILLLVYKQRQAASNRRAQELVRMDSNTQGIENPGFEASSPAQGIL
EAKVRHPLSYVAQRQPSESGRHLLSEPGTPLSPPGPGDVFFPSLDPVPDSP
NFEVI
```

The amino acid sequence for chimeric protein encoded by the CC5 expression construct is shown below

```
(SEQ ID NO: 1246; C10orf54 Construct 5 (CC5) with
                human sequence underlined)
MGVPTALEAGSWRWGSLLFALFLAASLGPVAAFKVATPYSLYVCPEGQNVT
LTCRLLGPVDKGHDVTFYKTWYRSSRGEVQTCSERRPIRNLTFQDLHLHHG
GHQAANTSHDLAQRHGLESASDHHGNFSITMRNLTLLDSGLYCCLVVEIRH
HHSEHRVHGAMELQVQAGKGSGSTCMASNEQDSDSITAAALATGACIVGIL
CLPLILLLVYKQRQVASHRRAQELVRMDSSNTQGIENPGFETTPPFQGMPE
AKTRPPLSYVAQRQPSESGRYLLSDPSTPLSPPGPGDVFFPSLDPVPDSPN
SEAI
```

The amino acid sequence for chimeric protein encoded by the CC6 expression construct is shown below

```
(SEQ ID NO: 1247; C10orf54 Construct 6 (CC6) with
                human sequence underlined)
MGVPAVPEASSPRWGTLLLAIFLAASRGLVAAFKVTTPYSLYVCPEGQNAT
LTCRILGPVSKGHDVTIYKTWYLSSRGEVQMCKEHRPIRNFTLQHLHHGS
HLKANASHDQPQKHGLELASDHHGNFSITLRNVTPRDSGLYCCLVIELKNH
HPEQRFYGSMELQVQTGKDAPSNCVVYPSSSQDSENITAAALATGACIVGI
LCLPLILLLVYKQRQAASNRRAQELVRMDSNIQGIENPGFEASPPAQGIPE
AKVRHPLSYVAQRQPSESGRHLLSEPSTPLSPPGPGDVFFPSLDPVPDSPN
FEVI
```

The amino acid sequence for chimeric protein encoded by the CC7 expression construct is shown below

```
(SEQ ID NO: 1248; C10orf54 Construct 7 (CC7) with
                human sequence underlined)
MGVPTALEAGSWRWGSLLFALFLAASLGPVAAFKVATPYSLYVCPEGQNVT
LTCRLLGPVDKGHDVTFYKTWYRSSRGEVQTCKEHRPIRNFTLQHLQHHGS
HLKANASHDQPQKHGLELASDHHGNFSITLRNVTPRDSGLYCCLVIELKNH
HPEQRFYGSMELQVQAGKGSGSTCMASNEQDSDSITAAALATGACIVGILC
LPLILLLVYKQRQVASHRRAQELVRMDSSNTQGIENPGFETTPPFQGMPEA
KTRPPLSYVAQRQPSESGRYLLSDPSTPLSPPGPGDVFFPSLDPVPDSPNS
EAI
```

The amino acid sequence for chimeric protein encoded by the CC8 expression construct is shown below

```
(SEQ ID NO: 1249; C10orf54 Construct 8 (CC8) with
                human sequence underlined)
MGVPAVPEASSPRWGTLLLAIFLAASRGLVAAFKVTTPYSLYVCPEGQNAT
LTCRILGPVSKGHDVTIYKTWYLSSRGEVQMCSERRPIRNLTFQDLHLHHG
GHQAANTSHDLAQRHGLESASDHHGNFSITMRNLTLLDSGLYCCLVVEIRH
HHSEHRVHGAMELQVQTGKDAPSNCVVYPSSSQDSENITAAALATGACIVG
ILCLPLILLLVYKQRQAASNRRAQELVRMDSNIQGIENPGFEASPPAQGIP
EAKVRHPLSYVAQRQPSESGRHLLSEPSTPLSPPGPGDVFFPSLDPVPDSP
NFEVI
```

The amino acid sequence for chimeric protein encoded by the CC9 expression construct is shown below

```
(SEQ ID NO: 1250; C10orf54 Construct 9 (CC9) with
                mouse sequence underlined)
MGVPTALEAGSWRWGSLLFALFLAASLGPVAAFKVATPYSLYVCPEGQNVT
LTCRLLGPVDKGHDVTFYKTWYRSSRGEVQTCKEHRPIRNFTLQHLQHHGS
HLKANASHDQPQKHGLESASDHHGNFSITMRNLTLLDSGLYCCLVVEIRHH
HSEHRVHGAMELQVQTGKDAPSNCVVYPSSSQDSENITAAALATGACIVGI
LCLPLILLLVYKQRQAASNRRAQELVRMDSNIQGIENPGFEASPPAQGIPE
AKVRHPLSYVAQRQPSESGRHLLSEPSTPLSPPGPGDVFFPSLDPVPDSPN
FEVI
```

The amino acid sequence for chimeric protein encoded by the 0010 expression construct is shown below (SEQ ID NO: 1251; C10orf54 Construct 10 (CC10) with human sequence underlined)
MGVPAVPEASSPRWGTLLLAIFLAASRGLVAAFKVTTPYSLYVCPEGQNAT

LTCRILGPVSKGHDVTIYKTWYLSSRGEVQMCSERRPIRNLTFQDLHLHHG

GHQAANTSHDLAQRHGLELASDHHGNFSITLRNVTPRDSGLYCCLVIELKN

HHPEQRFYGSMELQVQAGKGSGSTCMASNEQDSDSITAAALATGACIVGIL

CLPLILLLVYKQRQVASHRRAQELVRMDSSNTQGIENPGFETTPPFQGMPE

AKTRPPLSYVAQRQPSESGRYLLSDPSTPLSPPGPGDVFFPSLDPVPDSPN

SEAI

TABLE 39

| Antibody Designation | C10orf54 Construct Bin | Staining of following Construct IDs |
| --- | --- | --- |
| 5B | a | CC1, CC4, CC5, CC8, CC10 |
| 46A | a | CC1, CC4, CC5, CC8, CC10 |
| 97A | | |
| 128A | a | CC1, CC4, CC5, CC8, CC10 |
| 146C | a | CC1, CC4, CC5, CC8, CC10 |
| 208A | a | CC1, CC4, CC5, CC8, CC10 |
| 215A | b | CC1, CC4, CC5, CC8 |
| 26A | a | CC1, CC4, CC5, CC8, CC10 |
| 164A | a | CC1, CC4, CC5, CC8, CC10 |
| 230A | a | CC1, CC4, CC5, CC8, CC10 |
| 76E1 | b | CC1, CC4, CC5, CC8 |
| 53A | b | CC1, CC4, CC5, CC8 |
| 259A | b | CC1, CC4, CC5, CC8 |
| 33A | a | CC1, CC4, CC5, CC8, CC10 |
| 39A | b | CC1, CC4, CC5, CC8 |
| 124A | b | CC1, CC4, CC5, CC8 |
| 175A | c | CC1, CC4, CC5 |
| 321D | a | CC1, CC4, CC5, CC8, CC10 |
| 141A | d | CC1, CC4, CC5, CC8, CC9 |
| 51A | d | CC1, CC4, CC5, CC8, CC9 |
| 353A | e | CC1, CC3, CC4, CC5, CC8, CC9 |
| 305A | f | CC1, CC4, CC5, CC7, CC9 |

Results of these experiments demonstrate that the anti-C10orf54 antibodies as described herein bind to various epitopes of human C10orf54, including aa33-169, aa84-169, aa115-169, and aa84-115.

Example 5—Preparation of Humanized Antibodies

Murine antibodies prepared as described in Example 3 were selected for sequencing. The selected monoclonal antibodies designated 76E1, 141A and 175A were humanized by two methods as follows. The results of humanization are shown in FIGS. 3-8.

In a first humanization method, most amino acids in each complementarity-determining region (CDR), as previously identified, in the variable heavy (VH) and variable light (VL) domain sequence were converted to alanine. The resulting sequence for VH and for VL as shown in FIG. 9 was used as input to the human subgroup identification algorithm on the website of Dr. Andrew C. R. Martin www.bioinf.org.uk/abs/; this method is a derivation of Deret, S. et al SUBIM: a Program for Analysing the Kabat Database and Determining the Variability Subgroup of a new Immunoglobulin Sequence Comput Appl Biosci 11:435-439 (1995). Antibody 76E1 VH, 141A VH and 175A VH were closest to human VH subgroup I, 76E1 VL and 175A VL were closest to human VL kappa subgroup II, and 141A VL was closest to human VL kappa subgroup III. For each murine 76E1, 141A and 175A VH and VL sequence, a single human VH or VL germline acceptor sequence was chosen from the corresponding human subgroup germline sequences and all human joining region sequences compiled at IMGT® the international ImMunoGeneTics information System® (founder and director: Marie-Paule Lefranc, Montpellier, France).

In a second humanization method (Carter et al., *Proc Natl Acad Sci USA* 89:4285-4289 (1992)), human VH subgroup III germline was used as acceptor for the murine VH sequences of 76E1 VH, 141A VH and 175A VH; human VL subgroup kappa I was used as acceptor for 76E1 VL, 141 A VL and 175A VL.

Alteration of human germline framework (e.g., non-CDR residues in VH and VL) positions to corresponding parental murine 76E1, 141A or 175A sequence might be required to optimize binding of the humanized antibody. Potential changes for each humanized sequence are noted in FIGS. 3-8. Potential changes in the CDR sequences of the humanized antibodies in order to alleviate complications due to deamidation of solvent-exposed asparagines, oxidation of solvent-exposed methionines, and formation of isoaspartic acid are also noted in FIGS. 3-8.

Computer-graphics models of murine 76E1, 141A and 175A VH and VL domains were generated to aid in selection of CDR and framework residues that might require alteration. The Swiss-PdB Viewer program was used (Guex, N and Peitsch, M C SWISS-MODEL and the Swiss-PdBViewer: An environment for comparative protein modeling. Electrophoresis 18:2714-2723 (1997) Expasy website. Crystal structures of antibodies were taken from the Protein Data Bank website (Berman, H M; Westbrook, J; Feng, Z; Gilliland, G; Bhat, T N; Weissig, H; Shindyalov, I N; Bourne P E, The Protein Data Bank Nucleic Acids Research 28:235-242 (2000). The sequences of humanized 76E1, 141A and 175A VH and VL domains are shown in FIGS. 3-8.

Additional humanized anti-C10orf54 antibodies are prepared comprising a VH domain, VL domain, VH CDR1, VH CDR2, VH CDR3, VL CDR1, VL CDR2, and/or VL CDR3 as shown in Tables 12-33. For example, selected murine monoclonal antibodies designated 26A, 128A, 124A and 259A were humanized by the following method, the results of which are shown in FIGS. 22A, 22B, 23A, 23B, 24A, 24B, 25A and 25B. The CDR sequences and VH/VL sequences for antibodies designated 26A, 128A, 124A and 259A are shown in Tables 19, 15, 27 and 24, respectively.

The sequences of the VH and VL of each murine monoclonal antibody was used as input to the IgBLAST program on the NCBI website (Ye, J. et al. Nucleic Acids Research 41:W34-W40 (2013)). IgBLAST takes a murine VH or VL sequence and compares it to a library of known human germline sequences. The databases used were IMGT human VH genes (F+ORF, 273 germline sequences) and IMGT human VLkappa genes (F+ORF, 74 germline sequences). IgBLAST returned the top 10 human germline sequences according to score.

For all four VHs of 26A, 128A, 124A and 259A, human germline IGHV1-46 (allele 1) was chosen as the acceptor sequence and the human heavy chain IGHJ4 (allele 1) joining region (J gene) was chosen from human joining region sequences compiled at IMGT® the international ImMunoGeneTics information System® www.imgt.org (see FIGS. 22A, 23A, 24A, and 25A).

For 26A VL, human germline IGKV43-11 (allele 1) was chosen as the acceptor sequence and human light chain IGKJ2 (allele 1) joining region (J gene) was chosen from human joining region sequences compiled at IMGT® the international ImMunoGeneTics information System® www.imgt.org (see FIG. 22B).

For 128A VL, human germline IGKV1-39 (allele 1) was chosen as the acceptor sequence and human light chain IGKJ2 (allele 1) as the joining region (J gene) (see FIG. 23B).

For 124A VL, human germline IGKV2-30 (allele 1) was chosen as the acceptor sequence and human light chain IGKJ2 (allele 1) as the joining region (J gene) (see FIG. 24B).

For 259A VL, human germline IGKV2-28 (allele 1) was chosen as the acceptor sequence and human light chain IGKJ2 (allele 1) as the joining region (J gene) (see FIG. 25B).

Example 6—Anti-Tumor Activity

Anti-C10orf54 antibodies were tested for their anti-tumor activity in an animal tumor model. For these studies, the cell line Kasumi-3 (acute myeloid leukemia), was obtained from ATCC© (CRL-2725) and cultured according to the suppliers' protocols. Animals were obtained from Taconic (Hudson, NY). Studies were conducted with anti-C10orf54 antibodies in an animal tumor model.

In these experiments, 4-6 week-old immunodeficient NOD-SCID female mice were used for the Kasumi-3 tumor model. Mice were subcutaneously injected on the right flank with $1.2 \times 10^6$ viable cells (Kasumi-3) in a mixture of PBS (without magnesium or calcium) and BD MATRIGEL® basement matrix (BD Biosciences) at a 1:1 ratio. The injected total volume per mouse was 200 µl with 50% being MATRIGEL® (BD Biosciences). Once the tumor reached a size between 65-200 mm³ mice were randomized. Antibodies were administered weekly at 15 mg/kg for four weeks, bodyweights and tumors measured once and twice weekly, respectively. Tumor volume was calculated as described (van der Horst et al., 2009, Neoplasia 11(4):355-364). Experiments were performed on groups of at least 8 animals per experimental point.

Statistical significance between treatment and control groups was calculated using the Graphpad Prism software package and applying Student's two-tailed t-test. A p-value of less than 0.05 was considered significant. The results of three exemplary experiments are shown in Table 40. For Experiment 1, tumor volumes at which treatment was initiated were 114.7 mm3 (day 96). For Experiment 2, tumor volumes at which treatment was initiated were 114.5 mm3 (day 103). For Experiment 3, tumor volumes at which treatment was initiated were 133 mm3 (day 34).

TABLE 40

| EXPERIMENT 1 | | | |
|---|---|---|---|
| Treatment | Volume ± SD [mm³] | TGI [%] | P-value |
| CTRL IgG | 3255 ± 1704 | — | — |
| 175A | 833 ± 429 | −77 | 0.0088 |
| 124A | 1305 ± 674 | −62 | 0.0363 |
| 33A | 1514 ± 1156 | −55 | 0.0447 |
| 51A | 1668 ± 638 | −51 | 0.0507 |
| 46A | 1925 ± 791 | −42 | 0.0937 |
| 26A | 1982 ± 997 | −41 | 0.1154 |
| 39A | 2039 ± 1102 | −39 | 0.1370 |

TABLE 40-continued

| EXPERIMENT 2 | | | |
|---|---|---|---|
| Treatment | Volume ± SD [mm³] | TGI [%] | P-value |
| CTRL IgG | 2689 ± 866 | — | — |
| 141A | 1271 ± 962 | −55 | 0.0079 |
| 164A | 1638 ± 553 | −41 | 0.0136 |
| 128A | 2119 ± 1340 | −22 | 0.3585 |
| 321D | 2588 ± 1371 | −4 | 0.8638 |

| EXPERIMENT 3 | | | |
|---|---|---|---|
| Treatment | Volume ± SD [mm³] | TGI [%] | P-value |
| CTRL IgG | 1961 ± 1060 | — | — |
| 175A | 344 ± 841 | −81 | 0.0342 |

Figure 10:
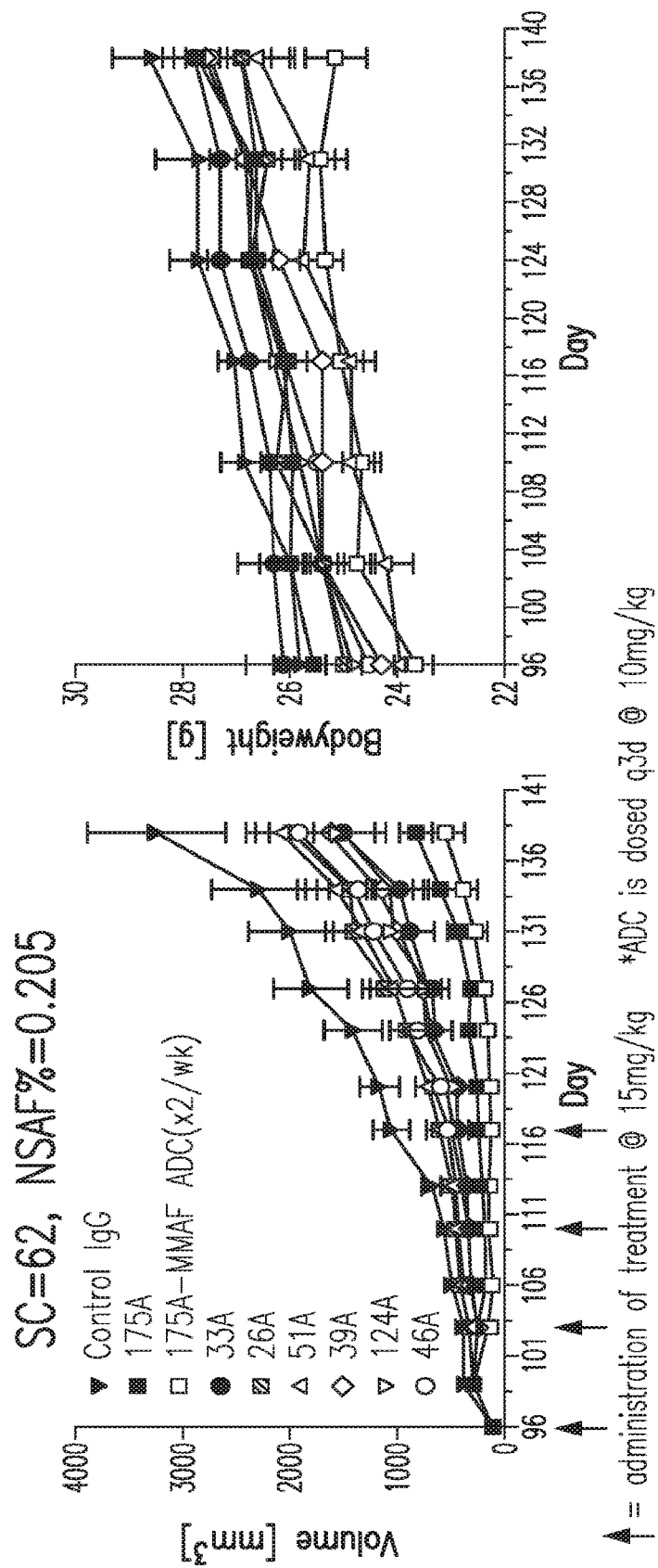
FIG. 10 shows anti-C10orf54 antibody treatment induces strong tumor growth inhibition in established Kasumi-3 tumors.
Figure 11:
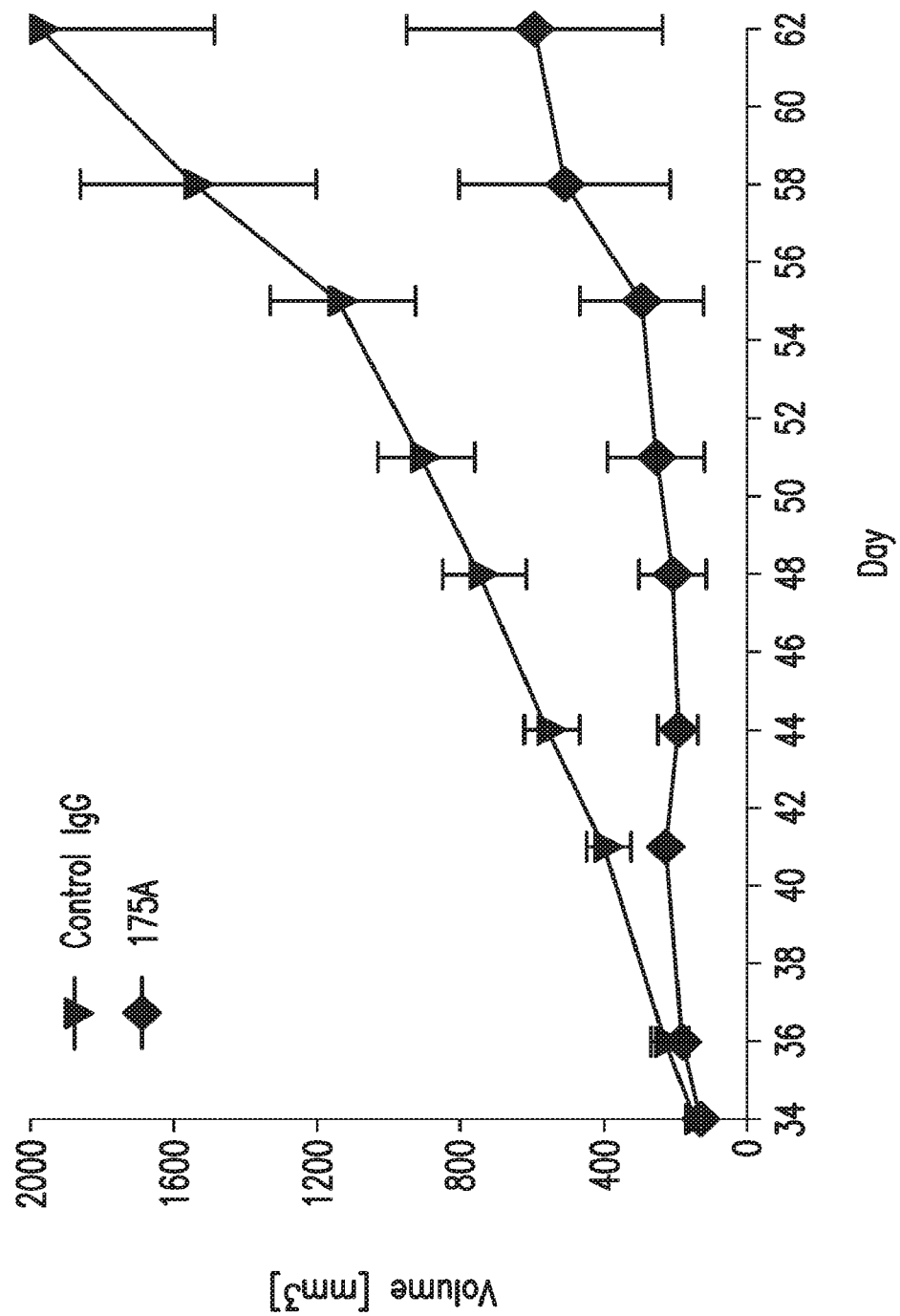
FIG. 11 shows murine 175A anti-C10orf54 antibody treatment induces strong tumor growth inhibition in established Kasumi-3 tumors.

As shown in FIG. 10 (see also, Table 40, Experiment 1), anti-C10orf54 antibody treatment induced strong tumor growth inhibition in established Kasumi-3 tumors. None of the antibody treatments had significant effect on bodyweight, which indicates that the antibody treatment was not toxic. As shown in FIG. 11 (see also, Table 40, Experiment 3), antibody treatment again with antibody 175A induces strong tumor growth inhibition in established Kasumi-3 tumors.

Example 7—Preparation and Use of Antibody-Drug Conjugates

Antibody-drug conjugates (ADCs) were prepared and used in secondary ADC assays and direct ADC assays with antibodies to C10orf54, as illustrated in the following exemplary generic Scheme A, where a maleimido group is attached through a linker (L) to a cytotoxin (CTX):

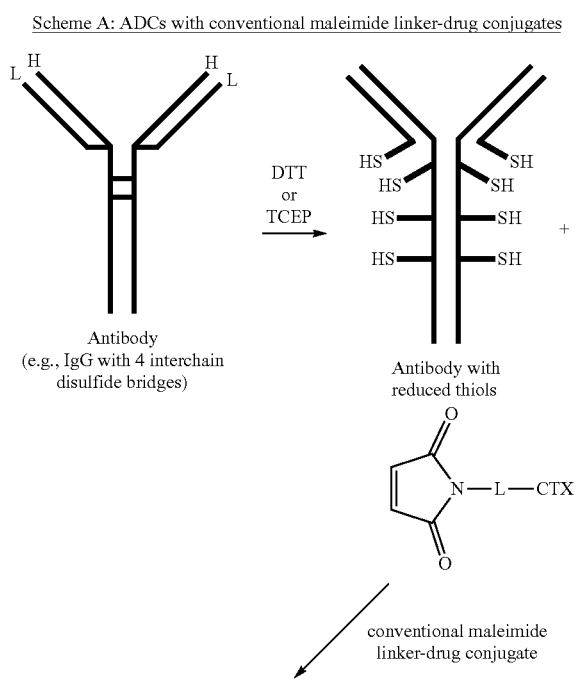

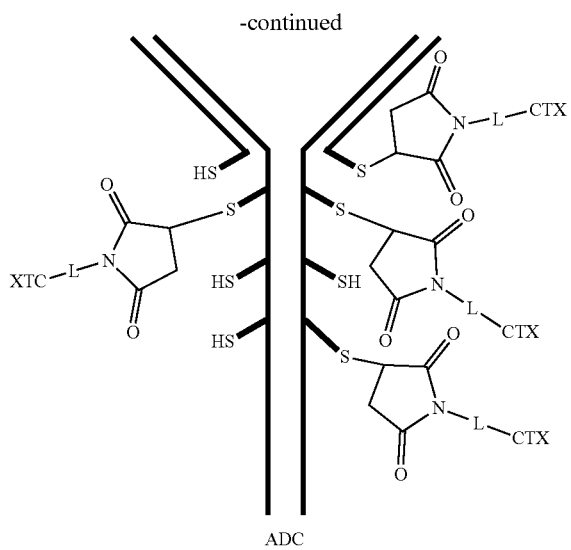

ADC

For example, according to Scheme A above, L may be one of the following:

(i) —(CH$_2$)$_5$-C(O)—; (ii) —(CH$_2$)$_5$—C(O)-Valine-Citrulline; (iii) —(CH$_2$)$_5$—C(O)-Valine-Alanine; (iv) —(CH$_2$)$_5$—C(O)-Valine-Citrulline-phenylenyl, where the phenylenyl is substituted by 2 substituents selected from the group consisting of —C(O)OH and —NH$_2$; (v) —(CH$_2$)$_5$—C(O)-Valine-Alanine-phenylenyl, where the phenylenyl is substituted by 2 substituents selected from the group consisting of —C(O)OH and —NH$_2$; (vi) —(CH$_2$CH$_2$)—(CH$_2$CH$_2$O)$_4$—C(O)-Valine-Citrulline-phenylenyl, where the phenylenyl is substituted by 2 substituents selected from the group consisting of —C(O)OH and —NH$_2$; or (vii) —(CH$_2$CH$_2$)—(CH$_2$CH$_2$O)$_4$-C(O)-Valine-Alanine-phenylenyl, where the phenylenyl is substituted by 2 substituents selected from the group consisting of —C(O)OH and —NH$_2$.

For example, according to Scheme A above, L may be one of the following: (i) caproyl ("c"); (ii) caproyl-Valine-Citrulline ("cValCit"); (iii) caproyl-Valine-Alanine ("cValAla"); (iv) caproyl-Valine-Citrulline-para aminobenzyl ("cValCit-PAB"); (v) caproyl-Valine-Alanine-para aminobenzyl ("cValAla-PAB"); (vi) (dPEG)$_4$-Valine-Citrulline-para aminobenzyl ("dPEG$_4$-ValCit-PAB"); or (vii) (dPEG)$_4$-Valine-Alanine-para aminobenzyl ("dPEG$_4$-ValAla-PAB").

For example, when the antibody-drug conjugate is prepared using a maleimido group ("m"), attached through the linker to a cytotoxin, CTX, as illustrated in Scheme A above, the antibody-drug conjugate may comprise one of the following: (i) maleimidocaproyl ("mc"); (ii) maleimidocaproyl-Valine-Citrulline ("mcValCit"); (iii) maleimidocaproyl-Valine-Alanine ("mcValAla"); (iv) maleimidocaproyl-Valine-Citrulline-para aminobenzyl ("mcValCit-PAB"); (v) maleimidocaproyl-Valine-Alanine-para aminobenzyl ("mcValAla-PAB"); (vi) maleimidocaproyl-(dPEG)$_4$-Valine-Citrulline-para aminobenzyl ("m-dPEG4-ValCit-PAB"); or (vii) maleimidocaproyl-(dPEG)$_4$-Valine-Alanine-para aminobenzyl ("m-dPEG4-ValAla-PAB").

As illustrated in the following Schemes B-F, the antibody-drug conjugate of Scheme A above may be prepared using maleimidocaproyl-monomethylauristatin F ("mc-MMAF"), maleimidocaproyl-Valine-Citrulline-para aminobenzyl-monomethylauristatin F ("mcValCit-PAB-MMAF"), maleimidocaproyl-Valine-Citrulline-para aminobenzyl-monomethylauristatin E ("mcValCit-PAB-MMAE"), maleimidocaproyl-(dPEG)$_4$-Valine-Citrulline-para aminobenzyl-CC1065 ("m-dPEG$_4$-ValCit-PAB-CC1065"), or maleimidocaproyl-Valine-Alanine-pyrrolobenzodiazepine ("mcValAla-PBD").

Exemplary antibody-drug conjugates are prepared using maleimidocaproyl-monomethylauristatin F (mc-MMAF), as illustrated in the following Scheme B, where the maleimido group is attached through a linker (L=caproyl group) to a cytotoxin (CTX=MMAF):

Scheme B ADCs conjugated with mc-MMAF

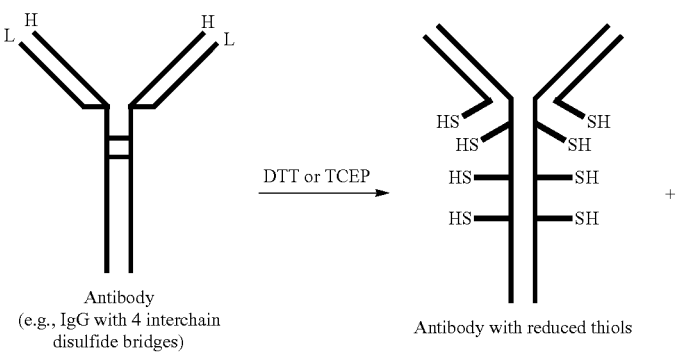

Antibody (e.g., IgG with 4 interchain disulfide bridges)

Antibody with reduced thiols

-continued

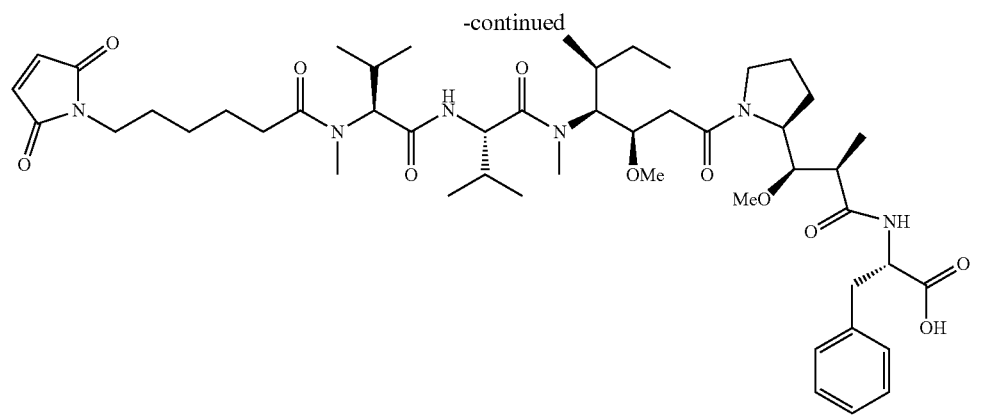

conventional maleimide linker-drug
conjugate (maleimidocaproyl-
monomethylauristatin F; mc-MMAF

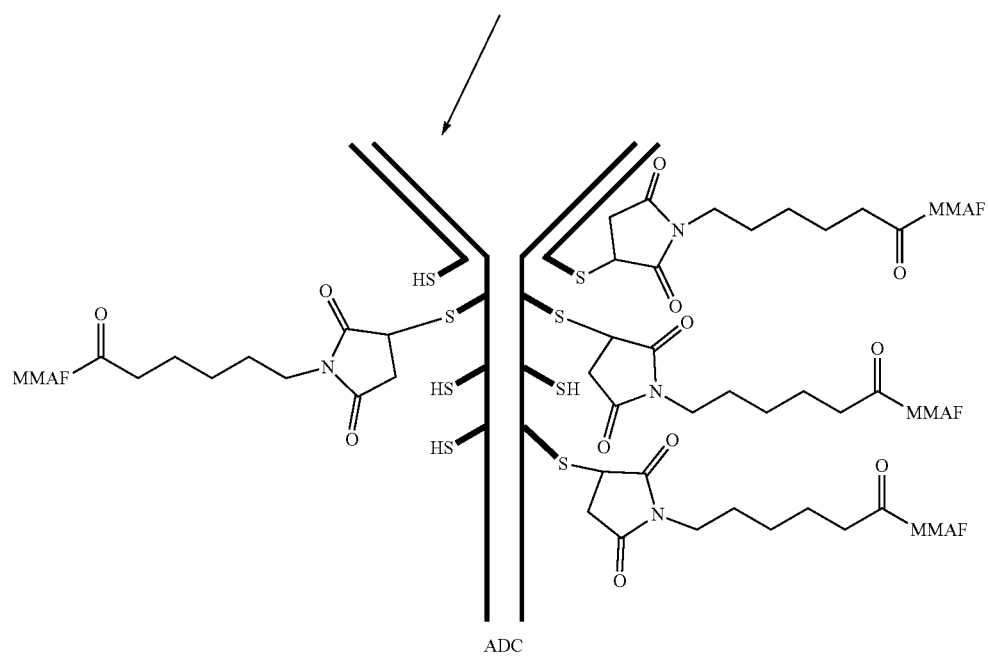

ADC

Exemplary antibody-drug conjugates are also prepared using maleimidocaproyl-Valine-Citrulline-para aminobenzyl-monomethylauristatin F (mcValCit-PAB-MMAF), as illustrated in the following Scheme C, where the maleimido group is attached through a linker (L=caproyl-Valine-Citrulline-para aminobenzyl) to a cytotoxin (CTX=MMAF):

Scheme C ADCs conjugated with mcValCit-PAB-MMAE

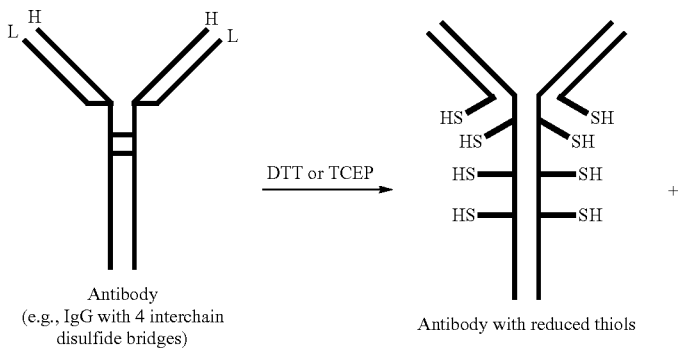

-continued

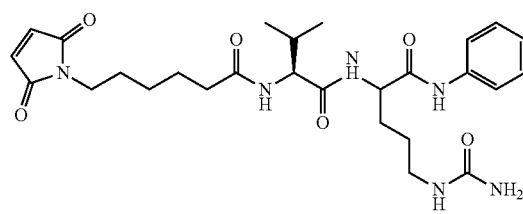
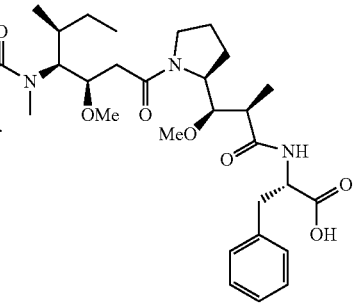

conventional maleimide
linker-drug conjugate
(maleimidocaproyl-Valine-Citrulline-
para aminobenzyl-
monomethylauristatin F;
mcValCit-PAB-MMAF)

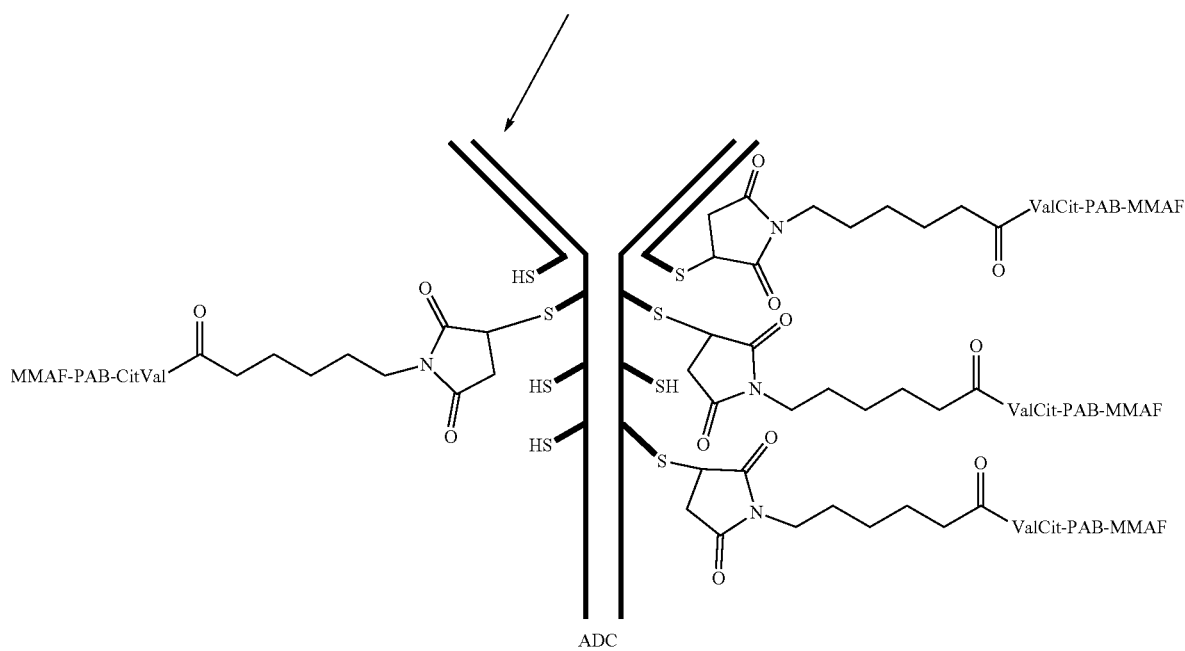

ADC

Exemplary antibody-drug conjugates are also prepared using maleimidocaproyl-Valine-Gitrulline-para aminobenzyl-monomethylauristatin E (mcValCit-PAB-MMAE), as illustrated in the following Scheme D, where the maleimido group is attached through a linker (L=caproyl-Valine-Gitrulline-para aminobenzyl) to a cytotoxin (CTX=MMAE):

Scheme D ADCs conjugated with mcValCit-PAB-MMAE

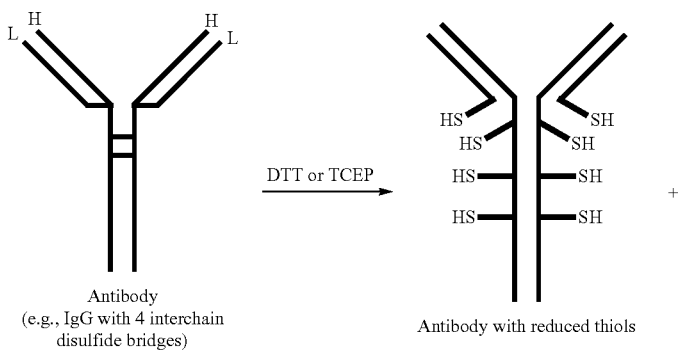

-continued

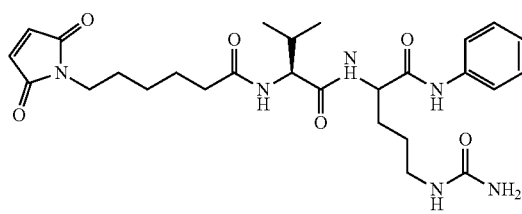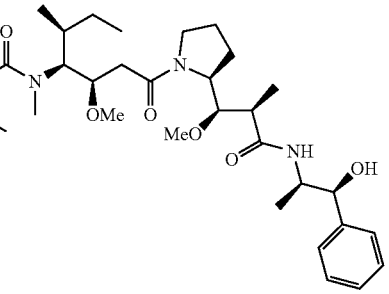

conventional maleimide
linker-drug conjugate
(maleimidocaproyl-Valine-Citrulline-
para aminobenzyl-
monomethylauristatin E;
mcValCit-PAB-MMAE)

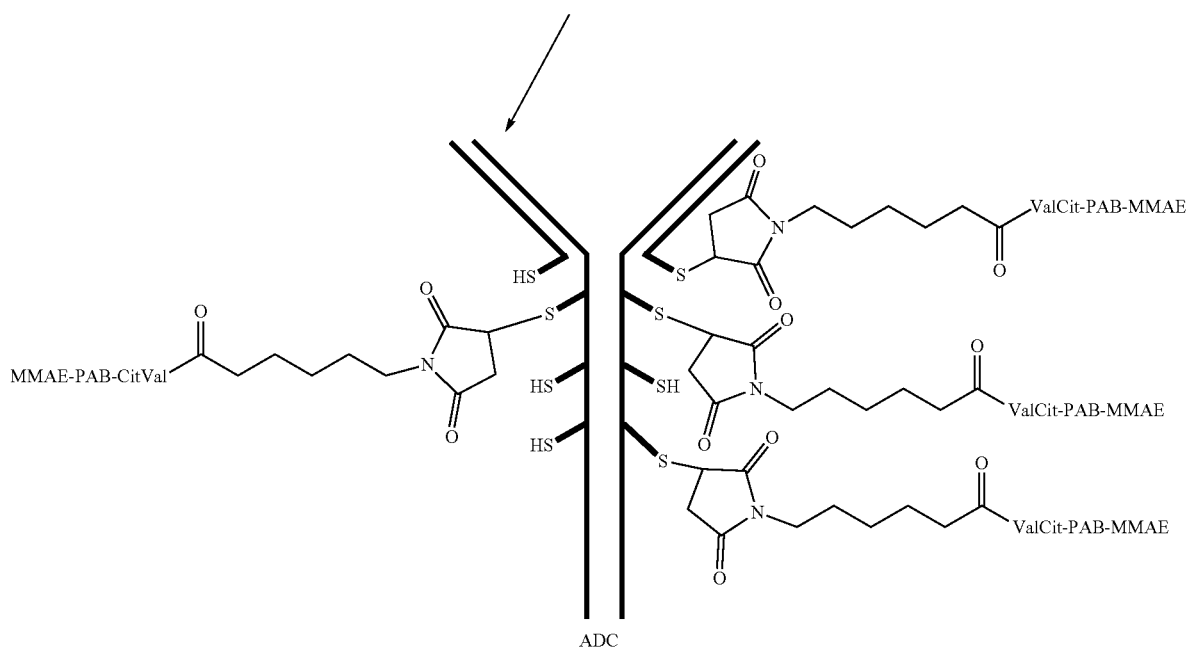

ADC

Exemplary antibody-drug conjugates are also prepared using maleimidocaproyl-(dPEG)$_4$-Valine-Citrulline-para aminobenzyl-CC1065 (m-dPEG4-ValCit-PAB-CC1065), as illustrated in the following Scheme E, where the maleimido group is attached through a linker (L=(dPEG)$_4$-Valine-Citrulline-para aminobenzyl) to a cytotoxin (CTX=CC1065):

Scheme E ADCs conjugated with m-dPEG4-ValCit-PAB-CC1065

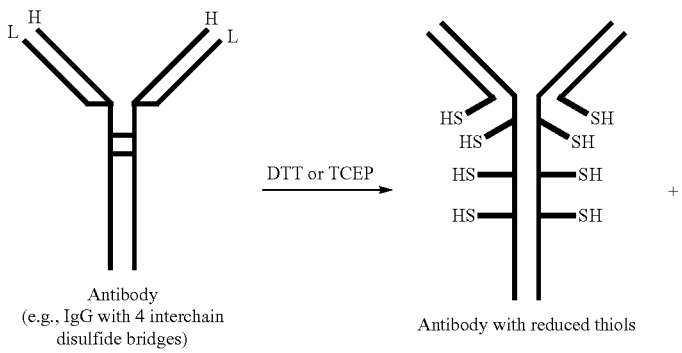

-continued

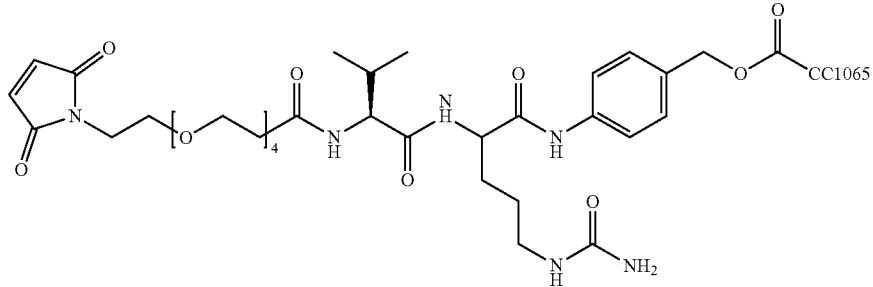

conventional maleimide
linker-drug conjugate
(maleimido-(dPEG)₄-Valine-Citrulline-
para aminobenzyl-CC1065;
m-dPEG₄-ValCit-PAB-CC1065)

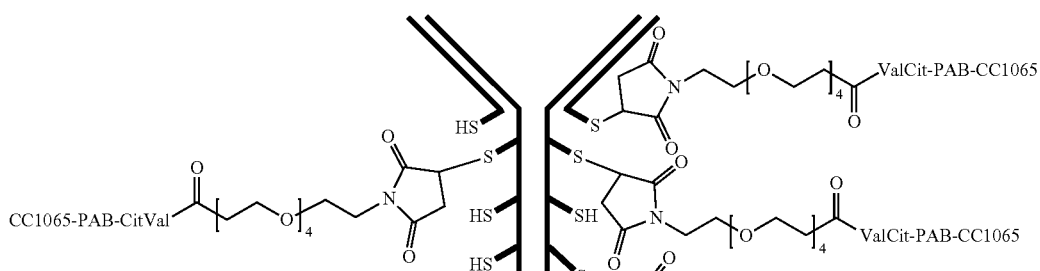

ADC

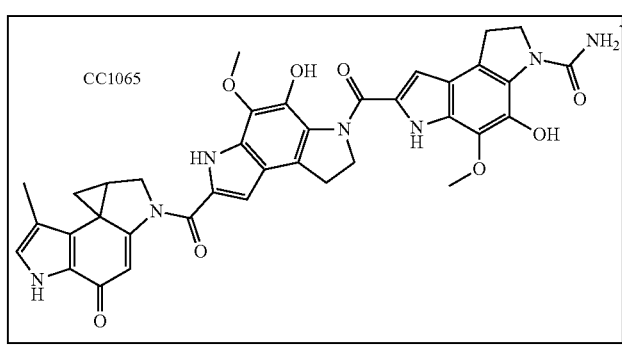

In Scheme E, the structure of the cyclophosphamide, CC1065, is depicted in the lower left-hand corner of the scheme, with an arrow indicating the point of attachment (e.g., via the free amino group on the CC1065 molecule) to the carbonyl group of the para aminobenzoate moiety of the linker.

Exemplary antibody-drug conjugates are also prepared using maleimidocaproyl-Valine-Alanine-pyrrolobenzodiazepine (mc-ValAla-PDB), as illustrated in the following Scheme F, where the maleimido group is attached through a linker (L=caproyl-Valine-Alanine) to a cytotoxin (CTX=PDB):

Scheme F: ADCs conjugated with mcValAla-PBD

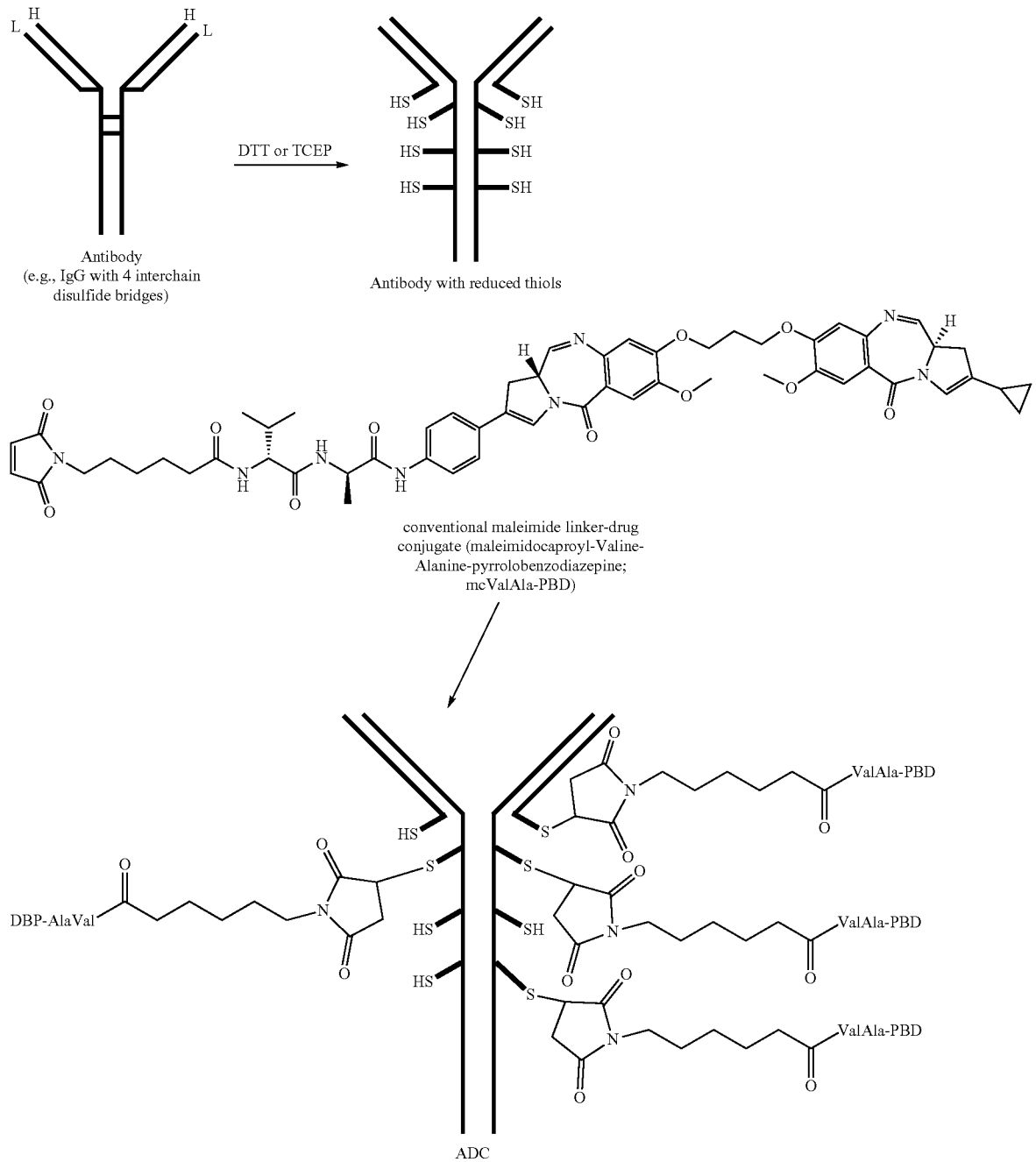

The ADCs of exemplary Schemes B-F were made as follows. In a sterile 1.7 ml eppendorf tube, 20 mg of antibody at 20 mg/ml concentration in phosphate buffered saline (PBS) pH 7.4 (Gibco, Mg and Ca free) was reacted with 1 mM diethylene triamine pentaacetic acid (DTPA) as the chelator. Then 2.75 eq. of tris(2-carboxyethyl)phosphine hydrochloride solution (TCEP HCl) (Sigma ampule 0.5M concentration) or 50 µL of 100 mM dithiothreitol (DTT) was added for an average drug-antibody ratio (DAR) of 4 drugs per antibody and incubated at 37° C. for 1 hour, with the aim of having less than 10% of the total antibody being in the unlabeled or naked antibody.

Dithiobisnitro-benzoate (DTNB; Ellman's reagent) colorimetric assay was used to assess free thiols available for conjugation (Ellman et al., *Biochemical Pharmacology* 7:88-95 (1961)). The reduced antibody solution was cooled in an ice-bath at ~ 0° C. for 15 minutes. Then, linker-cytotoxin conjugate was added to the reduced antibody solution as follows: (i) for Scheme B, 60 µL of mc-MMAF from a 10 mM stock solution in DMSO (9.74 mg in 1.074 ml of DMSO for 10 mM) was added; (ii) for Scheme C, 60 µL of mcValCit-PAB-MMAF from a 10 mM stock solution in DMSO (9.4 mg in 707 µL of DMSO for 10 mM) was added; (iii) for Scheme D, 60 µL of mcValCit-PAB-MMAE from a 10 mM stock solution in DMSO (3.24 mg in 247 µL of DMSO for 10 mM) was added; (iv) for Scheme E, 60 µL of mc-dPEG$_4$-ValCit-PAB-CC1065 from a 10 mM stock solution in DMSO (3.8 mg in 258 µL of DMSO for 10 mM) was added; and (v) for Scheme F, 60 µL of mc-ValAla-PBD from a 10 mM stock solution in DMSO is added. Once the linker-cytotoxin conjugate was added to the reduced antibody solution, the solution was incubated on a roller-plate in a refrigerator at 4° C. overnight (or alternatively at 37° C. for 2 hours) to produce the ADC. The DTNB assay was repeated to demonstrate no free thiols remaining (clear means no free thiol and a yellow color indicates remaining free thiols and incomplete conjugation of payload). The concentration of the ADC was obtained via the NanoDrop spectrophotometer. The crude ADC was purified using either PD-10 SEC separation or SEC chromatography via a SUPERDEX™ 200 column eluted with an appropriate working buffer or final formulation buffer. The purified ADC was stored at 4° C.

Hydrophobic Interaction Chromatography (HIC) HPLC method was used to determine average drug loads of the ADCs via HPLC. On an Agilent 1200 HPLC binary pump system attached to a Agilent 6130b Electrospray Mass Spectrometer, a Tosoh NPR Butyl-C4 column (2.1 mm×75 mm) was run with a binary gradient at 0.8 ml/min with diode-array UV-vis detection at 220 nm, 254 nm and 280 nm. Mobile phase A was 1.5M Sodium Sulfate in 1×PBS, Mobile phase B was 1×PBS with 25% isopropanol run on a 0-100% linear gradient for 10-12 column volumes with a 5 minute initial equilibration and 5 minute 100% mobile phase B wash at the end of each HPLC run. Unlabeled or naked antibody eluted first in the linear gradient with peaks representing increasing average drug loads in order of hydrophobicity which correlates with increasing loading of antibody with payloads. Retention times of the naked antibody were confirmed via running a standard injection of 20 µL of a 1 mg/ml stock solution of the antibody. Co-elution of the naked antibody and ADC definitively confirmed relative amounts of each.

Figure 12:
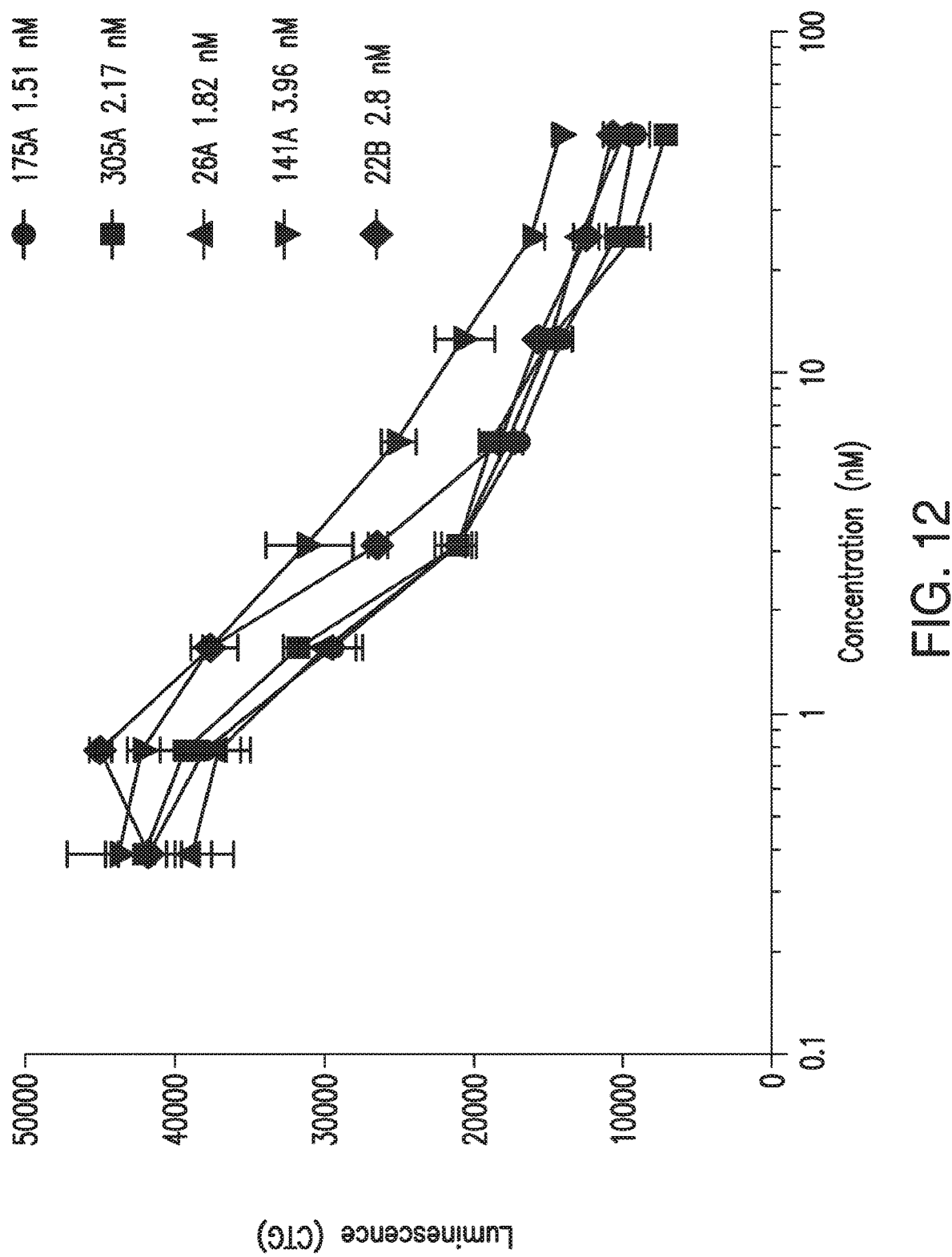
FIG. 12 shows results of a secondary ADC assay using anti-C10orf54 antibodies in a cell viability assay with C10orf54 expressing sarcoma line.

FIG. 12 shows the results of a secondary ADC assay using anti-C10orf54 antibodies in a cell viability assay using a C10orf54 expressing sarcoma line. Anti-C10orf54 antibodies were incubated at a 2:1 ratio with a secondary goat anti mouse antibody conjugated with MMAF. Cells were plated at 1000 cells/well and incubated in the presence of antibodies for 72 hours. The C10orf54 expressing sarcoma cells were killed by the anti-C10orf54 antibodies tested in a concentration-dependent manner.

Figure 13:
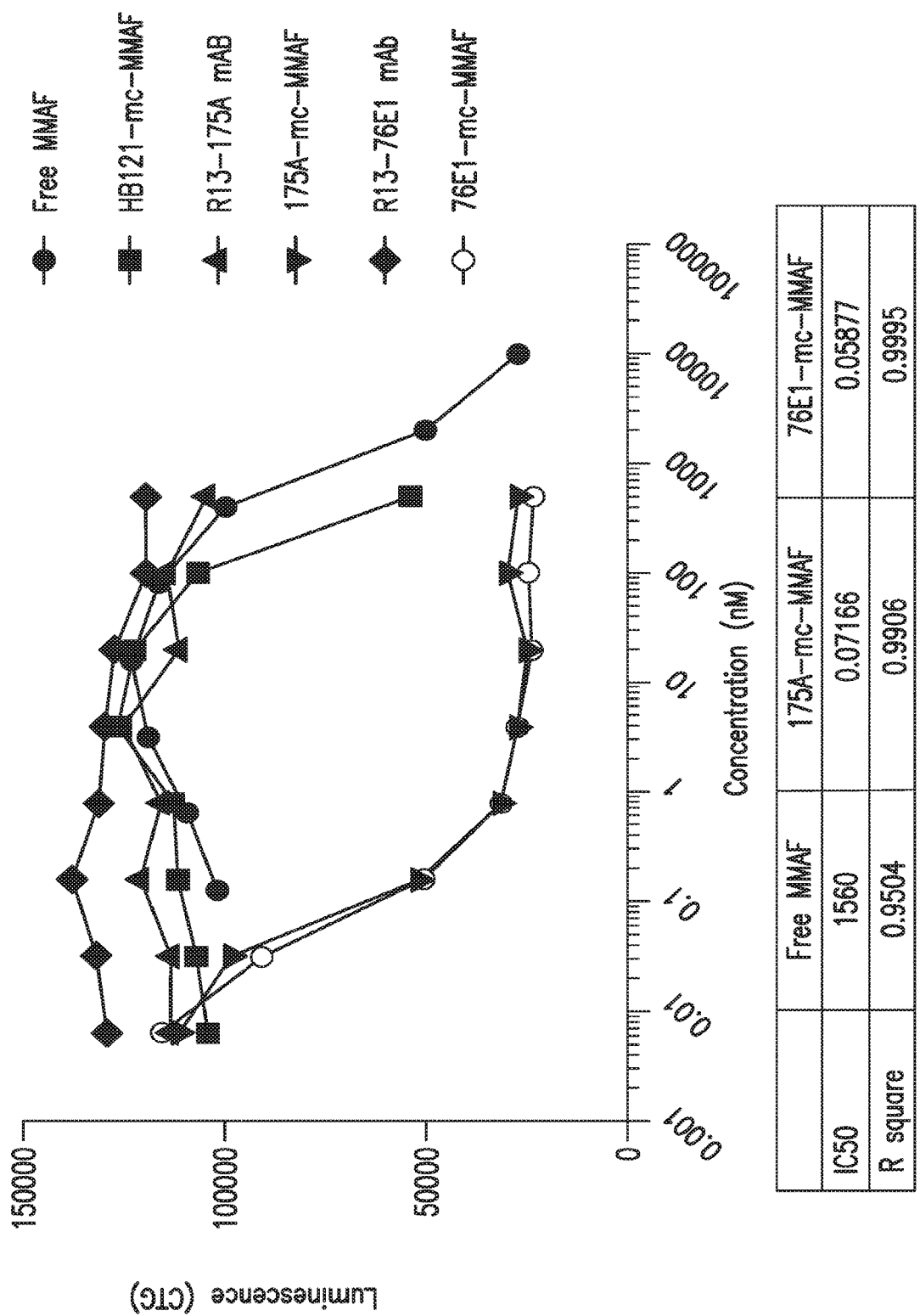
FIGS. 13 and 14 show activity of unconjugated and MMAF conjugated anti-C10orf54 antibodies in a cell viability assay using C10orf54 expressing sarcoma lines and parental sarcoma line.
Figure 14:
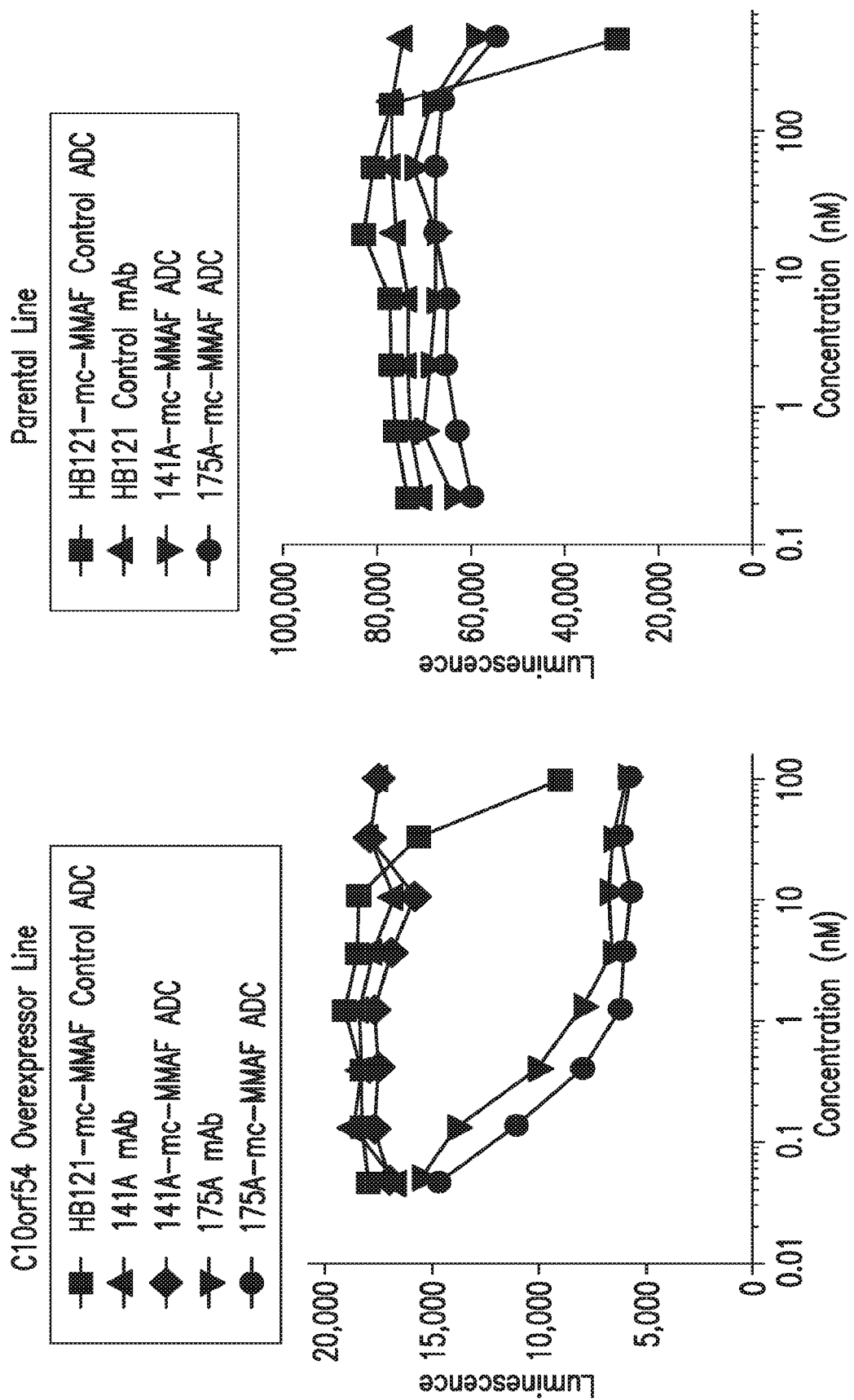
Figure 21A:
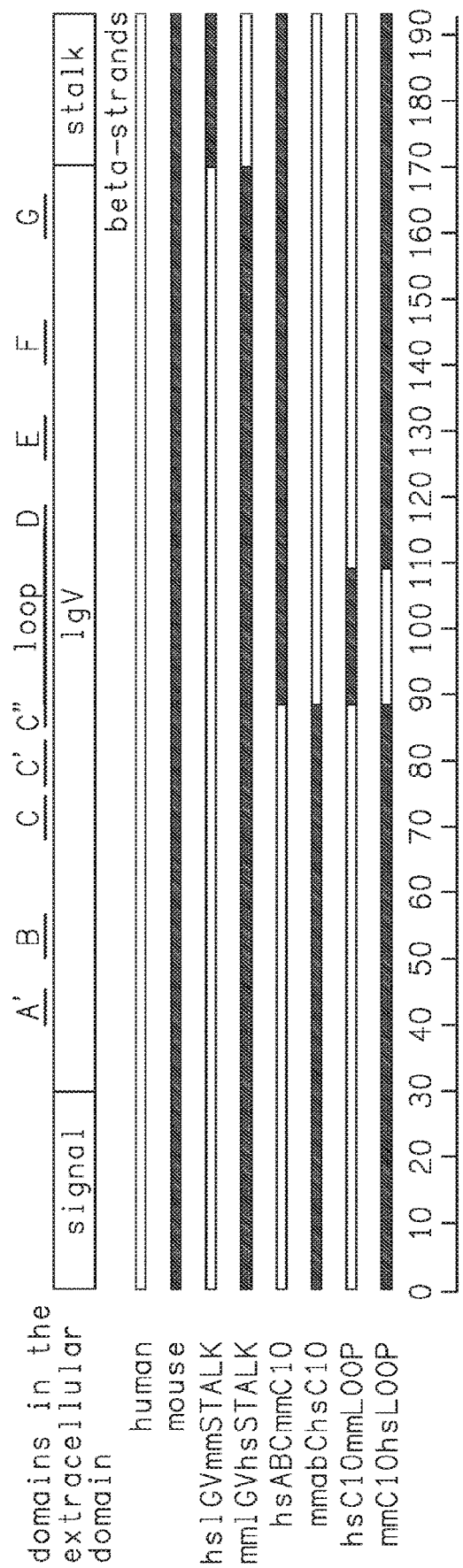
FIG. 21A shows a graphical depiction of C10orf54 protein and chimeric protein constructs. Designation "Human" refers to construct CC1; "Mouse" refers to construct CC2; "hsIGVmmSTALK" refers to construct CC5; "mmIGVhsSTALK" refers to construct CC6; "hsABCmmC10" refers to construct CC7; "mmabChsC10" refers to construct CC8; "hsC10mmLOOP" refers to construct CC9; and "mmC10hsLOOP" refers to construct CC10, as described in Example 3. A sequence alignment of amino acid sequences from human C10orf54 (residues 1 to 193 of SEQ ID NO:1079) and mouse C10orf54 (residues 1 to 190 of SEQ ID NO: 1243), including a consensus sequence of these residues (SEQ ID NO: 1914), are also depicted.
Figure 21B:
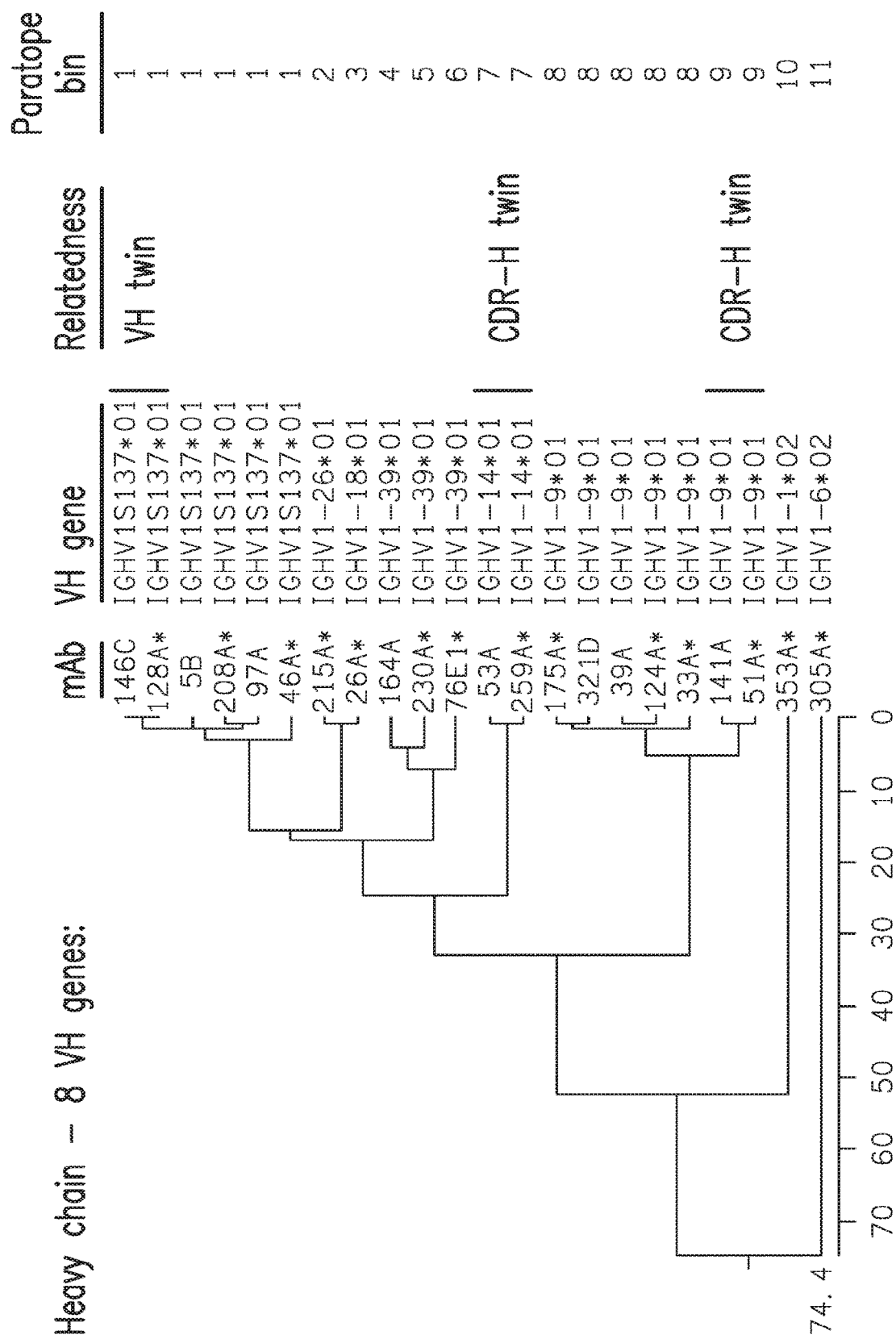
FIG. 21B shows a phylogenetic tree of C10orf54 antibodies for both VH and VL genes, including categorization of paratope bin and flow cluster analysis as described in Example 3. Designation "full-length human" refers to po CC1; "rat" refers to construct CC3; "full-length cyno" refers to construct CC4; "hsIGVmmSTALK" refers to construct CC5; "hsABCmmC10" refers to construct CC7; "mmABChsC10" refers to construct CC8; "hsC10mmLOOP" refers to construct CC9; and "mmC10hsLOOP" refers to construct CC10, as described in Example 3.
Figure 21B:
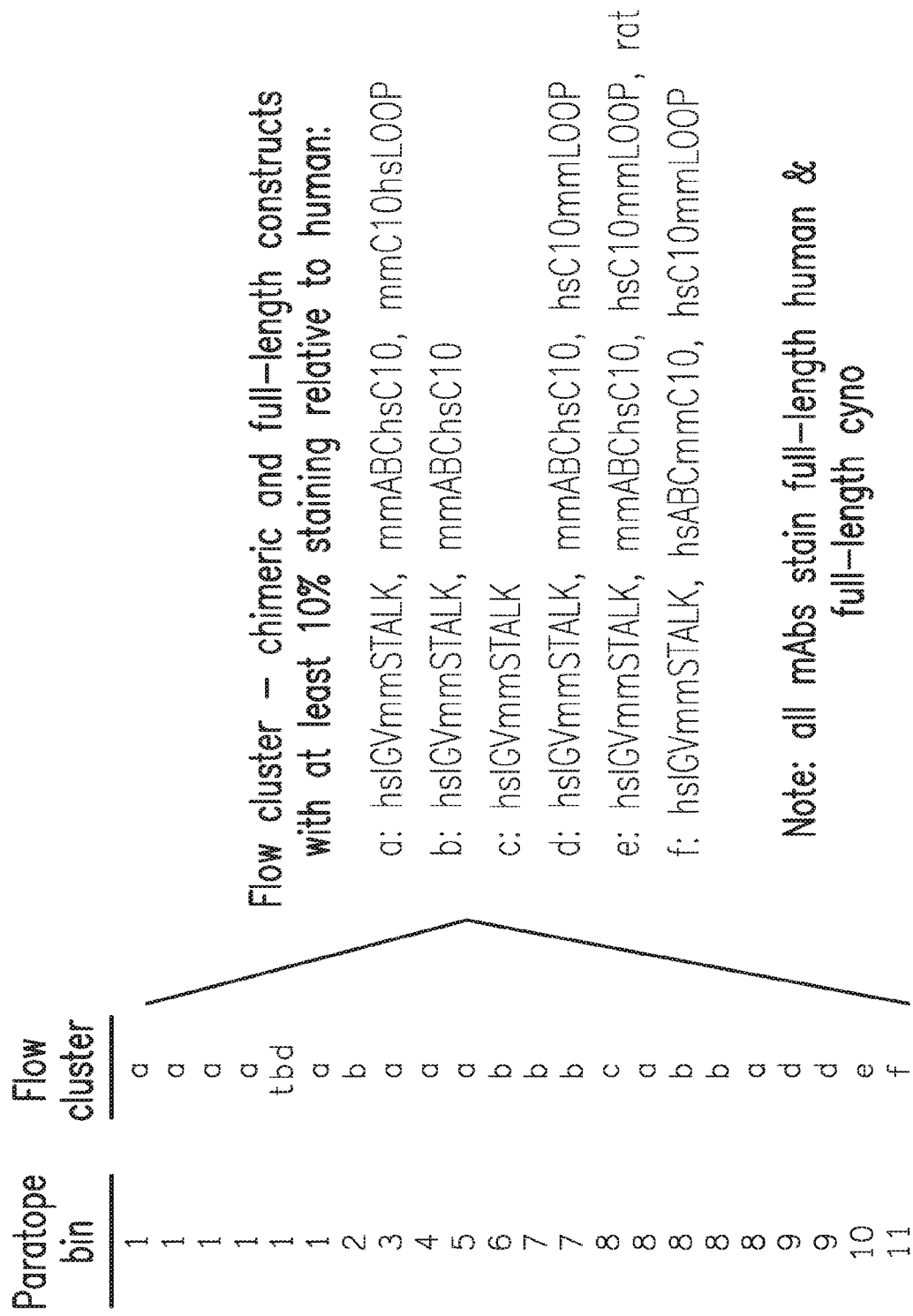
Figure 21B:
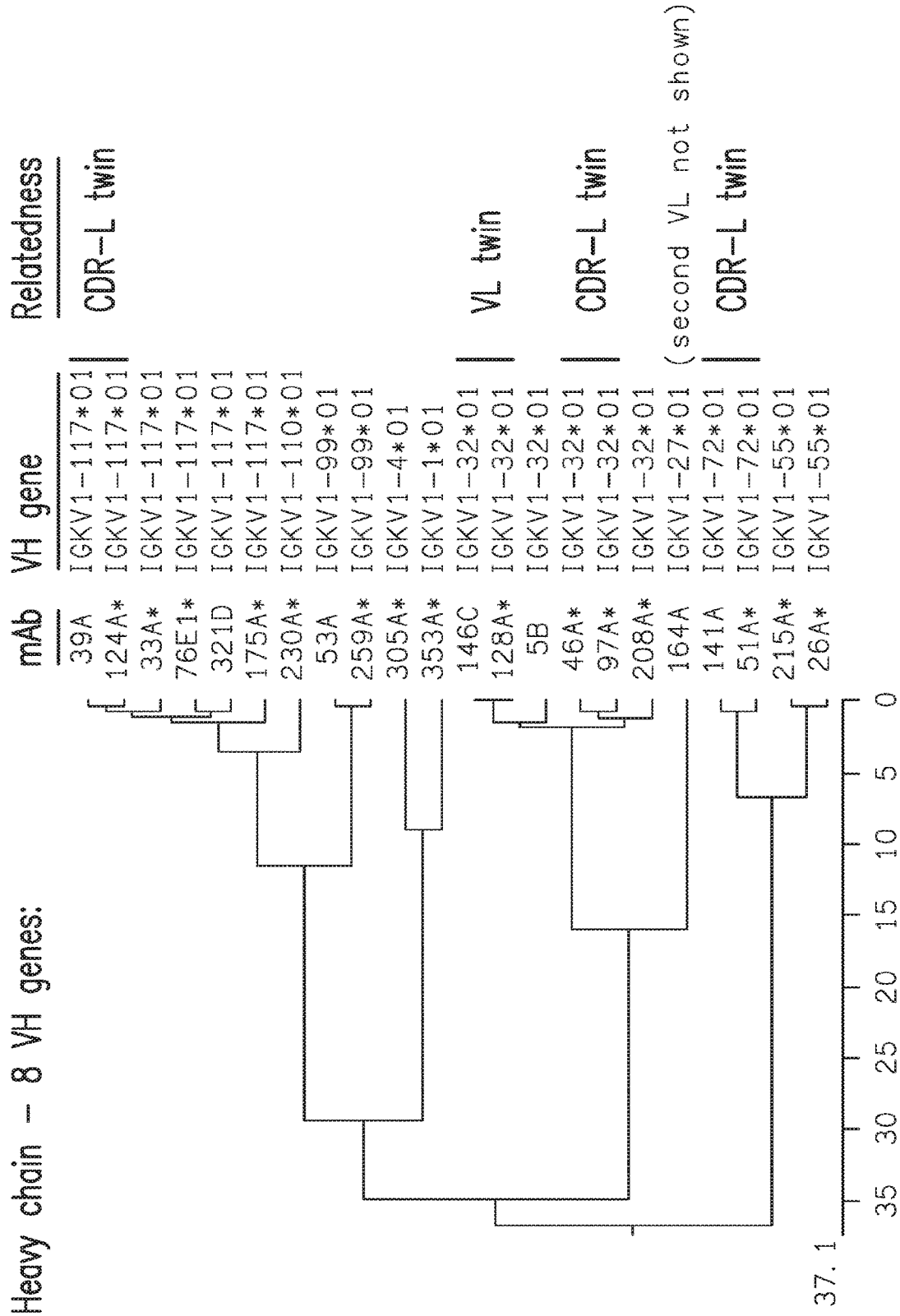

FIGS. 13-14 show the activity of unconjugated and anti-C10orf54 antibodies directly conjugated with MMAE in cell viability assays using C10orf54 expressing sarcoma lines. For these assays, cells may be plated in varying numbers in the wells and are incubated for various times in the presence or absence of anti-C10orf54 antibodies and ADCs. For example, for the assays shown in FIG. 13, cells were plated at 1000 cells/well and incubated in the presence of antibodies for 72 hours. In these in vitro cell-based assays, the MMAF conjugated anti-C10orf54 antibodies killed the sarcoma cells in a concentration-dependent manner.

FIG. 15 shows results of treatment with anti-C10orf54 antibodies and ADCs (e.g., unconjugated and MMAF conjugated anti-C10orf54 antibodies) in an animal tumor (e.g., xenograft) model, with C10orf54-expressing and parental sarcoma lines.

Example 8—Preparation and Use of Additional Antibody-Drug Conjugates

Additional antibody-drug conjugates of formula (Ia) or (Ib) of the present disclosure may be prepared as illustrated with formula (Ia) in the following Scheme G, and with formula (Ib) in the following Scheme H for:

Scheme G: ADCs of formula (Ia) of the present disclosure

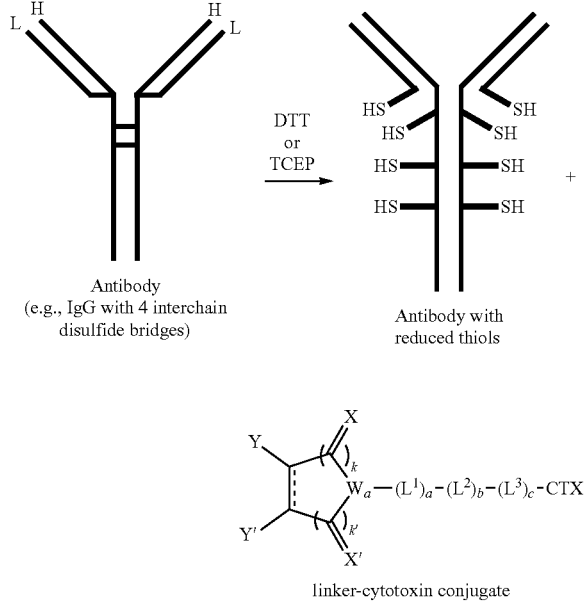

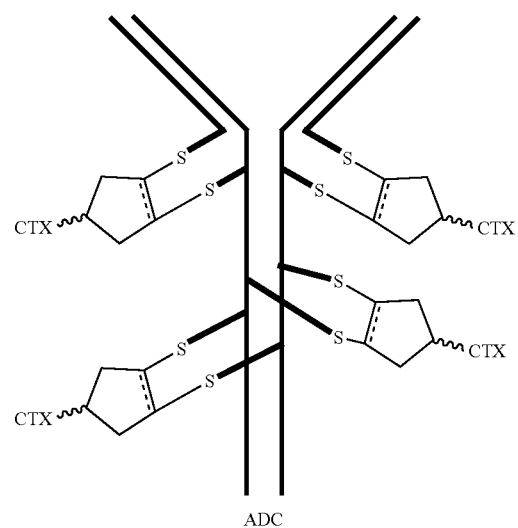

ADC

For ease of viewing, the linker-cytotoxin conjugate is represented by a cartoon, where the linker between $W_a$ and CTX is the squiggly line, k and k′ are both 0, and Y and Y′ are independently any electrophilic leaving group that reacts selectively with thiols.

427

Scheme H: ADCs of formula (Ib) of the present disclosure

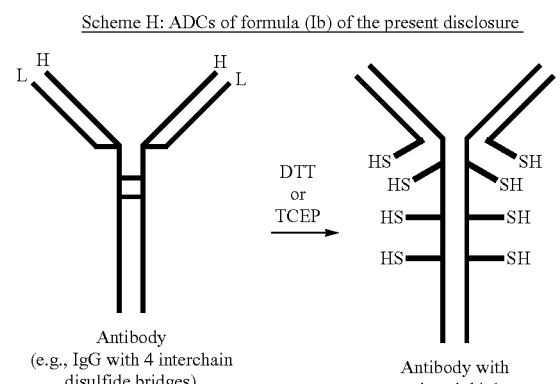

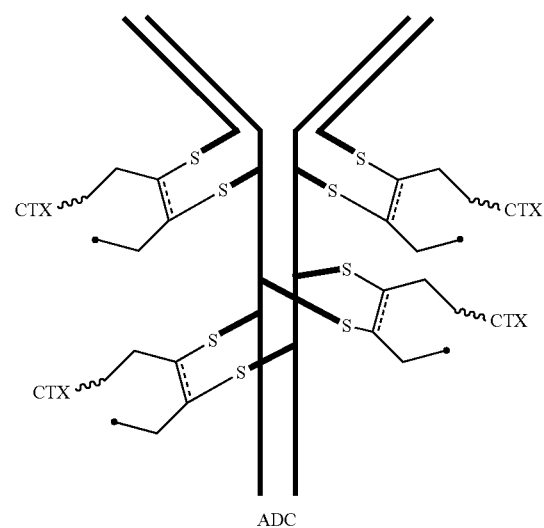

For ease of viewing, the linker-cytotoxin conjugate is represented by a cartoon, where the linker between $W_b$ and CTX is the squiggly line, k and k' are both 0, and Y and Y' are independently any electrophilic leaving group that reacts selectively with thiols.

428

Additional antibody-drug conjugates of the present disclosure may be prepared, wherein the antibody-drug conjugates are according to formula (Ic1):

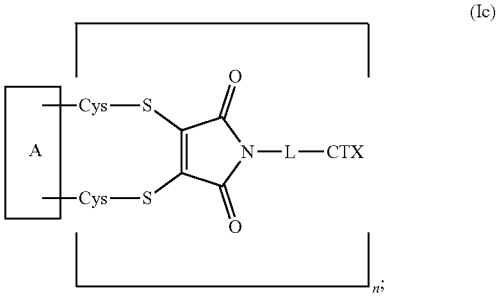

(Ic)

or a pharmaceutically acceptable salt thereof, wherein:

A is an antibody, wherein the antibody is an anti-C10orf54 antibody, optionally a humanized anti-C10orf54 antibody;

the two depicted cysteine residues are from an opened cysteine-cysteine disulfide bond in A;

L is a cleavable or a noncleavable linker;

CTX is cytotoxin bonded to L by an amide bond, a carbamate bond, a disulfide bond, an ether bond, a thioether bond, or an ester bond; and n is an integer of 1 to 4.

For example, the antibody-drug conjugates of formula (Ic1) are prepared where CTX is monomethylauristatin F (MMAF), L is —$(CH_2)_5C(O)$—, and n is 4.

For example, the antibody-drug conjugates of formula (Ic1) are prepared where the antibody-drug conjugate has the following formula:

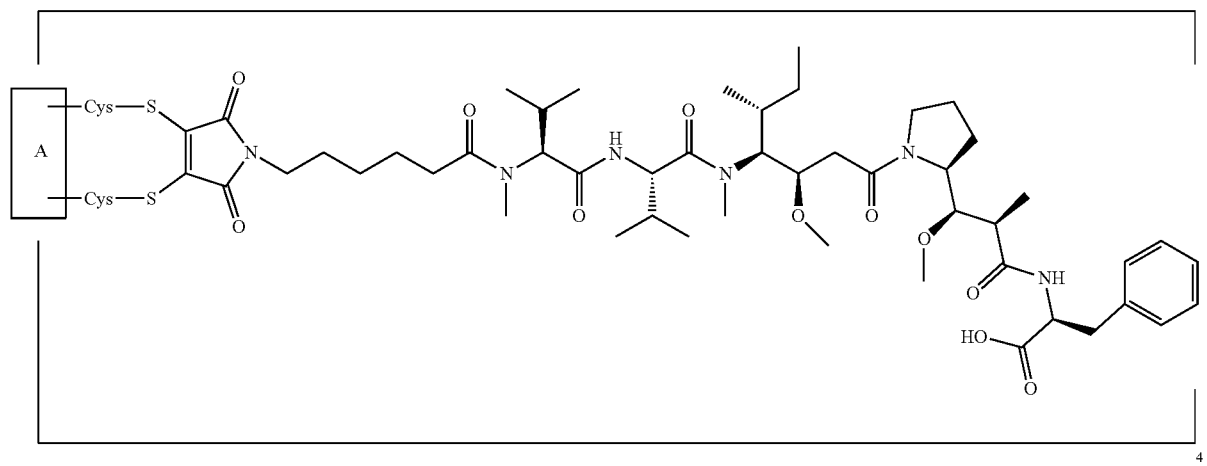

wherein A is an anti-C10orf54 antibody, optionally a humanized anti-C10orf54 antibody, and n is 4.

For example, the antibody-drug conjugates of formula (Ic1) are those where CTX is monomethylauristatin E (MMAE), L is —(CH$_2$)$_5$C(O)-Val-Ala-PAB-O—C(O)—, or —(CH$_2$)$_5$C(O)-Val-Cit-PAB-O—C(O)—, and n is 4.

For example, the antibody-drug conjugates of formula (Ic1) are those which have the following formula:

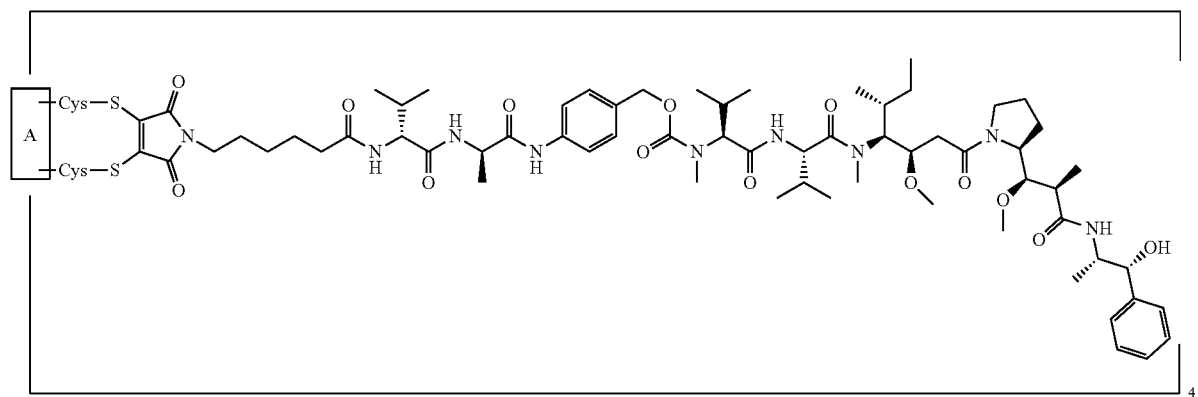

wherein A is an anti-C10orf54 antibody, optionally a humanized anti-C10orf54 antibody, and n is 4.

For example, the antibody-drug conjugates of formula (Ic1) are those where CTX is a pyrrolobenzodiazepine (PDB), L is —(CH$_2$)$_5$C(O)-Val-Ala-PAB-O—C(O)—, or —(CH$_2$)$_5$C(O)-Val-Cit-PAB-O—C(O)—, and n is 4.

For example, the antibody-drug conjugates of formula (Ic1) are those which have one of the following formulas:

431 432
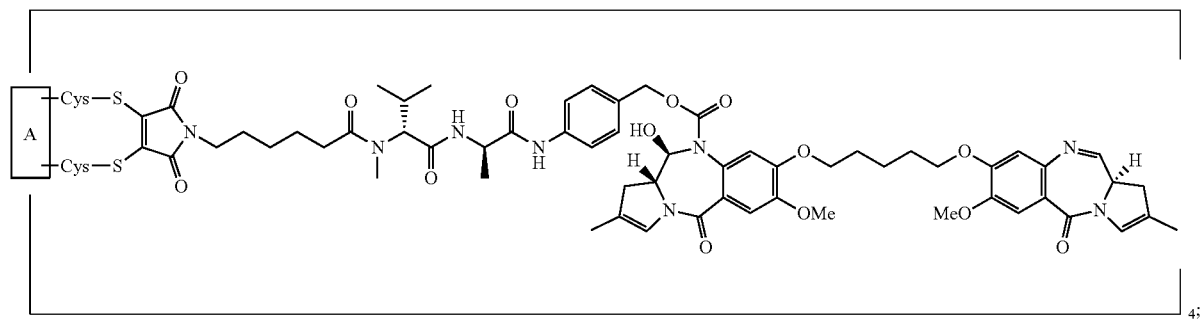
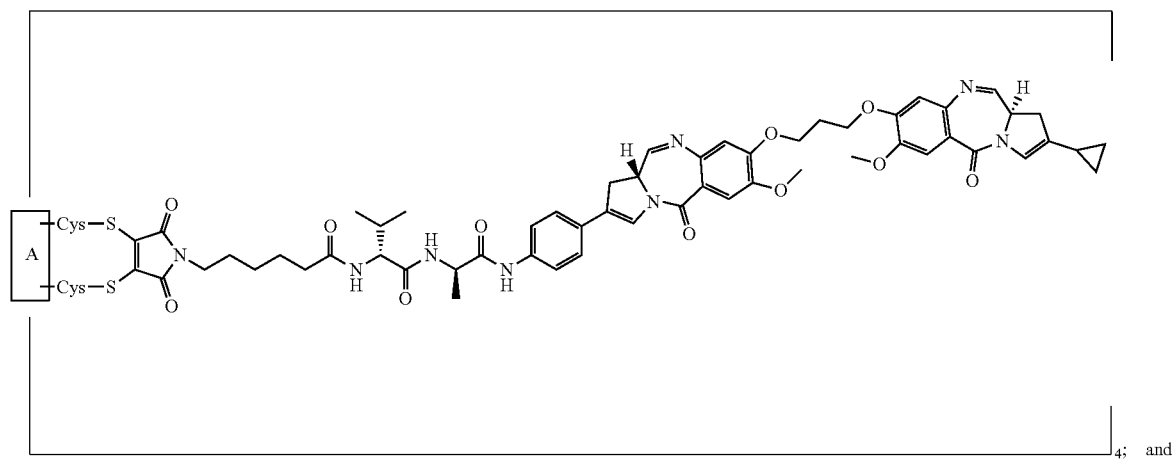
; and
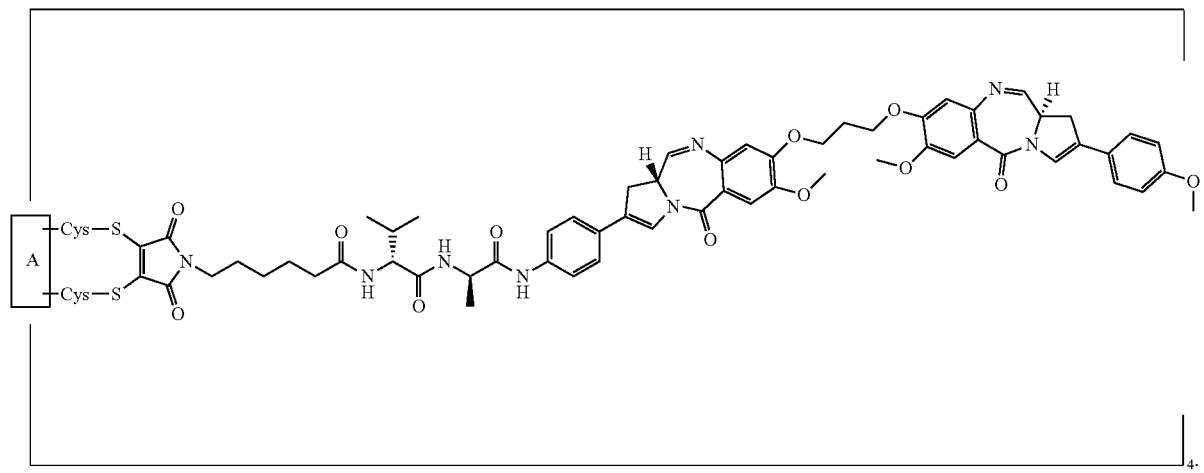

The antibody-drug conjugates of formula (Ic1) are prepared using linker-cytotoxin conjugates of the following formula (IIa):

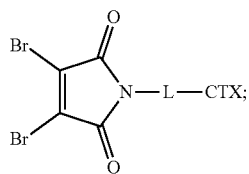

(IIa)

or an enantiomer, diasteriomer, or mixtures thereof;
wherein:
L is a cleavable or noncleavable linker; and
CTX is cytotoxin bonded to L by an amide bond, a carbamate bond, a disulfide bond, an ether bond, a thioether bond, or an ester bond.

For example, the antibody-drug conjugates of formula (Ic1) were prepared with anti-C10orf54 antibodies (e.g., humanized anti-C orf54 antibodies) using the linker-cytotoxin conjugate of formula (IIa), where CTX is MMAF, and L is —(CH$_2$)$_5$C(O)—.

For example, the antibody-drug conjugates of formula (Ic1) were prepared with anti-C10orf54 antibodies (e.g., humanized anti-C10orf54 antibodies) using the linker-cytotoxin conjugate which has the following structure:

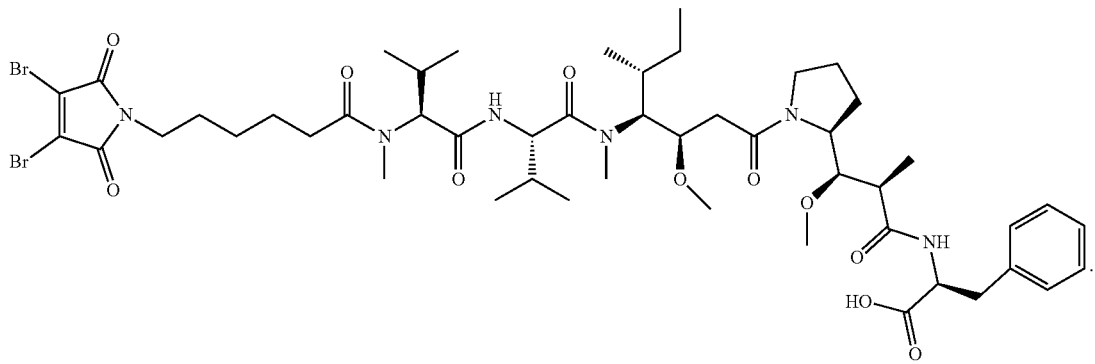 [SMILES: CC[C@@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@H](C(C)C)N(C)C(=O)CCCCCN1C(=O)C(Br)=C(Br)C1=O)C(C)C]

For example, the antibody-drug conjugates of formula (Ic1) are prepared with anti-16orf54 antibodies (e.g., humanized anti-C10orf54 antibodies) using the linker-cytotoxin conjugate of formula (IIa), where CTX is MMAE, and L is —(CH$_2$)$_5$C(O)-Val-Ala-PAB-O—C(O)—, or —(CH$_2$)$_5$C(O)-Val-Cit-PAB-O—C(O)—.

For example, the antibody-drug conjugates of formula (Ic1) are prepared with anti-C10orf54 antibodies (e.g., humanized anti-C10orf54 antibodies) using the linker-cytotoxin conjugate which has the following structure:

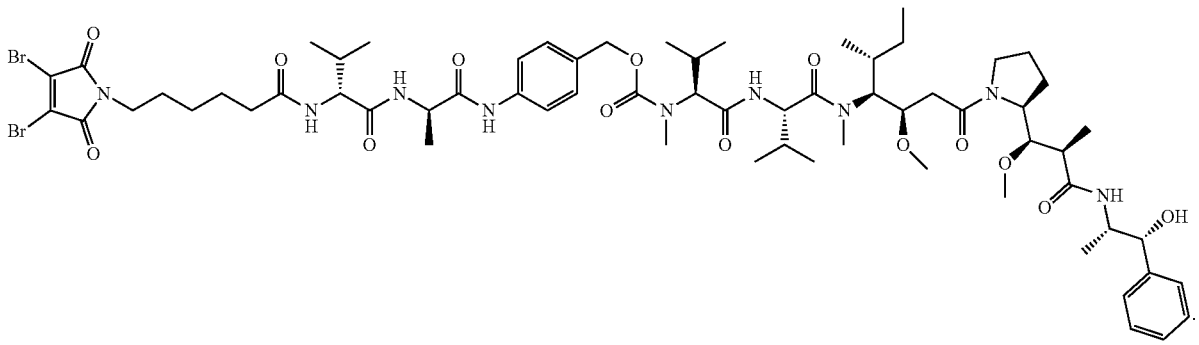 [SMILES: CC[C@@H](C)[C@@H]([C@@H](CC(=O)N1CCC[C@H]1[C@H](OC)[C@@H](C)C(=O)N[C@@H](C)[C@H](O)c1ccccc1)OC)N(C)C(=O)[C@@H](NC(=O)[C@H](C(C)C)N(C)C(=O)OCc1ccc(NC(=O)[C@@H](C)NC(=O)[C@H](NC(=O)CCCCCN2C(=O)C(Br)=C(Br)C2=O)C(C)C)cc1)C(C)C]

For example, the antibody-drug conjugates of formula (Ic1) are prepared with anti-16orf54 antibodies (e.g., humanized anti-C10orf54 antibodies) using the linker-cytotoxin conjugate of formula (IIa), where CTX is PDB, and L is —(CH$_2$)$_5$C(O)-Val-Ala-, —(CH$_2$)$_5$C(O)-Val-Cit-, —(CH$_2$)$_5$C(O)-Val-Ala-PAB-O—C(O)—, or —(CH$_2$)$_5$C(O)-Val-Cit-PAB-O—C(O)—.

For example, the antibody-drug conjugates of formula (Ic1) are prepared with anti-C10orf54 antibodies (e.g., humanized anti-C10orf54 antibodies) using the linker-cytotoxin conjugate which has one of the following structures:

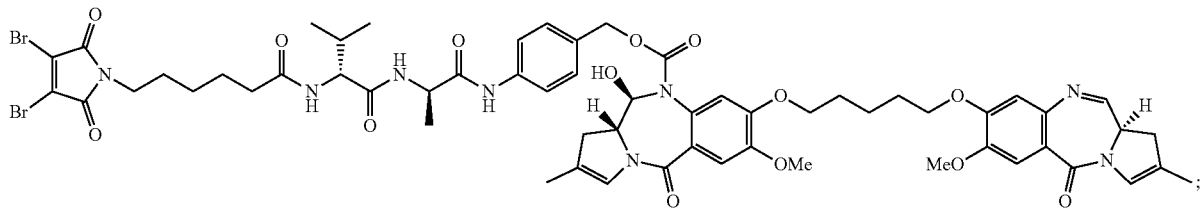

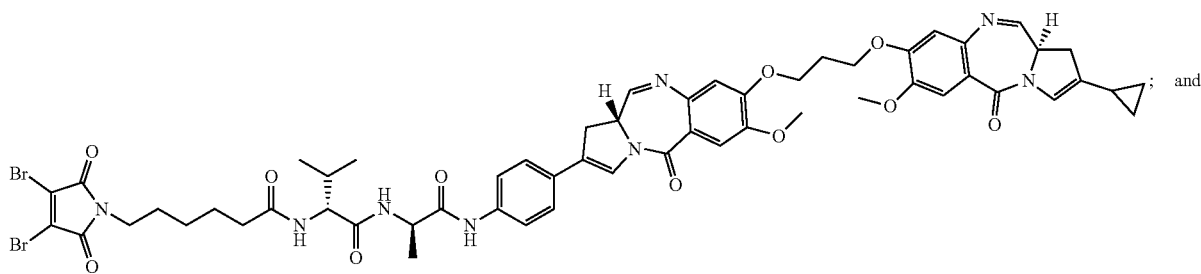

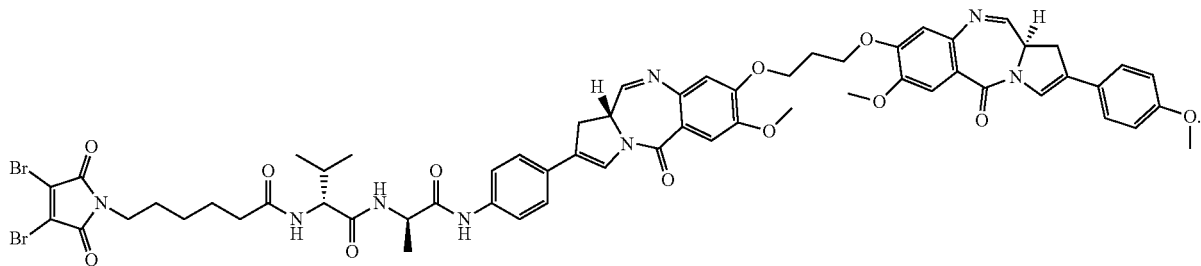

Additional antibody-drug conjugates of the present disclosure may be prepared, wherein the antibody-drug conjugates are according to formula (Ic2):

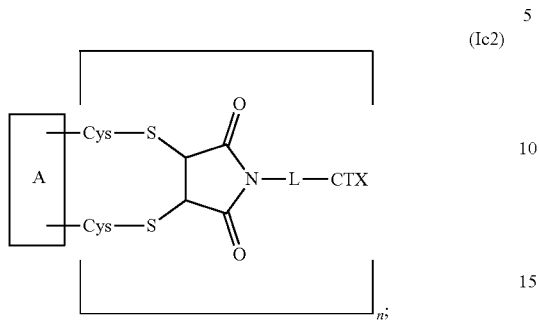

or a pharmaceutically acceptable salt thereof,
wherein:
A is an antibody, wherein the antibody is an anti-C10orf54 antibody, optionally a humanized anti-C10orf54 antibody;
the two depicted cysteine residues are from an opened cysteine-cysteine disulfide bond in A;
L is a cleavable or a noncleavable linker;
CTX is cytotoxin bonded to L by an amide bond, a carbamate bond, a disulfide bond, an ether bond, a thioether bond, or an ester bond; and
n is an integer of 1 to 4.

For example, the antibody-drug conjugates of formula (Ic2) are prepared where CTX is monomethylauristatin F (MMAF), L is —$(CH_2)_5C(O)$—, and n is 4.

For example, the antibody-drug conjugates of formula (Ic2) are prepared where the antibody-drug conjugate has the following formula:

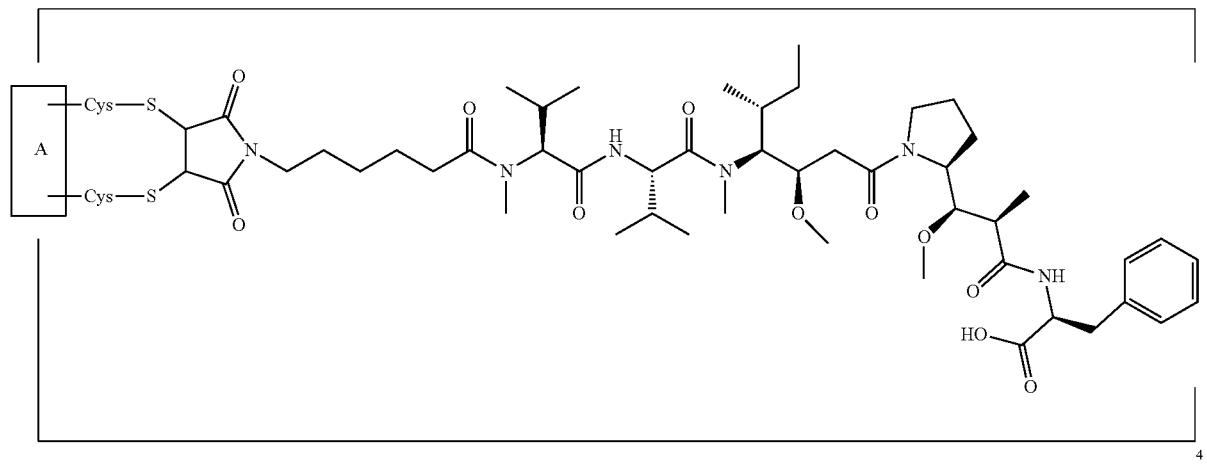

wherein A is an anti-C10orf54 antibody, optionally a humanized anti-C10orf54 antibody, and n is 4.

For example, the antibody-drug conjugates of formula (Ic2) are those where CTX is monomethylauristatin E (MMAE), L is —$(CH_2)_5C(O)$-Val-Ala-PAB-O—C(O)—, or —$(CH_2)_5C(O)$-Val-Cit-PAB-O—C(O)—, and n is 4.

For example, the antibody-drug conjugates of formula (Ic2) are those which have the following formula:

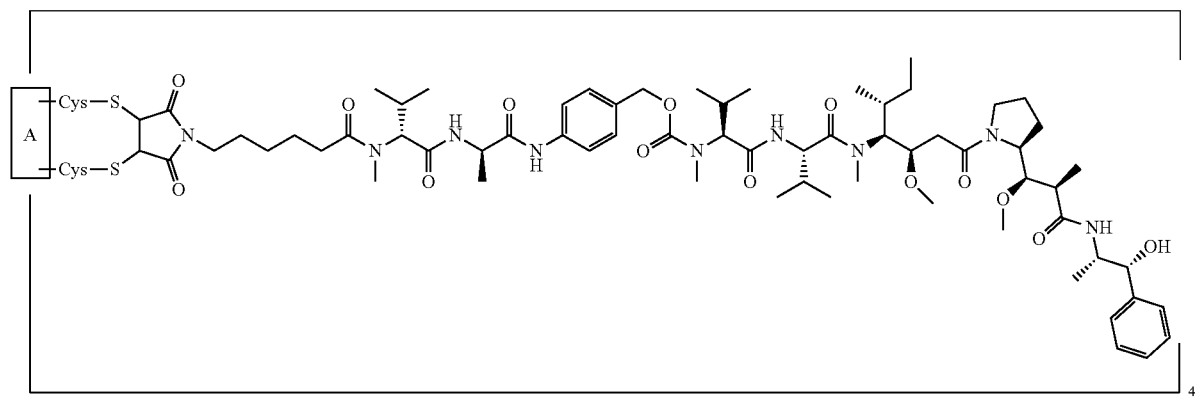

wherein A is an anti-C10orf54 antibody, optionally a humanized anti-C10orf54 antibody, and n is 4.

For example, the antibody-drug conjugates of formula (Ic2) are those where CTX is a pyrrolobenzodiazepine (PDB), L is —(CH$_2$)$_5$C(O)-Val-Ala-PAB-O—C(O)—, or —(CH$_2$)$_5$C(O)-Val-Cit-PAB-O—C(O)—, and n is 4.

For example, the antibody-drug conjugates of formula (Ic2) are those which have one of the following formulas:

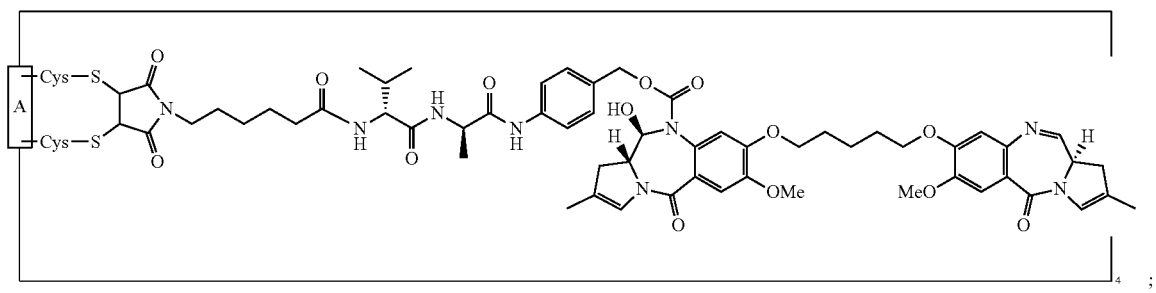

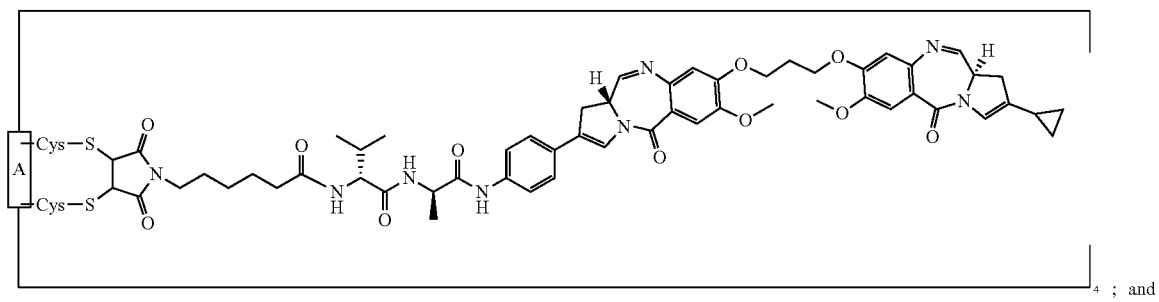
; and

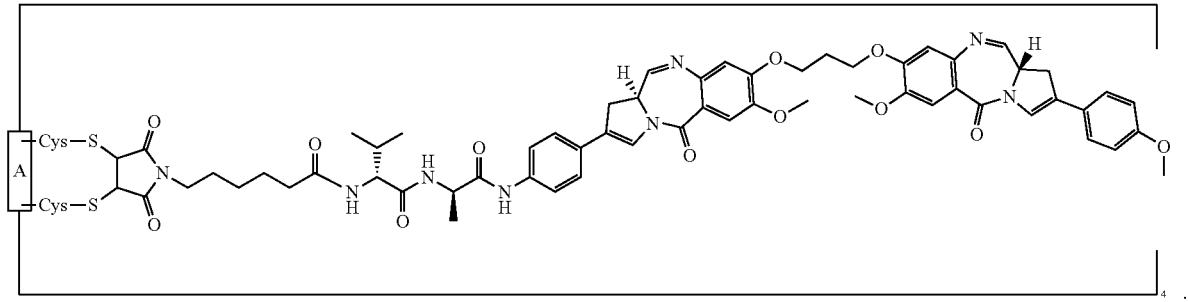
.

The antibody-drug conjugates of formula (Ic2) are prepared using linker-cytotoxin conjugates of one of the following formulas (IIb) and (IIc):

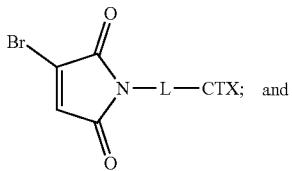
(IIb)

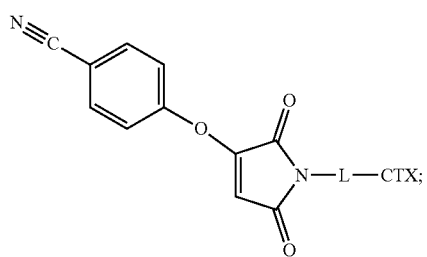
(IIc)

or an enantiomer, diasteriomer, or mixtures thereof;
wherein:
L is a cleavable or noncleavable linker; and
CTX is cytotoxin bonded to L by an amide bond, a carbamate bond, a disulfide bond, an ether bond, a thioether bond, or an ester bond.

For example, the antibody-drug conjugates of formula (Ic2) are prepared with anti C10orf54 antibodies (e.g., humanized anti-C10orf54 antibodies) using the linker-cytotoxin conjugate of formula (IIb) or (IIc), where CTX is MMAF, and L is —$(CH_2)_5C(O)$—.

For example, the antibody-drug conjugates of formula (Ic2) are prepared with anti-C10orf54 antibodies (e.g., humanized anti-C10orf54 antibodies) using the linker-cytotoxin conjugate which has one of the following structures:

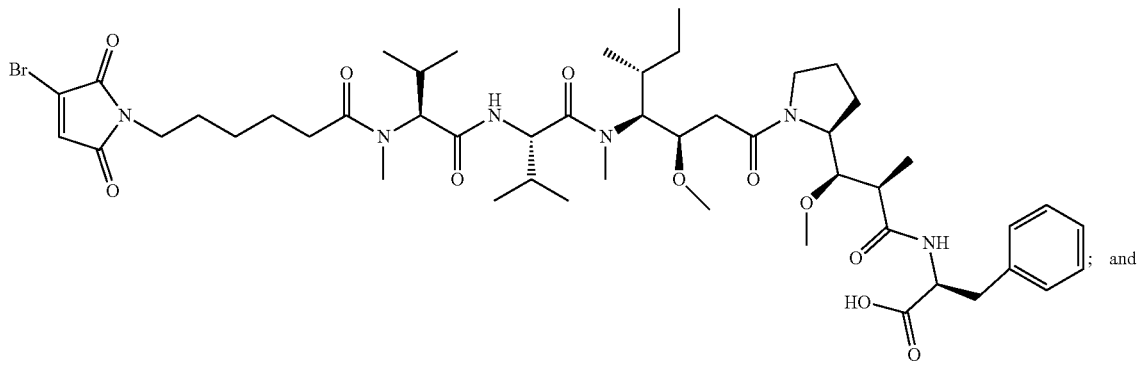
; and

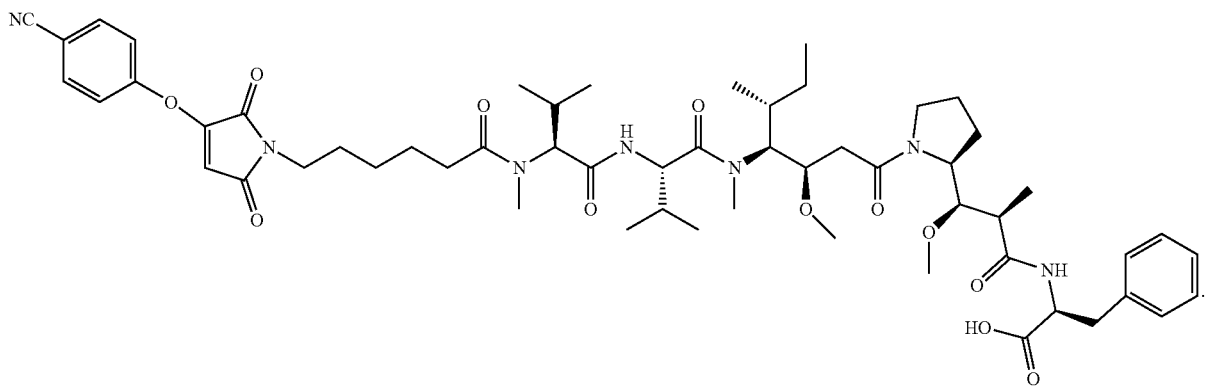

For example, the antibody-drug conjugates of formula (Ic2) are prepared with anti-16orf54 antibodies (e.g., humanized anti-C10orf54 antibodies) using the linker-cytotoxin conjugate of formula (IIb) or (IIc), where CTX is MMAE, and L is —(CH$_2$)$_5$C(O)-Val-Ala-PAB-O—C(O)—, or —(CH$_2$)$_5$C(O)-Val-Cit-PAB-O—C(O)—.

For example, the antibody-drug conjugates of formula (Ic2) are prepared with anti-C10orf54 antibodies (e.g., humanized anti-C10orf54 antibodies) using the linker-cytotoxin conjugate which has one of the following structures:

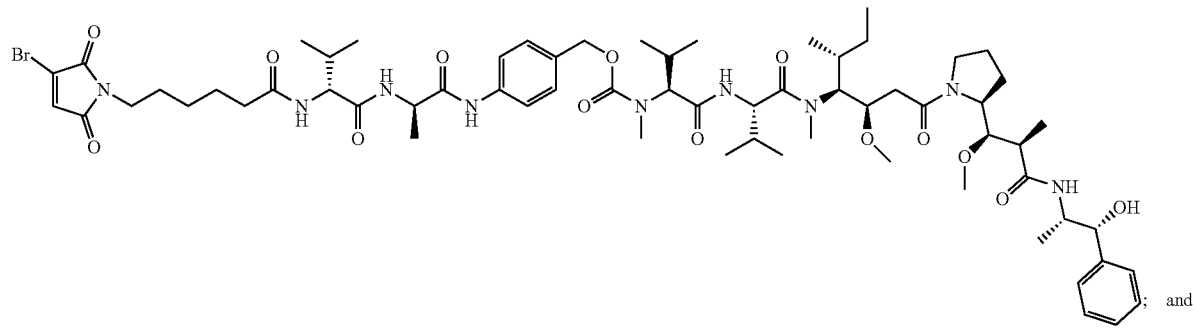

; and

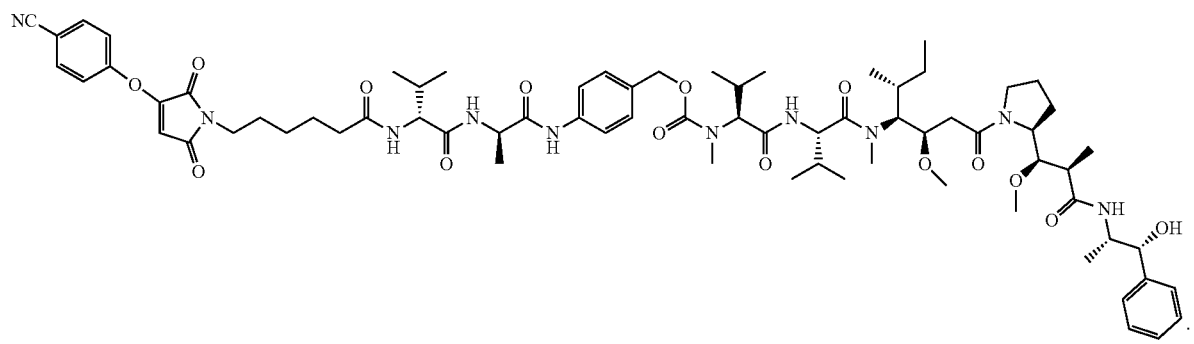

.

For example, the antibody-drug conjugates of formula (Ic2) are prepared with anti-16orf54 antibodies (e.g., humanized anti-C10orf54 antibodies) using the linker-cytotoxin conjugate of formula (IIb) or (IIc), where CTX is PDB, and L is —(CH$_2$)$_5$C(O)-Val-Ala-, —(CH$_2$)$_5$C(O)-Val-Cit-, —(CH$_2$)$_5$C(O)-Val-Ala-PAB-O—C(O)—, or (CH$_2$)$_5$C(O)-Val-Cit-PAB-O—C(O)—.

For example, the antibody-drug conjugates of formula (Ic2) are prepared with anti-C10orf54 antibodies (e.g., humanized anti-C10orf54 antibodies) using the linker-cytotoxin conjugate which has one of the following structures:

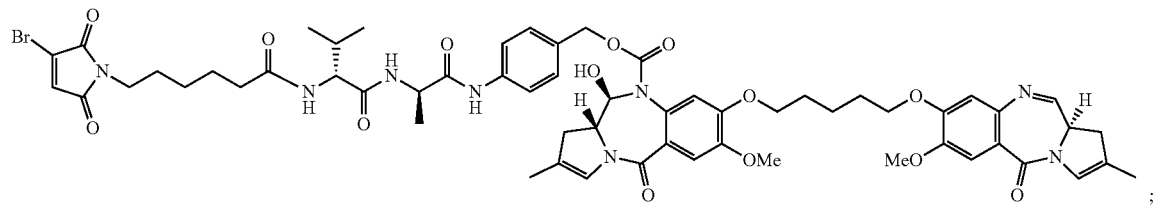

;

-continued

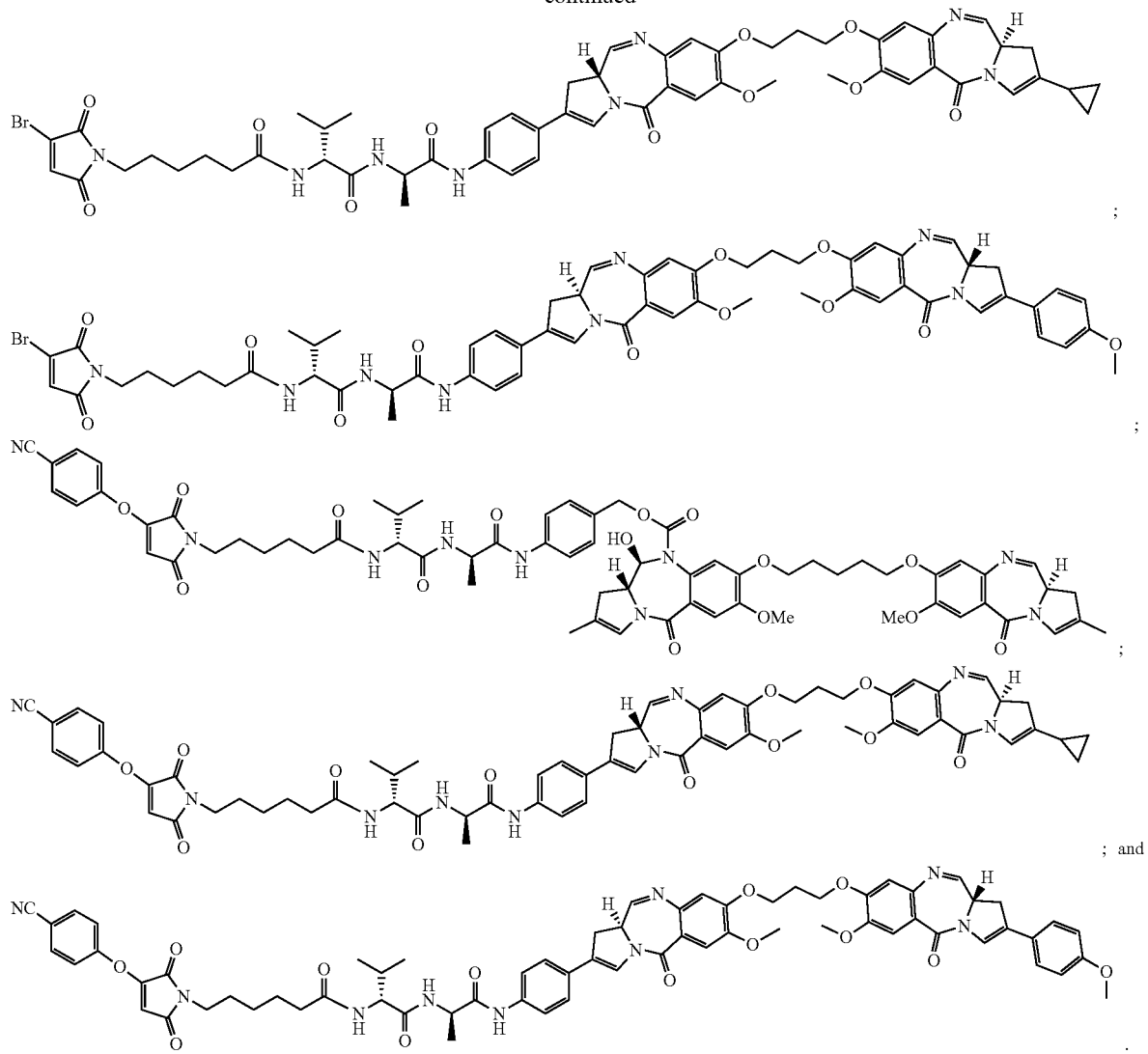

Antibody-drug conjugates, as described in this example and herein, are prepared wherein one or more interchain disulfide bonds of the antibody (e.g., four interchain disulfide bonds as depicted in exemplary Schemes F and G above) are conjugated. Antibody-drug conjugates, wherein one or more of the intrachain disulfide bonds of the antibody are conjugated, as described herein, have a preferred antibody-to-drug ratio of four.

Cell viability experiments were performed using human AML cell lines such as OCI/AML3, PL21 and P31/FUJ. For the primary ADC assays, myeloid cell lines were routinely passaged in RPMI or MEM media (LifeTech) supplemented with 10-20% fetal calf serum (LifeTech). To assay toxicity, cells were plated in 384-well plates (Greiner) at 3,000 cells per well in 50 μL of media.

For the primary ADC assays, DBM(C6)MMAF-conjugated anti-C10orf54 antibodies are serially-diluted from 100-300 nM in RPMI and added to appropriate wells in duplicate using an iPipette liquid handler (Apricot Designs). Cell plates are then incubated for three days, followed by lysis in Cell-Titer Glo assay reagent (Promega).

For primary ADC assays, luminescence is quantified on a SYNERGY™ HT plate reader (BioTek) and graphed. IC50s are calculated by fitting to a four-parameter sigmoidal fit (GraphPad). Results of exemplary primary ADC assays using three myeloid cell lines are shown as IC50 (nM) values in Table 41. For example, the ADCs represented in Table 41 were generated by conjugating the humanized variants of the antibodies to the DBM-(C6)-MMAF linker-toxin as described in this Example 8. The results indicate that the OCI/AML3 cell line and P31/FUJ were both sensitive to anti C10orf54 ADCs, while the PL21 cell line was less sensitive

TABLE 41

| | IC50 (nM) | | |
|---|---|---|---|
| Antibody* | OCI/AML3 | P31FUJ | PL21 |
| C1.18 DBM(C6)MMAF | >100 | >100 | >100 |
| 146C:DBM(C6):MMAF | 58.62 | <.001 | >100 |
| 164A:DBM(C6):MMAF | 0.30 | <.001 | 62.86 |
| 208A:DBM(C6):MMAF | 0.31 | <.001 | >100 |
| 215A:DBM(C6):MMAF | 0.43 | <.001 | >100 |
| 230A:DBM(C6):MMAF | 3.06 | <.001 | >100 |
| 259A:DBM(C6):MMAF | 1.56 | <.001 | >100 |

TABLE 41-continued

| Antibody* | IC50 (nM) | | |
|---|---|---|---|
| | OCI/AML3 | P31FUJ | PL21 |
| 305A:DBM(C6):MMAF | 0.81 | <.001 | >100 |
| 353A:DBM(C6):MMAF | 0.51 | <.001 | >100 |
| 53A:DBM(C6):MMAF | 0.34 | 0.16 | 4.97 |
| 5B:DBM(C6):MMAF | 1.01 | <.001 | >100 |
| 175A:DBM(C6):MMAF | 0.16 | <.001 | 7.83 |
| 76E1:DBM(C6):MMAF | 0.02 | 0.08 | 0.11 |

The embodiments of the present disclosure described above are intended to be merely exemplary, and those skilled in the art will recognize, or be able to ascertain using no more than routine experimentation, numerous equivalents to the specific procedures described herein. All such equivalents are considered to be within the scope of the present disclosure and are covered by the following claims.

Furthermore, as used in this specification and claims, the singular forms "a," "an" and "the" include plural forms unless the content clearly dictates otherwise. Thus, for example, reference to "an antibody" includes a mixture of two or more such antibodies, and the like. Additionally, ordinarily skilled artisans will recognize that operational sequences must be set forth in some specific order for the purpose of explanation and claiming, but the present disclosure contemplates various changes beyond such specific order.

Example 9—Functional Assays

In order to identify optimal conditions of cultivation and activation of naïve T-cells to the extent that this activation can be reversed by administration of anti-C10orf54 antibodies, the following experiments were conducted. Once optimal conditions are identified, they can be used in further anti-C10orf54 antibody screening, such as those described herein. Optimal concentrations of anti-CD3 antibodies, anti-CD28 antibodies, C10orf54-Fc, and T-cells have been determined.

CellTiter-Glo, a luminescent cell viability assay, was used to determine viability of T-cells cultivated at various conditions. T-cell activation was achieved by precoating of plates with anti-CD3 antibodies followed by co-stimulation with anti-CD28 antibodies in solution. The starting conditions were based on the data presented by Wang et al., Biofunctions of three new B7 family members (Reference: Wang, Jinghua, et al. "Biofunctions of three new B7 family members (IRM7P. 486)." (2014): 126-11).

T-cell concentration appeared to be important for anti-CD3/anti-CD28-dependent stimulation of T-cells. Only the highest amount tested, 50,000 cells per well of 384-well plate, demonstrated such dependence and was used for all further steps. Minimal anti-CD3 antibody concentration, at which activation close to maximal level was achieved, was 5 ug/ml. At the defined concentration of anti-CD3 antibody, a concentration-dependent C10orf54-Fc impact on T-cell proliferation was observed. With a stronger activation attained by CD2/CD3/CD28 magnetic beads, the effect was not observed.

Minimal anti-CD28 antibody concentration, at which T-cell proliferation close to maximal level was achieved, was shown to be about 3-4 ug/ml. Concentration-dependent impact of C10orf54-Fc on T-cell proliferation was observed within all the tested range of anti-CD28 antibody. Thus, a 3.2 ug/ml point has been chosen for the further steps.

Pan T-cells behaved similarly to naïve T-cells. However, naïve T-cells were more sensitive to C10orf54-Fc inhibition than pan T-cells (FIGS. 30A-30C).

In summary, based on the above analysis, the optimized conditions for cultivation and activation of naïve T-cells are 5 ug/ml of anti-CD3 antibodies and 3.2 ug/ml of anti-CD28 antibodies. The moderate level of activation made it possible to reverse this activation by C10orf54-Fc administration, making this assay helpful for assessing anti-C10orf54 antibodies.

Additional in vitro assays were conducted as described below to determine whether anti-C10orf54 antibodies enhanced T-cell stimulation.

Anti-C10orf54 antibodies described herein were immobilized on a plate at varying concentrations. Naïve T-cells were stimulated by the addition of soluble anti-CD28 antibodies at a concentration of 5 µg/ml and contacting the naïve T-cells to immobilized anti-CD3 antibodies at a concentration of 3.2 µg/ml on the same plate as the anti-C10orf54 antibodies. Enhancement of T-cell stimulation was monitored by IL-2 secretion, IFN-γ secretion and incorporation of $^3$H-thymidine (an indicator of cell proliferation).

The effects of the anti-C10orf54 antibodies on T-cell stimulation are summarized in Table 42 below.

TABLE 42

| mAb | KD [nM] | IL-2 [% of Mean] | IFN-γ [% of Mean] | 3H-Thymidine [% of Mean] | Paratope |
|---|---|---|---|---|---|
| 259A | 0.266 | 60 | 112 | 80 | 7 |
| 53A | 0.321 | 58 | 72 | 97 | 7 |
| 128A | 0.635 | 119 | 113 | 80 | 1 |
| 26A | 0.677 | 274 | 208 | 109 | 3 |
| 5B | 0.974 | 71 | 91 | 90 | 1 |
| 230A | 1.05 | 105 | 75 | 104 | 5 |
| 141A | 1.27 | 116 | 108 | 119 | 9 |
| 215A | 1.52 | 70 | 41 | 101 | 2 |
| 51A | 1.52 | 97 | 82 | 124 | 9 |
| 46A | 1.88 | 116 | 99 | 102 | 1 |
| 97A | 1.99 | 95 | 121 | 92 | 1 |
| 208A | 2.48 | 84 | 77 | 97 | 1 |
| 353A | 2.9 | 47 | 110 | 116 | 10 |
| 124A | 3.61 | 169 | 122 | 95 | 8 |
| 39A | 5.79 | 89 | 89 | 110 | 8 |
| 33A | 6.61 | 126 | 125 | 122 | 8 |
| 321D | 7.26 | 55 | 85 | 104 | 8 |
| 76E1 | 10.1 | 173 | 197 | 99 | 6 |
| 305A* | 20.8 | 10 | 35 | 61 | 11 |
| 175A* | 108 | 9 | 40 | 82 | 8 |

*Low affinity antibodies; 20 nM = 3 µg.

Still further, in vitro assays were conducted as described below to determine whether anti-C10orf54 antibodies induced T-cell proliferation.

The C10orf54-Fc construct, as described above, was immobilized on a plate at varying concentrations. As a positive control, an IgG-Fc construct was also immobilized on a separate plate. Naïve T-cells were stimulated by the addition of soluble anti-CD28 antibodies at a concentration of 5 µg/ml and contacting the naïve T-cells to immobilized anti-CD3 antibodies at a concentration of 3.2 µg/ml on the same plate as either the C10orf54-Fc construct or the IgG-Fc control. Additionally, soluble anti-C10orf54 antibodies (26A or 175A described herein) were added to further enhance T-cell stimulation. Enhancement of T-cell stimulation was monitored by IL-2 secretion, IFN-γ secretion and incorporation of $^3$H-thymidine (an indicator of cell proliferation).

Figure 29:
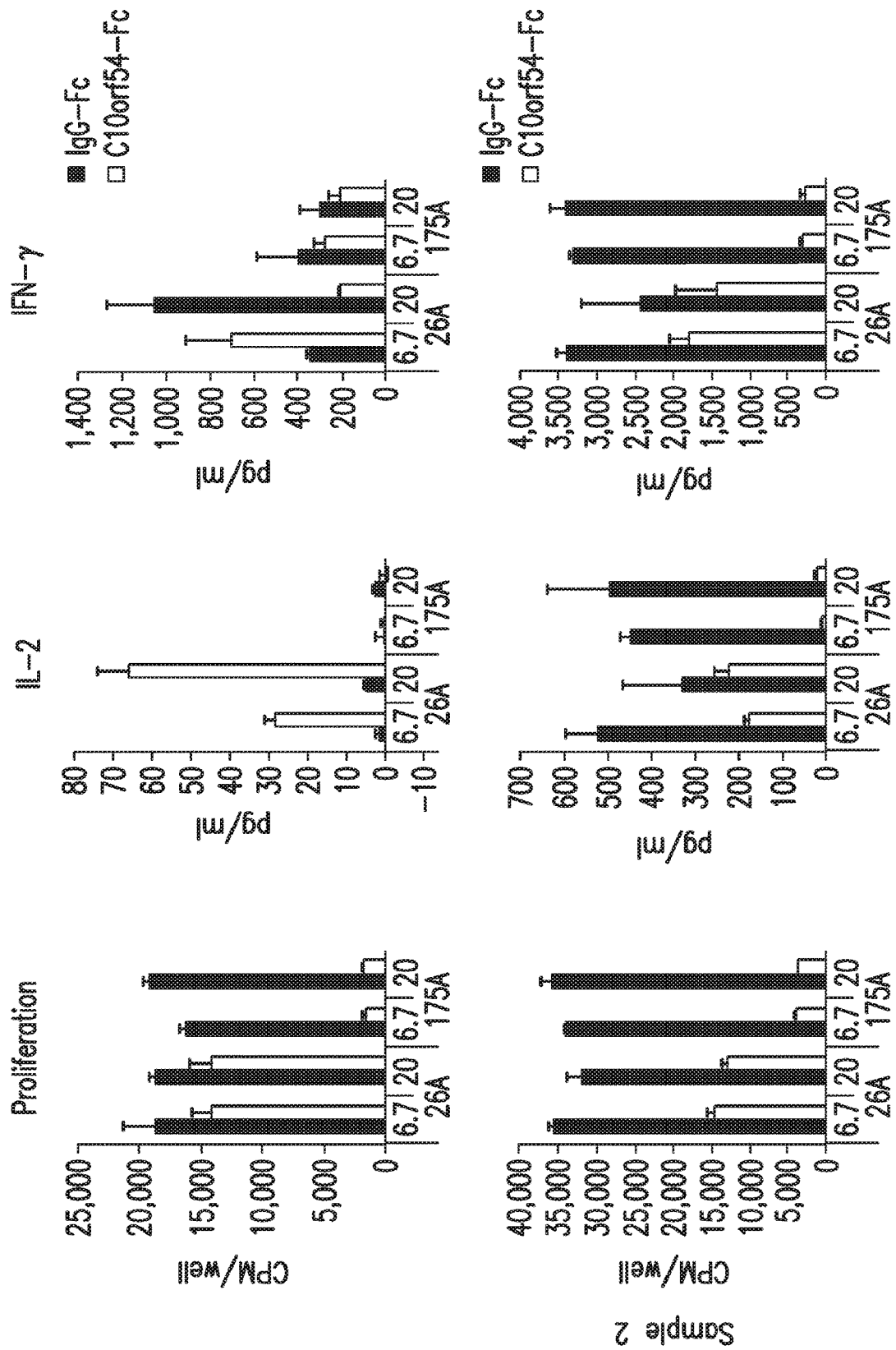
FIG. 29 shows bar graphs of the ability of anti-C10orf54 antibodies to attenuate C10orf54-mediated suppression of naïve T-cell proliferation and cytokine secretion.

The anti-C10orf54 antibody 26A attenuated C10orf54-mediated suppression of naïve T-cell proliferation, as well as secretion of IL-2 and IFN-γ. These results are shown in FIG. 29.

Still further in vitro assays were conducted as described below to determine whether C10orf54 inhibits T-cell stimulation in naïve T-cells, CD4+ T-cells and CD8+ T-cells.

The C10orf54-Fc construct, as described above, was immobilized on a plate at varying concentrations. As a positive control, an IgG-Fc construct was also immobilized on a separate plate. The T-cells were stimulated by the addition of soluble anti-CD28 antibodies at a concentration of 5 µg/ml and contacting the T-cells to immobilized anti-CD3 antibodies at a concentration of 3.2 µg/ml on the same plate as either the C10orf54-Fc construct or the IgG-Fc control. Inhibition of T-cell stimulation was monitored by incorporation of $^3$H-thymidine (an indicator of cell proliferation).

Figure 28:
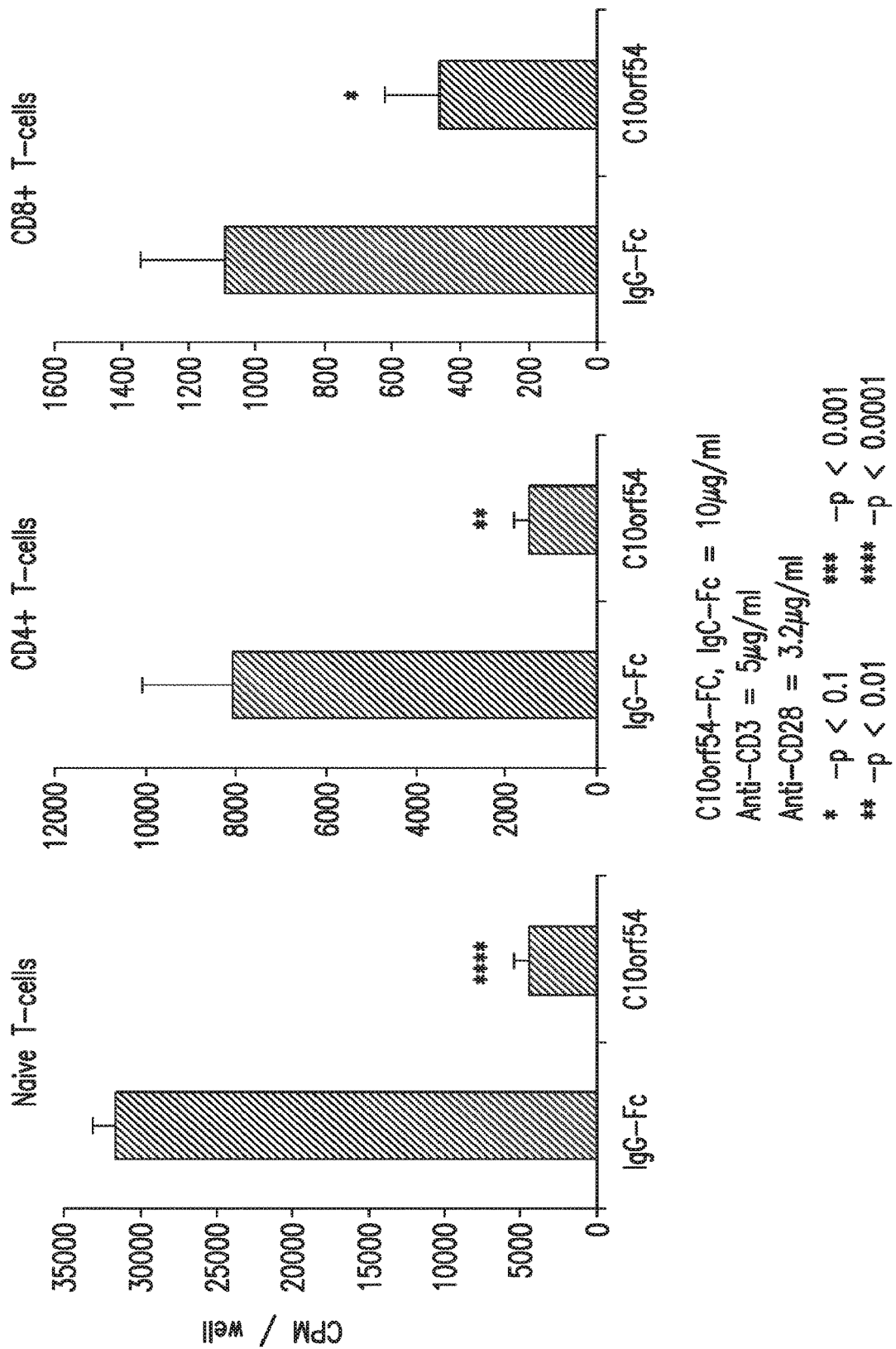
FIG. 28 shows bar graphs of T-cell proliferation being inhibited by exposure to a C10orf54-Fc construct. Incorporation of ³H-thymidine is depicted.

The immobilized C10orf54-Fc construct at a concentration of 10 µg/ml inhibited the anti-CD3/anti-CD28-stimulated naïve T-cells, as well as inhibited CD4+ or CD8+ T-cells, as measured by incorporation of $^3$H-thymidine. These results are shown in FIG. 28. In additional assays, anti-C10orf54 antibodies, such as 26A, are added to the assay to attenuate the C10orf54-mediated suppression of naïve T-cells, CD4$^+$ T-cells or CD8$^+$ T-cells.

The contents of all references described herein are hereby incorporated by reference. Other embodiments are within the following claims.

SEQUENCE LISTING

The patent contains a lengthy sequence listing. A copy of the sequence listing is available in electronic form from the USPTO web site (https://seqdata.uspto.gov/?pageRequest=docDetail&DocID=US11873339B2). An electronic copy of the sequence listing will also be available from the USPTO upon request and payment of the fee set forth in 37 CFR 1.19(b)(3).

What is claimed:

1. An isolated antibody, or antigen-binding fragment thereof, that binds to a first group of C10orf54 proteins or chimeric proteins designated CC1 (SEQ ID NO: 1079), CC4 (SEQ ID NO: 1245), CC5 (SEQ ID NO: 1246), CC8 (SEQ ID NO: 1249), and CC10 (SEQ ID NO: 1251), and does not bind to a second group of C10orf54 proteins or chimeric proteins designated CC2 (SEQ ID NO: 1243), CC3 (SEQ ID NO: 1244), CC6 (SEQ ID NO: 1247), CC7 (SEQ ID NO: 1248), and CC9 (SEQ ID NO: 1250);
wherein the antibody is the antibody 230A, comprising:
a heavy chain variable domain comprising the following three CDRs, respectively CDR-H1 having the sequence SEQ ID NO: 1302, CDR-H2 having the sequence SEQ ID NO: 1365 and CDR-H3 having the sequence SEQ ID NO: 1402, and a light chain variable domain comprising the following three CDRs, respectively CDR-L1 having the sequence SEQ ID NO: 1455, CDR-L2 having the sequence SEQ ID NO: 1103 and CDR-L3 having the sequence SEQ ID NO: 1505.

2. The isolated antibody, or antigen-binding fragment thereof, of claim 1, wherein the antibody comprises a heavy chain variable domain comprising the sequence of SEQ ID NO: 1271, and a light chain variable domain comprising the sequence of SEQ ID NO: 1272.

3. The antibody, or antigen-binding fragment thereof, of claim 1, wherein the antibody is a monoclonal antibody.

4. The antibody, or antigen-binding fragment thereof, of claim 1, wherein the antibody is humanized.

5. The antibody, or antigen-binding fragment thereof, of claim 1, wherein the antibody is a Fab fragment, a F(ab')2 fragment, a single chain Fv (sFv), a diabody, a triabody, or a minibody.

6. The antibody, or antigen-binding fragment thereof, of claim 1, wherein the antibody is conjugated or recombinantly fused to a detectable agent.

7. The antibody, or antigen-binding fragment thereof, of claim 6, wherein the detectable agent is selected from the group consisting of an enzyme, a fluorescent compound, a bioluminescent compound, a chemiluminescent compound, a radioisotope, a prosthetic group, a positron emitting metal, and a non-radioactive paramagnetic metal ion.

8. The antibody, or antigen-binding fragment thereof, of claim 7, wherein
the enzyme is selected from the group consisting of horseradish peroxidase, alkaline phosphatase, beta-galactosidase, and acetylcholinesterase,
the fluorescent compound is selected from the group consisting of umbelliferone, fluorescein, fluorescein isothiocynate, rhodamine, dichlorotriazinylamine fluorescein, dansyl chloride and phycoerythrin,
the bioluminescent compound is selected from the group consisting of luciferase, luciferin, and aequorin,
the chemiluminescent compound is luminol, or
the radioisotope is selected from the group consisting of $^{131}$I, $^{125}$I, $^{123}$I, $^{121}$I, $^{14}$C $^{35}$S, $^{3}$H, $^{115}$In, $^{113}$In, $^{112}$In, $^{111}$In, $^{99}$Tc, $^{201}$Ti, $^{68}$Ga, $^{67}$Ga, $^{103}$Pd, $^{99}$Mo, $^{133}$Xe, $^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn.

9. A polynucleotide comprising a nucleic acid sequence encoding the antibody or antigen-binding fragment thereof of claim 1.

10. An expression vector comprising the polynucleotide of claim 9.

11. An isolated host cell comprising the expression vector of claim 10.

12. A method of producing the antibody or antigen-binding fragment thereof of claim 1, the method comprising a step of culturing an isolated host cell comprising an expression vector comprising a polynucleotide comprising a nucleic acid sequence encoding the antibody or antigen-binding fragment thereof of claim 1 under conditions that promote the production of the antibody.

13. An in vitro method for detecting a C10orf54 protein in a sample comprising contacting the sample with the antibody or antigen-binding fragment thereof of claim 1.

14. An in vitro method of detecting a C10orf54-mediated disease in a subject comprising:
(a) assaying the level of a human C10orf54 antigen in cells or a tissue sample of a subject using the antibody or antigen-binding fragment thereof of claim 1, the antibody being conjugated or recombinantly fused to a detectable agent; and (b) comparing the level of the human C10orf54 antigen with a control level of the antigen, wherein an increase in the assayed human C10orf54 antigen level as compared to the control level of the human C10orf54 antigen is indicative of a C10orf54-mediated disease.

15. The method of claim 14, wherein assaying the level of C10orf54 antigen is determined by a method selected from the group consisting of: an immunohistochemistry assay, an enzyme linked immunosorbent assay (ELISA), a radioimmunoassay (RIA), and fluorescence activated cell sorting (FACS).

16. The method of claim 14 wherein the C10orf54-mediated disease is a cell proliferative disorder, a cancer, a tumor, or graft-versus-host disease.

17. A kit comprising the antibody, or antigen-binding fragment thereof, of claim 1.

18. The kit of claim 17, further comprising a substantially isolated human C10orf54 protein.

19. The kit of claim 18, wherein the human C10orf54 protein is attached to a solid support.

20. An in vitro method of monitoring a C10orf54-mediated disease comprising:

(a) assaying the level of a human C10orf54 antigen in cells or a tissue sample of a subject using an antibody or antigen-binding fragment thereof, the antibody comprising:

a heavy chain variable domain comprising the following three CDRs, respectively CDR-H1 having the sequence SEQ ID NO: 1302, CDR-H2 having the sequence SEQ ID NO: 1365 and CDR-H3 having the sequence SEQ ID NO: 1402, and a light chain variable domain comprising the following three CDRs, respectively CDR-L1 having the sequence SEQ ID NO: 1455, CDR-L2 having the sequence SEQ ID NO: 1103 and CDR-L3 having the sequence SEQ ID NO: 1505, wherein the antibody is conjugated or recombinantly fused to a detectable agent;

(b) comparing the level of the human C10orf54 antigen with a control level of the antigen, wherein an increase in the assayed human C10orf54 antigen level as compared to the control level of the human C10orf54 antigen is indicative of a C10orf54-mediated disease; and (c) repeating steps (a) and (b) one month, six months, or one year after initial diagnosis of the C10orf54-mediated disease.

21. The method of claim 14, wherein the detectable agent is selected from the group consisting of an enzyme, a fluorescent compound, a bioluminescent compound, a chemiluminescent compound, a radioisotope, a prosthetic group, a positron emitting metal, and a non-radioactive paramagnetic metal ion.

22. The method of claim 21, wherein the enzyme is selected from the group consisting of horseradish peroxidase, alkaline phosphatase, beta-galactosidase, and acetylcholinesterase, the fluorescent compound is selected from the group consisting of umbelliferone, fluorescein, fluorescein isothiocynate, rhodamine, dichlorotriazinylamine fluorescein, dansyl chloride and phycoerythrin, the bioluminescent compound is selected from the group consisting of luciferase, luciferin, and aequorin, the chemiluminescent compound is luminol, or the radioisotope is selected from the group consisting of $^{131}$I, $^{125}$I, $^{123}$I, $^{121}$I, $^{14}$C, $^{35}$S, $^{3}$H, $^{115}$In, $^{113}$In, $^{112}$In, $^{111}$In, $^{99}$Tc, $^{201}$Ti, $^{68}$Ga, $^{67}$Ga, $^{103}$Pd, $^{99}$Mo, $^{133}$Xe, $^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn.

23. The method of claim 20, wherein the detectable agent is selected from the group consisting of an enzyme, a fluorescent compound, a bioluminescent compound, a chemiluminescent compound, a radioisotope, a prosthetic group, a positron emitting metal, and a non-radioactive paramagnetic metal ion.

24. The method of claim 23, wherein the enzyme is selected from the group consisting of horseradish peroxidase, alkaline phosphatase, beta-galactosidase, and acetylcholinesterase, the fluorescent compound is selected from the group consisting of umbelliferone, fluorescein, fluorescein isothiocynate, rhodamine, dichlorotriazinylamine fluorescein, dansyl chloride and phycoerythrin, the bioluminescent compound is selected from the group consisting of luciferase, luciferin, and aequorin, the chemiluminescent compound is luminol, or the radioisotope is selected from the group consisting of $^{131}$I, $^{125}$I, $^{123}$I, $^{121}$I, $^{14}$C, $^{35}$S, $^{3}$H, $^{115}$In, $^{113}$In, $^{112}$In, $^{111}$In, $^{99}$Tc, $^{201}$Ti, $^{68}$Ga, $^{67}$Ga, $^{103}$Pd, $^{99}$Mo, $^{133}$Xe, $^{18}$F, $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn.

* * * * *